US011033593B2

(12) United States Patent
Senger et al.

(10) Patent No.: US 11,033,593 B2
(45) Date of Patent: Jun. 15, 2021

(54) ***BRASSICA* EVENTS LBFLFK AND LBFDAU AND METHODS FOR DETECTION THEREOF**

(71) Applicant: BASF PLANT SCIENCE COMPANY GMBH, Ludwigshafen (DE)

(72) Inventors: Toralf Senger, Durham, NC (US); Laurent Marty, Heidelberg (DE); Irene Kunze, Gatersleben (DE); Dietrich Rein, Berlin (DE); Joerg Bauer, Durham, NC (US); Carl Andre, Raleigh, NC (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 592 days.

(21) Appl. No.: 15/526,443

(22) PCT Filed: Nov. 13, 2015

(86) PCT No.: PCT/EP2015/076596

§ 371 (c)(1),
(2) Date: May 12, 2017

(87) PCT Pub. No.: WO2016/075303

PCT Pub. Date: May 19, 2016

(65) Prior Publication Data

US 2018/0298400 A1 Oct. 18, 2018

Related U.S. Application Data

(60) Provisional application No. 62/234,373, filed on Sep. 29, 2015, provisional application No. 62/079,622, filed on Nov. 14, 2014.

(51) Int. Cl.

| | |
|---|---|
| ***A61K 36/31*** | (2006.01) |
| ***C12N 15/82*** | (2006.01) |
| ***C12Q 1/6895*** | (2018.01) |
| *C12N 9/02* | (2006.01) |
| *C12N 9/00* | (2006.01) |
| *A61K 31/202* | (2006.01) |

(52) U.S. Cl.

CPC ............ *A61K 36/31* (2013.01); *C12Q 1/6895* (2013.01); *A61K 31/202* (2013.01); *C12N 9/0071* (2013.01); *C12N 9/93* (2013.01); *C12N 15/8247* (2013.01); *C12Y 114/19* (2013.01); *C12Y 114/19003* (2013.01); *C12Y 114/19006* (2013.01); *C12Y 602/01003* (2013.01)

(58) Field of Classification Search

CPC ...................................................... A61K 36/31

See application file for complete search history.

(56) References Cited

U.S. PATENT DOCUMENTS

| | | | | |
|---|---|---|---|---|
| 5,627,289 | A | 5/1997 | Jeromin et al. | |
| 6,303,849 | B1 | 10/2001 | Potts et al. | |
| 6,689,880 | B2 | 2/2004 | Chen et al. | |
| 6,733,974 | B1 | 5/2004 | Feazel | |
| 6,740,488 | B2 | 5/2004 | Rangwala et al. | |
| 6,818,807 | B2 | 11/2004 | Trolinder et al. | |
| 6,825,400 | B2 | 11/2004 | Behr et al. | |
| 6,893,826 | B1 | 5/2005 | Hillyard et al. | |
| 6,900,014 | B1 | 5/2005 | Weston et al. | |
| 7,371,930 | B1 * | 5/2008 | Knerr | A01H 5/12 435/410 |
| 7,423,198 | B2 | 9/2008 | Yao et al. | |
| 8,999,411 | B2 | 4/2015 | Froman et al. | |
| 2013/0288377 | A1 * | 10/2013 | Champagne | C12N 15/8274 435/471 |
| 2015/0299676 | A1 | 10/2015 | Walsh et al. | |

FOREIGN PATENT DOCUMENTS

| | | | |
|---|---|---|---|
| AU | 2011289381 | A1 | 1/2013 |
| WO | WO-93/10241 | A1 | 5/1993 |
| WO | WO-94/13814 | A1 | 6/1994 |
| WO | WO-95/27791 | A1 | 10/1995 |
| WO | WO-96/24674 | A1 | 8/1996 |
| WO | WO-98/55631 | A1 | 12/1998 |
| WO | WO-98/55632 | A1 | 12/1998 |
| WO | WO-99/64616 | A2 | 12/1999 |
| WO | WO-00/18889 | A2 | 4/2000 |
| WO | WO-01/059128 | A2 | 8/2001 |
| WO | WO-02/26946 | A2 | 4/2002 |

(Continued)

OTHER PUBLICATIONS

Vrinten etal (Production of Polyunsaturated Fatty Acids in Transgenic Plants. Biotechnology and Genetic Engineering Reviews—vol. 24, 263-280, 2007).*

Ruiz-Lopez et al (Nutritional and Bioactive Compounds in Mexican Lupin Beans Species: A Mini-Review. Nutrients. 1-19, 2019) (Year: 2019).*

Ruiz-Lopez et al (Modifying the lipid content and composition of plant seeds: engineering the production of LC-PUFA. Appl Microbiol Biotechnol 99:143-154, 2015) (Year: 2015).*

(Continued)

*Primary Examiner* — Ashley K Buran
*Assistant Examiner* — Wayne Zhong
(74) *Attorney, Agent, or Firm* — Marshall, Gerstein & Borun LLP

(57) ABSTRACT

The present invention provides transgenic *Brassica* events LBFLFK and LBFDAU and progeny thereof, and cells, seeds, plants comprising DNA diagnostic for these events. The invention also provides artificial oligonucleotide primers and probes that are diagnostic for the LBFLFK and LBFDAU events and their progeny in a sample, and methods for detecting the presence of the LBFLFK and LBFDAU events and their progeny in a sample. The invention further provides oil and commodity products derived from the LBFLFK and LBFDAU events.

13 Claims, 8 Drawing Sheets

Specification includes a Sequence Listing.

(56) References Cited

FOREIGN PATENT DOCUMENTS

| | | | |
|---|---|---|---|
| WO | WO-2002/052024 | A2 | 7/2002 |
| WO | WO-2003/078639 | A2 | 9/2003 |
| WO | WO-2003/089452 | A2 | 10/2003 |
| WO | WO-2003/093482 | A2 | 11/2003 |
| WO | WO-2004/071467 | A2 | 8/2004 |
| WO | WO-2004/087902 | A2 | 10/2004 |
| WO | WO-2004/090123 | A2 | 10/2004 |
| WO | WO-2005/007845 | A2 | 1/2005 |
| WO | WO-2005/012316 | A2 | 2/2005 |
| WO | WO-2005/083053 | A2 | 9/2005 |
| WO | WO-2005/083093 | A2 | 9/2005 |
| WO | WO-2006/008099 | A2 | 1/2006 |
| WO | WO-2006/012325 | A1 | 2/2006 |
| WO | WO-2006/024509 | A2 | 3/2006 |
| WO | WO-2006/069710 | A1 | 7/2006 |
| WO | WO-2006/100241 | A2 | 9/2006 |
| WO | WO-2007/096387 | A1 | 8/2007 |
| WO | WO-2008/022963 | A2 | 2/2008 |
| WO | WO-2009/111263 | A1 | 9/2009 |
| WO | WO-2010/023202 | A2 | 3/2010 |
| WO | WO-2010/066703 | A2 | 6/2010 |
| WO | WO-2011/006948 | A1 | 1/2011 |
| WO | WO-2011/161093 | A1 | 12/2011 |
| WO | WO-2013/049227 | A2 | 4/2013 |
| WO | WO-2013/153404 | A1 | 10/2013 |
| WO | WO-2013/185184 | A2 | 12/2013 |
| WO | WO-2015/089587 | A1 | 6/2015 |

OTHER PUBLICATIONS

Multari et al (Effects of Aromatic Herb Flavoring on Carotenoids and Volatile Compounds in Edible Oil from Blue Sweet Lupin (*Lupinus angustifolius*). Eur. J. Lipid Sci. Technol. 1-10, 2018) (Year: 2018).*

Abidi et al., "Effect of Genetic Modification on the Distribution of Minor Constituents in Canola Oil", Journal of the American Oil Chemists' Society, vol. 76, Issue 4, pp. 463-467 (Apr. 1999).

Arondel, et al., "Map-based Cloning of a Gene Controlling Omega-3 Fatty Acid Desaturation in Arabidopsisc", Science vol. 258, Issue 5086, Nov. 20, 1992, pp. 1353-1355.

Bai, et al., "X-ray Structure of a Mammalian Stearoyl-CoA Desaturase", Nature, Aug. 2015, vol. 524, pp. 252-256.

Bligh, et al., "A Rapid Method of Total Lipid Extraction and Purification", Canadian Journal of Biochemistry and Physiology, vol. 37, Issue 1, 1959, pp. 911-917.

Browse et al., Fatty acid composition of leaf lipids determined after combined digestion and fatty acid methyl ester formation from fresh tissue, Anal. Biochem., 152(1):141-5 (1986).

Cahoon et al., Biosynthetic origin of conjugated double bonds: production of fatty acid components of high-value drying oils in transgenic soybean embryos, Proc. Natl. Acad. Sci. USA, 96(22):12935-40 (1999).

Cutler, et al., "Abscisic Acid: Emergence of a Core Signaling Network", Annual Review of Plant Biology, vol. 61, 2010, pp. 651-679.

Database EMBL [Online] 5, "Rattus Norvegicus clone CH230-506F12, Working Draft Sequence, Unordered Pieces.", XP002754369, retrieved from EBI accession No. EM_HTG:AC142370 (Mar. 29, 2003).

Database EMBL [Online], "Mus Musculus Domesticus DNA, BAG Clone: B6Ng01-175K07, 3' End.", XP002754370, retrieved from EBI accession No. EM_GSS:GA003396, created Feb. 6, 2011).

Datar et al. Cell and Cell Debris Removal: Centrifugation and Crossflow Filtration, pp. 472-503 In: Rehm et al. (eds.), Biotechnology, Second, Completely Revised Edition, vol. 3 (Bioprocessing) edited by Stephanopoulos, Weinheim, Germany: VCH (1993).

De Block, et al., "Transformation of *Brassica napus* and *Brassica oleracea* Using Agrobacterium Tumefaciens and the Expression of the Bar and Neo Genes in the Transgenic Plants", Plant Physiol., v.91(2):694-701 (1989).

Dolde, et al., "Tocopherols in Breeding Lines and Effects of Planting Location, Fatty Acid Composition, and Temperature During Development", JAOCS, 76:349-55 (Mar. 1999).

Domergue, et al., Acyl Carriers Used as Substrates by the Desaturases and Elongases Involved in Very Long-chain Polyunsaturated Fatty Acids Biosynthesis Reconstituted in Yeast, J. Biol. Chem., 278(37):35115-26 (2003).

Domergue, et al., "In Vivo Characterization of the First Acyl-CoA Δ6-Desaturase from a Member of the Plant Kingdom, the Microalga Ostreococcus Tauri", Biochem. J., 389(Pt. 2):483-90 (2005).

Dubos, et al., "Integrating Bioinformatic Resources to Predict Transcription Factors Interacting with Cis-Sequences Conserved in Co-Regulated Genes", BMC Genomics, 15:317 (2014).

Focks, et al., "Wrinkled1: A Novel, Low-Seed-Oil Mutant of *Arabidopsis* with a Deficiency in the Seed-Specific Regulation of Carbohydrate Metabolism", Plant Physiol., 118(1):91-101 (1998).

Fujiwara et al., Seed-specific repression of GUS activity in tobacco plants by antisense RNA, Plant Mol. Biol., 20(6):1059-69 (1992).

Griffiths, et al., Delta 6- and Delta 12-desaturase Activities and Phosphatidic Acid Formation in Microsomal Preparations from the Developing Cotyledons of Common Borage (*Borango officinalis*), Biochem. J., 252(3):641-7 (1988).

Hull et al., Analysis of the promoter of an abscisic acid responsive late embryogenesis abundant gene of *Arabidopsis thaliana*, Plant Sci., 14:181-92 (1996).

International Preliminary Report on Patentability, International Application No. PCT/EP2015/076596, dated May 16, 2017.

International Preliminary Report on Patentability, International Application No. PCT/EP2015/076630, dated May 16, 2017.

International Preliminary Report on Patentability, PCT Application No. PCT/EP2015/076608, completed Feb. 28, 2017.

International Preliminary Report on Patentability, PCT application No. PCT/EP2015/076605, dated May 16, 2017.

International Search Report and Written Opinion for PCT Patent Application No. PCT/EP2015/076596, dated Mar. 11, 2016, 15 pages.

International Search Report and Written Opinion for PCT Patent Application No. PCT/EP2015/076605, dated Feb. 24, 2016, 13 pages.

International Search Report and Written Opinion for PCT Patent Application No. PCT/EP2015/076608, dated Mar. 9, 2016, 13 pages.

International Search Report and Written Opinion, International Application No. PCT/EP2015/076630, dated Mar. 7, 2016.

Jain, et al., "Identification of a Novel Lysophospholipid Acyltransferase in *Saccharomyces cerevisiae*", J. Biol. Chem., 282(42):30562-9 (2007).

Kargiotidou, et al., "Low Temperature and Light Regulate Delta 12 Fatty Acid Desaturases (FAD2) at a Transcriptional Level in Cotton (*Gossypium hirsutum*)", J. Exp. Bot., 49(8):2043-56 (2008).

Knutzon, et al., "Identification of Delta5-dehydratase from Mortierella Alpina by Heterologous Expression in Bakers' Yeast and Canola", J. Biol. Chem., 273(45):29360-6 (1998).

Li, et al., "Correlations between Tocopherol and Fatty Acid Components in Germplasm Collections of *Brassica* Oilseeds", Journal of Agricultural and Food Chemistry, 61:34-40 (2013).

Livak et al., Analysis of relative gene expression data using real-time quantitative PCR and the 2(-Delta Delta C(T)) Method, Methods, 25(4):402-8 (2001).

Meesapyodsuk, et al., "The Front-end Desaturase: Structure, Function, Evolution and Biotechnological Use", Lipids, vol. 47, Issue 3, Mar. 2012, pp. 227-237.

O'Malley, et al., "An Adapter Ligation-Mediated Pcr Method for High-Throughput Mapping of T-DNA Inserts in the *Arabidopsis* Genome", Nature Protocols, vol. 2, Issue 11, 2007, pp. 2910-2917.

Okayasu, et al., "Purification and Partial Characterization of Linoleoyl-CoA Desaturase from Rat Liver Microsomes", Archives of Biochemistry and Biophysics, 206(1):21-8 (1981).

Okuley, et al., "*Arabidopsis* FAD2 Gene Encodes the Enzyme that is Essential for Polyunsaturated Lipid Synthesis", The Plant Cell Online, vol. 6, Issue 1, Jan. 1994, pp. 147-158.

(56) References Cited

OTHER PUBLICATIONS

Paul, et al., "Members of the *Arabidopsis* FAE1-like 3-Ketoacyl-CoA Synthase Gene Family Substitute for the Elop Proteins of *Saccharomyces cerevisiae*", J. Biol. Chem., 281(14):9018-29 (2006).
Qi, et al., "Production of Very Long Chain Polyunsaturated Omega-3 and Omega-6 Fatty Acids in Plants", Nature Biotechnology, vol. 22, Issue 6, Jun. 2004, pp. 739-745.
Quek, et al., "Commercial Extraction of Vitamin E from Food Sources" The Encyclopedia of Vitamin E, Eds. Preedy, et al., CABI Publishers, Oxford, U.K., 2007, pp. 140-152.
Riekhof, et al., "Lysophosphatidylcholine Metabolism in *Saccharomyces cerevisiae* The Role of P-Type Atpases in Transport and in Broad Specificity Acyltransferase in Acylation", J. Biol. Chem., 282(51):36853-61 (2007).
Ruiz-Lopez, et al., "Successful High-level Accumulation of Fish Oil Omega-3 Long-Chain Polyunsaturated Fatty Acids in a Transgenic Oilseed Crop",Plant J., 77(2):198-208 (2014).
Ruuska, et al., "Contrapuntal Networks of Gene Expression during *Arabidopsis* Seed Filling", The Plant Cell Online, vol. 14, Issue 6, Jun. 2002, pp. 1191-1206.
Rychlik, et al, "A computer program for choosing optimal oligonudeotides for filter hybridization, sequencing and in vitro amplification of DNA", Nucleic Acids Research, 17(21):8543-51 (1989).
Sarkar, et al., "Specificity Determinants for the Abscisic Acid Response Element", FEBS Open Bio, vol. 3, Issue 1, Jan. 1, 2013, pp. 101-105.
Shanklin, et al., "Desaturation and Related Modifications of Fatty Acids1", Annual Review of Plant Physiology and Plant Molecular Biology, vol. 49, Jun. 1998, pp. 611-641.
Shanklin, et al., "Stearoyl-acyl-carrier-protein desaturase from Higher Plants is Structurally Unrelated to the Animal and Fungal Homologs", Proc. Natl. Acad. Sci. USA, 88(6):2510-4 (1991).
Strittmatter et al., "Purification and Properties of Rat Liver Microsomal Stearyl Coenzyme A Desaturase", Proc. Natl. Acad. Sci. USA, 71(11):4565-9 (1974).
Stymne, et al., "Biosynthesis of γ-linolenic Acid in Cotyledons and Microsomal Preparations of the Developing Seeds of Common Borage (*Borago officinalis*)", Biochem. J., 240(2):385-93 (1986).
Tamaki, et al., "LPT1 Encodes a Membrane-bound O-Acyltransferase Involved in the Acylation of Lysophospholipids in the Yeast *Saccharomyces cerevisiae*", J. Biol. Chem., 282(47):34288-98 (2007).
Tang, et al., "Oleate Desaturase Enzymes of Soybean: Evidence of Regulation Through Differential Stability and Phosphorylation", Plant J., 44(3):433-46 (2005).
Vilardell et al., Regulation of the rab17 gene promoter in transgenic *Arabidopsis* wild-type, ABA-deficient and ABA-insensitive mutants, Plant Mol. Biol., 24(4):561-9 (1994).
Wang, et al., "Crystal Structure of Human Stearoyl-Coenzyme a Desaturase in Complex with Substrate", Nature Structural & Molecular Biology, vol. 22, 2015, pp. 581-585.
Wu, et al., "Stepwise Engineering to Produce High Yields of Very Long-Chain Polyunsaturated Fatty Acids in Plants", Nature Biotechnology, vol. 23, Issue 8, 2005, pp. 1013-1017.
Xiao, et al., "Characterization of the Promoter and 5'-UTR Intron of Oleic Acid Desaturase (FAD2) Gene in *Brassica napus*", Gene, vol. 545, Issue 1, Jul. 2014, pp. 45-55.
Akermoun et al., Complex lipid biosynthesis: phospholipid synthesis, Biochemical Society Transactions 28: 713-5 (2000).
Bafor et al., Ricinoleic acid biosynthesis and triacylglycerol assembly in microsomal preparations from developing castor-bean (*Ricinus communis*) endosperm, Biochem. J., 280(Pt.2):507-14 (Dec. 1991).
Banas et al., Biosynthesis of an Acetylenic Fatty Acid in Microsomal Preparations from Developing Seeds of *Crepis alpina*. In: *Physiology, Biochemistry and Molecular Biology of Plant Lipids* (Williams et al. eds.) pp. 57-59. Kluwer Academic Press, Dordrecht (1997).
Bates et al., Acyl Editing and Headgroup Exchange Are the Major Mechanisms That Direct Polyunsaturated Fatty Acid Flux into Triacylglycerols. Plant Physiology 160: 1530-1539 (2012).
Bernert et al., Analysis of Partial Reactions in the Overall Chain Elongation of Saturated and Unsaturated Fatty Acids by Rat Liver Microsomes. J. Biol. Chem. 252, 6736-6744 (1977).
Blombach et al., Acetohydroxyacid synthase, a novel target for improvement of L-lysine production by Corynebacterium glutamicum, Appl. Environ. Microbiol., 75(2):419-27 (Jan. 2009).
Broadwater et al., Desaturation and hydroxylation. Residues 148 and 324 of *Arabidopsis* FAD2, in addition to substrate chain length, exert a major influence in partitioning of catalytic specificity, J. Biol. Chem., 277(18):15613-20 (May 2002).
Broun et al., Catalytic plasticity of fatty acid modification enzymes underlying chemical diversity of plant lipids, Science, 282(5392):1315-7 (Nov. 1998).
Brown et al., Synthetic promoters for CHO cell engineering, Biotechnol. Bioeng., 111(8):1638-47 (Aug. 2014).
Calvo et al., Genetic connection between fatty acid metabolism and sporulation in Aspergillus nidulans, J. Biol. Chem., 276(28):25766-74 (Jul. 2001).
Certik et al., Desaturase-defective fungal mutants: useful tools for the regulation and overproduction of polyunsaturated fatty acids, Trends in Biotechnology, vol. 16, No. 12, Dec. 1, 1998, pp. 500-505.
Deal et al., Histone variants and modifications in plant gene regulation, Curr. Opin. Plant Biol., 14(2):116-22 (Apr. 2011).
Demeke et al., Influence of DNA extraction methods, PCR inhibitors and quantification methods on real-time PCR assay of biotechnology-derived traits, Anal. Bioanal. Chem., 396(6):1977-90 (Mar. 2010).
Denic et al., A molecular caliper mechanism for determining very long-chain fatty acid length, Cell, 130(4):663-77 (Aug. 2007).
Eiamsa-ard et al., Two novel Physcomitrella patens fatty acid elongases (ELOs): identification and functional characterization, Appl. Microbiol. Biotechnol., 97:3485-3497 (2013).
Fraser et al., Partial purification and photoaffinity labelling of sunflower acyl-CoA:lysophosphatidylcholine acyltransferase, Biochem. Soc. Trans., 28(6):715-8 (Dec. 2000).
Fukuda, Characterization of matrix attachment sites in the upstream region of a tobacco chitinase gene, Plant Mol. Biol., 39(5):1051-62 (Mar. 1999).
Giusto et al., Lipid metabolism in vertebrate retinal rod outer segments, Prog. Lipid Res., 39(4):315-91 (Jul. 2000).
Goffman, et al., "Genetic variation of tocopherol content in a germplasm collection of *Brassica napus* L.", Euphytica, vol. 125, May 2002, pp. 189-196.
Hamilton, A binary-BAC system for plant transformation with high-molecular-weight DNA, Gene, 200(1-2):107-16 (Oct. 1997).
Hattori et al., Experimentally determined sequence requirement of ACGT-containing abscisic acid response element, Plant Cell Physiol., 43(1):136-40 (Jan. 2002).
He et al, Agrobacterium-Mediated Transformation of Large DNA Fragments Using a BIBAC Vector System in Rice, Plant Molecular Biology Reporter, vol. 28, No. 4, Mar. 2, 2010, pp. 613-619.
Higo et al., Plant cis-acting regulatory DNA elements (PLACE) database: 1999, Nucleic Acids Res., 27(1):297-300 (Jan. 1999).
Hinnebusch, The scanning mechanism of eukaryotic translation initiation, Annu. Rev. Biochem., 83:779-812 (2014).
Horrocks et al., Health benefits of Docosahexaenoic acid (DHA), Pharmacol. Res., 40(3):211-25 (Sep. 1999).
Keller et al., Crystal structure of a bZIP/DNA complex at 2.2 A: determinants of DNA specific recognition, J. Mol. Biol., 254(4):657-67 (Dec. 1995).
Kim et al., Transcription factors that directly regulate the expression of CSLA9 encoding mannan synthase in *Arabidopsis thaliana*, Plant Mol. Biol., 84(4-5):577-87 (Mar. 2014).
Komori et al., Current status of binary vectors and superbinary vectors, Plant Physiol., 145(4):1155-60 (Dec. 2007).
Kong et al., Expression levels of domestic cDNA cassettes integrated in the nuclear genomes of various Chlamydomonas reinhardtii strains, J. Biosci. Bioeng., 117(5):613-6 (May 2014).
Kozak, Initiation of translation in prokaryotes and eukaryotes, Gene, 234(2):187-208 (Jul. 1999).
Lopez et al., Identification of novel motif patterns to decipher the promoter architecture of co-expressed genes in *Arabidopsis thaliana*, BMC Syst. Biol., 7 Suppl 3:S10 (Oct. 2013).

(56) References Cited

OTHER PUBLICATIONS

Lowenthal et al., Quantitative bottom-up proteomics depends on digestion conditions, Anal. Chem., 86(1):551-8 (Jan. 2014).
Machens et al., Identification of a novel type of WRKY transcription factor binding site in elicitor-responsive cis-sequences from *Arabidopsis thaliana*, Plant Mol. Biol., 84(4-5):371-85 (2014).
Makriyannis et al., Design and study of peptide-ligand affinity chromatography adsorbents: application to the case of trypsin purification from bovine pancreas, Biotechnol. Bioeng., 53(1):49-57 (Jan. 1997).
Mantle et al., Differentiation of Claviceps purpurea in axenic culture, J. Gen. Microbiol., 93(2):321-34 (Apr. 1976).
Meggendorfer et al., Functional nuclear topography of transcriptionally inducible extra-chromosomal transgene clusters, CHromosome Res., 18(4):401-17 (Jun. 2010).
Mendel, *Versuche über Pflanzenhybriden* Verhandlungen des naturforschenden Vereines in Brünn, Bd. IV für das Jahr, 1865 Abhandlungen:3-47 (1866).
Mey et al., The biotrophic, non-appressorium-forming grass pathogen Claviceps purpurea needs a Fus3/Pmk1 homologous mitogen-activated protein kinase for colonization of rye ovarian tissue, Mol. Plant Microbe Interact., 15(4):303-12 (Apr. 2002).
Meyer et al., Novel fatty acid elongases and their use for the reconstitution of docosahexaenoic acid biosynthesis, Journal of Lipid Research, 45:1899-1909 (2004).
Muino et al., Structural determinants of DNA recognition by plant MADS-domain transcription factors, Nucleic Acids Res., 42(4):2138-46 (Feb. 2014).
Murashige et al., A Revised Medium for Rapid Growth and Bio Assays with Tobacco Tissue Cultures. Physiologia Plantarum 15, 3:473-497 (1962).
Nakagawa et al., Diversity of preferred nucleotide sequences around the translation initiation codon in eukaryote genomes, Nucleic Acids Res., 36(3):861-71 (Feb. 2008).
Nishikata et al., Database construction for PromoterCAD: synthetic promoter design for mammals and plants, ACS Synth. Biol., 3(3):192-6 (Mar. 2014).
Parker et al., Local DNA topography correlates with functional noncoding regions of the human genome, Science, 324(5925):389-92 (Apr. 2009).
Petrie et al., Metabolic engineering *Camelina sativa* with fish oil-like levels of DHA, PLoS One, 9(1):e85061 (Jan. 2014).
Potts et al., Inheritance of fatty acid composition in *Brassica juncea*, Proceedings of the 10th International Rapeseed Congress, Sep. 26, 1999.
Proc et al., A quantitative study of the effects of chaotropic agents, surfactants, and solvents on the digestion efficiency of human plasma proteins by trypsin, J> Proteome Res., 9(10):5422-37 (Oct. 2010).
Ramamoorthy et al., Length and sequence dependent accumulation of simple sequence repeats in vertebrates: potential role in genome organization and regulation, Gene, 551(2):167-75 (Nov. 2014).
Schwender et al., “Rubisco without the Calvin cycle improves the carbon efficiency of developing green seeds”, Nature, 432:779-82 (2004).
Shrestha et al., Int. J. Mol. Sci., Comparison of the substrate preferences of ω3 fatty acid desaturases for long chain polyunsaturated fatty acids, 20:3058 (2019).
Smith et al., Measurement of protein using bicinchoninic acid, Anal. Biochem., 150(1):76-85 (Oct. 1985).
Spector, Essentiality of fatty acids, Lipids, 34 Suppl: S1-3 (1999).
Stymne et al., Evidence for the reversibility of the acyl-CoA:lysophosphatidylcholine acyltransferase in microsomal preparations from developing safflower (*Carthamus tinctorius* L.) cotyledons and rat liver, Biochem. J., 233(2):305-14 (1984).
Sánchez-García et al., Differential temperature regulation of three sunflower microsomal oleate desaturase (FAD2) isoforms overexpressed in *Saccharomyces cerevisia*, Eur. J. Lipid Sci. Tech., 106:583-590 (2004).
Tudzynski et al., Biotechnology and genetics of ergot alkaloids, Appl. Microbiol. Biotechnol., 57(5-6):593-605 (Dec. 2001).
Tumaney et al., Synthesis of azidophospholipids and labeling of lysophosphatidylcholine acyltransferase from developing soybean cotyledons, Biochim. Biophys. Acta, 1439(1):47-56 (Jul. 1999).
Wachter et al., Synthetic CpG islands reveal DNA sequence determinants of chromatin structure, Elife, 3:e03397 (Sep. 2014).
Wang et al., ?3 fatty acid desaturases from microorganisms: structure, function, evolution, and biotechnological use, App. Microbiol., 97:10255-62 (2013).
Wijesundra, the influence of triacylglycerol structure on the oxidative stability of polyunsaturated oils, Lipid Technology, 20:199-202 (2008).
Yamashita et al., ATP-independent fatty acyl-coenzyme A synthesis from phospholipid: coenzyme A-dependent transacylation activity toward lysophosphatidic acid catalyzed by acyl-coenzyme A:lysophosphatidic acid acyltransferase, J. Biol. Chem., 276(29):26745-52 (Jul. 2001).

* cited by examiner

*BRASSICA* EVENTS LBFLFK AND LBFDAU AND METHODS FOR DETECTION THEREOF

This application is a National Stacie application of International Application No. PCT/EP2015/076596, filed Nov. 13, 2015, which claims the benefit of U.S. Provisional Patent Application No. 62/079,622, filed Nov. 14, 2014, and 62/234,373, filed Sep. 29, 2015, the entire disclosure of which is incorporated herein by reference.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "150221_Seqlisting.txt", which was created on May 9, 2017 and is 560,632 bytes in size. The subject matter of the Sequence Listing is incorporated herein in its entirety by reference.

FIELD OF THE INVENTION

The present invention relates to the field of biotechnology and agriculture, and more specifically, to transgenic *Brassica* plants comprising event LBFLFK or event LBFDAU, progeny plants, seed thereof, and oil and meal derived therefrom. The invention also relates to methods for detecting the presence of event LBFLFK or event LBFDAU in biological samples which employ nucleotide sequences that are unique to each event.

BACKGROUND OF THE INVENTION

The health benefits of the Very Long Chain Polyunsaturated Fatty Acids ("VLC-PUFA" or "PUFA") to human and animal nutrition have become increasingly established in recent years. In particular, the ω3 PUFA eicosapentaenoic acid (EPA) and docosahexaenoic acid (DHA) play roles in neural development, immune responses, and inflammatory responses. In addition, dietary supplements containing EPA and DHA are used to alleviate cardiovascular and neurological pathology, and may be useful in treating some cancers.

The current commercial source of EPA and DHA is fish oil. However, marine stocks are diminishing, and alternative sources of EPA and DHA are needed to meet increasing demand. Numerous efforts have been made to develop transgenic oilseed plants that produce VLC-PUFAs, including EPA and DHA. See, e.g., WO 2004/071467, WO 2013/185184, WO 2015/089587, Ruiz-Lopez, et al. (2014) Plant J. 77, 198-208. However, no transgenic oilseed plant has been commercialized which produces EPA and DHA at commercially relevant levels.

Polynucleotides encoding polypeptides which exhibit delta-6-elongase activity have been described in WO2001/059128, WO2004/087902 and WO2005/012316, said documents, describing this enzyme from *Physcomitrella patens*.

Polynucleotides encoding polypeptides which exhibit delta-5-desaturase activity have been described in WO2002026946 and WO2003/093482, said documents, describing this enzyme from *Thraustochytrium* sp.

Polynucleotides encoding polypeptides which exhibit delta-6-desaturase activity have been described in WO2005/012316, WO2005/083093, WO2006/008099 and WO2006/069710, said documents, describing this enzyme from *Ostreococcus tauri*.

Polynucleotides encoding polypeptides which exhibit delta-6-elongase activity have been described in WO2005/012316, WO2005/007845 and WO2006/069710, said documents, describing this enzyme from *Thalassiosira pseudonana*.

Polynucleotides encoding polypeptides which exhibit delta-12-desaturase activity have been described for example in WO2006100241, said documents, describing this enzyme from *Phytophthora sojae*.

Polynucleotides encoding polypeptides which exhibit delta-5-elongase activity have been described for example in WO2005/012316 and WO2007/096387, said documents, describing this enzyme from *Ostreococcus tauri*.

Polynucleotides encoding polypeptides which exhibit omega 3-desaturase activity have been described for example in WO2008/022963, said documents, describing this enzyme from *Phytium irregulare*.

Polynucleotides encoding polypeptides which exhibit omega 3-desaturase activity have been described for example in WO2005012316 and WO2005083053, said documents, describing this enzyme from *Phytophthora infestans*.

Polynucleotides encoding polypeptides which exhibit delta-4-desaturase activity have been described for example in WO2002026946, said documents, describing this enzyme from *Thraustochytrium* sp.

Polynucleotides coding for a delta-4 desaturase from *Pavlova lutheri* are described in WO2003078639 and WO2005007845.

The expression of foreign gene constructs in plants is known to be influenced by the chromosomal location at which the genes are inserted, and the presence of the transgenic construct at different locations in the plant's genome can influence expression of endogenous genes and the phenotype of the plant. For these reasons, it is necessary to screen large numbers of transgenic events made from a particular construct, in order to identify one or more "elite" events for commercialization that exhibit optimal expression of the transgene without undesirable characteristics. An elite event has the desired levels and patterns of transgenic expression and may be used to introgress the transgenic construct into commercially relevant genetic backgrounds, by sexual outcrossing using conventional breeding methods. Progeny of such crosses maintain the transgenic construct expression characteristics of the original elite event. This strategy is used to ensure reliable gene expression in a number of varieties that are adapted to local growing conditions.

For introgression, deregulation, and quality control purposes, it is necessary to be able to detect the presence of the transgenic construct in an elite event, both in the progeny of sexual crosses and in other plants. In addition, grain, meal, and foodstuffs may also be monitored for adventitious presence of transgenic constructs to ensure compliance with regulatory requirements.

The presence of a transgenic construct may be detected using known nucleic acid detection methods such as the polymerase chain reaction (PCR) or DNA hybridization using nucleic acid probes. These detection methods may be directed to frequently used genetic elements, such as promoters, terminators, marker genes, etc. Such methods may not be useful for discriminating between different events that contain the same genetic elements, unless the sequence of the chromosomal DNA adjacent to the inserted construct ("flanking DNA") is also known. Event-specific assays are known for numerous genetically modified products which have been commercialized. Event-specific detection assays are also required by regulatory agencies responsible for approving use of transgenic plants comprising a particular elite event. Transgenic plant event-specific assays have been described, for example, in U.S. Pat. Nos. 6,893,826; 6,825,400; 6,740,488; 6,733,974; 6,689,880; 6,900,014; 6,818,807; and 8,999,411.

SUMMARY OF THE INVENTION

In one embodiment, the present invention provides *Brassica* plants comprising transgenic *Brassica* event LBFLFK deposited as ATCC Designation "PTA-121703". *Brassica* event LBFLFK contains two insertions of the binary T-plasmid VC-LTM593-1qcz rc, the insertions being designated LBFLFK Locus 1 and LBFLFK Locus 2. The *Brassica* plants of this embodiment include progeny that are indistinguishable from *Brassica* event LBFLFK (to the extent that such progeny also contain at least one allele corresponding to LBKLFK Locus 1 or LBFLFK Locus 2). The *Brassica* plants of this embodiment comprise unique genomic DNA/transgene junction points, and consequently unique junction regions, for each LBFLFK insertion: the junction region for LBFLFK Locus 1 having at least the polynucleotide sequence of SEQ ID NO:4 or at least the polynucleotide sequence of SEQ ID NO:5, and the junction region for LBFLFK Locus 2 having at least the polynucleotide sequence of SEQ ID NO:13 or at least the polynucleotide sequence of SEQ ID NO:14. Also included in this embodiment are seeds, plant parts, plant cells, and plant products derived from *Brassica* event LBFLFK and progeny thereof.

In another embodiment, compositions and methods are provided for detecting the presence of the *Brassica* event LBFLFK genomic DNA/transgene junction regions for each LBFLFK insertion: the junction region for LBFLFK Locus 1 having at least the polynucleotide sequence of SEQ ID NO:4 or at least the polynucleotide sequence of SEQ ID NO:5, and the junction region for LBFLFK Locus 2 having at least the polynucleotide sequence of SEQ ID NO:13 or at least the polynucleotide sequence of SEQ ID NO:14.

In another embodiment, the invention provides commodity products, including canola oil and meal, produced from *Brassica* event LBFLFK and/or its progeny.

In another embodiment, the invention provides *Brassica* plants comprising transgenic *Brassica* event LBFDAU deposited as ATCC Designation "PTA-122340". *Brassica* event LBFDAU contains two insertions of the binary T-plasmid VC-LTM593-1qcz rc, the insertions being designated LBFDAU Locus 1 and LBFDAU Locus 2. The *Brassica* plants of this embodiment include and progeny thereof that are indistinguishable from *Brassica* event LBFDAU (to the extent that such progeny also contain at least one allele that corresponds to the inserted transgenic DNA). The *Brassica* plants of this embodiment comprise unique genomic DNA/transgene junction points, and consequently two unique junction regions, for each LBFDAU insertion: the junction region for LBFDAU Locus 1 having at least the polynucleotide sequence of SEQ ID NO:22 or at least the polynucleotide sequence of SEQ ID NO:23 and the junction region for LBFDAU Locus 2 having at least the polynucleotide sequence of SEQ ID NO:31 or at least the polynucleotide sequence of SEQ ID NO:32. Also included in this embodiment are seeds, plant parts, plant cells, and plant products derived from *Brassica* event LBFDAU and progeny thereof.

In another embodiment, compositions and methods are provided for detecting the presence of the *Brassica* event LBFDAU genomic DNA/transgene junction regions; the junction region for LBFDAU Locus 1 having at least the polynucleotide sequence of SEQ ID NO:22 or at least the polynucleotide sequence of SEQ ID NO:23 and the junction region for LBFDAU Locus 2 having at least the polynucleotide sequence of SEQ ID NO:31 or at least the polynucleotide sequence of SEQ ID NO:32.

In another embodiment, the invention provides commodity products, including canola oil and meal, produced from *Brassica* event LBFDAU and/or its progeny.

BRIEF DESCRIPTION OF THE SEQUENCES

Figure 1:
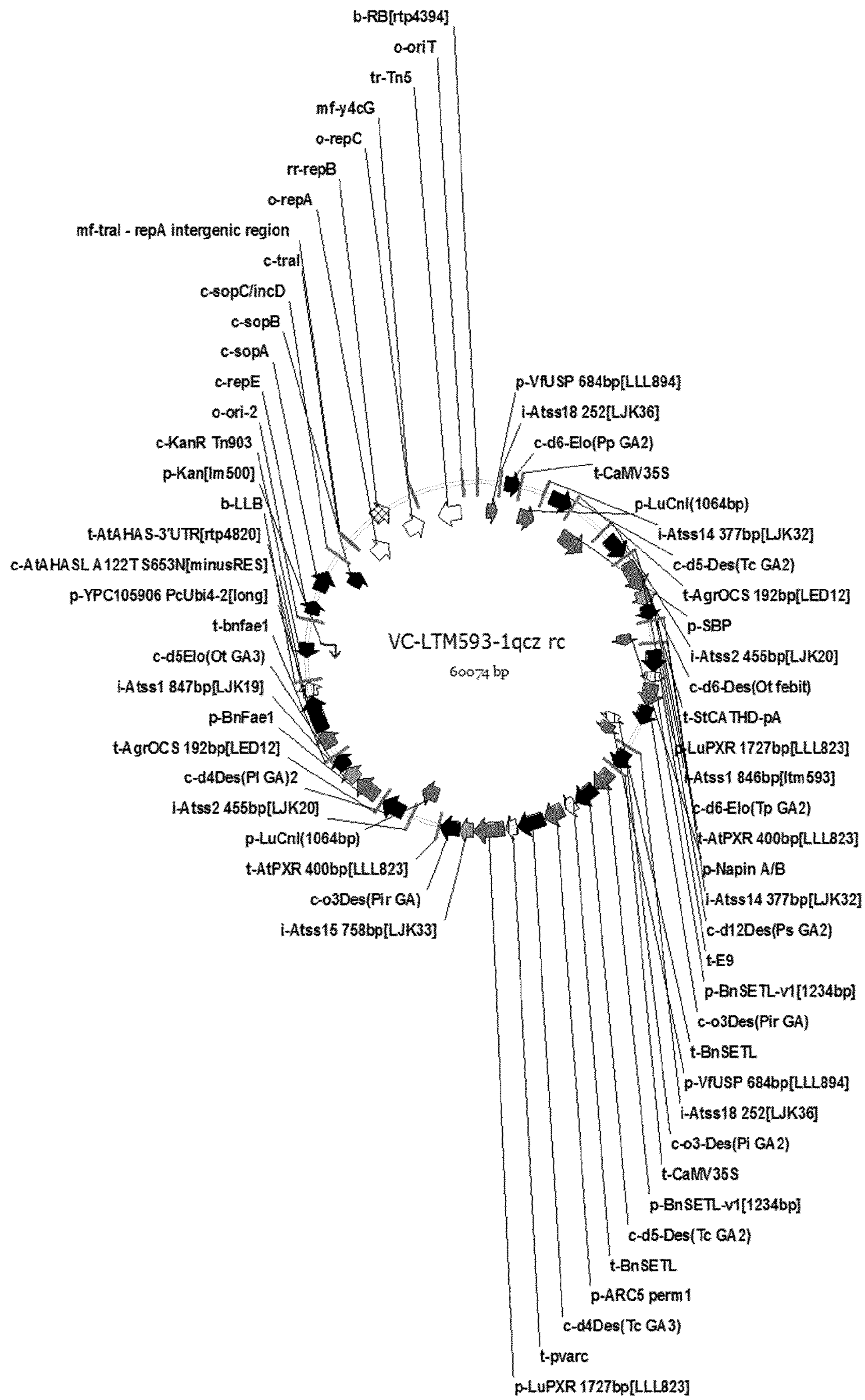
FIG. 1 is a map of binary transformation vector VC-LTM593-1qcz rc, used to generate *Brassica* plants comprising event LBFLFK and *Brassica* plants comprising event LBFDAU.

SEQ ID NO:1 is the sequence of vector VC-LTM593-1qcz rc used for transformation (see FIG. 1)

Figure 2:
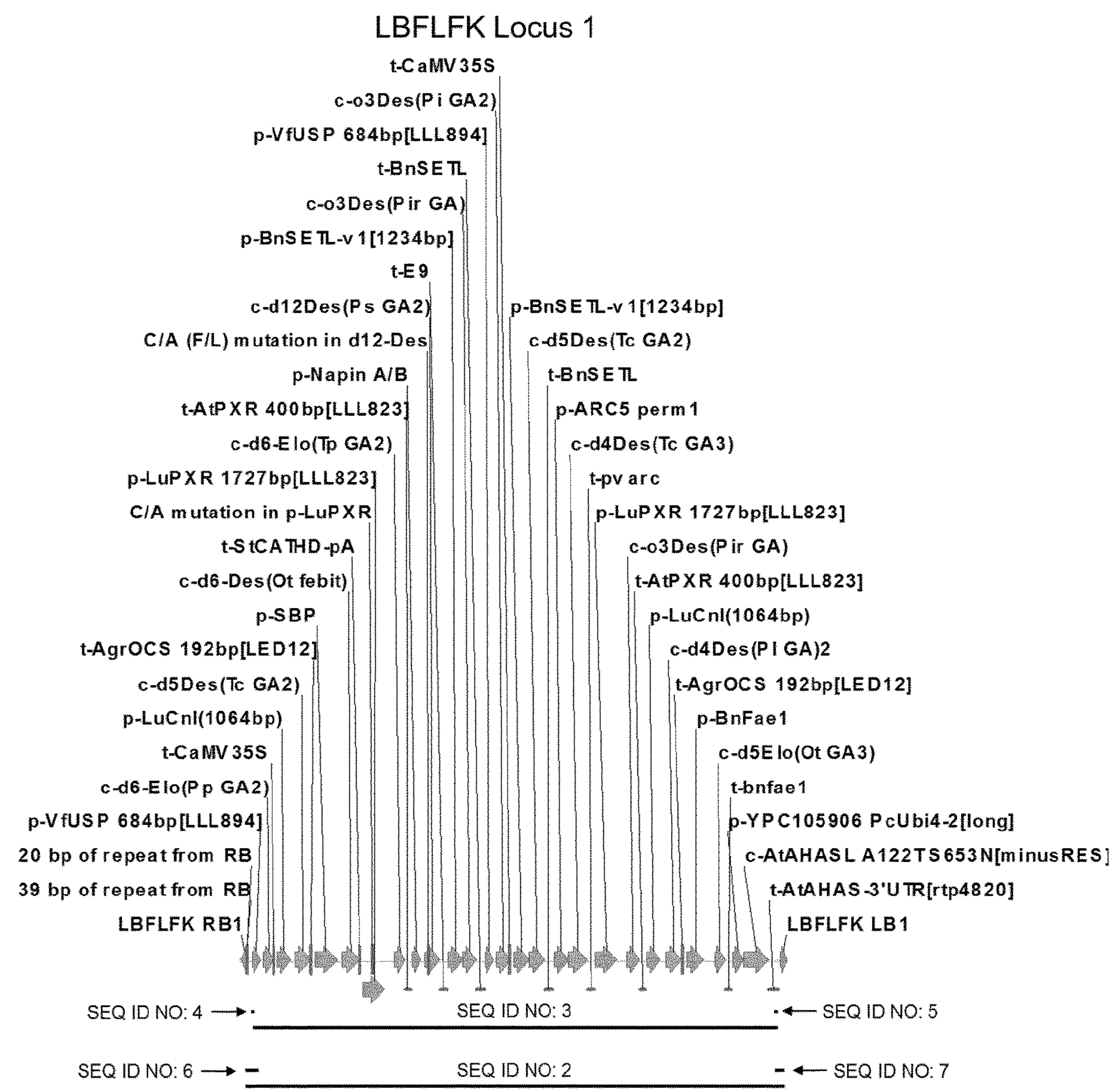
FIG. 2 shows the organization T-DNA locus 1 in the genome of a plant comprising *Brassica* event LBFLFK. SEQ ID NO:4 corresponds to the junction region of the Locus 1 T-DNA insert SEQ ID NO:3 and the right border flanking sequence SEQ ID NO:6. SEQ ID NO:5 corresponds to the junction region between the Locus 1 T-DNA insert SEQ ID NO:3 and left border flanking sequence SEQ ID NO:7.

SEQ ID NO:2 is a 44910 bp sequence assembled from the insert sequence of LBFLFK T-DNA Locus 1 (SEQ ID NO:3) and flanking sequences represented by SEQ ID NO:6 and SEQ ID NO:7 (See FIG. 2).

SEQ ID NO:3 is the sequence of the T-DNA insertion in Locus 1 of event LBFLFK, including left and right border sequences (See FIG. 2).

SEQ ID NO:4 is the LBFLFK Locus 1 RB junction region sequence including 10 bp of flanking genomic DNA and bp 1-10 of SEQ ID NO:3 (See FIG. 2).

SEQ ID NO:5 is the LBFLFK Locus 1 LB junction region sequence including bp 43748-43757 of SEQ ID NO:3 and 10 bp of flanking genomic DNA (See FIG. 2).

SEQ ID NO:6 is the flanking sequence up to and including the right border of the T-DNA in LBFLFK Locus 1. Nucleotides 1-570 are genomic DNA (See FIG. 2).

SEQ ID NO:7 is the flanking sequence up to and including the left border of the T-DNA in LBFLFK Locus 1. Nucleotides 229-811 are genomic DNA (See FIG. 2).

SEQ ID NO:8 is an LBFLFK Locus 1_Forward primer suitable for identifying Locus 1 of LBFLFK events. A PCR amplicon using the combination of SEQ ID NO:8 and SEQ ID NO:9 is positive for the presence of LBFLFK Locus 1.

SEQ ID NO:9 is an LBFLFK Locus 1_Reverse primer suitable for identifying Locus 1 of LBFLFK events. A PCR amplicon using the combination of SEQ ID NO:8 and SEQ ID NO:9 is positive for the presence of LBFLFK Locus 1.

SEQ ID NO:10 is an LBFLFK locus 1_Probe is a FAM™-labeled synthetic oligonucleotide that when used in an amplification reaction with SEQ ID NO:8 and SEQ ID NO:9 will release a fluorescent signal when positive for the presence of LBFLFK Locus 1.

Figure 3:
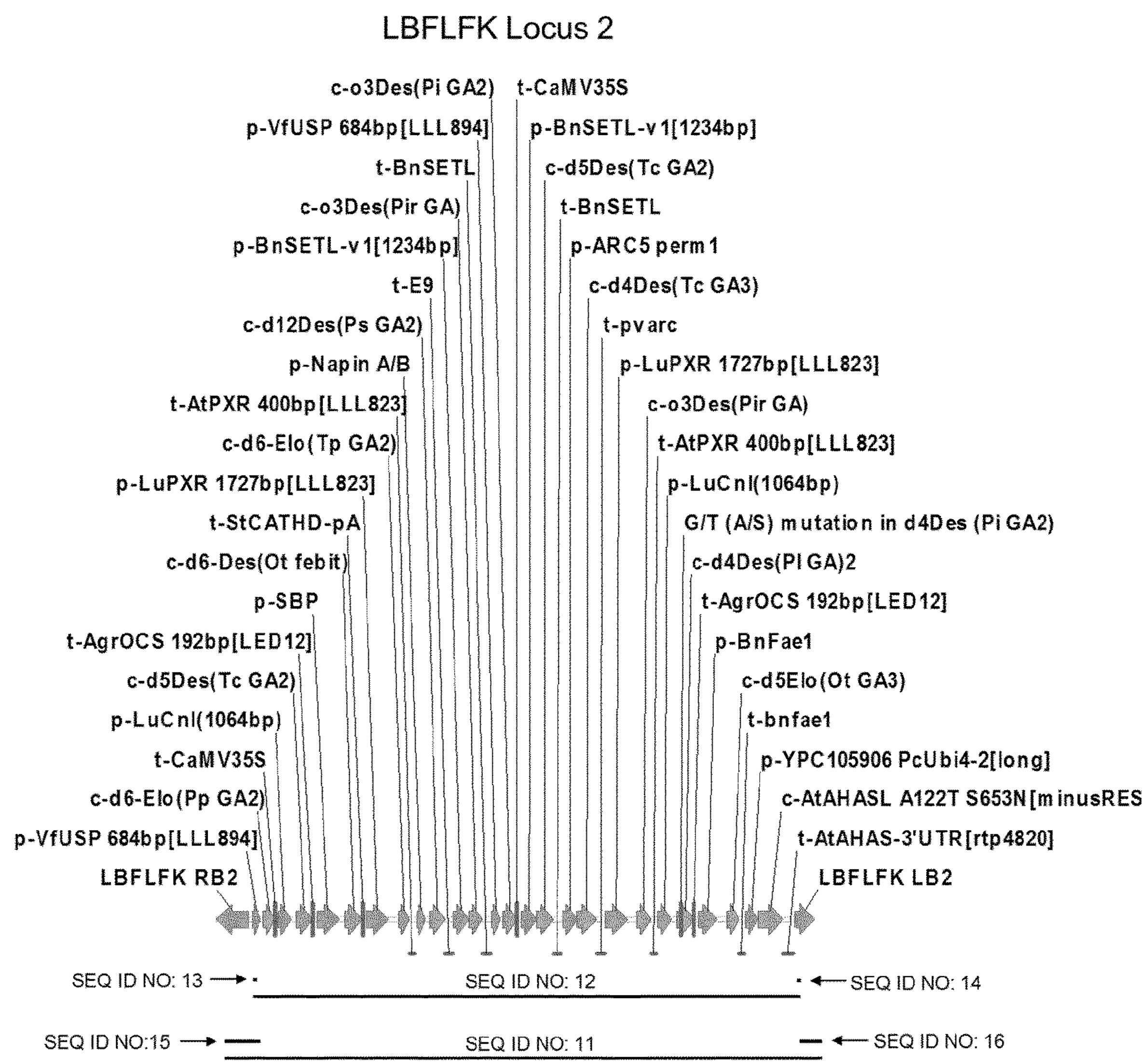
FIG. 3 shows the organization of T-DNA Locus 2 in the genome of a plant comprising *Brassica* event LBFLFK. SEQ ID NO:13 corresponds to the junction region of the Locus 2 T-DNA insert SEQ ID NO:12 and the right border flanking sequence SEQ ID NO:15. SEQ ID NO:14 corresponds to the junction region of the Locus 2 T-DNA insert SEQ ID NO:12 and left border flanking sequence SEQ ID NO:16.

SEQ ID NO:11 is a 47800 bp sequence assembled from the insert sequence of LBFLFK T-DNA Locus 2 (SEQ ID NO: 12) and flanking sequences represented by SEQ ID NO:15 and SEQ ID NO:16 (See FIG. 3).

SEQ ID NO:12 is the sequence of the T-DNA insertion in Locus 2 of event LBFLFK, including left and right border sequences (See FIG. 3).

SEQ ID NO:13 is the LBFLFK Locus 2 RB junction sequence including 10 bp of flanking genomic DNA and bp 1-10 of SEQ ID NO:12 (See FIG. 3).

SEQ ID NO:14 is the LBFLFK Locus 2 LB junction sequence including bp 43764-43773 of SEQ ID NO:12 and 10 bp of flanking genomic DNA (See FIG. 3).

SEQ ID NO:15 is the flanking sequence up to and including the right border of the T-DNA in LBFLFK Locus 2. Nucleotides 1-2468 are genomic DNA (See FIG. 3).

SEQ ID NO:16 is the flanking sequence up to and including the left border of the T-DNA in LBFLFK Locus 2. Nucleotides 242-1800 are genomic DNA (See FIG. 3).

SEQ ID NO:17 is the LBFLFK locus 2_Forward primer suitable for identifying Locus 2 of LBFLFK events. A PCR amplicon using the combination of SEQ ID NO:17 and SEQ ID NO:18 is positive for the presence of LBFLFK Locus 2.

SEQ ID NO:18 is the LBFLFK locus 2_Reverse primer suitable for identifying Locus 2 of LBFLFK events. A PCR amplicon using the combination of SEQ ID NO:17 and SEQ ID NO:18 is positive for the presence of LBFLFK Locus 2.

SEQ ID NO:19 is the LBFLFK locus 2_Probe is a FAM™-labeled synthetic oligonucleotide that when used in an amplification reaction with SEQ ID NO:17 and SEQ ID NO:18 will release a fluorescent signal when positive for the presence of LBFLFK Locus 2.

Figure 4:
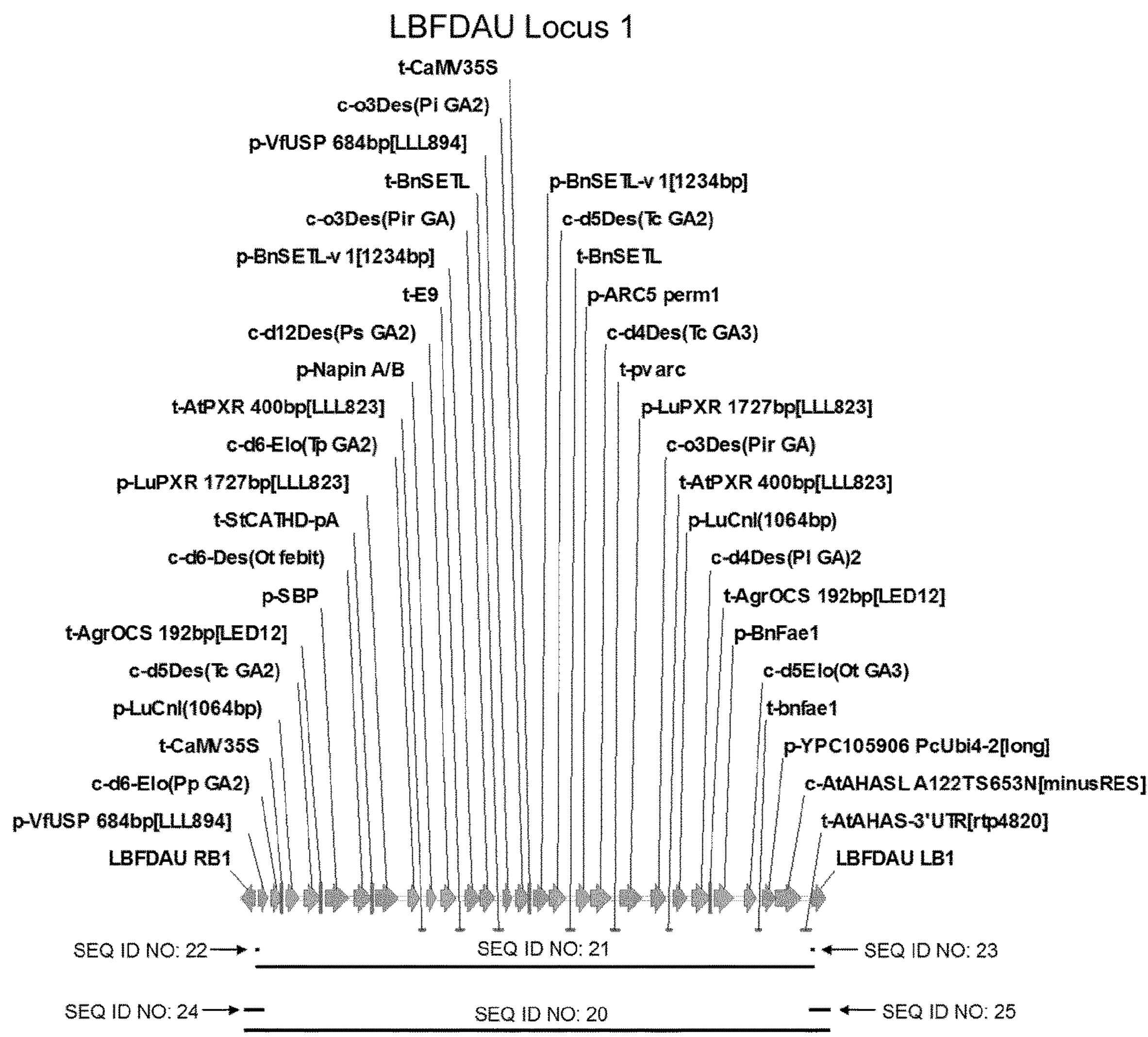
FIG. 4 shows the organization of T-DNA Locus 1 in the genome of a plant comprising *Brassica* event LBFDAU. SEQ ID NO:22 corresponds to the junction region of the Locus 1 T-DNA insert SEQ ID NO:21 and the right border flanking sequence SEQ ID NO:24. SEQ ID NO:23 corresponds to the junction region of the Locus 1 T-DNA insert SEQ ID NO:21 and left border flanking sequence SEQ ID NO:25.

SEQ ID NO:20 is a 45777 bp sequence assembled from the insert sequence of LBFDAU T-DNA Locus 1 (SEQ ID NO:21) and flanking sequences represented by SEQ ID NO:24 and SEQ ID NO:25 (See FIG. 4).

SEQ ID NO:21 is the sequence of the T-DNA insertion in Locus 1 of event LBFDAU, including left and right border sequences (See FIG. 4).

SEQ ID NO:22 is the LBFDAU Locus 1 RB junction sequence including 10 bp of flanking genomic DNA and bp 1-10 of SEQ ID NO:21 (See FIG. 4).

SEQ ID NO:23 is the LBFDAU Locus 1 LB junction sequence including bp 43711-43720 of SEQ ID NO:21 and 10 bp of flanking genomic DNA (See FIG. 4).

SEQ ID NO:24 is the flanking sequence up to and including the right border of the T-DNA in LBFDAU Locus 1. Nucleotides 1-1017 are genomic DNA (See FIG. 4).

SEQ ID NO:25 is the flanking sequence up to and including the left border of the T-DNA in LBFDAU Locus 1. Nucleotides 637-1677 are genomic DNA (See FIG. 4).

SEQ ID NO:26 is an LBFDAU Locus 1_Forward primer suitable for identifying Locus 1 of LBFDAU events. A PCR amplicon using the combination of SEQ ID NO:26 and SEQ ID NO:27 is positive for the presence of LBFDAU Locus 1.

SEQ ID NO:27 is an LBFDAU Locus 1_Reverse primer suitable for identifying Locus locus 1 of LBFDAU events. A PCR amplicon using the combination of SEQ ID NO:26 and SEQ ID NO:27 is positive for the presence of LBFDAU Locus 1.

SEQ ID NO:28 is an LBFDAU locus 1_Probe is a FAM™-labeled synthetic oligonucleotide that when used in an amplification reaction with SEQ ID NO:26 and SEQ ID NO:27 will release a fluorescent signal when positive for the presence of LBFDAU Locus 1.

Figure 5:
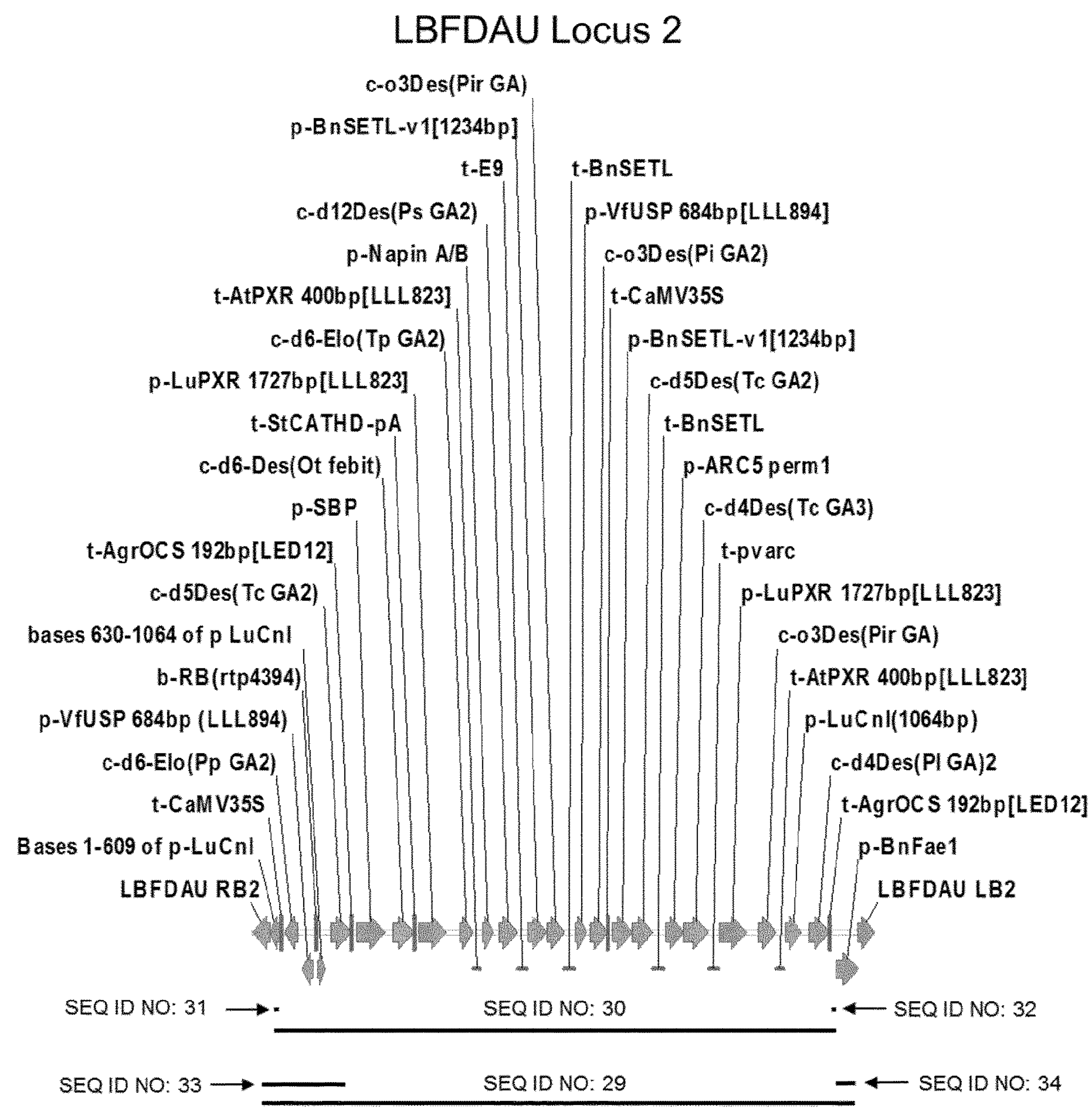
FIG. 5 shows the organization of T-DNA Locus 2 in the genome of a plant comprising *Brassica* event LBFDAU. SEQ ID NO:31 corresponds to the junction region of the Locus 2 T-DNA insert SEQ ID NO:30 and the right border flanking sequence SEQ ID NO:33. SEQ ID NO:32 corresponds to the junction region of the Locus 2 T-DNA insert SEQ ID NO:30 and left border flanking sequence SEQ ID NO:34.

SEQ ID NO:29 is a 39620 bp sequence assembled from the insert sequence of LBFDAU T-DNA Locus 2 (SEQ ID NO:30) and flanking sequences represented by SEQ ID NO:33 and SEQ ID NO:34 (See FIG. 5).

SEQ ID NO:30 is the sequence of the T-DNA insertion in Locus 2 of event LBFDAU, including left and right border sequences (See FIG. 5).

SEQ ID NO:31 is the LBFDAU Locus 2 RB junction sequence including 10 bp of flanking genomic DNA and bp 1-10 of SEQ ID NO: 30 (See FIG. 5).

SEQ ID NO:32 is the LBFDAU Locus 2 LB junction sequence including bp 37478-37487 of SEQ ID NO:30 and 10 bp of flanking genomic DNA (See FIG. 5).

SEQ ID NO:33 is the flanking sequence up to and including the right border of the T-DNA in LBFDAU Locus 2. Nucleotides 1-1099 are genomic DNA (See FIG. 5).

SEQ ID NO:34 is the flanking sequence up to and including the left border of the T-DNA in LBFLFK Locus 2. Nucleotides 288-1321 are genomic DNA (See FIG. 5).

SEQ ID NO:35 is an LBFDAU locus 2_Forward primer suitable for identifying Locus 2 of LBFDAU events. A PCR amplicon using the combination of SEQ ID NO:35 and SEQ ID NO:36 is positive for the presence of LBFDAU locus 2.

SEQ ID NO:36 is an LBFDAU locus 2_Reverse primer suitable for identifying Locus 2 of LBFDAU events. A PCR amplicon using the combination of SEQ ID NO:35 and SEQ ID NO:36 is positive for the presence of LBFDAU locus 2.

SEQ ID NO:37 is an LBFDAU locus 2_Probe is a FAM™-labeled synthetic oligonucleotide that when used in an amplification reaction with SEQ ID NO:35 and SEQ ID NO:36 will release a fluorescent signal when positive for the presence of LBFDAU Locus 2.

SEQ ID NO:38 is a primer suitable for determining zygosity of LBFLFK Locus 1. When used in combination with SEQ ID NO:39, production of a PCR amplicon of about 542 bp is positive for presence of WT at LBFLFK Locus 1.

SEQ ID NO:39 is a primer suitable for determining zygosity of LBFLFK Locus 1. When used in combination with SEQ ID NO:38, production of a PCR amplicon of about 542 bp is positive for presence of WT at LBFLFK Locus 1.

SEQ ID NO:40 is a primer suitable for determining zygosity of LBFLFK Locus 2. When used in combination with SEQ ID NO:41, production of a PCR amplicon of about 712 bp is positive for presence of WT at LBFLFK Locus 2.

SEQ ID NO:41 is a primer suitable for determining zygosity of LBFLFK Locus 2. When used in combination with SEQ ID NO:40, production of a PCR amplicon of about 712 bp is positive for presence of WT at LBFLFK Locus 2.

SEQ ID NO:42 is a primer suitable for determining zygosity of LBFDAU Locus 1. When used in combination with SEQ ID NO:43, production of a PCR amplicon of about 592 bp is positive for presence of WT at LBFDAU Locus 1.

SEQ ID NO:43 is a primer suitable for determining zygosity of LBFDAU Locus 1. When used in combination with SEQ ID NO:42, production of a PCR amplicon of about 592 bp is positive for presence of WT at LBFDAU Locus 1.

SEQ ID NO:44 is a primer suitable for determining zygosity of LBFDAU Locus 2. When used in combination with SEQ ID NO:45, production of a PCR amplicon of about 247 bp is positive for presence of WT at LBFDAU Locus 2.

SEQ ID NO:45 is a primer suitable for determining zygosity of LBFDAU Locus 2. When used in combination with SEQ ID NO:44, production of a PCR amplicon of about 247 bp is positive for presence of WT at LBFDAU Locus 2.

DETAILED DESCRIPTION OF THE INVENTION

The present invention is directed to transgenic *Brassica* events LBFLFK and LBFDAU, which are capable of producing oil comprising VLC-PUFAs, including EPA and DHA, for use as commodity products. *Brassica* plants of the invention have been modified by the insertion of the binary T-plasmid VC-LTM593-1qcz rc (SEQ ID NO:1) described in Example 1 comprising, in order, polynucleotides encoding the following enzymes of the VLC-PUFA biosynthetic pathway: Delta-6 ELONGASE from *Physcomitrella patens*; Delta-5 DESATURASE from *Thraustochytrium* sp. ATCC21685; Delta-6 DESATURASE from *Ostreococcus tauri*; Delta-6 ELONGASE from *Thalassiosira pseudonana*; Delta-12 DESATURASE from *Phythophthora sojae*; Omega-3 DESATURASE from *Pythium irregulare*; Omega-3-DESA TURASE from *Phythophthora infestans*; Delta-5 DESATURASE from *Thraustochytrium* sp. ATCC21685; Delta-4 DESATURASE from *Thraustochytrium* sp.; Omega-3 DESATURASE from *Pythium irregular*; Delta-4 DESATURASE from *Pavlova lutheri*; Delta-5 ELONGASE from *Ostreococcus tauri*. The VC-LTM593-1qcz rc binary T-plasmid (SEQ ID NO:1) further comprises a polynucleotide encoding the selectable marker acetohydroxy acid synthase, which confers tolerance to imidazolinone herbicides.

The invention further relates to the T-DNA insertions in each of *Brassica* events LBFLFK and LBFDAU, and to the genomic DNA/transgene insertions, i.e., the Locus 1 and Locus 2 junction regions found in *Brassica* plants or seeds comprising *Brassica* event LBFLFK, to the genomic DNA/transgene insertions, i.e., Locus 1 and Locus 2 junction regions found in *Brassica* plants or seeds comprising *Brassica* event LBFDAU, and the detection of the respective genomic DNA/transgene insertions, i.e., the respective Locus 1 and Locus 2 junction regions in *Brassica* plants or seed comprising event LBFLFK or event LBFDAU and progeny thereof.

As used herein, the term "*Brassica*" means any *Brassica* plant and includes all plant varieties that can be bred with *Brassica*. As defined herein, *Brassica* species include *B. napus, B. rapa, B. juncea, B. oleracea, B. nigra*, and *B. carinata*. Preferably, the species of the LBFLFK and LBFDAU events and their progeny is *B. napus*. As used herein, the term plant includes plant cells, plant organs, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, stalks, roots, root tips, anthers, and the like. Mature seed produced may be used for food, feed, fuel or other commercial or industrial purposes or for purposes of growing or reproducing the species. Progeny, variants and mutants of the regenerated plants are also included within the scope of the invention, provided that these parts comprise a LBFLFK or LBFDAU event.

A transgenic "event" is produced by transformation of plant cells with a heterologous DNA construct(s) including a nucleic acid expression cassette that comprises one or more transgene(s) of interest, the regeneration of a population of plants from cells which each comprise the inserted transgene(s) and selection of a particular plant characterized by insertion into a particular genome location. An event is characterized phenotypically by the expression of the transgene(s). At the genetic level, an event is part of the genetic makeup of a plant. The term "event" refers to the original transformant and progeny of the transformant that include the heterologous DNA. The term "event" also refers to progeny, produced by a sexual outcross between the transformant and another variety, that include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant comprising the inserted DNA and flanking sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA. In accordance with the invention, progeny of the *Brassica* LBFLFK event may comprise either LBFLFK Locus 1 or LBFLFK Locus 2, or both LBFLFK Locus 1 and LBFLFK Locus 2. Similarly, progeny of the *Brassica* LBFDAU event may comprise either LBFDAU Locus 1 or LBFDAU Locus 2, or both LBFDAU Locus 1 and LBFDAU Locus 2.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500 or 5000 base pairs or greater which is located either immediately upstream of and contiguous with, or immediately downstream of and contiguous with, the original foreign insert DNA molecule. Non-limiting examples of the flanking regions of the LBFLFK event comprise, for Locus 1, nucleotides 1 to 570 of SEQ ID NO: 6, nucleotides 229 to 811 of SEQ ID NO:7 and for Locus 2, nucleotides 1 to 2468 of SEQ ID NO:15, and/or nucleotides 242 to 1800 of SEQ ID NO:16 and variants and fragments thereof. Non-limiting examples of the flanking regions of the LBFDAU event comprise, for Locus 1, nucleotides 1 to 1017 of SEQ ID NO: 24, nucleotides 637 to 1677 of SEQ ID NO:25, and for Locus 2, nucleotides 1 to 1099 of SEQ ID NO:33 and/or nucleotides 288 to 1321 of SEQ ID NO: 34 and variants and fragments thereof.

Transformation procedures leading to random integration of the foreign DNA will result in transformants containing different flanking regions characteristic of and unique for each transformant. When recombinant DNA is introduced into a plant through traditional crossing, its flanking regions will generally not be changed. Transformants will also contain unique junctions between a piece of heterologous insert DNA and genomic DNA or two pieces of genomic DNA or two pieces of heterologous DNA. A "junction point" is a point where two specific DNA fragments join. For example, a junction point exists where insert DNA joins flanking DNA. A junction point also exists in a transformed organism where two DNA fragments join together in a manner that is modified from that found in the native organism. As used herein, "junction DNA" or "junction region" refers to DNA that comprises a junction point. Non-limiting examples of junction DNA from the LBFLFK event comprise, for Locus 1, SEQ ID NO:4, SEQ ID NO:5, and for Locus 2, SEQ ID NO:13, and/or SEQ ID NO:14, complements thereof, or variants and fragments thereof. Non-limiting examples of junction DNA from the LBFDAU event comprise, for Locus 1, SEQ ID NO:22, SEQ ID NO:23, and for Locus 2, SEQ ID NO:31 and/or SEQ ID NO:32, complements thereof, or variants and fragments thereof.

The term "germplasm" refers to an individual, a group of individuals or a clone representing a genotype, variety, species or culture or the genetic material thereof.

A "line" or "strain" is a group of individuals of identical parentage that are generally inbred to some degree and that are generally isogenic or near isogenic. Inbred lines tend to be highly homogeneous, homozygous and reproducible. Many analytical methods are available to determine the homozygosity and phenotypic stability of inbred lines.

The phrase "hybrid plants" refers to plants which result from a cross between genetically different individuals.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

The term "introgression" refers to the transmission of a desired allele of a genetic locus from one genetic background to another. In one method, the desired alleles can be introgressed through a sexual cross between two parents, wherein at least one of the parents has the desired allele in its genome.

The term "polynucleotide" according to the present invention refers to a deoxyribonucleic acid or ribonucleic acid. Unless stated otherwise, "polynucleotide" herein refers to a single strand of a DNA polynucleotide or to a double stranded DNA polynucleotide. The length of a polynucleotide is designated according to the invention by the specification of a number of base pairs ("bp") or nucleotides ("nt"). According to the invention, both designations are used interchangeably for single or double stranded nucleic acids. Also, as polynucleotides are defined by their respective nucleotide sequence, the terms nucleotide/polynucleotide and nucleotide sequence/polynucleotide sequence are used interchangeably, so that a reference to a nucleic acid sequence also is meant to define a nucleic acid comprising or consisting of a nucleic acid stretch the sequence of which is identical to the nucleic acid sequence.

As used herein, an "isolated DNA molecule", is an artificial polynucleotide corresponding to all or part of a flanking region, junction region, transgenic insert, amplicon, primer or probe that is unique to *Brassica* event LBFLFK or *Brassica* event LBFDAU, and which is not contained within the genome of *Brassica* event LBFLFK or the genome of *Brassica* event LBFDAU. Such isolated DNA molecules may be derived from the VC-LTM593-1qcz rc plasmid used to produce the LBFLFK and LBFDAU events, or from the genome of *Brassica* event LBFLFK or *Brassica* event LBFDAU, or from tissues, seeds, progeny, cells, plant organs, biological samples or commodity products derived from *Brassica* event LBFLFK or *Brassica* event LBFDAU. Such isolated DNA molecules can be extracted from cells, or tissues, or homogenates from a plant or seed or plant organ; or can be produced as an amplicon from extracted DNA or RNA from cells, or tissues, or homogenate from a plant or seed or plant organ, any of which is derived from *Brassica* event LBFLFK or *Brassica* event LBFDAU, or progeny, biological samples or commodity products derived therefrom.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from *Brassica* event LBFLFK or *Brassica* event LBFDAU, whether from a *Brassica* plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that can specifically anneal to a complementary target DNA strand by nucleic acid hybridization to form a hybrid between the primer and the target DNA strand, and then can be extended along the target DNA strand by a polymerase, e.g., a DNA polymerase. A primer pair or primer set of the present invention refers to two different primers that together are useful for amplification of a target nucleic acid sequence, e.g., by the polymerase chain reaction (PCR) or other conventional nucleic-acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods. Primers, primer pairs, or probes, may be produced by nucleotide synthesis, cloning, amplification, or other standard methods for producing a polynucleotide molecule. In accordance with the invention, one or more primer or probe sequences specific for target sequences in event LBFLFK Locus 1, LBFLFK Locus 2, LBFDAU Locus 1, and LBFDAU Locus 2, or complementary sequences thereto, may be selected using this disclosure and methods known in the art, for instance, via in silico analysis as described in Wojciech and Rhoads, NAR 17:8543-8551, 1989.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. The amplicon is of a length and has a sequence that is also diagnostic for the event. An amplicon may be of any length, and may range in length, for example, from the combined length of the primer pairs plus one nucleotide base pair, or the length of the primer pairs plus about fifty nucleotide base pairs, or the length of the primer pairs plus about two hundred nucleotide base pairs, the length of the primer pairs plus about five hundred nucleotide base pairs, or the length of the primer pairs plus about seven hundred fifty nucleotide base pairs, and the like. A primer pair can be derived from flanking sequence on both sides of the inserted DNA so as to produce an amplicon that includes the entire insert nucleotide sequence. Alternatively, a primer pair can be derived from flanking sequence on one side of an insert and sequence within the insert. A member of a primer pair derived from the plant genomic sequence may be located a distance from the inserted DNA molecule, and this distance can range from one nucleotide base pair up to about twenty thousand nucleotide base pairs. The use of the term "amplicon" specifically excludes primer-dimers that may be formed in the DNA thermal amplification reaction.

A "commodity product" refers to any product which is comprised of material derived from *Brassica* or *Brassica* oil and is sold to consumers.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. In accordance with the invention, the term relates to long chain PUFA (VLC-PUFA) having from 20 to 24 carbon atoms in the fatty acid chain. Systematic names of fatty acids including polyunsaturated fatty acids, their corresponding trivial names and shorthand notations used according to the present invention are given in Table 1.

TABLE 1

| Systematic name | Trivial Name | Short hand 1 | Short hand 2 |
|---|---|---|---|
| Hexadecanoic acid | Palmitic acid | 16:0 | |
| (Z)-7-Hexadecenoic acid | | 16:1n-9 | |
| (Z,Z,Z)-7,10,13-Hexadecatrienoic acid | | 16:3n-3 | |
| Octadecanoic acid | Stearic acid | 18:0 | |
| (Z)-9-Octadecenoic acid | Oleic acid | 18:1n-9 | OA |
| (Z,Z)-9,12-Octadecadienoic acid | Linoleic acid | 18:2n-6 | LA |
| (Z,Z)-6,9-Octadecadienoic acid | | 18:2n-9 | |
| (Z,Z,Z)-9,12,15-Octadecatrienoic acid | alpha-Linolenic acid | 18:3n-3 | ALA |
| (Z,Z,Z)-6,9,12-Octadecatrienoic acid | gamma-Linolenic acid | 18:3n-6 | GLA |
| (Z,Z,Z,Z)-6,9,12,15-Octadecatetraenoic acid | Stearidonic acid | 18:4n-3 | SDA |
| Eicosanoic acid | Arachidic acid | 20:0 | |
| (Z)-11-Eicosenoic acid | Gondoic acid | 20:1n-9 | |
| (Z,Z)-11,14-Eicosadienoic acid | | 20:2n-6 | |
| (Z,Z,Z)-11,14,17-Eicosatrienoic acid | | 20:3n-3 | |
| (Z,Z,Z)-8,11,14-Eicosatrienoic acid | Dihomo-gamma-linolenic acid | 20:3n-6 | DHGLA |
| (Z,Z,Z)-5,8,11-Eicosatrienoic acid | Mead acid | 20:3n-9 | |
| (Z,Z,Z,Z)-8,11,14,17-Eicosatetraenoic acid | | 20:4n-3 | ETA |
| (Z,Z,Z,Z)-5,8,11,14-Eicosatetraenoic acid | Arachidonic acid | 20:4n-6 | ARA |
| (Z,Z,Z,Z,Z)-5,8,11,14,17-Eicosapentaenoic acid | Timnodonic acid | 20:5n-3 | EPA |
| Docosanoic acid | Behenic acid | 22:0 | |
| (Z)-13-Docosenoic acid | Erucic acid | 22:1n-9 | |
| (Z,Z,Z,Z)-7,10,13,16-Docosatetraenoic acid | Adrenic acid | 22:4n-6 | DTA |
| (Z,Z,Z,Z,Z)-7,10,13,16,19-Docosapentaenoic acid | Clupanodonic acid | 22:5n-3 | DPAn-3 |
| (Z,Z,Z,Z,Z)-4,7,10,13,16-Docosapentaenoic acid | Osbond acid | 22:5n-6 | DPAn-6 |
| (Z,Z,Z,Z,Z,Z)-4,7,10,13,16,19-Docosahexaenoic acid | | 22:6n-3 | DHA |

Preferably, the VLC-PUFA produced by the LBFLFK and LBFDAU events and their progeny include DHGLA, ARA, ETA, EPA, DPA, DHA. More preferably, the VLC-PUFA produced by the LBFLFK and LBFDAU events and their progeny include ARA, EPA, and DHA. Most preferably, the VLC-PUFA produced by the LBFLFK and LBFDAU events and their progeny include EPA and/or DHA. Moreover, the LBFLFK and LBFDAU events and their progeny also produce intermediates of VLC-PUFA which occur during synthesis. Such intermediates may be formed from substrates by the desaturase, keto-acyl-CoA-synthase, keto-acyl-CoA-reductase, dehydratase and enoyl-CoA-reductase activity of the polypeptides of the present invention. Preferably, such substrates may include LA, GLA, DHGLA, ARA, eicosadienoic acid, ETA, and EPA.

In one embodiment, the transgenic *Brassica* plants of the invention comprise event LBFLFK (ATCC designation PTA-121703). Seed and progeny of event LBFLFK are also encompassed in this embodiment. In another embodiment, the transgenic *Brassica* plants of the invention comprise event LBFDAU (ATCC designation PTA-122340). Seed and progeny of event LBFDAU are also encompassed in this embodiment. Seeds of *Brassica* event LBFLFK (ATCC designation PTA-121703) and *Brassica* event LBFDAU (ATCC designation PTA-122340) have been deposited by applicant(s) at the American Type Culture Collection, Manassas, Va., USA, under the provisions of the Budapest Treaty on the International Recognition of the Deposit of Microorganisms for the Purposes of Patent Procedure. Applicants have no authority to waive any restrictions imposed by law on the transfer of biological material or its transportation in commerce. Applicants do not waive any infringement of their rights granted under this patent or rights applicable to the deposited events under the Plant Variety Protection Act (7 USC sec. 2321, et seq.), Unauthorized seed multiplication prohibited. This seed may be regulated according to national law. The deposition of seeds was made only for convenience of the person skilled in the art and does not constitute or imply any confession, admission, declaration or assertion that deposited seed are required to fully describe the invention, to fully enable the invention or for carrying out the invention or any part or aspect thereof.

The *Brassica* plants LBFLFK and LBFDAU can be used to manufacture commodities typically acquired from *Brassica*. Seeds of LBFLFK and LBFDAU can be processed into meal or oil as well as be used as an oil source in animal feeds for both terrestrial and aquatic animals. The VLC-PUFA-containing oil from events LBFLFK and LBFDAU may be used, for example, as a food additive to increase ω-3 fatty acid intake in humans and animals, or in pharmaceutical compositions to enhance therapeutic effects thereof, or as a component of cosmetic compositions, and the like.

An LBFLFK or LBFDAU plant can be bred by first sexually crossing a first parental *Brassica* plant grown from the transgenic LBFLFK or LBFDAU *Brassica* plant (or progeny thereof) and a second parental *Brassica* plant that lacks the EPA/DHA profile and imidazolinone tolerance of the LBFLFK or LBFDAU event, respectively, thereby producing a plurality of first progeny plants and then selecting a first progeny plant that displays the desired imidazolinone tolerance and selfing the first progeny plant, thereby producing a plurality of second progeny plants and then selecting from the second progeny plants which display the desired imidazolinone tolerance and EPA/DHA profile. These steps can further include the back-crossing of the first EPA/DHA producing progeny plant or the second EPA/DHA producing progeny plant to the second parental *Brassica* plant or a third parental *Brassica* plant, thereby producing a *Brassica* plant that displays the desired imidazolinone tolerance and EPA/DHA profile. It is further recognized that assaying progeny for phenotype is not required. Various methods and compositions, as disclosed elsewhere herein, can be used to detect and/or identify the LBFLFK or LBFDAU event.

Two different transgenic plants can also be sexually crossed to produce offspring that contain two independently-segregating exogenous genes. Selfing of appropriate progeny can produce plants that are homozygous for both exogenous transgenic inserts. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in Breeding Methods for Cultivar Development, Wilcos, ed., American Society of Agronomy, Madison Wis. (1987), and Buzza, Plant Breeding, in *Brassica* Oilseeds: Production and Utilization. D. S. Kimber and D. I. McGregor eds. Cab International, Wallingford, UK (1995).

In accordance with the invention embodied in *Brassica* event LBFLFK, the LBFLFK Locus 1 genomic DNA/transgene junction region and/or the LBFLFK Locus 2 genomic DNA/transgene junction region is present in *Brassica* plant LBFLFK (ATCC Accession No. PTA-121703) and progeny thereof. The LBFLFK Locus 1 DNA/transgene right border junction region comprises SEQ ID NO:4 and the LBFLFK Locus 1 left border junction region comprises SEQ ID NO:5, and the LBFLFK Locus 2 right border junction region comprises SEQ ID NO:13 and the LBFLFK left border junction region comprises SEQ ID NO:14. DNA sequences are provided that comprise at least one junction region sequence of event LBFLFK selected from the group consisting of SEQ ID NO:4 corresponding to positions 561 through 580 of SEQ ID NO:2 as shown in FIG. 2); SEQ ID NO:5 corresponding to positions 44318 through 44337 of SEQ ID NO:2, as shown in FIG. 2); SEQ ID NO:13 corresponding to positions 2459 through 2478 of SEQ ID NO:11 as shown in FIG. 3); and SEQ ID NO:14 corresponding to positions 46232 through 46251 of SEQ ID NO:11, as shown in FIG. 3), and complements thereof; wherein detection of these sequences in a biological sample containing *Brassica* DNA is diagnostic for the presence of *Brassica* event LBFLFK DNA in said sample. A *Brassica* event LBFLFK and *Brassica* seed comprising these DNA molecules is an aspect of this invention.

For example, to determine whether the *Brassica* plant resulting from a sexual cross contains transgenic DNA from event LBFLFK, DNA extracted from a *Brassica* plant tissue sample may be subjected to nucleic acid amplification method using (i) a first primer pair that includes: (a) a first primer derived from an LBFLFK Locus 1 flanking sequence and (b) a second primer derived from the LBFLFK Locus 1 inserted heterologous DNA, wherein amplification of the first and second primers produces an amplicon that is diagnostic for the presence of event LBFLFK Locus 1 DNA; and (ii) a second primer pair that includes (a) a third primer derived from an LBFLFK Locus 2 flanking sequence and (b) a fourth primer derived from the LBFLFK Locus 2 inserted heterologous DNA, wherein amplification of the third and fourth primers produces an amplicon that is diagnostic for the presence of event LBFLFK Locus 2 DNA.

The primer DNA molecules specific for target sequences in *Brassica* event LBFLFK comprise at least 11 contiguous nucleotides of any portion of the insert DNAs, flanking regions, and/or junction regions of LBFLFK Locus 1 and Locus 2. For example, LBFLFK Locus 1 primer DNA molecules may be derived from any of SEQ ID NO:2, SEQ ID NO:3, SEQ ID NO:4, or SEQ ID NO:5; SEQ ID NO:6, or SEQ ID NO:7, or complements thereof, to detect LBFLFK Locus 1. Similarly, LBFLFK Locus 2 primer DNA molecules may be derived from any of SEQ ID NO:15, SEQ ID NO:16, SEQ ID NO:13, or SEQ ID NO:14; SEQ ID NO:12, or SEQ ID NO:11, or complements thereof, to detect LBFLFK Locus 2. Those of skill in the art may use these primers to design primer pairs to produce LBFLFK Locus 1 and Locus 2 amplicons using known DNA amplification methods. The LBFLFK Locus 1 and Locus 2 amplicons produced using these DNA primers in the DNA amplification method are diagnostic for *Brassica* event LBFLFK when the amplification product contains an amplicon comprising an LBFLFK Locus 1 junction region SEQ ID NO:4 or SEQ ID NO:5, or complements thereof, and an amplicon comprising an LBFLFK Locus 2 junction region SEQ ID NO:13, or SEQ ID NO:14, or complements thereof.

Any LBFLFK amplicon produced by DNA primers homologous or complementary to any portion of SEQ ID NO:2 or SEQ ID NO:11, or complements thereof, is an aspect of the invention. Any amplicon that comprises SEQ ID NO:4 or SEQ ID NO:5 SEQ ID NO:13, or SEQ ID NO:14, or complements thereof, is an aspect of the invention.

According to another aspect of the invention, methods of detecting the presence of DNA corresponding to the *Brassica* event LBFLFK in a sample are provided. Such methods comprise the steps of: (a) contacting the sample comprising DNA with an LBFLFK Locus 1 primer pair and an LBFLFK Locus 2 primer pair that, when used in a nucleic acid amplification reaction with genomic DNA from *Brassica* event LBFLFK, produces a Locus 1 amplicon and a Locus 2 amplicon that are diagnostic for *Brassica* event LBFLFK; (b) performing a nucleic acid amplification reaction, thereby producing the Locus 1 and Locus 2 amplicons; and (c) detecting the amplicons, wherein one amplicon comprises the LBFLFK Locus 1 junction region SEQ ID NO:4 or SEQ ID NO:5, or the complements thereof, and one amplicon comprises the LBFLFK Locus 2 junction region SEQ ID NO:13 or SEQ ID NO:14, or the complements thereof.

The method of detecting the presence of DNA corresponding to the *Brassica* event LBFLFK in a sample may alternatively comprise the steps of: (a) contacting the sample comprising DNA with a primer pair that, when used in a nucleic acid amplification reaction with genomic DNA from *Brassica* event LBFLFK, produces a Locus 1 amplicon that is diagnostic for *Brassica* event LBFLFK; (b) performing a nucleic acid amplification reaction, thereby producing the amplicon; and (c) detecting the amplicon, wherein the amplicon comprises the LBFLFK Locus 1 junction region SEQ ID NO:4 or SEQ ID NO:5, or the complement thereof. The probe of SEQ ID NO:10 may be used to detect an LBFLFK Locus 1 amplicon.

The method of detecting the presence of DNA corresponding to the *Brassica* event LBFLFK in a sample may alternatively comprise the steps of: (a) contacting the sample comprising DNA with a primer pair that, when used in a nucleic acid amplification reaction with genomic DNA from *Brassica* event LBFLFK, produces a Locus 2 amplicon that is diagnostic for *Brassica* event LBFLFK; (b) performing a nucleic acid amplification reaction, thereby producing the amplicon; and (c) detecting the amplicon, wherein the amplicon comprises the LBFLFK Locus 2 junction region SEQ ID NO:13 or SEQ ID NO:14, or the complement thereof. The probe of SEQ ID NO:19 may be used to detect an LBFLFK Locus 2 amplicon.

According to another aspect of the invention, methods are provided for detecting the presence of a DNA corresponding to LBFLFK event Locus 1 in a sample. In one embodiment, the method comprises the steps of: (a) contacting the sample comprising DNA with a probe that hybridizes under stringent hybridization conditions with genomic DNA from Locus 1 of *Brassica* event LBFLFK and does not hybridize under the stringent hybridization conditions with genomic DNA from a control *Brassica* plant; (b) subjecting the sample and probe to stringent hybridization conditions; and (c) detecting hybridization of the probe to the *Brassica* event LBFLFK DNA, wherein said probe is specific for a target sequence comprising 11 contiguous nucleotides of SEQ ID NO:2 or the complement thereof. An exemplary probe for detecting LBFLFK Locus 1 is represented as SEQ ID NO:10.

The invention is also embodied in methods of detecting the presence of a DNA corresponding to LBFLFK event Locus 2 in a sample. In this embodiment, the method comprises the steps of: (a) contacting the sample comprising DNA with a probe that hybridizes under stringent hybridization conditions with genomic DNA from Locus 2 of *Brassica* event LBFLFK and does not hybridize under the stringent hybridization conditions with genomic DNA from a control *Brassica* plant; (b) subjecting the sample and probe to stringent hybridization conditions; and (c) detecting hybridization of the probe to the *Brassica* event LBFLFK DNA, wherein said probe is specific for a target sequence comprising 11 contiguous nucleotides of SEQ ID NO:11 or the complement thereof. An exemplary probe for detecting LBFLFK Locus 2 is represented as SEQ ID NO:19.

The methods for detecting *Brassica* event LBFLFK also encompass detecting *Brassica* event LBFLFK Locus 1 and Locus 2 in a single assay. In this embodiment, the method comprises the steps of: (a) contacting the sample comprising DNA with a first probe that hybridizes under stringent hybridization conditions with genomic DNA from Locus 1 of *Brassica* event LBFLFK and does not hybridize under the stringent hybridization conditions with genomic DNA from a control *Brassica* plant and a second probe that hybridizes under stringent hybridization conditions with genomic DNA from Locus 2 of *Brassica* event LBFLFK and does not hybridize under the stringent hybridization conditions with genomic DNA from a control *Brassica* plant; (b) subjecting the sample and probe to stringent hybridization conditions; and (c) detecting hybridization of the probes to the *Brassica* event LBFLFK Locus 1 DNA and Locus 2 DNA, wherein said first probe is specific for a target sequence comprising 11 contiguous nucleotides of SEQ ID NO:2 or the complement thereof and said second probe is specific for a target sequence comprising 11 contiguous nucleotides of SEQ ID NO:11 or the complement thereof.

Another aspect of the invention is a method of determining zygosity of the progeny of *Brassica* event LBFLFK, the method comprising performing the steps above for detecting LBFLFK Locus 1 and LBFLFK Locus 2, and performing the additional steps of: (d) contacting the sample comprising *Brassica* DNA with an LBFLFK wild type primer pair comprising at least 11 nucleotides of the *Brassica* genomic region of the LBFLFK Locus 1 transgene insertion and and LBFLFK Locus 2 wild type primer pair comprising at least 11 consecutive nucleotides of the *Brassica* genomic region of the LBFLFK Locus 2 transgene insertion, that when used in a nucleic acid amplification reaction with genomic DNA from wild type *Brassica* plants corresponding to the LBFLFK Locus 1 and/or LBFLFK Locus 2 transgene insertion region(s), produces amplicons that are diagnostic of the wild type *Brassica* genomic DNA homologous to the *Brassica* genomic region of the LBFLFK Locus 1 and Locus 2 transgene insertions; (e) performing a nucleic acid amplification reaction, thereby producing the second amplicon; (f) detecting the wild type *Brassica* amplicons; and (g) comparing the LBFLFK and wild type amplicons produced, wherein the presence of all amplicons indicates the sample is heterozygous for the transgene insertions. The zygosity detection method of the invention may employ any of the primers and probes described above which are specific for event LBFLFK Locus 1 and/or Locus 2. Exemplary primers for detection of wild type *Brassica* genomic DNA at the LBFLFK Locus 1 insertion site may be derived from SEQ ID NO:38 and SEQ ID NO:39, and suitable wild type Locus 1 probes may be designed from the wild type *Brassica* genomic sequence produced through amplification of SEQ ID NO:38 and SEQ ID NO:39. Exemplary primers for detection of wild type *Brassica* genomic DNA at the LBFLFK Locus 2 insertion site may be derived from SEQ ID NO:40 and SEQ ID NO:41, and suitable wild type Locus 2 probes may be designed from the wild type *Brassica* genomic sequence produced through amplification of SEQ ID NO:40 and SEQ ID NO:41.

Kits for the detection of *Brassica* event LBFLFK are provided which use primers designed from SEQ ID NO:2 and SEQ ID NO:11, or the complements thereof. An amplicon produced using said kit is diagnostic for LBFLFK when the amplicon (1) contains either nucleotide sequences set forth as SEQ ID NO:4, or SEQ ID NO:5, or complements thereof, and/or an amplicon comprising the Locus 2 junction region SEQ ID NO:13, or SEQ ID NO:14, or complements thereof.

In accordance with the invention embodied in *Brassica* event LBFDAU, the LBFDAU Locus 1 genomic DNA/transgene junction region and/or the LBFDAU Locus 2 genomic DNA/transgene junction region is present in *Brassica* event LBFDAU (ATCC Accession No. PTA-122340) and progeny thereof. The LBFDAU Locus 1 DNA/transgene right border junction region comprises SEQ ID NO:22 and the LBFDAU Locus 1 left border junction region comprises SEQ ID NO:23, and the LBFDAU Locus 2 right border junction region comprises SEQ ID NO:31 and the LBFDAU left border junction region comprises SEQ ID NO:32. DNA sequences are provided that comprise at least one junction region sequence of event LBFDAU selected from the group consisting of SEQ ID NO:22 (corresponding to positions 1008 through 1027 of SEQ ID NO:20, as shown in FIG. 4); SEQ ID NO:23 (corresponding to positions 44728 through 44747 of SEQ ID NO:20, as shown in FIG. 4); SEQ ID NO:31 (corresponding to positions 1090 through 1109 of SEQ ID NO:29, as shown in FIG. 5); and SEQ ID NO:32 (corresponding to positions 38577 through 38596 of SEQ ID NO:29, as shown in FIG. 5) and complements thereof; wherein detection of these sequences in a biological sample containing *Brassica* DNA is diagnostic for the presence of *Brassica* event LBFDAU DNA in said sample. A *Brassica* event LBFDAU and *Brassica* seed comprising these DNA molecules is an aspect of this invention.

For example, to determine whether the *Brassica* plant resulting from a sexual cross contains transgenic DNA from event LBFDAU, DNA extracted from a *Brassica* plant tissue sample may be subjected to nucleic acid amplification method using (i) a first primer pair that includes: (a) a first primer derived from an LBFDAU Locus 1 flanking sequence and (b) a second primer derived from the LBFDAU Locus 1 inserted heterologous DNA, wherein amplification of the first and second primers produces an amplicon that is diagnostic for the presence of event LBFDAU Locus 1 DNA; and/or (ii) a second primer pair that includes (a) a third primer derived from an LBFDAU Locus 2 flanking sequence and (b) a fourth primer derived from the LBFDAU Locus 2 inserted heterologous DNA, wherein amplification of the third and fourth primers produces an amplicon that is diagnostic for the presence of event LBFDAU Locus 2 DNA.

The primer DNA molecules specific for target sequences in *Brassica* event LBFDAU comprise 11 or more contiguous nucleotides of any portion of the insert DNAs, flanking regions, and/or junction regions of LBFDAU Locus 1 and Locus 2. For example, primer DNA molecules may be derived from any of SEQ ID NO:20, SEQ ID NO:21, SEQ ID NO:22, or SEQ ID NO:23; SEQ ID NO:24, or SEQ ID NO:25, or complements thereof, to detect LBFDAU Locus 1. Similarly, primer DNA molecules may be derived from any of SEQ ID NO:29, SEQ ID NO:30, SEQ ID NO:31, or SEQ ID NO:32; SEQ ID NO:33, or SEQ ID NO:34, or complements thereof, to detect LBFDAU Locus 2. Those of skill in the art may use these primers to design primer pairs to produce LBFDAU Locus 1 and Locus 2 amplicons using known DNA amplification methods The LBFDAU Locus 1 and Locus 2 amplicons produced using these DNA primers in the DNA amplification method is diagnostic for *Brassica* event LBFDAU when the amplification product contains an amplicon comprising the LBFDAU Locus 1 junction region SEQ ID NO:22 or SEQ ID NO:23 and/or an amplicon comprising the LBFDAU Locus 2 junction region SEQ ID NO:31, or SEQ ID NO:32.

Any LBFDAU amplicon produced by DNA primers homologous or complementary to any portion of SEQ ID NO:20 or SEQ ID NO:29, or complements thereof, is an aspect of the invention. Any amplicon that comprises the LBFDAU Locus 1 junction region SEQ ID NO:22, or SEQ ID NO:23, or complements thereof, and any amplicon comprising the LBFDAU Locus 2 junction region SEQ ID NO:31, or SEQ ID NO:32, or complements thereof, is an aspect of the invention.

According to another aspect of the invention, methods of detecting the presence of DNA corresponding to the *Brassica* event LBFDAU in a sample are provided. Such methods comprise: (a) contacting the sample comprising DNA with an LBFDAU Locus 1 primer pair and an LBFDAU Locus 2 primer pair that, when used in a nucleic acid amplification reaction with genomic DNA from *Brassica* event LBFDAU, produces a Locus 1 amplicon and a Locus 2 amplicon that are diagnostic for *Brassica* event LBFDAU; (b) performing a nucleic acid amplification reaction, thereby producing the amplicons; and (c) detecting the amplicons, wherein one amplicon comprises the LBFDAU Locus 1 junction region SEQ ID NO:22 or SEQ ID NO:23, or complements thereof, and one amplicon comprises the Locus 2 junction region SEQ ID NO:31 or SEQ ID NO:32, or complements thereof.

The method of detecting the presence of DNA corresponding to the *Brassica* event LBFDAU in a sample may alternatively comprise the steps of: (a) contacting the sample comprising DNA with a primer pair that, when used in a nucleic acid amplification reaction with genomic DNA from *Brassica* event LBFDAU, produces a Locus 1 amplicon that is diagnostic for *Brassica* event LBFDAU; (b) performing a nucleic acid amplification reaction, thereby producing the amplicon; and (c) detecting the amplicon, wherein the amplicon comprises the LBFDAU Locus 1 junction region SEQ ID NO:22 or SEQ ID NO:23, or a complement thereof. The probe of SEQ ID NO:28 may be used to detect an LBFDAU Locus 1 amplicon.

The method of detecting the presence of DNA corresponding to the *Brassica* event LBFDAU in a sample may alternatively comprise the steps of: (a) contacting the sample comprising DNA with a primer pair that, when used in a nucleic acid amplification reaction with genomic DNA from *Brassica* event LBFDAU, produces a Locus 2 amplicon that is diagnostic for *Brassica* event LBFDAU; (b) performing a nucleic acid amplification reaction, thereby producing the amplicon; and (c) detecting the amplicon, wherein the amplicon comprises the LBFDAU Locus 2 junction region SEQ ID NO:31 or SEQ ID NO:32, or a complement thereof. The probe of SEQ ID NO:37 may be used to detect an LBFDAU Locus 2 amplicon.

According to another aspect of the invention, methods are provided for detecting the presence of a DNA corresponding to LBFDAU event Locus 1 in a sample. In one embodiment, the method comprises the steps of: (a) contacting the sample comprising DNA with a probe that hybridizes under stringent hybridization conditions with genomic DNA from Locus 1 of *Brassica* event LBFDAU and does not hybridize under the stringent hybridization conditions with genomic DNA from a control *Brassica* plant; (b) subjecting the sample and probe to stringent hybridization conditions; and (c) detecting hybridization of the probe to the *Brassica* event LBFDAU DNA, wherein said probe is specific for a target sequence comprising 11 contiguous nucleotides of SEQ ID NO:20, or the complement thereof. An exemplary probe for detecting LBFDAU Locus 1 is represented as SEQ ID NO:28.

The invention is also embodied in methods of detecting the presence of a DNA corresponding to LBFDAU event Locus 2 in a sample. In this embodiment, the method comprises the steps of: (a) contacting the sample comprising DNA with a probe that hybridizes under stringent hybridization conditions with genomic DNA from Locus 2 of *Brassica* event LBFDAU and does not hybridize under the stringent hybridization conditions with genomic DNA from a control *Brassica* plant; (b) subjecting the sample and probe to stringent hybridization conditions; and (c) detecting hybridization of the probe to the *Brassica* event LBFDAU DNA, wherein said probe is specific for a target sequence comprising 11 contiguous nucleotides of SEQ ID NO:29, or the complement thereof. An exemplary probe for detecting LBFLFK Locus 2 is represented as SEQ ID NO:37.

The methods for detecting *Brassica* event LBFDAU also encompass detecting *Brassica* event LBFDAU Locus 1 and Locus 2 in a single assay. In this embodiment, the method comprises the steps of: (a) contacting the sample comprising DNA with a first probe that hybridizes under stringent hybridization conditions with genomic DNA from Locus 1 of *Brassica* event LBFDAU and does not hybridize under the stringent hybridization conditions with genomic DNA from a control *Brassica* plant and a second probe that hybridizes under stringent hybridization conditions with genomic DNA from Locus 2 of *Brassica* event LBFDAU and does not hybridize under the stringent hybridization conditions with genomic DNA from a control *Brassica* plant; (b) subjecting the sample and probe to stringent hybridization conditions; and (c) detecting hybridization of the probes to the *Brassica* event LBFDAU Locus 1 DNA and Locus 2 DNA, wherein said first probe is specific for a target sequence comprising 11 contiguous nucleotides of SEQ ID NO:20 or the complement thereof and said second probe is specific for a target sequence comprising 11 contiguous nucleotides of SEQ ID NO:29 or the complement thereof.

Another aspect of the invention is a method of determining zygosity of the progeny of *Brassica* event LBFDAU, the method comprising performing the steps above for detecting LBFDAU Locus 1 and LBFDAU Locus 2, and performing the additional steps of: (d) contacting the sample comprising *Brassica* DNA with an LBFDAU Locus 1 wild type primer pair comprising at least 11 consecutive nucleotides of the *Brassica* genomic region of the LBFDAU Locus 1 transgene insertion and an LBFDAU Locus 2 wild type primer pair comprising at least 11 consecutive nucleotides of the *Brassica* genomic region of the LBFDAU Locus 2 transgene insertion that when used in a nucleic acid amplification reaction with genomic DNA from wild type *Brassica* plants produces a second amplicon corresponding to the LBFDAU Locus 1 and/or LBFDAU Locus 2 transgene insertion region(s); (e) performing a nucleic acid amplification reaction, thereby producing the second amplicon and (f) detecting the *Brassica* wild type amplicons; and (g) comparing LBFDAU and wild type amplicons produced, wherein the presence of all amplicons indicates the sample is heterozygous for the transgene insertion. The zygosity detection method of the invention may employ any of the primers and probes described above which are specific for event LBFDAU Locus 1 and/or Locus 2. Exemplary primers for detection of wild type *Brassica* genomic DNA at the LBFDAU Locus 1 insertion site may be derived from SEQ ID NO:42 and SEQ ID NO:43, or the complements thereof and suitable wild type Locus 1 probes may be designed from the wild type *Brassica* genomic sequence produced through amplification of SEQ ID NO:42 and SEQ ID NO:43. Exemplary primers for detection of wild type *Brassica* genomic DNA at the LBFDAU Locus 2 insertion site may be derived from SEQ ID NO:44 and SEQ ID NO:45, and suitable wild type Locus 2 probes may be designed from the wild type *Brassica* genomic sequence produced through amplification of SEQ ID NO:44 and SEQ ID NO:45.

Kits for the detection of *Brassica* event LBFDAU are provided which use primers designed from SEQ ID NO:20 and SEQ ID NO:29, or the complements thereof. An amplicon produced using said kit is diagnostic for LBFDAU when the amplicon (1) contains either nucleotide sequences set forth as SEQ ID NO:22 or SEQ ID NO:23, or the complements thereof, and an amplicon comprising the Locus 2 junction region SEQ ID NO:31 or SEQ ID NO:32, or the complements thereof.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 (hereinafter, "Sambrook et al., 1989"); Current Protocols in Molecular Biology, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, .COPYRGT. 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

Regarding the amplification of a target nucleic acid sequence (e.g., by PCR) using a particular amplification primer pair, “stringent conditions” are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from a plant or seed tissue comprising *Brassica* event LBFLFK or *Brassica* event LBFDAU can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (e.g. Nikiforov, et al. Nucleic Acid Res. 22:4167-4175, 1994) where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that results in the production of a fluorescent signal. The fluorescent signal indicates the presence of the flanking/transgene insert sequence due to successful amplification and hybridization.

Other described methods, such as microfluidics (US Patent Pub. 2006068398, U.S. Pat. No. 6,544,734) provide methods and devices to separate and amplify DNA samples. Optical dyes are used to detect and quantitate specific DNA molecules (WO/05017181). Nanotube devices (WO/06024023) that comprise an electronic sensor for the detection of DNA molecules or nanobeads that bind specific DNA molecules and can then be detected.

Seed derived from *Brassica* event LBFLFK or *Brassica* event LBFDAU for sale for planting or for making commodity products is an aspect of the invention. Such commodity products include canola oil or meal containing VLC-PUFAs including but not limited to EPA and DHA. Commodity products derived from *Brassica* event LBFLFK comprise a detectable amount a DNA molecule comprising SEQ ID NO:4, SEQ ID NO:5, SEQ ID NO:13, and/or SEQ ID NO:14. Commodity products derived from *Brassica* event LBFDAU comprise a detectable amount a DNA molecule comprising SEQ ID NO:22, SEQ ID NO:23, SEQ ID NO:31, and/or SEQ ID NO:32. Exemplary commodity products derived from events LBFLFK and LBFDAU include, but are not limited to, cooking oil, salad oil, shortening, nutritionally enhanced foods, animal feed, pharmaceutical compositions, cosmetic compositions, hair care products, and the like.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

Example 1: Construction of BiBAC T-Plasmid VC-LTM593-1qcz rc

For synthesis of VLC-PUFA in seeds of *Brassica napus* events LBFLFK and LBFDAU, the set of genes encoding the proteins of the metabolic VLC-PUFA pathway were combined with expression elements (promoter, terminators and introns) onto a single binary T-plasmid designated VC-LTM593-1qcz rc (FIG. 1). The binary BAC (BiBAC) vector, suitable for transforming large T-DNAs into plants, is described in U.S. Pat. Nos. 5,733,744 and 5,977,439. Synthesis used in the construction of plasmid VC-LTM593-1qcz rc was performed by Life Technologies using the Geneart® technology described in WO2013049227. Plasmid VC-LTM593-1qcz rc (SEQ ID NO:1) has a total size of ~61.000 bp, and its structure is given in Table 2, which lists are the names of the elements, the nucleotide position in SEQ ID NO:1 (note: start position is larger than the stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to 43695 of VC-LTM593-1qcz rc). Elements outside of that region (=vector backbone) are required for cloning and stable maintenance in *E. coli* and/or agrobacteria.

The genetic elements of VC-LTM593-1qcz rc and the function of each element are listed in Table 2. For convenience, all enzymes expressed in seeds of plants carrying both T-DNA of VC-LTM593-1qcz rc that are required for EPA and DHA synthesis are additionally listed Table 3.

TABLE 2

Genetic Elements of plasmid VC-LTM593-1qcz rc.

| Genetic Elements of plasmid VC-LTM593-1qcz rc | From | To | Description, Function and Source of Element |
|---|---|---|---|
| p-VfUSP_684bp[LLL894] | 329 | 1012 | Promoter from UNKNOWN SEED PROTEIN gene USP (accession: X56240) from *Vicia faba* |
| i-Atss18_252[LJK36] | 1013 | 1264 | i-Atss18_252bp functional intron region; intron with partial 5' UTR, *Arabidopsis thaliana*, Locus At1g01170, +37 to +288 bp (numbering relative to start of transcription) (+72 to +282 bp 5'UTR-Intron only) |
| c-d6Elo(Pp_GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064 bp) | 2448 | 3511 | Promoter from CONLININ gene from *Linum usitatissimum* |
| i-Atss14_377bp[LJK32] | 3512 | 3888 | i-Atss14_377bp[LJK32] functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc_GA2) | 3892 | 5211 | Delta-5 DESATURASE from *Thraustochytrium* sp. ATCC21685 |
| t-AgrOCS 192 bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING PROTEIN-RELATED gene from *Vicia faba* |
| i-Atss2_455bp[LJK20] | 7338 | 7792 | i-Atss2_455bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d6Des(Ot_febit) | 7802 | 9172 | Delta-6 DESATURASE from *Ostreococcus tauri* |
| t-StCATHD-pA | 9200 | 9434 | Terminator from CATHEPSIN D INHIBITOR gene [CATHD] from *Solanum tuberosum* [Potato] |

TABLE 2-continued

| Genetic Elements of plasmid VC-LTM593-1qcz rc. | | | |
|---|---|---|---|
| Genetic Elements of plasmid VC-LTM593-1qcz rc | From | To | Description, Function and Source of Element |
| p-LuPXR 1727 bp[LLL823] | 9513 | 11239 | Promoter from PEROXIREDOXIN LIKE protein gene PXR from *Linum usitatissimum* |
| i-Atss1_846bp[ltm593] | 11240 | 12085 | i-Atss1_847bp functional intron region; intron with partial 5' UTR, *Arabidopsis thaliana*, Locus At1g62290 (aspartyl protease family protein), +1 to +847 bp (numbering relative to start of transcription) (+19 to +841 bp 5'UTR-Intron only); 1 bp at poly T stretch shorter compared to original i-Atss1_847bp |
| c-d6Elo(Tp_GA2) | 12099 | 12917 | Delta-6 ELONGASE from *Thalassiosira pseudonana* |
| t-AtPXR 400 bp[LLL823] | 12973 | 13372 | Terminator from peroxiredoxin like protein gene PXR (At1g48130) from *Arabidopsis thaliana* |
| p-Napin A/B | 13542 | 14205 | Promoter from napA/B gene (napin, seed storage protein) from *Brassica napus* |
| i-Atss14_377bp[LJK32] | 14206 | 14582 | i-Atss14_377bp[LJK32] functional intron region; intron with partial 5' UTR, *Arabidopsis thaliana*, Locus At5g63190, +166 to +542 bp (numbering relative to start of transcription) (+201 to +542 bp 5'UTR-Intron only) |
| c-d12Des(Ps_GA2) | 14589 | 15785 | Delta-12 DESATURASE from *Phythophthora sojae* |
| t-E9 | 15804 | 16361 | Terminator from Small Subunit of RuBisCo rbcS gene (E9) from *Pisum sativum* |
| p-BnSETL-v1[1234 bp] | 16454 | 17687 | SETL-v1 *Brassica napus* promoter |
| c-o3Des(Pir_GA) | 17690 | 18781 | Omega-3 DESATURASE from *Pythium irregulare* |
| t-BnSETL | 18803 | 19416 | SETL-v1 *Brassica napus* terminator |
| p-VfUSP_684bp[LLL894] | 19495 | 20178 | Promoter from UNKNOWN SEED PROTEIN gene USP (accession: X56240) from *Vicia faba* |
| i-Atss18_252[LJK36] | 20179 | 20430 | i-Atss18_252bp functional intron region; intron with partial 5' UTR, *Arabidopsis thaliana*, Locus At1g01170, +37 to +288 bp (numbering relative to start of transcription) (+72 to +282 bp 5'UTR-Intron only) |
| c-o3Des(Pi_GA2) | 20441 | 21526 | Omega-3-DESATURASE from *Phythophthora infestans* |
| t-CaMV35S | 21535 | 21750 | Terminator CaMV35S from 35S gene from Cauliflower mosaic virus |
| p-BnSETL-v1[1234 bp] | 21886 | 23119 | SETL-v1 *Brassica napus* promoter |
| c-d5Des(Tc_GA2) | 23122 | 24441 | Delta-5 DESATURASE from *Thraustochytrium* sp. ATCC21685 |
| t-BnSETL | 24463 | 25076 | SETL-v1 *Brassica napus* terminator |
| p-ARC5_perm1 | 25223 | 26373 | Promoter derived from a promoter from ARCILINE 5 gene from *Phaseolus vulgaris* |
| c-d4Des(Tc_GA3) | 26384 | 27943 | Delta-4 DESATURASE from *Thraustochytrium* sp. |
| t-pvarc | 27957 | 28556 | Terminator of ARC5 gene from *Phaseolus vulgaris* |
| p-LuPXR 1727 bp[LLL823] | 28649 | 30375 | Promoter from PEROXIREDOXIN LIKE protein gene PXR from *Linum usitatissimum* |
| i-Atss15_758bp[LJK33] | 30376 | 31133 | i-Atss15_758bp[LJK33] functional intron region; intron with partial 5'UTR, *Arabidopsis thaliana*, Locus At2g27040, +93 bp to +850 bp (numbering relative to start of transcription) (+128 to +847 bp 5'UTR-Intron only) |

TABLE 2-continued

| Genetic Elements of plasmid VC-LTM593-1qcz rc. | | | |
|---|---|---|---|
| Genetic Elements of plasmid VC-LTM593-1qcz rc | From | To | Description, Function and Source of Element |
| c-o3Des(Pir_GA) | 31149 | 32240 | Omega-3 DESATURASE from *Pythium irregulare* |
| t-AtPXR 400 bp[LLL823] | 32297 | 32696 | Terminator from PEROXIREDOXIN LIKE protein gene PXR (At1g48130) from *Arabidopsis thaliana* |
| p-LuCnl(1064 bp) | 32832 | 33895 | Promoter from CONLININ gene from *Linum usitatissimum* |
| i-Atss2_455bp[LJK20] | 33896 | 34350 | i-Atss2_455bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d4Des(PI_GA)2 | 34360 | 35697 | Delta-4 DESATURASE from *Pavlova lutheri* |
| t-AgrOCS 192 bp[LED12] | 35719 | 35910 | Terminator from OCTOPINE SYNTHASEgene OCS from *Agrobacterium tumefaciens* |
| p-BnFae1 | 36104 | 37533 | Promoter from Beta-KETOACYL-CoA SYNTHASE (FAE1.1) gene from *Brassica napus* |
| i-Atss1_847bp[LJK19] | 37534 | 38380 | i-Atss1_847bp functional intron region; intron with partial 5' UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 38388 | 39290 | Delta-5 ELONGASE from *Ostreococcus tauri* |
| t-bnFae1 | 39307 | 39706 | Terminator from FATTY ACID ELONGASE (FAE1, At4g34520) gene of *Arabidopsis thaliana* |
| p-YPC105906_PcUbi4-2[long] | 39830 | 40806 | MTX Parsley UBI4-2 promoter with internal intron |
| c-AtAHASL_A122T_S653N[minusRES] | 40814 | 42826 | ACETOHYDROXYACID SYNTHASE LARGE-SUBUNIT gene/CDS from *Arabidopsis* with S653N (csr1-2) mutation and A122T SDM mutation minus restriction sites |
| t-AtAHAS-3'UTR[rtp4820] | 42827 | 43606 | *Arabidopsis* (dicot) AtAHASL 3' Un-translated Region [trimmed] terminator for ACETOHYDROXYACID SYNTHASE gene |
| b-LLB | 43830 | 43695 | Left T-DNA Left border from pTi15955 [Genbank #AF242881] |
| c-KanR_Tn903 | 45777 | 44962 | Kanamycin Resistance selection gene/CDS |
| p-Kan[Im500] | 45898 | 45778 | Promoter for Kanamycin resistance gene |
| o-ori-2 | 47051 | 47267 | ori-2 origin of replication |
| c-repE | 47361 | 48116 | repE gene/CDS |
| c-sopA | 48695 | 49870 | sap/A gene/CDS |
| c-sopB | 49870 | 50841 | sopB gene/CDS |
| c-sopC/incD | 50914 | 51387 | incD/sopC partial gene/CDS |
| c-tral | 51890 | 51949 | tral gene/CDS |
| mf-tral - repA intergenic region | 51938 | 52300 | regulatory region of traR dependent quorum sensing regulon - containing 2 tra-boxes (see LI AND FARRAND JOURNAL OF BACTERIOLOGY, January 2000, p. 179-188) |
| o-repA | 52301 | 53518 | Rep-A gene from pTiC58 replicon (LI AND FARRAND JOURNAL OF BACTERIOLOGY, January 2000, p. 179 . . . 188) |

TABLE 2-continued

| Genetic Elements of plasmid VC-LTM593-1qcz rc | From | To | Description, Function and Source of Element |
|---|---|---|---|
| rr-repB | 53748 | 54758 | rep-B gene from pTiC58 replicon (LI AND FARRAND JOURNAL OF BACTERIOLOGY, January 2000, p. 179 . . . 188) |
| o-repC | 54973 | 56292 | rep-C gene from pTIC58 replicon (LI AND FARRAND JOURNAL OF BACTERIOLOGY, January 2000, p. 179 . . . 188) |
| mf-y4cG | 56771 | 56301 | fragment of DNA invertase homolog; similar to *Rhizobium* sp. NGR234 pNGR234a Y4CG |
| tr-Tn5 | 58811 | 57250 | Transposon Tn5 sequence |
| o-oriT | 59107 | 59275 | oriT from pRK310 genbank file |
| b-RB[rtp4394] | 148 | 59895 | Right T-DNA Right border |

Genetic Elements of plasmid VC-LTM593-1qcz rc.

TABLE 3

List of genes essential of EPA and DHA synthesis carried by the T-DNA of plasmid VC-LTM593-1qcz rc.

| Genes encoding enzymes for EPA and DHA synthesis | Length (bp) | Enzymatic function and source of encoded protein |
|---|---|---|
| c-d12Des(Ps_GA2) | 1197 | Delta-12 desaturase from *Phythophthora sojae* |
| c-d6Des(Ot_febit) | 1371 | Delta-6 desaturase from *Ostreococcus tauri* |
| c-d6Elo(Pp_GA2) | 873 | Delta-6 elongase from *Physcomitrella patens* |
| c-d6Elo(Tp_GA2) | 819 | Delta-6 elongase from *Thalassiosira pseudonana* |
| 2 copies of c-d5Des(Tc_GA2) | 1320 | Delta-5 desaturase from *Thraustochytrium* sp. ATCC21685 |
| c-o3Des(Pi_GA2) | 1086 | Omega-3-desaturase from *Phythophthora infestans* |
| 2 copies of c-o3Des(Pir_GA) | 1092 | Omega-3 desaturase from *Pythium irregulare* |
| c-d5Elo(Ot_GA3) | 903 | Delta-5 elongase from *Ostreococcus tauri* |
| c-d4Des(PI_GA)2 | 1338 | Delta-4 desaturase from *Pavlova lutheri* |
| c-d4Des(Tc_GA3) | 1560 | Delta-4 desaturase from *Thraustochytrium* sp. |

Example 2: Production and Selection of *B. napus* Events LBFLFK and LBFDAU

The LBFLFK and LBFDAU events were generated using a modified protocol according to DeBlock et al. 1989, Plant Physiology, 91:694-701). The binary vector VC-LTM593-1qcz rc (SEQ ID NO:1) was transformed into *Agrobacterium rhizogenes* SHA001 (WO2006024509), and co-cultivated with *Brassica* var. Kumily explants. Imidazolinone-tolerant plants were regenerated from transformed tissue.

Approximately 1543 hemizygous T0 transformation events were obtained, 68% of which contained the AHAS imidazolinone resistance selectable marker. In the T0 generation 335 events were screened for transgene copy number by qPCR and for EPA/DHA profile. Of these T0 events, 275 contained a single copy of VC-LTM593-1qcz rc, 49 contained two copies, and 11 contained three copies of the vector.

Figure 6:
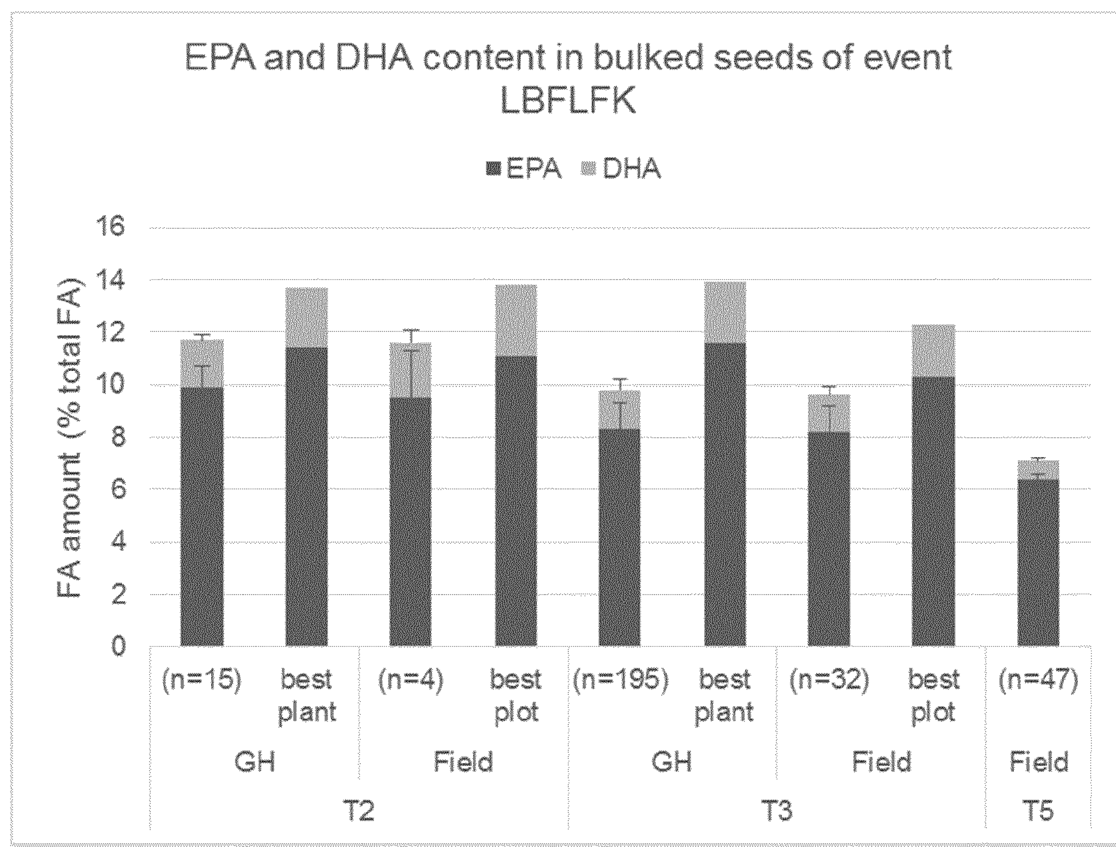
FIG. 6 shows the EPA and DHA content of bulked seed batches produced in the field and in the greenhouse from event LBFLFK.
Figure 7:
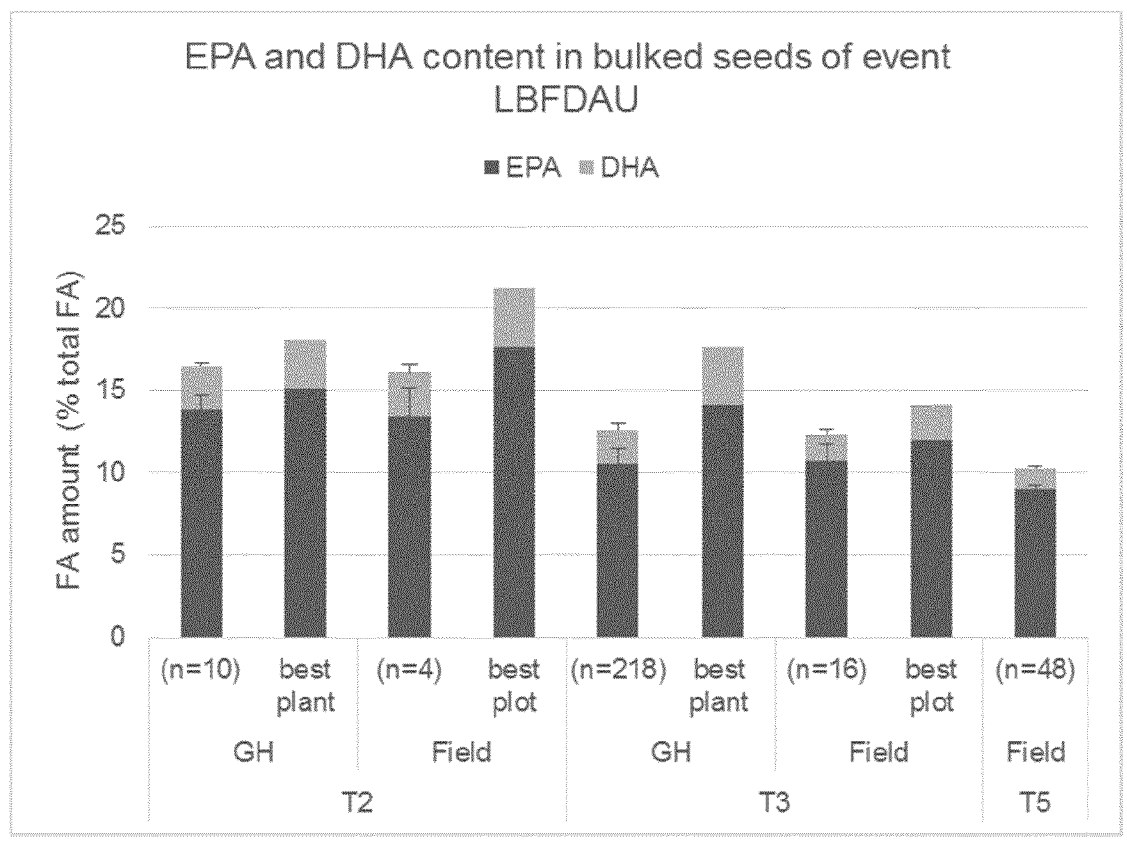
FIG. 7 shows the EPA and DHA content of bulked seed batches produced in the field and in the greenhouse from event LBFDAU.

In the T1 generation, 57 events were screened for copy number and EPA/DHA profile. Approximately 250 seeds from each event were destructively assayed for copy number at three locations on the T-DNA. The copy number segregation patterns were used to determine the number of T-DNA loci for each event. Both LBFLDK and LBFDAU were determined to have two independent T-DNA loci. A more extensive analysis was performed on additional plants for each event, where each gene in the T-DNA was assayed for copy number. The copy number results suggested that one T-DNA from LBFDAU was missing the genes c-AHAS and j-i-Atss1_c-d5Elo(Ot_GA3). Event LBFLFK has two full copies of the T-DNA. The results from the T1 generation were compared with the copy number results for the T0 generation in order to identify homozygous plants for each event. Homozygous T1 plants from all events were cultivated in the greenhouse and phenotypic observations were recorded including days to first flower, deformed flower rating, deformed leaf rating, deformed plant rating, deformed silique rating, flower color, leaf dentation, leaf color, fertility, number of leaf lobes, plant height. T2 seeds were collected from self-pollinated plants and thousand kernel weight, seed quality, oil content, protein content, and EPA and DHA content were measured (FIG. 6 and FIG. 7). Events LBFLFK and LBFDAU did not have any significant differences in the aerial phenotypes of T1 plants or a significant impact on total oil or protein accumulation in the T2 seed when compared to the WT Kumily controls. Both LBFDAU and LBFLFK were capable of synthesizing EPA and DHA in their seeds (FIG. 6 and FIG. 7), as determined by analysis of fatty acid methyl esters by gas chromatography.

Figure 8:
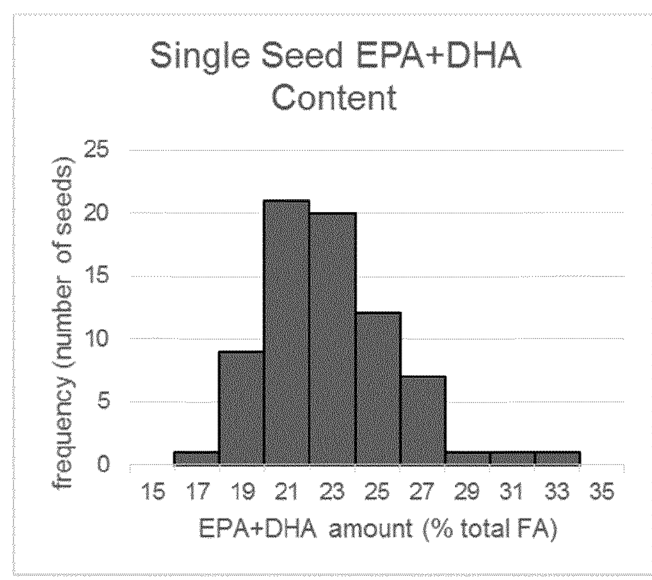
FIG. 8 shows the distribution of combined EPA plus DHA content in 95 T2 single seeds of event LBFDAU.

Certain events that had higher levels of EPA and DHA in the greenhouse, including LBFLFK and LBFDAU, were cultivated in field trials in USDA growth zone 11 during winter 2013 and examined for fatty acid profile, aerial phenotype (if any) and copy number in the T1 generation. There were no phenotypic or copy number abnormalities observed for LBFLFK and LBFDAU. EPA and DHA content in T2 seeds was roughly equal to EPA and DHA production in the greenhouse (FIG. 6 and FIG. 7). Single T2 seeds from a single plant of event LBFDAU were subjected to fatty acid analysis. The results indicate that there is a wide range of EPA/DHA content in the seeds of a single plants, but that all of the seeds contain at least some EPA and DHA, and some of the single seeds contain more than double the EPA/DHA seen in bulk seed batches (FIG. 8).

In the T2 generation, ten events were screened in the greenhouse. For each event, T2 seedbatches of two homozygous T1 plants where selected for seeding. Copy number analysis was performed on each T2 plant and the results confirmed that the T2 seed were indeed homozygous. T2 plants were observed in the greenhouse, and as with T1 plants, there was no significant impact on the phenotype of LBFLFK and LBFDAU T2 plants caused by the presence of the inserted T-DNA. Additional molecular characterization was performed on T2 plants grown in the greenhouse. qPCR and Southern blot analysis were used to confirm the absence of vector backbone. LBFLFK and LBFDAU were found to be free of vector backbone. T3 seed was collected from greenhouse-grown plants and EPA and DHA content were measured (FIG. 6 and FIG. 7).

Certain T2 events were also cultivated in field trials in USDA growth zones 3a-4b and 5a during the summer of 2014. Phenotypic ratings such as stand count, emergence vigor, days to first flower, days to last flower, days to seed maturity, plant height, lodging, and pod shatter were recorded. Some plants of event LBFLFK were slightly less vigorous and flowered two days later than WT Kumily, but was otherwise indistinguishable. The events grown in the field were also screened for imidazolinone tolerance. Table 4 shows the injury incurred by plants sprayed with imidazolinone herbicide. The events are indicated in the first column. IMI Injury: injury according to the scale detailed in Table 5 (DAT=days after treatment). Herbicide imazamox was applied at a 2× rate of 70 g imazamox/ha. *Brassica napus* cv Kumily, which is the non-transgenic comparator line that is otherwise isogenic to the events, was rated at 6 to 7, and was removed from the statistical analysis. ANOVA was conducted using the software JMP 11.0. Analysis was conducted at the 95% confidence level using Tukey test. Common letters between events in Table 4 indicate no significant difference in herbicide tolerance. T3 seeds were harvested from the field and were used for fatty acid analysis. FIG. 6 and FIG. 7 show that field produced T3 seed from LBFLFK and LBFDAU, respectively, are capable of EPA and DHA synthesis to the same levels observed for GH produced T3 seed.

A selection of events were cultivated in field trials in USDA growth zones 3a-4b and 5a during the summer. Homozygous T4 seeds were sown and the resulting T5 seeds were harvested and subjected to fatty acid analysis. T5 seeds of LBFLFK and LBFDAU maintained the ability to produce EPA and DHA (FIG. 6 and FIG. 7). Events LBFLFK and LBFDAU were selected based on EPA/DHA profile and imidazolinone tolerance.

TABLE 4

Herbicide tolerance of LBFLFK and LBFDAU T2 plants cultivated in USDA growth zones 3a-4b and 5a field trials

| Event | IMI Injury 7 DAT | | IMI Injury 14 DAT | | IMI Injury 21 DAT | |
|---|---|---|---|---|---|---|
| LBFDAU | 2 | a | 1 | ab | 1 | a |
| LBFLFK | 2 | a | 1 | b | 1 | a |
| Topas | 1 | a | 1 | b | 1 | a |
| Kumily | 6 | | 6 | | 7 | |

TABLE 5

Canola rating scale for herbicide

| % Injury | 1-7 Scale | Category | Injury Symptoms | Growth Rates and Recovery Effects |
|---|---|---|---|---|
| 0 | 1 | Excellent | None | None |
| 1-6 | 2 | Very Good | Leaf and petiole epinasty, chlorosis. | Minor or temporary growth effects. Injury and effects should be minor enough to not cause commercialization concerns. |
| 7-14 | 3 | Good | Leaf, petiole and stem epinasty, chlorosis, stem swelling. Leaf cupping may be observed. | This would be the maximum allowable injury for commercial evaluations. Fairly temporary in nature without any effect on final yield and minimal delay in maturity, |
| 15-20 | 4 | Fair | Above symptoms plus stunting in height, smaller leaf size or impact on LAI, in this class: Basal swelling may be observed. Expect recovery and seed production with this set of symptoms but delayed, reduced growth and reduced seed set. Plant stand may be non-uniform upon recovery. | Appearance of unaffected new growth impeded for <7 days. Slight delay in bolting and flower production. Yield impact minimal or small at harvest. |
| 21-40 | 5 | Poor | Injury in this class would be as above and more than evaluator's estimate of the level of commercial acceptance. | Significant delay in plant development, significant malformation s in growth and development vs. control. Malformations persist Serious reduction in maturity, height and harvest yield. |

TABLE 5-continued

| Canola rating scale for herbicide | | | | |
|---|---|---|---|---|
| % Injury | 1-7 Scale | Category | Injury Symptoms | Growth Rates and Recovery Effects |
| 41-79 | 6 | Non Tolerant | | Equivalent to suppression as a volunteer crop in a weed control assessment. Minimal regrowth following application. Plants survive but fail to flower and mature as normal. |
| 80-100 | 7 | Susceptible | Severe injury or death. | Severe injury or death. |

Example 3: Isolation of Genomic Flanking Sequences from Transgenic Events

Genomic DNA sequences flanking each T-DNA insertion in events LBFLFK and LBFDAU were determined. Leaf samples from greenhouse grown plants of events LBFLFK and LBFDAU were harvested and frozen. The leaf tissue was ground and genomic DNA was extracted using standard protocols for plant genomic DNA extraction. An aliquot amount of genomic DNA from each event was then used to isolate flanking sequences by adapter ligation-mediated PCR as described in O'Malley et al. 2007 Nature Protocols 2(11):2910-2917. Using this technique, PCR products were generated that contained sequence of the T-DNA border and adjacent genomic DNA. For each event, four distinct PCR products were obtained corresponding to the left and right border of each T-DNA locus. Individual PCR products were isolated and were sequenced using standard DNA sequencing protocols to determine sequence of the flanking regions. The flanking sequences were used to isolate and sequence the entire T-DNA insert from each locus of events LBFLFK and LBFDAU. A combination of methods known to those skilled in the art, such as long range PCR and Sanger sequencing, were used for this purpose. FIGS. 2-5 illustrate the T-DNA structure at each locus of events LBFLFK and LBFDAU.

The flanking sequence that extends into the right border of the T-DNA at Locus 1 in event LBFLFK is SEQ ID NO: 6, where nucleotides 1-570 are genomic DNA (FIG. 2). The flanking sequence that extends into the left border of the T-DNA at Locus 1 in event LBFLFK is SEQ ID NO: 7, where nucleotides 229-811 are genomic DNA (FIG. 2). A 44910 bp contig (SEQ ID NO: 2) was generated by aligning these flanking sequences with the sequence of the entire T-DNA insert at Locus 1 of event LBFLFK.

The flanking sequence that extends into the right border of the T-DNA at Locus 2 in event LBFLFK is SEQ ID NO: 15, where nucleotides 1-2468 are genomic DNA (FIG. 3). The flanking sequence that extends into the left border of the T-DNA at Locus 2 in event LBFLFK is SEQ ID NO: 16, where nucleotides 242-1800 are genomic DNA (FIG. 3). A 47800 bp contig (SEQ ID NO: 11) was generated by aligning these flanking sequences with the sequence of the entire T-DNA insert at Locus 2 of event LBFLFK (SEQ ID NO: 12).

The flanking sequence that extends into the right border of the T-DNA at Locus 1 in event LBFDAU is SEQ ID NO: 24, where nucleotides 1-1017 are genomic DNA (FIG. 4). The flanking sequence that extends into the left border of the T-DNA at Locus 1 in event LBFDAU is SEQ ID NO: 25, where nucleotides 637-1677 are genomic DNA (FIG. 4). A 45777 bp contig (SEQ ID NO: 21) was generated by aligning these flanking sequences with the sequence of the entire T-DNA insert at Locus 1 of event LBFDAU (SEQ ID NO: 21).

The flanking sequence that extends into the right border of the T-DNA at Locus 2 in event LBFDAU is SEQ ID NO: 33, where nucleotides 1-1099 are genomic DNA (FIG. 5). The flanking sequence that extends into the left border of the T-DNA at Locus 2 in event LBFDAU is SEQ ID NO: 34, where nucleotides 288-1321 are genomic DNA (FIG. 5). A 39620 bp contig (SEQ ID NO: 29) was generated by aligning these flanking sequences with the sequence of the entire T-DNA insert at Locus 2 of event LBFDAU (SEQ ID NO: 30).

Each flanking sequence from events LBFLFK and LBFDAU comprises the actual junction of the T-DNA borders with the adjacent genomic DNA. These junction regions can be described with 20 bp DNA sequences, where 10 bp of DNA corresponds to the right or left border, and the other 10 bp corresponds to the adjacent genomic DNA (Table 6).

TABLE 6

| 20 bp junction region sequences of LBFLFK and LBDFAU T-DNA loci. | | | | |
|---|---|---|---|---|
| Locus | Junction | SEQ ID NO: | Sequence | Details |
| LBFLFK locus 1 | LBFLFK RB1 | 4 | agctcgca atccagtc agca | bp 1-10 are genomic bp 11-20 are RB |
| LBFLFK locus 1 | LBFLFK LB1 | 5 | aagccata tatctgac ccta | bp 1-10 are LB bp 11-20 are genomic |
| LBFLFK locus 2 | LBFLFK RB2 | 13 | tatattta aaccagtc agca | bp 1-10 are genomic bp 11-20 are RB |
| LBFLFK locus 2 | LBFLFK LB2 | 14 | aatatatc ctcacata tgaa | bp 1-10 are LB bp 11-20 are genomic |
| LBFDAU locus 1 | LBFDAU RB1 | 22 | tataaata agcagtca gcat | bp 1-10 are genomic bp 11-20 are RB |
| LBFDAU locus 1 | LBFDAU LB1 | 23 | tactcatt gtaagaca caca | bp 1-10 are LB bp 11-20 are genomic |
| LBFDAU locus 2 | LBFDAU RB2 | 31 | caccctgg ctttgggg tgag | bp 1-10 are genomic bp 11-20 are RB |

TABLE 6-continued

| 20 bp junction region sequences of LBFLFK and LBDFAU T-DNA loci. | | | | |
|---|---|---|---|---|
| Locus | Junction | SEQ ID NO: | Sequence | Details |
| LBFDAU locus 2 | LBFDAU LB2 | 32 | tcctctac tattctcc gaca | bp 1-10 are LB bp 11-20 are genomic |

Example 4: Event-Specific Detection and Zygosity Assays

The flanking sequences isolated in Example 3 (SEQ ID NO: 6 and SEQ ID NO: 7 for LBFLFK Locus 1, SEQ ID NO: 15 and SEQ ID NO: 16 for LBFLFK Locus 2, SEQ ID NO: 24 and SEQ ID NO: 25 for LBFDAU Locus 1, and SEQ ID NO: 33 and SEQ ID NO: 34 for LBFDAU Locus 2) were used for the design of event specific detection assays to test for the presence of events LBFLFK and LBFDAU. Specific primer pairs are provided in this example, but the disclosed flanking sequences could be used to design different primer pairs for producing diagnostic amplicons for each locus of each event. Any primer pair that can be used to produce an amplicon including at least 11 consecutive bp of the junction sequences represented by SEQ ID NO: 4 and SEQ ID NO: 5 for LBFLFK Locus 1, SEQ ID NO: 13 and SEQ ID NO: 14 for LBFLFK Locus 2, SEQ ID NO: 22 and SEQ ID NO: 23 for LBFDAU Locus 1, and SEQ ID NO: 31 and SEQ ID NO:32 for LBFDAU Locus 2 can be used for the detection of events LBFLFK or LBFDAU and are within the scope of this invention.

Endpoint Taqman qPCR assays for locus detection were developed and are described in this example. Other methods may be known and used by those skilled in the art for the detection of events LBFLFK and LBFDAU. Oligonucleotide primers used for the assays are listed in Table 7 and endpoint Taqman qPCR assay conditions are provided in Table 8 and Table 9. Detection of each locus from LBFDAU and LBFLFK requires the use of a specific combination of forward primer, reverse primer, and probe. The TaqMan probes for targets of interest were labeled with FAM/BHQ1. The method described here is optimized for the Quantstudio™ 12 K Flex Real-Time PCR system from Life Technologies, although methods can be adapted to other systems with minor modification known to those skilled in the art. Endpoint Taqman qPCR assays were carried out with Jump-Start TagReadyMix (Sigma, P2893) in a 384-well plate (Life technologies, catalogue number 4309849) in a total volume of 10 microliters per well. Per reaction, 2 μl of template DNA is mixed with 8 microliters of qPCR reaction mixture according to Table 8 below. The plates were sealed with MicroAmp® Optical Adhesive Film (Life Technologies, catalogue number 4311971). The reactions were conducted using the cycling parameters described in Table 9.

TABLE 7

| Primers and Probes for event specific detection using endpoint Taqman qPCR assays. | | | |
|---|---|---|---|
| Event/ Locus | Forward Primer | Reverse Primer | Probe |
| LBFDAU Locus 1 | LBFDAU Locus 1_Forward primer SEQ ID NO: 26 gcggacatctacattt ttgaattg | LBFDAU Locus 1_Reverse primer SEQ ID NO: 27 gctatttgacttcttc atctgtgtgtct | LBFDAU Locus 1_Probe SEQ ID NO: 28 tttctccatattgacc atcata |
| LBFDAU Locus 2 | LBFDAU Locus 2_Forward primer SEQ ID NO: 35 cactgagcatggtgct taaacac | LBFDAU Locus 2_Reverse primer SEQ ID NO: 36 agagcgagagagagga agtaggtatataa | LBFDAU Locus 2_Probe SEQ ID NO: 37 ctggtgagttctagta ctt |
| LBFLFK Locus 1 | LBFLFK Locus 1_Forward primer SEQ ID NO: 8 ctctttctttttctcc atattgaccat | LBFLFK Locus 1_Reverse primer SEQ ID NO: 9 acatttttattcctgt atacgcacacat | LBFLFK Locus 1_Probe SEQ ID NO: 10 atactcattgctgatc cat |
| LBFLFK Locus 2 | LBFLFK Locus 2_Forward primer SEQ ID NO: 17 ccatattgaccatcat actcattgc | LBFLFK Locus 2_Reverse primer SEQ ID NO: 18 tggctgatagggttct ttcaaatata | LBFLFK Locus 2_Probe SEQ ID NO: 19 taaattatacttgatc ggtcatctg |

TABLE 8

| Reaction components for event specific Endpoint Taqman qPCR assays. Taqman endpoint qPCR reaction components | |
|---|---|
| PCR Component | Amount (μl) per reaction |
| 2X Jumpstart Taq Readymix | 5 |
| 25 mM MgSO4 | 0.4 |
| ROX (Sulforhodamine 101, 12 μM) | 0.1 |
| Forward Primer (10 μM) | 0.9 |
| Reverse Primer (10 μM) | 0.9 |
| Probe (10 μM) | 0.1 |
| gDNA (15-60 ng/μl) | 2 |
| Nuclease free water | 0.6 |
| volume final | 10 μl |

TABLE 9

| Endpoint Taqman qPCR cycling parameters | | | |
|---|---|---|---|
| | | KOD 1 | |
| | | Temp | Time |
| | step 1 | 95° C. | 5 min |
| 45 | step 2 | 95° C. | 18 sec |
| cycles | step 3 | 60° C. | 1 min |

The exemplified diagnostic amplicon for LBFLFK Locus 1 contains the junction sequence represented by SEQ ID NO: 5. The exemplified diagnostic amplicon for LBFLFK Locus 2 contains the junction sequence represented by SEQ ID NO: 14. The exemplified diagnostic amplicon for LBFDAU Locus 1 contains the junction sequence represented by SEQ ID NO: 23. The exemplified diagnostic amplicon for LBFDAU Locus 2 contains the junction sequence represented by SEQ ID NO: 32. In endpoint Taqman qPCR assay, the amplicons are detected by hybridization of the probe with its target amplicon, resulting in the release of a fluorescence signal. The controls for this analysis should include a positive control from a plant known to contain one or more loci of event LBFLFK or event LBFDAU DNA, a negative control from non-transgenic plant and a negative control that contains no template DNA.

Zygosity of transgenic plants can be determined by performing the endpoint Taqman qPCR assays described above concomitantly with PCR reactions that amplify the non-transgenic genomic insertion sites corresponding to each locus of events LBFLFK and LBFDAU. Oligonucleotide primers are listed in Table 10 along with the name of the polymerase and cycling conditions that should be used for each primer pair. PCR reaction components and cycling parameters are listed in Table 11, Table 12, and Table 13. Reactions were optimized to be carried out using either KOD Hot Start Polymerase (EMD Millipore 71086) or Phusion Hot Start DNA Polymerase (New England Biolabs M0535). Reaction volumes were 50 µL and were set up according to Tables 11 and 12. Cycling parameters to be used described in Table 13. The name of the cycling condition to use for each primer pair is listed in Table 10. PCR products can be visualized by a variety of methods known to those skilled in the art, such as agarose gel electrophoresis. The expected amplicon size for LBFDAU Locus 1 is about 592 bp. The expected amplicon size for LBFDAU locus 2 is about 247 bp. The expected amplicon size for LBFLFK locus 1 is about 542 bp. The expected amplicon size for LBFLFK locus 2 is about 712 bp.

TABLE 10

Primers used for zygosity testing using PCR.

| Event/ Locus | Forward Primer | Reverse Primer | Poly- merase | Cycling con- ditions |
|---|---|---|---|---|
| LBFDAU locus 1 | WT LBFDAU Locus 1 F SEQ ID NO: 42 GGCAGGCGTGATC TTATT | WT LBFDAU Locus 1 R SEQ ID NO: 43 CATAATTTGCAGT CGCTGATT | KOD | KOD 1 |
| LBFDAU locus 2 | WT LBFDAU Locus 2 F SEQ ID NO: 44 AGATAACGATACA TCCACGAA | WT LBFDAU Locus 2 R SEQ ID NO: 45 CGAACATAACAGA GCGAGAGA | KOD | KOD 2 |

TABLE 10-continued

Primers used for zygosity testing using PCR.

| Event/ Locus | Forward Primer | Reverse Primer | Poly- merase | Cycling con- ditions |
|---|---|---|---|---|
| LBFLFK locus 1 | WT LBFLFK Locus 1 F SEQ ID NO: 38 AGAAGTGTACGCG ACGAGA | WT LBFLFK Locus 1 R SEQ ID NO: 39 TCAGGAGCGAGAA TGCGAAAG | Phusion | Phusion |
| LBFLFK locus 2 | WT LBFLFK Locus 2 F SEQ ID NO: 40 ACCCATACATACG CATAAGTG | WT LBFLFK Locus 2 R SEQ ID NO: 41 AATATATGGGCTA CATTGA | Phusion | Phusion |

TABLE 11

PCR reaction components used for KOD Polymerase reactions
KOD Polymerase Reaction Components

| PCR Component | Amount (µl) per reaction |
|---|---|
| ddH2O | 15 |
| gDNA (15-60 ng/µl) | 2 |
| Primer-F (2.5 µM) | 4 |
| Primer-R (2.5 µM) | 4 |
| 10X KOD buffer | 5 |
| dNTP (2 mM each) | 5 |
| 25 mM MgSO4 | 3 |
| ddH2O | 10 |
| KOD Polymerase | 2 |
| volume final | 50 |

TABLE 12

PCR Reaction components used for Phusion Polymerase reactions
Phusion Polymerase Reaction Components

| PCR Component | Amount (µl) per reaction |
|---|---|
| ddH2O | 15 |
| gDNA (15-60 ng/µl) | 2 |
| Primer-F (2.5 µM) | 4 |
| Primer-R (2.5 µM) | 4 |
| 5x Phusion HF buffer | 10 |
| dNTP (10 mM each) | 1 |
| ddH2O | 13.5 |
| Phusion DNA Polymerase | 0.5 |
| volume final | 50 |

TABLE 13

| PCR thermocycler protocols for zygosity determination | | | | | | | |
|---|---|---|---|---|---|---|---|
| | | KOD 1 | | KOD 2 | | Phusion | |
| | | Temp | Time | Temp | Time | Temp | Time |
| 35 | step 1 | 95° C. | 2 min | 95° C. | 2 min | 98° C. | 30 sec |
| cycles | step 2 | 94° C. | 20 sec | 94° C. | 20 sec | 98° C. | 10 sec |
| | step 3 | 58° C. | 10 sec | 60° C. | 10 sec | 60° C. | 30 sec |

TABLE 13-continued

PCR thermocycler protocols for zygosity determination

| | KOD 1 | | KOD 2 | | Phusion | |
|---|---|---|---|---|---|---|
| | Temp | Time | Temp | Time | Temp | Time |
| step 4 | 70° C. | 1 min 20 sec | 70° C. | 1 min | 72° C. | 2.5 min |
| step 5 | 70° C. | 5 min | 70° C. | 5 min | 72° C. | 10 min |
| step 6 | 4° C. | Hold | 4° C. | Hold | 4° C. | Hold |

For a given locus, zygosity was determined by comparing the results of endpoint Taqman qPCR reactions using primers in table 7 with the results of PCR reactions using primers corresponding to the same locus in Table 10. For a given locus, a positive result for the endpoint Taqman qPCR assay combined with a negative result for the PCR indicates a homozygous transgenic plant. A positive result for the endpoint Taqman qPCR assay combined with a positive result for the PCR is indicative of a hemizygous plant for that specific locus. A negative result for the endpoint Taqman qPCR assay combined with a positive result for the PCR is indicative of a plant that is non-transgenic at that locus. Using these methods one can independently determine the zygosity of each T-DNA locus in events LBFLFK and LBFDAU in any plant.

The invention claimed is:

1. A *Brassica* plant or seed comprising event LBFLFK, a sample of seed comprising transformation event LBFLFK having been deposited under ATCC Accession No. PTA-121703.

2. An F1 progeny of the *Brassica* plant of claim 1, wherein the F1 progeny comprise polynucleotide having the sequence of SEQ ID NO:4, SEQ ID NO:5, SEQ ID NO:13, or SEQ ID NO:14.

3. An artificial DNA molecule comprising a sequence selected from the group consisting of SEQ ID NO:4, SEQ ID NO:5, and SEQ ID NO:13.

4. A method of detecting the presence of DNA corresponding to the *Brassica* event LBFLFK in a sample comprising DNA, the method comprising the steps of:

(a) contacting the sample with an LBFLFK Locus 1 primer pair and an LBFLFK Locus 2 primer pair that, when used in a nucleic acid amplification reaction with genomic DNA from *Brassica* event LBFLFK, produces a Locus 1 amplicon and a Locus 2 amplicon that are diagnostic for *Brassica* event LBFLFK;

(b) performing a nucleic acid amplification reaction, thereby producing the Locus 1 and Locus 2 amplicons; and (c) detecting the amplicons, wherein one amplicon comprises the LBFLFK Locus 1 junction region SEQ ID NO:4 or SEQ ID NO:5, or the complement thereof, and one amplicon comprises the LBFLFK Locus 2 junction region SEQ ID NO:13 or SEQ ID NO:14, or the complement thereof.

5. The method of claim 4, wherein (a) the LBFLFK Locus 1 primer pair comprises:

(i) a first primer selected from the group consisting of at least 11 consecutive nucleotides of SEQ ID NO:6, at least 11 consecutive nucleotides of the complement of SEQ ID NO:6, at least 11 consecutive nucleotides of SEQ ID NO:7, and at least 11 consecutive nucleotides of the complement of SEQ ID NO:7; and (ii) a second primer selected from the group consisting of at least 11 consecutive nucleotides of SEQ ID NO:3 and at least 11 consecutive nucleotides of the complement of SEQ ID NO:3, and (b) the LBFLFK Locus 2 primer pair comprises:

(i) a third primer selected from the group consisting of at least 11 consecutive nucleotides of SEQ ID NO:15 at least 11 consecutive nucleotides of the complement of SEQ ID NO:15, at least 11 consecutive nucleotides of SEQ ID NO:16, and at least 11 consecutive nucleotides of the complement of SEQ ID NO:16; and (ii) a fourth primer selected from the group consisting of at least 11 consecutive nucleotides of SEQ ID NO:12 and at least 11 consecutive nucleotides of the complement of SEQ ID NO:12.

6. The method of claim 5, wherein the first primer comprises SEQ ID NO:8, the second primer comprises SEQ ID NO:9, the third primer comprises SEQ ID NO:17, and the fourth primer comprises SEQ ID NO:18.

7. The method of claim 4, further comprising the steps of:

d) contacting the sample with an LBFLFK Locus 1 wild type primer pair comprising at least 11 consecutive nucleotides of the *Brassica* genomic region of the LBFLFK Locus 1 transgene insertion and an LBFLFK Locus 2 wild type primer pair comprising at least 11 consecutive nucleotides of the *Brassica* genomic region of the LBFLFK Locus 2 transgene insertion;

e) performing a nucleic acid amplification reaction, thereby producing amplicons of the homologous wild type *Brassica* genomic regions corresponding to LBFLFK Locus 1 and LBFLFK Locus 2 insertions;

f) detecting the wild type *Brassica* amplicons; and g) comparing the amplicons produced in step c) with the amplicons produced in step f), wherein the presence of both amplicons indicates that the sample is heterozygous for the LBFLFK Locus 1 and Locus 2 transgene insertions.

8. A meal derived from *Brassica* seed of claim 1 or progeny thereof, wherein the meal comprises a detectable amount of a nucleotide sequence diagnostic for *Brassica* event LBFLFK, wherein the sequence is selected from the group consisting of SEQ ID NO:4, SEQ ID NO:5, and SEQ ID NO:13.

9. A commodity product comprising the artificial DNA molecule of claim 3.

10. A method for producing a *Brassica* plant, the method comprising the step of crossing a plant comprising *Brassica* event LBFLFK with a *Brassica* plant lacking event LBFLFK to obtain a plant comprising the *Brassica* event LBFLFK, wherein a sample of event LBFLFK has been deposited under ATCC Accession No. PTA-121703.

11. A *Brassica* plant comprising an artificial DNA molecule comprising a sequence selected from the group consisting of SEQ ID NO:4, SEQ ID NO:5, SEQ ID NO:13, and SEQ ID NO:14, wherein the plant further comprises a polynucleotide comprising SEQ ID NO: 3 and/or a polynucleotide comprising SEQ ID NO: 12.

12. A *Brassica* seed comprising an artificial DNA molecule comprising a sequence selected from the group consisting of SEQ ID NO:4, SEQ ID NO:5, SEQ ID NO:13, and SEQ ID NO:14, wherein the seed further comprises a polynucleotide comprising SEQ ID NO: 3 and/or a polynucleotide comprising SEQ ID NO: 13.

13. An oil derived from *Brassica* seed of claim 1 or progeny thereof, wherein the oil comprises a detectable amount of a nucleotide sequence diagnostic for *Brassica* event LBFLFK, wherein the sequence is selected from the group consisting of SEQ ID NO:4, SEQ ID NO:5, and SEQ ID NO:13.

* * * * *

SEQUENCE LISTING

```
<160> NUMBER OF SEQ ID NOS: 45

<210> SEQ ID NO 1
<211> LENGTH: 60074
<212> TYPE: DNA
<213> ORGANISM: Artificial Sequence
<220> FEATURE:
<223> OTHER INFORMATION: vector VC-LTM593-1qcz rc

<400> SEQUENCE: 1

cctgccagtc agcatcatca caccaaaagt taggcccgaa tagtttgaaa ttagaaagct      60

cgcaattgag gtctacaggc caaattcgct cttagccgta caatattact caccggtgcg     120

atgcccccca tcgtaggtga aggtggaaat taatggcgcg cctgatcact gattagtaac     180

tattacgtaa gcctacgtag cgtcacgtga cgttagctaa cgctacgtag cctcagctga     240

cgttacgtaa gcctacgtag cgtcacgtga gcttagctaa cgctacctag gctcagctga     300

cgttacgtaa cgctagctag cgtcactcct gcagcaaatt tacacattgc cactaaacgt     360

ctaaaccctt gtaatttgtt tttgttttac tatgtgtgtt atgtatttga tttgcgataa     420

atttttatat ttggtactaa atttataaca ccttttatgc taacgtttgc caacacttag     480

caatttgcaa gttgattaat tgattctaaa ttatttttgt cttctaaata catatactaa     540

tcaactggaa atgtaaatat ttgctaatat ttctactata ggagaattaa agtgagtgaa     600

tatggtacca caaggtttgg agatttaatt gttgcaatgc tgcatggatg gcatatacac     660

caaacattca ataattcttg aggataataa tggtaccaca caagatttga ggtgcatgaa     720

cgtcacgtgg acaaaaggtt tagtaatttt tcaagacaac aatgttacca cacacaagtt     780

ttgaggtgca tgcatggatg ccctgtggaa agtttaaaaa tattttggaa atgatttgca     840

tggaagccat gtgtaaaacc atgacatcca cttggaggat gcaataatga agaaaactac     900

aaatttacat gcaactagtt atgcatgtag tctatataat gaggattttg caatactttc     960

attcatacac actcactaag ttttacacga ttataatttc ttcatagcca gtactgttta    1020

agcttcactg tctctgaatc ggcaaaggta aacgtatcaa ttattctaca aaccctttta    1080

tttttctttt gaattaccgt cttcattggt tatatgataa cttgataagt aaagcttcaa    1140

taattgaatt tgatctgtgt ttttttggcc ttaatactaa atccttacat aagctttgtt    1200

gcttctcctc ttgtgagttg agtgttaagt tgtaataatg gttcactttc agctttagaa    1260

gaaaccatgg aagttgttga gaggttctac ggagagttgg atggaaaggt ttcccaagga    1320

gtgaacgctt tgttgggatc tttcggagtt gagttgactg ataccccaac tactaaggga    1380

ttgccactcg ttgattctcc aactccaatt gtgttgggag tgtctgttta cttgaccatc    1440

gtgatcggag gattgctttg gatcaaggct agagatctca agccaagagc ttctgagcca    1500
```

```
ttcttgttgc aagctttggt gttggtgcac aacttgttct gcttcgcttt gtctctttac   1560
atgtgcgtgg gtatcgctta ccaagctatc acctggagat attccttgtg gggaaacgct   1620
tataacccaa agcacaagga gatggctatc ctcgtttacc tcttctacat gtccaagtac   1680
gtggagttca tggataccgt gatcatgatc ctcaagagat ccaccagaca gatttctttc   1740
ctccacgtgt accaccactc ttctatctcc cttatctggt gggctattgc tcaccacgct   1800
ccaggaggag aggcttattg gagtgctgct ctcaactctg gagtgcacgt gttgatgtac   1860
gcttactact tcttggctgc ttgcttgaga tcttccccaa agctcaagaa caagtacctc   1920
ttctggggaa gatacctcac ccaattccag atgttccagt tcatgctcaa cttggtgcaa   1980
gcttactacg atatgaaaac caacgctcca tatccacaat ggctcatcaa gatcctcttc   2040
tactacatga tctccctctt gttcctcttc ggaaacttct acgtgcaaaa gtacatcaag   2100
ccatccgatg gaaagcaaaa gggagctaag accgagtgat cgacaagctc gagtttctcc   2160
ataataatgt gtgagtagtt cccagataag ggaattaggg ttcctatagg gtttcgctca   2220
tgtgttgagc atataagaaa cccttagtat gtatttgtat ttgtaaaata cttctatcaa   2280
taaaatttct aattcctaaa accaaaatcc agtactaaaa tccagatccc ccgaattaat   2340
tcggcgttaa ttcagctagc tagcctcagc tgacgttacg taacgctagg tagcgtcacg   2400
tgacgttagc taacgctagg tagcgtcagc tgagcttacg taagcgctta gcagatattt   2460
ggtgtctaaa tgtttatttt gtgatatgtt catgtttgaa atggtggttt cgaaaccagg   2520
gacaacgttg ggatctgata gggtgtcaaa gagtattatg gattgggaca atttcggtca   2580
tgagttgcaa attcaagtat atcgttcgat tatgaaaatt ttcgaagaat atcccatttg   2640
agagagtctt tacctcatta atgtttttag attatgaaat tttatcatag ttcatcgtag   2700
tctttttggt gtaaaggctg taaaaagaaa ttgttcactt ttgttttcgt ttatgtgaag   2760
gctgtaaaag attgtaaaag actattttgg tgttttggat aaaatgatag tttttataga   2820
ttcttttgct tttagaagaa atacatttga aattttttcc atgttgagta taaaataccg   2880
aaatcgattg aagatcatag aaatatttta actgaaaaca aatttataac tgattcaatt   2940
ctctccattt ttatacctat ttaaccgtaa tcgattctaa tagatgatcg atttttttata  3000
taatcctaat taaccaacgg catgtattgg ataattaacc gatcaactct cacccctaat   3060
agaatcagta ttttccttcg acgttaattg atcctacact atgtaggtca tatccatcgt   3120
tttaattttt ggccaccatt caattctgtc ttgcctttag ggatgtgaat atgaacggcc   3180
aaggtaagag aataaaaata atccaaatta aagcaagaga ggccaagtaa gataatccaa   3240
atgtacactt gtcattgcca aaattagtaa aatactcggc atattgtatt cccacacatt   3300
attaaaatac cgtatatgta ttggctgcat ttgcatgaat aatactacgt gtaagcccaa   3360
aagaacccac gtgtagccca tgcaaagtta acactcacga ccccattcct cagtctccac   3420
tatataaacc caccatcccc aatctcacca aacccaccac acaactcaca actcactctc   3480
acaccttaaa gaaccaatca ccaccaaaaa atttcacgat ttggaatttg attcctgcga   3540
tcacaggtat gacaggttag attttgtttt gtatagttgt atacatactt ctttgtgatg   3600
ttttgtttac ttaatcgaat ttttggagtg ttttaaggtc tctcgtttag aaatcgtgga   3660
aaatatcact gtgtgtgtgt tcttatgatt cacagtgttt atgggtttca tgttctttgt   3720
tttatcattg aatgggaaga aatttcgttg ggatacaaat ttctcatgtt cttactgatc   3780
gttattagga gtttggggaa aaaggaagag tttttttggt tggttcgagt gattatgagg   3840
```

-continued

```
ttatttctgt atttgattta tgagttaatg gtcgttttaa tgttgtagac catgggaaaa   3900
ggatctgagg gaagatctgc tgctagagag atgactgctg aggctaacgg agataagaga   3960
aagaccatcc tcattgaggg agtgttgtac gatgctacca acttcaaaca cccaggaggt   4020
tccattatta acttcctcac cgagggagaa gctggagttg atgctaccca agcttacaga   4080
gagttccatc agagatccgg aaaggctgat aagtacctca agtccctccc aaagttggat   4140
gcttctaagg tggagtctag gttctctgct aaggagcagg ctagaaggga cgctatgacc   4200
agggattacg ctgctttcag agaggagttg gttgctgagg gatacttcga tccatctatc   4260
ccacacatga tctacagagt ggtggagatt gtggctttgt tcgctttgtc tttctggttg   4320
atgtctaagg cttctccaac ctctttggtt ttgggagtgg tgatgaacgg aatcgctcaa   4380
ggaagatgcg gatgggttat gcacgagatg ggacacggat ctttcactgg agttatctgg   4440
ctcgatgata ggatgtgcga gttcttctac ggagttggat gtggaatgtc tggacactac   4500
tggaagaacc agcactctaa gcaccacgct gctccaaaca gattggagca cgatgtggat   4560
ttgaacacct tgccactcgt tgctttcaac gagagagttg tgaggaaggt taagccagga   4620
tctttgttgg ctttgtggct cagagttcag gcttatttgt tcgctccagt gtcttgcttg   4680
ttgatcggat tgggatggac cttgtacttg cacccaagat atatgctcag gaccaagaga   4740
cacatggagt ttgtgtggat cttcgctaga tatatcggat ggttctcctt gatgggagct   4800
ttgggatatt ctcctggaac ttctgtggga atgtacctct gctctttcgg acttggatgc   4860
atctacatct tcctccaatt cgctgtgtct cacacccact tgccagttac caacccagag   4920
gatcaattgc actggcttga gtacgctgct gatcacaccg tgaacatctc taccaagtct   4980
tggttggtta cctggtggat gtctaacctc aacttccaaa tcgagcacca cttgttccca   5040
accgctccac aattcaggtt caaggagatc tctccaagag ttgaggctct cttcaagaga   5100
cacaacctcc cttactacga tttgccatac acctctgctg tttctactac cttcgctaac   5160
ctctactctg ttggacactc tgttggagct gataccaaga agcaggattg actgctttaa   5220
tgagatatgc gagacgccta tgatcgcatg atatttgctt tcaattctgt tgtgcacgtt   5280
gtaaaaaacc tgagcatgtg tagctcagat ccttaccgcc ggtttcggtt cattctaatg   5340
aatatatcac ccgttactat cgtattttta tgaataatat tctccgttca atttactgat   5400
tgtctacgta ggctcagctg agcttaccta aggctacgta ggctcacgtg acgttacgta   5460
aggctacgta gcgtcacgtg agcttaccta actctagcta gcctcacgtg accttagcta   5520
acactaggta gcgtcagctc gacggcccgg actgtatcca acttctgatc tttgaatctc   5580
tctgttccaa catgttctga aggagttcta agacttttca gaaagcttgt aacatgcttt   5640
gtagactttc tttgaattac tcttgcaaac tctgattgaa cctacgtgaa aactgctcca   5700
gaagttctaa ccaaattccg tcttgggaag gcccaaaatt tattgagtac ttcagtttca   5760
tggacgtgtc ttcaaagatt tataacttga aatcccatca tttttaagag aagttctgtt   5820
ccgcaatgtc ttagatctca ttgaaatcta caactcttgt gtcagaagtt cttccagaat   5880
caacttgcat catggtgaaa atctggccag aagttctgaa cttgtcatat ttcttaacag   5940
ttagaaaaat ttctaagtgt ttagaatttt gacttttcca aagcaaactt gacttttgac   6000
tttcttaata aaacaaactt catattctaa catgtcttga tgaaatgtga ttcttgaaat   6060
ttgatgttga tgcaaaagtc aaagtttgac ttttcagtgt gcaattgacc attttgctct   6120
tgtgccaatt ccaaacctaa attgatgtat cagtgctgca aacttgatgt catggaagat   6180
cttatgagaa aattcttgaa gactgagagg aaaaattttg tagtacaaca caaagaatcc   6240
```

```
tgtttttcat agtcggacta gacacattaa cataaaacac cacttcattc gaagagtgat   6300
tgaagaagga aatgtgcagt tacctttctg cagttcataa gagcaactta cagacacttt   6360
tactaaaata ctacaaagag gaagatttta acaacttaga gaagtaatgg gagttaaaga   6420
gcaacacatt aagggggagt gttaaaatta atgtgttgta accaccacta cctttagtaa   6480
gtattataag aaaattgtaa tcatcacatt ataattattg tccttattta aaattatgat   6540
aaagttgtat cattaagatt gagaaaacca aatagtcctc gtcttgattt ttgaattatt   6600
gttttctatg ttacttttct tcaagcctat ataaaaactt tgtaatgcta aattgtatgc   6660
tggaaaaaaa tgtgtaatga attgaataga aattatggta tttcaaagtc caaaatccat   6720
caatagaaat ttagtacaaa acgtaactca aaaatattct cttattttaa attttacaac   6780
aatataaaaa tattctctta ttttaaattt tacaataata taatttatca cctgtcacct   6840
ttagaatacc accaacaata ttaatactta gatattttat tcttaataat tttgagatct   6900
ctcaatatat ctgatattta ttttatattt gtgtcatatt ttcttatgtt ttagagttaa   6960
cccttatatc ttggtcaaac tagtaattca atatatgagt ttgtgaagga cacattgaca   7020
tcttgaaaca ttggttttaa ccttgttgga atgttaaagg taataaaaca ttcagaatta   7080
tgaccatcta ttaatatact tcctttgtct tttaaaaaag tgtgcatgaa aatgctctat   7140
ggtaagctag agtgtcttgc tggcctgtgt atatcaattc catttccaga tggtagaaac   7200
tgccactacg aataattagt cataagacac gtatgttaac acacgtcccc ttgcatgttt   7260
tttgccatat attccgtctc tttctttttc ttcacgtata aaacaatgaa ctaattaata   7320
gagcgatcaa gctgaacagt tctttgcttt cgaagttgcc gcaacctaaa caggtttttc   7380
cttcttcttt cttcttatta actacgacct tgtcctttgc ctatgtaaaa ttactaggtt   7440
ttcatcagtt acactgatta agttcgttat agtggaagat aaaatgccct caaagcattt   7500
tgcaggatat ctttgatttt tcaaagatat ggaactgtag agtttgatag tgttcttgaa   7560
tgtggttgca tgaagttttt ttggtctgca tgttattttt tcctcgaaat atgttttgag   7620
tccaacaagt gattcacttg ggattcagaa agttgttttc tcaatatgta acagtttttt   7680
tctatggaga aaaatcatag ggaccgttgg ttttggcttc tttaattttg agctcagatt   7740
aaacccattt tacccggtgt tcttggcaga attgaaaaca gtacgtagta ccgcgcctac   7800
catgtgtgtt gagaccgaga acaacgatgg aatccctact gtggagatcg ctttcgatgg   7860
agagagagaa agagctgagg ctaacgtgaa gttgtctgct gagaagatgg aacctgctgc   7920
tttggctaag accttcgcta gaagatacgt ggttatcgag ggagttgagt acgatgtgac   7980
cgatttcaaa catcctggag gaaccgtgat tttctacgct ctctctaaca ctggagctga   8040
tgctactgag gctttcaagg agttccacca cagatctaga aaggctagga aggctttggc   8100
tgctttgcct tctagacctg ctaagaccgc taaagtggat gatgctgaga tgctccagga   8160
tttcgctaag tggagaaagg agttggagag ggacggattc ttcaagcctt ctcctgctca   8220
tgttgcttac agattcgctg agttggctgc tatgtacgct ttgggaacct acttgatgta   8280
cgctagatac gttgtgtcct ctgtgttggt ttacgcttgc ttcttcggag ctagatgtgg   8340
atgggttcaa cacgagggag gacactcttc tttgaccgga aacatctggt gggataagag   8400
aatccaagct ttcactgctg gattcggatt ggctggatct ggagatatgt ggaactccat   8460
gcacaacaag caccacgcta ctcctcaaaa agtgaggcac gatatggatt tggataccac   8520
tcctgctgtt gctttcttca acaccgctgt ggaggataat agacctaggg gattctctaa   8580
```

```
gtactggctc agattgcaag cttggacctt cattcctgtg acttctggat tggtgttgct   8640
cttctggatg ttcttcctcc acccttctaa ggctttgaag ggaggaaagt acgaggagct   8700
tgtgtggatg ttggctgctc acgtgattag aacctggacc attaaggctg ttactggatt   8760
caccgctatg caatcctacg gactcttctt ggctacttct tgggtttccg gatgctactt   8820
gttcgctcac ttctctactt ctcacaccca cttggatgtt gttcctgctg atgagcactt   8880
gtcttgggtt aggtacgctg tggatcacac cattgatatc gatccttctc agggatgggt   8940
taactggttg atgggatact tgaactgcca agtgattcac cacctcttcc cttctatgcc   9000
tcaattcaga caacctgagg tgtccagaag attcgttgct ttcgctaaga agtggaacct   9060
caactacaag gtgatgactt atgctggagc ttggaaggct actttgggaa acctcgataa   9120
tgtgggaaag cactactacg tgcacggaca acactctgga aagaccgctt gattaatgaa   9180
ggccgcctcg accgtacccc ctgcagatag actatactat gttttagcct gcctgctggc   9240
tagctactat gttatgttat gttgtaaaat aaacacctgc taaggtatat ctatctatat   9300
tttagcatgg ctttctcaat aaattgtctt tccttatcgt ttactatctt atacctaata   9360
atgaaataat aatatcacat atgaggaacg gggcaggttt aggcatatat atacgagtgt   9420
agggcggagt ggggctacgt agcgtcacgt gacgttacct aagcctaggt agcctcagct   9480
gacgttacgt aacgctaggt aggctcagct gacacgggca ggacataggg actactacaa   9540
gcatagtatg cttcagacaa agagctagga aagaactctt gatggaggtt aagagaaaaa   9600
agtgctagag ggcatagta atcaaacttg tcaaaaccgt catcatgatg agggatgaca   9660
taatataaaa agttgactaa ggtcttggta gtactctttg attagtatta tatattggtg   9720
agaacatgag tcaagaggag acaagaaacc gaggaaccat agtttagcaa caagatggaa   9780
gttgcaaagt tgagctagcc gctcgattag ttacatctcc taagcagtac tacaaggaat   9840
ggtctctata ctttcatgtt tagcacatgg tagtgcggat tgacaagtta gaaacagtgc   9900
ttaggagaca aagagtcagt aaaggtattg aaagagtgaa gttgatgctc gacaggtcag   9960
gagaagtccc tccgccagat ggtgactacc aaggggttgg tatcagctga gacccaaata  10020
agattcttcg gttgaaccag tggttcgacc gagactctta gggtgggatt tcactgtaag  10080
atttgtgcat tttgttgaat ataaattgac aatttttttt atttaattat agattattta  10140
gaatgaatta catatttagt ttctaacaag gatagcaatg gatgggtatg ggtacaggtt  10200
aaacatatct attacccacc catctagtcg tcgggtttta cacgtaccca cccgtttaca  10260
taaaccagac cggaatttta aaccgtaccc gtccgttagc gggtttcaga tttacccgtt  10320
taatcgggta aaacctgatt actaaatata tatttttat ttgataaaca aaacaaaaat  10380
gttaatattt tcatattgga tgcaatttta agaaacacat attcataaat ttccatattt  10440
gtaggaaaat aaaaagaaaa atatattcaa gaacacaaat ttcaccgaca tgacttttat  10500
tacagagttg gaattagatc taacaattga aaaattaaaa ttaagataga atatgttgag  10560
gaacatgaca tagtataatg ctgggttacc cgtcgggtag gtatcgaggc ggatactact  10620
aaatccatcc cactcgctat ccgataatca ctggtttcgg gtatacccat tcccgtcaac  10680
aggccttttt aaccggataa tttcaactta tagtgaatga attttgaata aatagttaga  10740
ataccaaaat cctggattgc atttgcaatc aaattttgtg aaccgttaaa ttttgcatgt  10800
acttgggata gatataatag aaccgaattt tcattagttt aatttataac ttactttgtt  10860
caaagaaaaa aaatatctat ccaatttact tataataaaa aataatctat ccaagttact  10920
tattataatc aacttgtaaa aaggtaagaa tacaaatgtg gtagcgtacg tgtgattata  10980
```

```
tgtgacgaaa tgttatatct aacaaaagtc caaattccca tggtaaaaaa aatcaaaatg  11040
catggcaggc tgtttgtaac cttggaataa gatgttggcc aattctggag ccgccacgta  11100
cgcaagactc agggccacgt tctcttcatg caaggatagt agaacaccac tccacccacc  11160
tcctatatta gacctttgcc caaccctccc caactttccc atcccatcca caaagaaacc  11220
gacattttta tcataaatct ggtgcttaaa cactctggtg agttctagta cttctgctat  11280
gatcgatctc attaccattt cttaaatttc tctccctaaa tattccgagt tcttgatttt  11340
tgataacttc aggttttctc tttttgataa atctggtctt tccatttttt ttttttgtgg  11400
ttaatttagt ttcctatgtt cttcgattgt attatgcatg atctgtgttt ggattctgtt  11460
agattatgta ttggtgaata tgtatgtgtt tttgcatgtc tggttttggt cttaaaaatg  11520
ttcaaatctg atgatttgat tgaagctttt ttagtgttgg tttgattctt ctcaaaacta  11580
ctgttaattt actatcatgt tttccaactt tgattcatga tgacactttt gttctgcttt  11640
gttataaaat tttggttggt ttgattttgt aattatagtg taattttgtt aggaatgaac  11700
atgttttaat actctgtttt cgatttgtca cacattcgaa ttattaatcg ataatttaac  11760
tgaaaattca tggttctaga tcttgttgtc atcagattat ttgtttcgat aattcatcaa  11820
atatgtagtc cttttgctga tttgcgactg tttcattttt tctcaaaatt gtttttttgtt  11880
aagtttatct aacagttatc gttgtcaaaa gtctctttca ttttgcaaaa tcttcttttt  11940
tttttgttt gtaactttgt tttttaagct acacatttag tctgtaaaat agcatcgagg  12000
aacagttgtc ttagtagact tgcatgttct tgtaacttct atttgtttca gtttgttgat  12060
gactgctttg attttgtagg tcaaaggcgc accctaccat ggatgcttat aacgctgcta  12120
tggataagat tggagctgct atcatcgatt ggagtgatcc agatggaaag ttcagagctg  12180
atagggagga ttggtggttg tgcgatttca gatccgctat caccattgct ctcatctaca  12240
tcgctttcgt gatcttggga tctgctgtga tgcaatctct cccagctatg gacccatacc  12300
ctatcaagtt cctctacaac gtgtctcaaa tcttcctctg cgcttacatg actgttgagg  12360
ctggattcct cgcttatagg aacggataca ccgttatgcc atgcaaccac ttcaacgtga  12420
acgatccacc agttgctaac ttgctctggc tcttctacat ctccaaagtg tgggatttct  12480
gggataccat cttcattgtg ctcggaaaga agtggagaca actctctttc ttgcacgtgt  12540
accaccacac caccatcttc ctcttctact ggttgaacgc taacgtgctc tacgatggag  12600
atatcttctt gaccatcctc ctcaacggat tcattcacac cgtgatgtac acctactact  12660
tcatctgcat gcacaccaag gattctaaga ccggaaagtc tttgccaatc tggtggaagt  12720
catctttgac cgctttccaa ctcttgcaat tcaccatcat gatgtcccaa gctacctact  12780
tggttttcca cggatgcgat aaggtttccc tcagaatcac catcgtgtac ttcgtgtaca  12840
ttctctccct tttcttcctc ttcgctcagt tcttcgtgca atcctacatg gctccaaaga  12900
agaagaagtc cgcttgatgt taatgaaggc cgcagatatc agatctggtc gacctagagg  12960
atccccggcc gcaaagataa taacaaaagc ctactatata acgtacatgc aagtattgta  13020
tgatattaat gtttttacgt acgtgtaaac aaaaataatt acgtttgtaa cgtatggtga  13080
tgatgtggtg cactaggtgt aggccttgta ttaataaaaa gaagtttgtt ctatatagag  13140
tggtttagta cgacgattta tttactagtc ggattggaat agagaaccga attcttcaat  13200
ccttgctttt gatcaagaat tgaaaccgaa tcaaatgtaa aagttgatat atttgaaaaa  13260
cgtattgagc ttatgaaaat gctaatactc tcatctgtat ggaaaagtga ctttaaaacc  13320
```

-continued

```
gaacttaaaa gtgacaaaag gggaatatcg catcaaaccg aatgaaaccg atctacgtag  13380
gctcagctga gcttagctaa gcctacctag cctcacgtga gattatgtaa ggctaggtag  13440
cgtcacgtga cgttacctaa cactagctag cgtcagctga gcttagctaa ccctacgtag  13500
cctcacgtga gcttacctaa cgctacgtag cctcacgtga ctaaggatga cctacccatt  13560
cttgagacaa atgttacatt ttagtatcag agtaaaatgt gtacctataa ctcaaattcg  13620
attgacatgt atccattcaa cataaaatta aaccagcctg cacctgcatc cacatttcaa  13680
gtattttcaa accgttcggc tcctatccac cgggtgtaac aagacggatt ccgaatttgg  13740
aagattttga ctcaaattcc caatttatat tgaccgtgac taaatcaact ttaacttcta  13800
taattctgat taagctccca atttatattc ccaacggcac tacctccaaa atttatagac  13860
tctcatcccc ttttaaacca acttagtaaa cgtttttttt ttaattttat gaagttaagt  13920
ttttaccttg tttttaaaaa gaatcgttca taagatgcca tgccagaaca ttagctacac  13980
gttacacata gcatgcagcc gcggagaatt gtttttcttc gccacttgtc actcccttca  14040
aacacctaag agcttctctc tcacagcaca cacatacaat cacatgcgtg catgcattat  14100
tacacgtgat cgccatgcaa atctccttta tagcctataa attaactcat cggcttcact  14160
ctttactcaa accaaaactc atcaatacaa acaagattaa aaacatttca cgatttggaa  14220
tttgattcct gcgatcacag gtatgacagg ttagattttg ttttgtatag ttgtatacat  14280
acttctttgt gatgttttgt ttacttaatc gaatttttgg agtgttttaa ggtctctcgt  14340
ttagaaatcg tggaaaatat cactgtgtgt gtgttcttat gattcacagt gtttatgggt  14400
ttcatgttct ttgttttatc attgaatggg aagaaatttc gttgggatac aaatttctca  14460
tgttcttact gatcgttatt aggagtttgg ggaaaaagga agagtttttt tggttggttc  14520
gagtgattat gaggttattt ctgtatttga tttatgagtt aatggtcgtt ttaatgttgt  14580
agaccgccat ggctattttg aaccctgagg ctgattctgc tgctaacctc gctactgatt  14640
ctgaggctaa gcaaagacaa ttggctgagg ctggatacac tcacgttgag ggtgctcctg  14700
ctcctttgcc tttggagttg cctcacttct ctctcagaga tctcagagct gctattccta  14760
agcactgctt cgagagatct ttcgtgacct ccacctacta catgatcaag aacgtgttga  14820
cttgcgctgc tttgttctac gctgctacct tcattgatag agctggagct gctgcttatg  14880
ttttgtggcc tgtgtactgg ttcttccagg gatcttactt gactggagtg tgggttatcg  14940
ctcacgagtg tggacaccag gcttattgct cttctgaggt ggtgaacaac ttgattggac  15000
tcgtgttgca ctctgctttg ttggtgcctt accactcttg gagaatctct cacagaaagc  15060
accactccaa cactggatct tgcgagaacg atgaggtttt cgttcctgtg accagatctg  15120
tgttggcttc ttcttggaac gagaccttgg aggattctcc tctctaccaa ctctaccgta  15180
tcgtgtacat gttggttgtt ggatggatgc ctggatacct cttcttcaac gctactggac  15240
ctactaagta ctggggaaag tctaggtctc acttcaaccc ttactccgct atctatgctg  15300
atagggagag gtggatgatc gtgctctccg atattttctt ggtggctatg ttggctgttt  15360
tggctgcttt ggtgcacact ttctccttca acacgatggt gaagttctac gtggtgcctt  15420
acttcattgt gaacgcttac ttggtgttga ttacctacct ccaacacacc gatacctaca  15480
tccctcactt cagagaggga gagtggaatt ggttgagagg agctttgtgc actgtggata  15540
gatcatttgg tccattcctc gattctgtgg tgcatagaat cgtggatacc cacgtttgcc  15600
accatatctt ctccaagatg cctttctatc actgcgagga ggctaccaac gctattaagc  15660
ctctcctcgg aaagttctac ttgaaggata ctactcctgt tcctgttgct ctctggagat  15720
```

```
cttacaccca ctgcaagttc gttgaggatg atggaaaggt ggtgttctac aagaacaagt  15780
tatagttaat gaataattga ttggttcgag tattatggca ttgggaaaac tgtttttctt  15840
gtaccatttg ttgtgcttgt aatttactgt gtttttttatt cggttttcgc tatcgaactg  15900
tgaaatggaa atggatggag aagagttaat gaatgatatg gtccttttgt tcattctcaa  15960
attaatatta tttgtttttt ctcttatttg ttgtgtgttg aatttgaaat tataagagat  16020
atgcaaacat tttgttttga gtaaaaatgt gtcaaatcgt ggcctctaat gaccgaagtt  16080
aatatgagga gtaaaacact tgtagttgta ccattatgct tattcactag gcaacaaata  16140
tattttcaga cctagaaaag ctgcaaatgt tactgaatac aagtatgtcc tcttgtgttt  16200
tagacattta tgaactttcc tttatgtaat tttccagaat ccttgtcaga ttctaatcat  16260
tgctttataa ttatagttat actcatggat ttgtagttga gtatgaaaat atttttttaat  16320
gcattttatg acttgccaat tgattgacaa catgcatcaa tctagctagc ctcagctgac  16380
gttacgtaac gctaggtagc gtcacgtgac gttagctaac gctaggtagc gtcagctgag  16440
cttacgtaag cgcacagatg aatactagct gttgttcaca gttctagtgt ctcctcatta  16500
cgtgaattca agctacgatc actatctcaa ctcctacata aacatcagaa tgctacaaaa  16560
ctatgcacaa aaacaaaagc tacatctaat acgtgaatca attactctca tcacaagaaa  16620
gaagatttca atcaccgtcg agaaggagga ttcagttaat tgaatcaaag ttccgatcaa  16680
actcgaagac tggtgagcac gaggacgacg aagaagagtg tctcgaagat acaacaagca  16740
agaaatctac tgagtgacct cctgaagtta ttggcgcgat tgagagaatc aatccgaatt  16800
aatttcgggg aaaaagataa attagatact aagcgatggg cttgggctgg gctaagaaac  16860
aggtggcaat tgggctggag gaccccgcga ttcatagctt ccgatagccc aaaaaaaaac  16920
ggataacata tttatcgggt atttgaattt cagtgaaata agatattttc tttttgttag  16980
gaaaatttta gaaaataatg gaaattaaat agcgattatg ttacaagata cgatcagcat  17040
cgggcagtgc aaaatgctat agcttcccaa gatttgatcc ttttgggtta tctcctaatg  17100
acaattagtt taggattttg aaacttatat taatactatt atccgacaac acttgtttca  17160
gcttcttatt ttaacatttt ttgttttttt ctattcttct tcccatcagc attttctttt  17220
taaaaaattg aatactttaa ctttttaaaa atttcacaat gatcagatga tattatggaa  17280
gatctcaaga gttaaatgta tccatcttgg ggcattaaaa ccggtgtacg ggatgataaa  17340
tacagacttt atatcatatg atagctcagt aattcatatt tatcacgttg ctaaaaaaat  17400
tataaggtac tagtagtcaa caaaatcaat taaagagaaa gaaagaaacg catgtgaaga  17460
gagtttacaa ctggaaaagt aaaataaaaa ttaacgcatg ttgaatgctg acatgtcagt  17520
atgtccatga atccacgtat caagcgccat tcatcgatcg tcttcctctt tctaaatgaa  17580
aacaacttca cacatcacaa caaacaatac acacaagacc ccctctctct cgttgtctct  17640
ctgccagcga ccaaatcgaa gcttgagaag aacaagaagg ggtcaaacca tggcttctac  17700
atctgctgct caagacgctg ctccttacga gttcccttct ctcactgaga tcaagagggc  17760
tcttccttct gagtgtttcg aggcttctgt tcctctttct ctctactaca ccgctagatc  17820
tcttgctctt gctggatctc tcgctgttgc tctctcttac gctagagctt tgcctcttgt  17880
tcaggctaac gctcttcttg atgctactct ctgcactgga tacgttcttc tccagggaat  17940
cgttttctgg ggattcttca ccgttggtca cgattgtgga cacggagctt tctctagatc  18000
tcacgtgctc aacttctctg ttggaaccct catgcactct atcatcctta cccctttcga  18060
```

```
gtcttggaag ctctctcaca gacaccacca caagaacacc ggaaacatcg ataaggacga 18120
gatcttctac cctcaaagag aggctgattc tcaccctgtt tctagacacc ttgtgatgtc 18180
tcttggatct gcttggttcg cttacctttt cgctggattc cctcctagaa ccatgaacca 18240
cttcaaccct tgggaggcta tgtatgttag aagagtggct gctgtgatca tctctctcgg 18300
agttcttttc gctttcgctg gactctactc ttacctcacc ttcgttcttg gattcaccac 18360
tatggctatc tactacttcg gacctctctt catcttcgct accatgcttg ttgttaccac 18420
tttcctccac cacaacgatg aggagacacc ttggtacgct gattctgagt ggacttacgt 18480
gaagggaaac ctctcttctg tggacagatc ttacggtgct ctcatcgaca accttagcca 18540
caacatcgga actcaccaga tccaccacct cttccctatc atccctcact acaagctcaa 18600
cgatgctact gctgctttcg ctaaggcttt ccctgagctt gttaggaaaa acgctgctcc 18660
tatcatccca actttcttca ggatggctgc tatgtacgct aagtacggag ttgttgacac 18720
tgatgctaag accttcactc tcaaggaggc taaggctgct gctaagacta agtcatcttg 18780
atgattaatg aataattgat tgtacatact atatttttg tttaccttgt gttagtttaa 18840
tgttcagtgt cctctcttta ttgtggcacg tctctttgtt gtatgttgtg tctatacaaa 18900
gttgaaataa tggaaagaaa aggaagagtg taatttgttt tgttttaagt gtttataaat 18960
atatatatat aggtcattta gatagttcta ggtttctata aaactctctc tctggaagta 19020
gaatctgttt ttgagaggat ccagttgcct actaatctcc cccaaaaccc ttcaagctta 19080
accttcctct tcacaacaac agaggaaaca catctcttga gctctgagtt ctcttctttg 19140
agcatgtcta tcgctaaact catctgcctt atagcttccc tcttctcttc atctctctct 19200
ctcaccattt cgctgtaaaa cttattctcc tccctcagcc tctctatctc ttccttcagc 19260
atctcacaat tcccaccata atcgactgag gatgattcac cgtcatcaac ttcagactca 19320
gcgttgtagt cgtcatgagt ctcacaagcc ttggaccaag aagactcatc atcgcaagtt 19380
gatgatttat catgatgctt ctctgagccg tgtttgctac gtagcgtcac gtgacgttac 19440
ctaagcctag gtagcctcag ctgacgttac gtaacgctag gtaggctcag ctgactgcag 19500
caaatttaca cattgccact aaacgtctaa acccttgtaa tttgtttttg ttttactatg 19560
tgtgttatgt atttgatttg cgataaattt ttatatttgg tactaaattt ataacacctt 19620
ttatgctaac gtttgccaac acttagcaat ttgcaagttg attaattgat tctaaattat 19680
ttttgtcttc taaatacata tactaatcaa ctggaaatgt aaatatttgc taatatttct 19740
actataggag aattaaagtg agtgaatatg gtaccacaag gtttggagat ttaattgttg 19800
caatgctgca tggatggcat atacaccaaa cattcaataa ttcttgagga taataatggt 19860
accacacaag atttgaggtg catgaacgtc acgtggacaa aaggtttagt aatttttcaa 19920
gacaacaatg ttaccacaca caagttttga ggtgcatgca tggatgccct gtggaaagtt 19980
taaaaatatt ttggaaatga tttgcatgga agccatgtgt aaaaccatga catccacttg 20040
gaggatgcaa taatgaagaa aactacaaat ttacatgcaa ctagttatgc atgtagtcta 20100
tataatgagg attttgcaat actttcattc atacacactc actaagtttt acacgattat 20160
aatttcttca tagccagtac tgtttaagct tcactgtctc tgaatcggca aaggtaaacg 20220
tatcaattat tctacaaacc cttttatttt tcttttgaat taccgtcttc attggttata 20280
tgataacttg ataagtaaag cttcaataat tgaatttgat ctgtgttttt ttggccttaa 20340
tactaaatcc ttacataagc tttgttgctt ctcctcttgt gagttgagtg ttaagttgta 20400
ataatggttc actttcagct ttagaagaaa cgcgccttcc atggctacaa aggaggctta 20460
```

```
cgttttccca actctcaccg agatcaagag atctctccca aaggattgct tcgaggcttc  20520
tgtgcctttg tctctctact acactgtgag atgcttggtt attgctgtgg ctttgacctt  20580
cggattgaac tacgctagag ctttgccaga ggttgagtct ttctgggctt tggatgctgc  20640
tttgtgcact ggatatatcc tcctccaggg aattgtgttc tggggattct tcactgttgg  20700
acacgatgct ggacacggag ctttctctag ataccacctc ttgaacttcg ttgtgggaac  20760
cttcatgcac tctctcatct tgaccccatt cgagtcttgg aagttgaccc acagacacca  20820
ccacaagaac accggaaaca tcgatagaga tgaggtgttc tacccacaga gaaaggctga  20880
tgatcaccca ttgtccagga acttgatctt ggctttggga gctgcttggc ttgcttattt  20940
ggtggaggga ttcccaccaa gaaaggtgaa ccacttcaac ccattcgagc cactttttgt  21000
gagacaagtg tccgctgtgg ttatctcttt gctcgctcac ttcttcgttg ctggactctc  21060
tatctacttg tctctccagt tgggacttaa gaccatggct atctactact acggaccagt  21120
tttcgtgttc ggatctatgt tggtgattac caccttcttg caccacaacg atgaggagac  21180
tccatggtat gctgattctg agtggactta cgtgaaggga aacttgtcct ctgtggatag  21240
atcttacggt gctctcatcg ataacctctc ccacaacatc ggaactcacc agatccacca  21300
cctcttccca attatcccac actacaagct caagaaggct actgctgctt tccaccaagc  21360
tttcccagag cttgtgagaa agtccgatga gccaatcatc aaggctttct tcagagtggg  21420
aaggttgtat gctaactacg gagtggttga tcaagaggct aagctcttca ctttgaagga  21480
ggctaaggct gctactgaag ctgctgctaa gaccaagtct acctgattaa tgaatcgaca  21540
agctcgagtt tctccataat aatgtgtgag tagttcccag ataagggaat tagggttcct  21600
atagggtttc gctcatgtgt tgagcatata agaaaccctt agtatgtatt tgtatttgta  21660
aaatacttct atcaataaaa tttctaattc ctaaaaccaa aatccagtac taaaatccag  21720
atcccccgaa ttaattcggc gttaattcag ctacgtaggc tcagctgagc ttacctaagg  21780
ctacgtaggc tcacgtgacg ttacgtaagg ctacgtagcg tcacgtgagc ttacctaact  21840
ctagctagcc tcacgtgacc ttagctaaca ctaggtagcg tcagcacaga tgaatactag  21900
ctgttgttca cagttctagt gtctcctcat tacgtgaatt caagctacga tcactatctc  21960
aactcctaca taaacatcag aatgctacaa aactatgcac aaaaacaaaa gctacatcta  22020
atacgtgaat caattactct catcacaaga aagaagattt caatcaccgt cgagaaggag  22080
gattcagtta attgaatcaa agttccgatc aaactcgaag actggtgagc acgaggacga  22140
cgaagaagag tgtctcgaag atacaacaag caagaaatct actgagtgac ctcctgaagt  22200
tattggcgcg attgagagaa tcaatccgaa ttaatttcgg ggaaaaagat aaattagata  22260
ctaagcgatg ggcttgggct gggctaagaa acaggtggca attgggctgg aggaccccgc  22320
gattcatagc ttccgatagc ccaaaaaaaa acggataaca tatttatcgg gtatttgaat  22380
ttcagtgaaa taagatattt tctttttgtt aggaaaattt tagaaaataa tggaaattaa  22440
atagcgatta tgttacaaga tacgatcagc atcgggcagt gcaaaatgct atagcttccc  22500
aagatttgat ccttttgggt tatctcctaa tgacaattag tttaggattt tgaaacttat  22560
attaatacta ttatccgaca acacttgttt cagcttctta ttttaacatt ttttgttttt  22620
ttctattctt cttcccatca gcattttctt tttaaaaaat tgaatacttt aactttttaa  22680
aaatttcaca atgatcagat gatattatgg aagatctcaa gagttaaatg tatccatctt  22740
ggggcattaa aaccggtgta cgggatgata aatacagact ttatatcata tgatagctca  22800
```

```
gtaattcata tttatcacgt tgctaaaaaa attataaggt actagtagtc aacaaaatca  22860
attaaagaga aagaaagaaa cgcatgtgaa gagagtttac aactggaaaa gtaaaataaa  22920
aattaacgca tgttgaatgc tgacatgtca gtatgtccat gaatccacgt atcaagcgcc  22980
attcatcgat cgtcttcctc tttctaaatg aaaacaactt cacacatcac aacaaacaat  23040
acacacaaga ccccctctct ctcgttgtct ctctgccagc gaccaaatcg aagcttgaga  23100
agaacaagaa ggggtcaaac catgggaaaa ggatctgagg gaagatctgc tgctagagag  23160
atgactgctg aggctaacgg agataagaga aagaccatcc tcattgaggg agtgttgtac  23220
gatgctacca acttcaaaca cccaggaggt tccattatta acttcctcac cgagggagaa  23280
gctggagttg atgctaccca agcttacaga gagttccatc agagatccgg aaaggctgat  23340
aagtacctca agtccctccc aaagttggat gcttctaagg tggagtctag gttctctgct  23400
aaggagcagg ctagaaggga cgctatgacc agggattacg ctgctttcag agaggagttg  23460
gttgctgagg gatacttcga tccatctatc ccacacatga tctacagagt ggtggagatt  23520
gtggctttgt tcgctttgtc tttctggttg atgtctaagg cttctccaac ctctttggtt  23580
ttgggagtgg tgatgaacgg aatcgctcaa ggaagatgcg gatgggttat gcacgagatg  23640
ggacacggat ctttcactgg agttatctgg ctcgatgata ggatgtgcga gttcttctac  23700
ggagttggat gtggaatgtc tggacactac tggaagaacc agcactctaa gcaccacgct  23760
gctccaaaca gattggagca cgatgtggat ttgaacacct tgccactcgt tgctttcaac  23820
gagagagttg tgaggaaggt taagccagga tctttgttgg ctttgtggct cagagttcag  23880
gcttatttgt tcgctccagt gtcttgcttg ttgatcggat tgggatggac cttgtacttg  23940
cacccaagat atatgctcag gaccaagaga cacatggagt ttgtgtggat cttcgctaga  24000
tatatcggat ggttctcctt gatgggagct ttgggatatt ctcctggaac ttctgtggga  24060
atgtacctct gctctttcgg acttggatgc atctacatct tcctccaatt cgctgtgtct  24120
cacacccact tgccagttac caacccagag gatcaattgc actggcttga gtacgctgct  24180
gatcacaccg tgaacatctc taccaagtct tggttggtta cctggtggat gtctaacctc  24240
aacttccaaa tcgagcacca cttgttccca accgctccac aattcaggtt caaggagatc  24300
tctccaagag ttgaggctct cttcaagaga cacaacctcc cttactacga tttgccatac  24360
acctctgctg tttctactac cttcgctaac ctctactctg ttggacactc tgttggagct  24420
gataccaaga agcaggattg atgattaatg aataattgat tgtacatact atattttttg  24480
tttaccttgt gttagtttaa tgttcagtgt cctctcttta ttgtggcacg tctctttgtt  24540
gtatgttgtg tctatacaaa gttgaaataa tggaaagaaa aggaagagtg taatttgttt  24600
tgttttaagt gtttataaat atatatatat aggtcattta gatagttcta ggtttctata  24660
aaactctctc tctggaagta gaatctgttt ttgagaggat ccagttgcct actaatctcc  24720
cccaaaaccc ttcaagctta accttcctct tcacaacaac agaggaaaca catctcttga  24780
gctctgagtt ctcttctttg agcatgtcta tcgctaaact catctgcctt atagcttccc  24840
tcttctcttc atctctctct ctcaccattt cgctgtaaaa cttattctcc tccctcagcc  24900
tctctatctc ttccttcagc atctcacaat tcccaccata atcgactgag gatgattcac  24960
cgtcatcaac ttcagactca gcgttgtagt cgtcatgagt ctcacaagcc ttggaccaag  25020
aagactcatc atcgcaagtt gatgatttat catgatgctt ctctgagccg tgtttgctac  25080
ctagagtcag ctgagcttag ctaacgctag ctagtgtcag ctgacgttac gtaaggctaa  25140
ctagcgtcac gtgaccttac gtaacgctac gtaggctcag ctgagcttag ctaaccctag  25200
```

```
ctagtgtcac gtgagcttac gctactatag aaaatgtgtt atatcgacat gaccagacaa  25260
aggggcaaca gttaacaaaa caattaattc tttcatttga gattaaggaa ggtaaggtac  25320
taaaaagatt aaaaaaaatg agcttatctc tttgtttctg taataataat ataagtgtga  25380
taaactttta atataataat tgtaattagg ttttctacag atgagcacca ctcagagaca  25440
agataagaag aaaacaattt tgttaaacat gattatagaa acttttagtt aagtcttgaa  25500
gtatcaatat aacaaaaaaa agtacacacg actatgacaa taaacccact accgtcaggt  25560
tatcatttcg atgaaatgtt ttgatatcat taaatataac agtcacaaaa aatcatctaa  25620
ttataacaat ataacttata catatattta actaaaaact tagagttttt gtaatgattc  25680
taattgatga ttagagttta tagaaataca attaaataaa aaatataatt ttaaaaaaac  25740
atagtaaagt caatgagatc ctctctgacc tcagtgatca tttagtcatg tatgtacaac  25800
aatcattgtt catcacatga ctgtaaaata aataaggata aacttgggaa tatatataat  25860
atattgtatt aaataaaaaa gggaaataca aatatcaatt ttagattccc gagttgacac  25920
aactcaccat gcacgctgcc acctcagctc ccagctctcg tcacatgtct catgtcagtt  25980
aggtctttgg tttttagtct ttgacacaac tcgccatgca tgttgccacg tgagctcgtt  26040
cctcttccca tgatctcacc actgggcatg catgctgcca cctcagctgg cacctcttct  26100
ctatatgtcc ctagaggcca tgcacagtgc cacctcagca ctcctctcag aacccatacg  26160
tacctgccaa tcggcttctc tccataaata tctatttaaa ttataactaa ttatttcata  26220
tacttaattg atgacgtgga tgcattgcca tcgttgttta ataattgtta attacgacat  26280
gataaataaa atgaaagtaa aaagtacgaa agattttcca tttgttgttg tataaataga  26340
gaagtgagtg atgcataatg catgaatgca tgaccgcgcc accatgactg ttggatacga  26400
cgaggagatc ccattcgagc aagttagggc tcataacaag ccagacgacg cttggtgtgc  26460
tattcacgga cacgtgtacg acgttaccaa gttcgcttca gttcacccag gaggagatat  26520
tatcttgctc gctgctggaa aggaagctac tgtcctctac gagacctacc atgttagagg  26580
agtgtctgac gctgtgctca gaaagtacag aataggaaag ttgccagacg gacaaggagg  26640
agctaacgag aaggagaaga gaaccttgtc tggattgtcc tctgcttctt actacacctg  26700
gaactccgat ttctacagag tgatgaggga gagagttgtg gctagattga aggagagagg  26760
aaaggctaga agaggaggat acgaactctg gatcaaggct ttcttgctcc ttgttggatt  26820
ctggtcctct ctttactgga tgtgcaccct cgatccatct ttcggagcta tcttggctgc  26880
tatgtctttg ggagtgttcg ctgcttttgt tggaacctgc atccaacacg atggaaacca  26940
cggagctttc gctcaatcta gatgggttaa caaggtggca ggatggactt tggatatgat  27000
cggagcttct ggaatgactt gggagttcca acacgtgttg ggacaccacc catacactaa  27060
cttgatcgag gaggagaacg gattgcaaaa ggtgtccgga aagaagatgg ataccaagtt  27120
ggctgatcaa gagtctgatc cagatgtgtt ctccacctac ccaatgatga gattgcaccc  27180
ttggcaccag aagaggtggt atcacaggtt ccagcacatc tacggacctt tcatcttcgg  27240
attcatgacc atcaacaagg tggtgactca agatgttgga gtggtgttga gaaagagact  27300
cttccaaatc gatgctgagt gcagatatgc ttccccaatg tacgttgcta ggttctggat  27360
tatgaaggct ttgaccgtgt tgtatatggt tgctttgcct tgttatatgc aaggaccttg  27420
gcacggattg aaactcttcg ctatcgctca cttcacttgc ggagaggttt tggctaccat  27480
gttcatcgtg aaccacatta tcgagggagt gtcttacgct tctaaggatg ctgttaaggg  27540
```

-continued

```
aactatggct ccaccaaaga ctatgcacgg agtgacccca atgaacaaca ctagaaagga  27600
ggttgaggct gaggcttcta agtctggagc tgtggttaag tctgtgccat tggatgattg  27660
ggctgctgtt cagtgccaaa cctctgtgaa ctggtctgtt ggatcttggt tttggaacca  27720
cttctctgga ggactcaacc accaaatcga gcaccacctc ttcccaggat tgtctcacga  27780
gacctactac cacatccaag acgtggttca atctacctgt gctgagtacg gagttccata  27840
ccaacacgag ccatctttgt ggactgctta ctggaagatg ctcgaacacc ttagacaatt  27900
gggaaacgag gagactcacg agtcatggca gagagctgct tgattaatga actaagactc  27960
ccaaaaccac cttccctgtg acagttaaac cctgcttata cctttcctcc taataatgtt  28020
catctgtcac acaaactaaa ataaataaaa tgggagcaat aaataaaatg ggagctcata  28080
tatttacacc atttacactg tctattattc accatgccaa ttattacttc ataattttaa  28140
aattatgtca tttttaaaaa ttgcttaatg atggaaagga ttattataag ttaaaagtat  28200
aacatagata aactaaccac aaaacaaatc aatataaact aacttactct cccatctaat  28260
ttttatttaa atttctttac acttctcttc catttctatt tctacaacat tatttaacat  28320
ttttattgta tttttcttac tttctaactc tattcatttc aaaaatcaat atatgtttat  28380
caccacctct ctaaaaaaaa ctttacaatc attggtccag aaaagttaaa tcacgagatg  28440
gtcattttag cattaaaaca acgattcttg tatcactatt tttcagcatg tagtccattc  28500
tcttcaaaca aagacagcgg ctatataatc gttgtgttat attcagtcta aaacaactag  28560
ctagcctcag ctgacgttac gtaacgctag gtagcgtcac gtgacgttag ctaacgctag  28620
gtagcgtcag ctgagcttac gtaagcgcca cgggcaggac atagggacta ctacaagcat  28680
agtatgcttc agacaaagag ctaggaaaga actcttgatg gaggttaaga gaaaaaagtg  28740
ctagaggggc atagtaatca aacttgtcaa aaccgtcatc atgatgaggg atgacataat  28800
ataaaaagtt gactaaggtc ttggtagtac tctttgatta gtattatata ttggtgagaa  28860
catgagtcaa gaggagacaa gaaaccgagg aaccatagtt tagcaacaag atggaagttg  28920
caaagttgag ctagccgctc gattagttac atctcctaag cagtactaca aggaatggtc  28980
tctatacttt catgtttagc acatggtagt gcggattgac aagttagaaa cagtgcttag  29040
gagacaaaga gtcagtaaag gtattgaaag agtgaagttg atgctcgaca ggtcaggaga  29100
agtccctccg ccagatggtg actaccaagg ggttggtatc agctgagacc caaataagat  29160
tcttcggttg aaccagtggt tcgaccgaga ctcttagggt gggatttcac tgtaagattt  29220
gtgcattttg ttgaatataa attgacaatt ttttttattt aattatagat tatttagaat  29280
gaattacata tttagtttct aacaaggata gcaatggatg ggtatgggta caggttaaac  29340
atatctatta cccacccatc tagtcgtcgg gttttacacg tacccacccg tttacataaa  29400
ccagaccgga attttaaacc gtacccgtcc gttagcgggt ttcagattta cccgtttaat  29460
cgggtaaaac ctgattacta aatatatatt ttttatttga taaacaaaac aaaaatgtta  29520
atattttcat attggatgca attttaagaa acacatattc ataaatttcc atatttgtag  29580
gaaaataaaa agaaaaatat attcaagaac acaaatttca ccgacatgac ttttattaca  29640
gagttggaat tagatctaac aattgaaaaa ttaaaattaa gatagaatat gttgaggaac  29700
atgacatagt ataatgctgg gttacccgtc gggtaggtat cgaggcggat actactaaat  29760
ccatcccact cgctatccga taatcactgg tttcgggtat acccattccc gtcaacaggc  29820
ctttttaacc ggataatttc aacttatagt gaatgaattt tgaataaata gttagaatac  29880
caaaatcctg gattgcattt gcaatcaaat tttgtgaacc gttaaatttt gcatgtactt  29940
```

```
gggatagata taatagaacc gaattttcat tagtttaatt tataacttac tttgttcaaa  30000
gaaaaaaaat atctatccaa tttacttata ataaaaaata atctatccaa gttacttatt  30060
ataatcaact tgtaaaaagg taagaataca aatgtggtag cgtacgtgtg attatatgtg  30120
acgaaatgtt atatctaaca aaagtccaaa ttcccatggt aaaaaaaatc aaaatgcatg  30180
gcaggctgtt tgtaaccttg gaataagatg ttggccaatt ctggagccgc cacgtacgca  30240
agactcaggg ccacgttctc ttcatgcaag gatagtagaa caccactcca cccacctcct  30300
atattagacc tttgcccaac cctccccaac tttcccatcc catccacaaa gaaaccgaca  30360
tttttatcat aaatcagggt ttcgtttttg tttcatcgat aaactcaaag gtgatgattt  30420
tagggtcttg tgagtgtgct tttttgtttg attctactgt agggtttatg ttctttagct  30480
cataggtttt gtgtatttct tagaaatgtg gcttctttaa tctctgggtt tgtgactttt  30540
tgtgtggttt ctgtgttttt catatcaaaa acctattttt tccgagtttt tttttacaaa  30600
ttcttactct caagcttgaa tacttcacat gcagtgttct tttgtagatt ttagagttaa  30660
tgtgttaaaa agtttggatt tttcttgctt atagagcttc ttcactttga ttttgtgggt  30720
ttttttgttt taaaggtgag atttttgatg aggtttttgc ttcaaagatg tcacctttct  30780
gggtttgtct tttgaataaa gctatgaact gtcacatggc tgacgcaatt ttgttactat  30840
gtcatgaaag ctgacgtttt tccgtgttat acatgtttgc ttacacttgc atgcgtcaaa  30900
aaaattgggg ctttttagtt ttagtcaaag attttacttc tcttttggga tttatgaagg  30960
aaagttgcaa actttctcaa attttaccat ttttgctttg atgtttgttt agattgcgac  31020
agaacaaact catatatgtt gaaatttttg cttggttttg tataggattg tgtcttttgc  31080
ttataaatgt tgaaatctga actttttttt tgtttggttt ctttgagcag gagataaggc  31140
gcaccaccat ggcttctaca tctgctgctc aagacgctgc tccttacgag ttcccttctc  31200
tcactgagat caagagggct cttccttctg agtgtttcga ggcttctgtt cctctttctc  31260
tctactacac cgctagatct cttgctcttg ctggatctct cgctgttgct ctctcttacg  31320
ctagagcttt gcctcttgtt caggctaacg ctcttcttga tgctactctc tgcactggat  31380
acgttcttct ccagggaatc gttttctggg gattcttcac cgttggtcac gattgtggac  31440
acggagcttt ctctagatct cacgtgctca acttctctgt tggaaccctc atgcactcta  31500
tcatccttac ccctttcgag tcttggaagc tctctcacag acaccaccac aagaacaccg  31560
gaaacatcga taaggacgag atcttctacc ctcaaagaga ggctgattct caccctgttt  31620
ctagacacct tgtgatgtct cttggatctg cttggttcgc ttacctttc gctggattcc  31680
ctcctagaac catgaaccac ttcaaccctt gggaggctat gtatgttaga agagtggctg  31740
ctgtgatcat ctctctcgga gttcttttcg ctttcgctgg actctactct tacctcacct  31800
tcgttcttgg attcaccact atggctatct actacttcgg acctctcttc atcttcgcta  31860
ccatgcttgt tgttaccact ttcctccacc acaacgatga ggagacacct tggtacgctg  31920
attctgagtg gacttacgtg aagggaaacc tctcttctgt ggacagatct tacggtgctc  31980
tcatcgacaa ccttagccac aacatcggaa ctcaccagat ccaccacctc ttccctatca  32040
tccctcacta caagctcaac gatgctactg ctgctttcgc taaggctttc cctgagcttg  32100
ttaggaaaaa cgctgctcct atcatcccaa ctttcttcag gatggctgct atgtacgcta  32160
agtacggagt tgttgacact gatgctaaga ccttcactct caaggaggct aaggctgctg  32220
ctaagactaa gtcatcttga tgattaatga aggccgcaga tatcagatct ggtcgaccta  32280
```

-continued

```
gaggatcccc ggccgcaaag ataataacaa aagcctacta tataacgtac atgcaagtat  32340
tgtatgatat taatgttttt acgtacgtgt aaacaaaaat aattacgttt gtaacgtatg  32400
gtgatgatgt ggtgcactag gtgtaggcct tgtattaata aaaagaagtt tgttctatat  32460
agagtggttt agtacgacga tttatttact agtcggattg gaatagagaa ccgaattctt  32520
caatccttgc ttttgatcaa gaattgaaac cgaatcaaat gtaaaagttg atatatttga  32580
aaaacgtatt gagcttatga aaatgctaat actctcatct gtatggaaaa gtgactttaa  32640
aaccgaactt aaaagtgaca aaaggggaat atcgcatcaa accgaatgaa accgatctac  32700
gtaggctcag ctgagcttac ctaaggctac gtaggctcac gtgacgttac gtaaggctac  32760
gtagcgtcac gtgagcttac ctaactctag ctagcctcac gtgaccttag ctaacactag  32820
gtagcgtcag cttagcagat atttggtgtc taaatgttta ttttgtgata tgttcatgtt  32880
tgaaatggtg gtttcgaaac cagggacaac gttgggatct gatagggtgt caaagagtat  32940
tatggattgg gacaatttcg gtcatgagtt gcaaattcaa gtatatcgtt cgattatgaa  33000
aattttcgaa gaatatccca tttgagagag tctttacctc attaatgttt ttagattatg  33060
aaattttatc atagttcatc gtagtctttt tggtgtaaag gctgtaaaaa gaaattgttc  33120
acttttgttt tcgtttatgt gaaggctgta aaagattgta aaagactatt ttggtgtttt  33180
ggataaaatg atagttttta tagattcttt tgcttttaga agaaatacat ttgaaatttt  33240
ttccatgttg agtataaaat accgaaatcg attgaagatc atagaaatat tttaactgaa  33300
aacaaattta taactgattc aattctctcc atttttatac ctatttaacc gtaatcgatt  33360
ctaatagatg atcgattttt tatataatcc taattaacca acggcatgta ttggataatt  33420
aaccgatcaa ctctcacccc taatagaatc agtattttcc ttcgacgtta attgatccta  33480
cactatgtag gtcatatcca tcgttttaat ttttggccac cattcaattc tgtcttgcct  33540
ttagggatgt gaatatgaac ggccaaggta agagaataaa aataatccaa attaaagcaa  33600
gagaggccaa gtaagataat ccaaatgtac acttgtcatt gccaaaatta gtaaaatact  33660
cggcatattg tattcccaca cattattaaa ataccgtata tgtattggct gcatttgcat  33720
gaataatact acgtgtaagc ccaaaagaac ccacgtgtag cccatgcaaa gttaacactc  33780
acgaccccat tcctcagtct ccactatata aacccaccat ccccaatctc accaaaccca  33840
ccacacaact cacaactcac tctcacacct taaagaacca atcaccacca aaaaaagttc  33900
tttgctttcg aagttgccgc aacctaaaca ggtttttcct tcttctttct tcttattaac  33960
tacgaccttg tcctttgcct atgtaaaatt actaggtttt catcagttac actgattaag  34020
ttcgttatag tggaagataa aatgccctca aagcattttg caggatatct ttgatttttc  34080
aaagatatgg aactgtagag tttgatagtg ttcttgaatg tggttgcatg aagttttttt  34140
ggtctgcatg ttattttttc ctcgaaatat gttttgagtc caacaagtga ttcacttggg  34200
attcagaaag ttgttttctc aatatgtaac agttttttte tatggagaaa aatcataggg  34260
accgttggtt ttggcttctt taattttgag ctcagattaa acccatttta cccggtgttc  34320
ttggcagaat tgaaaacagt acgtagtacc gcgcctacca tgccacctag tgctgctagt  34380
gaaggtggtg ttgctgaact tagagctgct gaagttgcta gctacactag aaaggctgtt  34440
gacgaaagac ctgacctcac tatagttggt gacgctgttt acgacgctaa ggcttttagg  34500
gacgagcacc ctggtggtgc tcacttcgtt agccttttcg gaggtaggga cgctactgag  34560
gcttttatgg aatatcaccg tagagcttgg cctaaggcta ggatgtctaa gttcttcgtt  34620
ggttcacttg acgctagcga gaagcctact caagctgatt cagcttacct tagactttgc  34680
```

```
gctgaggtta acgctctttt gcctaagggt agcggaggat tcgctcctcc tagctactgg  34740
cttaaggctg ctgctcttgt tgttgctgct gttagtatag agggttatat gctccttagg  34800
ggtaagaccc ttttgcttag cgttttcctt ggactcgtgt tcgcttggat aggacttaat  34860
attcagcacg acgctaatca cggtgctctt agtagacact cagtgattaa ctactgcctc  34920
ggttacgctc aggattggat aggtggtaat atggtgcttt ggcttcaaga gcacgttgtg  34980
atgcaccacc tccacactaa cgacgttgac gctgatcctg atcaaaaggc tcacggtgtt  35040
cttagactta agcctactga cggttggatg ccttggcacg cacttcaaca actctatatc  35100
cttcctggtg aggctatgta cgcttttaag cttcttttct tggacgccct tgagcttctt  35160
gcttggaggt gggagggtga gaagattagc cctcttgcta gagctttgtt cgctcctgct  35220
gttgcttgta agcttggatt ctgggctaga ttcgttgctc tccctctctg gcttcaacct  35280
actgttcaca ctgctttgtg tatctgtgct actgtgtgta ctggtagctt ctacctcgcc  35340
ttcttcttct ttatctctca caacttcgac ggtgttggta gcgttggacc taagggatca  35400
cttcctagat cagctacttt cgttcaacgt caggttgaga ctagctctaa cgttggtggt  35460
tactggcttg gagttcttaa cggtggactt aactttcaga tagagcacca cttgttccct  35520
aggcttcacc actcttacta cgctcaaata gctcctgtgg ttaggactca catagagaag  35580
ctcggtttta agtaccgtca cttccctacc gttggatcta accttagctc aatgcttcag  35640
catatgggta agatgggaac tagacctggt gctgagaagg gtggtaaggc tgagtagtga  35700
ttaatgaata attgattgct gctttaatga gatatgcgag acgcctatga tcgcatgata  35760
tttgctttca attctgttgt gcacgttgta aaaaacctga gcatgtgtag ctcagatcct  35820
taccgccggt ttcggttcat tctaatgaat atatcacccg ttactatcgt atttttatga  35880
ataatattct ccgttcaatt tactgattgt ctacgtagcg tcacctgacg ttacgtaagg  35940
ctacctaggc tcacgtgacg ttacgtaacg ctacgtagcg tcaggtgagg ttagctaacg  36000
ctagctagcc tcacctgacg ttaggtaagg ctacgtagcg tcacctgaga ttagctaagc  36060
ctacctagac tcacgtgacc ttaggtaacg ctacgtagcg tcaaagcttt acaacgctac  36120
acaaaactta taaccgtaat caccattcat taacttaact actatcacat gcattcatga  36180
attgaaacga gaaggatgta aatagttggg aagttatctc cacgttgaag agatcgttag  36240
cgagagctga aagaccgagg gaggagacgc cgtcaacacg gacagagtcg tcgaccctca  36300
catgaagtag gaggaatctc cgtgaggagc cagagagacg tctttggtct tcggtttcga  36360
tccttgatct gacggagaag acgagagaag tgcgactgga ctccgtgagg accaacagag  36420
tcgtcctcgg tttcgatcgt cggtattggt ggagaaggcg gaggaatctc cgtgacgagc  36480
cagagagatg tcgtcggtct tcggtttcga tccttgatct gacggagaag acgagagaag  36540
tgcgacgaga ctccgtgagg accaacagag ttgtcctcgg tttcgatcgt cggtttcggc  36600
ggagaaggcg gaggaatctc cgtgaggagc cagagagacg tcgttggtct tcggtttcga  36660
tccttgatct gttggagaag acgagacaag tgggacgaga ctcaacgacg gagtcagaga  36720
cgtcgtcggt cttcggtttc ggccgagaag gcggagtcgg tcttcggttt cggccgagaa  36780
ggcggaggag acgtcttcga tttgggtctc tcctcttgac gaagaaaaca aagaacacga  36840
gaaataatga gaaagagaac aaaagaaaaa aaaataaaaa taaaaataaa atttggtcct  36900
cttatgtggt gacacgtggt ttgaaaccca ccaaataatc gatcacaaaa aacctaagtt  36960
aaggatcggt aataaccttt ctaattaatt ttgatttata ttaaatcact ctttttattt  37020
```

-continued

```
ataaacccca ctaaattatg cgatattgat tgtctaagta caaaaattct ctcgaattca  37080
atacacatgt ttcatatatt tagccctgtt catttaatat tactagcgca tttttaattt  37140
aaaattttgt aaactttttt ggtcaaagaa cattttttta attagagaca gaaatctaga  37200
ctctttattt ggaataatag taataaagat atattaggca atgagtttat gatgttatgt  37260
ttatatagtt tatttcattt taaattgaaa agcattattt ttatcgaaat gaatctagta  37320
tacaatcaat atttatgttt tttcatcaga tactttccta tttttggca cctttcatcg  37380
gactactgat ttatttcaat gtgtatgcat gcatgagcat gagtatacac atgtctttta  37440
aaatgcatgt aaagcgtaac ggaccacaaa agaggatcca tacaaataca tctcatcgct  37500
tcctctacta ttctccgaca cacacactga gcatggtgct taaacactct ggtgagttct  37560
agtacttctg ctatgatcga tctcattacc atttcttaaa tttctctccc taaatattcc  37620
gagttcttga tttttgataa cttcaggttt tctctttttg ataaatctgg tctttccatt  37680
ttttttttt tgtggttaat ttagtttcct atgttcttcg attgtattat gcatgatctg  37740
tgtttggatt ctgttagatt atgtattggt gaatatgtat gtgtttttgc atgtctggtt  37800
ttggtcttaa aaatgttcaa atctgatgat ttgattgaag ctttttagt gttggtttga  37860
ttcttctcaa aactactgtt aatttactat catgttttcc aactttgatt catgatgaca  37920
cttttgttct gctttgttat aaaattttgg ttggtttgat tttgtaatta tagtgtaatt  37980
ttgttaggaa tgaacatgtt ttaatactct gttttcgatt tgtcacacat tcgaattatt  38040
aatcgataat ttaactgaaa attcatggtt ctagatcttg ttgtcatcag attatttgtt  38100
tcgataattc atcaaatatg tagtcctttt gctgatttgc gactgtttca ttttttctca  38160
aaattgtttt ttgttaagtt tatctaacag ttatcgttgt caaaagtctc tttcattttg  38220
caaaatcttc ttttttttt tgtttgtaac tttgtttttt aagctacaca tttagtctgt  38280
aaaatagcat cgaggaacag ttgtcttagt agacttgcat gttcttgtaa cttctatttg  38340
tttcagtttg ttgatgactg ctttgatttt gtaggtcaaa ccgcgccatg tctgctagcg  38400
gagctttgtt gcctgctata gctttcgctg cttacgctta cgctacctac gcttatgctt  38460
tcgagtggag ccacgctaac ggaatcgata acgtggatgc tagagagtgg attggagctt  38520
tgtctttgag actccctgca attgcaacca caatgtacct cttgttctgc cttgtgggac  38580
ctagattgat ggctaagagg gaggcttttg atcctaaggg atttatgctc gcttacaacg  38640
cttaccaaac cgctttcaac gttgtggtgc tcggaatgtt cgctagagag atctctggat  38700
tgggacaacc tgtttgggga tctactatgc cttggagcga taggaagtcc ttcaagattt  38760
tgttgggagt gtggctccac tacaacaata agtacctcga gttgttggat actgtgttca  38820
tggtggctag gaaaaagacc aagcagctct ctttcttgca cgtgtaccac cacgctttgt  38880
tgatttgggc ttggtggctt gtttgtcacc tcatggctac caacgattgc atcgatgctt  38940
atttcggagc tgcttgcaac tctttcatcc acatcgtgat gtactcctac tacctcatgt  39000
ctgctttggg aattaggtgc ccttggaaga gatatatcac ccaggctcag atgttgcaat  39060
tcgtgatcgt gttcgctcac gctgttttcg tgctcagaca aaagcactgc cctgttactt  39120
tgccttgggc acaaatgttc gtgatgacaa atatgttggt gctcttcgga aacttctacc  39180
tcaaggctta ctctaacaag tctaggggag atggagcttc ttctgttaag cctgctgaga  39240
ctactagagc accttctgtg agaagaacca ggtcaaggaa gatcgattga tagttaatga  39300
actaagtttg atgtatctga gtgccaacgt ttactttgtc tttcctttct tttattggtt  39360
atgattagat gtttactatg ttctctcttt ttcgttataa ataaagaagt tcaattcttc  39420
```

```
tatagtttca aacgcgattt taagcgtttc tatttaggtt tacatgattt cttttacaaa  39480
atcatcttta aaatacagta tatttttagt tttcataaaa tatttaaaga aatgaaagtt  39540
tataaacatt cactcctatt ctctaattaa ggatttgtaa aacaaaaatt ttgtaagcat  39600
atcgatttat gcgttttgtc ttaattagct cactaaataa taaataatag cttatgttgt  39660
gggactgttt aattacctaa cttagaacta aaatcaactc tttgtgctag ctagcctcag  39720
ctgacgttac gtaacgctag gtagcgtcac gtgacgttag ctaacgctag gtagcgtcag  39780
ctgagcttac gtaagcgctt aattaaagta ctgatatcgg taccaaatcg aatccaaaaa  39840
ttacggatat gaatataggc atatccgtat ccgaattatc cgtttgacag ctagcaacga  39900
ttgtacaatt gcttctttaa aaaaggaaga aagaaagaaa gaaaagaatc aacatcagcg  39960
ttaacaaacg gccccgttac ggcccaaacg gtcatataga gtaacggcgt taagcgttga  40020
aagactccta tcgaaatacg taaccgcaaa cgtgtcatag tcagatcccc tcttccttca  40080
ccgcctcaaa cacaaaaata atcttctaca gcctatatat acaacccccc cttctatctc  40140
tcctttctca caattcatca tctttctttc tctacccca attttaagaa atcctctctt  40200
ctcctcttca ttttcaaggt aaatctctct ctctctctct ctctctgtta ttccttgttt  40260
taattaggta tgtattattg ctagtttgtt aatctgctta tcttatgtat gccttatgtg  40320
aatatcttta tcttgttcat ctcatccgtt tagaagctat aaatttgttg atttgactgt  40380
gtatctacac gtggttatgt ttatatctaa tcagatatga atttcttcat attgttgcgt  40440
ttgtgtgtac caatccgaaa tcgttgattt ttttcattta atcgtgtagc taattgtacg  40500
tatacatatg gatctacgta tcaattgttc atctgtttgt gtttgtatgt atacagatct  40560
gaaaacatca cttctctcat ctgattgtgt tgttacatac atagatatag atctgttata  40620
tcattttttt tattaattgt gtatatatat atgtgcatag atctggatta catgattgtg  40680
attatttaca tgattttgtt atttacgtat gtatatatgt agatctggac tttttggagt  40740
tgttgacttg attgtatttg tgtgtgtata tgtgtgttct gatcttgata tgttatgtat  40800
gtgcagctga accatggcgg cggcaacaac aacaacaaca acatcttctt cgatctcctt  40860
ctccaccaaa ccatctcctt cctcctccaa atcaccatta ccaatctcca gattctccct  40920
cccattctcc ctaaacccca acaaatcatc ctcctcctcc cgccgccgcg gtatcaaatc  40980
cagctctccc tcctccatct ccgccgtgct caacacaacc accaatgtca caaccactcc  41040
ctctccaacc aaacctacca aacccgaaac attcatctcc cgattcgctc cagatcaacc  41100
ccgcaaaggc gctgatatcc tcgtcgaggc tttagaacgt caaggcgtag aaaccgtatt  41160
cgcttaccct ggaggtacat caatggagat tcaccaagcc ttaacccgct cttcctcaat  41220
ccgtaacgtc cttcctcgtc acgaacaagg aggtgtattc gcagcagaag gatacgctcg  41280
atcctcaggt aaaccaggta tctgtatagc cacttcaggt cccggagcta caaatctcgt  41340
tagcggatta gccgatgcgt tgttagatag tgttcctctt gtagcaatca caggacaagt  41400
ccctcgtcgt atgattggta cagatgcgtt tcaagagact ccgattgttg aggtaacgcg  41460
ttcgattacg aagcataact atcttgtgat ggatgttgaa gatatcccaa ggattattga  41520
agaggctttc tttttagcta cttctggtag acctggacct gttttggttg atgttcctaa  41580
agatattcaa caacagcttg cgattcctaa ttgggaacag gctatgagat tacctggtta  41640
tatgtctagg atgcctaaac ctccggaaga ttctcatttg gagcagattg ttaggttgat  41700
ttctgagtct aagaagcctg tgttgtatgt tggtggtggt tgtcttaatt ctagcgatga  41760
```

```
attgggtagg tttgttgagc ttacgggcat ccctgttgcg agtacgttga tggggctggg  41820
atcttatcct tgtgatgatg agttgtcgtt acatatgctt ggaatgcatg ggactgtgta  41880
tgcaaattac gctgtggagc atagtgattt gttgttggcg tttggggtaa ggtttgatga  41940
tcgtgtcacg ggtaaacttg aggcttttgc tagtagggct aagattgttc atattgatat  42000
tgactcggct gagattggga agaataagac tcctcatgtg tctgtgtgtg gtgatgttaa  42060
gctggctttg caagggatga ataaggttct tgagaaccga gcggaggagc ttaaacttga  42120
ttttggagtt tggaggaatg agttgaacgt acagaaacag aagtttccgt tgagctttaa  42180
gacgtttggg gaagctattc ctccacagta tgcgattaag gtccttgatg agttgactga  42240
tggaaaagcc ataataagta ctggtgtcgg gcaacatcaa atgtgggcgg cgcagttcta  42300
caattacaag aaaccaaggc agtggctatc atcaggaggc cttggagcta tgggatttgg  42360
acttcctgct gcgattggag cgtctgttgc taaccctgat gcgatagttg tggatattga  42420
cggagatgga agttttataa tgaatgtgca agagctagcc actattcgtg tagagaatct  42480
tccagtgaag gtacttttat taaacaacca gcatcttggc atggttatgc aatgggaaga  42540
tcggttctac aaagctaacc gagctcacac atttctcggg gacccggctc aggaggacga  42600
gatattcccg aacatgttgc tgtttgcagc agcttgcggg attccagcgg cgagggtgac  42660
aaagaaagca gatctccgag aagctattca gacaatgctg gatacaccag gaccttacct  42720
gttggatgtg atttgtccgc accaagaaca tgtgttgccg atgatcccga atggtggcac  42780
tttcaacgat gtcataacgg aaggagatgg ccggattaaa tactgagaga tgaaaccggt  42840
gattatcaga accttttatg gtctttgtat gcatatggta aaaaaactta gtttgcaatt  42900
tcctgtttgt tttggtaatt tgagtttctt ttagttgttg atctgcctgc tttttggttt  42960
acgtcagact actactgctg ttgttgtttg gtttcctttc tttcatttta taaataaata  43020
atccggttcg gtttactcct tgtgactggc tcagtttggt tattgcgaaa tgcgaatggt  43080
aaattgagta attgaaattc gttattaggg ttctaagctg ttttaacagt cactgggtta  43140
atatctctcg aatcttgcat ggaaaatgct cttaccattg gtttttaatt gaaatgtgct  43200
catatgggcc gtggtttcca aattaaataa aactacgatg tcatcgagaa gtaaaatcaa  43260
ctgtgtccac attatcagtt ttgtgtatac gatgaaatag ggtaattcaa aatctagctt  43320
gatatgcctt ttggttcatt ttaaccttct gtaaacattt tttcagattt tgaacaagta  43380
aatccaaaaa aaaaaaaaaa aatctcaact caacactaaa ttattttaat gtataaaaga  43440
tgcttaaaac atttggctta aaagaaagaa gctaaaaaca tagagaactc ttgtaaattg  43500
aagtatgaaa atatactgaa ttgggtatta tatgaatttt tctgatttag gattcacatg  43560
atccaaaaag gaaatccaga agcactaatc agacattgga agtaggatta atcagtgatc  43620
agtaactatt aaattcaatt aaccgcggac atctacattt ttgaattgaa aaaaaattgg  43680
taattactct ttctttttct ccatattgac catcatactc attgctgatc catgtagatt  43740
tcccggacat gaagccattt acaattgaat atatcctgcc gccgctgccg ctttgcaccc  43800
ggtggagctt gcatgttggt ttctacgcag aactgagccg gttaggcaga taatttccat  43860
tgagaactga gccatgtgca ccttcccccc aacacggtga gcgacggggc aacggagtga  43920
tccacatggg acttttaaac atcatccgtc ggatggcgtt gcgagagaag cagtcgatcc  43980
gtgagatcag tcgaccaatt ctcatgtttg acagcttatc atcgaatttc tgccattcat  44040
ccgcttatta tcacttattc aggcgtagca accaggcgtt taagggcacc aataactgcc  44100
ttaaaaaaat tacgccccgc cctgccactc atcgcagtac tgttgtaatt cattaagcat  44160
```

```
tctgccgaca tggaagccat cacaaacggc atgatgaacc tgaatcgcca gcggcatcag  44220
caccttgtcg ccttgcgtat aatatttgcc catggtgaaa acgggggcga agaagttgtc  44280
catattggcc acgtttaaat caaaactggt gaaactcacc cagggattgg ctgagacgaa  44340
aaacatattc tcaataaacc ctttagggaa ataggccagg ttttcaccgt aacacgccac  44400
atcttgcgaa tatatgtgta gaaactgccg gaaatcgtcg tggtattcac tccagagcga  44460
tgaaaacgtt tcagtttgct catggaaaac ggtgtaacaa gggtgaacac tatcccatat  44520
caccagctca ccgtctttca ttgccatacg gaattccgga tgagcattca tcaggcgggc  44580
aagaatgtga ataaaggccg gataaaactt gtgcttattt ttctttacgg tctttaaaaa  44640
ggccgtaata tccaggacct gcaggggggg gggggcgctg aggtctgcct cgtgaagaag  44700
gtgttgctga ctcataccag gcctgaatcg ccccatcatc cagccagaaa gtgagggagc  44760
cacggttgat gagagctttg ttgtaggtgg accagttggt gattttgaac ttttgctttg  44820
ccacggaacg gtctgcgttg tcgggaagat gcgtgatctg atccttcaac tcagcaaaag  44880
ttcgatttat tcaacaaagc cgccgtcccg tcaagtcagc gtaatgctct gccagtgtta  44940
caaccaatta accaattctg attagaaaaa ctcatcgagc atcaaatgaa actgcaattt  45000
attcatatca ggattatcaa taccatattt ttgaaaaagc cgtttctgta atgaaggaga  45060
aaactcaccg aggcagttcc ataggatggc aagatcctgg tatcggtctg cgattccgac  45120
tcgtccaaca tcaatacaac ctattaattt cccctcgtca aaaataaggt tatcaagtga  45180
gaaatcacca tgagtgacga ctgaatccgg tgagaatggc aaaagcttat gcatttcttt  45240
ccagacttgt tcaacaggcc agccattacg ctcgtcatca aaatcactcg catcaaccaa  45300
accgttattc attcgtgatt gcgcctgagc gagacgaaat acgcgatcgc tgttaaaagg  45360
acaattacaa acaggaatcg aatgcaaccg gcgcaggaac actgccagcg catcaacaat  45420
attttcacct gaatcaggat attcttctaa tacctggaat gctgttttcc cggggatcgc  45480
agtggtgagt aaccatgcat catcaggagt acggataaaa tgcttgatgg tcggaagagg  45540
cataaattcc gtcagccagt ttagtctgac catctcatct gtaacatcat tggcaacgct  45600
acctttgcca tgtttcagaa acaactctgg cgcatcgggc ttcccataca atcgatagat  45660
tgtcgcacct gattgcccga cattatcgcg agcccattta tacccatata aatcagcatc  45720
catgttggaa tttaatcgcg gcctcgagca agacgtttcc cgttgaatat ggctcataac  45780
accccttgta ttactgttta tgtaagcaga cagttttatt gttcatgatg atatattttt  45840
atcttgtgca atgtaacatc agagattttg agacacaacg tggctttccc cccccccct  45900
gcaggtcctg aacggtctgg ttataggtac attgagcaac tgactgaaat gcctcaaaat  45960
gttctttacg atgccattgg gatatatcaa cggtggtata tccagtgatt tttttctcca  46020
ttttagcttc cttagctcct gaaaatctcg ataactcaaa aaatacgccc ggtagtgatc  46080
ttatttcatt atggtgaaag ttggaacctc ttacgtgccg atcaacgtct cattttcgcc  46140
aaaagttggc ccagggcttc ccggtatcaa cagggacacc aggatttatt tattctgcga  46200
agtgatcttc cgtcacaggt atttattcgc gataagctca tggagcggcg taaccgtcgc  46260
acaggaagga cagagaaagc gcggatctgg gaagtgacgg acagaacggt caggacctgg  46320
attggggagg cggttgccgc cgctgctgct gacggtgtga cgttctctgt tccggtcaca  46380
ccacatacgt tccgccattc ctatgcgatg cacatgctgt atgccggtat accgctgaaa  46440
gttctgcaaa gcctgatggg acataagtcc atcagttcaa cggaagtcta cacgaaggtt  46500
```

```
tttgcgctgg atgtggctgc ccggcaccgg gtgcagtttg cgatgccgga gtctgatgcg  46560
gttgcgatgc tgaaacaatt atcctgagaa taaatgcctt ggcctttata tggaaatgtg  46620
gaactgagtg gatatgctgt ttttgtctgt taaacagaga agctggctgt tatccactga  46680
gaagcgaacg aaacagtcgg gaaaatctcc cattatcgta gagatccgca ttattaatct  46740
caggagcctg tgtagcgttt ataggaagta gtgttctgtc atgatgcctg caagcggtaa  46800
cgaaaacgat ttgaatatgc cttcaggaac aatagaaatc ttcgtgcggt gttacgttga  46860
agtggagcgg attatgtcag caatggacag aacaacctaa tgaacacaga accatgatgt  46920
ggtctgtcct tttacagcca gtagtgctcg ccgcagtcga gcgacagggc gaagccctcg  46980
agtgagcgag gaagcaccag ggaacagcac ttatatattc tgcttacaca cgatgcctga  47040
aaaaacttcc cttggggtta tccacttatc cacggggata tttttataat tatttttttt  47100
atagttttta gatcttcttt tttagagcgc cttgtaggcc tttatccatg ctggttctag  47160
agaaggtgtt gtgacaaatt gccctttcag tgtgacaaat caccctcaaa tgacagtcct  47220
gtctgtgaca aattgccctt aaccctgtga caaattgccc tcagaagaag ctgttttttc  47280
acaaagttat ccctgcttat tgactctttt ttatttagtg tgacaatcta aaaacttgtc  47340
acacttcaca tggatctgtc atggcggaaa cagcggttat caatcacaag aaacgtaaaa  47400
atagcccgcg aatcgtccag tcaaacgacc tcactgaggc ggcatatagt ctctcccggg  47460
atcaaaaacg tatgctgtat ctgttcgttg accagatcag aaaatctgat ggcaccctac  47520
aggaacatga cggtatctgc gagatccatg ttgctaaata tgctgaaata ttcggattga  47580
cctctgcgga agccagtaag gatatacggc aggcattgaa gagtttcgcg gggaaggaag  47640
tggtttttta tcgccctgaa gaggatgccg gcgatgaaaa aggctatgaa tcttttcctt  47700
ggtttatcaa acgtgcgcac agtccatcca gagggcttta cagtgtacat atcaacccat  47760
atctcattcc cttctttatc gggttacaga accggtttac gcagtttcgg cttagtgaaa  47820
caaaagaaat caccaatccg tatgccatgc gtttatacga atccctgtgt cagtatcgta  47880
agccggatgg ctcaggcatc gtctctctga aaatcgactg gatcatagag cgttaccagc  47940
tgcctcaaag ttaccagcgt atgcctgact tccgccgccg cttcctgcag gtctgtgtta  48000
atgagatcaa cagcagaact ccaatgcgcc tctcatacat tgagaaaaag aaaggccgcc  48060
agacgactca tatcgtattt tccttccgcg atatcacttc catgacgaca ggatagtctg  48120
agggttatct gtcacagatt tgagggtggt tcgtcacatt tgttctgacc tactgagggt  48180
aatttgtcac agttttgctg tttccttcag cctgcatgga ttttctcata ctttttgaac  48240
tgtaattttt aaggaagcca aatttgaggg cagtttgtca cagttgattt ccttctcttt  48300
cccttcgtca tgtgacctga tatcgggggt tagttcgtca tcattgatga gggttgatta  48360
tcacagttta ttactctgaa ttggctatcc gcgtgtgtac ctctacctgg agtttttccc  48420
acggtggata tttcttcttg cgctgagcgt aagagctatc tgacagaaca gttcttcttt  48480
gcttcctcgc cagttcgctc gctatgctcg gttacacggc tgcggcgagc gctagtgata  48540
ataagtgact gaggtatgtg ctcttcttat ctccttttgt agtgttgctc ttattttaaa  48600
caactttgcg gtttttttgat gactttgcga ttttgttgtt gctttgcagt aaattgcaag  48660
atttaataaa aaaacgcaaa gcaatgatta aaggatgttc agaatgaaac tcatggaaac  48720
acttaaccag tgcataaacg ctggtcatga aatgacgaag gctatcgcca ttgcacagtt  48780
taatgatgac agcccggaag cgaggaaaat aacccggcgc tggagaatag gtgaagcagc  48840
ggatttagtt ggggtttctt ctcaggctat cagagatgcc gagaaagcag ggcgactacc  48900
```

```
gcacccggat atggaaattc gaggacgggt tgagcaacgt gttggttata caattgaaca  48960
aattaatcat atgcgtgatg tgtttggtac gcgattgcga cgtgctgaag acgtatttcc  49020
accggtgatc ggggttgctg cccataaagg tggcgtttac aaaacctcag tttctgttca  49080
tcttgctcag gatctggctc tgaaggggct acgtgttttg ctcgtggaag gtaacgaccc  49140
ccagggaaca gcctcaatgt atcacggatg ggtaccagat cttcatattc atgcagaaga  49200
cactctcctg cctttctatc ttggggaaaa ggacgatgtc acttatgcaa taaagcccac  49260
ttgctggccg gggcttgaca ttattccttc ctgtctggct ctgcaccgta ttgaaactga  49320
gttaatgggc aaatttgatg aaggtaaact gcccaccgat ccacacctga tgctccgact  49380
ggccattgaa actgttgctc atgactatga tgtcatagtt attgacagcg cgcctaacct  49440
gggtatcggc acgattaatg tcgtatgtgc tgctgatgtg ctgattgttc ccacgcctgc  49500
tgagttgttt gactacacct ccgcactgca gtttttcgat atgcttcgtg atctgctcaa  49560
gaacgttgat cttaaagggt tcgagcctga tgtacgtatt ttgcttacca aatacagcaa  49620
tagtaatggc tctcagtccc cgtggatgga ggagcaaatt cgggatgcct ggggaagcat  49680
ggttctaaaa aatgttgtac gtgaaacgga tgaagttggt aaaggtcaga tccggatgag  49740
aactgttttt gaacaggcca ttgatcaacg ctcttcaact ggtgcctgga gaaatgctct  49800
ttctatttgg gaacctgtct gcaatgaaat tttcgatcgt ctgattaaac cacgctggga  49860
gattagataa tgaagcgtgc gcctgttatt ccaaaacata cgctcaatac tcaaccggtt  49920
gaagatactt cgttatcgac accagctgcc ccgatggtgg attcgttaat tgcgcgcgta  49980
ggagtaatgg ctcgcggtaa tgccattact ttgcctgtat gtggtcggga tgtgaagttt  50040
actcttgaag tgctccgggg tgatagtgtt gagaagacct ctcgggtatg gtcaggtaat  50100
gaacgtgacc aggagctgct tactgaggac gcactggatg atctcatccc ttcttttcta  50160
ctgactggtc aacagacacc ggcgttcggt cgaagagtat ctggtgtcat agaaattgcc  50220
gatgggagtc gccgtcgtaa agctgctgca cttaccgaaa gtgattatcg tgttctggtt  50280
ggcgagctgg atgatgagca gatggctgca ttatccagat tgggtaacga ttatcgccca  50340
acaagtgctt atgaacgtgg tcagcgttat gcaagccgat tgcagaatga atttgctgga  50400
aatatttctg cgctggctga tgcggaaaat atttcacgta agattattac ccgctgtatc  50460
aacaccgcca aattgcctaa atcagttgtt gctctttttt ctcaccccgg tgaactatct  50520
gcccggtcag gtgatgcact tcaaaaagcc tttacagata aagaggaatt acttaagcag  50580
caggcatcta accttcatga gcagaaaaaa gctggggtga tatttgaagc tgaagaagtt  50640
atcactcttt taacttctgt gcttaaaacg tcatctgcat caagaactag tttaagctca  50700
cgacatcagt ttgctcctgg agcgacagta ttgtataagg gcgataaaat ggtgcttaac  50760
ctggacaggt ctcgtgttcc aactgagtgt atagagaaaa ttgaggccat tcttaaggaa  50820
cttgaaaagc cagcaccctg atgcgaccac gttttagtct acgtttatct gtctttactt  50880
aatgtccttt gttacaggcc agaaagcata actggcctga atattctctc tgggcccact  50940
gttccacttg tatcgtcggt ctgataatca gactgggacc acggtcccac tcgtatcgtc  51000
ggtctgatta ttagtctggg accacggtcc cactcgtatc gtcggtctga ttattagtct  51060
gggaccacgg tcccactcgt atcgtcggtc tgataatcag actgggacca cggtcccact  51120
cgtatcgtcg gtctgattat tagtctggga ccatggtccc actcgtatcg tcggtctgat  51180
tattagtctg ggaccacggt cccactcgta tcgtcggtct gattattagt ctggaaccac  51240
```

```
ggtcccactc gtatcgtcgg tctgattatt agtctgggac cacggtccca ctcgtatcgt  51300
cggtctgatt attagtctgg gaccacgatc ccactcgtgt tgtcggtctg attatcggtc  51360
tgggaccacg gtcccacttg tattgtcgat cagactatca gcgtgagact acgattccat  51420
caatgcctgt caagggcaag tattgacatg tcgtcgtaac ctgtagaacg gagtaacctc  51480
ggtgtgcggt tgtatgcctg ctgtggattg ctgctgtgtc ctgcttatcc acaacatttt  51540
gcgcacggtt atgtggacaa aatacctggt tacccaggcc gtgccggcac gtttcctaca  51600
aggtagaatc cgcctgagtc gcaagggtga cttcgcctat attggacgac ggcgcgcaga  51660
gggcgacctc tttttgggtt acgattgtag gattatcact aaaacaatac atgaacatat  51720
tcaaatggca atctctctaa ggcattggaa ataaatacaa ataacagttg ggtggagttt  51780
ttcgacctga gggcgttaac tcttcaagga caacaagacc gtggacgtcg agcggctctc  51840
cgacaagcat gtcgcccgcc tggtcaagca gaccgcactc gccgccggcg cttcgatacc  51900
gttcgtattg gtccggcgaa actgtgagta tccgcatcgt aatctccgca tgaacaggtc  51960
atgcgaacag aaatcatctc acggtgcgtt tgcctacgtg cagatttgca cctcaggtga  52020
ttctaccgag tcggtgttcc aaggcgcgaa atgcgagcgg gtgaggccga ccagacgccg  52080
acaaggttgt gcagatctgc acttggtgcc acgtcgcaca gaagaaggga atcggtctaa  52140
ctcacagata gcatttgaag aatcgggatt tagtgtgatt tcgattgaaa cgcgcgtaac  52200
cgttcattaa ccaaaaacgt cttgcaacct cacccgcatt aggtaatcgt cacggataaa  52260
tggcaatacg cgccaattaa ccgtgacaag agataacacc gtgagcaaag ccgctgccat  52320
atcccgaaat gatcgcccgt cggtagatgt taccattggt gagcatgctg agcagctcag  52380
ctctcagctt caagcgatga gcgaggcttt gtttcctccg acgtcgcaca agagcttgcg  52440
caaattcacc tcgggtgaag ccgcacgctt gatgaaaata tctgactcaa ctcttcgaaa  52500
gatgacactg gctggcgaag ggccgcaacc tgaactcgcc agcaacggac ggcgctttta  52560
caccctcggt cagataaacg aaatccggca gatgcttgcc ggctcgactc gaggacgtga  52620
aagcattgat tttgtgcctc atcgccgagg ttctgagcat ttgcaagtcg ttgctgtaac  52680
caacttcaaa ggtggctctg ggaagacgac gacgtccgct catcttgcac agtatctggc  52740
gttgcaaggt tacagggttc tcgcagtcga tctcgatccg caggctagtc tttcagcact  52800
cctcggcgtt ctgccagaaa ctgatgtcgg tgcaaacgaa acgctctatg cggctattcg  52860
gtacgacgac acacgtcgtc cgttgcgaga tgtgatccga ccgacgtatt ttgatggtct  52920
tcaccttgtt cctggaaatc tcgagcttat ggagttcgag cataccaccc cgaaagcatt  52980
gactgacaaa ggtacgcgcg acggattgtt cttcactcgc gtggcccaag cctttgatga  53040
ggtcgccgac gattacgatg tcgtggtcat cgactgccct cctcagcttg ggtttttgac  53100
tctcagcggg ttgtgtgctg caacatcaat ggtaatcacc gtacatcctc agatgctgga  53160
tatcgcttcc atgagccagt ttctcctcat gacacgcgac cttctgggtg tcgtgaaaga  53220
ggcgggggc aatctccagt acgatttcat acgctatctc ttgacgcgct atgagcccca  53280
ggacgcgccg cagacgaaag tgacggcact gctgcgcaac atgttcgagg atcacgtcct  53340
tacaaatcct atggtcaagt cggcagcggt atctgatgcc ggtttaacca agcagacgct  53400
ctatgagata gggcgagaga accttacgcg atcgacatac gaccgggcga tggaatcttt  53460
agatgcggtg aattcggaga tcgaggcttt gatcaagatg gcgtgggggc gggtctaatg  53520
aaaggctttg cgttcctcac agatctgttg ggagctccca acagacaggt gttgattcgc  53580
cccctggaca tggggcactg gagaagccgg ggtaatttga gacgacgacg cacgcccatc  53640
```

```
gctaattggc cagggtgcag ttgtcttgtc ttgttgggag ctcccaacca agcgcatttg  53700
caatcaaaaa tgcgacgcca cgacgccaaa cccaagaggc cgatatcatg agccgcaaag  53760
acgcaatcga tactttgttc ctcaagaagc aacctgcgac cgatagagca gcagtcgaca  53820
agtcgaccgc tcgtgttcgt accggagcga tttcggccat gggttcgtct ttgcaagaga  53880
tggctgaggg cgcaaaggct gcagctcggc tgcaggatca actggctaca ggcgaagccg  53940
tcgtgtccct ggatccatcc atgatcgacg ggtcgccgat cgcggatcgg ctgccctcag  54000
acgtggatcc gaaattcgag cagcttgagg cgagcatttc gcaggagggg cagcaggtgc  54060
cggttcttgt cagaccgcac cctgaggctg ccggtcgata tcagatcgta tatggaaggc  54120
ggcggctgcg cgcggcagta aatctgcgga gagaggtttc tgccattgtt cgaaatctca  54180
cggactgtga actggtcgtg gcccagggcc gcgaaaatct taaccgcgct gacctctcgt  54240
tcattgagaa ggctctcttc gccctgcgcc tcgaagatgc gggttttgat agagccacca  54300
tcattgccgc gctatccact gacaaggccg acctcagccg ctacataact gtagcaaggg  54360
gcataccgct gaacctcgcc acacaaatcg gcccagcgtc gaaagcgggt cgatcgcgtt  54420
gggtcgtact tgccgagggg cttgggaagc ctaaggcaac ggacgcaatc gaagcgatgc  54480
ttgggtcaga gcagttcaag caatctgata gcgatacccg ctttaacctc attttcaacg  54540
ccgtttcaag gccacctgcg aagactccaa aaaaggtaag ggcctggagc acgccaaagg  54600
ggaaaaaggc agcgacgatc cgacaagaaa ctggacgaac ggcgctggtt ttcgacgaga  54660
gactggtgcc aacttttggc gaatatgtcg ctgaccagtt ggacagtctg tacgcccagt  54720
tcattgaaac caacggagga ggcaagctcg accaatagtc agggtttcat ccaatttaaa  54780
gctccgctcg actgagatgg actggctctc accgcaaaag aaaaaggccc ccgaaacggc  54840
gttccggaag accttctctg tagtctcgca gctaagagaa tcgcatttcc aggaatcgta  54900
gtcaagggtc ccgtaaggga aagcgtcatt tcgacgggcg gatttcaatt gcctaacaaa  54960
aggtaaaagg aaatgcagac gcatatctca acgacgtcct ttgggcggcg gccgatgaca  55020
ctcggccata ttgcaagcca gatggcagca aaagcggtcg catcagacac tgtcgcccac  55080
aaatggcagg tcttccagca catccgtgaa tcccggggac tgatcggagc cacggaccgc  55140
tcactctcga tcctgaacgc gctgttgacg ttttacccgg agaccgcctt gactggtggt  55200
gccgaactgg tcgtatggcc ttctaacgaa cagctgatgg ctcgcgccaa cggcatgccc  55260
gccacgacac tgcgccggca tcttgccata ctggttgatt gcgggctcat cattcgccgc  55320
gacagcccca atggcaagcg gttcgcccgc aagggaaggg gaggggagat tgagcaggcc  55380
tatgggttcg atctgtcgcc gatcgtcgcg cgggccgagg agttccgaga tctggcccag  55440
acagtgcaag ctgaaaaaaa ggccttccgg gtggccaagg agcgcttgac tcttcttcgt  55500
cgtgacattg tcaaaatgat cgaaactggc gtcgaagaga gcgttcctgg aaactgggga  55560
agagttaccc agacctatca ggggatcatc ggccgcctgc cacgctcggc acctcggcag  55620
cttgtcgaga gtattgggca agagcttcag gaactctgca tcgagatccg tgacgtattg  55680
gaatctttca caaaaacgat gaatctggac gccaatgagt cccatatcgg tcgccacaaa  55740
cagaattcaa atccagactc taaatttgaa tctgaataca gctctggaaa aaaagatgaa  55800
gcgggcggca gcgttgcgga aaccgacaat gtacggagct tgccgaaacg cgagctgcct  55860
ttgggaatcg tgctggatgc ctgccccgaa atgcgggaat tggcccaggg aggtccaatt  55920
cggcattggc gcgacttgct ggcggcggct gagcttgccc ggccgatgct ggggattagt  55980
```

```
ccgagcgcct ggcgggaggc ccgcgaaacc atgggcgatc aacacgcggc gatcacgctg  56040
gcttcgatct atcagcgggc cggtcagatc aataacgctg gggctatct gcgcagcctg  56100
accgaccggg ccaaggatgg gaagttttcg acctggccga tggtcatggc gttgctccgg  56160
gcaaagctgg acgagcagaa gaatgcagtt ggcgctggaa agccgcgaac tgctgaggag  56220
gtcgaggatg acagccgcct ccacgtatcg gaatcgctgc tcaaaaacct gcgaaagccg  56280
agatcttggt gatcctctcg ctattcagcc gcggcgatgt cgacgtcggt gatcaacccg  56340
gaacgtcggg cgcggtcgat caggttcttg acggacgagg gcgcccattt ggatccaccg  56400
cgcggcgtgc gctcgtgcag tctttcaagc tggccggcga tctcgcggag cttcaggtct  56460
gggttcgaag aatggatgcc ggccacaagc gtcatcaggc gatcttcggg aagacgggga  56520
ggagattttt tcaggagcgc tgcatccacc aggcgttccg tcaccatcca cttcacggct  56580
cggcgaagac gttctggcgt ccagtcgagg ccccgctgct tgagcattcg ggcgatgtcg  56640
tcccatgtgt gatccggtcg catgcgacga acggtaggaa gccattggtt cgcggacgcc  56700
tgaatcctat cgccatatgc cgctttctgg gccgcggtca tccttgccag cgcctccggg  56760
cgcttttccc ggatgcccgg gttgccggaa agcttcccta ggcacaaacg ttgactcttg  56820
gatcgagctg gcagacaaag caataaccca cacagaggac gattaatggc tgacgaagag  56880
atccagaatc cgccggacgg tactgctgct gccgaagttg agccggctgc tcctagaggt  56940
agaagagcaa agaaagcacc agccgaaaca gcccgcacgg gatcgttcaa atccgtgaag  57000
ccgaaaaccc gcggcctcag caaccgagaa aaactggaga agatcggtca aatcgaagct  57060
caggtcgctg gcggcgcaac cttgaaggac gccgttaaga tcgtgggtat ttccgttcag  57120
acctattatc aatggaagag agctgcggtt caacctgtct cacagaatcc ggccgtgtct  57180
gtttcagttg acgatgaact cggcgagttc atccaactcg aggaggaaaa tcggcggctc  57240
agaaagcttc acgctgccgc aagcactcag ggcgcaaggg ctgctaaagg aagcggaaca  57300
cgtagaaagc cagtccgcag aaacggtgct gaccccggat gaatgtcagc tactgggcta  57360
tctggacaag ggaaaacgca agcgcaaaga gaaagcaggt agcttgcagt gggcttacat  57420
ggcgatagct agactgggcg gttttatgga cagcaagcga accggaattg ccagctgggg  57480
cgccctctgg gaaggttggg aagccctgca aagtaaactg gatggctttc ttgccgccaa  57540
ggatctgatg gcgcagggga tcaagatctg atcaagagac aggggccggc ccacgctgtc  57600
gtccaatctc ccaagacacg ccgccaccgc gcaccgtcgc ggcgagctgc tccccaagcc  57660
gctgttcgat gggcttccac cgcacgaggc tggacccctt ggcgtcatca agcatcccat  57720
ttcgcccgct ggcgagcatg acggggcgcc ggtagacgcc ggcaacgcgc tggccgtcgg  57780
ccacggggcg atgctccagg ccggtatcgg cggcaatgtc cttcgcggcc tgcgccagtt  57840
cccgagcccg ctgctgccca gcagattccg gtgaggatca cgcgctgccc gcgccgctcg  57900
gccagtccct gttcggccag gaagtccgcg cgctgctgta tcgcctactt ggcctcactg  57960
ctaaagccca ggtcgcccaa gcccgagcca ccgtcgatca actgctggtc aagccaggtg  58020
gcaccgatca cgcgggcctg ccgctcgatg ggcaggtgcg atttcagctc caccgtcacg  58080
ccaccaagac gctgggcgtc atagcggcgg ccctgctcgg gcagatcgtc cggcaccttc  58140
catagtccct cggccacgca caccacgatg ccggcctggt gcagggcttc gaggcggcgg  58200
gtgtggcccg caacgacttc cagcggatca cgcccgacac ggcctgacct agctcgacga  58260
ccaggtgaga tcggtgaccg cgctagtcaa gcaaccggcg tgccatggcg tttacggcca  58320
gatcaatcgc agcgccctcg ccctcgccgt cgccgtcgcc gatgaaccag gctgccgaca  58380
```

```
agcccgtcca tgcaatgatc cagcgaagaa gccgttcggg ctcaaacccg gtcgtcgcga  58440

ccacaatgct gagtcgagcc tccagcctgc ccggcaggat cgcaagcggg cgaccggggt  58500

cgctgagatc gggattcgtg aagatgttgg catagtcgaa ggtgcgctcg ccgagcagtc  58560

cgtgcgggtc gatggccagc cagccgcggt cgccgaagtc gagcacgttc tcgtggtgca  58620

ggtcgccgtg gagcgggcac acctcgcgcg gcgccgccag aagttggcgc gctacgctgg  58680

cggcgggcgc aagtgccgcg tgctcagcgg ccaaccggaa aagcggctgg aaccattcct  58740

gtagcggatg gagatcgggc ggcggtccgg accgcggcgc gtgcagacga gcggcggtgt  58800

cgcagaggat cgtggcatca ccgaaccgcg ccgtgcgcgg gtcgtcggtg agccagagtt  58860

tcagcaggcc gcccaggcgg cccaggtcgc cattgatgcg ggccagctcg cggacgtgct  58920

catagtccac gacgcccgtg attttgtagc cctggccgac ggccagcagg taggccgaca  58980

ggctcatgcc ggccgccgcc gccttttcct caatcgctct tcgttcgtct ggaaggcagt  59040

acaccttgat aggtgggctg cccttcctgg ttggcttggt ttcatcagcc atccgcttgc  59100

cctcatctgt tacgccggcg gtagccggcc agcctcgcag agcaggattc ccgttgagca  59160

ccgccaggtg cgaataaggg acagtgaaga aggaacaccc gctcgcgggt gggcctactt  59220

cacctatcct gcccggctga cgccgttgga tacaccaagg aaagtctaca cgaacccttt  59280

ggcaaaatcc tgtatatcgt gcgaaaaagg atggatatac cgaaaaaatc gctataatga  59340

ccccgaagca gggttatgca gcggaaaagc gctgcttccc tgctgttttg tggaatatct  59400

accgactgga aacaggcaaa tgcaggaaat tactgaactg aggggacagg cgagagacga  59460

tgccaaagag ctacaccgac gagctggccg agtgggttga atcccgcgcg gccaagaagc  59520

gccggcgtga tgaggctgcg gttgcgttcc tggcggtgag ggcggatgtc gaggcggcgt  59580

tagcgtccgg ctatgcgctc gtcaccattt gggagcacat gcgggaaacg gggaaggtca  59640

agttctccta cgagacgttc cgctcgcacg ccaggcggca catcaaggcc aagcccgccg  59700

atgtgcccgc accgcaggcc aaggctgcgg aacccgcgcc ggcacccaag acgccggagc  59760

cacggcggcc gaagcagggg ggcaaggctg aaaagccggc ccccgctgcg gccccgaccg  59820

gcttcacctt caacccaaca ccggacaaaa aggatcaacc gggctgcatc cgatgcaagt  59880

gtgtcgctgt cgactcgttg tacaacgaaa tccattccca ttccgcgctc aagatggctt  59940

cccctcggca gttcatcagg gctaaatcaa tctagccgac ttgtccggtg aaatgggctg  60000

cactccaaca gaaacaatca aacaaacata cacagcgact tattcacacg agctcaaatt  60060

acaacggtat atat                                                    60074
```

<210> SEQ ID NO 2
<211> LENGTH: 44910
<212> TYPE: DNA
<213> ORGANISM: Artificial Sequence
<220> FEATURE:
<223> OTHER INFORMATION: contig of insert and flanking sequences of LBFLFK T-DNA Locus 1

<400> SEQUENCE: 2

```
tatttttgtt catgtcttat tttctttttt cctaatgtaa ctatgagagg cttaaaaact     60

gtaaaatcag caaaacaata tacaattaca gtaaaaaatg tcacatacta agttctatat    120

atgactacaa gtctacaact caactaatca tccacataaa taattagttt tgtcataatt    180

atattatagt aagtacctga agaaaagata aagccatttc tggacaacat catctcgtat    240

tggcatcttt atacgtggac gacaaaatct atcacaataa tagttgctag atatagatac    300
```

```
atgaattttg taatatgatt aattaattgg cgcttcataa ctaaaataac taataaaggg    360
taaatgttct taaagtttca taattaatta tgtttcagag tggttgcatt atagtagttt    420
aaaattcaga agtgtacgcg acgagaaaag agatttgctg gtgactattg catcatcttt    480
gacatggaaa aaatcttaga taagaatagt ttgaaattag aaagctcgca attgaggtct    540
accaaaatta gaaattagaa agctcgcaat ccagtcagca tcatcacacc aaaagttagg    600
cccgaatagt ttgaaattag aaagctcgca attgaggtct acaggccaaa ttcgctctta    660
gccgtacaat attactcacc ggtgcgatgc cccccatcgt aggtgaaggt ggaaattaat    720
ggcgcgcctg atcactgatt agtaactatt acgtaagcct acgtagcgtc acgtgacgtt    780
agctaacgct acgtagcctc agctgacgtt acgtaagcct acgtagcgtc acgtgagctt    840
agctaacgct acctaggctc agctgacgtt acgtaacgct agctagcgtc actcctgcag    900
caaatttaca cattgccact aaacgtctaa acccttgtaa tttgtttttg ttttactatg    960
tgtgttatgt atttgatttg cgataaattt ttatatttgg tactaaattt ataacacctt   1020
ttatgctaac gtttgccaac acttagcaat ttgcaagttg attaattgat tctaaattat   1080
ttttgtcttc taaatacata tactaatcaa ctggaaatgt aaatatttgc taatatttct   1140
actataggag aattaaagtg agtgaatatg gtaccacaag gtttggagat ttaattgttg   1200
caatgctgca tggatggcat atacaccaaa cattcaataa ttcttgagga taataatggt   1260
accacacaag atttgaggtg catgaacgtc acgtggacaa aaggtttagt aatttttcaa   1320
gacaacaatg ttaccacaca caagttttga ggtgcatgca tggatgccct gtggaaagtt   1380
taaaaatatt ttggaaatga tttgcatgga agccatgtgt aaaaccatga catccacttg   1440
gaggatgcaa taatgaagaa aactacaaat ttacatgcaa ctagttatgc atgtagtcta   1500
tataatgagg attttgcaat actttcattc atacacactc actaagtttt acacgattat   1560
aatttcttca tagccagtac tgtttaagct tcactgtctc tgaatcggca aaggtaaacg   1620
tatcaattat tctacaaacc cttttatttt tcttttgaat taccgtcttc attggttata   1680
tgataacttg ataagtaaag cttcaataat tgaatttgat ctgtgttttt ttggccttaa   1740
tactaaatcc ttacataagc tttgttgctt ctcctcttgt gagttgagtg ttaagttgta   1800
ataatggttc actttcagct ttagaagaaa ccatggaagt tgttgagagg ttctacggag   1860
agttggatgg aaaggtttcc caaggagtga acgctttgtt gggatctttc ggagttgagt   1920
tgactgatac cccaactact aagggattgc cactcgttga ttctccaact ccaattgtgt   1980
tgggagtgtc tgtttacttg accatcgtga tcggaggatt gctttggatc aaggctagag   2040
atctcaagcc aagagcttct gagccattct tgttgcaagc tttggtgttg gtgcacaact   2100
tgttctgctt cgctttgtct ctttacatgt gcgtgggtat cgcttaccaa gctatcacct   2160
ggagatattc cttgtgggga aacgcttata acccaaagca caaggagatg gctatcctcg   2220
tttacctctt ctacatgtcc aagtacgtgg agttcatgga taccgtgatc atgatcctca   2280
agagatccac cagacagatt tctttcctcc acgtgtacca ccactcttct atctccctta   2340
tctggtgggc tattgctcac cacgctccag gaggagaggc ttattggagt gctgctctca   2400
actctggagt gcacgtgttg atgtacgctt actacttctt ggctgcttgc ttgagatctt   2460
ccccaaagct caagaacaag tacctcttct ggggaagata cctcacccaa ttccagatgt   2520
tccagttcat gctcaacttg gtgcaagctt actacgatat gaaaaccaac gctccatatc   2580
cacaatggct catcaagatc ctcttctact acatgatctc cctcttgttc ctcttcggaa   2640
```

```
acttctacgt gcaaaagtac atcaagccat ccgatggaaa gcaaaaggga gctaagaccg   2700
agtgatcgac aagctcgagt ttctccataa taatgtgtga gtagttccca gataagggaa   2760
ttagggttcc tatagggttt cgctcatgtg ttgagcatat aagaaaccct tagtatgtat   2820
ttgtatttgt aaaatacttc tatcaataaa atttctaatt cctaaaacca aaatccagta   2880
ctaaaatcca gatcccccga attaattcgg cgttaattca gctagctagc ctcagctgac   2940
gttacgtaac gctaggtagc gtcacgtgac gttagctaac gctaggtagc gtcagctgag   3000
cttacgtaag cgcttagcag atatttggtg tctaaatgtt tattttgtga tatgttcatg   3060
tttgaaatgg tggtttcgaa accagggaca acgttgggat ctgatagggt gtcaaagagt   3120
attatggatt gggacaattt cggtcatgag ttgcaaattc aagtatatcg ttcgattatg   3180
aaaattttcg aagaatatcc catttgagag agtctttacc tcattaatgt ttttagatta   3240
tgaaatttta tcatagttca tcgtagtctt tttggtgtaa aggctgtaaa aagaaattgt   3300
tcacttttgt tttcgtttat gtgaaggctg taaaagattg taaaagacta ttttggtgtt   3360
ttggataaaa tgatagtttt tatagattct tttgctttta gaagaaatac atttgaaatt   3420
ttttccatgt tgagtataaa ataccgaaat cgattgaaga tcatagaaat attttaactg   3480
aaaacaaatt tataactgat tcaattctct ccatttttat acctatttaa ccgtaatcga   3540
ttctaataga tgatcgattt tttatataat cctaattaac caacggcatg tattggataa   3600
ttaaccgatc aactctcacc cctaatagaa tcagtatttt ccttcgacgt taattgatcc   3660
tacactatgt aggtcatatc catcgtttta atttttggcc accattcaat tctgtcttgc   3720
ctttagggat gtgaatatga acggccaagg taagagaata aaaataatcc aaattaaagc   3780
aagagaggcc aagtaagata atccaaatgt acacttgtca ttgccaaaat tagtaaaata   3840
ctcggcatat tgtattccca cacattatta aaataccgta tatgtattgg ctgcatttgc   3900
atgaataata ctacgtgtaa gcccaaaaga acccacgtgt agcccatgca aagttaacac   3960
tcacgacccc attcctcagt ctccactata taaacccacc atccccaatc tcaccaaacc   4020
caccacacaa ctcacaactc actctcacac cttaaagaac caatcaccac caaaaaattt   4080
cacgatttgg aatttgattc ctgcgatcac aggtatgaca ggttagattt tgttttgtat   4140
agttgtatac atacttcttt gtgatgtttt gtttacttaa tcgaattttt ggagtgtttt   4200
aaggtctctc gtttagaaat cgtggaaaat atcactgtgt gtgtgttctt atgattcaca   4260
gtgtttatgg gtttcatgtt ctttgtttta tcattgaatg ggaagaaatt tcgttgggat   4320
acaaatttct catgttctta ctgatcgtta ttaggagttt ggggaaaaag gaagagtttt   4380
tttggttggt tcgagtgatt atgaggttat ttctgtattt gatttatgag ttaatggtcg   4440
ttttaatgtt gtagaccatg ggaaaaggat ctgagggaag atctgctgct agagagatga   4500
ctgctgaggc taacggagat aagagaaaga ccatcctcat tgagggagtg ttgtacgatg   4560
ctaccaactt caaacaccca ggaggttcca ttattaactt cctcaccgag ggagaagctg   4620
gagttgatgc tacccaagct tacagagagt tccatcagag atccggaaag gctgataagt   4680
acctcaagtc cctcccaaag ttggatgctt ctaaggtgga gtctaggttc tctgctaagg   4740
agcaggctag aagggacgct atgaccaggg attacgctgc tttcagagag gagttggttg   4800
ctgagggata cttcgatcca tctatcccac acatgatcta cagagtggtg gagattgtgg   4860
ctttgttcgc tttgtctttc tggttgatgt ctaaggcttc tccaacctct ttggttttgg   4920
gagtggtgat gaacggaatc gctcaaggaa gatgcggatg ggttatgcac gagatgggac   4980
acggatcttt cactggagtt atctggctcg atgataggat gtgcgagttc ttctacggag   5040
```

```
ttggatgtgg aatgtctgga cactactgga agaaccagca ctctaagcac cacgctgctc   5100
caaacagatt ggagcacgat gtggatttga acaccttgcc actcgttgct ttcaacgaga   5160
gagttgtgag gaaggttaag ccaggatctt tgttggcttt gtggctcaga gttcaggctt   5220
atttgttcgc tccagtgtct tgcttgttga tcggattggg atggaccttg tacttgcacc   5280
caagatatat gctcaggacc aagagacaca tggagtttgt gtggatcttc gctagatata   5340
tcggatggtt ctccttgatg ggagctttgg gatattctcc tggaacttct gtgggaatgt   5400
acctctgctc tttcggactt ggatgcatct acatcttcct ccaattcgct gtgtctcaca   5460
cccacttgcc agttaccaac ccagaggatc aattgcactg gcttgagtac gctgctgatc   5520
acaccgtgaa catctctacc aagtcttggt tggttacctg gtggatgtct aacctcaact   5580
tccaaatcga gcaccacttg ttcccaaccg ctccacaatt caggttcaag gagatctctc   5640
caagagttga ggctctcttc aagagacaca acctccctta ctacgatttg ccatacacct   5700
ctgctgtttc tactaccttc gctaacctct actctgttgg acactctgtt ggagctgata   5760
ccaagaagca ggattgactg ctttaatgag atatgcgaga cgcctatgat cgcatgatat   5820
ttgctttcaa ttctgttgtg cacgttgtaa aaaacctgag catgtgtagc tcagatcctt   5880
accgccggtt tcggttcatt ctaatgaata tatcacccgt tactatcgta tttttatgaa   5940
taatattctc cgttcaattt actgattgtc tacgtaggct cagctgagct tacctaaggc   6000
tacgtaggct cacgtgacgt tacgtaaggc tacgtagcgt cacgtgagct tacctaactc   6060
tagctagcct cacgtgacct tagctaacac taggtagcgt cagctcgacg gcccggactg   6120
tatccaactt ctgatctttg aatctctctg ttccaacatg ttctgaagga gttctaagac   6180
ttttcagaaa gcttgtaaca tgctttgtag actttctttg aattactctt gcaaactctg   6240
attgaaccta cgtgaaaact gctccagaag ttctaaccaa attccgtctt gggaaggccc   6300
aaaatttatt gagtacttca gtttcatgga cgtgtcttca aagatttata acttgaaatc   6360
ccatcatttt taagagaagt tctgttccgc aatgtcttag atctcattga aatctacaac   6420
tcttgtgtca gaagttcttc cagaatcaac ttgcatcatg gtgaaaatct ggccagaagt   6480
tctgaacttg tcatatttct taacagttag aaaaatttct aagtgtttag aattttgact   6540
tttccaaagc aaacttgact tttgactttc ttaataaaac aaacttcata ttctaacatg   6600
tcttgatgaa atgtgattct tgaaatttga tgttgatgca aaagtcaaag tttgactttt   6660
cagtgtgcaa ttgaccattt tgctcttgtg ccaattccaa acctaaattg atgtatcagt   6720
gctgcaaact tgatgtcatg gaagatctta tgagaaaatt cttgaagact gagaggaaaa   6780
attttgtagt acaacacaaa gaatcctgtt tttcatagtc ggactagaca cattaacata   6840
aaacaccact tcattcgaag agtgattgaa gaaggaaatg tgcagttacc tttctgcagt   6900
tcataagagc aacttacaga cacttttact aaaatactac aaagaggaag attttaacaa   6960
cttagagaag taatgggagt taaagagcaa cacattaagg gggagtgtta aaattaatgt   7020
gttgtaacca ccactacctt tagtaagtat tataagaaaa ttgtaatcat cacattataa   7080
ttattgtcct tatttaaaat tatgataaag ttgtatcatt aagattgaga aaaccaaata   7140
gtcctcgtct tgatttttga attattgttt tctatgttac ttttcttcaa gcctatataa   7200
aaactttgta atgctaaatt gtatgctgga aaaaaatgtg taatgaattg aatagaaatt   7260
atggtatttc aaagtccaaa atccatcaat agaaatttag tacaaaacgt aactcaaaaa   7320
tattctctta ttttaaattt tacaacaata taaaaatatt ctcttatttt aaattttaca   7380
```

```
ataatataat ttatcacctg tcacctttag aataccacca acaatattaa tacttagata   7440
ttttattctt aataattttg agatctctca atatatctga tatttatttt atatttgtgt   7500
catattttct tatgttttag agttaaccct tatatcttgg tcaaactagt aattcaatat   7560
atgagtttgt gaaggacaca ttgacatctt gaaacattgg ttttaacctt gttggaatgt   7620
taaaggtaat aaaacattca gaattatgac catctattaa tatacttcct ttgtctttta   7680
aaaaagtgtg catgaaaatg ctctatggta agctagagtg tcttgctggc ctgtgtatat   7740
caattccatt tccagatggt agaaactgcc actacgaata attagtcata agacacgtat   7800
gttaacacac gtccccttgc atgtttttttg ccatatattc cgtctctttc tttttcttca   7860
cgtataaaac aatgaactaa ttaatagagc gatcaagctg aacagttctt tgctttcgaa   7920
gttgccgcaa cctaaacagg tttttccttc ttctttcttc ttattaacta cgaccttgtc   7980
ctttgcctat gtaaaattac taggttttca tcagttacac tgattaagtt cgttatagtg   8040
gaagataaaa tgccctcaaa gcattttgca ggatatcttt gatttttcaa agatatggaa   8100
ctgtagagtt tgatagtgtt cttgaatgtg gttgcatgaa gttttttttgg tctgcatgtt   8160
attttttcct cgaaatatgt tttgagtcca acaagtgatt cacttgggat tcagaaagtt   8220
gttttctcaa tatgtaacag tttttttcta tggagaaaaa tcatagggac cgttggtttt   8280
ggcttcttta attttgagct cagattaaac ccattttacc cggtgttctt ggcagaattg   8340
aaaacagtac gtagtaccgc gcctaccatg tgtgttgaga ccgagaacaa cgatggaatc   8400
cctactgtgg agatcgcttt cgatggagag agagaaagag ctgaggctaa cgtgaagttg   8460
tctgctgaga agatggaacc tgctgctttg gctaagacct tcgctagaag atacgtggtt   8520
atcgagggag ttgagtacga tgtgaccgat ttcaaacatc ctggaggaac cgtgattttc   8580
tacgctctct ctaacactgg agctgatgct actgaggctt tcaaggagtt ccaccacaga   8640
tctagaaagg ctaggaaggc tttggctgct ttgccttcta gacctgctaa gaccgctaaa   8700
gtggatgatg ctgagatgct ccaggatttc gctaagtgga gaaaggagtt ggagagggac   8760
ggattcttca agccttctcc tgctcatgtt gcttacagat tcgctgagtt ggctgctatg   8820
tacgctttgg gaacctactt gatgtacgct agatacgttg tgtcctctgt gttggtttac   8880
gcttgcttct tcggagctag atgtggatgg gttcaacacg agggaggaca ctcttctttg   8940
accggaaaca tctggtggga taagagaatc caagctttca ctgctggatt cggattggct   9000
ggatctggag atatgtggaa ctccatgcac aacaagcacc acgctactcc tcaaaaagtg   9060
aggcacgata tggatttgga taccactcct gctgttgctt tcttcaacac cgctgtggag   9120
gataatagac ctaggggatt ctctaagtac tggctcagat tgcaagcttg gaccttcatt   9180
cctgtgactt ctggattggt gttgctcttc tggatgttct tcctccaccc ttctaaggct   9240
ttgaagggag gaaagtacga ggagcttgtg tggatgttgg ctgctcacgt gattagaacc   9300
tggaccatta aggctgttac tggattcacc gctatgcaat cctacggact cttcttggct   9360
acttcttggg tttccggatg ctacttgttc gctcacttct ctacttctca cacccacttg   9420
gatgttgttc ctgctgatga gcacttgtct tgggttaggt acgctgtgga tcacaccatt   9480
gatatcgatc cttctcaggg atgggttaac tggttgatgg gatacttgaa ctgccaagtg   9540
attcaccacc tcttcccttc tatgcctcaa ttcagacaac ctgaggtgtc cagaagattc   9600
gttgctttcg ctaagaagtg gaacctcaac tacaaggtga tgacttatgc tggagcttgg   9660
aaggctactt tgggaaacct cgataatgtg ggaaagcact actacgtgca cggacaacac   9720
tctggaaaga ccgcttgatt aatgaaggcc gcctcgaccg tacccccctgc agatagacta   9780
```

```
tactatgttt tagcctgcct gctggctagc tactatgtta tgttatgttg taaaataaac   9840
acctgctaag gtatatctat ctatatttta gcatggcttt ctcaataaat tgtctttcct   9900
tatcgtttac tatcttatac ctaataatga aataataata tcacatatga ggaacggggc   9960
aggtttaggc atatatatac gagtgtaggg cggagtgggg ctacgtagcg tcacgtgacg  10020
ttacctaagc ctaggtagcc tcagctgacg ttacgtaacg ctaggtaggc tcagctgaca  10080
cgggcaggac atagggacta ctacaagcat agtatgcttc agacaaagag ctaggaaaga  10140
actcttgatg gaggttaaga gaaaaaagtg ctagaggggc atagtaatca aacttgtcaa  10200
aaccgtcatc atgatgaggg atgacataat ataaaaagtt gactaaggtc ttggtagtac  10260
tctttgatta gtattatata ttggtgagaa catgagtcaa gaggagacaa gaaaccgagg  10320
aaccatagtt tagcaacaag atggaagttg caaagttgag ctagccgctc gattagttac  10380
atctcctaag cagtactaca aggaatggtc tctatacttt catgtttagc acatggtagt  10440
gcggattgac aagttagaaa cagtgcttag gagacaaaga gtcagtaaag gtattgaaag  10500
agtgaagttg atgctcgaca ggtcaggaga agtccctccg ccagatggtg actaccaagg  10560
ggttggtatc agctgagacc caaataagat tcttcggttg aaccagtggt tcgaccgaga  10620
ctcttagggt gggatttcac tgtaagattt gtgcattttg ttgaatataa attgacaatt  10680
tttttatttt aattatagat tatttagaat gaattacata tttagtttct aacaaggata  10740
gcaatggatg ggtatgggta caggttaaac atatctatta cccacccatc tagtcgtcgg  10800
gttttacacg tacccacccg tttacataaa ccagaccgga attttaaacc gtacccgtcc  10860
gttagcgggt ttcagattta cccgtttaat cgggtaaaac ctgattacta aatatatatt  10920
ttttatttga taaacaaaac aaaaatgtta atattttcat attggatgca attttaagaa  10980
acacatattc ataaatttcc atatttgtag gaaaataaaa agaaaaatat attcaagaac  11040
acaaatttca ccgacatgac ttttattaca gagttggaat tagatctaac aattgaaaaa  11100
ttaaaattaa gatagaatat gttgaggaac atgacatagt ataatgctgg gttacccgtc  11160
gggtaggtat cgaggcggat actactaaat ccatcccact cgctatccga taatcactgg  11220
tttcgggtat acccattccc gtcaacaggc ctttttaacc ggataatttc aacttatagt  11280
gaatgaattt tgaataaata gttagaatac caaaatcctg gattgcattt gcaatcaaat  11340
tttgtgaacc gttaaatttt gcatgtactt gggatagata taatagaacc gaattttcat  11400
tagtttaatt tataacttac tttgttcaaa gaaaaaaaat atctatccaa tttacttata  11460
ataaaaaata atctatccaa gttacttatt ataatcaact tgtaaaaagg taagaataca  11520
aatgtggtag cgtacgtgtg attatatgtg acgaaatgtt atatctaaca aaagtccaaa  11580
ttcccatggt aaaaaaaatc aaaatgcatg gcaggctgtt tgtaaccttg gaataagatg  11640
ttggccaatt ctggagccgc cacgtacgca agactcaggg ccacgttctc ttcatgcaag  11700
gatagtagaa caccactcca cccacctcct atattagacc tttgcccaac cctccccaac  11760
tttcccatcc catccacaaa gaaaccgaca tttttatcat aaatctggtg cttaaacact  11820
ctggtgagtt ctagtacttc tgctatgatc gatctcatta ccatttctta aatttctctc  11880
cctaaatatt ccgagttctt gatttttgat aacttcaggt tttctctttt tgataaatct  11940
ggtctttcca tttttttttt ttgtggttaa tttagtttcc tatgttcttc gattgtatta  12000
tgcatgatct gtgtttggat tctgttagat tatgtattgg tgaatatgta tgtgtttttg  12060
catgtctggt tttggtctta aaaatgttca aatctgatga tttgattgaa gctttttttag  12120
```

-continued

```
tgttggtttg attcttctca aaactactgt taatttacta tcatgttttc caactttgat  12180
tcatgatgac acttttgttc tgctttgtta taaaattttg gttggtttga ttttgtaatt  12240
atagtgtaat tttgttagga atgaacatgt tttaatactc tgttttcgat ttgtcacaca  12300
ttcgaattat taatcgataa tttaactgaa aattcatggt tctagatctt gttgtcatca  12360
gattatttgt ttcgataatt catcaaatat gtagtccttt tgctgatttg cgactgtttc  12420
atttttctc aaaattgttt tttgttaagt ttatctaaca gttatcgttg tcaaaagtct  12480
ctttcatttt gcaaaatctt cttttttttt ttgtttgtaa ctttgttttt taagctacac  12540
atttagtctg taaaatagca tcgaggaaca gttgtcttag tagacttgca tgttcttgta  12600
acttctattt gtttcagttt gttgatgact gctttgattt tgtaggtcaa aggcgcaccc  12660
taccatggat gcttataacg ctgctatgga taagattgga gctgctatca tcgattggag  12720
tgatccagat ggaaagttca gagctgatag ggaggattgg tggttgtgcg atttcagatc  12780
cgctatcacc attgctctca tctacatcgc tttcgtgatc ttgggatctg ctgtgatgca  12840
atctctccca gctatggacc catacccctat caagttcctc tacaacgtgt ctcaaatctt  12900
cctctgcgct tacatgactg ttgaggctgg attcctcgct tataggaacg gatacaccgt  12960
tatgccatgc aaccacttca acgtgaacga tccaccagtt gctaacttgc tctggctctt  13020
ctacatctcc aaagtgtggg atttctggga taccatcttc attgtgctcg gaaagaagtg  13080
gagacaactc tctttcttgc acgtgtacca ccacaccacc atcttcctct tctactggtt  13140
gaacgctaac gtgctctacg atggagatat cttcttgacc atcctcctca acggattcat  13200
tcacaccgtg atgtacacct actacttcat ctgcatgcac accaaggatt ctaagaccgg  13260
aaagtctttg ccaatctggt ggaagtcatc tttgaccgct ttccaactct tgcaattcac  13320
catcatgatg tcccaagcta cctacttggt tttccacgga tgcgataagg tttccctcag  13380
aatcaccatc gtgtacttcg tgtacattct ctcccttttc ttcctcttcg ctcagttctt  13440
cgtgcaatcc tacatggctc caaagaagaa gaagtccgct tgatgttaat gaaggccgca  13500
gatatcagat ctggtcgacc tagaggatcc ccggccgcaa agataataac aaaagcctac  13560
tatataacgt acatgcaagt attgtatgat attaatgttt ttacgtacgt gtaaacaaaa  13620
ataattacgt ttgtaacgta tggtgatgat gtggtgcact aggtgtaggc cttgtattaa  13680
taaaaagaag tttgttctat atagagtggt ttagtacgac gatttattta ctagtcggat  13740
tggaatagag aaccgaattc ttcaatcctt gcttttgatc aagaattgaa accgaatcaa  13800
atgtaaaagt tgatatattt gaaaaacgta ttgagcttat gaaaatgcta atactctcat  13860
ctgtatggaa aagtgacttt aaaaccgaac ttaaaagtga caaaagggga atatcgcatc  13920
aaaccgaatg aaaccgatct acgtaggctc agctgagctt agctaagcct acctagcctc  13980
acgtgagatt atgtaaggct aggtagcgtc acgtgacgtt acctaacact agctagcgtc  14040
agctgagctt agctaaccct acgtagcctc acgtgagctt acctaacgct acgtagcctc  14100
acgtgactaa ggatgaccta cccattcttg agacaaatgt tacattttag tatcagagta  14160
aaatgtgtac ctataactca aattcgattg acatgtatcc attcaacata aaattaaacc  14220
agcctgcacc tgcatccaca tttcaagtat tttcaaaccg ttcggctcct atccaccggg  14280
tgtaacaaga cggattccga atttggaaga ttttgactca aattcccaat ttatattgac  14340
cgtgactaaa tcaactttaa cttctataat tctgattaag ctcccaattt atattcccaa  14400
cggcactacc tccaaaattt atagactctc atccccttttt aaaccaactt agtaaacgtt  14460
ttttttttaa ttttatgaag ttaagttttt accttgtttt taaaaagaat cgttcataag  14520
```

```
atgccatgcc agaacattag ctacacgtta cacatagcat gcagccgcgg agaattgttt  14580
ttcttcgcca cttgtcactc ccttcaaaca cctaagagct tctctctcac agcacacaca  14640
tacaatcaca tgcgtgcatg cattattaca cgtgatcgcc atgcaaatct cctttatagc  14700
ctataaatta actcatcggc ttcactcttt actcaaacca aaactcatca atacaaacaa  14760
gattaaaaac atttcacgat ttggaatttg attcctgcga tcacaggtat gacaggttag  14820
attttgtttt gtatagttgt atacatactt ctttgtgatg ttttgtttac ttaatcgaat  14880
ttttggagtg ttttaaggtc tctcgtttag aaatcgtgga aaatatcact gtgtgtgtgt  14940
tcttatgatt cacagtgttt atgggtttca tgttctttgt tttatcattg aatgggaaga  15000
aatttcgttg ggatacaaat ttctcatgtt cttactgatc gttattagga gtttggggaa  15060
aaaggaagag tttttttggt tggttcgagt gattatgagg ttatttctgt atttgattta  15120
tgagttaatg gtcgttttaa tgttgtagac cgccatggct attttgaacc ctgaggctga  15180
ttctgctgct aacctcgcta ctgattctga ggctaagcaa agacaattgg ctgaggctgg  15240
atacactcac gttgagggtg ctcctgctcc tttgcctttg gagttgcctc acttctctct  15300
cagagatctc agagctgcta ttcctaagca ctgcttcgag agatctttcg tgacctccac  15360
ctactacatg atcaagaacg tgttgacttg cgctgctttg ttatacgctg ctaccttcat  15420
tgatagagct ggagctgctg cttatgtttt gtggcctgtg tactggttct tccagggatc  15480
ttacttgact ggagtgtggg ttatcgctca cgagtgtgga caccaggctt attgctcttc  15540
tgaggtggtg aacaacttga ttggactcgt gttgcactct gctttgttgg tgccttacca  15600
ctcttggaga atctctcaca gaaagcacca ctccaacact ggatcttgcg agaacgatga  15660
ggttttcgtt cctgtgacca gatctgtgtt ggcttcttct tggaacgaga ccttggagga  15720
ttctcctctc taccaactct accgtatcgt gtacatgttg gttgttggat ggatgcctgg  15780
atacctcttc ttcaacgcta ctggacctac taagtactgg ggaaagtcta ggtctcactt  15840
caacccttac tccgctatct atgctgatag ggagaggtgg atgatcgtgc tctccgatat  15900
tttcttggtg gctatgttgg ctgttttggc tgctttggtg cacactttct ccttcaacac  15960
gatggtgaag ttctacgtgg tgccttactt cattgtgaac gcttacttgg tgttgattac  16020
ctacctccaa cacaccgata cctacatccc tcacttcaga gagggagagt ggaattggtt  16080
gagaggagct ttgtgcactg tggatagatc atttggtcca ttcctcgatt ctgtggtgca  16140
tagaatcgtg gatacccacg tttgccacca tatcttctcc aagatgcctt tctatcactg  16200
cgaggaggct accaacgcta ttaagcctct cctcggaaag ttctacttga aggatactac  16260
tcctgttcct gttgctctct ggagatctta cacccactgc aagttcgttg aggatgatgg  16320
aaaggtggtg ttctacaaga acaagttata gttaatgaat aattgattgg ttcgagtatt  16380
atggcattgg gaaaactgtt tttcttgtac catttgttgt gcttgtaatt tactgtgttt  16440
tttattcggt tttcgctatc gaactgtgaa atggaaatgg atggagaaga gttaatgaat  16500
gatatggtcc ttttgttcat tctcaaatta atattatttg ttttttctct tatttgttgt  16560
gtgttgaatt tgaaattata agagatatgc aaacattttg ttttgagtaa aaatgtgtca  16620
aatcgtggcc tctaatgacc gaagttaata tgaggagtaa aacacttgta gttgtaccat  16680
tatgcttatt cactaggcaa caaatatatt ttcagaccta gaaaagctgc aaatgttact  16740
gaatacaagt atgtcctctt gtgttttaga catttatgaa ctttccttta tgtaattttc  16800
cagaatcctt gtcagattct aatcattgct ttataattat agttatactc atggatttgt  16860
```

```
agttgagtat gaaaatattt tttaatgcat tttatgactt gccaattgat tgacaacatg  16920
catcaatcta gctagcctca gctgacgtta cgtaacgcta ggtagcgtca cgtgacgtta  16980
gctaacgcta ggtagcgtca gctgagctta cgtaagcgca cagatgaata ctagctgttg  17040
ttcacagttc tagtgtctcc tcattacgtg aattcaagct acgatcacta tctcaactcc  17100
tacataaaca tcagaatgct acaaaactat gcacaaaaac aaaagctaca tctaatacgt  17160
gaatcaatta ctctcatcac aagaaagaag atttcaatca ccgtcgagaa ggaggattca  17220
gttaattgaa tcaaagttcc gatcaaactc gaagactggt gagcacgagg acgacgaaga  17280
agagtgtctc gaagatacaa caagcaagaa atctactgag tgacctcctg aagttattgg  17340
cgcgattgag agaatcaatc cgaattaatt tcggggaaaa agataaatta gatactaagc  17400
gatgggcttg ggctgggcta agaaacaggt ggcaattggg ctggaggacc ccgcgattca  17460
tagcttccga tagcccaaaa aaaaacggat aacatattta tcgggtattt gaatttcagt  17520
gaaataagat attttctttt tgttaggaaa attttagaaa ataatggaaa ttaaatagcg  17580
attatgttac aagatacgat cagcatcggg cagtgcaaaa tgctatagct tcccaagatt  17640
tgatcctttt gggttatctc ctaatgacaa ttagtttagg attttgaaac ttatattaat  17700
actattatcc gacaacactt gtttcagctt cttattttaa catttttgt ttttttctat  17760
tcttcttccc atcagcattt tctttttaaa aaattgaata ctttaacttt ttaaaaattt  17820
cacaatgatc agatgatatt atggaagatc tcaagagtta aatgtatcca tcttggggca  17880
ttaaaaccgg tgtacgggat gataaataca gactttatat catatgatag ctcagtaatt  17940
catatttatc acgttgctaa aaaaattata aggtactagt agtcaacaaa atcaattaaa  18000
gagaaagaaa gaaacgcatg tgaagagagt ttacaactgg aaaagtaaaa taaaaattaa  18060
cgcatgttga atgctgacat gtcagtatgt ccatgaatcc acgtatcaag cgccattcat  18120
cgatcgtctt cctctttcta aatgaaaaca acttcacaca tcacaacaaa caatacacac  18180
aagacccccct ctctctcgtt gtctctctgc cagcgaccaa atcgaagctt gagaagaaca  18240
agaaggggtc aaaccatggc ttctacatct gctgctcaag acgctgctcc ttacgagttc  18300
ccttctctca ctgagatcaa gagggctctt ccttctgagt gtttcgaggc ttctgttcct  18360
ctttctctct actacaccgc tagatctctt gctcttgctg gatctctcgc tgttgctctc  18420
tcttacgcta gagctttgcc tcttgttcag gctaacgctc ttcttgatgc tactctctgc  18480
actggatacg ttcttctcca gggaatcgtt ttctggggat tcttcaccgt tggtcacgat  18540
tgtggacacg gagctttctc tagatctcac gtgctcaact tctctgttgg aaccctcatg  18600
cactctatca tccttacccc tttcgagtct tggaagctct ctcacagaca ccaccacaag  18660
aacaccggaa acatcgataa ggacgagatc ttctaccctc aaagagaggc tgattctcac  18720
cctgtttcta gacaccttgt gatgtctctt ggatctgctt ggttcgctta cctttttcgct  18780
ggattccctc ctagaaccat gaaccacttc aacccttggg aggctatgta tgttagaaga  18840
gtggctgctg tgatcatctc tctcggagtt cttttcgctt tcgctggact ctactcttac  18900
ctcaccttcg ttcttggatt caccactatg gctatctact acttcggacc tctcttcatc  18960
ttcgctacca tgcttgttgt taccactttc ctccaccaca acgatgagga gacaccttgg  19020
tacgctgatt ctgagtggac ttacgtgaag ggaaacctct cttctgtgga cagatcttac  19080
ggtgctctca tcgacaacct tagccacaac atcggaactc accagatcca ccacctcttc  19140
cctatcatcc ctcactacaa gctcaacgat gctactgctg ctttcgctaa ggctttccct  19200
gagcttgtta ggaaaaacgc tgctcctatc atcccaactt tcttcaggat ggctgctatg  19260
```

```
tacgctaagt acggagttgt tgacactgat gctaagacct tcactctcaa ggaggctaag  19320
gctgctgcta agactaagtc atcttgatga ttaatgaata attgattgta catactatat  19380
tttttgttta ccttgtgtta gtttaatgtt cagtgtcctc tctttattgt ggcacgtctc  19440
tttgttgtat gttgtgtcta tacaaagttg aaataatgga aagaaaagga agagtgtaat  19500
ttgttttgtt ttaagtgttt ataaatatat atatataggt catttagata gttctaggtt  19560
tctataaaac tctctctctg gaagtagaat ctgtttttga gaggatccag ttgcctacta  19620
atctccccca aaacccttca agcttaacct tcctcttcac aacaacagag gaaacacatc  19680
tcttgagctc tgagttctct tctttgagca tgtctatcgc taaactcatc tgccttatag  19740
cttccctctt ctcttcatct ctctctctca ccatttcgct gtaaaactta ttctcctccc  19800
tcagcctctc tatctcttcc ttcagcatct cacaattccc accataatcg actgaggatg  19860
attcaccgtc atcaacttca gactcagcgt tgtagtcgtc atgagtctca caagccttgg  19920
accaagaaga ctcatcatcg caagttgatg atttatcatg atgcttctct gagccgtgtt  19980
tgctacgtag cgtcacgtga cgttacctaa gcctaggtag cctcagctga cgttacgtaa  20040
cgctaggtag gctcagctga ctgcagcaaa tttacacatt gccactaaac gtctaaaccc  20100
ttgtaatttg tttttgtttt actatgtgtg ttatgtattt gatttgcgat aaatttttat  20160
atttggtact aaatttataa caccttttat gctaacgttt gccaacactt agcaatttgc  20220
aagttgatta attgattcta aattattttt gtcttctaaa tacatatact aatcaactgg  20280
aaatgtaaat atttgctaat atttctacta taggagaatt aaagtgagtg aatatggtac  20340
cacaaggttt ggagatttaa ttgttgcaat gctgcatgga tggcatatac accaaacatt  20400
caataattct tgaggataat aatggtacca cacaagattt gaggtgcatg aacgtcacgt  20460
ggacaaaagg tttagtaatt tttcaagaca acaatgttac cacacacaag ttttgaggtg  20520
catgcatgga tgccctgtgg aaagtttaaa aatattttgg aaatgatttg catggaagcc  20580
atgtgtaaaa ccatgacatc cacttggagg atgcaataat gaagaaaact acaaatttac  20640
atgcaactag ttatgcatgt agtctatata atgaggattt tgcaatactt tcattcatac  20700
acactcacta agttttacac gattataatt tcttcatagc cagtactgtt taagcttcac  20760
tgtctctgaa tcggcaaagg taaacgtatc aattattcta caaacccttt tatttttctt  20820
ttgaattacc gtcttcattg gttatatgat aacttgataa gtaaagcttc aataattgaa  20880
tttgatctgt gttttttttgg ccttaatact aaatccttac ataagctttg ttgcttctcc  20940
tcttgtgagt tgagtgttaa gttgtaataa tggttcactt tcagctttag aagaaacgcg  21000
ccttccatgg ctacaaagga ggcttacgtt ttcccaactc tcaccgagat caagagatct  21060
ctcccaaagg attgcttcga ggcttctgtg cctttgtctc tctactacac tgtgagatgc  21120
ttggttattg ctgtggcttt gaccttcgga ttgaactacg ctagagcttt gccagaggtt  21180
gagtctttct gggctttgga tgctgctttg tgcactggat atatcctcct ccagggaatt  21240
gtgttctggg gattcttcac tgttggacac gatgctggac acggagcttt ctctagatac  21300
cacctcttga acttcgttgt gggaaccttc atgcactctc tcatcttgac cccattcgag  21360
tcttggaagt tgacccacag acaccaccac aagaacaccg gaaacatcga tagagatgag  21420
gtgttctacc cacagagaaa ggctgatgat cacccattgt ccaggaactt gatcttggct  21480
ttgggagctg cttggcttgc ttatttggtg gagggattcc caccaagaaa ggtgaaccac  21540
ttcaacccat tcgagccact tttgtgaga caagtgtccg ctgtggttat ctctttgctc  21600
```

```
gctcacttct tcgttgctgg actctctatc tacttgtctc tccagttggg acttaagacc  21660
atggctatct actactacgg accagttttc gtgttcggat ctatgttggt gattaccacc  21720
ttcttgcacc acaacgatga ggagactcca tggtatgctg attctgagtg gacttacgtg  21780
aagggaaact tgtcctctgt ggatagatct tacggtgctc tcatcgataa cctctcccac  21840
aacatcggaa ctcaccagat ccaccacctc ttcccaatta tcccacacta caagctcaag  21900
aaggctactg ctgctttcca ccaagctttc ccagagcttg tgagaaagtc cgatgagcca  21960
atcatcaagg ctttcttcag agtgggaagg ttgtatgcta actacggagt ggttgatcaa  22020
gaggctaagc tcttcacttt gaaggaggct aaggctgcta ctgaagctgc tgctaagacc  22080
aagtctacct gattaatgaa tcgacaagct cgagtttctc cataataatg tgtgagtagt  22140
tcccagataa gggaattagg gttcctatag ggtttcgctc atgtgttgag catataagaa  22200
acccttagta tgtatttgta tttgtaaaat acttctatca ataaaatttc taattcctaa  22260
aaccaaaatc cagtactaaa atccagatcc cccgaattaa ttcggcgtta attcagctac  22320
gtaggctcag ctgagcttac ctaaggctac gtaggctcac gtgacgttac gtaaggctac  22380
gtagcgtcac gtgagcttac ctaactctag ctagcctcac gtgaccttag ctaacactag  22440
gtagcgtcag cacagatgaa tactagctgt tgttcacagt tctagtgtct cctcattacg  22500
tgaattcaag ctacgatcac tatctcaact cctacataaa catcagaatg ctacaaaact  22560
atgcacaaaa acaaaagcta catctaatac gtgaatcaat tactctcatc acaagaaaga  22620
agatttcaat caccgtcgag aaggaggatt cagttaattg aatcaaagtt ccgatcaaac  22680
tcgaagactg gtgagcacga ggacgacgaa gaagagtgtc tcgaagatac aacaagcaag  22740
aaatctactg agtgacctcc tgaagttatt ggcgcgattg agagaatcaa tccgaattaa  22800
tttcggggaa aaagataaat tagatactaa gcgatgggct tgggctgggc taagaaacag  22860
gtggcaattg ggctggagga ccccgcgatt catagcttcc gatagcccaa aaaaaaacgg  22920
ataacatatt tatcgggtat ttgaatttca gtgaaataag atattttctt tttgttagga  22980
aaattttaga aaataatgga aattaaatag cgattatgtt acaagatacg atcagcatcg  23040
ggcagtgcaa aatgctatag cttcccaaga tttgatcctt ttgggttatc tcctaatgac  23100
aattagttta ggattttgaa acttatatta atactattat ccgacaacac ttgtttcagc  23160
ttcttatttt aacatttttt gttttttct attcttcttc ccatcagcat tttcttttta  23220
aaaaattgaa tactttaact ttttaaaaat ttcacaatga tcagatgata ttatggaaga  23280
tctcaagagt taaatgtatc catcttgggg cattaaaacc ggtgtacggg atgataaata  23340
cagactttat atcatatgat agctcagtaa ttcatattta tcacgttgct aaaaaaatta  23400
taaggtacta gtagtcaaca aaatcaatta aagagaaaga aagaaacgca tgtgaagaga  23460
gtttacaact ggaaaagtaa aataaaaatt aacgcatgtt gaatgctgac atgtcagtat  23520
gtccatgaat ccacgtatca agcgccattc atcgatcgtc ttcctctttc taaatgaaaa  23580
caacttcaca catcacaaca aacaatacac acaagacccc ctctctctcg ttgtctctct  23640
gccagcgacc aaatcgaagc ttgagaagaa caagaagggg tcaaaccatg ggaaaaggat  23700
ctgagggaag atctgctgct agagagatga ctgctgaggc taacggagat aagagaaaga  23760
ccatcctcat tgagggagtg ttgtacgatg ctaccaactt caaacaccca ggaggttcca  23820
ttattaactt cctcaccgag ggagaagctg gagttgatgc tacccaagct tacagagagt  23880
tccatcagag atccggaaag gctgataagt acctcaagtc cctcccaaag ttggatgctt  23940
ctaaggtgga gtctaggttc tctgctaagg agcaggctag aagggacgct atgaccaggg  24000
```

```
attacgctgc tttcagagag gagttggttg ctgagggata cttcgatcca tctatcccac  24060
acatgatcta cagagtggtg gagattgtgg ctttgttcgc tttgtctttc tggttgatgt  24120
ctaaggcttc tccaacctct ttggttttgg gagtggtgat gaacggaatc gctcaaggaa  24180
gatgcggatg ggttatgcac gagatgggac acggatcttt cactggagtt atctggctcg  24240
atgataggat gtgcgagttc ttctacggag ttggatgtgg aatgtctgga cactactgga  24300
agaaccagca ctctaagcac cacgctgctc caaacagatt ggagcacgat gtggatttga  24360
acaccttgcc actcgttgct ttcaacgaga gagttgtgag gaaggttaag ccaggatctt  24420
tgttggcttt gtggctcaga gttcaggctt atttgttcgc tccagtgtct tgcttgttga  24480
tcggattggg atggaccttg tacttgcacc caagatatat gctcaggacc aagagacaca  24540
tggagtttgt gtggatcttc gctagatata tcggatggtt ctccttgatg ggagctttgg  24600
gatattctcc tggaacttct gtgggaatgt acctctgctc tttcggactt ggatgcatct  24660
acatcttcct ccaattcgct gtgtctcaca cccacttgcc agttaccaac ccagaggatc  24720
aattgcactg gcttgagtac gctgctgatc acaccgtgaa catctctacc aagtcttggt  24780
tggttacctg gtggatgtct aacctcaact tccaaatcga gcaccacttg ttcccaaccg  24840
ctccacaatt caggttcaag gagatctctc caagagttga ggctctcttc aagagacaca  24900
acctccctta ctacgatttg ccatacacct ctgctgtttc tactaccttc gctaacctct  24960
actctgttgg acactctgtt ggagctgata ccaagaagca ggattgatga ttaatgaata  25020
attgattgta catactatat tttttgttta ccttgtgtta gtttaatgtt cagtgtcctc  25080
tctttattgt ggcacgtctc tttgttgtat gttgtgtcta tacaaagttg aaataatgga  25140
aagaaaagga agagtgtaat ttgttttgtt ttaagtgttt ataaatatat atatataggt  25200
catttagata gttctaggtt tctataaaac tctctctctg gaagtagaat ctgtttttga  25260
gaggatccag ttgcctacta atctccccca aaacccttca agcttaacct tcctcttcac  25320
aacaacagag gaaacacatc tcttgagctc tgagttctct tctttgagca tgtctatcgc  25380
taaactcatc tgccttatag cttccctctt ctcttcatct ctctctctca ccatttcgct  25440
gtaaaactta ttctcctccc tcagcctctc tatctcttcc ttcagcatct cacaattccc  25500
accataatcg actgaggatg attcaccgtc atcaacttca gactcagcgt tgtagtcgtc  25560
atgagtctca caagccttgg accaagaaga ctcatcatcg caagttgatg atttatcatg  25620
atgcttctct gagccgtgtt tgctacctag agtcagctga gcttagctaa cgctagctag  25680
tgtcagctga cgttacgtaa ggctaactag cgtcacgtga ccttacgtaa cgctacgtag  25740
gctcagctga gcttagctaa ccctagctag tgtcacgtga gcttacgcta ctatagaaaa  25800
tgtgttatat cgacatgacc agacaaaggg gcaacagtta acaaaacaat taattctttc  25860
atttgagatt aaggaaggta aggtactaaa aagattaaaa aaaatgagct tatctctttg  25920
tttctgtaat aataatataa gtgtgataaa cttttaatat aataattgta attaggtttt  25980
ctacagatga gcaccactca gagacaagat aagaagaaaa caattttgtt aaacatgatt  26040
atagaaactt ttagttaagt cttgaagtat caatataaca aaaaaaagta cacacgacta  26100
tgacaataaa cccactaccg tcaggttatc atttcgatga aatgttttga tatcattaaa  26160
tataacagtc acaaaaaatc atctaattat aacaatataa cttatacata tatttaacta  26220
aaaacttaga gtttttgtaa tgattctaat tgatgattag agtttataga aatacaatta  26280
aataaaaaat ataattttaa aaaaacatag taaagtcaat gagatcctct ctgacctcag  26340
```

```
tgatcattta gtcatgtatg tacaacaatc attgttcatc acatgactgt aaaataaata  26400
aggataaact tgggaatata tataatatat tgtattaaat aaaaaaggga aatacaaata  26460
tcaattttag attcccgagt tgacacaact caccatgcac gctgccacct cagctcccag  26520
ctctcgtcac atgtctcatg tcagttaggt ctttggtttt tagtctttga cacaactcgc  26580
catgcatgtt gccacgtgag ctcgttcctc ttcccatgat ctcaccactg ggcatgcatg  26640
ctgccacctc agctggcacc tcttctctat atgtccctag aggccatgca cagtgccacc  26700
tcagcactcc tctcagaacc catacgtacc tgccaatcgg cttctctcca taaatatcta  26760
tttaaattat aactaattat ttcatatact taattgatga cgtggatgca ttgccatcgt  26820
tgtttaataa ttgttaatta cgacatgata aataaaatga aagtaaaaag tacgaaagat  26880
tttccatttg ttgttgtata aatagagaag tgagtgatgc ataatgcatg aatgcatgac  26940
cgcgccacca tgactgttgg atacgacgag gagatcccat tcgagcaagt tagggctcat  27000
aacaagccag acgacgcttg gtgtgctatt cacggacacg tgtacgacgt taccaagttc  27060
gcttcagttc acccaggagg agatattatc ttgctcgctg ctggaaagga agctactgtc  27120
ctctacgaga cctaccatgt tagaggagtg tctgacgctg tgctcagaaa gtacagaata  27180
ggaaagttgc cagacggaca aggaggagct aacgagaagg agaagagaac cttgtctgga  27240
ttgtcctctg cttcttacta cacctggaac tccgatttct acagagtgat gagggagaga  27300
gttgtggcta gattgaagga gagaggaaag gctagaagag gaggatacga actctggatc  27360
aaggctttct tgctccttgt tggattctgg tcctctcttt actggatgtg caccctcgat  27420
ccatctttcg gagctatctt ggctgctatg tctttgggag tgttcgctgc ttttgttgga  27480
acctgcatcc aacacgatgg aaaccacgga gctttcgctc aatctagatg ggttaacaag  27540
gtggcaggat ggactttgga tatgatcgga gcttctggaa tgacttggga gttccaacac  27600
gtgttgggac accacccata cactaacttg atcgaggagg agaacggatt gcaaaaggtg  27660
tccggaaaga agatggatac caagttggct gatcaagagt ctgatccaga tgtgttctcc  27720
acctacccaa tgatgagatt gcacccttgg caccagaaga ggtggtatca caggttccag  27780
cacatctacg gacctttcat cttcggattc atgaccatca acaaggtggt gactcaagat  27840
gttggagtgg tgttgagaaa gagactcttc caaatcgatg ctgagtgcag atatgcttcc  27900
ccaatgtacg ttgctaggtt ctggattatg aaggctttga ccgtgttgta tatggttgct  27960
ttgccttgtt atatgcaagg accttggcac ggattgaaac tcttcgctat cgctcacttc  28020
acttgcggag aggttttggc taccatgttc atcgtgaacc acattatcga gggagtgtct  28080
tacgcttcta aggatgctgt taagggaact atggctccac caaagactat gcacggagtg  28140
accccaatga acaacactag aaaggaggtt gaggctgagg cttctaagtc tggagctgtg  28200
gttaagtctg tgccattgga tgattgggct gctgttcagt gccaaacctc tgtgaactgg  28260
tctgttggat cttggttttg gaaccacttc tctggaggac tcaaccacca aatcgagcac  28320
cacctcttcc caggattgtc tcacgagacc tactaccaca tccaagacgt ggttcaatct  28380
acctgtgctg agtacggagt tccataccaa cacgagccat ctttgtggac tgcttactgg  28440
aagatgctcg aacaccttag acaattggga aacgaggaga ctcacgagtc atggcagaga  28500
gctgcttgat taatgaacta agactcccaa aaccaccttc cctgtgacag ttaaaccctg  28560
cttatacctt tcctcctaat aatgttcatc tgtcacacaa actaaaataa ataaaatggg  28620
agcaataaat aaaatgggag ctcatatatt tacaccattt acactgtcta ttattcacca  28680
tgccaattat tacttcataa ttttaaaatt atgtcatttt taaaaattgc ttaatgatgg  28740
```

```
aaaggattat tataagttaa aagtataaca tagataaact aaccacaaaa caaatcaata  28800
taaactaact tactctccca tctaattttt atttaaattt ctttacactt ctcttccatt  28860
tctatttcta caacattatt taacattttt attgtatttt tcttactttc taactctatt  28920
catttcaaaa atcaatatat gtttatcacc acctctctaa aaaaaacttt acaatcattg  28980
gtccagaaaa gttaaatcac gagatggtca ttttagcatt aaaacaacga ttcttgtatc  29040
actatttttc agcatgtagt ccattctctt caaacaaaga cagcggctat ataatcgttg  29100
tgttatattc agtctaaaac aactagctag cctcagctga cgttacgtaa cgctaggtag  29160
cgtcacgtga cgttagctaa cgctaggtag cgtcagctga gcttacgtaa gcgccacggg  29220
caggacatag ggactactac aagcatagta tgcttcagac aaagagctag gaaagaactc  29280
ttgatggagg ttaagagaaa aaagtgctag aggggcatag taatcaaact tgtcaaaacc  29340
gtcatcatga tgagggatga cataatataa aaagttgact aaggtcttgg tagtactctt  29400
tgattagtat tatatattgg tgagaacatg agtcaagagg agacaagaaa ccgaggaacc  29460
atagtttagc aacaagatgg aagttgcaaa gttgagctag ccgctcgatt agttacatct  29520
cctaagcagt actacaagga atggtctcta tactttcatg tttagcacat ggtagtgcgg  29580
attgacaagt tagaaacagt gcttaggaga caaagagtca gtaaaggtat tgaaagagtg  29640
aagttgatgc tcgacaggtc aggagaagtc cctccgccag atggtgacta ccaaggggtt  29700
ggtatcagct gagacccaaa taagattctt cggttgaacc agtggttcga ccgagactct  29760
tagggtggga tttcactgta agatttgtgc attttgttga atataaattg acaatttttt  29820
ttatttaatt atagattatt tagaatgaat tacatattta gtttctaaca aggatagcaa  29880
tggatgggta tgggtacagg ttaaacatat ctattaccca cccatctagt cgtcgggttt  29940
tacacgtacc cacccgttta cataaaccag aacggaattt taaaccgtac ccgtccgtta  30000
gcgggtttca gatttacccg tttaatcggg taaaacctga ttactaaata tatatttttt  30060
atttgataaa caaaacaaaa atgttaatat tttcatattg gatgcaattt taagaaacac  30120
atattcataa atttccatat ttgtaggaaa ataaaaagaa aaatatattc aagaacacaa  30180
atttcaccga catgactttt attacagagt tggaattaga tctaacaatt gaaaaattaa  30240
aattaagata gaatatgttg aggaacatga catagtataa tgctgggtta cccgtcgggt  30300
aggtatcgag gcggatacta ctaaatccat cccactcgct atccgataat cactggtttc  30360
gggtataccc attcccgtca acaggccttt ttaaccggat aatttcaact tatagtgaat  30420
gaattttgaa taaatagtta gaataccaaa atcctggatt gcatttgcaa tcaaattttg  30480
tgaaccgtta aattttgcat gtacttggga tagatataat agaaccgaat tttcattagt  30540
ttaatttata acttactttg ttcaaagaaa aaaaatatct atccaattta cttataataa  30600
aaaataatct atccaagtta cttattataa tcaacttgta aaaaggtaag aatacaaatg  30660
tggtagcgta cgtgtgatta tatgtgacga aatgttatat ctaacaaaag tccaaattcc  30720
catggtaaaa aaaatcaaaa tgcatggcag gctgtttgta accttggaat aagatgttgg  30780
ccaattctgg agccgccacg tacgcaagac tcagggccac gttctcttca tgcaaggata  30840
gtagaacacc actccaccca cctcctatat tagacctttg cccaaccctc cccaactttc  30900
ccatcccatc cacaaagaaa ccgacatttt tatcataaat cagggtttcg tttttgtttc  30960
atcgataaac tcaaaggtga tgattttagg gtcttgtgag tgtgcttttt tgtttgattc  31020
tactgtaggg tttatgttct ttagctcata ggttttgtgt atttcttaga aatgtggctt  31080
```

```
ctttaatctc tgggtttgtg actttttgtg tggtttctgt gtttttcata tcaaaaacct  31140
atttttccg agtttttttt tacaaattct tactctcaag cttgaatact tcacatgcag  31200
tgttcttttg tagattttag agttaatgtg ttaaaaagtt tggatttttc ttgcttatag  31260
agcttcttca ctttgatttt gtgggttttt ttgttttaaa ggtgagattt ttgatgaggt  31320
ttttgcttca aagatgtcac ctttctgggt ttgtcttttg aataaagcta tgaactgtca  31380
catggctgac gcaattttgt tactatgtca tgaaagctga cgtttttccg tgttatacat  31440
gtttgcttac acttgcatgc gtcaaaaaaa ttggggcttt ttagttttag tcaaagattt  31500
tacttctctt ttgggattta tgaaggaaag ttgcaaactt tctcaaattt taccattttt  31560
gctttgatgt ttgtttagat tgcgacagaa caaactcata tatgttgaaa tttttgcttg  31620
gttttgtata ggattgtgtc ttttgcttat aaatgttgaa atctgaactt tttttttgtt  31680
tggtttcttt gagcaggaga taaggcgcac caccatggct tctacatctg ctgctcaaga  31740
cgctgctcct tacgagttcc cttctctcac tgagatcaag agggctcttc cttctgagtg  31800
tttcgaggct tctgttcctc tttctctcta ctacaccgct agatctcttg ctcttgctgg  31860
atctctcgct gttgctctct cttacgctag agctttgcct cttgttcagg ctaacgctct  31920
tcttgatgct actctctgca ctggatacgt tcttctccag ggaatcgttt tctggggatt  31980
cttcaccgtt ggtcacgatt gtggacacgg agctttctct agatctcacg tgctcaactt  32040
ctctgttgga accctcatgc actctatcat ccttacccct ttcgagtctt ggaagctctc  32100
tcacagacac caccacaaga acaccggaaa catcgataag gacgagatct tctaccctca  32160
aagagaggct gattctcacc ctgtttctag acaccttgtg atgtctcttg gatctgcttg  32220
gttcgcttac cttttcgctg gattccctcc tagaaccatg aaccacttca acccttggga  32280
ggctatgtat gttagaagag tggctgctgt gatcatctct ctcggagttc ttttcgcttt  32340
cgctggactc tactcttacc tcaccttcgt tcttggattc accactatgg ctatctacta  32400
cttcggacct ctcttcatct tcgctaccat gcttgttgtt accactttcc tccaccacaa  32460
cgatgaggag acaccttggt acgctgattc tgagtggact tacgtgaagg gaaacctctc  32520
ttctgtggac agatcttacg gtgctctcat cgacaacctt agccacaaca tcggaactca  32580
ccagatccac cacctcttcc ctatcatccc tcactacaag ctcaacgatg ctactgctgc  32640
tttcgctaag gctttccctg agcttgttag gaaaaacgct gctcctatca tcccaacttt  32700
cttcaggatg gctgctatgt acgctaagta cggagttgtt gacactgatg ctaagacctt  32760
cactctcaag gaggctaagg ctgctgctaa gactaagtca tcttgatgat taatgaaggc  32820
cgcagatatc agatctggtc gacctagagg atccccggcc gcaaagataa taacaaaagc  32880
ctactatata acgtacatgc aagtattgta tgatattaat gtttttacgt acgtgtaaac  32940
aaaaataatt acgtttgtaa cgtatggtga tgatgtggtg cactaggtgt aggccttgta  33000
ttaataaaaa gaagtttgtt ctatatagag tggtttagta cgacgattta tttactagtc  33060
ggattggaat agagaaccga attcttcaat ccttgctttt gatcaagaat tgaaaccgaa  33120
tcaaatgtaa aagttgatat atttgaaaaa cgtattgagc ttatgaaaat gctaatactc  33180
tcatctgtat ggaaaagtga ctttaaaacc gaacttaaaa gtgacaaaag gggaatatcg  33240
catcaaaccg aatgaaaccg atctacgtag gctcagctga gcttacctaa ggctacgtag  33300
gctcacgtga cgttacgtaa ggctacgtag cgtcacgtga gcttacctaa ctctagctag  33360
cctcacgtga ccttagctaa cactaggtag cgtcagctta gcagatattt ggtgtctaaa  33420
tgtttatttt gtgatatgtt catgtttgaa atggtggttt cgaaaccagg gacaacgttg  33480
```

```
ggatctgata gggtgtcaaa gagtattatg gattgggaca atttcggtca tgagttgcaa  33540
attcaagtat atcgttcgat tatgaaaatt ttcgaagaat atcccatttg agagagtctt  33600
tacctcatta atgtttttag attatgaaat tttatcatag ttcatcgtag tctttttggt  33660
gtaaaggctg taaaaagaaa ttgttcactt ttgttttcgt ttatgtgaag gctgtaaaag  33720
attgtaaaag actattttgg tgttttggat aaaatgatag tttttataga ttcttttgct  33780
tttagaagaa atacatttga aattttttcc atgttgagta taaaataccg aaatcgattg  33840
aagatcatag aaatatttta actgaaaaca aatttataac tgattcaatt ctctccattt  33900
ttatacctat ttaaccgtaa tcgattctaa tagatgatcg attttttata taatcctaat  33960
taaccaacgg catgtattgg ataattaacc gatcaactct cacccctaat agaatcagta  34020
ttttccttcg acgttaattg atcctacact atgtaggtca tatccatcgt tttaattttt  34080
ggccaccatt caattctgtc ttgcctttag ggatgtgaat atgaacggcc aaggtaagag  34140
aataaaaata atccaaatta aagcaagaga ggccaagtaa gataatccaa atgtacactt  34200
gtcattgcca aaattagtaa aatactcggc atattgtatt cccacacatt attaaaatac  34260
cgtatatgta ttggctgcat ttgcatgaat aatactacgt gtaagcccaa aagaacccac  34320
gtgtagccca tgcaaagtta acactcacga ccccattcct cagtctccac tatataaacc  34380
caccatcccc aatctcacca aacccaccac acaactcaca actcactctc acaccttaaa  34440
gaaccaatca ccaccaaaaa aagttctttg ctttcgaagt tgccgcaacc taaacaggtt  34500
tttccttctt ctttcttctt attaactacg accttgtcct ttgcctatgt aaaattacta  34560
ggttttcatc agttacactg attaagttcg ttatagtgga agataaaatg ccctcaaagc  34620
attttgcagg atatctttga tttttcaaag atatggaact gtagagtttg atagtgttct  34680
tgaatgtggt tgcatgaagt ttttttggtc tgcatgttat tttttcctcg aaatatgttt  34740
tgagtccaac aagtgattca cttgggattc agaaagttgt tttctcaata tgtaacagtt  34800
tttttctatg gagaaaaatc atagggaccg ttggttttgg cttctttaat tttgagctca  34860
gattaaaccc attttacccg gtgttcttgg cagaattgaa aacagtacgt agtaccgcgc  34920
ctaccatgcc acctagtgct gctagtgaag gtggtgttgc tgaacttaga gctgctgaag  34980
ttgctagcta cactagaaag gctgttgacg aaagacctga cctcactata gttggtgacg  35040
ctgtttacga cgctaaggct tttagggacg agcaccctgg tggtgctcac ttcgttagcc  35100
ttttcggagg tagggacgct actgaggctt ttatggaata tcaccgtaga gcttggccta  35160
aggctaggat gtctaagttc ttcgttggtt cacttgacgc tagcgagaag cctactcaag  35220
ctgattcagc ttaccttaga ctttgcgctg aggttaacgc tcttttgcct aagggtagcg  35280
gaggattcgc tcctcctagc tactggctta aggctgctgc tcttgttgtt gctgctgtta  35340
gtatagaggg ttatatgctc cttaggggta agaccctttt gcttagcgtt ttccttggac  35400
tcgtgttcgc ttggatagga cttaatattc agcacgacgc taatcacggt gctcttagta  35460
gacactcagt gattaactac tgcctcggtt acgctcagga ttggataggt ggtaatatgg  35520
tgctttggct tcaagagcac gttgtgatgc accacctcca cactaacgac gttgacgctg  35580
atcctgatca aaaggctcac ggtgttctta gacttaagcc tactgacggt tggatgcctt  35640
ggcacgcact tcaacaactc tatatccttc ctggtgaggc tatgtacgct tttaagcttc  35700
ttttcttgga cgcccttgag cttcttgctt ggaggtggga gggtgagaag attagccctc  35760
ttgctagagc tttgttcgct cctgctgttg cttgtaagct tggattctgg gctagattcg  35820
```

```
ttgctctccc tctctggctt caacctactg ttcacactgc tttgtgtatc tgtgctactg  35880
tgtgtactgg tagcttctac ctcgccttct tcttctttat ctctcacaac ttcgacggtg  35940
ttggtagcgt tggacctaag ggatcacttc ctagatcagc tactttcgtt caacgtcagg  36000
ttgagactag ctctaacgtt ggtggttact ggcttggagt tcttaacggt ggacttaact  36060
ttcagataga gcaccacttg ttccctaggc ttcaccactc ttactacgct caaatagctc  36120
ctgtggttag gactcacata gagaagctcg gttttaagta ccgtcacttc cctaccgttg  36180
gatctaacct tagctcaatg cttcagcata tgggtaagat gggaactaga cctggtgctg  36240
agaagggtgg taaggctgag tagtgattaa tgaataattg attgctgctt taatgagata  36300
tgcgagacgc ctatgatcgc atgatatttg ctttcaattc tgttgtgcac gttgtaaaaa  36360
acctgagcat gtgtagctca gatccttacc gccggtttcg gttcattcta atgaatatat  36420
cacccgttac tatcgtattt ttatgaataa tattctccgt tcaatttact gattgtctac  36480
gtagcgtcac ctgacgttac gtaaggctac ctaggctcac gtgacgttac gtaacgctac  36540
gtagcgtcag gtgaggttag ctaacgctag ctagcctcac ctgacgttag gtaaggctac  36600
gtagcgtcac ctgagattag ctaagcctac ctagactcac gtgaccttag gtaacgctac  36660
gtagcgtcaa agctttacaa cgctacacaa aacttataac cgtaatcacc attcattaac  36720
ttaactacta tcacatgcat tcatgaattg aaacgagaag gatgtaaata gttgggaagt  36780
tatctccacg ttgaagagat cgttagcgag agctgaaaga ccgagggagg agacgccgtc  36840
aacacggaca gagtcgtcga ccctcacatg aagtaggagg aatctccgtg aggagccaga  36900
gagacgtctt tggtcttcgg tttcgatcct tgatctgacg gagaagacga gagaagtgcg  36960
actggactcc gtgaggacca acagagtcgt cctcggtttc gatcgtcggt attggtggag  37020
aaggcggagg aatctccgtg acgagccaga gagatgtcgt cggtcttcgg tttcgatcct  37080
tgatctgacg gagaagacga gagaagtgcg acgagactcc gtgaggacca acagagttgt  37140
cctcggtttc gatcgtcggt ttcggcggag aaggcggagg aatctccgtg aggagccaga  37200
gagacgtcgt tggtcttcgg tttcgatcct tgatctgttg gagaagacga gacaagtggg  37260
acgagactca acgacggagt cagagacgtc gtcggtcttc ggtttcggcc gagaaggcgg  37320
agtcggtctt cggtttcggc cgagaaggcg gaggagacgt cttcgatttg ggtctctcct  37380
cttgacgaag aaaacaaaga acacgagaaa taatgagaaa gagaacaaaa gaaaaaaaaa  37440
taaaaataaa aataaaattt ggtcctctta tgtggtgaca cgtggtttga aacccaccaa  37500
ataatcgatc acaaaaaacc taagttaagg atcggtaata acctttctaa ttaattttga  37560
tttatattaa atcactcttt ttatttataa accccactaa attatgcgat attgattgtc  37620
taagtacaaa aattctctcg aattcaatac acatgtttca tatatttagc cctgttcatt  37680
taatattact agcgcatttt taatttaaaa ttttgtaaac ttttttggtc aaagaacatt  37740
tttttaatta gagacagaaa tctagactct ttatttggaa taatagtaat aaagatatat  37800
taggcaatga gtttatgatg ttatgtttat atagtttatt tcattttaaa ttgaaaagca  37860
ttatttttat cgaaatgaat ctagtataca atcaatattt atgttttttc atcagatact  37920
ttcctatttt ttggcacctt tcatcggact actgatttat ttcaatgtgt atgcatgcat  37980
gagcatgagt atacacatgt cttttaaaat gcatgtaaag cgtaacggac cacaaaagag  38040
gatccataca aatacatctc atcgcttcct ctactattct ccgacacaca cactgagcat  38100
ggtgcttaaa cactctggtg agttctagta cttctgctat gatcgatctc attaccattt  38160
cttaaatttc tctccctaaa tattccgagt tcttgatttt tgataacttc aggttttctc  38220
```

```
tttttgataa atctggtctt tccatttttt tttttttgtg gttaatttag tttcctatgt  38280
tcttcgattg tattatgcat gatctgtgtt tggattctgt tagattatgt attggtgaat  38340
atgtatgtgt ttttgcatgt ctggttttgg tcttaaaaat gttcaaatct gatgatttga  38400
ttgaagcttt tttagtgttg gtttgattct tctcaaaact actgttaatt tactatcatg  38460
ttttccaact ttgattcatg atgacacttt tgttctgctt tgttataaaa ttttggttgg  38520
tttgattttg taattatagt gtaattttgt taggaatgaa catgttttaa tactctgttt  38580
tcgatttgtc acacattcga attattaatc gataatttaa ctgaaaattc atggttctag  38640
atcttgttgt catcagatta tttgtttcga taattcatca aatatgtagt ccttttgctg  38700
atttgcgact gtttcatttt ttctcaaaat tgttttttgt taagtttatc taacagttat  38760
cgttgtcaaa agtctctttc attttgcaaa atcttctttt tttttttgtt tgtaactttg  38820
ttttttaagc tacacattta gtctgtaaaa tagcatcgag gaacagttgt cttagtagac  38880
ttgcatgttc ttgtaacttc tatttgtttc agtttgttga tgactgcttt gattttgtag  38940
gtcaaaccgc gccatgtctg ctagcggagc tttgttgcct gctatagctt tcgctgctta  39000
cgcttacgct acctacgctt atgctttcga gtggagccac gctaacggaa tcgataacgt  39060
ggatgctaga gagtggattg gagctttgtc tttgagactc cctgcaattg caaccacaat  39120
gtacctcttg ttctgccttg tgggacctag attgatggct aagagggagg cttttgatcc  39180
taagggattt atgctcgctt acaacgctta ccaaaccgct ttcaacgttg tggtgctcgg  39240
aatgttcgct agagagatct ctggattggg acaacctgtt tggggatcta ctatgccttg  39300
gagcgatagg aagtccttca agattttgtt gggagtgtgg ctccactaca acaataagta  39360
cctcgagttg ttggatactg tgttcatggt ggctaggaaa aagaccaagc agctctcttt  39420
cttgcacgtg taccaccacg ctttgttgat ttgggcttgg tggcttgttt gtcacctcat  39480
ggctaccaac gattgcatcg atgcttattt cggagctgct tgcaactctt tcatccacat  39540
cgtgatgtac tcctactacc tcatgtctgc tttgggaatt aggtgccctt ggaagagata  39600
tatcacccag gctcagatgt tgcaattcgt gatcgtgttc gctcacgctg ttttcgtgct  39660
cagacaaaag cactgccctg ttactttgcc ttgggcacaa atgttcgtga tgacaaatat  39720
gttggtgctc ttcggaaact tctacctcaa ggcttactct aacaagtcta ggggagatgg  39780
agcttcttct gttaagcctg ctgagactac tagagcacct tctgtgagaa gaaccaggtc  39840
aaggaagatc gattgatagt taatgaacta agtttgatgt atctgagtgc caacgtttac  39900
tttgtctttc ctttctttta ttggttatga ttagatgttt actatgttct ctctttttcg  39960
ttataaataa agaagttcaa ttcttctata gtttcaaacg cgattttaag cgtttctatt  40020
taggtttaca tgatttcttt tacaaaatca tctttaaaat acagtatatt tttagttttc  40080
ataaaatatt taaagaaatg aaagtttata aacattcact cctattctct aattaaggat  40140
ttgtaaaaca aaaattttgt aagcatatcg atttatgcgt tttgtcttaa ttagctcact  40200
aaataataaa taatagctta tgttgtggga ctgtttaatt acctaactta gaactaaaat  40260
caactctttg tgctagctag cctcagctga cgttacgtaa cgctaggtag cgtcacgtga  40320
cgttagctaa cgctaggtag cgtcagctga gcttacgtaa gcgcttaatt aaagtactga  40380
tatcggtacc aaatcgaatc caaaaattac ggatatgaat ataggcatat ccgtatccga  40440
attatccgtt tgacagctag caacgattgt acaattgctt ctttaaaaaa ggaagaaaga  40500
aagaaagaaa agaatcaaca tcagcgttaa caaacggccc cgttacggcc caaacggtca  40560
```

```
tatagagtaa cggcgttaag cgttgaaaga ctcctatcga aatacgtaac cgcaaacgtg  40620
tcatagtcag atcccctctt ccttcaccgc ctcaaacaca aaaataatct tctacagcct  40680
atatatacaa cccccccttc tatctctcct ttctcacaat tcatcatctt tctttctcta  40740
cccccaattt taagaaatcc tctcttctcc tcttcatttt caaggtaaat ctctctctct  40800
ctctctctct ctgttattcc ttgttttaat taggtatgta ttattgctag tttgttaatc  40860
tgcttatctt atgtatgcct tatgtgaata tctttatctt gttcatctca tccgtttaga  40920
agctataaat ttgttgattt gactgtgtat ctacacgtgg ttatgtttat atctaatcag  40980
atatgaattt cttcatattg ttgcgtttgt gtgtaccaat ccgaaatcgt tgattttttt  41040
catttaatcg tgtagctaat tgtacgtata catatggatc tacgtatcaa ttgttcatct  41100
gtttgtgttt gtatgtatac agatctgaaa acatcacttc tctcatctga ttgtgttgtt  41160
acatacatag atatagatct gttatatcat tttttttatt aattgtgtat atatatatgt  41220
gcatagatct ggattacatg attgtgatta tttacatgat tttgttattt acgtatgtat  41280
atatgtagat ctggactttt tggagttgtt gacttgattg tatttgtgtg tgtatatgtg  41340
tgttctgatc ttgatatgtt atgtatgtgc agctgaacca tggcggcggc aacaacaaca  41400
acaacaacat cttcttcgat ctccttctcc accaaaccat ctccttcctc ctccaaatca  41460
ccattaccaa tctccagatt ctccctccca ttctccctaa accccaacaa atcatcctcc  41520
tcctcccgcc gccgcggtat caaatccagc tctccctcct ccatctccgc cgtgctcaac  41580
acaaccacca atgtcacaac cactccctct ccaaccaaac ctaccaaacc cgaaacattc  41640
atctcccgat tcgctccaga tcaaccccgc aaaggcgctg atatcctcgt cgaggcttta  41700
gaacgtcaag gcgtagaaac cgtattcgct taccctggag gtacatcaat ggagattcac  41760
caagccttaa cccgctcttc ctcaatccgt aacgtccttc ctcgtcacga acaaggaggt  41820
gtattcgcag cagaaggata cgctcgatcc tcaggtaaac caggtatctg tatagccact  41880
tcaggtcccg gagctacaaa tctcgttagc ggattagccg atgcgttgtt agatagtgtt  41940
cctcttgtag caatcacagg acaagtccct cgtcgtatga ttggtacaga tgcgtttcaa  42000
gagactccga ttgttgaggt aacgcgttcg attacgaagc ataactatct tgtgatggat  42060
gttgaagata tcccaaggat tattgaagag gctttctttt tagctacttc tggtagacct  42120
ggacctgttt tggttgatgt tcctaaagat attcaacaac agcttgcgat tcctaattgg  42180
gaacaggcta tgagattacc tggttatatg tctaggatgc ctaaacctcc ggaagattct  42240
catttggagc agattgttag gttgatttct gagtctaaga agcctgtgtt gtatgttggt  42300
ggtggttgtc ttaattctag cgatgaattg ggtaggtttg ttgagcttac gggcatccct  42360
gttgcgagta cgttgatggg gctgggatct tatccttgtg atgatgagtt gtcgttacat  42420
atgcttggaa tgcatgggac tgtgtatgca aattacgctg tggagcatag tgatttgttg  42480
ttggcgtttg gggtaaggtt tgatgatcgt gtcacgggta aacttgaggc ttttgctagt  42540
agggctaaga ttgttcatat tgatattgac tcggctgaga ttgggaagaa taagactcct  42600
catgtgtctg tgtgtggtga tgttaagctg gctttgcaag ggatgaataa ggttcttgag  42660
aaccgagcgg aggagcttaa acttgatttt ggagtttgga ggaatgagtt gaacgtacag  42720
aaacagaagt ttccgttgag ctttaagacg tttggggaag ctattcctcc acagtatgcg  42780
attaaggtcc ttgatgagtt gactgatgga aaagccataa taagtactgg tgtcgggcaa  42840
catcaaatgt gggcggcgca gttctacaat tacaagaaac caaggcagtg gctatcatca  42900
ggaggccttg gagctatggg atttggactt cctgctgcga ttggagcgtc tgttgctaac  42960
```

```
cctgatgcga tagttgtgga tattgacgga gatggaagtt ttataatgaa tgtgcaagag  43020
ctagccacta ttcgtgtaga gaatcttcca gtgaaggtac ttttattaaa caaccagcat  43080
cttggcatgg ttatgcaatg ggaagatcgg ttctacaaag ctaaccgagc tcacacattt  43140
ctcggggacc cggctcagga ggacgagata ttcccgaaca tgttgctgtt tgcagcagct  43200
tgcgggattc cagcggcgag ggtgacaaag aaagcagatc tccgagaagc tattcagaca  43260
atgctggata caccaggacc ttacctgttg gatgtgattt gtccgcacca agaacatgtg  43320
ttgccgatga tcccgaatgg tggcactttc aacgatgtca taacggaagg agatggccgg  43380
attaaatact gagagatgaa accggtgatt atcagaacct tttatggtct ttgtatgcat  43440
atggtaaaaa aacttagttt gcaatttcct gtttgttttg gtaatttgag tttcttttag  43500
ttgttgatct gcctgctttt tggtttacgt cagactacta ctgctgttgt tgtttggttt  43560
cctttctttc attttataaa taaataatcc ggttcggttt actccttgtg actggctcag  43620
tttggttatt gcgaaatgcg aatggtaaat tgagtaattg aaattcgtta ttagggttct  43680
aagctgtttt aacagtcact gggttaatat ctctcgaatc ttgcatggaa aatgctctta  43740
ccattggttt ttaattgaaa tgtgctcata tgggccgtgg tttccaaatt aaataaaact  43800
acgatgtcat cgagaagtaa aatcaactgt gtccacatta tcagttttgt gtatacgatg  43860
aaatagggta attcaaaatc tagcttgata tgccttttgg ttcattttaa ccttctgtaa  43920
acatttttc agattttgaa caagtaaatc caaaaaaaaa aaaaaaaatc tcaactcaac  43980
actaaattat tttaatgtat aaaagatgct taaaacattt ggcttaaaag aaagaagcta  44040
aaaacataga gaactcttgt aaattgaagt atgaaaatat actgaattgg gtattatatg  44100
aatttttctg atttaggatt cacatgatcc aaaaaggaaa tccagaagca ctaatcagac  44160
attggaagta ggattaatca gtgatcagta actattaaat tcaattaacc gcggacatct  44220
acatttttga attgaaaaaa aattggtaat tactctttct ttttctccat attgaccatc  44280
atactcattg ctgatccatg tagatttccc ggacatgaag ccatatatct gaccctactc  44340
cacaaatata tttttattta taaaaaggtg gccattgtat actatgtgtg cgtatacagg  44400
aataaaaatg tgtcaatgta tatgtaaact gattccatct tatatgtaat gtgcgtgtgt  44460
aaatgaagat actagtatcc atgtgtcgcc tacttgattt gttcaactgt aactcataat  44520
atctcaagat tctttctttt ttttctacga atatcgcaat ctataatacc attaaattat  44580
tgtaacaaaa ttggttgaca tttataaaat gaaaaagaag agaagagcat ttaaacacga  44640
ctgatgaaag tccaatgtag ctagataaac cacgcgtggt ggtcaatgcg ttccattcca  44700
aaaggatccg agttcgaatc cgcaccacac cagattttca ctgcgcgtgg ccatgaagct  44760
ttcgcattct cgctcctgag aatggttctc catttttttt ttccagtgta gctagatacc  44820
ggtctgaatc taggtttata atatgctgac aatgtaatga taattaatac atcaaaacat  44880
gtgtttctga accaaaataa aaactttttt                                   44910
```

<210> SEQ ID NO 3
<211> LENGTH: 43757
<212> TYPE: DNA
<213> ORGANISM: Artificial Sequence
<220> FEATURE:
<223> OTHER INFORMATION: T-DNA insertion in LBFLFK Locus 1, including left and right border sequences

<400> SEQUENCE: 3

```
ccagtcagca tcatcacacc aaaagttagg cccgaatagt ttgaaattag aaagctcgca     60
```

```
attgaggtct acaggccaaa ttcgctctta gccgtacaat attactcacc ggtgcgatgc    120
cccccatcgt aggtgaaggt ggaaattaat ggcgcgcctg atcactgatt agtaactatt    180
acgtaagcct acgtagcgtc acgtgacgtt agctaacgct acgtagcctc agctgacgtt    240
acgtaagcct acgtagcgtc acgtgagctt agctaacgct acctaggctc agctgacgtt    300
acgtaacgct agctagcgtc actcctgcag caaatttaca cattgccact aaacgtctaa    360
acccttgtaa tttgtttttg ttttactatg tgtgttatgt atttgatttg cgataaattt    420
ttatatttgg tactaaattt ataacacctt ttatgctaac gtttgccaac acttagcaat    480
ttgcaagttg attaattgat tctaaattat ttttgtcttc taaatacata tactaatcaa    540
ctggaaatgt aaatatttgc taatatttct actataggag aattaaagtg agtgaatatg    600
gtaccacaag gtttggagat ttaattgttg caatgctgca tggatggcat atacaccaaa    660
cattcaataa ttcttgagga taataatggt accacacaag atttgaggtg catgaacgtc    720
acgtggacaa aaggtttagt aatttttcaa gacaacaatg ttaccacaca caagttttga    780
ggtgcatgca tggatgccct gtggaaagtt taaaaatatt ttggaaatga tttgcatgga    840
agccatgtgt aaaaccatga catccacttg gaggatgcaa taatgaagaa aactacaaat    900
ttacatgcaa ctagttatgc atgtagtcta tataatgagg attttgcaat actttcattc    960
atacacactc actaagtttt acacgattat aatttcttca tagccagtac tgtttaagct   1020
tcactgtctc tgaatcggca aaggtaaacg tatcaattat tctacaaacc cttttatttt   1080
tcttttgaat taccgtcttc attggttata tgataacttg ataagtaaag cttcaataat   1140
tgaatttgat ctgtgttttt ttggccttaa tactaaatcc ttacataagc tttgttgctt   1200
ctcctcttgt gagttgagtg ttaagttgta ataatggttc actttcagct ttagaagaaa   1260
ccatggaagt tgttgagagg ttctacggag agttggatgg aaaggtttcc caaggagtga   1320
acgctttgtt gggatctttc ggagttgagt tgactgatac cccaactact aagggattgc   1380
cactcgttga ttctccaact ccaattgtgt tgggagtgtc tgtttacttg accatcgtga   1440
tcggaggatt gctttggatc aaggctagag atctcaagcc aagagcttct gagccattct   1500
tgttgcaagc tttggtgttg gtgcacaact tgttctgctt cgctttgtct ctttacatgt   1560
gcgtgggtat cgcttaccaa gctatcacct ggagatattc cttgtgggga aacgcttata   1620
acccaaagca caaggagatg gctatcctcg tttacctctt ctacatgtcc aagtacgtgg   1680
agttcatgga taccgtgatc atgatcctca agagatccac cagacagatt tctttcctcc   1740
acgtgtacca ccactcttct atctccctta tctggtgggc tattgctcac cacgctccag   1800
gaggagaggc ttattggagt gctgctctca actctggagt gcacgtgttg atgtacgctt   1860
actacttctt ggctgcttgc ttgagatctt ccccaaagct caagaacaag tacctcttct   1920
ggggaagata cctcacccaa ttccagatgt tccagttcat gctcaacttg gtgcaagctt   1980
actacgatat gaaaaccaac gctccatatc cacaatggct catcaagatc ctcttctact   2040
acatgatctc cctcttgttc ctcttcggaa acttctacgt gcaaaagtac atcaagccat   2100
ccgatggaaa gcaaaaggga gctaagaccg agtgatcgac aagctcgagt ttctccataa   2160
taatgtgtga gtagttccca gataagggaa ttagggttcc tatagggttt cgctcatgtg   2220
ttgagcatat aagaaaccct tagtatgtat ttgtatttgt aaaatacttc tatcaataaa   2280
atttctaatt cctaaaacca aaatccagta ctaaaatcca gatcccccga attaattcgg   2340
cgttaattca gctagctagc ctcagctgac gttacgtaac gctaggtagc gtcacgtgac   2400
```

```
gttagctaac gctaggtagc gtcagctgag cttacgtaag cgcttagcag atatttggtg   2460
tctaaatgtt tattttgtga tatgttcatg tttgaaatgg tggtttcgaa accagggaca   2520
acgttgggat ctgatagggt gtcaaagagt attatggatt gggacaattt cggtcatgag   2580
ttgcaaattc aagtatatcg ttcgattatg aaaattttcg aagaatatcc catttgagag   2640
agtctttacc tcattaatgt ttttagatta tgaaatttta tcatagttca tcgtagtctt   2700
tttggtgtaa aggctgtaaa aagaaattgt tcacttttgt tttcgtttat gtgaaggctg   2760
taaaagattg taaaagacta ttttggtgtt ttggataaaa tgatagtttt tatagattct   2820
tttgctttta gaagaaatac atttgaaatt ttttccatgt tgagtataaa ataccgaaat   2880
cgattgaaga tcatagaaat attttaactg aaaacaaatt tataactgat tcaattctct   2940
ccatttttat acctatttaa ccgtaatcga ttctaataga tgatcgattt tttatataat   3000
cctaattaac caacggcatg tattggataa ttaaccgatc aactctcacc cctaatagaa   3060
tcagtatttt ccttcgacgt taattgatcc tacactatgt aggtcatatc catcgtttta   3120
atttttggcc accattcaat tctgtcttgc ctttagggat gtgaatatga acggccaagg   3180
taagagaata aaaataatcc aaattaaagc aagagaggcc aagtaagata atccaaatgt   3240
acacttgtca ttgccaaaat tagtaaaata ctcggcatat tgtattccca cacattatta   3300
aaataccgta tatgtattgg ctgcatttgc atgaataata ctacgtgtaa gcccaaaaga   3360
acccacgtgt agcccatgca aagttaacac tcacgacccc attcctcagt ctccactata   3420
taaacccacc atccccaatc tcaccaaacc caccacacaa ctcacaactc actctcacac   3480
cttaaagaac caatcaccac caaaaaattt cacgatttgg aatttgattc ctgcgatcac   3540
aggtatgaca ggttagattt tgttttgtat agttgtatac atacttcttt gtgatgtttt   3600
gtttacttaa tcgaattttt ggagtgtttt aaggtctctc gtttagaaat cgtggaaaat   3660
atcactgtgt gtgtgttctt atgattcaca gtgtttatgg gtttcatgtt ctttgtttta   3720
tcattgaatg ggaagaaatt tcgttgggat acaaatttct catgttctta ctgatcgtta   3780
ttaggagttt ggggaaaaag gaagagtttt tttggttggt tcgagtgatt atgaggttat   3840
ttctgtattt gatttatgag ttaatggtcg ttttaatgtt gtagaccatg ggaaaaggat   3900
ctgagggaag atctgctgct agagagatga ctgctgaggc taacggagat aagagaaaga   3960
ccatcctcat tgagggagtg ttgtacgatg ctaccaactt caaacaccca ggaggttcca   4020
ttattaactt cctcaccgag ggagaagctg gagttgatgc tacccaagct tacagagagt   4080
tccatcagag atccggaaag gctgataagt acctcaagtc cctcccaaag ttggatgctt   4140
ctaaggtgga gtctaggttc tctgctaagg agcaggctag aagggacgct atgaccaggg   4200
attacgctgc tttcagagag gagttggttg ctgagggata cttcgatcca tctatcccac   4260
acatgatcta cagagtggtg gagattgtgg ctttgttcgc tttgtctttc tggttgatgt   4320
ctaaggcttc tccaacctct ttggttttgg gagtggtgat gaacggaatc gctcaaggaa   4380
gatgcggatg ggttatgcac gagatgggac acggatcttt cactggagtt atctggctcg   4440
atgataggat gtgcgagttc ttctacggag ttggatgtgg aatgtctgga cactactgga   4500
agaaccagca ctctaagcac cacgctgctc caaacagatt ggagcacgat gtggatttga   4560
acaccttgcc actcgttgct ttcaacgaga gagttgtgag gaaggttaag ccaggatctt   4620
tgttggcttt gtggctcaga gttcaggctt atttgttcgc tccagtgtct tgcttgttga   4680
tcggattggg atggaccttg tacttgcacc caagatatat gctcaggacc aagagacaca   4740
tggagtttgt gtggatcttc gctagatata tcggatggtt ctccttgatg ggagctttgg   4800
```

```
gatattctcc tggaacttct gtgggaatgt acctctgctc tttcggactt ggatgcatct   4860

acatcttcct ccaattcgct gtgtctcaca cccacttgcc agttaccaac ccagaggatc   4920

aattgcactg gcttgagtac gctgctgatc acaccgtgaa catctctacc aagtcttggt   4980

tggttacctg gtggatgtct aacctcaact tccaaatcga gcaccacttg ttcccaaccg   5040

ctccacaatt caggttcaag gagatctctc caagagttga ggctctcttc aagagacaca   5100

acctccctta ctacgatttg ccatacacct ctgctgtttc tactaccttc gctaacctct   5160

actctgttgg acactctgtt ggagctgata ccaagaagca ggattgactg ctttaatgag   5220

atatgcgaga cgcctatgat cgcatgatat ttgctttcaa ttctgttgtg cacgttgtaa   5280

aaaacctgag catgtgtagc tcagatcctt accgccggtt tcggttcatt ctaatgaata   5340

tatcacccgt tactatcgta tttttatgaa taatattctc cgttcaattt actgattgtc   5400

tacgtaggct cagctgagct tacctaaggc tacgtaggct cacgtgacgt tacgtaaggc   5460

tacgtagcgt cacgtgagct tacctaactc tagctagcct cacgtgacct tagctaacac   5520

taggtagcgt cagctcgacg gcccggactg tatccaactt ctgatctttg aatctctctg   5580

ttccaacatg ttctgaagga gttctaagac ttttcagaaa gcttgtaaca tgctttgtag   5640

actttctttg aattactctt gcaaactctg attgaaccta cgtgaaaact gctccagaag   5700

ttctaaccaa attccgtctt gggaaggccc aaaatttatt gagtacttca gtttcatgga   5760

cgtgtcttca aagatttata acttgaaatc ccatcatttt taagagaagt tctgttccgc   5820

aatgtcttag atctcattga aatctacaac tcttgtgtca gaagttcttc cagaatcaac   5880

ttgcatcatg gtgaaaatct ggccagaagt tctgaacttg tcatatttct taacagttag   5940

aaaaatttct aagtgtttag aattttgact tttccaaagc aaacttgact tttgactttc   6000

ttaataaaac aaacttcata ttctaacatg tcttgatgaa atgtgattct tgaaatttga   6060

tgttgatgca aaagtcaaag tttgactttt cagtgtgcaa ttgaccattt tgctcttgtg   6120

ccaattccaa acctaaattg atgtatcagt gctgcaaact tgatgtcatg gaagatctta   6180

tgagaaaatt cttgaagact gagaggaaaa attttgtagt acaacacaaa gaatcctgtt   6240

tttcatagtc ggactagaca cattaacata aaacaccact tcattcgaag agtgattgaa   6300

gaaggaaatg tgcagttacc tttctgcagt tcataagagc aacttacaga cacttttact   6360

aaaatactac aaagaggaag attttaacaa cttagagaag taatgggagt taaagagcaa   6420

cacattaagg gggagtgtta aaattaatgt gttgtaacca ccactacctt tagtaagtat   6480

tataagaaaa ttgtaatcat cacattataa ttattgtcct tatttaaaat tatgataaag   6540

ttgtatcatt aagattgaga aaaccaaata gtcctcgtct tgatttttga attattgttt   6600

tctatgttac ttttcttcaa gcctatataa aaactttgta atgctaaatt gtatgctgga   6660

aaaaaatgtg taatgaattg aatagaaatt atggtatttc aaagtccaaa atccatcaat   6720

agaaatttag tacaaaacgt aactcaaaaa tattctctta ttttaaattt tacaacaata   6780

taaaaatatt ctcttatttt aaattttaca ataatataat ttatcacctg tcacctttag   6840

aataccacca acaatattaa tacttagata ttttattctt aataattttg agatctctca   6900

atatatctga tatttatttt atatttgtgt catattttct tatgttttag agttaaccct   6960

tatatcttgg tcaaactagt aattcaatat atgagtttgt gaaggacaca ttgacatctt   7020

gaaacattgg ttttaacctt gttggaatgt taaaggtaat aaaacattca gaattatgac   7080

catctattaa tatacttcct ttgtctttta aaaaagtgtg catgaaaatg ctctatggta   7140
```

```
agctagagtg tcttgctggc ctgtgtatat caattccatt tccagatggt agaaactgcc   7200
actacgaata attagtcata agacacgtat gttaacacac gtccccttgc atgtttttg    7260
ccatatattc cgtctctttc tttttcttca cgtataaaac aatgaactaa ttaatagagc   7320
gatcaagctg aacagttctt tgctttcgaa gttgccgcaa cctaaacagg tttttccttc   7380
ttctttcttc ttattaacta cgaccttgtc ctttgcctat gtaaaattac taggttttca   7440
tcagttacac tgattaagtt cgttatagtg gaagataaaa tgccctcaaa gcattttgca   7500
ggatatcttt gatttttcaa agatatggaa ctgtagagtt tgatagtgtt cttgaatgtg   7560
gttgcatgaa gtttttttgg tctgcatgtt attttttcct cgaaatatgt tttgagtcca   7620
acaagtgatt cacttgggat tcagaaagtt gttttctcaa tatgtaacag tttttttcta   7680
tggagaaaaa tcatagggac cgttggtttt ggcttcttta attttgagct cagattaaac   7740
ccattttacc cggtgttctt ggcagaattg aaaacagtac gtagtaccgc gcctaccatg   7800
tgtgttgaga ccgagaacaa cgatggaatc cctactgtgg agatcgcttt cgatggagag   7860
agagaaagag ctgaggctaa cgtgaagttg tctgctgaga agatggaacc tgctgctttg   7920
gctaagacct tcgctagaag atacgtggtt atcgagggag ttgagtacga tgtgaccgat   7980
ttcaaacatc ctggaggaac cgtgattttc tacgctctct ctaacactgg agctgatgct   8040
actgaggctt tcaaggagtt ccaccacaga tctagaaagg ctaggaaggc tttggctgct   8100
ttgccttcta gacctgctaa gaccgctaaa gtggatgatg ctgagatgct ccaggatttc   8160
gctaagtgga gaaaggagtt ggagagggac ggattcttca agccttctcc tgctcatgtt   8220
gcttacagat tcgctgagtt ggctgctatg tacgctttgg gaacctactt gatgtacgct   8280
agatacgttg tgtcctctgt gttggtttac gcttgcttct tcggagctag atgtggatgg   8340
gttcaacacg agggaggaca ctcttctttg accggaaaca tctggtggga taagagaatc   8400
caagctttca ctgctggatt cggattggct ggatctggag atatgtggaa ctccatgcac   8460
aacaagcacc acgctactcc tcaaaaagtg aggcacgata tggatttgga taccactcct   8520
gctgttgctt tcttcaacac cgctgtggag gataatagac ctaggggatt ctctaagtac   8580
tggctcagat tgcaagcttg gaccttcatt cctgtgactt ctggattggt gttgctcttc   8640
tggatgttct tcctccaccc ttctaaggct ttgaagggag gaaagtacga ggagcttgtg   8700
tggatgttgg ctgctcacgt gattagaacc tggaccatta aggctgttac tggattcacc   8760
gctatgcaat cctacggact cttcttggct acttcttggg tttccggatg ctacttgttc   8820
gctcacttct ctacttctca cacccacttg gatgttgttc ctgctgatga gcacttgtct   8880
tgggttaggt acgctgtgga tcacaccatt gatatcgatc cttctcaggg atgggttaac   8940
tggttgatgg gatacttgaa ctgccaagtg attcaccacc tcttcccttc tatgcctcaa   9000
ttcagacaac ctgaggtgtc cagaagattc gttgctttcg ctaagaagtg gaacctcaac   9060
tacaaggtga tgacttatgc tggagcttgg aaggctactt tgggaaacct cgataatgtg   9120
ggaaagcact actacgtgca cggacaacac tctggaaaga ccgcttgatt aatgaaggcc   9180
gcctcgaccg taccccctgc agatagacta tactatgttt tagcctgcct gctggctagc   9240
tactatgtta tgttatgttg taaaataaac acctgctaag gtatatctat ctatatttta   9300
gcatggcttt ctcaataaat tgtctttcct tatcgtttac tatcttatac ctaataatga   9360
aataataata tcacatatga ggaacggggc aggtttaggc atatatatac gagtgtaggg   9420
cggagtgggg ctacgtagcg tcacgtgacg ttacctaagc ctaggtagcc tcagctgacg   9480
ttacgtaacg ctaggtaggc tcagctgaca cgggcaggac atagggacta ctacaagcat   9540
```

```
agtatgcttc agacaaagag ctaggaaaga actcttgatg gaggttaaga gaaaaaagtg   9600
ctagaggggc atagtaatca aacttgtcaa aaccgtcatc atgatgaggg atgacataat   9660
ataaaaagtt gactaaggtc ttggtagtac tctttgatta gtattatata ttggtgagaa   9720
catgagtcaa gaggagacaa gaaaccgagg aaccatagtt tagcaacaag atggaagttg   9780
caaagttgag ctagccgctc gattagttac atctcctaag cagtactaca aggaatggtc   9840
tctatacttt catgtttagc acatggtagt gcggattgac aagttagaaa cagtgcttag   9900
gagacaaaga gtcagtaaag gtattgaaag agtgaagttg atgctcgaca ggtcaggaga   9960
agtccctccg ccagatggtg actaccaagg ggttggtatc agctgagacc caaataagat  10020
tcttcggttg aaccagtggt tcgaccgaga ctcttagggt gggatttcac tgtaagattt  10080
gtgcattttg ttgaatataa attgacaatt ttttttattt aattatagat tatttagaat  10140
gaattacata tttagtttct aacaaggata gcaatggatg ggtatgggta caggttaaac  10200
atatctatta cccacccatc tagtcgtcgg gttttacacg tacccacccg tttacataaa  10260
ccagaccgga attttaaacc gtacccgtcc gttagcgggt ttcagattta cccgtttaat  10320
cgggtaaaac ctgattacta aatatatatt ttttatttga taaacaaaac aaaaatgtta  10380
atattttcat attggatgca attttaagaa acacatattc ataaatttcc atatttgtag  10440
gaaaataaaa agaaaaatat attcaagaac acaaatttca ccgacatgac ttttattaca  10500
gagttggaat tagatctaac aattgaaaaa ttaaaattaa gatagaatat gttgaggaac  10560
atgacatagt ataatgctgg gttacccgtc gggtaggtat cgaggcggat actactaaat  10620
ccatcccact cgctatccga taatcactgg tttcgggtat acccattccc gtcaacaggc  10680
ctttttaacc ggataatttc aacttatagt gaatgaattt tgaataaata gttagaatac  10740
caaaatcctg gattgcattt gcaatcaaat tttgtgaacc gttaaatttt gcatgtactt  10800
gggatagata taatagaacc gaattttcat tagtttaatt tataacttac tttgttcaaa  10860
gaaaaaaaat atctatccaa tttacttata ataaaaaata atctatccaa gttacttatt  10920
ataatcaact tgtaaaaagg taagaataca aatgtggtag cgtacgtgtg attatatgtg  10980
acgaaatgtt atatctaaca aaagtccaaa ttcccatggt aaaaaaaatc aaaatgcatg  11040
gcaggctgtt tgtaaccttg gaataagatg ttggccaatt ctggagccgc cacgtacgca  11100
agactcaggg ccacgttctc ttcatgcaag gatagtagaa caccactcca cccacctcct  11160
atattagacc tttgcccaac cctccccaac tttcccatcc catccacaaa gaaaccgaca  11220
tttttatcat aaatctggtg cttaaacact ctggtgagtt ctagtacttc tgctatgatc  11280
gatctcatta ccatttctta aatttctctc cctaaatatt ccgagttctt gatttttgat  11340
aacttcaggt tttctctttt tgataaatct ggtctttcca ttttttttt ttgtggttaa  11400
tttagtttcc tatgttcttc gattgtatta tgcatgatct gtgtttggat tctgttagat  11460
tatgtattgg tgaatatgta tgtgtttttg catgtctggt tttggtctta aaaatgttca  11520
aatctgatga tttgattgaa gctttttag tgttggtttg attcttctca aaactactgt  11580
taatttacta tcatgttttc caactttgat tcatgatgac acttttgttc tgctttgtta  11640
taaaattttg gttggtttga ttttgtaatt atagtgtaat tttgttagga atgaacatgt  11700
tttaatactc tgttttcgat ttgtcacaca ttcgaattat taatcgataa tttaactgaa  11760
aattcatggt tctagatctt gttgtcatca gattatttgt ttcgataatt catcaaatat  11820
gtagtccttt tgctgatttg cgactgtttc attttttctc aaaattgttt tttgttaagt  11880
```

-continued

```
ttatctaaca gttatcgttg tcaaaagtct ctttcatttt gcaaaatctt cttttttttt  11940
ttgtttgtaa ctttgttttt taagctacac atttagtctg taaaatagca tcgaggaaca  12000
gttgtcttag tagacttgca tgttcttgta acttctattt gtttcagttt gttgatgact  12060
gctttgattt tgtaggtcaa aggcgcaccc taccatggat gcttataacg ctgctatgga  12120
taagattgga gctgctatca tcgattggag tgatccagat ggaaagttca gagctgatag  12180
ggaggattgg tggttgtgcg atttcagatc cgctatcacc attgctctca tctacatcgc  12240
tttcgtgatc ttgggatctg ctgtgatgca atctctccca gctatggacc catacccta t  12300
caagttcctc tacaacgtgt ctcaaatctt cctctgcgct tacatgactg ttgaggctgg  12360
attcctcgct tataggaacg gatacaccgt tatgccatgc aaccacttca acgtgaacga  12420
tccaccagtt gctaacttgc tctggctctt ctacatctcc aaagtgtggg atttctggga  12480
taccatcttc attgtgctcg gaaagaagtg gagacaactc tctttcttgc acgtgtacca  12540
ccacaccacc atcttcctct tctactggtt gaacgctaac gtgctctacg atggagatat  12600
cttcttgacc atcctcctca acggattcat tcacaccgtg atgtacacct actacttcat  12660
ctgcatgcac accaaggatt ctaagaccgg aaagtctttg ccaatctggt ggaagtcatc  12720
tttgaccgct ttccaactct tgcaattcac catcatgatg tcccaagcta cctacttggt  12780
tttccacgga tgcgataagg tttccctcag aatcaccatc gtgtacttcg tgtacattct  12840
ctccctttc ttcctcttcg ctcagttctt cgtgcaatcc tacatggctc caaagaagaa  12900
gaagtccgct tgatgttaat gaaggccgca gatatcagat ctggtcgacc tagaggatcc  12960
ccggccgcaa agataataac aaaagcctac tatataacgt acatgcaagt attgtatgat  13020
attaatgttt ttacgtacgt gtaaacaaaa ataattacgt ttgtaacgta tggtgatgat  13080
gtggtgcact aggtgtaggc cttgtattaa taaaaagaag tttgttctat atagagtggt  13140
ttagtacgac gatttattta ctagtcggat tggaatagag aaccgaattc ttcaatcctt  13200
gcttttgatc aagaattgaa accgaatcaa atgtaaaagt tgatatattt gaaaaacgta  13260
ttgagcttat gaaaatgcta atactctcat ctgtatggaa aagtgacttt aaaaccgaac  13320
ttaaaagtga caaaagggga atatcgcatc aaaccgaatg aaaccgatct acgtaggctc  13380
agctgagctt agctaagcct acctagcctc acgtgagatt atgtaaggct aggtagcgtc  13440
acgtgacgtt acctaacact agctagcgtc agctgagctt agctaaccct acgtagcctc  13500
acgtgagctt acctaacgct acgtagcctc acgtgactaa ggatgaccta cccattcttg  13560
agacaaatgt tacattttag tatcagagta aaatgtgtac ctataactca aattcgattg  13620
acatgtatcc attcaacata aaattaaacc agcctgcacc tgcatccaca tttcaagtat  13680
tttcaaaccg ttcggctcct atccaccggg tgtaacaaga cggattccga atttggaaga  13740
ttttgactca aattcccaat ttatattgac cgtgactaaa tcaactttaa cttctataat  13800
tctgattaag ctcccaattt atattcccaa cggcactacc tccaaaattt atagactctc  13860
atccccttt aaaccaactt agtaaacgtt tttttttaa ttttatgaag ttaagtttt  13920
accttgtttt taaaaagaat cgttcataag atgccatgcc agaacattag ctacacgtta  13980
cacatagcat gcagccgcgg agaattgttt ttcttcgcca cttgtcactc ccttcaaaca  14040
cctaagagct tctctctcac agcacacaca tacaatcaca tgcgtgcatg cattattaca  14100
cgtgatcgcc atgcaaatct cctttatagc ctataaatta actcatcggc ttcactcttt  14160
actcaaacca aaactcatca atacaaacaa gattaaaaac atttcacgat ttggaatttg  14220
attcctgcga tcacaggtat gacaggttag attttgtttt gtatagttgt atacatactt  14280
```

```
ctttgtgatg ttttgtttac ttaatcgaat ttttggagtg ttttaaggtc tctcgtttag  14340
aaatcgtgga aaatatcact gtgtgtgtgt tcttatgatt cacagtgttt atgggtttca  14400
tgttctttgt tttatcattg aatgggaaga aatttcgttg ggatacaaat ttctcatgtt  14460
cttactgatc gttattagga gtttggggaa aaaggaagag ttttttggt tggttcgagt  14520
gattatgagg ttatttctgt atttgattta tgagttaatg gtcgttttaa tgttgtagac  14580
cgccatggct attttgaacc ctgaggctga ttctgctgct aacctcgcta ctgattctga  14640
ggctaagcaa agacaattgg ctgaggctgg atacactcac gttgagggtg ctcctgctcc  14700
tttgcctttg gagttgcctc acttctctct cagagatctc agagctgcta ttcctaagca  14760
ctgcttcgag agatctttcg tgacctccac ctactacatg atcaagaacg tgttgacttg  14820
cgctgctttg ttatacgctg ctaccttcat tgatagagct ggagctgctg cttatgtttt  14880
gtggcctgtg tactggttct tccagggatc ttacttgact ggagtgtggg ttatcgctca  14940
cgagtgtgga caccaggctt attgctcttc tgaggtggtg aacaacttga ttggactcgt  15000
gttgcactct gctttgttgg tgccttacca ctcttggaga atctctcaca gaaagcacca  15060
ctccaacact ggatcttgcg agaacgatga ggttttcgtt cctgtgacca gatctgtgtt  15120
ggcttcttct tggaacgaga ccttggagga ttctcctctc taccaactct accgtatcgt  15180
gtacatgttg gttgttggat ggatgcctgg atacctcttc ttcaacgcta ctggacctac  15240
taagtactgg ggaaagtcta ggtctcactt caacccttac tccgctatct atgctgatag  15300
ggagaggtgg atgatcgtgc tctccgatat ttcttggtg gctatgttgg ctgttttggc  15360
tgctttggtg cacactttct ccttcaacac gatggtgaag ttctacgtgg tgccttactt  15420
cattgtgaac gcttacttgg tgttgattac ctacctccaa cacaccgata cctacatccc  15480
tcacttcaga gagggagagt ggaattggtt gagaggagct ttgtgcactg tggatagatc  15540
atttggtcca ttcctcgatt ctgtggtgca tagaatcgtg gatacccacg tttgccacca  15600
tatcttctcc aagatgcctt tctatcactg cgaggaggct accaacgcta ttaagcctct  15660
cctcggaaag ttctacttga aggatactac tcctgttcct gttgctctct ggagatctta  15720
cacccactgc aagttcgttg aggatgatgg aaaggtggtg ttctacaaga acaagttata  15780
gttaatgaat aattgattgg ttcgagtatt atggcattgg gaaaactgtt tttcttgtac  15840
catttgttgt gcttgtaatt tactgtgttt tttattcggt tttcgctatc gaactgtgaa  15900
atggaaatgg atggagaaga gttaatgaat gatatggtcc ttttgttcat tctcaaatta  15960
atattatttg tttttctct tatttgttgt gtgttgaatt tgaaattata agagatatgc  16020
aaacattttg ttttgagtaa aaatgtgtca aatcgtggcc tctaatgacc gaagttaata  16080
tgaggagtaa aacacttgta gttgtaccat tatgcttatt cactaggcaa caaatatatt  16140
ttcagaccta gaaaagctgc aaatgttact gaatacaagt atgtcctctt gtgttttaga  16200
catttatgaa ctttccttta tgtaattttc cagaatcctt gtcagattct aatcattgct  16260
ttataattat agttatactc atggatttgt agttgagtat gaaaatattt tttaatgcat  16320
tttatgactt gccaattgat tgacaacatg catcaatcta gctagcctca gctgacgtta  16380
cgtaacgcta ggtagcgtca cgtgacgtta gctaacgcta ggtagcgtca gctgagctta  16440
cgtaagcgca cagatgaata ctagctgttg ttcacagttc tagtgtctcc tcattacgtg  16500
aattcaagct acgatcacta tctcaactcc tacataaaca tcagaatgct acaaaactat  16560
gcacaaaaac aaaagctaca tctaatacgt gaatcaatta ctctcatcac aagaaagaag  16620
```

```
atttcaatca ccgtcgagaa ggaggattca gttaattgaa tcaaagttcc gatcaaactc  16680
gaagactggt gagcacgagg acgacgaaga agagtgtctc gaagatacaa caagcaagaa  16740
atctactgag tgacctcctg aagttattgg cgcgattgag agaatcaatc cgaattaatt  16800
tcggggaaaa agataaatta gatactaagc gatgggcttg ggctgggcta agaaacaggt  16860
ggcaattggg ctggaggacc ccgcgattca tagcttccga tagcccaaaa aaaaacggat  16920
aacatattta tcgggtattt gaatttcagt gaaataagat atttcttttt tgttaggaaa  16980
attttagaaa ataatggaaa ttaaatagcg attatgttac aagatacgat cagcatcggg  17040
cagtgcaaaa tgctatagct tcccaagatt tgatcctttt gggttatctc ctaatgacaa  17100
ttagtttagg attttgaaac ttatattaat actattatcc gacaacactt gtttcagctt  17160
cttattttaa catttttgt tttttctat tcttcttccc atcagcattt tctttttaaa  17220
aaattgaata ctttaacttt ttaaaaattt cacaatgatc agatgatatt atggaagatc  17280
tcaagagtta aatgtatcca tcttggggca ttaaaaccgg tgtacgggat gataaataca  17340
gactttatat catatgatag ctcagtaatt catatttatc acgttgctaa aaaaattata  17400
aggtactagt agtcaacaaa atcaattaaa gagaaagaaa gaaacgcatg tgaagagagt  17460
ttacaactgg aaaagtaaaa taaaaattaa cgcatgttga atgctgacat gtcagtatgt  17520
ccatgaatcc acgtatcaag cgccattcat cgatcgtctt cctctttcta aatgaaaaca  17580
acttcacaca tcacaacaaa caatacacac aagacccccct ctctctcgtt gtctctctgc  17640
cagcgaccaa atcgaagctt gagaagaaca agaaggggtc aaaccatggc ttctacatct  17700
gctgctcaag acgctgctcc ttacgagttc ccttctctca ctgagatcaa gagggctctt  17760
ccttctgagt gtttcgaggc ttctgttcct ctttctctct actacaccgc tagatctctt  17820
gctcttgctg gatctctcgc tgttgctctc tcttacgcta gagctttgcc tcttgttcag  17880
gctaacgctc ttcttgatgc tactctctgc actggatacg ttcttctcca gggaatcgtt  17940
ttctggggat tcttcaccgt tggtcacgat tgtggacacg gagctttctc tagatctcac  18000
gtgctcaact tctctgttgg aaccctcatg cactctatca tccttacccc tttcgagtct  18060
tggaagctct ctcacagaca ccaccacaag aacaccggaa acatcgataa ggacgagatc  18120
ttctaccctc aaagagaggc tgattctcac cctgtttcta gacaccttgt gatgtctctt  18180
ggatctgctt ggttcgctta ccttttcgct ggattccctc ctagaaccat gaaccacttc  18240
aacccttggg aggctatgta tgttagaaga gtggctgctg tgatcatctc tctcggagtt  18300
cttttcgctt tcgctggact ctactcttac ctcaccttcg ttcttggatt caccactatg  18360
gctatctact acttcggacc tctcttcatc ttcgctacca tgcttgttgt taccactttc  18420
ctccaccaca acgatgagga gacaccttgg tacgctgatt ctgagtggac ttacgtgaag  18480
ggaaacctct cttctgtgga cagatcttac ggtgctctca tcgacaacct tagccacaac  18540
atcggaactc accagatcca ccacctcttc cctatcatcc ctcactacaa gctcaacgat  18600
gctactgctg ctttcgctaa ggctttccct gagcttgtta ggaaaaacgc tgctcctatc  18660
atcccaactt tcttcaggat ggctgctatg tacgctaagt acggagttgt tgacactgat  18720
gctaagacct tcactctcaa ggaggctaag gctgctgcta agactaagtc atcttgatga  18780
ttaatgaata attgattgta catactatat tttttgttta ccttgtgtta gtttaatgtt  18840
cagtgtcctc tctttattgt ggcacgtctc tttgttgtat gttgtgtcta tacaaagttg  18900
aaataatgga aagaaaagga agagtgtaat ttgttttgtt ttaagtgttt ataaatatat  18960
atatataggt catttagata gttctaggtt tctataaaac tctctctctg gaagtagaat  19020
```

```
ctgtttttga gaggatccag ttgcctacta atctccccca aaacccttca agcttaacct  19080
tcctcttcac aacaacagag gaaacacatc tcttgagctc tgagttctct tctttgagca  19140
tgtctatcgc taaactcatc tgccttatag cttccctctt ctcttcatct ctctctctca  19200
ccatttcgct gtaaaactta ttctcctccc tcagcctctc tatctcttcc ttcagcatct  19260
cacaattccc accataatcg actgaggatg attcaccgtc atcaacttca gactcagcgt  19320
tgtagtcgtc atgagtctca caagccttgg accaagaaga ctcatcatcg caagttgatg  19380
atttatcatg atgcttctct gagccgtgtt tgctacgtag cgtcacgtga cgttacctaa  19440
gcctaggtag cctcagctga cgttacgtaa cgctaggtag gctcagctga ctgcagcaaa  19500
tttacacatt gccactaaac gtctaaaccc ttgtaatttg tttttgtttt actatgtgtg  19560
ttatgtattt gatttgcgat aaatttttat atttggtact aaatttataa caccttttat  19620
gctaacgttt gccaacactt agcaatttgc aagttgatta attgattcta aattattttt  19680
gtcttctaaa tacatatact aatcaactgg aaatgtaaat atttgctaat atttctacta  19740
taggagaatt aaagtgagtg aatatggtac cacaaggttt ggagatttaa ttgttgcaat  19800
gctgcatgga tggcatatac accaaacatt caataattct tgaggataat aatggtacca  19860
cacaagattt gaggtgcatg aacgtcacgt ggacaaaagg tttagtaatt tttcaagaca  19920
acaatgttac cacacacaag ttttgaggtg catgcatgga tgccctgtgg aaagtttaaa  19980
aatattttgg aaatgatttg catggaagcc atgtgtaaaa ccatgacatc cacttggagg  20040
atgcaataat gaagaaaact acaaatttac atgcaactag ttatgcatgt agtctatata  20100
atgaggattt tgcaatactt tcattcatac acactcacta agttttacac gattataatt  20160
tcttcatagc cagtactgtt taagcttcac tgtctctgaa tcggcaaagg taaacgtatc  20220
aattattcta caaacccttt tatttttctt ttgaattacc gtcttcattg gttatatgat  20280
aacttgataa gtaaagcttc aataattgaa tttgatctgt gttttttttgg ccttaatact  20340
aaatccttac ataagctttg ttgcttctcc tcttgtgagt tgagtgttaa gttgtaataa  20400
tggttcactt tcagctttag aagaaacgcg ccttccatgg ctacaaagga ggcttacgtt  20460
ttcccaactc tcaccgagat caagagatct ctcccaaagg attgcttcga ggcttctgtg  20520
cctttgtctc tctactacac tgtgagatgc ttggttattg ctgtggcttt gaccttcgga  20580
ttgaactacg ctagagcttt gccagaggtt gagtctttct gggctttgga tgctgctttg  20640
tgcactggat atatcctcct ccagggaatt gtgttctggg gattcttcac tgttggacac  20700
gatgctggac acggagcttt ctctagatac cacctcttga acttcgttgt gggaaccttc  20760
atgcactctc tcatcttgac cccattcgag tcttggaagt tgacccacag acaccaccac  20820
aagaacaccg gaaacatcga tagagatgag gtgttctacc cacagagaaa ggctgatgat  20880
cacccattgt ccaggaactt gatcttggct ttgggagctg cttggcttgc ttatttggtg  20940
gagggattcc caccaagaaa ggtgaaccac ttcaacccat tcgagccact tttgtgaga  21000
caagtgtccg ctgtggttat ctctttgctc gctcacttct tcgttgctgg actctctatc  21060
tacttgtctc tccagttggg acttaagacc atggctatct actactacgg accagttttc  21120
gtgttcggat ctatgttggt gattaccacc ttcttgcacc acaacgatga ggagactcca  21180
tggtatgctg attctgagtg gacttacgtg aagggaaact tgtcctctgt ggatagatct  21240
tacggtgctc tcatcgataa cctctcccac aacatcggaa ctcaccagat ccaccacctc  21300
ttcccaatta tcccacacta caagctcaag aaggctactg ctgctttcca ccaagctttc  21360
```

```
ccagagcttg tgagaaagtc cgatgagcca atcatcaagg ctttcttcag agtgggaagg  21420
ttgtatgcta actacggagt ggttgatcaa gaggctaagc tcttcacttt gaaggaggct  21480
aaggctgcta ctgaagctgc tgctaagacc aagtctacct gattaatgaa tcgacaagct  21540
cgagtttctc cataataatg tgtgagtagt tcccagataa gggaattagg gttcctatag  21600
ggtttcgctc atgtgttgag catataagaa acccttagta tgtatttgta tttgtaaaat  21660
acttctatca ataaaatttc taattcctaa aaccaaaatc cagtactaaa atccagatcc  21720
cccgaattaa ttcggcgtta attcagctac gtaggctcag ctgagcttac ctaaggctac  21780
gtaggctcac gtgacgttac gtaaggctac gtagcgtcac gtgagcttac ctaactctag  21840
ctagcctcac gtgaccttag ctaacactag gtagcgtcag cacagatgaa tactagctgt  21900
tgttcacagt tctagtgtct cctcattacg tgaattcaag ctacgatcac tatctcaact  21960
cctacataaa catcagaatg ctacaaaact atgcacaaaa acaaaagcta catctaatac  22020
gtgaatcaat tactctcatc acaagaaaga agatttcaat caccgtcgag aaggaggatt  22080
cagttaattg aatcaaagtt ccgatcaaac tcgaagactg gtgagcacga ggacgacgaa  22140
gaagagtgtc tcgaagatac aacaagcaag aaatctactg agtgacctcc tgaagttatt  22200
ggcgcgattg agagaatcaa tccgaattaa tttcggggaa aaagataaat tagatactaa  22260
gcgatgggct tgggctgggc taagaaacag gtggcaattg ggctggagga ccccgcgatt  22320
catagcttcc gatagcccaa aaaaaaacgg ataacatatt tatcgggtat ttgaatttca  22380
gtgaaataag atattttctt tttgttagga aaattttaga aaataatgga aattaaatag  22440
cgattatgtt acaagatacg atcagcatcg ggcagtgcaa aatgctatag cttcccaaga  22500
tttgatcctt ttgggttatc tcctaatgac aattagttta ggattttgaa acttatatta  22560
atactattat ccgacaacac ttgtttcagc ttcttatttt aacatttttt gttttttct  22620
attcttcttc ccatcagcat tttcttttta aaaaattgaa tactttaact ttttaaaaat  22680
ttcacaatga tcagatgata ttatggaaga tctcaagagt taaatgtatc catcttgggg  22740
cattaaaacc ggtgtacggg atgataaata cagactttat atcatatgat agctcagtaa  22800
ttcatattta tcacgttgct aaaaaaatta taaggtacta gtagtcaaca aaatcaatta  22860
aagagaaaga aagaaacgca tgtgaagaga gtttacaact ggaaaagtaa aataaaaatt  22920
aacgcatgtt gaatgctgac atgtcagtat gtccatgaat ccacgtatca agcgccattc  22980
atcgatcgtc ttcctctttc taaatgaaaa caacttcaca catcacaaca aacaatacac  23040
acaagacccc ctctctctcg ttgtctctct gccagcgacc aaatcgaagc ttgagaagaa  23100
caagaagggg tcaaaccatg ggaaaaggat ctgagggaag atctgctgct agagagatga  23160
ctgctgaggc taacggagat aagagaaaga ccatcctcat tgagggagtg ttgtacgatg  23220
ctaccaactt caaacaccca ggaggttcca ttattaactt cctcaccgag ggagaagctg  23280
gagttgatgc tacccaagct tacagagagt tccatcagag atccggaaag gctgataagt  23340
acctcaagtc cctcccaaag ttggatgctt ctaaggtgga gtctaggttc tctgctaagg  23400
agcaggctag aagggacgct atgaccaggg attacgctgc tttcagagag gagttggttg  23460
ctgagggata cttcgatcca tctatcccac acatgatcta cagagtggtg gagattgtgg  23520
ctttgttcgc tttgtctttc tggttgatgt ctaaggcttc tccaacctct ttggttttgg  23580
gagtggtgat gaacggaatc gctcaaggaa gatgcggatg ggttatgcac gagatgggac  23640
acggatcttt cactggagtt atctggctcg atgataggat gtgcgagttc ttctacggag  23700
ttggatgtgg aatgtctgga cactactgga agaaccagca ctctaagcac cacgctgctc  23760
```

```
caaacagatt ggagcacgat gtggatttga acaccttgcc actcgttgct ttcaacgaga  23820
gagttgtgag gaaggttaag ccaggatctt tgttggcttt gtggctcaga gttcaggctt  23880
atttgttcgc tccagtgtct tgcttgttga tcggattggg atggaccttg tacttgcacc  23940
caagatatat gctcaggacc aagagacaca tggagtttgt gtggatcttc gctagatata  24000
tcggatggtt ctccttgatg ggagctttgg gatattctcc tggaacttct gtgggaatgt  24060
acctctgctc tttcggactt ggatgcatct acatcttcct ccaattcgct gtgtctcaca  24120
cccacttgcc agttaccaac ccagaggatc aattgcactg gcttgagtac gctgctgatc  24180
acaccgtgaa catctctacc aagtcttggt tggttacctg gtggatgtct aacctcaact  24240
tccaaatcga gcaccacttg ttcccaaccg ctccacaatt caggttcaag gagatctctc  24300
caagagttga ggctctcttc aagagacaca acctccctta ctacgatttg ccatacacct  24360
ctgctgtttc tactaccttc gctaacctct actctgttgg acactctgtt ggagctgata  24420
ccaagaagca ggattgatga ttaatgaata attgattgta catactatat tttttgttta  24480
ccttgtgtta gtttaatgtt cagtgtcctc tctttattgt ggcacgtctc tttgttgtat  24540
gttgtgtcta tacaaagttg aaataatgga aagaaaagga agagtgtaat ttgttttgtt  24600
ttaagtgttt ataaatatat atatataggt catttagata gttctaggtt tctataaaac  24660
tctctctctg gaagtagaat ctgtttttga gaggatccag ttgcctacta atctccccca  24720
aaacccttca agcttaacct tcctcttcac aacaacagag gaaacacatc tcttgagctc  24780
tgagttctct tctttgagca tgtctatcgc taaactcatc tgccttatag cttccctctt  24840
ctcttcatct ctctctctca ccatttcgct gtaaaactta ttctcctccc tcagcctctc  24900
tatctcttcc ttcagcatct cacaattccc accataatcg actgaggatg attcaccgtc  24960
atcaacttca gactcagcgt tgtagtcgtc atgagtctca caagccttgg accaagaaga  25020
ctcatcatcg caagttgatg atttatcatg atgcttctct gagccgtgtt tgctacctag  25080
agtcagctga gcttagctaa cgctagctag tgtcagctga cgttacgtaa ggctaactag  25140
cgtcacgtga ccttacgtaa cgctacgtag gctcagctga gcttagctaa ccctagctag  25200
tgtcacgtga gcttacgcta ctatagaaaa tgtgttatat cgacatgacc agacaaaggg  25260
gcaacagtta acaaaacaat taattctttc atttgagatt aaggaaggta aggtactaaa  25320
aagattaaaa aaaatgagct tatctctttg tttctgtaat aataatataa gtgtgataaa  25380
cttttaatat aataattgta attaggtttt ctacagatga gcaccactca gagacaagat  25440
aagaagaaaa caattttgtt aaacatgatt atagaaactt ttagttaagt cttgaagtat  25500
caatataaca aaaaaaagta cacacgacta tgacaataaa cccactaccg tcaggttatc  25560
atttcgatga aatgttttga tatcattaaa tataacagtc acaaaaaatc atctaattat  25620
aacaatataa cttatacata tatttaacta aaaacttaga gtttttgtaa tgattctaat  25680
tgatgattag agtttataga aatacaatta aataaaaaat ataattttaa aaaaacatag  25740
taaagtcaat gagatcctct ctgacctcag tgatcattta gtcatgtatg tacaacaatc  25800
attgttcatc acatgactgt aaaataaata aggataaact tgggaatata tataatatat  25860
tgtattaaat aaaaaaggga aatacaaata tcaattttag attcccgagt tgacacaact  25920
caccatgcac gctgccacct cagctcccag ctctcgtcac atgtctcatg tcagttaggt  25980
ctttggtttt tagtctttga cacaactcgc catgcatgtt gccacgtgag ctcgttcctc  26040
ttcccatgat ctcaccactg ggcatgcatg ctgccacctc agctggcacc tcttctctat  26100
```

```
atgtccctag aggccatgca cagtgccacc tcagcactcc tctcagaacc catacgtacc  26160
tgccaatcgg cttctctcca taaatatcta tttaaattat aactaattat ttcatatact  26220
taattgatga cgtggatgca ttgccatcgt tgtttaataa ttgttaatta cgacatgata  26280
aataaaatga aagtaaaaag tacgaaagat tttccatttg ttgttgtata aatagagaag  26340
tgagtgatgc ataatgcatg aatgcatgac cgcgccacca tgactgttgg atacgacgag  26400
gagatcccat tcgagcaagt tagggctcat aacaagccag acgacgcttg gtgtgctatt  26460
cacggacacg tgtacgacgt taccaagttc gcttcagttc acccaggagg agatattatc  26520
ttgctcgctg ctggaaagga agctactgtc ctctacgaga cctaccatgt tagaggagtg  26580
tctgacgctg tgctcagaaa gtacagaata ggaaagttgc cagacggaca aggaggagct  26640
aacgagaagg agaagagaac cttgtctgga ttgtcctctg cttcttacta cacctggaac  26700
tccgatttct acagagtgat gagggagaga gttgtggcta gattgaagga gagaggaaag  26760
gctagaagag gaggatacga actctggatc aaggctttct tgctccttgt tggattctgg  26820
tcctctcttt actggatgtg caccctcgat ccatctttcg gagctatctt ggctgctatg  26880
tctttgggag tgttcgctgc ttttgttgga acctgcatcc aacacgatgg aaaccacgga  26940
gctttcgctc aatctagatg ggttaacaag gtggcaggat ggactttgga tatgatcgga  27000
gcttctggaa tgacttggga gttccaacac gtgttgggac accacccata cactaacttg  27060
atcgaggagg agaacggatt gcaaaaggtg tccggaaaga agatggatac caagttggct  27120
gatcaagagt ctgatccaga tgtgttctcc acctacccaa tgatgagatt gcacccttgg  27180
caccagaaga ggtggtatca caggttccag cacatctacg gacctttcat cttcggattc  27240
atgaccatca acaaggtggt gactcaagat gttggagtgg tgttgagaaa gagactcttc  27300
caaatcgatg ctgagtgcag atatgcttcc ccaatgtacg ttgctaggtt ctggattatg  27360
aaggctttga ccgtgttgta tatggttgct ttgccttgtt atatgcaagg accttggcac  27420
ggattgaaac tcttcgctat cgctcacttc acttgcggag aggttttggc taccatgttc  27480
atcgtgaacc acattatcga gggagtgtct tacgcttcta aggatgctgt taagggaact  27540
atggctccac caaagactat gcacggagtg accccaatga acaacactag aaaggaggtt  27600
gaggctgagg cttctaagtc tggagctgtg gttaagtctg tgccattgga tgattgggct  27660
gctgttcagt gccaaacctc tgtgaactgg tctgttggat cttggttttg gaaccacttc  27720
tctggaggac tcaaccacca aatcgagcac cacctcttcc caggattgtc tcacgagacc  27780
tactaccaca tccaagacgt ggttcaatct acctgtgctg agtacggagt tccataccaa  27840
cacgagccat ctttgtggac tgcttactgg aagatgctcg aacaccttag acaattggga  27900
aacgaggaga ctcacgagtc atggcagaga gctgcttgat taatgaacta agactcccaa  27960
aaccaccttc cctgtgacag ttaaaccctg cttatacctt tcctcctaat aatgttcatc  28020
tgtcacacaa actaaaataa ataaaatggg agcaataaat aaaatgggag ctcatatatt  28080
tacaccattt acactgtcta ttattcacca tgccaattat tacttcataa ttttaaaatt  28140
atgtcatttt taaaaattgc ttaatgatgg aaaggattat tataagttaa aagtataaca  28200
tagataaact aaccacaaaa caaatcaata taaactaact tactctccca tctaattttt  28260
atttaaattt ctttacactt ctcttccatt tctatttcta caacattatt taacattttt  28320
attgtatttt tcttactttc taactctatt catttcaaaa atcaatatat gtttatcacc  28380
acctctctaa aaaaaacttt acaatcattg gtccagaaaa gttaaatcac gagatggtca  28440
ttttagcatt aaaacaacga ttcttgtatc actatttttc agcatgtagt ccattctctt  28500
```

```
caaacaaaga cagcggctat ataatcgttg tgttatattc agtctaaaac aactagctag  28560
cctcagctga cgttacgtaa cgctaggtag cgtcacgtga cgttagctaa cgctaggtag  28620
cgtcagctga gcttacgtaa gcgccacggg caggacatag ggactactac aagcatagta  28680
tgcttcagac aaagagctag gaaagaactc ttgatggagg ttaagagaaa aaagtgctag  28740
aggggcatag taatcaaact tgtcaaaacc gtcatcatga tgagggatga cataatataa  28800
aaagttgact aaggtcttgg tagtactctt tgattagtat tatatattgg tgagaacatg  28860
agtcaagagg agacaagaaa ccgaggaacc atagtttagc aacaagatgg aagttgcaaa  28920
gttgagctag ccgctcgatt agttacatct cctaagcagt actacaagga atggtctcta  28980
tactttcatg tttagcacat ggtagtgcgg attgacaagt tagaaacagt gcttaggaga  29040
caaagagtca gtaaaggtat tgaaagagtg aagttgatgc tcgacaggtc aggagaagtc  29100
cctccgccag atggtgacta ccaaggggtt ggtatcagct gagacccaaa taagattctt  29160
cggttgaacc agtggttcga ccgagactct tagggtggga tttcactgta agatttgtgc  29220
attttgttga atataaattg acaatttttt ttatttaatt atagattatt tagaatgaat  29280
tacatattta gtttctaaca aggatagcaa tggatgggta tgggtacagg ttaaacatat  29340
ctattaccca cccatctagt cgtcgggttt tacacgtacc cacccgttta cataaaccag  29400
aacggaattt taaaccgtac ccgtccgtta gcgggtttca gatttacccg tttaatcggg  29460
taaaacctga ttactaaata tatatttttt atttgataaa caaaacaaaa atgttaatat  29520
tttcatattg gatgcaattt taagaaacac atattcataa atttccatat ttgtaggaaa  29580
ataaaaagaa aaatatattc aagaacacaa atttcaccga catgactttt attacagagt  29640
tggaattaga tctaacaatt gaaaaattaa aattaagata gaatatgttg aggaacatga  29700
catagtataa tgctgggtta cccgtcgggt aggtatcgag gcggatacta ctaaatccat  29760
cccactcgct atccgataat cactggtttc gggtataccc attcccgtca acaggccttt  29820
ttaaccggat aatttcaact tatagtgaat gaattttgaa taaatagtta gaataccaaa  29880
atcctggatt gcatttgcaa tcaaattttg tgaaccgtta aattttgcat gtacttggga  29940
tagatataat agaaccgaat tttcattagt ttaatttata acttactttg ttcaaagaaa  30000
aaaaatatct atccaattta cttataataa aaaataatct atccaagtta cttattataa  30060
tcaacttgta aaaaggtaag aatacaaatg tggtagcgta cgtgtgatta tatgtgacga  30120
aatgttatat ctaacaaaag tccaaattcc catggtaaaa aaaatcaaaa tgcatggcag  30180
gctgtttgta accttggaat aagatgttgg ccaattctgg agccgccacg tacgcaagac  30240
tcagggccac gttctcttca tgcaaggata gtagaacacc actccaccca cctcctatat  30300
tagacctttg cccaaccctc cccaactttc ccatcccatc cacaaagaaa ccgacatttt  30360
tatcataaat cagggtttcg tttttgtttc atcgataaac tcaaaggtga tgattttagg  30420
gtcttgtgag tgtgcttttt tgtttgattc tactgtaggg tttatgttct ttagctcata  30480
ggttttgtgt atttcttaga aatgtggctt ctttaatctc tgggtttgtg actttttgtg  30540
tggtttctgt gtttttcata tcaaaaacct attttttccg agtttttttt tacaaattct  30600
tactctcaag cttgaatact tcacatgcag tgttcttttg tagattttag agttaatgtg  30660
ttaaaaagtt tggatttttc ttgcttatag agcttcttca ctttgatttt gtgggttttt  30720
ttgttttaaa ggtgagattt ttgatgaggt ttttgcttca aagatgtcac ctttctgggt  30780
ttgtcttttg aataaagcta tgaactgtca catggctgac gcaattttgt tactatgtca  30840
```

```
tgaaagctga cgtttttccg tgttatacat gtttgcttac acttgcatgc gtcaaaaaaa  30900
ttggggcttt ttagttttag tcaaagattt tacttctctt ttgggattta tgaaggaaag  30960
ttgcaaactt tctcaaattt taccattttt gctttgatgt ttgtttagat tgcgacagaa  31020
caaactcata tatgttgaaa tttttgcttg gttttgtata ggattgtgtc ttttgcttat  31080
aaatgttgaa atctgaactt tttttttgtt tggtttcttt gagcaggaga taaggcgcac  31140
caccatggct tctacatctg ctgctcaaga cgctgctcct tacgagttcc cttctctcac  31200
tgagatcaag agggctcttc cttctgagtg tttcgaggct tctgttcctc tttctctcta  31260
ctacaccgct agatctcttg ctcttgctgg atctctcgct gttgctctct cttacgctag  31320
agctttgcct cttgttcagg ctaacgctct tcttgatgct actctctgca ctggatacgt  31380
tcttctccag ggaatcgttt tctggggatt cttcaccgtt ggtcacgatt gtggacacgg  31440
agctttctct agatctcacg tgctcaactt ctctgttgga accctcatgc actctatcat  31500
ccttacccct ttcgagtctt ggaagctctc tcacagacac caccacaaga acaccggaaa  31560
catcgataag gacgagatct tctaccctca aagagaggct gattctcacc ctgtttctag  31620
acaccttgtg atgtctcttg gatctgcttg gttcgcttac cttttcgctg gattccctcc  31680
tagaaccatg aaccacttca acccttggga ggctatgtat gttagaagag tggctgctgt  31740
gatcatctct ctcggagttc ttttcgcttt cgctggactc tactcttacc tcaccttcgt  31800
tcttggattc accactatgg ctatctacta cttcggacct ctcttcatct tcgctaccat  31860
gcttgttgtt accactttcc tccaccacaa cgatgaggag acaccttggt acgctgattc  31920
tgagtggact tacgtgaagg gaaacctctc ttctgtggac agatcttacg gtgctctcat  31980
cgacaacctt agccacaaca tcggaactca ccagatccac cacctcttcc ctatcatccc  32040
tcactacaag ctcaacgatg ctactgctgc tttcgctaag gctttccctg agcttgttag  32100
gaaaaacgct gctcctatca tcccaacttt cttcaggatg gctgctatgt acgctaagta  32160
cggagttgtt gacactgatg ctaagacctt cactctcaag gaggctaagg ctgctgctaa  32220
gactaagtca tcttgatgat taatgaaggc cgcagatatc agatctggtc gacctagagg  32280
atccccggcc gcaaagataa taacaaaagc ctactatata acgtacatgc aagtattgta  32340
tgatattaat gtttttacgt acgtgtaaac aaaaataatt acgtttgtaa cgtatggtga  32400
tgatgtggtg cactaggtgt aggccttgta ttaataaaaa gaagtttgtt ctatatagag  32460
tggtttagta cgacgattta tttactagtc ggattggaat agagaaccga attcttcaat  32520
ccttgctttt gatcaagaat tgaaaccgaa tcaaatgtaa aagttgatat atttgaaaaa  32580
cgtattgagc ttatgaaaat gctaatactc tcatctgtat ggaaaagtga ctttaaaacc  32640
gaacttaaaa gtgacaaaag gggaatatcg catcaaaccg aatgaaaccg atctacgtag  32700
gctcagctga gcttacctaa ggctacgtag gctcacgtga cgttacgtaa ggctacgtag  32760
cgtcacgtga gcttacctaa ctctagctag cctcacgtga ccttagctaa cactaggtag  32820
cgtcagctta gcagatattt ggtgtctaaa tgtttatttt gtgatatgtt catgtttgaa  32880
atggtggttt cgaaaccagg gacaacgttg ggatctgata gggtgtcaaa gagtattatg  32940
gattgggaca atttcggtca tgagttgcaa attcaagtat atcgttcgat tatgaaaatt  33000
ttcgaagaat atcccatttg agagagtctt tacctcatta atgtttttag attatgaaat  33060
tttatcatag ttcatcgtag tctttttggt gtaaaggctg taaaaagaaa ttgttcactt  33120
ttgttttcgt ttatgtgaag gctgtaaaag attgtaaaag actattttgg tgttttggat  33180
aaaatgatag tttttataga ttcttttgct tttagaagaa atacatttga aatttttttcc  33240
```

```
atgttgagta taaaataccg aaatcgattg aagatcatag aaatatttta actgaaaaca  33300
aatttataac tgattcaatt ctctccattt ttatacctat ttaaccgtaa tcgattctaa  33360
tagatgatcg attttttata taatcctaat taaccaacgg catgtattgg ataattaacc  33420
gatcaactct cacccctaat agaatcagta ttttccttcg acgttaattg atcctacact  33480
atgtaggtca tatccatcgt tttaattttt ggccaccatt caattctgtc ttgcctttag  33540
ggatgtgaat atgaacggcc aaggtaagag aataaaaata atccaaatta aagcaagaga  33600
ggccaagtaa gataatccaa atgtacactt gtcattgcca aaattagtaa aatactcggc  33660
atattgtatt cccacacatt attaaaatac cgtatatgta ttggctgcat ttgcatgaat  33720
aatactacgt gtaagcccaa aagaacccac gtgtagccca tgcaaagtta acactcacga  33780
ccccattcct cagtctccac tatataaacc caccatcccc aatctcacca aacccaccac  33840
acaactcaca actcactctc acaccttaaa gaaccaatca ccaccaaaaa aagttctttg  33900
ctttcgaagt tgccgcaacc taaacaggtt tttccttctt ctttcttctt attaactacg  33960
accttgtcct ttgcctatgt aaaattacta ggttttcatc agttacactg attaagttcg  34020
ttatagtgga agataaaatg ccctcaaagc attttgcagg atatctttga tttttcaaag  34080
atatggaact gtagagtttg atagtgttct tgaatgtggt tgcatgaagt ttttttggtc  34140
tgcatgttat tttttcctcg aaatatgttt tgagtccaac aagtgattca cttgggattc  34200
agaaagttgt tttctcaata tgtaacagtt tttttctatg gagaaaaatc atagggaccg  34260
ttggttttgg cttctttaat tttgagctca gattaaaccc attttacccg gtgttcttgg  34320
cagaattgaa aacagtacgt agtaccgcgc ctaccatgcc acctagtgct gctagtgaag  34380
gtggtgttgc tgaacttaga gctgctgaag ttgctagcta cactagaaag gctgttgacg  34440
aaagacctga cctcactata gttggtgacg ctgtttacga cgctaaggct tttagggacg  34500
agcaccctgg tggtgctcac ttcgttagcc ttttcggagg tagggacgct actgaggctt  34560
ttatggaata tcaccgtaga gcttggccta aggctaggat gtctaagttc ttcgttggtt  34620
cacttgacgc tagcgagaag cctactcaag ctgattcagc ttaccttaga ctttgcgctg  34680
aggttaacgc tcttttgcct aagggtagcg gaggattcgc tcctcctagc tactggctta  34740
aggctgctgc tcttgttgtt gctgctgtta gtatagaggg ttatatgctc cttaggggta  34800
agaccctttt gcttagcgtt ttccttggac tcgtgttcgc ttggatagga cttaatattc  34860
agcacgacgc taatcacggt gctcttagta gacactcagt gattaactac tgcctcggtt  34920
acgctcagga ttggataggt ggtaatatgg tgctttggct tcaagagcac gttgtgatgc  34980
accacctcca cactaacgac gttgacgctg atcctgatca aaaggctcac ggtgttctta  35040
gacttaagcc tactgacggt tggatgcctt ggcacgcact tcaacaactc tatatccttc  35100
ctggtgaggc tatgtacgct tttaagcttc ttttcttgga cgcccttgag cttcttgctt  35160
ggaggtggga gggtgagaag attagccctc ttgctagagc tttgttcgct cctgctgttg  35220
cttgtaagct tggattctgg gctagattcg ttgctctccc tctctggctt caacctactg  35280
ttcacactgc tttgtgtatc tgtgctactg tgtgtactgg tagcttctac ctcgccttct  35340
tcttctttat ctctcacaac ttcgacggtg ttggtagcgt tggacctaag ggatcacttc  35400
ctagatcagc tactttcgtt caacgtcagg ttgagactag ctctaacgtt ggtggttact  35460
ggcttggagt tcttaacggt ggacttaact ttcagataga gcaccacttg ttccctaggc  35520
ttcaccactc ttactacgct caaatagctc ctgtggttag gactcacata gagaagctcg  35580
```

```
gttttaagta ccgtcacttc cctaccgttg gatctaacct tagctcaatg cttcagcata  35640
tgggtaagat gggaactaga cctggtgctg agaagggtgg taaggctgag tagtgattaa  35700
tgaataattg attgctgctt taatgagata tgcgagacgc ctatgatcgc atgatatttg  35760
ctttcaattc tgttgtgcac gttgtaaaaa acctgagcat gtgtagctca gatccttacc  35820
gccggtttcg gttcattcta atgaatatat cacccgttac tatcgtattt ttatgaataa  35880
tattctccgt tcaatttact gattgtctac gtagcgtcac ctgacgttac gtaaggctac  35940
ctaggctcac gtgacgttac gtaacgctac gtagcgtcag gtgaggttag ctaacgctag  36000
ctagcctcac ctgacgttag gtaaggctac gtagcgtcac ctgagattag ctaagcctac  36060
ctagactcac gtgaccttag gtaacgctac gtagcgtcaa agctttacaa cgctacacaa  36120
aacttataac cgtaatcacc attcattaac ttaactacta tcacatgcat tcatgaattg  36180
aaacgagaag gatgtaaata gttgggaagt tatctccacg ttgaagagat cgttagcgag  36240
agctgaaaga ccgagggagg agacgccgtc aacacggaca gagtcgtcga ccctcacatg  36300
aagtaggagg aatctccgtg aggagccaga gagacgtctt tggtcttcgg tttcgatcct  36360
tgatctgacg gagaagacga gagaagtgcg actggactcc gtgaggacca acagagtcgt  36420
cctcggtttc gatcgtcggt attggtggag aaggcggagg aatctccgtg acgagccaga  36480
gagatgtcgt cggtcttcgg tttcgatcct tgatctgacg gagaagacga gagaagtgcg  36540
acgagactcc gtgaggacca acagagttgt cctcggtttc gatcgtcggt ttcggcggag  36600
aaggcggagg aatctccgtg aggagccaga gagacgtcgt tggtcttcgg tttcgatcct  36660
tgatctgttg gagaagacga gacaagtggg acgagactca acgacggagt cagagacgtc  36720
gtcggtcttc ggtttcggcc gagaaggcgg agtcggtctt cggtttcggc cgagaaggcg  36780
gaggagacgt cttcgatttg ggtctctcct cttgacgaag aaaacaaaga acacgagaaa  36840
taatgagaaa gagaacaaaa gaaaaaaaaa taaaaataaa aataaaattt ggtcctctta  36900
tgtggtgaca cgtggtttga aacccaccaa ataatcgatc acaaaaaacc taagttaagg  36960
atcggtaata acctttctaa ttaattttga tttatattaa atcactcttt ttatttataa  37020
accccactaa attatgcgat attgattgtc taagtacaaa aattctctcg aattcaatac  37080
acatgtttca tatatttagc cctgttcatt taatattact agcgcatttt taatttaaaa  37140
ttttgtaaac ttttttggtc aaagaacatt tttttaatta gagacagaaa tctagactct  37200
ttatttggaa taatagtaat aaagatatat taggcaatga gtttatgatg ttatgtttat  37260
atagtttatt tcattttaaa ttgaaaagca ttatttttat cgaaatgaat ctagtataca  37320
atcaatattt atgtttttc atcagatact ttcctatttt ttggcacctt tcatcggact  37380
actgatttat ttcaatgtgt atgcatgcat gagcatgagt atacacatgt cttttaaaat  37440
gcatgtaaag cgtaacggac cacaaaagag gatccataca aatacatctc atcgcttcct  37500
ctactattct ccgacacaca cactgagcat ggtgcttaaa cactctggtg agttctagta  37560
cttctgctat gatcgatctc attaccattt cttaaatttc tctccctaaa tattccgagt  37620
tcttgatttt tgataacttc aggttttctc tttttgataa atctggtctt tccatttttt  37680
ttttttgtg gttaatttag tttcctatgt tcttcgattg tattatgcat gatctgtgtt  37740
tggattctgt tagattatgt attggtgaat atgtatgtgt ttttgcatgt ctggttttgg  37800
tcttaaaaat gttcaaatct gatgatttga ttgaagcttt tttagtgttg gtttgattct  37860
tctcaaaact actgttaatt tactatcatg ttttccaact ttgattcatg atgacacttt  37920
tgttctgctt tgttataaaa ttttggttgg tttgattttg taattatagt gtaattttgt  37980
```

```
taggaatgaa catgttttaa tactctgttt tcgatttgtc acacattcga attattaatc  38040
gataatttaa ctgaaaattc atggttctag atcttgttgt catcagatta tttgtttcga  38100
taattcatca aatatgtagt ccttttgctg atttgcgact gtttcatttt ttctcaaaat  38160
tgtttttttgt taagtttatc taacagttat cgttgtcaaa agtctctttc attttgcaaa  38220
atcttctttt tttttttgtt tgtaactttg ttttttaagc tacacattta gtctgtaaaa  38280
tagcatcgag gaacagttgt cttagtagac ttgcatgttc ttgtaacttc tatttgtttc  38340
agtttgttga tgactgcttt gattttgtag gtcaaaccgc gccatgtctg ctagcggagc  38400
tttgttgcct gctatagctt tcgctgctta cgcttacgct acctacgctt atgctttcga  38460
gtggagccac gctaacggaa tcgataacgt ggatgctaga gagtggattg gagctttgtc  38520
tttgagactc cctgcaattg caaccacaat gtacctcttg ttctgccttg tgggacctag  38580
attgatggct aagagggagg cttttgatcc taagggattt atgctcgctt acaacgctta  38640
ccaaaccgct ttcaacgttg tggtgctcgg aatgttcgct agagagatct ctggattggg  38700
acaacctgtt tggggatcta ctatgccttg gagcgatagg aagtccttca agattttgtt  38760
gggagtgtgg ctccactaca acaataagta cctcgagttg ttggatactg tgttcatggt  38820
ggctaggaaa aagaccaagc agctctcttt cttgcacgtg taccaccacg ctttgttgat  38880
ttgggcttgg tggcttgttt gtcacctcat ggctaccaac gattgcatcg atgcttattt  38940
cggagctgct tgcaactctt tcatccacat cgtgatgtac tcctactacc tcatgtctgc  39000
tttgggaatt aggtgccctt ggaagagata tatcacccag gctcagatgt tgcaattcgt  39060
gatcgtgttc gctcacgctg ttttcgtgct cagacaaaag cactgccctg ttactttgcc  39120
ttgggcacaa atgttcgtga tgacaaatat gttggtgctc ttcggaaact tctacctcaa  39180
ggcttactct aacaagtcta ggggagatgg agcttcttct gttaagcctg ctgagactac  39240
tagagcacct tctgtgagaa gaaccaggtc aaggaagatc gattgatagt taatgaacta  39300
agtttgatgt atctgagtgc caacgtttac tttgtctttc ctttctttta ttggttatga  39360
ttagatgttt actatgttct ctctttttcg ttataaataa agaagttcaa ttcttctata  39420
gtttcaaacg cgattttaag cgtttctatt taggtttaca tgatttcttt tacaaaatca  39480
tctttaaaat acagtatatt tttagttttc ataaaatatt taaagaaatg aaagtttata  39540
aacattcact cctattctct aattaaggat ttgtaaaaca aaaattttgt aagcatatcg  39600
atttatgcgt tttgtcttaa ttagctcact aaataataaa taatagctta tgttgtggga  39660
ctgtttaatt acctaactta gaactaaaat caactctttg tgctagctag cctcagctga  39720
cgttacgtaa cgctaggtag cgtcacgtga cgttagctaa cgctaggtag cgtcagctga  39780
gcttacgtaa gcgcttaatt aaagtactga tatcggtacc aaatcgaatc caaaaattac  39840
ggatatgaat ataggcatat ccgtatccga attatccgtt tgacagctag caacgattgt  39900
acaattgctt ctttaaaaaa ggaagaaaga aagaaagaaa agaatcaaca tcagcgttaa  39960
caaacggccc cgttacggcc caaacggtca tatagagtaa cggcgttaag cgttgaaaga  40020
ctcctatcga aatacgtaac cgcaaacgtg tcatagtcag atcccctctt ccttcaccgc  40080
ctcaaacaca aaaataatct tctacagcct atatatacaa cccccccttc tatctctcct  40140
ttctcacaat tcatcatctt tctttctcta cccccaattt taagaaatcc tctcttctcc  40200
tcttcatttt caaggtaaat ctctctctct ctctctctct ctgttattcc ttgttttaat  40260
taggtatgta ttattgctag tttgttaatc tgcttatctt atgtatgcct tatgtgaata  40320
```

```
tctttatctt gttcatctca tccgtttaga agctataaat ttgttgattt gactgtgtat  40380
ctacacgtgg ttatgtttat atctaatcag atatgaattt cttcatattg ttgcgtttgt  40440
gtgtaccaat ccgaaatcgt tgattttttt catttaatcg tgtagctaat tgtacgtata  40500
catatggatc tacgtatcaa ttgttcatct gtttgtgttt gtatgtatac agatctgaaa  40560
acatcacttc tctcatctga ttgtgttgtt acatacatag atatagatct gttatatcat  40620
tttttttatt aattgtgtat atatatatgt gcatagatct ggattacatg attgtgatta  40680
tttacatgat tttgttattt acgtatgtat atatgtagat ctggactttt tggagttgtt  40740
gacttgattg tatttgtgtg tgtatatgtg tgttctgatc ttgatatgtt atgtatgtgc  40800
agctgaacca tggcggcggc aacaacaaca acaacaacat cttcttcgat ctccttctcc  40860
accaaaccat ctccttcctc ctccaaatca ccattaccaa tctccagatt ctccctccca  40920
ttctccctaa accccaacaa atcatcctcc tcctcccgcc gccgcggtat caaatccagc  40980
tctccctcct ccatctccgc cgtgctcaac acaaccacca atgtcacaac cactccctct  41040
ccaaccaaac ctaccaaacc cgaaacattc atctcccgat tcgctccaga tcaaccccgc  41100
aaaggcgctg atatcctcgt cgaggcttta gaacgtcaag gcgtagaaac cgtattcgct  41160
taccctggag gtacatcaat ggagattcac caagccttaa cccgctcttc ctcaatccgt  41220
aacgtccttc ctcgtcacga acaaggaggt gtattcgcag cagaaggata cgctcgatcc  41280
tcaggtaaac caggtatctg tatagccact tcaggtcccg gagctacaaa tctcgttagc  41340
ggattagccg atgcgttgtt agatagtgtt cctcttgtag caatcacagg acaagtccct  41400
cgtcgtatga ttggtacaga tgcgtttcaa gagactccga ttgttgaggt aacgcgttcg  41460
attacgaagc ataactatct tgtgatggat gttgaagata tcccaaggat tattgaagag  41520
gctttctttt tagctacttc tggtagacct ggacctgttt tggttgatgt tcctaaagat  41580
attcaacaac agcttgcgat tcctaattgg gaacaggcta tgagattacc tggttatatg  41640
tctaggatgc ctaaacctcc ggaagattct catttggagc agattgttag gttgatttct  41700
gagtctaaga agcctgtgtt gtatgttggt ggtggttgtc ttaattctag cgatgaattg  41760
ggtaggtttg ttgagcttac gggcatccct gttgcgagta cgttgatggg gctgggatct  41820
tatccttgtg atgatgagtt gtcgttacat atgcttggaa tgcatgggac tgtgtatgca  41880
aattacgctg tggagcatag tgatttgttg ttggcgtttg gggtaaggtt tgatgatcgt  41940
gtcacgggta aacttgaggc ttttgctagt agggctaaga ttgttcatat tgatattgac  42000
tcggctgaga ttgggaagaa taagactcct catgtgtctg tgtgtggtga tgttaagctg  42060
gctttgcaag ggatgaataa ggttcttgag aaccgagcgg aggagcttaa acttgatttt  42120
ggagtttgga ggaatgagtt gaacgtacag aaacagaagt ttccgttgag ctttaagacg  42180
tttggggaag ctattcctcc acagtatgcg attaaggtcc ttgatgagtt gactgatgga  42240
aaagccataa taagtactgg tgtcgggcaa catcaaatgt gggcggcgca gttctacaat  42300
tacaagaaac caaggcagtg gctatcatca ggaggccttg gagctatggg atttggactt  42360
cctgctgcga ttggagcgtc tgttgctaac cctgatgcga tagttgtgga tattgacgga  42420
gatggaagtt ttataatgaa tgtgcaagag ctagccacta ttcgtgtaga gaatcttcca  42480
gtgaaggtac ttttattaaa caaccagcat cttggcatgg ttatgcaatg ggaagatcgg  42540
ttctacaaag ctaaccgagc tcacacattt ctcggggacc cggctcagga ggacgagata  42600
ttcccgaaca tgttgctgtt tgcagcagct tgcgggattc cagcggcgag ggtgacaaag  42660
aaagcagatc tccgagaagc tattcagaca atgctggata caccaggacc ttacctgttg  42720
```

```
gatgtgattt gtccgcacca agaacatgtg ttgccgatga tcccgaatgg tggcactttc  42780

aacgatgtca taacggaagg agatggccgg attaaatact gagagatgaa accggtgatt  42840

atcagaacct tttatggtct ttgtatgcat atggtaaaaa aacttagttt gcaatttcct  42900

gtttgttttg gtaatttgag tttcttttag ttgttgatct gcctgctttt tggtttacgt  42960

cagactacta ctgctgttgt tgtttggttt cctttctttc attttataaa taaataatcc  43020

ggttcggttt actccttgtg actggctcag tttggttatt gcgaaatgcg aatggtaaat  43080

tgagtaattg aaattcgtta ttagggttct aagctgtttt aacagtcact gggttaatat  43140

ctctcgaatc ttgcatggaa aatgctctta ccattggttt ttaattgaaa tgtgctcata  43200

tgggccgtgg tttccaaatt aaataaaact acgatgtcat cgagaagtaa aatcaactgt  43260

gtccacatta tcagttttgt gtatacgatg aaatagggta attcaaaatc tagcttgata  43320

tgccttttgg ttcattttaa ccttctgtaa acatttttc agattttgaa caagtaaatc  43380

caaaaaaaaa aaaaaaaatc tcaactcaac actaaattat tttaatgtat aaaagatgct  43440

taaaacattt ggcttaaaag aaagaagcta aaaacataga gaactcttgt aaattgaagt  43500

atgaaaatat actgaattgg gtattatatg aatttttctg atttaggatt cacatgatcc  43560

aaaaaggaaa tccagaagca ctaatcagac attggaagta ggattaatca gtgatcagta  43620

actattaaat tcaattaacc gcggacatct acatttttga attgaaaaaa aattggtaat  43680

tactctttct ttttctccat attgaccatc atactcattg ctgatccatg tagatttccc  43740

ggacatgaag ccatata                                                 43757


<210> SEQ ID NO 4
<211> LENGTH: 20
<212> TYPE: DNA
<213> ORGANISM: Artificial sequence
<220> FEATURE:
<223> OTHER INFORMATION: LBFLFK Locus 1 RB junction region

<400> SEQUENCE: 4

agctcgcaat ccagtcagca                                                 20


<210> SEQ ID NO 5
<211> LENGTH: 20
<212> TYPE: DNA
<213> ORGANISM: Artificial sequence
<220> FEATURE:
<223> OTHER INFORMATION: LBFLFK Locus 1 LB junction region

<400> SEQUENCE: 5

aagccatata tctgacccta                                                 20


<210> SEQ ID NO 6
<211> LENGTH: 1100
<212> TYPE: DNA
<213> ORGANISM: Artificial sequence
<220> FEATURE:
<223> OTHER INFORMATION: LBFLFK Locus 1 flanking sequence up to and
      including the right border of the T-DNA

<400> SEQUENCE: 6

tatttttgtt catgtcttat tttctttttt cctaatgtaa ctatgagagg cttaaaaact     60

gtaaaatcag caaaacaata tacaattaca gtaaaaaatg tcacatacta agttctatat    120

atgactacaa gtctacaact caactaatca tccacataaa taattagttt tgtcataatt    180

atattatagt aagtacctga agaaaagata aagccatttc tggacaacat catctcgtat    240
```

```
tggcatcttt atacgtggac gacaaaatct atcacaataa tagttgctag atatagatac    300

atgaattttg taatatgatt aattaattgg cgcttcataa ctaaaataac taataaaggg    360

taaatgttct taaagtttca taattaatta tgtttcagag tggttgcatt atagtagttt    420

aaaattcaga agtgtacgcg acgagaaaag agatttgctg gtgactattg catcatcttt    480

gacatggaaa aaatcttaga taagaatagt ttgaaattag aaagctcgca attgaggtct    540

accaaaatta gaaattagaa agctcgcaat ccagtcagca tcatcacacc aaaagttagg    600

cccgaatagt ttgaaattag aaagctcgca attgaggtct acaggccaaa ttcgctctta    660

gccgtacaat attactcacc ggtgcgatgc cccccatcgt aggtgaaggt ggaaattaat    720

ggcgcgcctg atcactgatt agtaactatt acgtaagcct acgtagcgtc acgtgacgtt    780

agctaacgct acgtagcctc agctgacgtt acgtaagcct acgtagcgtc acgtgagctt    840

agctaacgct acctaggctc agctgacgtt acgtaacgct agctagcgtc actcctgcag    900

caaatttaca cattgccact aaacgtctaa acccttgtaa tttgtttttg ttttactatg    960

tgtgttatgt atttgatttg cgataaattt ttatatttgg tactaaattt ataacacctt   1020

ttatgctaac gtttgccaac acttagcaat ttgcaagttg attaattgat tctaaattat   1080

ttttgtcttc taaatacata                                                1100
```

```
<210> SEQ ID NO 7
<211> LENGTH: 811
<212> TYPE: DNA
<213> ORGANISM: Artificial sequence
<220> FEATURE:
<223> OTHER INFORMATION: LBFLFK Locus 1 flanking sequence up to and
      including the left border of the T-DNA

<400> SEQUENCE: 7
```

```
aatttttctg atttaggatt cacatgatcc aaaaaggaaa tccagaagca ctaatcagac     60

attggaagta ggattaatca gtgatcagta actattaaat tcaattaacc gcggacatct    120

acatttttga attgaaaaaa aattggtaat tactctttct ttttctccat attgaccatc    180

atactcattg ctgatccatg tagatttccc ggacatgaag ccatttactc tgaccctact    240

ccacaaatat atttttattt ataaaaaggt ggccattgta tactatgtgt gcgtatacag    300

gaataaaaat gtgtcaatgt atatgtaaac tgattccatc ttatatgtaa tgtgcgtgtg    360

taaatgaaga tactagtatc catgtgtcgc ctacttgatt tgttcaactg taactcataa    420

tatctcaaga ttctttcttt tttttctacg aatatcgcaa tctataatac cattaaatta    480

ttgtaacaaa attggttgac atttataaaa tgaaaaagaa gagaagagca tttaaacacg    540

actgatgaaa gtccaatgta gctagataaa ccacgcgtgg tggtcaatgc gttccattcc    600

aaaaggatcc gagttcgaat ccgcaccaca ccagattttc actgcgcgtg gccatgaagc    660

tttcgcattc tcgctcctga gaatggttct ccattttttt tttccagtgt agctagatac    720

cggtctgaat ctaggtttat aatatgctga caatgtaatg ataattaata catcaaaaca    780

tgtgtttctg aaccaaaata aaaacttttt t                                   811
```

```
<210> SEQ ID NO 8
<211> LENGTH: 27
<212> TYPE: DNA
<213> ORGANISM: Artificial sequence
<220> FEATURE:
<223> OTHER INFORMATION: LBFLFK Locus 1_Forward primer

<400> SEQUENCE: 8
```

ctctttcttt ttctccatat tgaccat 27

<210> SEQ ID NO 9
<211> LENGTH: 28
<212> TYPE: DNA
<213> ORGANISM: Artificial sequence
<220> FEATURE:
<223> OTHER INFORMATION: LBFLFK Locus 1_Reverse primer

<400> SEQUENCE: 9
acatttttat tcctgtatac gcacacat 28

<210> SEQ ID NO 10
<211> LENGTH: 19
<212> TYPE: DNA
<213> ORGANISM: Artificial sequence
<220> FEATURE:
<223> OTHER INFORMATION: LBFLFK locus 1_Probe

<400> SEQUENCE: 10
atactcattg ctgatccat 19

<210> SEQ ID NO 11
<211> LENGTH: 47800
<212> TYPE: DNA
<213> ORGANISM: Artificial sequence
<220> FEATURE:
<223> OTHER INFORMATION: contig of insert and flanking sequences of LBFLFK T-DNA Locus 2

<400> SEQUENCE: 11
gaaaaacctg catctccaaa aatgttcaaa tggcttaaaa acagagaaaa tgagtggaat 60
attagataga tctaccttta tagaacacac aaaaatacat atctaaaatt attaaatctt 120
cctttaaatg agtggaagat gagaaccatg tgatgaaaaa cctgcaaaac aagataaatt 180
agtaagaaaa acatgagaca gaaacaataa attgatataa agtttgatgt ttataagttc 240
aaagggatta aagagaggtt tgagagtttt agaacgagga acataccatt tttgttgcag 300
ccatttgaga ggagaagaga gaatgtgtaa atgttttttt atataaggag acaaaaattc 360
caataaggtt aaatattttt gatcagaaga cttactagac gacttacttg taagtcgccc 420
agaagacttc aatattttta gcgggaaact aaaatatttt tagcgggagt tagaagaccc 480
taaacataac ccttaaacta aattaactaa ctaaatactt cataaaatca aattaaactt 540
aaaaagtgtt tactatacac agaaataatc acatgtagat ataaatttaa tttttcaaaa 600
aaacatttaa gctttccaaa atctaaccct aagaatacat acaatactac aacatatgtt 660
gccaaaccct agaccaaaga atatcatgat tcactacttt cactcatcta tgttgaaaac 720
aattcaattt tattatatct taatttatat cacttaaaac tgtttataat tacatgattt 780
taattttccg tttatcaaaa tattttttac aaaatttata aattattttt aggatcaact 840
ataccagacg acttccatgg acgccgtaca gaagactaaa cagaatctca caagactcag 900
aagacgtagc ggggatatat tcataaaaat gagttctgtt tttttgtttg gtcacaaggg 960
gctggttgta atttcacaag gcttttggat tacttttgca tttgattcaa gtttgggtat 1020
acttttgcaa tcaaaatcaa gttttgagtc atatttggta aatcgcccta tataaaataa 1080
aattttaaaa agtaatgaat ctacatattt tgtaattttt aaaaaattta gttaacaatt 1140
ataataacac aaaacttaag aaaaagttat aattgtcgta tttttttctc ttttcttttc 1200
tatgtaatat ttttatataa gtaataatgt gaatagaatt tatcaaatca tatgttagaa 1260

-continued

```
taattattat ataattttat acatttaaaa atttaaatat aatcaagata tatacatgta   1320
tttatatatt accagatcag agcagatatc cgtttcccaa aattttaata tttgtgattt   1380
gcttcgattt taatggatat tgatttttag tattttttg cttcaaaagt ttatggatat   1440
tcggaatttt cggatcgaat cgaaacgaat aacgcatcaa atcaaattta acggataaaa   1500
ccttagtaac acatgcataa accttagtga acttctcaag ctttcgattc tctatcttat   1560
ttatctatga aattaattaa cataattttc cttgaattaa cataattgga ctaacgcata   1620
ttcgagctga agtcaaaatt cccaaaactt gttcttgata tgagtaaaac tgttcgtctg   1680
atgtaaactc ttactgtagt tgtattacaa actaatgata aagtatgcat tttctatttt   1740
attataaatt tacattacta gttgataaca tattgacaac tagaaagcgt gagagagaga   1800
tactcggtaa gccgagatgt atatccacag ttggagtctt tggatttcat atccagaatt   1860
gggtcgcaaa ctttcagtac aaagttatga catctccatg gtatatatcg acgtgtctat   1920
atatcatatt aaagaaaggt ttgtagtatt tggttaggta caaatgcgat caacttttga   1980
atttatatcc atgtacatat atacccttgg ttacaaggac acctacccat acatacgcat   2040
aagtgacaaa tagcaaaata tctacacatc gcatgacccc gttctttttt atgataaggt   2100
tgtgattttt gtggttcttt tttttcatct cttacattga ttcagtatgt tgtccaaaaa   2160
aaaaacagtg attcagtatt atatcgagta aattcacaag aacgtagcta caatgtagat   2220
gatttattaa caattttaca agagacaagc aaatgtcgag caatcatatt ctataatatc   2280
aacctaaaag agttaaatcc ataaaattag ttggcaacga gcgatagtat gaaagttagg   2340
tgatgacaaa agttgctata ttgcttcaac tatattttca taaatttatt tgtctggatg   2400
aaaaccacaa aattttaaaa atataatttt gattggtaat atgtaaataa cgggatccta   2460
tatttaaacc agtcagcatc atcacaccaa aagttaggcc cgaatagttt gaaattagaa   2520
agctcgcaat tgaggtctac aggccaaatt cgctcttagc cgtacaatat tactcaccgg   2580
tgcgatgccc cccatcgtag gtgaaggtgg aaattaatgg cgcgcctgat cactgattag   2640
taactattac gtaagcctac gtagcgtcac gtgacgttag ctaacgctac gtagcctcag   2700
ctgacgttac gtaagcctac gtagcgtcac gtgagcttag ctaacgctac ctaggctcag   2760
ctgacgttac gtaacgctag ctagcgtcac tcctgcagca aatttacaca ttgccactaa   2820
acgtctaaac ccttgtaatt tgtttttgtt ttactatgtg tgttatgtat ttgatttgcg   2880
ataaattttt atatttggta ctaaatttat aacacctttt atgctaacgt ttgccaacac   2940
ttagcaattt gcaagttgat taattgattc taaattattt ttgtcttcta aatacatata   3000
ctaatcaact ggaaatgtaa atatttgcta atatttctac tataggagaa ttaaagtgag   3060
tgaatatggt accacaaggt ttggagattt aattgttgca atgctgcatg gatggcatat   3120
acaccaaaca ttcaataatt cttgaggata ataatggtac cacacaagat ttgaggtgca   3180
tgaacgtcac gtggacaaaa ggtttagtaa tttttcaaga caacaatgtt accacacaca   3240
agttttgagg tgcatgcatg gatgccctgt ggaaagttta aaaatatttt ggaaatgatt   3300
tgcatggaag ccatgtgtaa aaccatgaca tccacttgga ggatgcaata atgaagaaaa   3360
ctacaaattt acatgcaact agttatgcat gtagtctata taatgaggat tttgcaatac   3420
tttcattcat acacactcac taagttttac acgattataa tttcttcata gccagtactg   3480
tttaagcttc actgtctctg aatcggcaaa ggtaaacgta tcaattattc tacaaaccct   3540
tttatttttc ttttgaatta ccgtcttcat tggttatatg ataacttgat aagtaaagct   3600
```

```
tcaataattg aatttgatct gtgttttttt ggccttaata ctaaatcctt acataagctt   3660
tgttgcttct cctcttgtga gttgagtgtt aagttgtaat aatggttcac tttcagcttt   3720
agaagaaacc atggaagttg ttgagaggtt ctacggagag ttggatggaa aggtttccca   3780
aggagtgaac gctttgttgg gatctttcgg agttgagttg actgataccc caactactaa   3840
gggattgcca ctcgttgatt ctccaactcc aattgtgttg ggagtgtctg tttacttgac   3900
catcgtgatc ggaggattgc tttggatcaa ggctagagat ctcaagccaa gagcttctga   3960
gccattcttg ttgcaagctt tggtgttggt gcacaacttg ttctgcttcg ctttgtctct   4020
ttacatgtgc gtgggtatcg cttaccaagc tatcacctgg agatattcct tgtggggaaa   4080
cgcttataac cccaaagcaca aggagatggc tatcctcgtt tacctcttct acatgtccaa   4140
gtacgtggag ttcatggata ccgtgatcat gatcctcaag agatccacca gacagatttc   4200
tttcctccac gtgtaccacc actcttctat ctcccttatc tggtgggcta ttgctcacca   4260
cgctccagga ggagaggctt attggagtgc tgctctcaac tctggagtgc acgtgttgat   4320
gtacgcttac tacttcttgg ctgcttgctt gagatcttcc ccaaagctca agaacaagta   4380
cctcttctgg ggaagatacc tcacccaatt ccagatgttc cagttcatgc tcaacttggt   4440
gcaagcttac tacgatatga aaaccaacgc tccatatcca caatggctca tcaagatcct   4500
cttctactac atgatctccc tcttgttcct cttcggaaac ttctacgtgc aaaagtacat   4560
caagccatcc gatggaaagc aaaagggagc taagaccgag tgatcgacaa gctcgagttt   4620
ctccataata atgtgtgagt agttcccaga taagggaatt agggttccta tagggtttcg   4680
ctcatgtgtt gagcatataa gaaaccctta gtatgtattt gtatttgtaa aatacttcta   4740
tcaataaaat ttctaattcc taaaaccaaa atccagtact aaaatccaga tcccccgaat   4800
taattcggcg ttaattcagc tagctagcct cagctgacgt tacgtaacgc taggtagcgt   4860
cacgtgacgt tagctaacgc taggtagcgt cagctgagct tacgtaagcg cttagcagat   4920
atttggtgtc taaatgttta ttttgtgata tgttcatgtt tgaaatggtg gtttcgaaac   4980
cagggacaac gttgggatct gatagggtgt caaagagtat tatggattgg gacaatttcg   5040
gtcatgagtt gcaaattcaa gtatatcgtt cgattatgaa aattttcgaa gaatatccca   5100
tttgagagag tctttacctc attaatgttt ttagattatg aaattttatc atagttcatc   5160
gtagtctttt tggtgtaaag gctgtaaaaa gaaattgttc acttttgttt tcgtttatgt   5220
gaaggctgta aaagattgta aaagactatt ttggtgtttt ggataaaatg atagttttta   5280
tagattcttt tgcttttaga agaaatacat ttgaaatttt ttccatgttg agtataaaat   5340
accgaaatcg attgaagatc atagaaatat tttaactgaa aacaaattta taactgattc   5400
aattctctcc atttttatac ctatttaacc gtaatcgatt ctaatagatg atcgattttt   5460
tatataatcc taattaacca acggcatgta ttggataatt aaccgatcaa ctctcacccc   5520
taatagaatc agtattttcc ttcgacgtta attgatccta cactatgtag gtcatatcca   5580
tcgttttaat ttttggccac cattcaattc tgtcttgcct ttagggatgt gaatatgaac   5640
ggccaaggta agagaataaa aataatccaa attaaagcaa gagaggccaa gtaagataat   5700
ccaaatgtac acttgtcatt gccaaaatta gtaaaatact cggcatattg tattcccaca   5760
cattattaaa ataccgtata tgtattggct gcatttgcat gaataatact acgtgtaagc   5820
ccaaaagaac ccacgtgtag cccatgcaaa gttaacactc acgaccccat tcctcagtct   5880
ccactatata aacccaccat ccccaatctc accaaaccca ccacacaact cacaactcac   5940
tctcacacct taaagaacca atcaccacca aaaaatttca cgatttggaa tttgattcct   6000
```

```
gcgatcacag gtatgacagg ttagattttg ttttgtatag ttgtatacat acttctttgt   6060
gatgttttgt ttacttaatc gaatttttgg agtgttttaa ggtctctcgt ttagaaatcg   6120
tggaaaatat cactgtgtgt gtgttcttat gattcacagt gtttatgggt ttcatgttct   6180
ttgttttatc attgaatggg aagaaatttc gttgggatac aaatttctca tgttcttact   6240
gatcgttatt aggagtttgg ggaaaaagga agagtttttt tggttggttc gagtgattat   6300
gaggttattt ctgtatttga tttatgagtt aatggtcgtt ttaatgttgt agaccatggg   6360
aaaaggatct gagggaagat ctgctgctag agagatgact gctgaggcta acggagataa   6420
gagaaagacc atcctcattg agggagtgtt gtacgatgct accaacttca aacacccagg   6480
aggttccatt attaacttcc tcaccgaggg agaagctgga gttgatgcta cccaagctta   6540
cagagagttc catcagagat ccggaaaggc tgataagtac ctcaagtccc tcccaaagtt   6600
ggatgcttct aaggtggagt ctaggttctc tgctaaggag caggctagaa gggacgctat   6660
gaccagggat tacgctgctt tcagagagga gttggttgct gagggatact tcgatccatc   6720
tatcccacac atgatctaca gagtggtgga gattgtggct ttgttcgctt tgtctttctg   6780
gttgatgtct aaggcttctc caacctcttt ggttttggga gtggtgatga acggaatcgc   6840
tcaaggaaga tgcggatggg ttatgcacga gatgggacac ggatctttca ctggagttat   6900
ctggctcgat gataggatgt gcgagttctt ctacggagtt ggatgtggaa tgtctggaca   6960
ctactggaag aaccagcact ctaagcacca cgctgctcca aacagattgg agcacgatgt   7020
ggatttgaac accttgccac tcgttgcttt caacgagaga gttgtgagga aggttaagcc   7080
aggatctttg ttggctttgt ggctcagagt tcaggcttat ttgttcgctc cagtgtcttg   7140
cttgttgatc ggattgggat ggaccttgta cttgcaccca agatatatgc tcaggaccaa   7200
gagacacatg gagtttgtgt ggatcttcgc tagatatatc ggatggttct ccttgatggg   7260
agctttggga tattctcctg gaacttctgt gggaatgtac ctctgctctt tcggacttgg   7320
atgcatctac atcttcctcc aattcgctgt gtctcacacc cacttgccag ttaccaaccc   7380
agaggatcaa ttgcactggc ttgagtacgc tgctgatcac accgtgaaca tctctaccaa   7440
gtcttggttg gttacctggt ggatgtctaa cctcaacttc caaatcgagc accacttgtt   7500
cccaaccgct ccacaattca ggttcaagga gatctctcca agagttgagg ctctcttcaa   7560
gagacacaac ctcccttact acgatttgcc atacacctct gctgtttcta ctaccttcgc   7620
taacctctac tctgttggac actctgttgg agctgatacc aagaagcagg attgactgct   7680
ttaatgagat atgcgagacg cctatgatcg catgatattt gctttcaatt ctgttgtgca   7740
cgttgtaaaa aacctgagca tgtgtagctc agatccttac cgccggtttc ggttcattct   7800
aatgaatata tcacccgtta ctatcgtatt tttatgaata atattctccg ttcaatttac   7860
tgattgtcta cgtaggctca gctgagctta cctaaggcta cgtaggctca cgtgacgtta   7920
cgtaaggcta cgtagcgtca cgtgagctta cctaactcta gctagcctca cgtgacctta   7980
gctaacacta ggtagcgtca gctcgacggc ccggactgta tccaacttct gatctttgaa   8040
tctctctgtt ccaacatgtt ctgaaggagt tctaagactt ttcagaaagc ttgtaacatg   8100
ctttgtagac tttctttgaa ttactcttgc aaactctgat tgaacctacg tgaaaactgc   8160
tccagaagtt ctaaccaaat tccgtcttgg gaaggcccaa aatttattga gtacttcagt   8220
ttcatggacg tgtcttcaaa gatttataac ttgaaatccc atcattttta agagaagttc   8280
tgttccgcaa tgtcttagat ctcattgaaa tctacaactc ttgtgtcaga agttcttcca   8340
```

```
gaatcaactt gcatcatggt gaaaatctgg ccagaagttc tgaacttgtc atatttctta   8400
acagttagaa aaatttctaa gtgtttagaa ttttgacttt tccaaagcaa acttgacttt   8460
tgactttctt aataaaacaa acttcatatt ctaacatgtc ttgatgaaat gtgattcttg   8520
aaatttgatg ttgatgcaaa agtcaaagtt tgacttttca gtgtgcaatt gaccattttg   8580
ctcttgtgcc aattccaaac ctaaattgat gtatcagtgc tgcaaacttg atgtcatgga   8640
agatcttatg agaaaattct tgaagactga gaggaaaaat tttgtagtac aacacaaaga   8700
atcctgtttt tcatagtcgg actagacaca ttaacataaa acaccacttc attcgaagag   8760
tgattgaaga aggaaatgtg cagttacctt tctgcagttc ataagagcaa cttacagaca   8820
cttttactaa aatactacaa agaggaagat tttaacaact tagagaagta atgggagtta   8880
aagagcaaca cattaagggg gagtgttaaa attaatgtgt tgtaaccacc actaccttta   8940
gtaagtatta taagaaaatt gtaatcatca cattataatt attgtcctta tttaaaatta   9000
tgataaagtt gtatcattaa gattgagaaa accaaatagt cctcgtcttg atttttgaat   9060
tattgttttc tatgttactt ttcttcaagc ctatataaaa actttgtaat gctaaattgt   9120
atgctggaaa aaaatgtgta atgaattgaa tagaaattat ggtatttcaa agtccaaaat   9180
ccatcaatag aaatttagta caaaacgtaa ctcaaaaata ttctcttatt ttaaatttta   9240
caacaatata aaaatattct cttattttaa attttacaat aatataattt atcacctgtc   9300
acctttagaa taccaccaac aatattaata cttagatatt ttattcttaa taattttgag   9360
atctctcaat atatctgata tttattttat atttgtgtca tattttctta tgttttagag   9420
ttaaccctta tatcttggtc aaactagtaa ttcaatatat gagtttgtga aggacacatt   9480
gacatcttga aacattggtt ttaaccttgt tggaatgtta aaggtaataa aacattcaga   9540
attatgacca tctattaata tacttccttt gtcttttaaa aaagtgtgca tgaaaatgct   9600
ctatggtaag ctagagtgtc ttgctggcct gtgtatatca attccatttc cagatggtag   9660
aaactgccac tacgaataat tagtcataag acacgtatgt taacacacgt ccccttgcat   9720
gtttttttgcc atatattccg tctctttctt tttcttcacg tataaaacaa tgaactaatt   9780
aatagagcga tcaagctgaa cagttctttg ctttcgaagt tgccgcaacc taaacaggtt   9840
tttccttctt ctttcttctt attaactacg accttgtcct ttgcctatgt aaaattacta   9900
ggttttcatc agttacactg attaagttcg ttatagtgga agataaaatg ccctcaaagc   9960
attttgcagg atatctttga tttttcaaag atatggaact gtagagtttg atagtgttct  10020
tgaatgtggt tgcatgaagt ttttttggtc tgcatgttat tttttcctcg aaatatgttt  10080
tgagtccaac aagtgattca cttgggattc agaaagttgt tttctcaata tgtaacagtt  10140
tttttctatg gagaaaaatc atagggaccg ttggttttgg cttctttaat tttgagctca  10200
gattaaaccc attttacccg gtgttcttgg cagaattgaa aacagtacgt agtaccgcgc  10260
ctaccatgtg tgttgagacc gagaacaacg atggaatccc tactgtggag atcgctttcg  10320
atggagagag agaaagagct gaggctaacg tgaagttgtc tgctgagaag atggaacctg  10380
ctgctttggc taagaccttc gctagaagat acgtggttat cgagggagtt gagtacgatg  10440
tgaccgattt caaacatcct ggaggaaccg tgattttcta cgctctctct aacactggag  10500
ctgatgctac tgaggctttc aaggagttcc accacagatc tagaaaggct aggaaggctt  10560
tggctgcttt gccttctaga cctgctaaga ccgctaaagt ggatgatgct gagatgctcc  10620
aggatttcgc taagtggaga aaggagttgg agagggacgg attcttcaag ccttctcctg  10680
ctcatgttgc ttacagattc gctgagttgg ctgctatgta cgctttggga acctacttga  10740
```

```
tgtacgctag atacgttgtg tcctctgtgt tggtttacgc ttgcttcttc ggagctagat  10800
gtggatgggt tcaacacgag ggaggacact cttctttgac cggaaacatc tggtgggata  10860
agagaatcca agctttcact gctggattcg gattggctgg atctggagat atgtggaact  10920
ccatgcacaa caagcaccac gctactcctc aaaaagtgag gcacgatatg gatttggata  10980
ccactcctgc tgttgctttc ttcaacaccg ctgtggagga taatagacct aggggattct  11040
ctaagtactg gctcagattg caagcttgga ccttcattcc tgtgacttct ggattggtgt  11100
tgctcttctg gatgttcttc ctccaccctt ctaaggcttt gaagggagga aagtacgagg  11160
agcttgtgtg gatgttggct gctcacgtga ttagaacctg gaccattaag gctgttactg  11220
gattcaccgc tatgcaatcc tacggactct tcttggctac ttcttgggtt tccggatgct  11280
acttgttcgc tcacttctct acttctcaca cccacttgga tgttgttcct gctgatgagc  11340
acttgtcttg ggttaggtac gctgtggatc acaccattga tatcgatcct tctcagggat  11400
gggttaactg gttgatggga tacttgaact gccaagtgat tcaccacctc ttcccttcta  11460
tgcctcaatt cagacaacct gaggtgtcca gaagattcgt tgctttcgct aagaagtgga  11520
acctcaacta caaggtgatg acttatgctg gagcttggaa ggctactttg ggaaacctcg  11580
ataatgtggg aaagcactac tacgtgcacg gacaacactc tggaaagacc gcttgattaa  11640
tgaaggccgc ctcgaccgta ccccctgcag atagactata ctatgtttta gcctgcctgc  11700
tggctagcta ctatgttatg ttatgttgta aaataaacac ctgctaaggt atatctatct  11760
atattttagc atggctttct caataaattg tctttcctta tcgtttacta tcttatacct  11820
aataatgaaa taataatatc acatatgagg aacggggcag gtttaggcat atatatacga  11880
gtgtagggcg gagtggggct acgtagcgtc acgtgacgtt acctaagcct aggtagcctc  11940
agctgacgtt acgtaacgct aggtaggctc agctgacacg ggcaggacat agggactact  12000
acaagcatag tatgcttcag acaaagagct aggaaagaac tcttgatgga ggttaagaga  12060
aaaaagtgct agaggggcat agtaatcaaa cttgtcaaaa ccgtcatcat gatgagggat  12120
gacataatat aaaaagttga ctaaggtctt ggtagtactc tttgattagt attatatatt  12180
ggtgagaaca tgagtcaaga ggagacaaga aaccgaggaa ccatagttta gcaacaagat  12240
ggaagttgca aagttgagct agccgctcga ttagttacat ctcctaagca gtactacaag  12300
gaatggtctc tatactttca tgtttagcac atggtagtgc ggattgacaa gttagaaaca  12360
gtgcttagga gacaaagagt cagtaaaggt attgaaagag tgaagttgat gctcgacagg  12420
tcaggagaag tccctccgcc agatggtgac taccaagggg ttggtatcag ctgagaccca  12480
aataagattc ttcggttgaa ccagtggttc gaccgagact cttagggtgg gatttcactg  12540
taagatttgt gcattttgtt gaatataaat tgacaatttt ttttatttaa ttatagatta  12600
tttagaatga attacatatt tagtttctaa caaggatagc aatggatggg tatgggtaca  12660
ggttaaacat atctattacc cacccatcta gtcgtcgggt tttacacgta cccacccgtt  12720
tacataaacc agaccggaat tttaaaccgt acccgtccgt tagcgggttt cagatttacc  12780
cgtttaatcg ggtaaaacct gattactaaa tatatatttt ttatttgata aacaaaacaa  12840
aaatgttaat attttcatat tggatgcaat tttaagaaac acatattcat aaatttccat  12900
atttgtagga aaataaaaag aaaaatatat tcaagaacac aaatttcacc gacatgactt  12960
ttattacaga gttggaatta gatctaacaa ttgaaaaatt aaaattaaga tagaatatgt  13020
tgaggaacat gacatagtat aatgctgggt tacccgtcgg gtaggtatcg aggcggatac  13080
```

```
tactaaatcc atcccactcg ctatccgata atcactggtt tcgggtatac ccattcccgt  13140
caacaggcct ttttaaccgg ataatttcaa cttatagtga atgaattttg aataaatagt  13200
tagaatacca aaatcctgga ttgcatttgc aatcaaattt tgtgaaccgt taaattttgc  13260
atgtacttgg gatagatata atagaaccga attttcatta gtttaattta taacttactt  13320
tgttcaaaga aaaaaaatat ctatccaatt tacttataat aaaaaaataat ctatccaagt  13380
tacttattat aatcaacttg taaaaaggta agaatacaaa tgtggtagcg tacgtgtgat  13440
tatatgtgac gaaatgttat atctaacaaa agtccaaatt cccatggtaa aaaaaatcaa  13500
aatgcatggc aggctgtttg taaccttgga ataagatgtt ggccaattct ggagccgcca  13560
cgtacgcaag actcagggcc acgttctctt catgcaagga tagtagaaca ccactccacc  13620
cacctcctat attagacctt tgcccaaccc tccccaactt tcccatccca tccacaaaga  13680
aaccgacatt tttatcataa atctggtgct taaacactct ggtgagttct agtacttctg  13740
ctatgatcga tctcattacc atttcttaaa tttctctccc taaatattcc gagttcttga  13800
tttttgataa cttcaggttt tctctttttg ataaatctgg tctttccatt tttttttttt  13860
gtggttaatt tagtttccta tgttcttcga ttgtattatg catgatctgt gtttggattc  13920
tgttagatta tgtattggtg aatatgtatg tgtttttgca tgtctggttt tggtcttaaa  13980
aatgttcaaa tctgatgatt tgattgaagc ttttttagtg ttggtttgat tcttctcaaa  14040
actactgtta atttactatc atgttttcca actttgattc atgatgacac ttttgttctg  14100
ctttgttata aaattttggt tggtttgatt ttgtaattat agtgtaattt tgttaggaat  14160
gaacatgttt taatactctg ttttcgattt gtcacacatt cgaattatta atcgataatt  14220
taactgaaaa ttcatggttc tagatcttgt tgtcatcaga ttatttgttt cgataattca  14280
tcaaatatgt agtccttttg ctgatttgcg actgtttcat tttttctcaa aattgttttt  14340
tgttaagttt atctaacagt tatcgttgtc aaaagtctct ttcattttgc aaaatcttct  14400
tttttttttt gtttgtaact ttgtttttta agctacacat ttagtctgta aaatagcatc  14460
gaggaacagt tgtcttagta gacttgcatg ttcttgtaac ttctatttgt ttcagtttgt  14520
tgatgactgc tttgattttg taggtcaaag gcgcacccta ccatggatgc ttataacgct  14580
gctatggata agattggagc tgctatcatc gattggagtg atccagatgg aaagttcaga  14640
gctgataggg aggattggtg gttgtgcgat ttcagatccg ctatcaccat tgctctcatc  14700
tacatcgctt tcgtgatctt gggatctgct gtgatgcaat ctctcccagc tatggaccca  14760
taccctatca agttcctcta caacgtgtct caaatcttcc tctgcgctta catgactgtt  14820
gaggctggat tcctcgctta taggaacgga tacaccgtta tgccatgcaa ccacttcaac  14880
gtgaacgatc caccagttgc taacttgctc tggctcttct acatctccaa agtgtgggat  14940
ttctgggata ccatcttcat tgtgctcgga aagaagtgga gacaactctc tttcttgcac  15000
gtgtaccacc acaccaccat cttcctcttc tactggttga acgctaacgt gctctacgat  15060
ggagatatct tcttgaccat cctcctcaac ggattcattc acaccgtgat gtacacctac  15120
tacttcatct gcatgcacac caaggattct aagaccggaa agtctttgcc aatctggtgg  15180
aagtcatctt tgaccgcttt ccaactcttg caattcacca tcatgatgtc ccaagctacc  15240
tacttggttt tccacggatg cgataaggtt tccctcagaa tcaccatcgt gtacttcgtg  15300
tacattctct ccctttcctt cctcttcgct cagttcttcg tgcaatccta catggctcca  15360
aagaagaaga agtccgcttg atgttaatga aggccgcaga tatcagatct ggtcgaccta  15420
gaggatcccc ggccgcaaag ataataacaa aagcctacta tataacgtac atgcaagtat  15480
```

```
tgtatgatat taatgttttt acgtacgtgt aaacaaaaat aattacgttt gtaacgtatg  15540
gtgatgatgt ggtgcactag gtgtaggcct tgtattaata aaaagaagtt tgttctatat  15600
agagtggttt agtacgacga tttatttact agtcggattg gaatagagaa ccgaattctt  15660
caatccttgc ttttgatcaa gaattgaaac cgaatcaaat gtaaaagttg atatatttga  15720
aaaacgtatt gagcttatga aaatgctaat actctcatct gtatggaaaa gtgactttaa  15780
aaccgaactt aaaagtgaca aaaggggaat atcgcatcaa accgaatgaa accgatctac  15840
gtaggctcag ctgagcttag ctaagcctac ctagcctcac gtgagattat gtaaggctag  15900
gtagcgtcac gtgacgttac ctaacactag ctagcgtcag ctgagcttag ctaaccctac  15960
gtagcctcac gtgagcttac ctaacgctac gtagcctcac gtgactaagg atgacctacc  16020
cattcttgag acaaatgtta cattttagta tcagagtaaa atgtgtacct ataactcaaa  16080
ttcgattgac atgtatccat tcaacataaa attaaaccag cctgcacctg catccacatt  16140
tcaagtattt tcaaaccgtt cggctcctat ccaccgggtg taacaagacg gattccgaat  16200
ttggaagatt ttgactcaaa ttcccaattt atattgaccg tgactaaatc aactttaact  16260
tctataattc tgattaagct cccaatttat attcccaacg gcactacctc caaaatttat  16320
agactctcat ccccttttaa accaacttag taaacgtttt ttttttaatt ttatgaagtt  16380
aagtttttac cttgttttta aaaagaatcg ttcataagat gccatgccag aacattagct  16440
acacgttaca catagcatgc agccgcggag aattgttttt cttcgccact tgtcactccc  16500
ttcaaacacc taagagcttc tctctcacag cacacacata caatcacatg cgtgcatgca  16560
ttattacacg tgatcgccat gcaaatctcc tttatagcct ataaattaac tcatcggctt  16620
cactctttac tcaaaccaaa actcatcaat acaaacaaga ttaaaaacat ttcacgattt  16680
ggaatttgat tcctgcgatc acaggtatga caggttagat tttgttttgt atagttgtat  16740
acatacttct ttgtgatgtt ttgtttactt aatcgaattt ttggagtgtt ttaaggtctc  16800
tcgtttagaa atcgtggaaa atatcactgt gtgtgtgttc ttatgattca cagtgtttat  16860
gggtttcatg ttctttgttt tatcattgaa tgggaagaaa tttcgttggg atacaaattt  16920
ctcatgttct tactgatcgt tattaggagt ttggggaaaa aggaagagtt tttttggttg  16980
gttcgagtga ttatgaggtt atttctgtat ttgatttatg agttaatggt cgttttaatg  17040
ttgtagaccg ccatggctat tttgaaccct gaggctgatt ctgctgctaa cctcgctact  17100
gattctgagg ctaagcaaag acaattggct gaggctggat acactcacgt tgagggtgct  17160
cctgctcctt tgcctttgga gttgcctcac ttctctctca gagatctcag agctgctatt  17220
cctaagcact gcttcgagag atctttcgtg acctccacct actacatgat caagaacgtg  17280
ttgacttgcg ctgctttgtt ctacgctgct accttcattg atagagctgg agctgctgct  17340
tatgttttgt ggcctgtgta ctggttcttc cagggatctt acttgactgg agtgtgggtt  17400
atcgctcacg agtgtggaca ccaggcttat tgctcttctg aggtggtgaa caacttgatt  17460
ggactcgtgt tgcactctgc tttgttggtg ccttaccact cttggagaat ctctcacaga  17520
aagcaccact ccaacactgg atcttgcgag aacgatgagg ttttcgttcc tgtgaccaga  17580
tctgtgttgg cttcttcttg gaacgagacc ttggaggatt ctcctctcta ccaactctac  17640
cgtatcgtgt acatgttggt tgttggatgg atgcctggat acctcttctt caacgctact  17700
ggacctacta agtactgggg aaagtctagg tctcacttca acccttactc cgctatctat  17760
gctgataggg agaggtggat gatcgtgctc tccgatattt tcttggtggc tatgttggct  17820
```

```
gttttggctg ctttggtgca cactttctcc ttcaacacga tggtgaagtt ctacgtggtg  17880
ccttacttca ttgtgaacgc ttacttggtg ttgattacct acctccaaca caccgatacc  17940
tacatccctc acttcagaga gggagagtgg aattggttga gaggagcttt gtgcactgtg  18000
gatagatcat ttggtccatt cctcgattct gtggtgcata gaatcgtgga tacccacgtt  18060
tgccaccata tcttctccaa gatgcctttc tatcactgcg aggaggctac caacgctatt  18120
aagcctctcc tcggaaagtt ctacttgaag gatactactc ctgttcctgt tgctctctgg  18180
agatcttaca cccactgcaa gttcgttgag gatgatggaa aggtggtgtt ctacaagaac  18240
aagttatagt taatgaataa ttgattggtt cgagtattat ggcattggga aaactgtttt  18300
tcttgtacca tttgttgtgc ttgtaattta ctgtgttttt tattcggttt tcgctatcga  18360
actgtgaaat ggaaatggat ggagaagagt taatgaatga tatggtcctt ttgttcattc  18420
tcaaattaat attatttgtt ttttctctta tttgttgtgt gttgaatttg aaattataag  18480
agatatgcaa acattttgtt ttgagtaaaa atgtgtcaaa tcgtggcctc taatgaccga  18540
agttaatatg aggagtaaaa cacttgtagt tgtaccatta tgcttattca ctaggcaaca  18600
aatatatttt cagacctaga aaagctgcaa atgttactga atacaagtat gtcctcttgt  18660
gttttagaca tttatgaact ttcctttatg taattttcca gaatccttgt cagattctaa  18720
tcattgcttt ataattatag ttatactcat ggatttgtag ttgagtatga aaatattttt  18780
taatgcattt tatgacttgc caattgattg acaacatgca tcaatctagc tagcctcagc  18840
tgacgttacg taacgctagg tagcgtcacg tgacgttagc taacgctagg tagcgtcagc  18900
tgagcttacg taagcgcaca gatgaatact agctgttgtt cacagttcta gtgtctcctc  18960
attacgtgaa ttcaagctac gatcactatc tcaactccta cataaacatc agaatgctac  19020
aaaactatgc acaaaaacaa aagctacatc taatacgtga atcaattact ctcatcacaa  19080
gaaagaagat ttcaatcacc gtcgagaagg aggattcagt taattgaatc aaagttccga  19140
tcaaactcga agactggtga gcacgaggac gacgaagaag agtgtctcga agatacaaca  19200
agcaagaaat ctactgagtg acctcctgaa gttattggcg cgattgagag aatcaatccg  19260
aattaatttc ggggaaaaag ataaattaga tactaagcga tgggcttggg ctgggctaag  19320
aaacaggtgg caattgggct ggaggacccc gcgattcata gcttccgata gcccaaaaaa  19380
aaacggataa catatttatc gggtatttga atttcagtga aataagatat tttctttttg  19440
ttaggaaaat tttagaaaat aatggaaatt aaatagcgat tatgttacaa gatacgatca  19500
gcatcgggca gtgcaaaatg ctatagcttc ccaagatttg atccttttgg gttatctcct  19560
aatgacaatt agtttaggat tttgaaactt atattaatac tattatccga caacacttgt  19620
ttcagcttct tattttaaca ttttttgttt ttttctattc ttcttcccat cagcattttc  19680
tttttaaaaa attgaatact ttaacttttt aaaaatttca caatgatcag atgatattat  19740
ggaagatctc aagagttaaa tgtatccatc ttggggcatt aaaaccggtg tacgggatga  19800
taaatacaga ctttatatca tatgatagct cagtaattca tatttatcac gttgctaaaa  19860
aaattataag gtactagtag tcaacaaaat caattaaaga gaaagaaaga aacgcatgtg  19920
aagagagttt acaactggaa aagtaaaata aaaattaacg catgttgaat gctgacatgt  19980
cagtatgtcc atgaatccac gtatcaagcg ccattcatcg atcgtcttcc tctttctaaa  20040
tgaaaacaac ttcacacatc acaacaaaca atacacacaa gaccccctct ctctcgttgt  20100
ctctctgcca gcgaccaaat cgaagcttga gaagaacaag aaggggtcaa accatggctt  20160
ctacatctgc tgctcaagac gctgctcctt acgagttccc ttctctcact gagatcaaga  20220
```

```
gggctcttcc ttctgagtgt ttcgaggctt ctgttcctct ttctctctac tacaccgcta  20280
gatctcttgc tcttgctgga tctctcgctg ttgctctctc ttacgctaga gctttgcctc  20340
ttgttcaggc taacgctctt cttgatgcta ctctctgcac tggatacgtt cttctccagg  20400
gaatcgtttt ctggggattc ttcaccgttg gtcacgattg tggacacgga gctttctcta  20460
gatctcacgt gctcaacttc tctgttggaa ccctcatgca ctctatcatc cttacccctt  20520
tcgagtcttg gaagctctct cacagacacc accacaagaa caccggaaac atcgataagg  20580
acgagatctt ctaccctcaa agagaggctg attctcaccc tgtttctaga caccttgtga  20640
tgtctcttgg atctgcttgg ttcgcttacc ttttcgctgg attccctcct agaaccatga  20700
accacttcaa cccttgggag gctatgtatg ttagaagagt ggctgctgtg atcatctctc  20760
tcggagttct tttcgctttc gctggactct actcttacct caccttcgtt cttggattca  20820
ccactatggc tatctactac ttcggacctc tcttcatctt cgctaccatg cttgttgtta  20880
ccactttcct ccaccacaac gatgaggaga caccttggta cgctgattct gagtggactt  20940
acgtgaaggg aaacctctct tctgtggaca gatcttacgg tgctctcatc gacaacctta  21000
gccacaacat cggaactcac cagatccacc acctcttccc tatcatccct cactacaagc  21060
tcaacgatgc tactgctgct ttcgctaagg ctttccctga gcttgttagg aaaaacgctg  21120
ctcctatcat cccaactttc ttcaggatgg ctgctatgta cgctaagtac ggagttgttg  21180
acactgatgc taagaccttc actctcaagg aggctaaggc tgctgctaag actaagtcat  21240
cttgatgatt aatgaataat tgattgtaca tactatattt tttgtttacc ttgtgttagt  21300
ttaatgttca gtgtcctctc tttattgtgg cacgtctctt tgttgtatgt tgtgtctata  21360
caaagttgaa ataatggaaa gaaaaggaag agtgtaattt gttttgtttt aagtgtttat  21420
aaatatatat atataggtca tttagatagt tctaggtttc tataaaactc tctctctgga  21480
agtagaatct gtttttgaga ggatccagtt gcctactaat ctcccccaaa acccttcaag  21540
cttaaccttc ctcttcacaa caacagagga aacacatctc ttgagctctg agttctcttc  21600
tttgagcatg tctatcgcta aactcatctg ccttatagct tccctcttct cttcatctct  21660
ctctctcacc atttcgctgt aaaacttatt ctcctccctc agcctctcta tctcttcctt  21720
cagcatctca caattcccac cataatcgac tgaggatgat tcaccgtcat caacttcaga  21780
ctcagcgttg tagtcgtcat gagtctcaca agccttggac caagaagact catcatcgca  21840
agttgatgat ttatcatgat gcttctctga gccgtgtttg ctacgtagcg tcacgtgacg  21900
ttacctaagc ctaggtagcc tcagctgacg ttacgtaacg ctaggtaggc tcagctgact  21960
gcagcaaatt tacacattgc cactaaacgt ctaaaccctt gtaatttgtt tttgttttac  22020
tatgtgtgtt atgtatttga tttgcgataa atttttatat ttggtactaa atttataaca  22080
ccttttatgc taacgtttgc caacacttag caatttgcaa gttgattaat tgattctaaa  22140
ttatttttgt cttctaaata catatactaa tcaactggaa atgtaaatat ttgctaatat  22200
ttctactata ggagaattaa agtgagtgaa tatggtacca caaggtttgg agatttaatt  22260
gttgcaatgc tgcatggatg gcatatacac caaacattca ataattcttg aggataataa  22320
tggtaccaca caagatttga ggtgcatgaa cgtcacgtgg acaaaaggtt tagtaatttt  22380
tcaagacaac aatgttacca cacacaagtt ttgaggtgca tgcatggatg ccctgtggaa  22440
agtttaaaaa tattttggaa atgatttgca tggaagccat gtgtaaaacc atgacatcca  22500
cttggaggat gcaataatga agaaaactac aaatttacat gcaactagtt atgcatgtag  22560
```

-continued

```
tctatataat gaggattttg caatactttc attcatacac actcactaag ttttacacga  22620
ttataatttc ttcatagcca gtactgttta agcttcactg tctctgaatc ggcaaaggta  22680
aacgtatcaa ttattctaca aaccctttta tttttctttt gaattaccgt cttcattggt  22740
tatatgataa cttgataagt aaagcttcaa taattgaatt tgatctgtgt ttttttggcc  22800
ttaatactaa atccttacat aagctttgtt gcttctcctc ttgtgagttg agtgttaagt  22860
tgtaataatg gttcactttc agctttagaa gaaacgcgcc ttccatggct acaaaggagg  22920
cttacgtttt cccaactctc accgagatca agagatctct cccaaaggat tgcttcgagg  22980
cttctgtgcc tttgtctctc tactacactg tgagatgctt ggttattgct gtggctttga  23040
ccttcggatt gaactacgct agagctttgc cagaggttga gtctttctgg gctttggatg  23100
ctgctttgtg cactggatat atcctcctcc agggaattgt gttctgggga ttcttcactg  23160
ttggacacga tgctggacac ggagctttct ctagatacca cctcttgaac ttcgttgtgg  23220
gaaccttcat gcactctctc atcttgaccc cattcgagtc ttggaagttg acccacagac  23280
accaccacaa gaacaccgga aacatcgata gagatgaggt gttctaccca cagagaaagg  23340
ctgatgatca cccattgtcc aggaacttga tcttggcttt gggagctgct tggcttgctt  23400
atttggtgga gggattccca ccaagaaagg tgaaccactt caacccattc gagccacttt  23460
ttgtgagaca agtgtccgct gtggttatct ctttgctcgc tcacttcttc gttgctggac  23520
tctctatcta cttgtctctc cagttgggac ttaagaccat ggctatctac tactacggac  23580
cagttttcgt gttcggatct atgttggtga ttaccacctt cttgcaccac aacgatgagg  23640
agactccatg gtatgctgat tctgagtgga cttacgtgaa gggaaacttg tcctctgtgg  23700
atagatctta cggtgctctc atcgataacc tctcccacaa catcggaact caccagatcc  23760
accacctctt cccaattatc ccacactaca agctcaagaa ggctactgct gctttccacc  23820
aagctttccc agagcttgtg agaaagtccg atgagccaat catcaaggct ttcttcagag  23880
tgggaaggtt gtatgctaac tacggagtgg ttgatcaaga ggctaagctc ttcactttga  23940
aggaggctaa ggctgctact gaagctgctg ctaagaccaa gtctacctga ttaatgaatc  24000
gacaagctcg agtttctcca taataatgtg tgagtagttc ccagataagg gaattagggt  24060
tcctataggg tttcgctcat gtgttgagca tataagaaac ccttagtatg tatttgtatt  24120
tgtaaaatac ttctatcaat aaaatttcta attcctaaaa ccaaaatcca gtactaaaat  24180
ccagatcccc cgaattaatt cggcgttaat tcagctacgt aggctcagct gagcttacct  24240
aaggctacgt aggctcacgt gacgttacgt aaggctacgt agcgtcacgt gagcttacct  24300
aactctagct agcctcacgt gaccttagct aacactaggt agcgtcagca cagatgaata  24360
ctagctgttg ttcacagttc tagtgtctcc tcattacgtg aattcaagct acgatcacta  24420
tctcaactcc tacataaaca tcagaatgct acaaaactat gcacaaaaac aaaagctaca  24480
tctaatacgt gaatcaatta ctctcatcac aagaaagaag atttcaatca ccgtcgagaa  24540
ggaggattca gttaattgaa tcaaagttcc gatcaaactc gaagactggt gagcacgagg  24600
acgacgaaga agagtgtctc gaagatacaa caagcaagaa atctactgag tgacctcctg  24660
aagttattgg cgcgattgag agaatcaatc cgaattaatt tcggggaaaa agataaatta  24720
gatactaagc gatgggcttg ggctgggcta agaaacaggt ggcaattggg ctggaggacc  24780
ccgcgattca tagcttccga tagcccaaaa aaaaacggat aacatattta tcgggtattt  24840
gaatttcagt gaaataagat attttctttt tgttaggaaa attttagaaa ataatggaaa  24900
ttaaatagcg attatgttac aagatacgat cagcatcggg cagtgcaaaa tgctatagct  24960
```

```
tcccaagatt tgatcctttt gggttatctc ctaatgacaa ttagtttagg attttgaaac  25020
ttatattaat actattatcc gacaacactt gtttcagctt cttattttaa catttttttgt  25080
tttttctat tcttcttccc atcagcattt tctttttaaa aaattgaata ctttaacttt  25140
ttaaaaattt cacaatgatc agatgatatt atggaagatc tcaagagtta aatgtatcca  25200
tcttggggca ttaaaaccgg tgtacgggat gataaataca gactttatat catatgatag  25260
ctcagtaatt catatttatc acgttgctaa aaaaattata aggtactagt agtcaacaaa  25320
atcaattaaa gagaaagaaa gaaacgcatg tgaagagagt ttacaactgg aaaagtaaaa  25380
taaaaattaa cgcatgttga atgctgacat gtcagtatgt ccatgaatcc acgtatcaag  25440
cgccattcat cgatcgtctt cctctttcta aatgaaaaca acttcacaca tcacaacaaa  25500
caatacacac aagacccccct ctctctcgtt gtctctctgc cagcgaccaa atcgaagctt  25560
gagaagaaca agaaggggtc aaaccatggg aaaaggatct gagggaagat ctgctgctag  25620
agagatgact gctgaggcta acggagataa gagaaagacc atcctcattg agggagtgtt  25680
gtacgatgct accaacttca aacacccagg aggttccatt attaacttcc tcaccgaggg  25740
agaagctgga gttgatgcta cccaagctta cagagagttc catcagagat ccggaaaggc  25800
tgataagtac ctcaagtccc tcccaaagtt ggatgcttct aaggtggagt ctaggttctc  25860
tgctaaggag caggctagaa gggacgctat gaccagggat tacgctgctt tcagagagga  25920
gttggttgct gagggatact tcgatccatc tatcccacac atgatctaca gagtggtgga  25980
gattgtggct ttgttcgctt tgtctttctg gttgatgtct aaggcttctc caacctcttt  26040
ggttttggga gtggtgatga acggaatcgc tcaaggaaga tgcggatggg ttatgcacga  26100
gatgggacac ggatctttca ctggagttat ctggctcgat gataggatgt gcgagttctt  26160
ctacggagtt ggatgtggaa tgtctggaca ctactggaag aaccagcact ctaagcacca  26220
cgctgctcca aacagattgg agcacgatgt ggatttgaac accttgccac tcgttgcttt  26280
caacgagaga gttgtgagga aggttaagcc aggatctttg ttggctttgt ggctcagagt  26340
tcaggcttat ttgttcgctc cagtgtcttg cttgttgatc ggattgggat ggaccttgta  26400
cttgcaccca agatatatgc tcaggaccaa gagacacatg gagtttgtgt ggatcttcgc  26460
tagatatatc ggatggttct ccttgatggg agctttggga tattctcctg gaacttctgt  26520
gggaatgtac ctctgctctt tcggacttgg atgcatctac atcttcctcc aattcgctgt  26580
gtctcacacc cacttgccag ttaccaaccc agaggatcaa ttgcactggc ttgagtacgc  26640
tgctgatcac accgtgaaca tctctaccaa gtcttggttg gttacctggt ggatgtctaa  26700
cctcaacttc caaatcgagc accacttgtt cccaaccgct ccacaattca ggttcaagga  26760
gatctctcca agagttgagg ctctcttcaa gagacacaac ctcccttact acgatttgcc  26820
atacacctct gctgtttcta ctaccttcgc taacctctac tctgttggac actctgttgg  26880
agctgatacc aagaagcagg attgatgatt aatgaataat tgattgtaca tactatattt  26940
tttgtttacc ttgtgttagt ttaatgttca gtgtcctctc tttattgtgg cacgtctctt  27000
tgttgtatgt tgtgtctata caaagttgaa ataatggaaa gaaaaggaag agtgtaattt  27060
gttttgtttt aagtgtttat aaatatatat atataggtca tttagatagt tctaggtttc  27120
tataaaactc tctctctgga agtagaatct gtttttgaga ggatccagtt gcctactaat  27180
ctcccccaaa acccttcaag cttaaccttc ctcttcacaa caacagagga aacacatctc  27240
ttgagctctg agttctcttc tttgagcatg tctatcgcta aactcatctg ccttatagct  27300
```

```
tccctcttct cttcatctct ctctctcacc atttcgctgt aaaacttatt ctcctccctc  27360
agcctctcta tctcttcctt cagcatctca caattcccac cataatcgac tgaggatgat  27420
tcaccgtcat caacttcaga ctcagcgttg tagtcgtcat gagtctcaca agccttggac  27480
caagaagact catcatcgca agttgatgat ttatcatgat gcttctctga gccgtgtttg  27540
ctacctagag tcagctgagc ttagctaacg ctagctagtg tcagctgacg ttacgtaagg  27600
ctaactagcg tcacgtgacc ttacgtaacg ctacgtaggc tcagctgagc ttagctaacc  27660
ctagctagtg tcacgtgagc ttacgctact atagaaaatg tgttatatcg acatgaccag  27720
acaaaggggc aacagttaac aaaacaatta attctttcat ttgagattaa ggaaggtaag  27780
gtactaaaaa gattaaaaaa aatgagctta tctctttgtt tctgtaataa taatataagt  27840
gtgataaact tttaatataa taattgtaat taggttttct acagatgagc accactcaga  27900
gacaagataa gaagaaaaca attttgttaa acatgattat agaaactttt agttaagtct  27960
tgaagtatca atataacaaa aaaaagtaca cacgactatg acaataaacc cactaccgtc  28020
aggttatcat ttcgatgaaa tgttttgata tcattaaata taacagtcac aaaaaatcat  28080
ctaattataa caatataact tatacatata tttaactaaa aacttagagt ttttgtaatg  28140
attctaattg atgattagag tttatagaaa tacaattaaa taaaaaatat aattttaaaa  28200
aaacatagta aagtcaatga gatcctctct gacctcagtg atcatttagt catgtatgta  28260
caacaatcat tgttcatcac atgactgtaa aataaataag gataaacttg ggaatatata  28320
taatatattg tattaaataa aaaagggaaa tacaaatatc aattttagat tcccgagttg  28380
acacaactca ccatgcacgc tgccacctca gctcccagct ctcgtcacat gtctcatgtc  28440
agttaggtct ttggttttta gtctttgaca caactcgcca tgcatgttgc cacgtgagct  28500
cgttcctctt cccatgatct caccactggg catgcatgct gccacctcag ctggcacctc  28560
ttctctatat gtccctagag gccatgcaca gtgccacctc agcactcctc tcagaaccca  28620
tacgtacctg ccaatcggct tctctccata aatatctatt taaattataa ctaattattt  28680
catatactta attgatgacg tggatgcatt gccatcgttg tttaataatt gttaattacg  28740
acatgataaa taaaatgaaa gtaaaaagta cgaaagattt tccatttgtt gttgtataaa  28800
tagagaagtg agtgatgcat aatgcatgaa tgcatgaccg cgccaccatg actgttggat  28860
acgacgagga gatcccattc gagcaagtta gggctcataa caagccagac gacgcttggt  28920
gtgctattca cggacacgtg tacgacgtta ccaagttcgc ttcagttcac ccaggaggag  28980
atattatctt gctcgctgct ggaaaggaag ctactgtcct ctacgagacc taccatgtta  29040
gaggagtgtc tgacgctgtg ctcagaaagt acagaatagg aaagttgcca gacggacaag  29100
gaggagctaa cgagaaggag aagagaacct tgtctggatt gtcctctgct tcttactaca  29160
cctggaactc cgatttctac agagtgatga gggagagagt tgtggctaga ttgaaggaga  29220
gaggaaaggc tagaagagga ggatacgaac tctggatcaa ggctttcttg ctccttgttg  29280
gattctggtc ctctctttac tggatgtgca ccctcgatcc atctttcgga gctatcttgg  29340
ctgctatgtc tttgggagtg ttcgctgctt ttgttggaac ctgcatccaa cacgatggaa  29400
accacggagc tttcgctcaa tctagatggg ttaacaaggt ggcaggatgg actttggata  29460
tgatcggagc ttctggaatg acttgggagt tccaacacgt gttgggacac cacccataca  29520
ctaacttgat cgaggaggag aacggattgc aaaaggtgtc cggaaagaag atggatacca  29580
agttggctga tcaagagtct gatccagatg tgttctccac ctacccaatg atgagattgc  29640
acccttggca ccagaagagg tggtatcaca ggttccagca catctacgga cctttcatct  29700
```

```
tcggattcat gaccatcaac aaggtggtga ctcaagatgt tggagtggtg ttgagaaaga  29760
gactcttcca aatcgatgct gagtgcagat atgcttcccc aatgtacgtt gctaggttct  29820
ggattatgaa ggctttgacc gtgttgtata tggttgcttt gccttgttat atgcaaggac  29880
cttggcacgg attgaaactc ttcgctatcg ctcacttcac ttgcggagag gttttggcta  29940
ccatgttcat cgtgaaccac attatcgagg gagtgtctta cgcttctaag gatgctgtta  30000
agggaactat ggctccacca aagactatgc acggagtgac cccaatgaac aacactagaa  30060
aggaggttga ggctgaggct tctaagtctg gagctgtggt taagtctgtg ccattggatg  30120
attgggctgc tgttcagtgc caaacctctg tgaactggtc tgttggatct tggttttgga  30180
accacttctc tggaggactc aaccaccaaa tcgagcacca cctcttccca ggattgtctc  30240
acgagaccta ctaccacatc caagacgtgg ttcaatctac ctgtgctgag tacggagttc  30300
cataccaaca cgagccatct ttgtggactg cttactggaa gatgctcgaa caccttagac  30360
aattgggaaa cgaggagact cacgagtcat ggcagagagc tgcttgatta atgaactaag  30420
actcccaaaa ccaccttccc tgtgacagtt aaaccctgct tatacctttc ctcctaataa  30480
tgttcatctg tcacacaaac taaaataaat aaaatgggag caataaataa aatgggagct  30540
catatattta caccatttac actgtctatt attcaccatg ccaattatta cttcataatt  30600
ttaaaattat gtcattttta aaaattgctt aatgatggaa aggattatta taagttaaaa  30660
gtataacata gataaactaa ccacaaaaca aatcaatata aactaactta ctctcccatc  30720
taatttttat ttaaatttct ttacacttct cttccatttc tatttctaca acattattta  30780
acatttttat tgtatttttc ttactttcta actctattca tttcaaaaat caatatatgt  30840
ttatcaccac ctctctaaaa aaaactttac aatcattggt ccagaaaagt taaatcacga  30900
gatggtcatt ttagcattaa aacaacgatt cttgtatcac tatttttcag catgtagtcc  30960
attctcttca aacaaagaca gcggctatat aatcgttgtg ttatattcag tctaaaacaa  31020
ctagctagcc tcagctgacg ttacgtaacg ctaggtagcg tcacgtgacg ttagctaacg  31080
ctaggtagcg tcagctgagc ttacgtaagc gccacgggca ggacataggg actactacaa  31140
gcatagtatg cttcagacaa agagctagga aagaactctt gatggaggtt aagagaaaaa  31200
agtgctagag gggcatagta atcaaacttg tcaaaaccgt catcatgatg agggatgaca  31260
taatataaaa agttgactaa ggtcttggta gtactctttg attagtatta tatattggtg  31320
agaacatgag tcaagaggag acaagaaacc gaggaaccat agtttagcaa caagatggaa  31380
gttgcaaagt tgagctagcc gctcgattag ttacatctcc taagcagtac tacaaggaat  31440
ggtctctata ctttcatgtt tagcacatgg tagtgcggat tgacaagtta gaaacagtgc  31500
ttaggagaca aagagtcagt aaaggtattg aaagagtgaa gttgatgctc gacaggtcag  31560
gagaagtccc tccgccagat ggtgactacc aaggggttgg tatcagctga gacccaaata  31620
agattcttcg gttgaaccag tggttcgacc gagactctta gggtgggatt tcactgtaag  31680
atttgtgcat tttgttgaat ataaattgac aattttttt atttaattat agattattta  31740
gaatgaatta catatttagt ttctaacaag gatagcaatg gatgggtatg ggtacaggtt  31800
aaacatatct attacccacc catctagtcg tcgggtttta cacgtaccca cccgtttaca  31860
taaaccagac cggaatttta aaccgtaccc gtccgttagc gggtttcaga tttacccgtt  31920
taatcgggta aaacctgatt actaaatata tatttttat ttgataaaca aaacaaaaat  31980
gttaatattt tcatattgga tgcaatttta agaaacacat attcataaat ttccatattt  32040
```

-continued

```
gtaggaaaat aaaaagaaaa atatattcaa gaacacaaat ttcaccgaca tgacttttat 32100
tacagagttg gaattagatc taacaattga aaaattaaaa ttaagataga atatgttgag 32160
gaacatgaca tagtataatg ctgggttacc cgtcgggtag gtatcgaggc ggatactact 32220
aaatccatcc cactcgctat ccgataatca ctggtttcgg gtatacccat tcccgtcaac 32280
aggccttttt aaccggataa tttcaactta tagtgaatga attttgaata aatagttaga 32340
ataccaaaat cctggattgc atttgcaatc aaattttgtg aaccgttaaa ttttgcatgt 32400
acttgggata gatataatag aaccgaattt tcattagttt aatttataac ttactttgtt 32460
caaagaaaaa aaatatctat ccaatttact tataataaaa aataatctat ccaagttact 32520
tattataatc aacttgtaaa aaggtaagaa tacaaatgtg gtagcgtacg tgtgattata 32580
tgtgacgaaa tgttatatct aacaaaagtc caaattccca tggtaaaaaa aatcaaaatg 32640
catggcaggc tgtttgtaac cttggaataa gatgttggcc aattctggag ccgccacgta 32700
cgcaagactc agggccacgt tctcttcatg caaggatagt agaacaccac tccacccacc 32760
tcctatatta gacctttgcc caaccctccc caactttccc atcccatcca caaagaaacc 32820
gacattttta tcataaatca gggtttcgtt tttgtttcat cgataaactc aaaggtgatg 32880
attttagggt cttgtgagtg tgctttttttg tttgattcta ctgtagggtt tatgttcttt 32940
agctcatagg ttttgtgtat ttcttagaaa tgtggcttct ttaatctctg ggtttgtgac 33000
tttttgtgtg gtttctgtgt ttttcatatc aaaaacctat tttttccgag ttttttttta 33060
caaattctta ctctcaagct tgaatacttc acatgcagtg ttcttttgta gattttagag 33120
ttaatgtgtt aaaaagtttg gatttttctt gcttatagag cttcttcact ttgattttgt 33180
gggttttttt gttttaaagg tgagattttt gatgaggttt ttgcttcaaa gatgtcacct 33240
ttctgggttt gtcttttgaa taaagctatg aactgtcaca tggctgacgc aattttgtta 33300
ctatgtcatg aaagctgacg tttttccgtg ttatacatgt ttgcttacac ttgcatgcgt 33360
caaaaaaatt ggggcttttt agttttagtc aaagatttta cttctctttt gggatttatg 33420
aaggaaagtt gcaaactttc tcaaatttta ccatttttgc tttgatgttt gtttagattg 33480
cgacagaaca aactcatata tgttgaaatt tttgcttggt tttgtatagg attgtgtctt 33540
ttgcttataa atgttgaaat ctgaactttt tttttgtttg gtttctttga gcaggagata 33600
aggcgcacca ccatggcttc tacatctgct gctcaagacg ctgctcctta cgagttccct 33660
tctctcactg agatcaagag ggctcttcct tctgagtgtt tcgaggcttc tgttcctctt 33720
tctctctact acaccgctag atctcttgct cttgctggat ctctcgctgt tgctctctct 33780
tacgctagag ctttgcctct tgttcaggct aacgctcttc ttgatgctac tctctgcact 33840
ggatacgttc ttctccaggg aatcgttttc tggggattct tcaccgttgg tcacgattgt 33900
ggacacggag ctttctctag atctcacgtg ctcaacttct ctgttggaac cctcatgcac 33960
tctatcatcc ttaccccttt cgagtcttgg aagctctctc acagacacca ccacaagaac 34020
accggaaaca tcgataagga cgagatcttc taccctcaaa gagaggctga ttctcaccct 34080
gtttctagac accttgtgat gtctcttgga tctgcttggt tcgcttacct tttcgctgga 34140
ttccctccta gaaccatgaa ccacttcaac ccttgggagg ctatgtatgt tagaagagtg 34200
gctgctgtga tcatctctct cggagttctt ttcgctttcg ctggactcta ctcttacctc 34260
accttcgttc ttggattcac cactatggct atctactact tcggacctct cttcatcttc 34320
gctaccatgc ttgttgttac cactttcctc caccacaacg atgaggagac accttggtac 34380
gctgattctg agtggactta cgtgaaggga aacctctctt ctgtggacag atcttacggt 34440
```

```
gctctcatcg acaaccttag ccacaacatc ggaactcacc agatccacca cctcttccct  34500
atcatccctc actacaagct caacgatgct actgctgctt tcgctaaggc tttccctgag  34560
cttgttagga aaaacgctgc tcctatcatc ccaactttct tcaggatggc tgctatgtac  34620
gctaagtacg gagttgttga cactgatgct aagaccttca ctctcaagga ggctaaggct  34680
gctgctaaga ctaagtcatc ttgatgatta atgaaggccg cagatatcag atctggtcga  34740
cctagaggat ccccggccgc aaagataata acaaaagcct actatataac gtacatgcaa  34800
gtattgtatg atattaatgt ttttacgtac gtgtaaacaa aaataattac gtttgtaacg  34860
tatggtgatg atgtggtgca ctaggtgtag gccttgtatt aataaaaaga agtttgttct  34920
atatagagtg gtttagtacg acgatttatt tactagtcgg attggaatag agaaccgaat  34980
tcttcaatcc ttgcttttga tcaagaattg aaaccgaatc aaatgtaaaa gttgatatat  35040
ttgaaaaacg tattgagctt atgaaaatgc taatactctc atctgtatgg aaaagtgact  35100
ttaaaaccga acttaaaagt gacaaaaggg gaatatcgca tcaaaccgaa tgaaaccgat  35160
ctacgtaggc tcagctgagc ttacctaagg ctacgtaggc tcacgtgacg ttacgtaagg  35220
ctacgtagcg tcacgtgagc ttacctaact ctagctagcc tcacgtgacc ttagctaaca  35280
ctaggtagcg tcagcttagc agatatttgg tgtctaaatg tttattttgt gatatgttca  35340
tgtttgaaat ggtggtttcg aaaccaggga caacgttggg atctgatagg gtgtcaaaga  35400
gtattatgga ttgggacaat ttcggtcatg agttgcaaat tcaagtatat cgttcgatta  35460
tgaaaatttt cgaagaatat cccatttgag agagtcttta cctcattaat gtttttagat  35520
tatgaaattt tatcatagtt catcgtagtc tttttggtgt aaaggctgta aaaagaaatt  35580
gttcactttt gttttcgttt atgtgaaggc tgtaaaagat tgtaaaagac tattttggtg  35640
ttttggataa aatgatagtt tttatagatt cttttgcttt tagaagaaat acatttgaaa  35700
ttttttccat gttgagtata aaataccgaa atcgattgaa gatcatagaa atattttaac  35760
tgaaaacaaa tttataactg attcaattct ctccattttt atacctattt aaccgtaatc  35820
gattctaata gatgatcgat tttttatata atcctaatta accaacggca tgtattggat  35880
aattaaccga tcaactctca cccctaatag aatcagtatt ttccttcgac gttaattgat  35940
cctacactat gtaggtcata tccatcgttt taatttttgg ccaccattca attctgtctt  36000
gcctttaggg atgtgaatat gaacggccaa ggtaagagaa taaaaataat ccaaattaaa  36060
gcaagagagg ccaagtaaga taatccaaat gtacacttgt cattgccaaa attagtaaaa  36120
tactcggcat attgtattcc cacacattat taaaataccg tatatgtatt ggctgcattt  36180
gcatgaataa tactacgtgt aagcccaaaa gaacccacgt gtagcccatg caaagttaac  36240
actcacgacc ccattcctca gtctccacta tataaaccca ccatccccaa tctcaccaaa  36300
cccaccacac aactcacaac tcactctcac accttaaaga accaatcacc accaaaaaaa  36360
gttctttgct ttcgaagttg ccgcaaccta aacaggtttt tccttcttct ttcttcttat  36420
taactacgac cttgtccttt gcctatgtaa aattactagg ttttcatcag ttacactgat  36480
taagttcgtt atagtggaag ataaaatgcc ctcaaagcat tttgcaggat atctttgatt  36540
tttcaaagat atggaactgt agagtttgat agtgttcttg aatgtggttg catgaagttt  36600
ttttggtctg catgttattt tttcctcgaa atatgttttg agtccaacaa gtgattcact  36660
tgggattcag aaagttgttt tctcaatatg taacagtttt tttctatgga gaaaaatcat  36720
agggaccgtt ggttttggct tctttaattt tgagctcaga ttaaacccat tttacccggt  36780
```

-continued

```
gttcttggca gaattgaaaa cagtacgtag taccgcgcct accatgccac ctagtgctgc  36840
tagtgaaggt ggtgttgctg aacttagagc tgctgaagtt gctagctaca ctagaaaggc  36900
tgttgacgaa agacctgacc tcactatagt tggtgacgct gtttacgacg ctaaggcttt  36960
tagggacgag caccctggtg gtgctcactt cgttagcctt ttcggaggta gggacgctac  37020
tgaggctttt atggaatatc accgtagagc ttggcctaag gctaggatgt ctaagttctt  37080
cgttggttca cttgacgcta gcgagaagcc tactcaagct gattcatctt accttagact  37140
ttgcgctgag gttaacgctc ttttgcctaa gggtagcgga ggattcgctc ctcctagcta  37200
ctggcttaag gctgctgctc ttgttgttgc tgctgttagt atagagggtt atatgctcct  37260
taggggtaag acccttttgc ttagcgtttt ccttggactc gtgttcgctt ggataggact  37320
taatattcag cacgacgcta atcacggtgc tcttagtaga cactcagtga ttaactactg  37380
cctcggttac gctcaggatt ggataggtgg taatatggtg ctttggcttc aagagcacgt  37440
tgtgatgcac cacctccaca ctaacgacgt tgacgctgat cctgatcaaa aggctcacgg  37500
tgttcttaga cttaagccta ctgacggttg gatgccttgg cacgcacttc aacaactcta  37560
tatccttcct ggtgaggcta tgtacgcttt taagcttctt ttcttggacg cccttgagct  37620
tcttgcttgg aggtgggagg gtgagaagat tagccctctt gctagagctt tgttcgctcc  37680
tgctgttgct tgtaagcttg gattctgggc tagattcgtt gctctccctc tctggcttca  37740
acctactgtt cacactgctt tgtgtatctg tgctactgtg tgtactggta gcttctacct  37800
cgccttcttc ttctttatct ctcacaactt cgacggtgtt ggtagcgttg gacctaaggg  37860
atcacttcct agatcagcta ctttcgttca acgtcaggtt gagactagct ctaacgttgg  37920
tggttactgg cttggagttc ttaacggtgg acttaacttt cagatagagc accacttgtt  37980
ccctaggctt caccactctt actacgctca aatagctcct gtggttagga ctcacataga  38040
gaagctcggt tttaagtacc gtcacttccc taccgttgga tctaacctta gctcaatgct  38100
tcagcatatg ggtaagatgg gaactagacc tggtgctgag aagggtggta aggctgagta  38160
gtgattaatg aataattgat tgctgcttta atgagatatg cgagacgcct atgatcgcat  38220
gatatttgct ttcaattctg ttgtgcacgt tgtaaaaaac ctgagcatgt gtagctcaga  38280
tccttaccgc cggtttcggt tcattctaat gaatatatca cccgttacta tcgtattttt  38340
atgaataata ttctccgttc aatttactga ttgtctacgt agcgtcacct gacgttacgt  38400
aaggctacct aggctcacgt gacgttacgt aacgctacgt agcgtcaggt gaggttagct  38460
aacgctagct agcctcacct gacgttaggt aaggctacgt agcgtcacct gagattagct  38520
aagcctacct agactcacgt gaccttaggt aacgctacgt agcgtcaaag ctttacaacg  38580
ctacacaaaa cttataaccg taatcaccat tcattaactt aactactatc acatgcattc  38640
atgaattgaa acgagaagga tgtaaatagt tgggaagtta tctccacgtt gaagagatcg  38700
ttagcgagag ctgaaagacc gagggaggag acgccgtcaa cacggacaga gtcgtcgacc  38760
ctcacatgaa gtaggaggaa tctccgtgag gagccagaga gacgtctttg gtcttcggtt  38820
tcgatccttg atctgacgga gaagacgaga gaagtgcgac tggactccgt gaggaccaac  38880
agagtcgtcc tcggtttcga tcgtcggtat tggtggagaa ggcggaggaa tctccgtgac  38940
gagccagaga gatgtcgtcg gtcttcggtt tcgatccttg atctgacgga gaagacgaga  39000
gaagtgcgac gagactccgt gaggaccaac agagttgtcc tcggtttcga tcgtcggttt  39060
cggcggagaa ggcggaggaa tctccgtgag gagccagaga gacgtcgttg gtcttcggtt  39120
tcgatccttg atctgttgga gaagacgaga caagtgggac gagactcaac gacggagtca  39180
```

```
gagacgtcgt cggtcttcgg tttcggccga gaaggcggag tcggtcttcg gtttcggccg  39240
agaaggcgga ggagacgtct tcgatttggg tctctcctct tgacgaagaa aacaaagaac  39300
acgagaaata atgagaaaga gaacaaaaga aaaaaaaata aaaataaaaa taaaatttgg  39360
tcctcttatg tggtgacacg tggtttgaaa cccaccaaat aatcgatcac aaaaaaccta  39420
agttaaggat cggtaataac ctttctaatt aattttgatt tatattaaat cactcttttt  39480
atttataaac cccactaaat tatgcgatat tgattgtcta agtacaaaaa ttctctcgaa  39540
ttcaatacac atgtttcata tatttagccc tgttcattta atattactag cgcattttta  39600
atttaaaatt ttgtaaactt ttttggtcaa agaacatttt tttaattaga gacagaaatc  39660
tagactcttt atttggaata atagtaataa agatatatta ggcaatgagt ttatgatgtt  39720
atgtttatat agtttatttc attttaaatt gaaaagcatt atttttatcg aaatgaatct  39780
agtatacaat caatatttat gtttttttcat cagatacttt cctatttttt ggcacctttc  39840
atcggactac tgatttattt caatgtgtat gcatgcatga gcatgagtat acacatgtct  39900
tttaaaatgc atgtaaagcg taacggacca caaaagagga tccatacaaa tacatctcat  39960
cgcttcctct actattctcc gacacacaca ctgagcatgg tgcttaaaca ctctggtgag  40020
ttctagtact tctgctatga tcgatctcat taccatttct taaatttctc tccctaaata  40080
ttccgagttc ttgatttttg ataacttcag gttttctctt tttgataaat ctggtctttc  40140
catttttttt tttttgtggt taatttagtt tcctatgttc ttcgattgta ttatgcatga  40200
tctgtgtttg gattctgtta gattatgtat tggtgaatat gtatgtgttt ttgcatgtct  40260
ggttttggtc ttaaaaatgt tcaaatctga tgatttgatt gaagcttttt tagtgttggt  40320
ttgattcttc tcaaaactac tgttaattta ctatcatgtt ttccaacttt gattcatgat  40380
gacacttttg ttctgctttg ttataaaatt ttggttggtt tgattttgta attatagtgt  40440
aattttgtta ggaatgaaca tgttttaata ctctgtttc gatttgtcac acattcgaat  40500
tattaatcga taatttaact gaaaattcat ggttctagat cttgttgtca tcagattatt  40560
tgtttcgata attcatcaaa tatgtagtcc ttttgctgat ttgcgactgt ttcatttttt  40620
ctcaaaattg ttttttgtta agtttatcta acagttatcg ttgtcaaaag tctctttcat  40680
tttgcaaaat cttctttttt tttttgtttg taactttgtt ttttaagcta cacatttagt  40740
ctgtaaaata gcatcgagga acagttgtct tagtagactt gcatgttctt gtaacttcta  40800
tttgtttcag tttgttgatg actgctttga ttttgtaggt caaaccgcgc catgtctgct  40860
agcggagctt tgttgcctgc tatagctttc gctgcttacg cttacgctac ctacgcttat  40920
gctttcgagt ggagccacgc taacggaatc gataacgtgg atgctagaga gtggattgga  40980
gctttgtctt tgagactccc tgcaattgca accacaatgt acctcttgtt ctgccttgtg  41040
ggacctagat tgatggctaa gagggaggct tttgatccta agggatttat gctcgcttac  41100
aacgcttacc aaaccgcttt caacgttgtg gtgctcggaa tgttcgctag agagatctct  41160
ggattgggac aacctgtttg gggatctact atgccttgga gcgataggaa gtccttcaag  41220
attttgttgg gagtgtggct ccactacaac aataagtacc tcgagttgtt ggatactgtg  41280
ttcatggtgg ctaggaaaaa gaccaagcag ctctctttct tgcacgtgta ccaccacgct  41340
ttgttgattt gggcttggtg gcttgtttgt cacctcatgg ctaccaacga ttgcatcgat  41400
gcttatttcg gagctgcttg caactctttc atccacatcg tgatgtactc ctactacctc  41460
atgtctgctt tgggaattag gtgcccttgg aagagatata tcacccaggc tcagatgttg  41520
```

```
caattcgtga tcgtgttcgc tcacgctgtt ttcgtgctca gacaaaagca ctgccctgtt  41580
actttgcctt gggcacaaat gttcgtgatg acaaatatgt tggtgctctt cggaaacttc  41640
tacctcaagg cttactctaa caagtctagg ggagatggag cttcttctgt taagcctgct  41700
gagactacta gagcaccttc tgtgagaaga accaggtcaa ggaagatcga ttgatagtta  41760
atgaactaag tttgatgtat ctgagtgcca acgtttactt tgtctttcct ttcttttatt  41820
ggttatgatt agatgtttac tatgttctct ctttttcgtt ataaataaag aagttcaatt  41880
cttctatagt ttcaaacgcg attttaagcg tttctattta ggtttacatg atttctttta  41940
caaaatcatc tttaaaatac agtatatttt tagttttcat aaaatattta aagaaatgaa  42000
agtttataaa cattcactcc tattctctaa ttaaggattt gtaaaacaaa aattttgtaa  42060
gcatatcgat ttatgcgttt tgtcttaatt agctcactaa ataataaata atagcttatg  42120
ttgtgggact gtttaattac ctaacttaga actaaaatca actctttgtg ctagctagcc  42180
tcagctgacg ttacgtaacg ctaggtagcg tcacgtgacg ttagctaacg ctaggtagcg  42240
tcagctgagc ttacgtaagc gcttaattaa agtactgata tcggtaccaa atcgaatcca  42300
aaaattacgg atatgaatat aggcatatcc gtatccgaat tatccgtttg acagctagca  42360
acgattgtac aattgcttct ttaaaaaagg aagaaagaaa gaaagaaaag aatcaacatc  42420
agcgttaaca aacggccccg ttacggccca aacggtcata tagagtaacg gcgttaagcg  42480
ttgaaagact cctatcgaaa tacgtaaccg caaacgtgtc atagtcagat cccctcttcc  42540
ttcaccgcct caaacacaaa aataatcttc tacagcctat atatacaacc ccccttcta  42600
tctctccttt ctcacaattc atcatctttc tttctctacc cccaatttta agaaatcctc  42660
tcttctcctc ttcattttca aggtaaatct ctctctctct ctctctctct gttattcctt  42720
gttttaatta ggtatgtatt attgctagtt tgttaatctg cttatcttat gtatgcctta  42780
tgtgaatatc tttatcttgt tcatctcatc cgtttagaag ctataaattt gttgatttga  42840
ctgtgtatct acacgtggtt atgtttatat ctaatcagat atgaatttct tcatattgtt  42900
gcgtttgtgt gtaccaatcc gaaatcgttg attttttca tttaatcgtg tagctaattg  42960
tacgtataca tatggatcta cgtatcaatt gttcatctgt ttgtgtttgt atgtatacag  43020
atctgaaaac atcacttctc tcatctgatt gtgttgttac atacatagat atagatctgt  43080
tatatcattt tttttattaa ttgtgtatat atatatgtgc atagatctgg attacatgat  43140
tgtgattatt tacatgattt tgttatttac gtatgtatat atgtagatct ggactttttg  43200
gagttgttga cttgattgta tttgtgtgtg tatatgtgtg ttctgatctt gatatgttat  43260
gtatgtgcag ctgaaccatg gcggcggcaa caacaacaac aacaacatct tcttcgatct  43320
ccttctccac caaaccatct ccttcctcct ccaaatcacc attaccaatc tccagattct  43380
ccctcccatt ctccctaaac cccaacaaat catcctcctc ctcccgccgc cgcggtatca  43440
aatccagctc tccctcctcc atctccgccg tgctcaacac aaccaccaat gtcacaacca  43500
ctccctctcc aaccaaacct accaaacccg aaacattcat ctcccgattc gctccagatc  43560
aaccccgcaa aggcgctgat atcctcgtcg aggctttaga acgtcaaggc gtagaaaccg  43620
tattcgctta ccctggaggt acatcaatgg agattcacca agccttaacc cgctcttcct  43680
caatccgtaa cgtccttcct cgtcacgaac aaggaggtgt attcgcagca gaaggatacg  43740
ctcgatcctc aggtaaacca ggtatctgta tagccacttc aggtcccgga gctacaaatc  43800
tcgttagcgg attagccgat gcgttgttag atagtgttcc tcttgtagca atcacaggac  43860
aagtccctcg tcgtatgatt ggtacagatg cgtttcaaga gactccgatt gttgaggtaa  43920
```

```
cgcgttcgat tacgaagcat aactatcttg tgatggatgt tgaagatatc ccaaggatta  43980
ttgaagaggc tttcttttta gctacttctg gtagacctgg acctgttttg gttgatgttc  44040
ctaaagatat tcaacaacag cttgcgattc ctaattggga acaggctatg agattacctg  44100
gttatatgtc taggatgcct aaacctccgg aagattctca tttggagcag attgttaggt  44160
tgatttctga gtctaagaag cctgtgttgt atgttggtgg tggttgtctt aattctagcg  44220
atgaattggg taggtttgtt gagcttacgg gcatccctgt tgcgagtacg ttgatggggc  44280
tgggatctta tccttgtgat gatgagttgt cgttacatat gcttggaatg catgggactg  44340
tgtatgcaaa ttacgctgtg gagcatagtg atttgttgtt ggcgtttggg gtaaggtttg  44400
atgatcgtgt cacgggtaaa cttgaggctt ttgctagtag ggctaagatt gttcatattg  44460
atattgactc ggctgagatt gggaagaata agactcctca tgtgtctgtg tgtggtgatg  44520
ttaagctggc tttgcaaggg atgaataagg ttcttgagaa ccgagcggag gagcttaaac  44580
ttgattttgg agtttggagg aatgagttga acgtacagaa acagaagttt ccgttgagct  44640
ttaagacgtt tggggaagct attcctccac agtatgcgat taaggtcctt gatgagttga  44700
ctgatggaaa agccataata agtactggtg tcgggcaaca tcaaatgtgg gcggcgcagt  44760
tctacaatta caagaaacca aggcagtggc tatcatcagg aggccttgga gctatgggat  44820
ttggacttcc tgctgcgatt ggagcgtctg ttgctaaccc tgatgcgata gttgtggata  44880
ttgacggaga tggaagtttt ataatgaatg tgcaagagct agccactatt cgtgtagaga  44940
atcttccagt gaaggtactt ttattaaaca accagcatct tggcatggtt atgcaatggg  45000
aagatcggtt ctacaaagct aaccgagctc acacatttct cggggacccg gctcaggagg  45060
acgagatatt cccgaacatg ttgctgtttg cagcagcttg cgggattcca gcggcgaggg  45120
tgacaaagaa agcagatctc cgagaagcta ttcagacaat gctggataca ccaggacctt  45180
acctgttgga tgtgatttgt ccgcaccaag aacatgtgtt gccgatgatc ccgaatggtg  45240
gcactttcaa cgatgtcata acggaaggag atggccggat taaatactga gagatgaaac  45300
cggtgattat cagaaccttt tatggtcttt gtatgcatat ggtaaaaaaa cttagtttgc  45360
aatttcctgt ttgttttggt aatttgagtt tcttttagtt gttgatctgc ctgctttttg  45420
gtttacgtca gactactact gctgttgttg tttggtttcc tttctttcat tttataaata  45480
aataatccgg ttcggtttac tccttgtgac tggctcagtt tggttattgc gaaatgcgaa  45540
tggtaaattg agtaattgaa attcgttatt agggttctaa gctgttttaa cagtcactgg  45600
gttaatatct ctcgaatctt gcatggaaaa tgctcttacc attggttttt aattgaaatg  45660
tgctcatatg ggccgtggtt tccaaattaa ataaaactac gatgtcatcg agaagtaaaa  45720
tcaactgtgt ccacattatc agttttgtgt atacgatgaa atagggtaat tcaaaatcta  45780
gcttgatatg ccttttggtt cattttaacc ttctgtaaac attttttcag attttgaaca  45840
agtaaatcca aaaaaaaaaa aaaaaatctc aactcaacac taaattattt taatgtataa  45900
aagatgctta aaacatttgg cttaaaagaa agaagctaaa aacatagaga actcttgtaa  45960
attgaagtat gaaaatatac tgaattgggt attatatgaa tttttctgat ttaggattca  46020
catgatccaa aaaggaaatc cagaagcact aatcagacat tggaagtagg attaatcagt  46080
gatcagtaac tattaaattc aattaaccgc ggacatctac atttttgaat tgaaaaaaaa  46140
ttggtaatta ctctttcttt ttctccatat tgaccatcat actcattgct gatccatgta  46200
gatttcccgg acatgaagcc atttacaatt gaatatatcc tcacatatga aatatatttt  46260
```

```
tttttacaa attacaccta ttaaattata cttgatcggt catctgatat atttgaaaga  46320
accctatcag ccagctattc ataatttaca taaaagaaaa ttacgtgctt aaaatctctc  46380
taaaaaaaaa aaaagacaaa gacatcaaac tgatccatga aagtaaaatg gagtgtattt  46440
taattttatc ttcagaccaa tgttatcaat gtagcccata tattaatact aaaacaactt  46500
ctgcacaaac acacgaatca aagcctcgtg tttcatcgta gctttagcta aaatttccca  46560
aaagcaaatt caatagtatt ttactaggtc aaacccacaa gagaaaaaga aagtcaatcc  46620
caaggatcaa gaaatgagaa gtgagaggag aatgctttat tgggtttgct aataactaat  46680
aagacatgaa gcagactgaa aacatctggt tttgtccaaa aaagaaggaa gtcagattcc  46740
aaaactgcgc acctacattg tttaatactc actcacacat acattcatgt ttttactgtt  46800
tatacacagt caataattta tacacagctc catgttttaa tatttaccca tctctctttt  46860
gtagtctatc gtagactttc acttgtgtcc ccctcatgcg gcaacatcct cagcaacttg  46920
atttactata tacaataata caaatcataa gatatttgtt aggagctggt ttgtaaatta  46980
tttcgataca atactgaagc gaagggacca gcaatctttt tagctgatca gaacaatctt  47040
actaacgtgt gtctttgtaa gaaaatccaa cttttacttt ttcaggaggg agtgtagcgg  47100
attatgtata aataactcga agagtggtgc acaaagttca agtgtttgtg taaaatgttc  47160
gacaagacat tgactaaagc attccgaaca tgtcaacaaa actacaattc taaaattgca  47220
aaaagctgct aaacggtgga atagcattta acacgcattc tataccaaac atttttttc  47280
ttgaacacca aagaaaccaa acctaatgtc aaccatcgta tggaaactat agaactaaat  47340
caaactaaca aattcttatt gtatattctt aaaaacatcc ttataagaca gtttttccaa  47400
atgaatcttt agacttcatt gtactaatat gtttaaaata atataattat gtatttaatt  47460
tcttgaaagt ttcgctgcta agaggcaatt atctttttat atttttttct ctcttatttt  47520
caaattctaa ttaattttct tggagagttt atccgatgat gatattctta tttcaactca  47580
atccacgagt aaatgtgtta gcaccacatc taaccatttg gagcttgtac tagctctatc  47640
tttccaaact taactttctt gagtgcttat ttatataaag catcagtata tggcccaacc  47700
caagaaaagc tgaacaaaat tagcaacaat agcaagggac gaactgcagc tcttcttggt  47760
tgtcgtgcct tccaattctc gactttccgt ggaagaacat                       47800
```

```
<210> SEQ ID NO 12
<211> LENGTH: 43773
<212> TYPE: DNA
<213> ORGANISM: Artificial sequence
<220> FEATURE:
<223> OTHER INFORMATION: T-DNA insertion in LBFLFK Locus 2, including
      left and right border sequences

<400> SEQUENCE: 12
```

```
ccagtcagca tcatcacacc aaaagttagg cccgaatagt ttgaaattag aaagctcgca     60
attgaggtct acaggccaaa ttcgctctta gccgtacaat attactcacc ggtgcgatgc    120
cccccatcgt aggtgaaggt ggaaattaat ggcgcgcctg atcactgatt agtaactatt    180
acgtaagcct acgtagcgtc acgtgacgtt agctaacgct acgtagcctc agctgacgtt    240
acgtaagcct acgtagcgtc acgtgagctt agctaacgct acctaggctc agctgacgtt    300
acgtaacgct agctagcgtc actcctgcag caaatttaca cattgccact aaacgtctaa    360
acccttgtaa tttgtttttg ttttactatg tgtgttatgt atttgatttg cgataaattt    420
ttatatttgg tactaaattt ataacacctt ttatgctaac gtttgccaac acttagcaat    480
```

```
ttgcaagttg attaattgat tctaaattat ttttgtcttc taaatacata tactaatcaa    540
ctggaaatgt aaatatttgc taatatttct actataggag aattaaagtg agtgaatatg    600
gtaccacaag gtttggagat ttaattgttg caatgctgca tggatggcat atacaccaaa    660
cattcaataa ttcttgagga taataatggt accacacaag atttgaggtg catgaacgtc    720
acgtggacaa aaggtttagt aatttttcaa gacaacaatg ttaccacaca caagttttga    780
ggtgcatgca tggatgccct gtggaaagtt taaaaatatt ttggaaatga tttgcatgga    840
agccatgtgt aaaaccatga catccacttg gaggatgcaa taatgaagaa aactacaaat    900
ttacatgcaa ctagttatgc atgtagtcta tataatgagg attttgcaat actttcattc    960
atacacactc actaagtttt acacgattat aatttcttca tagccagtac tgtttaagct   1020
tcactgtctc tgaatcggca aaggtaaacg tatcaattat tctacaaacc cttttatttt   1080
tcttttgaat taccgtcttc attggttata tgataacttg ataagtaaag cttcaataat   1140
tgaatttgat ctgtgttttt ttggccttaa tactaaatcc ttacataagc tttgttgctt   1200
ctcctcttgt gagttgagtg ttaagttgta ataatggttc actttcagct ttagaagaaa   1260
ccatggaagt tgttgagagg ttctacggag agttggatgg aaaggtttcc caaggagtga   1320
acgctttgtt gggatctttc ggagttgagt tgactgatac cccaactact aagggattgc   1380
cactcgttga ttctccaact ccaattgtgt tgggagtgtc tgtttacttg accatcgtga   1440
tcggaggatt gctttggatc aaggctagag atctcaagcc aagagcttct gagccattct   1500
tgttgcaagc tttggtgttg gtgcacaact tgttctgctt cgctttgtct ctttacatgt   1560
gcgtgggtat cgcttaccaa gctatcacct ggagatattc cttgtgggga aacgcttata   1620
acccaaagca caaggagatg gctatcctcg tttacctctt ctacatgtcc aagtacgtgg   1680
agttcatgga taccgtgatc atgatcctca agagatccac cagacagatt tctttcctcc   1740
acgtgtacca ccactcttct atctccctta tctggtgggc tattgctcac cacgctccag   1800
gaggagaggc ttattggagt gctgctctca actctggagt gcacgtgttg atgtacgctt   1860
actacttctt ggctgcttgc ttgagatctt ccccaaagct caagaacaag tacctcttct   1920
ggggaagata cctcacccaa ttccagatgt tccagttcat gctcaacttg gtgcaagctt   1980
actacgatat gaaaaccaac gctccatatc cacaatggct catcaagatc ctcttctact   2040
acatgatctc cctcttgttc ctcttcggaa acttctacgt gcaaaagtac atcaagccat   2100
ccgatggaaa gcaaaaggga gctaagaccg agtgatcgac aagctcgagt ttctccataa   2160
taatgtgtga gtagttccca gataagggaa ttagggttcc tatagggttt cgctcatgtg   2220
ttgagcatat aagaaaccct tagtatgtat ttgtatttgt aaaatacttc tatcaataaa   2280
atttctaatt cctaaaacca aaatccagta ctaaaatcca gatcccccga attaattcgg   2340
cgttaattca gctagctagc ctcagctgac gttacgtaac gctaggtagc gtcacgtgac   2400
gttagctaac gctaggtagc gtcagctgag cttacgtaag cgcttagcag atatttggtg   2460
tctaaatgtt tattttgtga tatgttcatg tttgaaatgg tggtttcgaa accagggaca   2520
acgttgggat ctgatagggt gtcaaagagt attatggatt gggacaattt cggtcatgag   2580
ttgcaaattc aagtatatcg ttcgattatg aaaattttcg aagaatatcc catttgagag   2640
agtctttacc tcattaatgt ttttagatta tgaaatttta tcatagttca tcgtagtctt   2700
tttggtgtaa aggctgtaaa aagaaattgt tcacttttgt tttcgtttat gtgaaggctg   2760
taaaagattg taaaagacta ttttggtgtt ttggataaaa tgatagtttt tatagattct   2820
tttgctttta gaagaaatac atttgaaatt ttttccatgt tgagtataaa ataccgaaat   2880
```

```
cgattgaaga tcatagaaat attttaactg aaaacaaatt tataactgat tcaattctct   2940

ccatttttat acctatttaa ccgtaatcga ttctaataga tgatcgattt tttatataat   3000

cctaattaac caacggcatg tattggataa ttaaccgatc aactctcacc cctaatagaa   3060

tcagtatttt ccttcgacgt taattgatcc tacactatgt aggtcatatc catcgtttta   3120

atttttggcc accattcaat tctgtcttgc ctttagggat gtgaatatga acggccaagg   3180

taagagaata aaaataatcc aaattaaagc aagagaggcc aagtaagata atccaaatgt   3240

acacttgtca ttgccaaaat tagtaaaata ctcggcatat tgtattccca cacattatta   3300

aaataccgta tatgtattgg ctgcatttgc atgaataata ctacgtgtaa gcccaaaaga   3360

acccacgtgt agcccatgca aagttaacac tcacgacccc attcctcagt ctccactata   3420

taaacccacc atccccaatc tcaccaaacc caccacacaa ctcacaactc actctcacac   3480

cttaaagaac caatcaccac caaaaaattt cacgatttgg aatttgattc ctgcgatcac   3540

aggtatgaca ggttagattt tgttttgtat agttgtatac atacttcttt gtgatgtttt   3600

gtttacttaa tcgaattttt ggagtgtttt aaggtctctc gtttagaaat cgtggaaaat   3660

atcactgtgt gtgtgttctt atgattcaca gtgtttatgg gtttcatgtt ctttgtttta   3720

tcattgaatg ggaagaaatt tcgttgggat acaaatttct catgttctta ctgatcgtta   3780

ttaggagttt ggggaaaaag gaagagtttt tttggttggt tcgagtgatt atgaggttat   3840

ttctgtattt gatttatgag ttaatggtcg ttttaatgtt gtagaccatg ggaaaaggat   3900

ctgagggaag atctgctgct agagagatga ctgctgaggc taacggagat aagagaaaga   3960

ccatcctcat tgagggagtg ttgtacgatg ctaccaactt caaacaccca ggaggttcca   4020

ttattaactt cctcaccgag ggagaagctg gagttgatgc tacccaagct tacagagagt   4080

tccatcagag atccggaaag gctgataagt acctcaagtc cctcccaaag ttggatgctt   4140

ctaaggtgga gtctaggttc tctgctaagg agcaggctag aagggacgct atgaccaggg   4200

attacgctgc tttcagagag gagttggttg ctgagggata cttcgatcca tctatcccac   4260

acatgatcta cagagtggtg gagattgtgg ctttgttcgc tttgtctttc tggttgatgt   4320

ctaaggcttc tccaacctct ttggttttgg gagtggtgat gaacggaatc gctcaaggaa   4380

gatgcggatg ggttatgcac gagatgggac acggatcttt cactggagtt atctggctcg   4440

atgataggat gtgcgagttc ttctacggag ttggatgtgg aatgtctgga cactactgga   4500

agaaccagca ctctaagcac cacgctgctc caaacagatt ggagcacgat gtggatttga   4560

acaccttgcc actcgttgct ttcaacgaga gagttgtgag gaaggttaag ccaggatctt   4620

tgttggcttt gtggctcaga gttcaggctt atttgttcgc tccagtgtct tgcttgttga   4680

tcggattggg atggaccttg tacttgcacc caagatatat gctcaggacc aagagacaca   4740

tggagtttgt gtggatcttc gctagatata tcggatggtt ctccttgatg ggagctttgg   4800

gatattctcc tggaacttct gtgggaatgt acctctgctc tttcggactt ggatgcatct   4860

acatcttcct ccaattcgct gtgtctcaca cccacttgcc agttaccaac ccagaggatc   4920

aattgcactg gcttgagtac gctgctgatc acaccgtgaa catctctacc aagtcttggt   4980

tggttacctg gtggatgtct aacctcaact tccaaatcga gcaccacttg ttcccaaccg   5040

ctccacaatt caggttcaag gagatctctc caagagttga ggctctcttc aagagacaca   5100

acctccctta ctacgatttg ccatacacct ctgctgtttc tactaccttc gctaacctct   5160

actctgttgg acactctgtt ggagctgata ccaagaagca ggattgactg ctttaatgag   5220
```

```
atatgcgaga cgcctatgat cgcatgatat ttgctttcaa ttctgttgtg cacgttgtaa   5280
aaaacctgag catgtgtagc tcagatcctt accgccggtt tcggttcatt ctaatgaata   5340
tatcacccgt tactatcgta tttttatgaa taatattctc cgttcaattt actgattgtc   5400
tacgtaggct cagctgagct tacctaaggc tacgtaggct cacgtgacgt tacgtaaggc   5460
tacgtagcgt cacgtgagct tacctaactc tagctagcct cacgtgacct tagctaacac   5520
taggtagcgt cagctcgacg gcccggactg tatccaactt ctgatctttg aatctctctg   5580
ttccaacatg ttctgaagga gttctaagac ttttcagaaa gcttgtaaca tgctttgtag   5640
actttctttg aattactctt gcaaactctg attgaaccta cgtgaaaact gctccagaag   5700
ttctaaccaa attccgtctt gggaaggccc aaaatttatt gagtacttca gtttcatgga   5760
cgtgtcttca aagatttata acttgaaatc ccatcatttt taagagaagt tctgttccgc   5820
aatgtcttag atctcattga aatctacaac tcttgtgtca gaagttcttc cagaatcaac   5880
ttgcatcatg gtgaaaatct ggccagaagt tctgaacttg tcatatttct taacagttag   5940
aaaaatttct aagtgtttag aattttgact tttccaaagc aaacttgact tttgactttc   6000
ttaataaaac aaacttcata ttctaacatg tcttgatgaa atgtgattct tgaaatttga   6060
tgttgatgca aaagtcaaag tttgactttt cagtgtgcaa ttgaccattt tgctcttgtg   6120
ccaattccaa acctaaattg atgtatcagt gctgcaaact tgatgtcatg gaagatctta   6180
tgagaaaatt cttgaagact gagaggaaaa attttgtagt acaacacaaa gaatcctgtt   6240
tttcatagtc ggactagaca cattaacata aaacaccact tcattcgaag agtgattgaa   6300
gaaggaaatg tgcagttacc tttctgcagt tcataagagc aacttacaga cacttttact   6360
aaaatactac aaagaggaag attttaacaa cttagagaag taatgggagt taaagagcaa   6420
cacattaagg gggagtgtta aaattaatgt gttgtaacca ccactacctt tagtaagtat   6480
tataagaaaa ttgtaatcat cacattataa ttattgtcct tatttaaaat tatgataaag   6540
ttgtatcatt aagattgaga aaaccaaata gtcctcgtct tgatttttga attattgttt   6600
tctatgttac ttttcttcaa gcctatataa aaactttgta atgctaaatt gtatgctgga   6660
aaaaaatgtg taatgaattg aatagaaatt atggtatttc aaagtccaaa atccatcaat   6720
agaaatttag tacaaaacgt aactcaaaaa tattctctta ttttaaattt tacaacaata   6780
taaaaatatt ctcttatttt aaattttaca ataatataat ttatcacctg tcacctttag   6840
aataccacca acaatattaa tacttagata ttttattctt aataattttg agatctctca   6900
atatatctga tatttatttt atatttgtgt catattttct tatgttttag agttaaccct   6960
tatatcttgg tcaaactagt aattcaatat atgagtttgt gaaggacaca ttgacatctt   7020
gaaacattgg ttttaacctt gttggaatgt taaaggtaat aaaacattca gaattatgac   7080
catctattaa tatacttcct ttgtctttta aaaaagtgtg catgaaaatg ctctatggta   7140
agctagagtg tcttgctggc ctgtgtatat caattccatt tccagatggt agaaactgcc   7200
actacgaata attagtcata agacacgtat gttaacacac gtccccttgc atgtttttttg   7260
ccatatattc cgtctctttc tttttcttca cgtataaaac aatgaactaa ttaatagagc   7320
gatcaagctg aacagttctt tgctttcgaa gttgccgcaa cctaaacagg tttttccttc   7380
ttctttcttc ttattaacta cgaccttgtc ctttgcctat gtaaaattac taggttttca   7440
tcagttacac tgattaagtt cgttatagtg gaagataaaa tgccctcaaa gcattttgca   7500
ggatatcttt gatttttcaa agatatggaa ctgtagagtt tgatagtgtt cttgaatgtg   7560
gttgcatgaa gtttttttgg tctgcatgtt attttttcct cgaaatatgt tttgagtcca   7620
```

```
acaagtgatt cacttgggat tcagaaagtt gttttctcaa tatgtaacag tttttttcta   7680
tggagaaaaa tcatagggac cgttggtttt ggcttcttta attttgagct cagattaaac   7740
ccattttacc cggtgttctt ggcagaattg aaaacagtac gtagtaccgc gcctaccatg   7800
tgtgttgaga ccgagaacaa cgatggaatc cctactgtgg agatcgcttt cgatggagag   7860
agagaaagag ctgaggctaa cgtgaagttg tctgctgaga agatggaacc tgctgctttg   7920
gctaagacct tcgctagaag atacgtggtt atcgagggag ttgagtacga tgtgaccgat   7980
ttcaaacatc ctggaggaac cgtgattttc tacgctctct ctaacactgg agctgatgct   8040
actgaggctt tcaaggagtt ccaccacaga tctagaaagg ctaggaaggc tttggctgct   8100
ttgccttcta gacctgctaa gaccgctaaa gtggatgatg ctgagatgct ccaggatttc   8160
gctaagtgga gaaaggagtt ggagagggac ggattcttca agccttctcc tgctcatgtt   8220
gcttacagat tcgctgagtt ggctgctatg tacgctttgg gaacctactt gatgtacgct   8280
agatacgttg tgtcctctgt gttggtttac gcttgcttct tcggagctag atgtggatgg   8340
gttcaacacg agggaggaca ctcttctttg accggaaaca tctggtggga taagagaatc   8400
caagctttca ctgctggatt cggattggct ggatctggag atatgtggaa ctccatgcac   8460
aacaagcacc acgctactcc tcaaaaagtg aggcacgata tggatttgga taccactcct   8520
gctgttgctt tcttcaacac cgctgtggag gataatagac ctaggggatt ctctaagtac   8580
tggctcagat tgcaagcttg gaccttcatt cctgtgactt ctggattggt gttgctcttc   8640
tggatgttct tcctccaccc ttctaaggct ttgaagggag gaaagtacga ggagcttgtg   8700
tggatgttgg ctgctcacgt gattagaacc tggaccatta aggctgttac tggattcacc   8760
gctatgcaat cctacggact cttcttggct acttcttggg tttccggatg ctacttgttc   8820
gctcacttct ctacttctca cacccacttg gatgttgttc ctgctgatga gcacttgtct   8880
tgggttaggt acgctgtgga tcacaccatt gatatcgatc cttctcaggg atgggttaac   8940
tggttgatgg gatacttgaa ctgccaagtg attcaccacc tcttcccttc tatgcctcaa   9000
ttcagacaac ctgaggtgtc cagaagattc gttgctttcg ctaagaagtg gaacctcaac   9060
tacaaggtga tgacttatgc tggagcttgg aaggctactt tgggaaacct cgataatgtg   9120
ggaaagcact actacgtgca cggacaacac tctggaaaga ccgcttgatt aatgaaggcc   9180
gcctcgaccg taccccctgc agatagacta tactatgttt tagcctgcct gctggctagc   9240
tactatgtta tgttatgttg taaaataaac acctgctaag gtatatctat ctatatttta   9300
gcatggcttt ctcaataaat tgtctttcct tatcgtttac tatcttatac ctaataatga   9360
aataataata tcacatatga ggaacggggc aggtttaggc atatatatac gagtgtaggg   9420
cggagtgggg ctacgtagcg tcacgtgacg ttacctaagc ctaggtagcc tcagctgacg   9480
ttacgtaacg ctaggtaggc tcagctgaca cgggcaggac atagggacta ctacaagcat   9540
agtatgcttc agacaaagag ctaggaaaga actcttgatg gaggttaaga gaaaaaagtg   9600
ctagaggggc atagtaatca aacttgtcaa aaccgtcatc atgatgaggg atgacataat   9660
ataaaaagtt gactaaggtc ttggtagtac tctttgatta gtattatata ttggtgagaa   9720
catgagtcaa gaggagacaa gaaaccgagg aaccatagtt tagcaacaag atggaagttg   9780
caaagttgag ctagccgctc gattagttac atctcctaag cagtactaca aggaatggtc   9840
tctatacttt catgtttagc acatggtagt gcggattgac aagttagaaa cagtgcttag   9900
gagacaaaga gtcagtaaag gtattgaaag agtgaagttg atgctcgaca ggtcaggaga   9960
```

```
agtccctccg ccagatggtg actaccaagg ggttggtatc agctgagacc caaataagat  10020
tcttcggttg aaccagtggt tcgaccgaga ctcttagggt gggatttcac tgtaagattt  10080
gtgcattttg ttgaatataa attgacaatt ttttttattt aattatagat tatttagaat  10140
gaattacata tttagtttct aacaaggata gcaatggatg ggtatgggta caggttaaac  10200
atatctatta cccacccatc tagtcgtcgg gttttacacg tacccacccg tttacataaa  10260
ccagaccgga attttaaacc gtacccgtcc gttagcgggt ttcagattta cccgtttaat  10320
cgggtaaaac ctgattacta aatatatatt ttttatttga taaacaaaac aaaaatgtta  10380
atattttcat attggatgca attttaagaa acacatattc ataaatttcc atatttgtag  10440
gaaaataaaa agaaaaatat attcaagaac acaaatttca ccgacatgac ttttattaca  10500
gagttggaat tagatctaac aattgaaaaa ttaaaattaa gatagaatat gttgaggaac  10560
atgacatagt ataatgctgg gttacccgtc gggtaggtat cgaggcggat actactaaat  10620
ccatcccact cgctatccga taatcactgg tttcgggtat acccattccc gtcaacaggc  10680
ctttttaacc ggataatttc aacttatagt gaatgaattt tgaataaata gttagaatac  10740
caaaatcctg gattgcattt gcaatcaaat tttgtgaacc gttaaatttt gcatgtactt  10800
gggatagata taatagaacc gaattttcat tagtttaatt tataacttac tttgttcaaa  10860
gaaaaaaaat atctatccaa tttacttata ataaaaaata atctatccaa gttacttatt  10920
ataatcaact tgtaaaaagg taagaataca aatgtggtag cgtacgtgtg attatatgtg  10980
acgaaatgtt atatctaaca aaagtccaaa ttcccatggt aaaaaaaatc aaaatgcatg  11040
gcaggctgtt tgtaaccttg gaataagatg ttggccaatt ctggagccgc cacgtacgca  11100
agactcaggg ccacgttctc ttcatgcaag gatagtagaa caccactcca cccacctcct  11160
atattagacc tttgcccaac cctccccaac tttcccatcc catccacaaa gaaaccgaca  11220
tttttatcat aaatctggtg cttaaacact ctggtgagtt ctagtacttc tgctatgatc  11280
gatctcatta ccatttctta aatttctctc cctaaatatt ccgagttctt gatttttgat  11340
aacttcaggt tttctctttt tgataaatct ggtctttcca tttttttttt ttgtggttaa  11400
tttagtttcc tatgttcttc gattgtatta tgcatgatct gtgtttggat tctgttagat  11460
tatgtattgg tgaatatgta tgtgtttttg catgtctggt tttggtctta aaaatgttca  11520
aatctgatga tttgattgaa gctttttttag tgttggtttg attcttctca aaactactgt  11580
taatttacta tcatgttttc caactttgat tcatgatgac acttttgttc tgctttgtta  11640
taaaattttg gttggtttga ttttgtaatt atagtgtaat tttgttagga atgaacatgt  11700
tttaatactc tgttttcgat ttgtcacaca ttcgaattat taatcgataa tttaactgaa  11760
aattcatggt tctagatctt gttgtcatca gattatttgt ttcgataatt catcaaatat  11820
gtagtccttt tgctgatttg cgactgtttc attttttctc aaaattgttt tttgttaagt  11880
ttatctaaca gttatcgttg tcaaaagtct ctttcatttt gcaaaatctt cttttttttt  11940
ttgtttgtaa ctttgttttt taagctacac atttagtctg taaaatagca tcgaggaaca  12000
gttgtcttag tagacttgca tgttcttgta acttctattt gtttcagttt gttgatgact  12060
gctttgattt tgtaggtcaa aggcgcaccc taccatggat gcttataacg ctgctatgga  12120
taagattgga gctgctatca tcgattggag tgatccagat ggaaagttca gagctgatag  12180
ggaggattgg tggttgtgcg atttcagatc cgctatcacc attgctctca tctacatcgc  12240
tttcgtgatc ttgggatctg ctgtgatgca atctctccca gctatggacc catacccta t  12300
caagttcctc tacaacgtgt ctcaaatctt cctctgcgct tacatgactg ttgaggctgg  12360
```

```
attcctcgct tataggaacg gatacaccgt tatgccatgc aaccacttca acgtgaacga  12420
tccaccagtt gctaacttgc tctggctctt ctacatctcc aaagtgtggg atttctggga  12480
taccatcttc attgtgctcg gaaagaagtg gagacaactc tctttcttgc acgtgtacca  12540
ccacaccacc atcttcctct tctactggtt gaacgctaac gtgctctacg atggagatat  12600
cttcttgacc atcctcctca acggattcat tcacaccgtg atgtacacct actacttcat  12660
ctgcatgcac accaaggatt ctaagaccgg aaagtctttg ccaatctggt ggaagtcatc  12720
tttgaccgct ttccaactct tgcaattcac catcatgatg tcccaagcta cctacttggt  12780
tttccacgga tgcgataagg tttccctcag aatcaccatc gtgtacttcg tgtacattct  12840
ctccctttc ttcctcttcg ctcagttctt cgtgcaatcc tacatggctc caaagaagaa  12900
gaagtccgct tgatgttaat gaaggccgca gatatcagat ctggtcgacc tagaggatcc  12960
ccggccgcaa agataataac aaaagcctac tatataacgt acatgcaagt attgtatgat  13020
attaatgttt ttacgtacgt gtaaacaaaa ataattacgt ttgtaacgta tggtgatgat  13080
gtggtgcact aggtgtaggc cttgtattaa taaaaagaag tttgttctat atagagtggt  13140
ttagtacgac gatttattta ctagtcggat tggaatagag aaccgaattc ttcaatcctt  13200
gcttttgatc aagaattgaa accgaatcaa atgtaaaagt tgatatattt gaaaaacgta  13260
ttgagcttat gaaaatgcta atactctcat ctgtatggaa aagtgacttt aaaaccgaac  13320
ttaaaagtga caaaagggga atatcgcatc aaaccgaatg aaaccgatct acgtaggctc  13380
agctgagctt agctaagcct acctagcctc acgtgagatt atgtaaggct aggtagcgtc  13440
acgtgacgtt acctaacact agctagcgtc agctgagctt agctaaccct acgtagcctc  13500
acgtgagctt acctaacgct acgtagcctc acgtgactaa ggatgaccta cccattcttg  13560
agacaaatgt tacattttag tatcagagta aaatgtgtac ctataactca aattcgattg  13620
acatgtatcc attcaacata aaattaaacc agcctgcacc tgcatccaca tttcaagtat  13680
tttcaaaccg ttcggctcct atccaccggg tgtaacaaga cggattccga atttggaaga  13740
ttttgactca aattcccaat ttatattgac cgtgactaaa tcaactttaa cttctataat  13800
tctgattaag ctcccaattt atattcccaa cggcactacc tccaaaattt atagactctc  13860
atccccttt aaaccaactt agtaaacgtt tttttttaa ttttatgaag ttaagttttt  13920
accttgtttt taaaaagaat cgttcataag atgccatgcc agaacattag ctacacgtta  13980
cacatagcat gcagccgcgg agaattgttt ttcttcgcca cttgtcactc ccttcaaaca  14040
cctaagagct tctctctcac agcacacaca tacaatcaca tgcgtgcatg cattattaca  14100
cgtgatcgcc atgcaaatct cctttatagc ctataaatta actcatcggc ttcactcttt  14160
actcaaacca aaactcatca atacaaacaa gattaaaaac atttcacgat ttggaatttg  14220
attcctgcga tcacaggtat gacaggttag attttgtttt gtatagttgt atacatactt  14280
ctttgtgatg ttttgtttac ttaatcgaat ttttggagtg ttttaaggtc tctcgtttag  14340
aaatcgtgga aaatatcact gtgtgtgtgt tcttatgatt cacagtgttt atgggtttca  14400
tgttctttgt tttatcattg aatgggaaga aatttcgttg ggatacaaat ttctcatgtt  14460
cttactgatc gttattagga gtttggggaa aaaggaagag ttttttttggt tggttcgagt  14520
gattatgagg ttatttctgt atttgattta tgagttaatg gtcgttttaa tgttgtagac  14580
cgccatggct attttgaacc ctgaggctga ttctgctgct aacctcgcta ctgattctga  14640
ggctaagcaa agacaattgg ctgaggctgg atacactcac gttgagggtg ctcctgctcc  14700
```

```
tttgcctttg gagttgcctc acttctctct cagagatctc agagctgcta ttcctaagca  14760
ctgcttcgag agatctttcg tgacctccac ctactacatg atcaagaacg tgttgacttg  14820
cgctgctttg ttctacgctg ctaccttcat tgatagagct ggagctgctg cttatgtttt  14880
gtggcctgtg tactggttct tccagggatc ttacttgact ggagtgtggg ttatcgctca  14940
cgagtgtgga caccaggctt attgctcttc tgaggtggtg aacaacttga ttggactcgt  15000
gttgcactct gctttgttgg tgccttacca ctcttggaga atctctcaca gaaagcacca  15060
ctccaacact ggatcttgcg agaacgatga ggttttcgtt cctgtgacca gatctgtgtt  15120
ggcttcttct tggaacgaga ccttggagga ttctcctctc taccaactct accgtatcgt  15180
gtacatgttg gttgttggat ggatgcctgg atacctcttc ttcaacgcta ctggacctac  15240
taagtactgg ggaaagtcta ggtctcactt caacccttac tccgctatct atgctgatag  15300
ggagaggtgg atgatcgtgc tctccgatat tttcttggtg gctatgttgg ctgttttggc  15360
tgctttggtg cacactttct ccttcaacac gatggtgaag ttctacgtgg tgccttactt  15420
cattgtgaac gcttacttgg tgttgattac ctacctccaa cacaccgata cctacatccc  15480
tcacttcaga gagggagagt ggaattggtt gagaggagct ttgtgcactg tggatagatc  15540
atttggtcca ttcctcgatt ctgtggtgca tagaatcgtg gatacccacg tttgccacca  15600
tatcttctcc aagatgcctt tctatcactg cgaggaggct accaacgcta ttaagcctct  15660
cctcggaaag ttctacttga aggatactac tcctgttcct gttgctctct ggagatctta  15720
cacccactgc aagttcgttg aggatgatgg aaaggtggtg ttctacaaga acaagttata  15780
gttaatgaat aattgattgg ttcgagtatt atggcattgg gaaaactgtt tttcttgtac  15840
catttgttgt gcttgtaatt tactgtgttt tttattcggt tttcgctatc gaactgtgaa  15900
atggaaatgg atggagaaga gttaatgaat gatatggtcc ttttgttcat tctcaaatta  15960
atattatttg tttttttctct tatttgttgt gtgttgaatt tgaaattata agagatatgc  16020
aaacattttg ttttgagtaa aaatgtgtca aatcgtggcc tctaatgacc gaagttaata  16080
tgaggagtaa aacacttgta gttgtaccat tatgcttatt cactaggcaa caaatatatt  16140
ttcagaccta gaaaagctgc aaatgttact gaatacaagt atgtcctctt gtgttttaga  16200
catttatgaa ctttccttta tgtaattttc cagaatcctt gtcagattct aatcattgct  16260
ttataattat agttatactc atggatttgt agttgagtat gaaaatattt tttaatgcat  16320
tttatgactt gccaattgat tgacaacatg catcaatcta gctagcctca gctgacgtta  16380
cgtaacgcta ggtagcgtca cgtgacgtta gctaacgcta ggtagcgtca gctgagctta  16440
cgtaagcgca cagatgaata ctagctgttg ttcacagttc tagtgtctcc tcattacgtg  16500
aattcaagct acgatcacta tctcaactcc tacataaaca tcagaatgct acaaaactat  16560
gcacaaaaac aaaagctaca tctaatacgt gaatcaatta ctctcatcac aagaaagaag  16620
atttcaatca ccgtcgagaa ggaggattca gttaattgaa tcaaagttcc gatcaaactc  16680
gaagactggt gagcacgagg acgacgaaga agagtgtctc gaagatacaa caagcaagaa  16740
atctactgag tgacctcctg aagttattgg cgcgattgag agaatcaatc cgaattaatt  16800
tcggggaaaa agataaatta gatactaagc gatgggcttg ggctgggcta agaaacaggt  16860
ggcaattggg ctggaggacc ccgcgattca tagcttccga tagcccaaaa aaaaacggat  16920
aacatattta tcgggtattt gaatttcagt gaaataagat attttctttt tgttaggaaa  16980
attttagaaa ataatggaaa ttaaatagcg attatgttac aagatacgat cagcatcggg  17040
cagtgcaaaa tgctatagct tcccaagatt tgatcctttt gggttatctc ctaatgacaa  17100
```

```
ttagtttagg attttgaaac ttatattaat actattatcc gacaacactt gtttcagctt  17160
cttattttaa catttttgt tttttctat tcttcttccc atcagcattt tctttttaaa  17220
aaattgaata ctttaacttt ttaaaaattt cacaatgatc agatgatatt atggaagatc  17280
tcaagagtta aatgtatcca tcttggggca ttaaaaccgg tgtacgggat gataaataca  17340
gactttatat catatgatag ctcagtaatt catatttatc acgttgctaa aaaaattata  17400
aggtactagt agtcaacaaa atcaattaaa gagaaagaaa gaaacgcatg tgaagagagt  17460
ttacaactgg aaaagtaaaa taaaaattaa cgcatgttga atgctgacat gtcagtatgt  17520
ccatgaatcc acgtatcaag cgccattcat cgatcgtctt cctctttcta aatgaaaaca  17580
acttcacaca tcacaacaaa caatacacac aagacccct ctctctcgtt gtctctctgc  17640
cagcgaccaa atcgaagctt gagaagaaca agaaggggtc aaaccatggc ttctacatct  17700
gctgctcaag acgctgctcc ttacgagttc ccttctctca ctgagatcaa gagggctctt  17760
ccttctgagt gtttcgaggc ttctgttcct ctttctctct actacaccgc tagatctctt  17820
gctcttgctg gatctctcgc tgttgctctc tcttacgcta gagctttgcc tcttgttcag  17880
gctaacgctc ttcttgatgc tactctctgc actggatacg ttcttctcca gggaatcgtt  17940
ttctggggat tcttcaccgt tggtcacgat tgtggacacg gagctttctc tagatctcac  18000
gtgctcaact tctctgttgg aaccctcatg cactctatca tccttacccc tttcgagtct  18060
tggaagctct ctcacagaca ccaccacaag aacaccggaa acatcgataa ggacgagatc  18120
ttctaccctc aaagagaggc tgattctcac cctgtttcta gacaccttgt gatgtctctt  18180
ggatctgctt ggttcgctta ccttttcgct ggattccctc ctagaaccat gaaccacttc  18240
aacccttggg aggctatgta tgttagaaga gtggctgctg tgatcatctc tctcggagtt  18300
cttttcgctt tcgctggact ctactcttac ctcaccttcg ttcttggatt caccactatg  18360
gctatctact acttcggacc tctcttcatc ttcgctacca tgcttgttgt taccactttc  18420
ctccaccaca acgatgagga gacaccttgg tacgctgatt ctgagtggac ttacgtgaag  18480
ggaaacctct cttctgtgga cagatcttac ggtgctctca tcgacaacct tagccacaac  18540
atcggaactc accagatcca ccacctcttc cctatcatcc ctcactacaa gctcaacgat  18600
gctactgctg ctttcgctaa ggctttccct gagcttgtta ggaaaaacgc tgctcctatc  18660
atcccaactt tcttcaggat ggctgctatg tacgctaagt acggagttgt tgacactgat  18720
gctaagacct tcactctcaa ggaggctaag gctgctgcta agactaagtc atcttgatga  18780
ttaatgaata attgattgta catactatat tttttgttta ccttgtgtta gtttaatgtt  18840
cagtgtcctc tctttattgt ggcacgtctc tttgttgtat gttgtgtcta tacaaagttg  18900
aaataatgga aagaaaagga agagtgtaat ttgttttgtt ttaagtgttt ataaatatat  18960
atatataggt catttagata gttctaggtt tctataaaac tctctctctg gaagtagaat  19020
ctgtttttga gaggatccag ttgcctacta atctccccca aaacccttca agcttaacct  19080
tcctcttcac aacaacagag gaaacacatc tcttgagctc tgagttctct tctttgagca  19140
tgtctatcgc taaactcatc tgccttatag cttccctctt ctcttcatct ctctctctca  19200
ccatttcgct gtaaaactta ttctcctccc tcagcctctc tatctcttcc ttcagcatct  19260
cacaattccc accataatcg actgaggatg attcaccgtc atcaacttca gactcagcgt  19320
tgtagtcgtc atgagtctca caagccttgg accaagaaga ctcatcatcg caagttgatg  19380
atttatcatg atgcttctct gagccgtgtt tgctacgtag cgtcacgtga cgttacctaa  19440
```

```
gcctaggtag cctcagctga cgttacgtaa cgctaggtag gctcagctga ctgcagcaaa  19500
tttacacatt gccactaaac gtctaaaccc ttgtaatttg tttttgtttt actatgtgtg  19560
ttatgtattt gatttgcgat aaatttttat atttggtact aaatttataa cacctttttat  19620
gctaacgttt gccaacactt agcaatttgc aagttgatta attgattcta aattattttt  19680
gtcttctaaa tacatatact aatcaactgg aaatgtaaat atttgctaat atttctacta  19740
taggagaatt aaagtgagtg aatatggtac cacaaggttt ggagatttaa ttgttgcaat  19800
gctgcatgga tggcatatac accaaacatt caataattct tgaggataat aatggtacca  19860
cacaagattt gaggtgcatg aacgtcacgt ggacaaaagg tttagtaatt tttcaagaca  19920
acaatgttac cacacacaag ttttgaggtg catgcatgga tgccctgtgg aaagtttaaa  19980
aatattttgg aaatgatttg catggaagcc atgtgtaaaa ccatgacatc cacttggagg  20040
atgcaataat gaagaaaact acaaatttac atgcaactag ttatgcatgt agtctatata  20100
atgaggattt tgcaatactt tcattcatac acactcacta agttttacac gattataatt  20160
tcttcatagc cagtactgtt taagcttcac tgtctctgaa tcggcaaagg taaacgtatc  20220
aattattcta caaacccttt tatttttctt ttgaattacc gtcttcattg gttatatgat  20280
aacttgataa gtaaagcttc aataattgaa tttgatctgt gtttttttgg ccttaatact  20340
aaatccttac ataagctttg ttgcttctcc tcttgtgagt tgagtgttaa gttgtaataa  20400
tggttcactt tcagctttag aagaaacgcg ccttccatgg ctacaaagga ggcttacgtt  20460
ttcccaactc tcaccgagat caagagatct ctcccaaagg attgcttcga ggcttctgtg  20520
cctttgtctc tctactacac tgtgagatgc ttggttattg ctgtggcttt gaccttcgga  20580
ttgaactacg ctagagcttt gccagaggtt gagtctttct gggctttgga tgctgctttg  20640
tgcactggat atatcctcct ccagggaatt gtgttctggg gattcttcac tgttggacac  20700
gatgctggac acggagcttt ctctagatac cacctcttga acttcgttgt gggaaccttc  20760
atgcactctc tcatcttgac cccattcgag tcttggaagt tgacccacag acaccaccac  20820
aagaacaccg gaaacatcga tagagatgag gtgttctacc cacagagaaa ggctgatgat  20880
cacccattgt ccaggaactt gatcttggct ttgggagctg cttggcttgc ttatttggtg  20940
gagggattcc caccaagaaa ggtgaaccac ttcaacccat tcgagccact tttgtgaga  21000
caagtgtccg ctgtggttat ctctttgctc gctcacttct tcgttgctgg actctctatc  21060
tacttgtctc tccagttggg acttaagacc atggctatct actactacgg accagttttc  21120
gtgttcggat ctatgttggt gattaccacc ttcttgcacc acaacgatga ggagactcca  21180
tggtatgctg attctgagtg gacttacgtg aagggaaact tgtcctctgt ggatagatct  21240
tacggtgctc tcatcgataa cctctcccac aacatcggaa ctcaccagat ccaccacctc  21300
ttcccaatta tcccacacta caagctcaag aaggctactg ctgctttcca ccaagctttc  21360
ccagagcttg tgagaaagtc cgatgagcca atcatcaagg ctttcttcag agtgggaagg  21420
ttgtatgcta actacggagt ggttgatcaa gaggctaagc tcttcacttt gaaggaggct  21480
aaggctgcta ctgaagctgc tgctaagacc aagtctacct gattaatgaa tcgacaagct  21540
cgagtttctc cataataatg tgtgagtagt tcccagataa gggaattagg gttcctatag  21600
ggtttcgctc atgtgttgag catataagaa acccttagta tgtatttgta tttgtaaaat  21660
acttctatca ataaaatttc taattcctaa aaccaaaatc cagtactaaa atccagatcc  21720
cccgaattaa ttcggcgtta attcagctac gtaggctcag ctgagcttac ctaaggctac  21780
gtaggctcac gtgacgttac gtaaggctac gtagcgtcac gtgagcttac ctaactctag  21840
```

```
ctagcctcac gtgaccttag ctaacactag gtagcgtcag cacagatgaa tactagctgt  21900
tgttcacagt tctagtgtct cctcattacg tgaattcaag ctacgatcac tatctcaact  21960
cctacataaa catcagaatg ctacaaaact atgcacaaaa acaaaagcta catctaatac  22020
gtgaatcaat tactctcatc acaagaaaga agatttcaat caccgtcgag aaggaggatt  22080
cagttaattg aatcaaagtt ccgatcaaac tcgaagactg gtgagcacga ggacgacgaa  22140
gaagagtgtc tcgaagatac aacaagcaag aaatctactg agtgacctcc tgaagttatt  22200
ggcgcgattg agagaatcaa tccgaattaa tttcggggaa aaagataaat tagatactaa  22260
gcgatgggct tgggctgggc taagaaacag gtggcaattg ggctggagga ccccgcgatt  22320
catagcttcc gatagcccaa aaaaaaacgg ataacatatt tatcgggtat ttgaatttca  22380
gtgaaataag atattttctt tttgttagga aaattttaga aaataatgga aattaaatag  22440
cgattatgtt acaagatacg atcagcatcg ggcagtgcaa aatgctatag cttcccaaga  22500
tttgatcctt ttgggttatc tcctaatgac aattagttta ggattttgaa acttatatta  22560
atactattat ccgacaacac ttgtttcagc ttcttatttt aacatttttt gttttttttct  22620
attcttcttc ccatcagcat tttcttttta aaaaattgaa tactttaact ttttaaaaat  22680
ttcacaatga tcagatgata ttatggaaga tctcaagagt taaatgtatc catcttgggg  22740
cattaaaacc ggtgtacggg atgataaata cagactttat atcatatgat agctcagtaa  22800
ttcatattta tcacgttgct aaaaaaaatta taaggtacta gtagtcaaca aaatcaatta  22860
aagagaaaga aagaaacgca tgtgaagaga gtttacaact ggaaaagtaa aataaaaatt  22920
aacgcatgtt gaatgctgac atgtcagtat gtccatgaat ccacgtatca agcgccattc  22980
atcgatcgtc ttcctctttc taaatgaaaa caacttcaca catcacaaca aacaatacac  23040
acaagacccc ctctctctcg ttgtctctct gccagcgacc aaatcgaagc ttgagaagaa  23100
caagaagggg tcaaaccatg ggaaaaggat ctgagggaag atctgctgct agagagatga  23160
ctgctgaggc taacggagat aagagaaaga ccatcctcat tgagggagtg ttgtacgatg  23220
ctaccaactt caaacaccca ggaggttcca ttattaactt cctcaccgag ggagaagctg  23280
gagttgatgc tacccaagct tacagagagt tccatcagag atccggaaag gctgataagt  23340
acctcaagtc cctcccaaag ttggatgctt ctaaggtgga gtctaggttc tctgctaagg  23400
agcaggctag aagggacgct atgaccaggg attacgctgc tttcagagag gagttggttg  23460
ctgagggata cttcgatcca tctatcccac acatgatcta cagagtggtg gagattgtgg  23520
ctttgttcgc tttgtctttc tggttgatgt ctaaggcttc tccaacctct ttggttttgg  23580
gagtggtgat gaacggaatc gctcaaggaa gatgcggatg ggttatgcac gagatgggac  23640
acggatcttt cactggagtt atctggctcg atgataggat gtgcgagttc ttctacggag  23700
ttggatgtgg aatgtctgga cactactgga agaaccagca ctctaagcac cacgctgctc  23760
caaacagatt ggagcacgat gtggatttga acaccttgcc actcgttgct ttcaacgaga  23820
gagttgtgag gaaggttaag ccaggatctt tgttggcttt gtggctcaga gttcaggctt  23880
atttgttcgc tccagtgtct tgcttgttga tcggattggg atggaccttg tacttgcacc  23940
caagatatat gctcaggacc aagagacaca tggagtttgt gtggatcttc gctagatata  24000
tcggatggtt ctccttgatg ggagctttgg gatattctcc tggaacttct gtgggaatgt  24060
acctctgctc tttcggactt ggatgcatct acatcttcct ccaattcgct gtgtctcaca  24120
cccacttgcc agttaccaac ccagaggatc aattgcactg gcttgagtac gctgctgatc  24180
```

-continued

```
acaccgtgaa catctctacc aagtcttggt tggttacctg gtggatgtct aacctcaact  24240
tccaaatcga gcaccacttg ttcccaaccg ctccacaatt caggttcaag gagatctctc  24300
caagagttga ggctctcttc aagagacaca acctccctta ctacgatttg ccatacacct  24360
ctgctgtttc tactaccttc gctaacctct actctgttgg acactctgtt ggagctgata  24420
ccaagaagca ggattgatga ttaatgaata attgattgta catactatat tttttgttta  24480
ccttgtgtta gtttaatgtt cagtgtcctc tctttattgt ggcacgtctc tttgttgtat  24540
gttgtgtcta tacaaagttg aaataatgga aagaaaagga agagtgtaat ttgttttgtt  24600
ttaagtgttt ataaatatat atatataggt catttagata gttctaggtt tctataaaac  24660
tctctctctg gaagtagaat ctgtttttga gaggatccag ttgcctacta atctccccca  24720
aaacccttca agcttaacct tcctcttcac aacaacagag gaaacacatc tcttgagctc  24780
tgagttctct tctttgagca tgtctatcgc taaactcatc tgccttatag cttccctctt  24840
ctcttcatct ctctctctca ccatttcgct gtaaaactta ttctcctccc tcagcctctc  24900
tatctcttcc ttcagcatct cacaattccc accataatcg actgaggatg attcaccgtc  24960
atcaacttca gactcagcgt tgtagtcgtc atgagtctca caagccttgg accaagaaga  25020
ctcatcatcg caagttgatg atttatcatg atgcttctct gagccgtgtt tgctacctag  25080
agtcagctga gcttagctaa cgctagctag tgtcagctga cgttacgtaa ggctaactag  25140
cgtcacgtga ccttacgtaa cgctacgtag gctcagctga gcttagctaa ccctagctag  25200
tgtcacgtga gcttacgcta ctatagaaaa tgtgttatat cgacatgacc agacaaaggg  25260
gcaacagtta acaaaacaat taattctttc atttgagatt aaggaaggta aggtactaaa  25320
aagattaaaa aaaatgagct tatctctttg tttctgtaat aataatataa gtgtgataaa  25380
cttttaatat aataattgta attaggtttt ctacagatga gcaccactca gagacaagat  25440
aagaagaaaa caattttgtt aaacatgatt atagaaactt ttagttaagt cttgaagtat  25500
caatataaca aaaaaaagta cacacgacta tgacaataaa cccactaccg tcaggttatc  25560
atttcgatga aatgttttga tatcattaaa tataacagtc acaaaaaatc atctaattat  25620
aacaatataa cttatacata tatttaacta aaaacttaga gtttttgtaa tgattctaat  25680
tgatgattag agtttataga aatacaatta aataaaaaat ataattttaa aaaaacatag  25740
taaagtcaat gagatcctct ctgacctcag tgatcattta gtcatgtatg tacaacaatc  25800
attgttcatc acatgactgt aaaataaata aggataaact tgggaatata tataatatat  25860
tgtattaaat aaaaaaggga aatacaaata tcaattttag attcccgagt tgacacaact  25920
caccatgcac gctgccacct cagctcccag ctctcgtcac atgtctcatg tcagttaggt  25980
ctttggtttt tagtctttga cacaactcgc catgcatgtt gccacgtgag ctcgttcctc  26040
ttcccatgat ctcaccactg ggcatgcatg ctgccacctc agctggcacc tcttctctat  26100
atgtccctag aggccatgca cagtgccacc tcagcactcc tctcagaacc catacgtacc  26160
tgccaatcgg cttctctcca taaatatcta tttaaattat aactaattat ttcatatact  26220
taattgatga cgtggatgca ttgccatcgt tgtttaataa ttgttaatta cgacatgata  26280
aataaaatga aagtaaaaag tacgaaagat tttccatttg ttgttgtata aatagagaag  26340
tgagtgatgc ataatgcatg aatgcatgac cgcgccacca tgactgttgg atacgacgag  26400
gagatcccat tcgagcaagt tagggctcat aacaagccag acgacgcttg gtgtgctatt  26460
cacggacacg tgtacgacgt taccaagttc gcttcagttc acccaggagg agatattatc  26520
ttgctcgctg ctggaaagga agctactgtc ctctacgaga cctaccatgt tagaggagtg  26580
```

```
tctgacgctg tgctcagaaa gtacagaata ggaaagttgc cagacggaca aggaggagct  26640
aacgagaagg agaagagaac cttgtctgga ttgtcctctg cttcttacta cacctggaac  26700
tccgatttct acagagtgat gagggagaga gttgtggcta gattgaagga gagaggaaag  26760
gctagaagag gaggatacga actctggatc aaggctttct tgctccttgt tggattctgg  26820
tcctctcttt actggatgtg caccctcgat ccatctttcg gagctatctt ggctgctatg  26880
tctttgggag tgttcgctgc ttttgttgga acctgcatcc aacacgatgg aaaccacgga  26940
gctttcgctc aatctagatg ggttaacaag gtggcaggat ggactttgga tatgatcgga  27000
gcttctggaa tgacttggga gttccaacac gtgttgggac accacccata cactaacttg  27060
atcgaggagg agaacggatt gcaaaaggtg tccggaaaga agatggatac caagttggct  27120
gatcaagagt ctgatccaga tgtgttctcc acctacccaa tgatgagatt gcacccttgg  27180
caccagaaga ggtggtatca caggttccag cacatctacg gacctttcat cttcggattc  27240
atgaccatca acaaggtggt gactcaagat gttggagtgg tgttgagaaa gagactcttc  27300
caaatcgatg ctgagtgcag atatgcttcc ccaatgtacg ttgctaggtt ctggattatg  27360
aaggctttga ccgtgttgta tatggttgct ttgccttgtt atatgcaagg accttggcac  27420
ggattgaaac tcttcgctat cgctcacttc acttgcggag aggttttggc taccatgttc  27480
atcgtgaacc acattatcga gggagtgtct tacgcttcta aggatgctgt taagggaact  27540
atggctccac caaagactat gcacggagtg accccaatga acaacactag aaaggaggtt  27600
gaggctgagg cttctaagtc tggagctgtg gttaagtctg tgccattgga tgattgggct  27660
gctgttcagt gccaaacctc tgtgaactgg tctgttggat cttggttttg gaaccacttc  27720
tctggaggac tcaaccacca aatcgagcac cacctcttcc caggattgtc tcacgagacc  27780
tactaccaca tccaagacgt ggttcaatct acctgtgctg agtacggagt tccataccaa  27840
cacgagccat ctttgtggac tgcttactgg aagatgctcg aacaccttag acaattggga  27900
aacgaggaga ctcacgagtc atggcagaga gctgcttgat taatgaacta agactcccaa  27960
aaccaccttc cctgtgacag ttaaaccctg cttatacctt tcctcctaat aatgttcatc  28020
tgtcacacaa actaaaataa ataaaatggg agcaataaat aaaatgggag ctcatatatt  28080
tacaccattt acactgtcta ttattcacca tgccaattat tacttcataa ttttaaaatt  28140
atgtcatttt taaaaattgc ttaatgatgg aaaggattat tataagttaa aagtataaca  28200
tagataaact aaccacaaaa caaatcaata taaactaact tactctccca tctaattttt  28260
atttaaattt ctttacactt ctcttccatt tctatttcta caacattatt taacattttt  28320
attgtatttt tcttactttc taactctatt catttcaaaa atcaatatat gtttatcacc  28380
acctctctaa aaaaaacttt acaatcattg gtccagaaaa gttaaatcac gagatggtca  28440
ttttagcatt aaaacaacga ttcttgtatc actatttttc agcatgtagt ccattctctt  28500
caaacaaaga cagcggctat ataatcgttg tgttatattc agtctaaaac aactagctag  28560
cctcagctga cgttacgtaa cgctaggtag cgtcacgtga cgttagctaa cgctaggtag  28620
cgtcagctga gcttacgtaa gcgccacggg caggacatag ggactactac aagcatagta  28680
tgcttcagac aaagagctag gaaagaactc ttgatggagg ttaagagaaa aaagtgctag  28740
aggggcatag taatcaaact tgtcaaaacc gtcatcatga tgagggatga cataatataa  28800
aaagttgact aaggtcttgg tagtactctt tgattagtat tatatattgg tgagaacatg  28860
agtcaagagg agacaagaaa ccgaggaacc atagtttagc aacaagatgg aagttgcaaa  28920
```

```
gttgagctag ccgctcgatt agttacatct cctaagcagt actacaagga atggtctcta  28980
tactttcatg tttagcacat ggtagtgcgg attgacaagt tagaaacagt gcttaggaga  29040
caaagagtca gtaaaggtat tgaaagagtg aagttgatgc tcgacaggtc aggagaagtc  29100
cctccgccag atggtgacta ccaaggggtt ggtatcagct gagacccaaa taagattctt  29160
cggttgaacc agtggttcga ccgagactct tagggtggga tttcactgta agatttgtgc  29220
attttgttga atataaattg acaatttttt ttatttaatt atagattatt tagaatgaat  29280
tacatattta gtttctaaca aggatagcaa tggatgggta tgggtacagg ttaaacatat  29340
ctattaccca cccatctagt cgtcgggttt tacacgtacc cacccgttta cataaaccag  29400
accggaattt taaaccgtac ccgtccgtta gcgggtttca gatttacccg tttaatcggg  29460
taaaacctga ttactaaata tatatttttt atttgataaa caaaacaaaa atgttaatat  29520
tttcatattg gatgcaattt taagaaacac atattcataa atttccatat ttgtaggaaa  29580
ataaaaagaa aaatatattc aagaacacaa atttcaccga catgactttt attacagagt  29640
tggaattaga tctaacaatt gaaaaattaa aattaagata gaatatgttg aggaacatga  29700
catagtataa tgctgggtta cccgtcgggt aggtatcgag gcggatacta ctaaatccat  29760
cccactcgct atccgataat cactggtttc gggtataccc attcccgtca acaggccttt  29820
ttaaccggat aatttcaact tatagtgaat gaattttgaa taaatagtta gaataccaaa  29880
atcctggatt gcatttgcaa tcaaattttg tgaaccgtta aattttgcat gtacttggga  29940
tagatataat agaaccgaat tttcattagt ttaatttata acttactttg ttcaaagaaa  30000
aaaaatatct atccaattta cttataataa aaaataatct atccaagtta cttattataa  30060
tcaacttgta aaaaggtaag aatacaaatg tggtagcgta cgtgtgatta tatgtgacga  30120
aatgttatat ctaacaaaag tccaaattcc catggtaaaa aaaatcaaaa tgcatggcag  30180
gctgtttgta accttggaat aagatgttgg ccaattctgg agccgccacg tacgcaagac  30240
tcagggccac gttctcttca tgcaaggata gtagaacacc actccaccca cctcctatat  30300
tagacctttg cccaaccctc cccaactttc ccatcccatc cacaaagaaa ccgacatttt  30360
tatcataaat cagggtttcg tttttgtttc atcgataaac tcaaaggtga tgattttagg  30420
gtcttgtgag tgtgcttttt tgtttgattc tactgtaggg tttatgttct ttagctcata  30480
ggttttgtgt atttcttaga aatgtggctt ctttaatctc tgggtttgtg actttttgtg  30540
tggtttctgt gtttttcata tcaaaaacct atttttttccg agttttttttt tacaaattct  30600
tactctcaag cttgaatact tcacatgcag tgttcttttg tagattttag agttaatgtg  30660
ttaaaaagtt tggatttttc ttgcttatag agcttcttca ctttgatttt gtgggttttt  30720
ttgttttaaa ggtgagattt ttgatgaggt ttttgcttca aagatgtcac ctttctgggt  30780
ttgtcttttg aataaagcta tgaactgtca catggctgac gcaattttgt tactatgtca  30840
tgaaagctga cgtttttccg tgttatacat gtttgcttac acttgcatgc gtcaaaaaaa  30900
ttggggcttt ttagttttag tcaaagattt tacttctctt ttgggattta tgaaggaaag  30960
ttgcaaactt tctcaaattt taccattttt gctttgatgt ttgtttagat tgcgacagaa  31020
caaactcata tatgttgaaa tttttgcttg gttttgtata ggattgtgtc ttttgcttat  31080
aaatgttgaa atctgaactt ttttttgtt tggtttcttt gagcaggaga taaggcgcac  31140
caccatggct tctacatctg ctgctcaaga cgctgctcct tacgagttcc cttctctcac  31200
tgagatcaag agggctcttc cttctgagtg tttcgaggct tctgttcctc tttctctcta  31260
ctacaccgct agatctcttg ctcttgctgg atctctcgct gttgctctct cttacgctag  31320
```

```
agctttgcct cttgttcagg ctaacgctct tcttgatgct actctctgca ctggatacgt  31380
tcttctccag ggaatcgttt tctggggatt cttcaccgtt ggtcacgatt gtggacacgg  31440
agctttctct agatctcacg tgctcaactt ctctgttgga accctcatgc actctatcat  31500
ccttacccct ttcgagtctt ggaagctctc tcacagacac caccacaaga acaccggaaa  31560
catcgataag gacgagatct tctaccctca aagagaggct gattctcacc ctgtttctag  31620
acaccttgtg atgtctcttg gatctgcttg gttcgcttac cttttcgctg gattccctcc  31680
tagaaccatg aaccacttca acccttggga ggctatgtat gttagaagag tggctgctgt  31740
gatcatctct ctcggagttc ttttcgcttt cgctggactc tactcttacc tcaccttcgt  31800
tcttggattc accactatgg ctatctacta cttcggacct ctcttcatct tcgctaccat  31860
gcttgttgtt accactttcc tccaccacaa cgatgaggag acaccttggt acgctgattc  31920
tgagtggact tacgtgaagg gaaacctctc ttctgtggac agatcttacg gtgctctcat  31980
cgacaacctt agccacaaca tcggaactca ccagatccac cacctcttcc ctatcatccc  32040
tcactacaag ctcaacgatg ctactgctgc tttcgctaag gctttccctg agcttgttag  32100
gaaaaacgct gctcctatca tcccaacttt cttcaggatg gctgctatgt acgctaagta  32160
cggagttgtt gacactgatg ctaagacctt cactctcaag gaggctaagg ctgctgctaa  32220
gactaagtca tcttgatgat taatgaaggc cgcagatatc agatctggtc gacctagagg  32280
atccccggcc gcaaagataa taacaaaagc ctactatata acgtacatgc aagtattgta  32340
tgatattaat gtttttacgt acgtgtaaac aaaaataatt acgtttgtaa cgtatggtga  32400
tgatgtggtg cactaggtgt aggccttgta ttaataaaaa gaagtttgtt ctatatagag  32460
tggtttagta cgacgattta tttactagtc ggattggaat agagaaccga attcttcaat  32520
ccttgctttt gatcaagaat tgaaaccgaa tcaaatgtaa aagttgatat atttgaaaaa  32580
cgtattgagc ttatgaaaat gctaatactc tcatctgtat ggaaaagtga ctttaaaacc  32640
gaacttaaaa gtgacaaaag gggaatatcg catcaaaccg aatgaaaccg atctacgtag  32700
gctcagctga gcttacctaa ggctacgtag gctcacgtga cgttacgtaa ggctacgtag  32760
cgtcacgtga gcttacctaa ctctagctag cctcacgtga ccttagctaa cactaggtag  32820
cgtcagctta gcagatattt ggtgtctaaa tgtttatttt gtgatatgtt catgtttgaa  32880
atggtggttt cgaaaccagg gacaacgttg ggatctgata gggtgtcaaa gagtattatg  32940
gattgggaca atttcggtca tgagttgcaa attcaagtat atcgttcgat tatgaaaatt  33000
ttcgaagaat atcccatttg agagagtctt tacctcatta atgtttttag attatgaaat  33060
tttatcatag ttcatcgtag tctttttggt gtaaaggctg taaaaagaaa ttgttcactt  33120
ttgttttcgt ttatgtgaag gctgtaaaag attgtaaaag actattttgg tgttttggat  33180
aaaatgatag tttttataga ttcttttgct tttagaagaa atacatttga aatttttttcc  33240
atgttgagta taaaataccg aaatcgattg aagatcatag aaatatttta actgaaaaca  33300
aatttataac tgattcaatt ctctccattt ttatacctat ttaaccgtaa tcgattctaa  33360
tagatgatcg attttttata taatcctaat taaccaacgg catgtattgg ataattaacc  33420
gatcaactct cacccctaat agaatcagta ttttccttcg acgttaattg atcctacact  33480
atgtaggtca tatccatcgt tttaattttt ggccaccatt caattctgtc ttgcctttag  33540
ggatgtgaat atgaacggcc aaggtaagag aataaaaata atccaaatta aagcaagaga  33600
ggccaagtaa gataatccaa atgtacactt gtcattgcca aaattagtaa aatactcggc  33660
```

```
atattgtatt cccacacatt attaaaatac cgtatatgta ttggctgcat ttgcatgaat  33720
aatactacgt gtaagcccaa aagaacccac gtgtagccca tgcaaagtta acactcacga  33780
ccccattcct cagtctccac tatataaacc caccatcccc aatctcacca aacccaccac  33840
acaactcaca actcactctc acaccttaaa gaaccaatca ccaccaaaaa aagttctttg  33900
ctttcgaagt tgccgcaacc taaacaggtt tttccttctt ctttcttctt attaactacg  33960
accttgtcct ttgcctatgt aaaattacta ggttttcatc agttacactg attaagttcg  34020
ttatagtgga agataaaatg ccctcaaagc attttgcagg atatctttga tttttcaaag  34080
atatggaact gtagagtttg atagtgttct tgaatgtggt tgcatgaagt ttttttggtc  34140
tgcatgttat tttttcctcg aaatatgttt tgagtccaac aagtgattca cttgggattc  34200
agaaagttgt tttctcaata tgtaacagtt tttttctatg gagaaaaatc atagggaccg  34260
ttggttttgg cttctttaat tttgagctca gattaaaccc attttacccg gtgttcttgg  34320
cagaattgaa aacagtacgt agtaccgcgc ctaccatgcc acctagtgct gctagtgaag  34380
gtggtgttgc tgaacttaga gctgctgaag ttgctagcta cactagaaag gctgttgacg  34440
aaagacctga cctcactata gttggtgacg ctgtttacga cgctaaggct tttagggacg  34500
agcaccctgg tggtgctcac ttcgttagcc ttttcggagg tagggacgct actgaggctt  34560
ttatggaata tcaccgtaga gcttggccta aggctaggat gtctaagttc ttcgttggtt  34620
cacttgacgc tagcgagaag cctactcaag ctgattcatc ttaccttaga ctttgcgctg  34680
aggttaacgc tcttttgcct aagggtagcg gaggattcgc tcctcctagc tactggctta  34740
aggctgctgc tcttgttgtt gctgctgtta gtatagaggg ttatatgctc cttaggggta  34800
agaccctttt gcttagcgtt ttccttggac tcgtgttcgc ttggatagga cttaatattc  34860
agcacgacgc taatcacggt gctcttagta gacactcagt gattaactac tgcctcggtt  34920
acgctcagga ttggataggt ggtaatatgg tgctttggct tcaagagcac gttgtgatgc  34980
accacctcca cactaacgac gttgacgctg atcctgatca aaaggctcac ggtgttctta  35040
gacttaagcc tactgacggt tggatgcctt ggcacgcact tcaacaactc tatatccttc  35100
ctggtgaggc tatgtacgct tttaagcttc ttttcttgga cgcccttgag cttcttgctt  35160
ggaggtggga gggtgagaag attagccctc ttgctagagc tttgttcgct cctgctgttg  35220
cttgtaagct tggattctgg gctagattcg ttgctctccc tctctggctt caacctactg  35280
ttcacactgc tttgtgtatc tgtgctactg tgtgtactgg tagcttctac ctcgccttct  35340
tcttctttat ctctcacaac ttcgacggtg ttggtagcgt tggacctaag ggatcacttc  35400
ctagatcagc tactttcgtt caacgtcagg ttgagactag ctctaacgtt ggtggttact  35460
ggcttggagt tcttaacggt ggacttaact ttcagataga gcaccacttg ttccctaggc  35520
ttcaccactc ttactacgct caaatagctc ctgtggttag gactcacata gagaagctcg  35580
gttttaagta ccgtcacttc cctaccgttg gatctaacct tagctcaatg cttcagcata  35640
tgggtaagat gggaactaga cctggtgctg agaagggtgg taaggctgag tagtgattaa  35700
tgaataattg attgctgctt taatgagata tgcgagacgc ctatgatcgc atgatatttg  35760
ctttcaattc tgttgtgcac gttgtaaaaa acctgagcat gtgtagctca gatccttacc  35820
gccggtttcg gttcattcta atgaatatat cacccgttac tatcgtattt ttatgaataa  35880
tattctccgt tcaatttact gattgtctac gtagcgtcac ctgacgttac gtaaggctac  35940
ctaggctcac gtgacgttac gtaacgctac gtagcgtcag gtgaggttag ctaacgctag  36000
ctagcctcac ctgacgttag gtaaggctac gtagcgtcac ctgagattag ctaagcctac  36060
```

```
ctagactcac gtgaccttag gtaacgctac gtagcgtcaa agctttacaa cgctacacaa  36120
aacttataac cgtaatcacc attcattaac ttaactacta tcacatgcat tcatgaattg  36180
aaacgagaag gatgtaaata gttgggaagt tatctccacg ttgaagagat cgttagcgag  36240
agctgaaaga ccgagggagg agacgccgtc aacacggaca gagtcgtcga ccctcacatg  36300
aagtaggagg aatctccgtg aggagccaga gagacgtctt tggtcttcgg tttcgatcct  36360
tgatctgacg gagaagacga gagaagtgcg actggactcc gtgaggacca acagagtcgt  36420
cctcggtttc gatcgtcggt attggtggag aaggcggagg aatctccgtg acgagccaga  36480
gagatgtcgt cggtcttcgg tttcgatcct tgatctgacg gagaagacga gagaagtgcg  36540
acgagactcc gtgaggacca acagagttgt cctcggtttc gatcgtcggt ttcggcggag  36600
aaggcggagg aatctccgtg aggagccaga gagacgtcgt tggtcttcgg tttcgatcct  36660
tgatctgttg gagaagacga gacaagtggg acgagactca acgacggagt cagagacgtc  36720
gtcggtcttc ggtttcggcc gagaaggcgg agtcggtctt cggtttcggc cgagaaggcg  36780
gaggagacgt cttcgatttg ggtctctcct cttgacgaag aaaacaaaga acacgagaaa  36840
taatgagaaa gagaacaaaa gaaaaaaaaa taaaaataaa aataaaattt ggtcctctta  36900
tgtggtgaca cgtggtttga aacccaccaa ataatcgatc acaaaaaacc taagttaagg  36960
atcggtaata acctttctaa ttaattttga tttatattaa atcactcttt ttatttataa  37020
accccactaa attatgcgat attgattgtc taagtacaaa aattctctcg aattcaatac  37080
acatgtttca tatatttagc cctgttcatt taatattact agcgcatttt taatttaaaa  37140
ttttgtaaac ttttttggtc aaagaacatt tttttaatta gagacagaaa tctagactct  37200
ttatttggaa taatagtaat aaagatatat taggcaatga gtttatgatg ttatgtttat  37260
atagtttatt tcattttaaa ttgaaaagca ttatttttat cgaaatgaat ctagtataca  37320
atcaatattt atgtttttc atcagatact ttcctatttt ttggcacctt tcatcggact  37380
actgatttat ttcaatgtgt atgcatgcat gagcatgagt atacacatgt cttttaaaat  37440
gcatgtaaag cgtaacggac cacaaaagag gatccataca aatacatctc atcgcttcct  37500
ctactattct ccgacacaca cactgagcat ggtgcttaaa cactctggtg agttctagta  37560
cttctgctat gatcgatctc attaccattt cttaaatttc tctccctaaa tattccgagt  37620
tcttgatttt tgataacttc aggttttctc tttttgataa atctggtctt tccatttttt  37680
tttttttgtg gttaatttag tttcctatgt tcttcgattg tattatgcat gatctgtgtt  37740
tggattctgt tagattatgt attggtgaat atgtatgtgt ttttgcatgt ctggttttgg  37800
tcttaaaaat gttcaaatct gatgatttga ttgaagcttt tttagtgttg gtttgattct  37860
tctcaaaact actgttaatt tactatcatg ttttccaact ttgattcatg atgacacttt  37920
tgttctgctt tgttataaaa ttttggttgg tttgattttg taattatagt gtaattttgt  37980
taggaatgaa catgttttaa tactctgttt tcgatttgtc acacattcga attattaatc  38040
gataatttaa ctgaaaattc atggttctag atcttgttgt catcagatta tttgtttcga  38100
taattcatca aatatgtagt ccttttgctg atttgcgact gtttcatttt ttctcaaaat  38160
tgttttttgt taagtttatc taacagttat cgttgtcaaa agtctctttc attttgcaaa  38220
atcttctttt tttttttgtt tgtaactttg ttttttaagc tacacattta gtctgtaaaa  38280
tagcatcgag gaacagttgt cttagtagac ttgcatgttc ttgtaacttc tatttgtttc  38340
agtttgttga tgactgcttt gattttgtag gtcaaaccgc gccatgtctg ctagcggagc  38400
```

```
tttgttgcct gctatagctt tcgctgctta cgcttacgct acctacgctt atgctttcga  38460
gtggagccac gctaacggaa tcgataacgt ggatgctaga gagtggattg gagctttgtc  38520
tttgagactc cctgcaattg caaccacaat gtacctcttg ttctgccttg tgggacctag  38580
attgatggct aagagggagg cttttgatcc taagggattt atgctcgctt acaacgctta  38640
ccaaaccgct ttcaacgttg tggtgctcgg aatgttcgct agagagatct ctggattggg  38700
acaacctgtt tggggatcta ctatgccttg gagcgatagg aagtccttca agattttgtt  38760
gggagtgtgg ctccactaca acaataagta cctcgagttg ttggatactg tgttcatggt  38820
ggctaggaaa aagaccaagc agctctcttt cttgcacgtg taccaccacg ctttgttgat  38880
ttgggcttgg tggcttgttt gtcacctcat ggctaccaac gattgcatcg atgcttattt  38940
cggagctgct tgcaactctt tcatccacat cgtgatgtac tcctactacc tcatgtctgc  39000
tttgggaatt aggtgccctt ggaagagata tatcacccag gctcagatgt tgcaattcgt  39060
gatcgtgttc gctcacgctg ttttcgtgct cagacaaaag cactgccctg ttactttgcc  39120
ttgggcacaa atgttcgtga tgacaaatat gttggtgctc ttcggaaact tctacctcaa  39180
ggcttactct aacaagtcta ggggagatgg agcttcttct gttaagcctg ctgagactac  39240
tagagcacct tctgtgagaa gaaccaggtc aaggaagatc gattgatagt taatgaacta  39300
agtttgatgt atctgagtgc caacgtttac tttgtctttc ctttctttta ttggttatga  39360
ttagatgttt actatgttct ctctttttcg ttataaataa agaagttcaa ttcttctata  39420
gtttcaaacg cgattttaag cgtttctatt taggtttaca tgatttcttt tacaaaatca  39480
tctttaaaat acagtatatt tttagttttc ataaaatatt taaagaaatg aaagtttata  39540
aacattcact cctattctct aattaaggat ttgtaaaaca aaaattttgt aagcatatcg  39600
atttatgcgt tttgtcttaa ttagctcact aaataataaa taatagctta tgttgtggga  39660
ctgtttaatt acctaactta gaactaaaat caactctttg tgctagctag cctcagctga  39720
cgttacgtaa cgctaggtag cgtcacgtga cgttagctaa cgctaggtag cgtcagctga  39780
gcttacgtaa gcgcttaatt aaagtactga tatcggtacc aaatcgaatc caaaaattac  39840
ggatatgaat ataggcatat ccgtatccga attatccgtt tgacagctag caacgattgt  39900
acaattgctt ctttaaaaaa ggaagaaaga aagaaagaaa agaatcaaca tcagcgttaa  39960
caaacggccc cgttacggcc caaacggtca tatagagtaa cggcgttaag cgttgaaaga  40020
ctcctatcga aatacgtaac cgcaaacgtg tcatagtcag atcccctctt ccttcaccgc  40080
ctcaaacaca aaaataatct tctacagcct atatatacaa cccccccttc tatctctcct  40140
ttctcacaat tcatcatctt tctttctcta cccccaattt taagaaatcc tctcttctcc  40200
tcttcatttt caaggtaaat ctctctctct ctctctctct ctgttattcc ttgttttaat  40260
taggtatgta ttattgctag tttgttaatc tgcttatctt atgtatgcct tatgtgaata  40320
tctttatctt gttcatctca tccgtttaga agctataaat ttgttgattt gactgtgtat  40380
ctacacgtgg ttatgtttat atctaatcag atatgaattt cttcatattg ttgcgtttgt  40440
gtgtaccaat ccgaaatcgt tgattttttt catttaatcg tgtagctaat tgtacgtata  40500
catatggatc tacgtatcaa ttgttcatct gtttgtgttt gtatgtatac agatctgaaa  40560
acatcacttc tctcatctga ttgtgttgtt acatacatag atatagatct gttatatcat  40620
tttttttatt aattgtgtat atatatatgt gcatagatct ggattacatg attgtgatta  40680
tttacatgat tttgttattt acgtatgtat atatgtagat ctggactttt tggagttgtt  40740
gacttgattg tatttgtgtg tgtatatgtg tgttctgatc ttgatatgtt atgtatgtgc  40800
```

```
agctgaacca tggcggcggc aacaacaaca acaacaacat cttcttcgat ctccttctcc  40860
accaaaccat ctccttcctc ctccaaatca ccattaccaa tctccagatt ctccctccca  40920
ttctccctaa accccaacaa atcatcctcc tcctcccgcc gccgcggtat caaatccagc  40980
tctccctcct ccatctccgc cgtgctcaac acaaccacca atgtcacaac cactccctct  41040
ccaaccaaac ctaccaaacc cgaaacattc atctcccgat tcgctccaga tcaaccccgc  41100
aaaggcgctg atatcctcgt cgaggcttta gaacgtcaag gcgtagaaac cgtattcgct  41160
taccctggag gtacatcaat ggagattcac caagccttaa cccgctcttc ctcaatccgt  41220
aacgtccttc ctcgtcacga acaaggaggt gtattcgcag cagaaggata cgctcgatcc  41280
tcaggtaaac caggtatctg tatagccact tcaggtcccg gagctacaaa tctcgttagc  41340
ggattagccg atgcgttgtt agatagtgtt cctcttgtag caatcacagg acaagtccct  41400
cgtcgtatga ttggtacaga tgcgtttcaa gagactccga ttgttgaggt aacgcgttcg  41460
attacgaagc ataactatct tgtgatggat gttgaagata tcccaaggat tattgaagag  41520
gctttctttt tagctacttc tggtagacct ggacctgttt tggttgatgt tcctaaagat  41580
attcaacaac agcttgcgat tcctaattgg gaacaggcta tgagattacc tggttatatg  41640
tctaggatgc ctaaacctcc ggaagattct catttggagc agattgttag gttgatttct  41700
gagtctaaga agcctgtgtt gtatgttggt ggtggttgtc ttaattctag cgatgaattg  41760
ggtaggtttg ttgagcttac gggcatccct gttgcgagta cgttgatggg gctgggatct  41820
tatccttgtg atgatgagtt gtcgttacat atgcttggaa tgcatgggac tgtgtatgca  41880
aattacgctg tggagcatag tgatttgttg ttggcgtttg gggtaaggtt tgatgatcgt  41940
gtcacgggta aacttgaggc ttttgctagt agggctaaga ttgttcatat tgatattgac  42000
tcggctgaga ttgggaagaa taagactcct catgtgtctg tgtgtggtga tgttaagctg  42060
gctttgcaag ggatgaataa ggttcttgag aaccgagcgg aggagcttaa acttgatttt  42120
ggagtttgga ggaatgagtt gaacgtacag aaacagaagt ttccgttgag ctttaagacg  42180
tttggggaag ctattcctcc acagtatgcg attaaggtcc ttgatgagtt gactgatgga  42240
aaagccataa taagtactgg tgtcgggcaa catcaaatgt gggcggcgca gttctacaat  42300
tacaagaaac caaggcagtg gctatcatca ggaggccttg gagctatggg atttggactt  42360
cctgctgcga ttggagcgtc tgttgctaac cctgatgcga tagttgtgga tattgacgga  42420
gatggaagtt ttataatgaa tgtgcaagag ctagccacta ttcgtgtaga gaatcttcca  42480
gtgaaggtac ttttattaaa caaccagcat cttggcatgg ttatgcaatg ggaagatcgg  42540
ttctacaaag ctaaccgagc tcacacattt ctcggggacc cggctcagga ggacgagata  42600
ttcccgaaca tgttgctgtt tgcagcagct tgcgggattc cagcggcgag ggtgacaaag  42660
aaagcagatc tccgagaagc tattcagaca atgctggata caccaggacc ttacctgttg  42720
gatgtgattt gtccgcacca agaacatgtg ttgccgatga tcccgaatgg tggcactttc  42780
aacgatgtca taacggaagg agatggccgg attaaatact gagagatgaa accggtgatt  42840
atcagaacct tttatggtct ttgtatgcat atggtaaaaa aacttagttt gcaatttcct  42900
gtttgttttg gtaatttgag tttcttttag ttgttgatct gcctgctttt tggtttacgt  42960
cagactacta ctgctgttgt tgtttggttt cctttctttc attttataaa taaataatcc  43020
ggttcggttt actccttgtg actggctcag tttggttatt gcgaaatgcg aatggtaaat  43080
tgagtaattg aaattcgtta ttagggttct aagctgtttt aacagtcact gggttaatat  43140
```

```
ctctcgaatc ttgcatggaa aatgctctta ccattggttt ttaattgaaa tgtgctcata  43200

tgggccgtgg tttccaaatt aaataaaact acgatgtcat cgagaagtaa aatcaactgt  43260

gtccacatta tcagttttgt gtatacgatg aaatagggta attcaaaatc tagcttgata  43320

tgccttttgg ttcattttaa ccttctgtaa acatttttc agattttgaa caagtaaatc  43380

caaaaaaaaa aaaaaaaatc tcaactcaac actaaattat tttaatgtat aaaagatgct  43440

taaaacattt ggcttaaaag aaagaagcta aaaacataga gaactcttgt aaattgaagt  43500

atgaaaatat actgaattgg gtattatatg aatttttctg atttaggatt cacatgatcc  43560

aaaaaggaaa tccagaagca ctaatcagac attggaagta ggattaatca gtgatcagta  43620

actattaaat tcaattaacc gcggacatct acatttttga attgaaaaaa aattggtaat  43680

tactctttct ttttctccat attgaccatc atactcattg ctgatccatg tagatttccc  43740

ggacatgaag ccatttacaa ttgaatatat cct                               43773
```

<210> SEQ ID NO 13
<211> LENGTH: 20
<212> TYPE: DNA
<213> ORGANISM: Artificial sequence
<220> FEATURE:
<223> OTHER INFORMATION: LBFLFK Locus 2 RB junction region

<400> SEQUENCE: 13

```
tatatttaaa ccagtcagca                                                 20
```

<210> SEQ ID NO 14
<211> LENGTH: 20
<212> TYPE: DNA
<213> ORGANISM: Artificial sequence
<220> FEATURE:
<223> OTHER INFORMATION: LBFLFK Locus 2 LB junction region

<400> SEQUENCE: 14

```
aatatatcct cacatatgaa                                                 20
```

<210> SEQ ID NO 15
<211> LENGTH: 2900
<212> TYPE: DNA
<213> ORGANISM: Artificial sequence
<220> FEATURE:
<223> OTHER INFORMATION: LBFLFK Locus 2 flanking sequence up to and including the right border of the T-DNA

<400> SEQUENCE: 15

```
gaaaaacctg catctccaaa aatgttcaaa tggcttaaaa acagagaaaa tgagtggaat     60

attagataga tctaccttta tagaacacac aaaaatacat atctaaaatt attaaatctt    120

cctttaaatg agtggaagat gagaaccatg tgatgaaaaa cctgcaaaac aagataaatt    180

agtaagaaaa acatgagaca gaaacaataa attgatataa agtttgatgt ttataagttc    240

aaagggatta aagagaggtt tgagagtttt agaacgagga acataccatt tttgttgcag    300

ccatttgaga ggagaagaga gaatgtgtaa atgtttttt atataaggag acaaaaattc     360

caataaggtt aaatattttt gatcagaaga cttactagac gacttacttg taagtcgccc    420

agaagacttc aatattttta gcgggaaact aaaatatttt tagcgggagt tagaagaccc    480

taaacataac ccttaaacta aattaactaa ctaaatactt cataaaatca aattaaactt    540

aaaaagtgtt tactatacac agaaataatc acatgtagat ataaatttaa tttttcaaaa    600

aaacatttaa gctttccaaa atctaaccct aagaatacat acaatactac aacatatgtt    660
```

```
gccaaaccct agaccaaaga atatcatgat tcactacttt cactcatcta tgttgaaaac    720
aattcaattt tattatatct taatttatat cacttaaaac tgtttataat tacatgattt    780
taattttccg tttatcaaaa tattttttac aaaatttata aattattttt aggatcaact    840
ataccagacg acttccatgg acgccgtaca gaagactaaa cagaatctca caagactcag    900
aagacgtagc ggggatatat tcataaaaat gagttctgtt tttttgtttg gtcacaaggg    960
gctggttgta atttcacaag gcttttggat tacttttgca tttgattcaa gtttgggtat   1020
acttttgcaa tcaaaatcaa gttttgagtc atatttggta aatcgcccta tataaaataa   1080
aattttaaaa agtaatgaat ctacatattt tgtaattttt aaaaaattta gttaacaatt   1140
ataataacac aaaacttaag aaaaagttat aattgtcgta tttttttctc ttttcttttc   1200
tatgtaatat ttttatataa gtaataatgt gaatagaatt tatcaaatca tatgttagaa   1260
taattattat ataattttat acatttaaaa atttaaatat aatcaagata tatacatgta   1320
tttatatatt accagatcag agcagatatc cgtttcccaa aattttaata tttgtgattt   1380
gcttcgattt taatggatat tgatttttag tattttttg cttcaaaagt ttatggatat    1440
tcggaatttt cggatcgaat cgaaacgaat aacgcatcaa atcaaattta acggataaaa   1500
ccttagtaac acatgcataa accttagtga acttctcaag ctttcgattc tctatcttat   1560
ttatctatga aattaattaa cataattttc cttgaattaa cataattgga ctaacgcata   1620
ttcgagctga agtcaaaatt cccaaaactt gttcttgata tgagtaaaac tgttcgtctg   1680
atgtaaactc ttactgtagt tgtattacaa actaatgata aagtatgcat tttctatttt   1740
attataaatt tacattacta gttgataaca tattgacaac tagaaagcgt gagagagaga   1800
tactcggtaa gccgagatgt atatccacag ttggagtctt tggatttcat atccagaatt   1860
gggtcgcaaa ctttcagtac aaagttatga catctccatg gtatatatcg acgtgtctat   1920
atatcatatt aaagaaaggt ttgtagtatt tggttaggta caaatgcgat caacttttga   1980
atttatatcc atgtacatat ataccccttgg ttacaaggac acctacccat acatacgcat  2040
aagtgacaaa tagcaaaata tctacacatc gcatgacccc gttctttttt atgataaggt   2100
tgtgattttt gtggttcttt tttttcatct cttacattga ttcagtatgt tgtccaaaaa   2160
aaaaacagtg attcagtatt atatcgagta aattcacaag aacgtagcta caatgtagat   2220
gatttattaa caattttaca agagacaagc aaatgtcgag caatcatatt ctataatatc   2280
aacctaaaag agttaaatcc ataaaattag ttggcaacga gcgatagtat gaaagttagg   2340
tgatgacaaa agttgctata ttgcttcaac tatattttca taaatttatt tgtctggatg   2400
aaaaccacaa aattttaaaa atataatttt gattggtaat atgtaaataa cgggatccta   2460
tatttaaacc agtcagcatc atcacaccaa aagttaggcc cgaatagttt gaaattagaa   2520
agctcgcaat tgaggtctac aggccaaatt cgctcttagc cgtacaatat tactcaccgg   2580
tgcgatgccc cccatcgtag gtgaaggtgg aaattaatgg cgcgcctgat cactgattag   2640
taactattac gtaagcctac gtagcgtcac gtgacgttag ctaacgctac gtagcctcag   2700
ctgacgttac gtaagcctac gtagcgtcac gtgagcttag ctaacgctac ctaggctcag   2760
ctgacgttac gtaacgctag ctagcgtcac tcctgcagca aatttacaca ttgccactaa   2820
acgtctaaac ccttgtaatt tgtttttgtt ttactatgtg tgttatgtat ttgatttgcg   2880
ataaattttt atatttggta                                                2900
```

<210> SEQ ID NO 16
<211> LENGTH: 1800

<212> TYPE: DNA
<213> ORGANISM: Artificial sequence
<220> FEATURE:
<223> OTHER INFORMATION: LBFLFK Locus 2 flanking sequence up to and including the left border of the T-DNA

<400> SEQUENCE: 16

```
tttttctgat ttaggattca catgatccaa aaaggaaatc cagaagcact aatcagacat     60
tggaagtagg attaatcagt gatcagtaac tattaaattc aattaaccgc ggacatctac    120
atttttgaat tgaaaaaaaa ttggtaatta ctctttcttt ttctccatat tgaccatcat    180
actcattgct gatccatgta gatttcccgg acatgaagcc atttacaatt gaatatatcc    240
tcacatatga aatatatttt ttttttacaa attacaccta ttaaattata cttgatcggt    300
catctgatat atttgaaaga accctatcag ccagctattc ataatttaca taaaagaaaa    360
ttacgtgctt aaaatctctc taaaaaaaaa aaaagacaaa gacatcaaac tgatccatga    420
aagtaaaatg gagtgtattt taattttatc ttcagaccaa tgttatcaat gtagcccata    480
tattaatact aaaacaactt ctgcacaaac acacgaatca aagcctcgtg tttcatcgta    540
gctttagcta aaatttccca aaagcaaatt caatagtatt ttactaggtc aaacccacaa    600
gagaaaaaga aagtcaatcc caaggatcaa gaaatgagaa gtgagaggag aatgctttat    660
tgggtttgct aataactaat aagacatgaa gcagactgaa aacatctggt tttgtccaaa    720
aaagaaggaa gtcagattcc aaaactgcgc acctacattg tttaatactc actcacacat    780
acattcatgt ttttactgtt tatacacagt caataattta tacacagctc catgttttaa    840
tatttaccca tctctctttt gtagtctatc gtagactttc acttgtgtcc ccctcatgcg    900
gcaacatcct cagcaacttg atttactata tacaataata caaatcataa gatatttgtt    960
aggagctggt ttgtaaatta tttcgataca atactgaagc gaagggacca gcaatctttt   1020
tagctgatca gaacaatctt actaacgtgt gtctttgtaa gaaaatccaa cttttacttt   1080
ttcaggaggg agtgtagcgg attatgtata aataactcga agagtggtgc acaaagttca   1140
agtgtttgtg taaaatgttc gacaagacat tgactaaagc attccgaaca tgtcaacaaa   1200
actacaattc taaaattgca aaaagctgct aaacggtgga atagcattta acacgcattc   1260
tataccaaac attttttttc ttgaacacca aagaaaccaa acctaatgtc aaccatcgta   1320
tggaaactat agaactaaat caaactaaca aattcttatt gtatattctt aaaaacatcc   1380
ttataagaca gtttttccaa atgaatcttt agacttcatt gtactaatat gtttaaaata   1440
atataattat gtatttaatt tcttgaaagt ttcgctgcta agaggcaatt atctttttat   1500
atttttttct ctcttatttt caaattctaa ttaattttct tggagagttt atccgatgat   1560
gatattctta tttcaactca atccacgagt aaatgtgtta gcaccacatc taaccatttg   1620
gagcttgtac tagctctatc tttccaaact taactttctt gagtgcttat ttatataaag   1680
catcagtata tggcccaacc caagaaaagc tgaacaaaat tagcaacaat agcaagggac   1740
gaactgcagc tcttcttggt tgtcgtgcct tccaattctc gactttccgt ggaagaacat   1800
```

<210> SEQ ID NO 17
<211> LENGTH: 25
<212> TYPE: DNA
<213> ORGANISM: Artificial sequence
<220> FEATURE:
<223> OTHER INFORMATION: LBFLFK Locus 2_Forward primer

<400> SEQUENCE: 17

```
ccatattgac catcatactc attgc                                       25
```

<210> SEQ ID NO 18
<211> LENGTH: 26
<212> TYPE: DNA
<213> ORGANISM: Artificial sequence
<220> FEATURE:
<223> OTHER INFORMATION: LBFLFK Locus 2_Reverse primer

<400> SEQUENCE: 18
tggctgatag ggttctttca aatata 26

<210> SEQ ID NO 19
<211> LENGTH: 25
<212> TYPE: DNA
<213> ORGANISM: Artificial sequence
<220> FEATURE:
<223> OTHER INFORMATION: LBFLFK locus 2_Probe

<400> SEQUENCE: 19
taaattatac ttgatcggtc atctg 25

<210> SEQ ID NO 20
<211> LENGTH: 45777
<212> TYPE: DNA
<213> ORGANISM: Artificial sequence
<220> FEATURE:
<223> OTHER INFORMATION: contig of insert and flanking sequences of LBFDAU T-DNA locus 1

<400> SEQUENCE: 20
aaaagaaata taaaagaata tgaccaaaaa agtaaacgtg agtgagagaa taagaaaatg 60
actacaaaat ataatagcct caattatctt caaaactaag ttgacattta attatgcttt 120
tgcaagatat ttacttttgt tgttcgatca tatttaatga ttattttggt tttgaaacaa 180
atattaacat tatatatatt gtgtctatat tgaactgttg taaattataa acatcaaaat 240
tttaatgtta tcttaattat aatttctaat actagtatat tcaaaaatca aaataaacat 300
attttataaa atagtgccag tacgtagtat gggagataat actagtggct ttataaaggg 360
aaacattgtc tctaaaatct cagataaaat gttaaaacac acttattcac aattatgaag 420
atttgaaata tctgaaattt caaattgatg cacttggtag aaagcaaagg ttcaacgcta 480
agtctacaag gtgtaataat gaagtgaaaa tgctagttta gattaccctt gatatgtgac 540
tgaacatagg gtggagcgtc agtgagtcca tggagtacag aagctaaaca agagacatgg 600
ttaagcacca gaatcaactc gttctccata gagtccagct tttgagatat atgtgaatag 660
ccttgttgca atatacttgt gagtggcagg cgtgatctta ttaacgaaag tccaaattct 720
gaacaaagtt tatatcaagc tacgatggaa atatggaatc cgtatcaaaa tcaactgtac 780
tgtatcatac ggtgcagatt tttagctcga ctctaccacc ttgcgtttac ttttgtgatg 840
aacattgcga ttatatatga ggacctaaat agagggaaaa tgtatgaaga caggatccta 900
agaatgaaaa accagcatcc ccaagatgtg gcaccaagtg ctatcgacca caaactacgc 960
tggacatact ctgatatagt tcgttaagaa atcaaaatgt caacacatat aaataagcag 1020
tcagcatcat cacaccaaaa gttaggcccg aatagtttga aattagaaag ctcgcaattg 1080
aggtctacag gccaaattcg ctcttagccg tacaatatta ctcaccggtg cgatgccccc 1140
catcgtaggt gaaggtggaa attaatggcg cgcctgatca ctgattagta actattacgt 1200
aagcctacgt agcgtcacgt gacgttagct aacgctacgt agcctcagct gacgttacgt 1260
aagcctacgt agcgtcacgt gagcttagct aacgctacct aggctcagct gacgttacgt 1320

```
aacgctagct agcgtcactc ctgcagcaaa tttacacatt gccactaaac gtctaaaccc   1380
ttgtaatttg tttttgtttt actatgtgtg ttatgtattt gatttgcgat aaatttttat   1440
atttggtact aaatttataa caccttttat gctaacgttt gccaacactt agcaatttgc   1500
aagttgatta attgattcta aattattttt gtcttctaaa tacatatact aatcaactgg   1560
aaatgtaaat atttgctaat atttctacta taggagaatt aaagtgagtg aatatggtac   1620
cacaaggttt ggagatttaa ttgttgcaat gctgcatgga tggcatatac accaaacatt   1680
caataattct tgaggataat aatggtacca cacaagattt gaggtgcatg aacgtcacgt   1740
ggacaaaagg tttagtaatt tttcaagaca acaatgttac cacacacaag ttttgaggtg   1800
catgcatgga tgccctgtgg aaagtttaaa aatattttgg aaatgatttg catggaagcc   1860
atgtgtaaaa ccatgacatc cacttggagg atgcaataat gaagaaaact acaaatttac   1920
atgcaactag ttatgcatgt agtctatata atgaggattt tgcaatactt tcattcatac   1980
acactcacta agttttacac gattataatt tcttcatagc cagtactgtt taagcttcac   2040
tgtctctgaa tcggcaaagg taaacgtatc aattattcta caaacccttt tatttttctt   2100
ttgaattacc gtcttcattg gttatatgat aacttgataa gtaaagcttc aataattgaa   2160
tttgatctgt gttttttttgg ccttaatact aaatccttac ataagctttg ttgcttctcc   2220
tcttgtgagt tgagtgttaa gttgtaataa tggttcactt tcagctttag aagaaaccat   2280
ggaagttgtt gagaggttct acggagagtt ggatggaaag gtttcccaag gagtgaacgc   2340
tttgttggga tctttcggag ttgagttgac tgatacccca actactaagg gattgccact   2400
cgttgattct ccaactccaa ttgtgttggg agtgtctgtt tacttgacca tcgtgatcgg   2460
aggattgctt tggatcaagg ctagagatct caagccaaga gcttctgagc cattcttgtt   2520
gcaagctttg gtgttggtgc acaacttgtt ctgcttcgct ttgtctcttt acatgtgcgt   2580
gggtatcgct taccaagcta tcacctggag atattccttg tggggaaacg cttataaccc   2640
aaagcacaag gagatggcta tcctcgttta cctcttctac atgtccaagt acgtggagtt   2700
catggatacc gtgatcatga tcctcaagag atccaccaga cagatttctt tcctccacgt   2760
gtaccaccac tcttctatct ccccttatctg gtgggctatt gctcaccacg ctccaggagg   2820
agaggcttat tggagtgctg ctctcaactc tggagtgcac gtgttgatgt acgcttacta   2880
cttcttggct gcttgcttga gatcttcccc aaagctcaag aacaagtacc tcttctgggg   2940
aagatacctc acccaattcc agatgttcca gttcatgctc aacttggtgc aagcttacta   3000
cgatatgaaa accaacgctc catatccaca atggctcatc aagatcctct tctactacat   3060
gatctccctc ttgttcctct tcggaaactt ctacgtgcaa aagtacatca agccatccga   3120
tggaaagcaa aagggagcta agaccgagtg atcgacaagc tcgagtttct ccataataat   3180
gtgtgagtag ttcccagata agggaattag ggttcctata gggtttcgct catgtgttga   3240
gcatataaga aacccttagt atgtatttgt atttgtaaaa tacttctatc aataaaattt   3300
ctaattccta aaaccaaaat ccagtactaa aatccagatc ccccgaatta attcggcgtt   3360
aattcagcta gctagcctca gctgacgtta cgtaacgcta ggtagcgtca cgtgacgtta   3420
gctaacgcta ggtagcgtca gctgagctta cgtaagcgct tagcagatat ttggtgtcta   3480
aatgtttatt ttgtgatatg ttcatgtttg aaatggtggt ttcgaaacca gggacaacgt   3540
tgggatctga tagggtgtca aagagtatta tggattggga caatttcggt catgagttgc   3600
aaattcaagt atatcgttcg attatgaaaa ttttcgaaga atatcccatt tgagagagtc   3660
```

```
tttacctcat taatgttttt agattatgaa attttatcat agttcatcgt agtctttttg   3720
gtgtaaaggc tgtaaaaaga aattgttcac ttttgttttc gtttatgtga aggctgtaaa   3780
agattgtaaa agactatttt ggtgttttgg ataaaatgat agtttttata gattcttttg   3840
cttttagaag aaatacattt gaaatttttt ccatgttgag tataaaatac cgaaatcgat   3900
tgaagatcat agaaatattt taactgaaaa caaatttata actgattcaa ttctctccat   3960
ttttatacct atttaaccgt aatcgattct aatagatgat cgattttttta tataatccta   4020
attaaccaac ggcatgtatt ggataattaa ccgatcaact ctcacccccta atagaatcag   4080
tattttcctt cgacgttaat tgatcctaca ctatgtaggt catatccatc gttttaattt   4140
ttggccacca ttcaattctg tcttgccttt agggatgtga atatgaacgg ccaaggtaag   4200
agaataaaaa taatccaaat taaagcaaga gaggccaagt aagataatcc aaatgtacac   4260
ttgtcattgc caaaattagt aaaatactcg gcatattgta ttcccacaca ttattaaaat   4320
accgtatatg tattggctgc atttgcatga ataatactac gtgtaagccc aaaagaaccc   4380
acgtgtagcc catgcaaagt taacactcac gaccccattc ctcagtctcc actatataaa   4440
cccaccatcc ccaatctcac caaacccacc acacaactca caactcactc tcacacctta   4500
aagaaccaat caccaccaaa aaatttcacg atttggaatt tgattcctgc gatcacaggt   4560
atgacaggtt agattttgtt ttgtatagtt gtatacatac ttctttgtga tgttttgttt   4620
acttaatcga atttttggag tgttttaagg tctctcgttt agaaatcgtg gaaaatatca   4680
ctgtgtgtgt gttcttatga ttcacagtgt ttatgggttt catgttcttt gttttatcat   4740
tgaatgggaa gaaatttcgt tgggatacaa atttctcatg ttcttactga tcgttattag   4800
gagtttgggg aaaaaggaag agttttttttg gttggttcga gtgattatga ggttatttct   4860
gtatttgatt tatgagttaa tggtcgtttt aatgttgtag accatgggaa aaggatctga   4920
gggaagatct gctgctagag agatgactgc tgaggctaac ggagataaga gaaagaccat   4980
cctcattgag ggagtgttgt acgatgctac caacttcaaa cacccaggag gttccattat   5040
taacttcctc accgagggag aagctggagt tgatgctacc caagcttaca gagagttcca   5100
tcagagatcc ggaaaggctg ataagtacct caagtccctc ccaaagttgg atgcttctaa   5160
ggtggagtct aggttctctg ctaaggagca ggctagaagg gacgctatga ccagggatta   5220
cgctgctttc agagaggagt tggttgctga gggatacttc gatccatcta tcccacacat   5280
gatctacaga gtggtggaga ttgtggcttt gttcgctttg tctttctggt tgatgtctaa   5340
ggcttctcca acctctttgg ttttgggagt ggtgatgaac ggaatcgctc aaggaagatg   5400
cggatgggtt atgcacgaga tgggacacgg atctttcact ggagttatct ggctcgatga   5460
taggatgtgc gagttcttct acggagttgg atgtggaatg tctggacact actggaagaa   5520
ccagcactct aagcaccacg ctgctccaaa cagattggag cacgatgtgg atttgaacac   5580
cttgccactc gttgctttca acgagagagt tgtgaggaag gttaagccag gatctttgtt   5640
ggctttgtgg ctcagagttc aggcttattt gttcgctcca gtgtcttgct tgttgatcgg   5700
attgggatgg accttgtact tgcacccaag atatatgctc aggaccaaga gacacatgga   5760
gtttgtgtgg atcttcgcta gatatatcgg atggttctcc ttgatgggag ctttgggata   5820
ttctcctgga acttctgtgg gaatgtacct ctgctctttc ggacttggat gcatctacat   5880
cttcctccaa ttcgctgtgt ctcacaccca cttgccagtt accaacccag aggatcaatt   5940
gcactggctt gagtacgctg ctgatcacac cgtgaacatc tctaccaagt cttggttggt   6000
tacctggtgg atgtctaacc tcaacttcca aatcgagcac cacttgttcc caaccgctcc   6060
```

```
acaattcagg ttcaaggaga tctctccaag agttgaggct ctcttcaaga gacacaacct   6120
cccttactac gatttgccat acacctctgc tgtttctact accttcgcta acctctactc   6180
tgttggacac tctgttggag ctgataccaa gaagcaggat tgactgcttt aatgagatat   6240
gcgagacgcc tatgatcgca tgatatttgc tttcaattct gttgtgcacg ttgtaaaaaa   6300
cctgagcatg tgtagctcag atccttaccg ccggtttcgg ttcattctaa tgaatatatc   6360
acccgttact atcgtatttt tatgaataat attctccgtt caatttactg attgtctacg   6420
taggctcagc tgagcttacc taaggctacg taggctcacg tgacgttacg taaggctacg   6480
tagcgtcacg tgagcttacc taactctagc tagcctcacg tgaccttagc taacactagg   6540
tagcgtcagc tcgacggccc ggactgtatc caacttctga tctttgaatc tctctgttcc   6600
aacatgttct gaaggagttc taagactttt cagaaagctt gtaacatgct ttgtagactt   6660
tctttgaatt actcttgcaa actctgattg aacctacgtg aaaactgctc cagaagttct   6720
aaccaaattc cgtcttggga aggcccaaaa tttattgagt acttcagttt catggacgtg   6780
tcttcaaaga tttataactt gaaatcccat catttttaag agaagttctg ttccgcaatg   6840
tcttagatct cattgaaatc tacaactctt gtgtcagaag ttcttccaga atcaacttgc   6900
atcatggtga aaatctggcc agaagttctg aacttgtcat atttcttaac agttagaaaa   6960
atttctaagt gtttagaatt ttgacttttc caaagcaaac ttgacttttg actttcttaa   7020
taaaacaaac ttcatattct aacatgtctt gatgaaatgt gattcttgaa atttgatgtt   7080
gatgcaaaag tcaaagtttg acttttcagt gtgcaattga ccattttgct cttgtgccaa   7140
ttccaaacct aaattgatgt atcagtgctg caaacttgat gtcatggaag atcttatgag   7200
aaaattcttg aagactgaga ggaaaaattt tgtagtacaa cacaaagaat cctgtttttc   7260
atagtcggac tagacacatt aacataaaac accacttcat tcgaagagtg attgaagaag   7320
gaaatgtgca gttacctttc tgcagttcat aagagcaact tacagacact tttactaaaa   7380
tactacaaag aggaagattt taacaactta gagaagtaat gggagttaaa gagcaacaca   7440
ttaaggggga gtgttaaaat taatgtgttg taaccaccac tacctttagt aagtattata   7500
agaaaattgt aatcatcaca ttataattat tgtccttatt taaaattatg ataaagttgt   7560
atcattaaga ttgagaaaac caaatagtcc tcgtcttgat ttttgaatta ttgttttcta   7620
tgttactttt cttcaagcct atataaaaac tttgtaatgc taaattgtat gctggaaaaa   7680
aatgtgtaat gaattgaata gaaattatgg tatttcaaag tccaaaatcc atcaatagaa   7740
atttagtaca aaacgtaact caaaaatatt ctcttatttt aaattttaca acaatataaa   7800
aatattctct tattttaaat tttacaataa tataatttat cacctgtcac ctttagaata   7860
ccaccaacaa tattaatact tagatatttt attcttaata attttgagat ctctcaatat   7920
atctgatatt tattttatat ttgtgtcata ttttcttatg ttttagagtt aacccttata   7980
tcttggtcaa actagtaatt caatatatga gtttgtgaag gacacattga catcttgaaa   8040
cattggtttt aaccttgttg gaatgttaaa ggtaataaaa cattcagaat tatgaccatc   8100
tattaatata cttcctttgt cttttaaaaa agtgtgcatg aaaatgctct atggtaagct   8160
agagtgtctt gctggcctgt gtatatcaat tccatttcca gatggtagaa actgccacta   8220
cgaataatta gtcataagac acgtatgtta acacacgtcc ccttgcatgt tttttgccat   8280
atattccgtc tctttctttt tcttcacgta taaaacaatg aactaattaa tagagcgatc   8340
aagctgaaca gttctttgct ttcgaagttg ccgcaaccta aacaggtttt tccttcttct   8400
```

```
ttcttcttat taactacgac cttgtccttt gcctatgtaa aattactagg ttttcatcag   8460
ttacactgat taagttcgtt atagtggaag ataaaatgcc ctcaaagcat tttgcaggat   8520
atctttgatt tttcaaagat atggaactgt agagtttgat agtgttcttg aatgtggttg   8580
catgaagttt ttttggtctg catgttattt tttcctcgaa atatgttttg agtccaacaa   8640
gtgattcact tgggattcag aaagttgttt tctcaatatg taacagtttt tttctatgga   8700
gaaaaatcat agggaccgtt ggttttggct tctttaattt tgagctcaga ttaaacccat   8760
tttacccggt gttcttggca gaattgaaaa cagtacgtag taccgcgcct accatgtgtg   8820
ttgagaccga gaacaacgat ggaatcccta ctgtggagat cgctttcgat ggagagagag   8880
aaagagctga ggctaacgtg aagttgtctg ctgagaagat ggaacctgct gctttggcta   8940
agaccttcgc tagaagatac gtggttatcg agggagttga gtacgatgtg accgatttca   9000
aacatcctgg aggaaccgtg attttctacg ctctctctaa cactggagct gatgctactg   9060
aggctttcaa ggagttccac cacagatcta gaaaggctag gaaggctttg gctgctttgc   9120
cttctagacc tgctaagacc gctaaagtgg atgatgctga gatgctccag gatttcgcta   9180
agtggagaaa ggagttggag agggacggat tcttcaagcc ttctcctgct catgttgctt   9240
acagattcgc tgagttggct gctatgtacg ctttgggaac ctacttgatg tacgctagat   9300
acgttgtgtc ctctgtgttg gtttacgctt gcttcttcgg agctagatgt ggatgggttc   9360
aacacgaggg aggacactct tctttgaccg gaaacatctg gtgggataag agaatccaag   9420
ctttcactgc tggattcgga ttggctggat ctggagatat gtggaactcc atgcacaaca   9480
agcaccacgc tactcctcaa aaagtgaggc acgatatgga tttggatacc actcctgctg   9540
ttgctttctt caacaccgct gtggaggata atagacctag ggattctct aagtactggc   9600
tcagattgca agcttggacc ttcattcctg tgacttctgg attggtgttg ctcttctgga   9660
tgttcttcct ccacccttct aaggctttga agggaggaaa gtacgaggag cttgtgtgga   9720
tgttggctgc tcacgtgatt agaacctgga ccattaaggc tgttactgga ttcaccgcta   9780
tgcaatccta cggactcttc ttggctactt cttgggtttc cggatgctac ttgttcgctc   9840
acttctctac ttctcacacc cacttggatg ttgttcctgc tgatgagcac ttgtcttggg   9900
ttaggtacgc tgtggatcac accattgata tcgatccttc tcagggatgg gttaactggt   9960
tgatgggata cttgaactgc caagtgattc accacctctt cccttctatg cctcaattca  10020
gacaacctga ggtgtccaga agattcgttg ctttcgctaa gaagtggaac ctcaactaca  10080
aggtgatgac ttatgctgga gcttggaagg ctactttggg aaacctcgat aatgtgggaa  10140
agcactacta cgtgcacgga caacactctg gaaagaccgc ttgattaatg aaggccgcct  10200
cgaccgtacc ccctgcagat agactatact atgttttagc ctgcctgctg gctagctact  10260
atgttatgtt atgttgtaaa ataaacacct gctaaggtat atctatctat attttagcat  10320
ggctttctca ataaattgtc tttccttatc gtttactatc ttatacctaa taatgaaata  10380
ataatatcac atatgaggaa cggggcaggt ttaggcatat atatacgagt gtagggcgga  10440
gtggggctac gtagcgtcac gtgacgttac ctaagcctag gtagcctcag ctgacgttac  10500
gtaacgctag gtaggctcag ctgacacggg caggacatag ggactactac aagcatagta  10560
tgcttcagac aaagagctag gaaagaactc ttgatggagg ttaagagaaa aaagtgctag  10620
aggggcatag taatcaaact tgtcaaaacc gtcatcatga tgagggatga cataatataa  10680
aaagttgact aaggtcttgg tagtactctt tgattagtat tatatattgg tgagaacatg  10740
agtcaagagg agacaagaaa ccgaggaacc atagtttagc aacaagatgg aagttgcaaa  10800
```

```
gttgagctag ccgctcgatt agttacatct cctaagcagt actacaagga atggtctcta  10860
tactttcatg tttagcacat ggtagtgcgg attgacaagt tagaaacagt gcttaggaga  10920
caaagagtca gtaaaggtat tgaaagagtg aagttgatgc tcgacaggtc aggagaagtc  10980
cctccgccag atggtgacta ccaaggggtt ggtatcagct gagacccaaa taagattctt  11040
cggttgaacc agtggttcga ccgagactct tagggtggga tttcactgta agatttgtgc  11100
attttgttga atataaattg acaatttttt ttatttaatt atagattatt tagaatgaat  11160
tacatattta gtttctaaca aggatagcaa tggatgggta tgggtacagg ttaaacatat  11220
ctattaccca cccatctagt cgtcgggttt tacacgtacc cacccgttta cataaaccag  11280
accggaattt taaaccgtac ccgtccgtta gcgggtttca gatttacccg tttaatcggg  11340
taaaacctga ttactaaata tatatttttt atttgataaa caaaacaaaa atgttaatat  11400
tttcatattg gatgcaattt taagaaacac atattcataa atttccatat ttgtaggaaa  11460
ataaaaagaa aaatatattc aagaacacaa atttcaccga catgactttt attacagagt  11520
tggaattaga tctaacaatt gaaaaattaa aattaagata gaatatgttg aggaacatga  11580
catagtataa tgctgggtta cccgtcgggt aggtatcgag gcggatacta ctaaatccat  11640
cccactcgct atccgataat cactggtttc gggtataccc attcccgtca acaggccttt  11700
ttaaccggat aatttcaact tatagtgaat gaattttgaa taaatagtta gaataccaaa  11760
atcctggatt gcatttgcaa tcaaattttg tgaaccgtta aattttgcat gtacttggga  11820
tagatataat agaaccgaat tttcattagt ttaatttata acttactttg ttcaaagaaa  11880
aaaaatatct atccaattta cttataataa aaaataatct atccaagtta cttattataa  11940
tcaacttgta aaaaggtaag aatacaaatg tggtagcgta cgtgtgatta tatgtgacga  12000
aatgttatat ctaacaaaag tccaaattcc catggtaaaa aaaatcaaaa tgcatggcag  12060
gctgtttgta accttggaat aagatgttgg ccaattctgg agccgccacg tacgcaagac  12120
tcagggccac gttctcttca tgcaaggata gtagaacacc actccaccca cctcctatat  12180
tagacctttg cccaaccctc cccaactttc ccatcccatc cacaaagaaa ccgacatttt  12240
tatcataaat ctggtgctta aacactctgg tgagttctag tacttctgct atgatcgatc  12300
tcattaccat ttcttaaatt tctctcccta aatattccga gttcttgatt tttgataact  12360
tcaggttttc tctttttgat aaatctggtc tttccatttt tttttttgt ggttaattta  12420
gtttcctatg ttcttcgatt gtattatgca tgatctgtgt ttggattctg ttagattatg  12480
tattggtgaa tatgtatgtg tttttgcatg tctggttttg gtcttaaaaa tgttcaaatc  12540
tgatgatttg attgaagctt ttttagtgtt ggtttgattc ttctcaaaac tactgttaat  12600
ttactatcat gttttccaac tttgattcat gatgacactt ttgttctgct ttgttataaa  12660
attttggttg gtttgatttt gtaattatag tgtaattttg ttaggaatga acatgtttta  12720
atactctgtt ttcgatttgt cacacattcg aattattaat cgataattta actgaaaatt  12780
catggttcta gatcttgttg tcatcagatt atttgtttcg ataattcatc aaatatgtag  12840
tccttttgct gatttgcgac tgtttcattt tttctcaaaa ttgttttttg ttaagtttat  12900
ctaacagtta tcgttgtcaa aagtctcttt catttttgcaa aatcttcttt tttttttgt  12960
ttgtaacttt gttttttaag ctacacattt agtctgtaaa atagcatcga ggaacagttg  13020
tcttagtaga cttgcatgtt cttgtaactt ctatttgttt cagtttgttg atgactgctt  13080
tgattttgta ggtcaaaggc gcaccctacc atggatgctt ataacgctgc tatggataag  13140
```

```
attggagctg ctatcatcga ttggagtgat ccagatggaa agttcagagc tgatagggag  13200
gattggtggt tgtgcgattt cagatccgct atcaccattg ctctcatcta catcgctttc  13260
gtgatcttgg gatctgctgt gatgcaatct ctcccagcta tggacccata ccctatcaag  13320
ttcctctaca acgtgtctca aatcttcctc tgcgcttaca tgactgttga ggctggattc  13380
ctcgcttata ggaacggata caccgttatg ccatgcaacc acttcaacgt gaacgatcca  13440
ccagttgcta acttgctctg gctcttctac atctccaaag tgtgggattt ctgggatacc  13500
atcttcattg tgctcggaaa gaagtggaga caactctctt tcttgcacgt gtaccaccac  13560
accaccatct tcctcttcta ctggttgaac gctaacgtgc tctacgatgg agatatcttc  13620
ttgaccatcc tcctcaacgg attcattcac accgtgatgt acacctacta cttcatctgc  13680
atgcacacca aggattctaa gaccggaaag tctttgccaa tctggtggaa gtcatctttg  13740
accgctttcc aactcttgca attcaccatc atgatgtccc aagctaccta cttggttttc  13800
cacggatgcg ataaggtttc cctcagaatc accatcgtgt acttcgtgta cattctctcc  13860
cttttcttcc tcttcgctca gttcttcgtg caatcctaca tggctccaaa gaagaagaag  13920
tccgcttgat gttaatgaag gccgcagata tcagatctgg tcgacctaga ggatccccgg  13980
ccgcaaagat aataacaaaa gcctactata taacgtacat gcaagtattg tatgatatta  14040
atgtttttac gtacgtgtaa acaaaaataa ttacgtttgt aacgtatggt gatgatgtgg  14100
tgcactaggt gtaggccttg tattaataaa aagaagtttg ttctatatag agtggtttag  14160
tacgacgatt tatttactag tcggattgga atagagaacc gaattcttca atccttgctt  14220
ttgatcaaga attgaaaccg aatcaaatgt aaaagttgat atatttgaaa aacgtattga  14280
gcttatgaaa atgctaatac tctcatctgt atggaaaagt gactttaaaa ccgaacttaa  14340
aagtgacaaa aggggaatat cgcatcaaac cgaatgaaac cgatctacgt aggctcagct  14400
gagcttagct aagcctacct agcctcacgt gagattatgt aaggctaggt agcgtcacgt  14460
gacgttacct aacactagct agcgtcagct gagcttagct aaccctacgt agcctcacgt  14520
gagcttacct aacgctacgt agcctcacgt gactaaggat gacctaccca ttcttgagac  14580
aaatgttaca ttttagtatc agagtaaaat gtgtacctat aactcaaatt cgattgacat  14640
gtatccattc aacataaaat taaaccagcc tgcacctgca tccacatttc aagtattttc  14700
aaaccgttcg gctcctatcc accgggtgta acaagacgga ttccgaattt ggaagatttt  14760
gactcaaatt cccaatttat attgaccgtg actaaatcaa ctttaacttc tataattctg  14820
attaagctcc caatttatat tcccaacggc actacctcca aaatttatag actctcatcc  14880
ccttttaaac caacttagta aacgtttttt ttttaatttt atgaagttaa gtttttacct  14940
tgtttttaaa aagaatcgtt cataagatgc catgccagaa cattagctac acgttacaca  15000
tagcatgcag ccgcggagaa ttgtttttct tcgccacttg tcactccctt caaacaccta  15060
agagcttctc tctcacagca cacacataca atcacatgcg tgcatgcatt attacacgtg  15120
atcgccatgc aaatctcctt tatagcctat aaattaactc atcggcttca ctctttactc  15180
aaaccaaaac tcatcaatac aaacaagatt aaaaacattt cacgatttgg aatttgattc  15240
ctgcgatcac aggtatgaca ggttagattt tgttttgtat agttgtatac atacttcttt  15300
gtgatgtttt gtttacttaa tcgaattttt ggagtgtttt aaggtctctc gtttagaaat  15360
cgtggaaaat atcactgtgt gtgtgttctt atgattcaca gtgtttatgg gtttcatgtt  15420
ctttgtttta tcattgaatg ggaagaaatt tcgttgggat acaaatttct catgttctta  15480
ctgatcgtta ttaggagttt ggggaaaaag gaagagtttt tttggttggt tcgagtgatt  15540
```

```
atgaggttat ttctgtattt gatttatgag ttaatggtcg ttttaatgtt gtagaccgcc  15600
atggctattt tgaaccctga ggctgattct gctgctaacc tcgctactga ttctgaggct  15660
aagcaaagac aattggctga ggctggatac actcacgttg agggtgctcc tgctcctttg  15720
cctttggagt tgcctcactt ctctctcaga gatctcagag ctgctattcc taagcactgc  15780
ttcgagagat ctttcgtgac ctccacctac tacatgatca agaacgtgtt gacttgcgct  15840
gctttgttct acgctgctac cttcattgat agagctggag ctgctgctta tgttttgtgg  15900
cctgtgtact ggttcttcca gggatcttac ttgactggag tgtgggttat cgctcacgag  15960
tgtggacacc aggcttattg ctcttctgag gtggtgaaca acttgattgg actcgtgttg  16020
cactctgctt tgttggtgcc ttaccactct tggagaatct ctcacagaaa gcaccactcc  16080
aacactggat cttgcgagaa cgatgaggtt ttcgttcctg tgaccagatc tgtgttggct  16140
tcttcttgga acgagacctt ggaggattct cctctctacc aactctaccg tatcgtgtac  16200
atgttggttg ttggatggat gcctggatac ctcttcttca acgctactgg acctactaag  16260
tactggggaa agtctaggtc tcacttcaac ccttactccg ctatctatgc tgatagggag  16320
aggtggatga tcgtgctctc cgatattttc ttggtggcta tgttggctgt tttggctgct  16380
ttggtgcaca ctttctcctt caacacgatg gtgaagttct acgtggtgcc ttacttcatt  16440
gtgaacgctt acttggtgtt gattacctac ctccaacaca ccgataccta catccctcac  16500
ttcagagagg gagagtggaa ttggttgaga ggagctttgt gcactgtgga tagatcattt  16560
ggtccattcc tcgattctgt ggtgcataga atcgtggata cccacgtttg ccaccatatc  16620
ttctccaaga tgcctttcta tcactgcgag gaggctacca acgctattaa gcctctcctc  16680
ggaaagttct acttgaagga tactactcct gttcctgttg ctctctggag atcttacacc  16740
cactgcaagt tcgttgagga tgatggaaag gtggtgttct acaagaacaa gttatagtta  16800
atgaataatt gattggttcg agtattatgg cattgggaaa actgtttttc ttgtaccatt  16860
tgttgtgctt gtaatttact gtgtttttta ttcggttttc gctatcgaac tgtgaaatgg  16920
aaatggatgg agaagagtta atgaatgata tggtcctttt gttcattctc aaattaatat  16980
tatttgtttt ttctcttatt tgttgtgtgt tgaatttgaa attataagag atatgcaaac  17040
attttgtttt gagtaaaaat gtgtcaaatc gtggcctcta atgaccgaag ttaatatgag  17100
gagtaaaaca cttgtagttg taccattatg cttattcact aggcaacaaa tatattttca  17160
gacctagaaa agctgcaaat gttactgaat acaagtatgt cctcttgtgt tttagacatt  17220
tatgaacttt cctttatgta attttccaga atccttgtca gattctaatc attgctttat  17280
aattatagtt atactcatgg atttgtagtt gagtatgaaa atattttta atgcatttta  17340
tgacttgcca attgattgac aacatgcatc aatctagcta gcctcagctg acgttacgta  17400
acgctaggta gcgtcacgtg acgttagcta acgctaggta gcgtcagctg agcttacgta  17460
agcgcacaga tgaatactag ctgttgttca cagttctagt gtctcctcat tacgtgaatt  17520
caagctacga tcactatctc aactcctaca taaacatcag aatgctacaa aactatgcac  17580
aaaaacaaaa gctacatcta atacgtgaat caattactct catcacaaga aagaagattt  17640
caatcaccgt cgagaaggag gattcagtta attgaatcaa agttccgatc aaactcgaag  17700
actggtgagc acgaggacga cgaagaagag tgtctcgaag atacaacaag caagaaatct  17760
actgagtgac ctcctgaagt tattggcgcg attgagagaa tcaatccgaa ttaatttcgg  17820
ggaaaaagat aaattagata ctaagcgatg ggcttgggct gggctaagaa acaggtggca  17880
```

```
attgggctgg aggaccccgc gattcatagc ttccgatagc ccaaaaaaaa acggataaca  17940
tatttatcgg gtatttgaat ttcagtgaaa taagatattt tctttttgtt aggaaaattt  18000
tagaaaataa tggaaattaa atagcgatta tgttacaaga tacgatcagc atcgggcagt  18060
gcaaaatgct atagcttccc aagatttgat ccttttgggt tatctcctaa tgacaattag  18120
tttaggattt tgaaacttat attaatacta ttatccgaca acacttgttt cagcttctta  18180
ttttaacatt ttttgttttt ttctattctt cttcccatca gcattttctt tttaaaaaat  18240
tgaatacttt aactttttaa aaatttcaca atgatcagat gatattatgg aagatctcaa  18300
gagttaaatg tatccatctt ggggcattaa aaccggtgta cgggatgata aatacagact  18360
ttatatcata tgatagctca gtaattcata tttatcacgt tgctaaaaaa attataaggt  18420
actagtagtc aacaaaatca attaaagaga aagaaagaaa cgcatgtgaa gagagtttac  18480
aactggaaaa gtaaaataaa aattaacgca tgttgaatgc tgacatgtca gtatgtccat  18540
gaatccacgt atcaagcgcc attcatcgat cgtcttcctc tttctaaatg aaaacaactt  18600
cacacatcac aacaaacaat acacacaaga ccccctctct ctcgttgtct ctctgccagc  18660
gaccaaatcg aagcttgaga agaacaagaa ggggtcaaac catggcttct acatctgctg  18720
ctcaagacgc tgctccttac gagttccctt ctctcactga gatcaagagg gctcttcctt  18780
ctgagtgttt cgaggcttct gttcctcttt ctctctacta caccgctaga tctcttgctc  18840
ttgctggatc tctcgctgtt gctctctctt acgctagagc tttgcctctt gttcaggcta  18900
acgctcttct tgatgctact ctctgcactg gatacgttct tctccaggga atcgttttct  18960
ggggattctt caccgttggt cacgattgtg gacacggagc tttctctaga tctcacgtgc  19020
tcaacttctc tgttggaacc ctcatgcact ctatcatcct taccccttc gagtcttgga  19080
agctctctca cagacaccac cacaagaaca ccggaaacat cgataaggac gagatcttct  19140
accctcaaag agaggctgat tctcaccctg tttctagaca ccttgtgatg tctcttggat  19200
ctgcttggtt cgcttacctt ttcgctggat tccctcctag aaccatgaac cacttcaacc  19260
cttgggaggc tatgtatgtt agaagagtgg ctgctgtgat catctctctc ggagttcttt  19320
tcgctttcgc tggactctac tcttacctca ccttcgttct tggattcacc actatggcta  19380
tctactactt cggacctctc ttcatcttcg ctaccatgct tgttgttacc actttcctcc  19440
accacaacga tgaggagaca ccttggtacg ctgattctga gtggacttac gtgaagggaa  19500
acctctcttc tgtggacaga tcttacggtg ctctcatcga caaccttagc cacaacatcg  19560
gaactcacca gatccaccac ctcttcccta tcatccctca ctacaagctc aacgatgcta  19620
ctgctgcttt cgctaaggct ttccctgagc ttgttaggaa aaacgctgct cctatcatcc  19680
caactttctt caggatggct gctatgtacg ctaagtacgg agttgttgac actgatgcta  19740
agaccttcac tctcaaggag gctaaggctg ctgctaagac taagtcatct tgatgattaa  19800
tgaataattg attgtacata ctatattttt tgtttacctt gtgttagttt aatgttcagt  19860
gtcctctctt tattgtggca cgtctctttg ttgtatgttg tgtctataca aagttgaaat  19920
aatggaaaga aaaggaagag tgtaatttgt tttgttttaa gtgtttataa atatatatat  19980
ataggtcatt tagatagttc taggtttcta taaaactctc tctctggaag tagaatctgt  20040
ttttgagagg atccagttgc ctactaatct cccccaaaac ccttcaagct taaccttcct  20100
cttcacaaca acagaggaaa cacatctctt gagctctgag ttctcttctt tgagcatgtc  20160
tatcgctaaa ctcatctgcc ttatagcttc cctcttctct tcatctctct ctctcaccat  20220
ttcgctgtaa aacttattct cctccctcag cctctctatc tcttccttca gcatctcaca  20280
```

```
attcccacca taatcgactg aggatgattc accgtcatca acttcagact cagcgttgta  20340
gtcgtcatga gtctcacaag ccttggacca agaagactca tcatcgcaag ttgatgattt  20400
atcatgatgc ttctctgagc cgtgtttgct acgtagcgtc acgtgacgtt acctaagcct  20460
aggtagcctc agctgacgtt acgtaacgct aggtaggctc agctgactgc agcaaattta  20520
cacattgcca ctaaacgtct aaacccttgt aatttgtttt tgttttacta tgtgtgttat  20580
gtatttgatt tgcgataaat ttttatattt ggtactaaat ttataacacc ttttatgcta  20640
acgtttgcca acacttagca atttgcaagt tgattaattg attctaaatt atttttgtct  20700
tctaaataca tatactaatc aactggaaat gtaaatattt gctaatattt ctactatagg  20760
agaattaaag tgagtgaata tggtaccaca aggtttggag atttaattgt tgcaatgctg  20820
catggatggc atatacacca aacattcaat aattcttgag gataataatg gtaccacaca  20880
agatttgagg tgcatgaacg tcacgtggac aaaaggttta gtaatttttc aagacaacaa  20940
tgttaccaca cacaagtttt gaggtgcatg catggatgcc ctgtggaaag tttaaaaata  21000
ttttggaaat gatttgcatg gaagccatgt gtaaaaccat gacatccact tggaggatgc  21060
aataatgaag aaaactacaa atttacatgc aactagttat gcatgtagtc tatataatga  21120
ggattttgca atactttcat tcatacacac tcactaagtt ttacacgatt ataatttctt  21180
catagccagt actgtttaag cttcactgtc tctgaatcgg caaaggtaaa cgtatcaatt  21240
attctacaaa ccctttttatt tttcttttga attaccgtct tcattggtta tatgataact  21300
tgataagtaa agcttcaata attgaatttg atctgtgttt ttttggcctt aatactaaat  21360
ccttacataa gctttgttgc ttctcctctt gtgagttgag tgttaagttg taataatggt  21420
tcactttcag ctttagaaga aacgcgcctt ccatggctac aaaggaggct tacgttttcc  21480
caactctcac cgagatcaag agatctctcc caaaggattg cttcgaggct tctgtgcctt  21540
tgtctctcta ctacactgtg agatgcttgg ttattgctgt ggctttgacc ttcggattga  21600
actacgctag agctttgcca gaggttgagt ctttctgggc tttggatgct gctttgtgca  21660
ctggatatat cctcctccag ggaattgtgt tctggggatt cttcactgtt ggacacgatg  21720
ctggacacgg agctttctct agataccacc tcttgaactt cgttgtggga accttcatgc  21780
actctctcat cttgacccca ttcgagtctt ggaagttgac ccacagacac caccacaaga  21840
acaccggaaa catcgataga gatgaggtgt tctacccaca gagaaaggct gatgatcacc  21900
cattgtccag gaacttgatc ttggctttgg gagctgcttg gcttgcttat ttggtggagg  21960
gattcccacc aagaaaggtg aaccacttca acccattcga gccacttttt gtgagacaag  22020
tgtccgctgt ggttatctct ttgctcgctc acttcttcgt tgctggactc tctatctact  22080
tgtctctcca gttgggactt aagaccatgg ctatctacta ctacggacca gttttcgtgt  22140
tcggatctat gttggtgatt accaccttct tgcaccacaa cgatgaggag actccatggt  22200
atgctgattc tgagtggact tacgtgaagg gaaacttgtc ctctgtggat agatcttacg  22260
gtgctctcat cgataacctc tcccacaaca tcggaactca ccagatccac cacctcttcc  22320
caattatccc acactacaag ctcaagaagg ctactgctgc tttccaccaa gctttcccag  22380
agcttgtgag aaagtccgat gagccaatca tcaaggcttt cttcagagtg ggaaggttgt  22440
atgctaacta cggagtggtt gatcaagagg ctaagctctt cactttgaag gaggctaagg  22500
ctgctactga agctgctgct aagaccaagt ctacctgatt aatgaatcga caagctcgag  22560
tttctccata ataatgtgtg agtagttccc agataaggga attagggttc ctatagggtt  22620
```

tcgctcatgt gttgagcata taagaaaccc ttagtatgta tttgtatttg taaaatactt 22680
ctatcaataa aatttctaat tcctaaaacc aaaatccagt actaaaatcc agatccccg 22740
aattaattcg gcgttaattc agctacgtag gctcagctga gcttacctaa ggctacgtag 22800
gctcacgtga cgttacgtaa ggctacgtag cgtcacgtga gcttacctaa ctctagctag 22860
cctcacgtga ccttagctaa cactaggtag cgtcagcaca gatgaatact agctgttgtt 22920
cacagttcta gtgtctcctc attacgtgaa ttcaagctac gatcactatc tcaactccta 22980
cataaacatc agaatgctac aaaactatgc acaaaaacaa aagctacatc taatacgtga 23040
atcaattact ctcatcacaa gaaagaagat ttcaatcacc gtcgagaagg aggattcagt 23100
taattgaatc aaagttccga tcaaactcga agactggtga gcacgaggac gacgaagaag 23160
agtgtctcga agatacaaca agcaagaaat ctactgagtg acctcctgaa gttattggcg 23220
cgattgagag aatcaatccg aattaatttc ggggaaaaag ataaattaga tactaagcga 23280
tgggcttggg ctgggctaag aaacaggtgg caattgggct ggaggacccc gcgattcata 23340
gcttccgata gcccaaaaaa aaacggataa catatttatc gggtatttga atttcagtga 23400
aataagatat tttctttttg ttaggaaaat tttagaaaat aatggaaatt aaatagcgat 23460
tatgttacaa gatacgatca gcatcgggca gtgcaaaatg ctatagcttc ccaagatttg 23520
atccttttgg gttatctcct aatgacaatt agtttaggat tttgaaactt atattaatac 23580
tattatccga caacacttgt ttcagcttct tattttaaca ttttttgttt ttttctattc 23640
ttcttcccat cagcattttc tttttaaaaa attgaatact ttaacttttt aaaaatttca 23700
caatgatcag atgatattat ggaagatctc aagagttaaa tgtatccatc ttggggcatt 23760
aaaaccggtg tacgggatga taaatacaga ctttatatca tatgatagct cagtaattca 23820
tatttatcac gttgctaaaa aaattataag gtactagtag tcaacaaaat caattaaaga 23880
gaaagaaaga aacgcatgtg aagagagttt acaactggaa aagtaaaata aaaattaacg 23940
catgttgaat gctgacatgt cagtatgtcc atgaatccac gtatcaagcg ccattcatcg 24000
atcgtcttcc tctttctaaa tgaaaacaac ttcacacatc acaacaaaca atacacacaa 24060
gaccccctct ctctcgttgt ctctctgcca gcgaccaaat cgaagcttga gaagaacaag 24120
aaggggtcaa accatgggaa aaggatctga gggaagatct gctgctagag agatgactgc 24180
tgaggctaac ggagataaga gaaagaccat cctcattgag ggagtgttgt acgatgctac 24240
caacttcaaa cacccaggag gttccattat taacttcctc accgagggag aagctggagt 24300
tgatgctacc caagcttaca gagagttcca tcagagatcc ggaaaggctg ataagtacct 24360
caagtccctc ccaaagttgg atgcttctaa ggtggagtct aggttctctg ctaaggagca 24420
ggctagaagg gacgctatga ccagggatta cgctgctttc agagaggagt tggttgctga 24480
gggatacttc gatccatcta tcccacacat gatctacaga gtggtggaga ttgtggcttt 24540
gttcgctttg tctttctggt tgatgtctaa ggcttctcca acctctttgg ttttgggagt 24600
ggtgatgaac ggaatcgctc aaggaagatg cggatgggtt atgcacgaga tgggacacgg 24660
atctttcact ggagttatct ggctcgatga taggatgtgc gagttcttct acggagttgg 24720
atgtggaatg tctggacact actggaagaa ccagcactct aagcaccacg ctgctccaaa 24780
cagattggag cacgatgtgg atttgaacac cttgccactc gttgctttca acgagagagt 24840
tgtgaggaag gttaagccag gatctttgtt ggctttgtgg ctcagagttc aggcttattt 24900
gttcgctcca gtgtcttgct tgttgatcgg attgggatgg accttgtact tgcacccaag 24960
atatatgctc aggaccaaga gacacatgga gtttgtgtgg atcttcgcta gatatatcgg 25020

```
atggttctcc ttgatgggag ctttgggata ttctcctgga acttctgtgg gaatgtacct  25080
ctgctctttc ggacttggat gcatctacat cttcctccaa ttcgctgtgt ctcacaccca  25140
cttgccagtt accaacccag aggatcaatt gcactggctt gagtacgctg ctgatcacac  25200
cgtgaacatc tctaccaagt cttggttggt tacctggtgg atgtctaacc tcaacttcca  25260
aatcgagcac cacttgttcc caaccgctcc acaattcagg ttcaaggaga tctctccaag  25320
agttgaggct ctcttcaaga gacacaacct cccttactac gatttgccat acacctctgc  25380
tgtttctact accttcgcta acctctactc tgttggacac tctgttggag ctgataccaa  25440
gaagcaggat tgatgattaa tgaataattg attgtacata ctatattttt tgtttacctt  25500
gtgttagttt aatgttcagt gtcctctctt tattgtggca cgtctctttg ttgtatgttg  25560
tgtctataca aagttgaaat aatggaaaga aaaggaagag tgtaatttgt tttgttttaa  25620
gtgtttataa atatatatat ataggtcatt tagatagttc taggtttcta taaaactctc  25680
tctctggaag tagaatctgt ttttgagagg atccagttgc ctactaatct cccccaaaac  25740
ccttcaagct taaccttcct cttcacaaca acagaggaaa cacatctctt gagctctgag  25800
ttctcttctt tgagcatgtc tatcgctaaa ctcatctgcc ttatagcttc cctcttctct  25860
tcatctctct ctctcaccat ttcgctgtaa aacttattct cctccctcag cctctctatc  25920
tcttccttca gcatctcaca attcccacca taatcgactg aggatgattc accgtcatca  25980
acttcagact cagcgttgta gtcgtcatga gtctcacaag ccttggacca agaagactca  26040
tcatcgcaag ttgatgattt atcatgatgc ttctctgagc cgtgtttgct acctagagtc  26100
agctgagctt agctaacgct agctagtgtc agctgacgtt acgtaaggct aactagcgtc  26160
acgtgacctt acgtaacgct acgtaggctc agctgagctt agctaaccct agctagtgtc  26220
acgtgagctt acgctactat agaaaatgtg ttatatcgac atgaccagac aaaggggcaa  26280
cagttaacaa aacaattaat tctttcattt gagattaagg aaggtaaggt actaaaaaga  26340
ttaaaaaaaa tgagcttatc tctttgtttc tgtaataata atataagtgt gataaacttt  26400
taatataata attgtaatta ggttttctac agatgagcac cactcagaga caagataaga  26460
agaaaacaat tttgttaaac atgattatag aaacttttag ttaagtcttg aagtatcaat  26520
ataacaaaaa aaagtacaca cgactatgac aataaaccca ctaccgtcag gttatcattt  26580
cgatgaaatg ttttgatatc attaaatata acagtcacaa aaaatcatct aattataaca  26640
atataactta tacatatatt taactaaaaa cttagagttt ttgtaatgat tctaattgat  26700
gattagagtt tatagaaata caattaaata aaaaatataa ttttaaaaaa acatagtaaa  26760
gtcaatgaga tcctctctga cctcagtgat catttagtca tgtatgtaca acaatcattg  26820
ttcatcacat gactgtaaaa taaataagga taaacttggg aatatatata atatattgta  26880
ttaaataaaa aagggaaata caaatatcaa ttttagattc ccgagttgac acaactcacc  26940
atgcacgctg ccacctcagc tcccagctct cgtcacatgt ctcatgtcag ttaggtcttt  27000
ggtttttagt ctttgacaca actcgccatg catgttgcca cgtgagctcg ttcctcttcc  27060
catgatctca ccactgggca tgcatgctgc cacctcagct ggcacctctt ctctatatgt  27120
ccctagaggc catgcacagt gccacctcag cactcctctc agaacccata cgtacctgcc  27180
aatcggcttc tctccataaa tatctattta aattataact aattatttca tatacttaat  27240
tgatgacgtg gatgcattgc catcgttgtt taataattgt taattacgac atgataaata  27300
aaatgaaagt aaaaagtacg aaagattttc catttgttgt tgtataaata gagaagtgag  27360
```

```
tgatgcataa tgcatgaatg catgaccgcg ccaccatgac tgttggatac gacgaggaga  27420
tcccattcga gcaagttagg gctcataaca agccagacga cgcttggtgt gctattcacg  27480
gacacgtgta cgacgttacc aagttcgctt cagttcaccc aggaggagat attatcttgc  27540
tcgctgctgg aaaggaagct actgtcctct acgagaccta ccatgttaga ggagtgtctg  27600
acgctgtgct cagaaagtac agaataggaa agttgccaga cggacaagga ggagctaacg  27660
agaaggagaa gagaaccttg tctggattgt cctctgcttc ttactacacc tggaactccg  27720
atttctacag agtgatgagg gagagagttg tggctagatt gaaggagaga ggaaaggcta  27780
gaagaggagg atacgaactc tggatcaagg ctttcttgct ccttgttgga ttctggtcct  27840
ctctttactg gatgtgcacc ctcgatccat ctttcggagc tatcttggct gctatgtctt  27900
tgggagtgtt cgctgctttt gttggaacct gcatccaaca cgatggaaac cacggagctt  27960
tcgctcaatc tagatgggtt aacaaggtgg caggatggac tttggatatg atcggagctt  28020
ctggaatgac ttgggagttc caacacgtgt tgggacacca cccatacact aacttgatcg  28080
aggaggagaa cggattgcaa aaggtgtccg gaaagaagat ggataccaag ttggctgatc  28140
aagagtctga tccagatgtg ttctccacct acccaatgat gagattgcac ccttggcacc  28200
agaagaggtg gtatcacagg ttccagcaca tctacggacc tttcatcttc ggattcatga  28260
ccatcaacaa ggtggtgact caagatgttg gagtggtgtt gagaaagaga ctcttccaaa  28320
tcgatgctga gtgcagatat gcttccccaa tgtacgttgc taggttctgg attatgaagg  28380
ctttgaccgt gttgtatatg gttgctttgc cttgttatat gcaaggacct tggcacggat  28440
tgaaactctt cgctatcgct cacttcactt gcggagaggt tttggctacc atgttcatcg  28500
tgaaccacat tatcgaggga gtgtcttacg cttctaagga tgctgttaag ggaactatgg  28560
ctccaccaaa gactatgcac ggagtgaccc caatgaacaa cactagaaag gaggttgagg  28620
ctgaggcttc taagtctgga gctgtggtta agtctgtgcc attggatgat tgggctgctg  28680
ttcagtgcca aacctctgtg aactggtctg ttggatcttg gttttggaac cacttctctg  28740
gaggactcaa ccaccaaatc gagcaccacc tcttcccagg attgtctcac gagacctact  28800
accacatcca agacgtggtt caatctacct gtgctgagta cggagttcca taccaacacg  28860
agccatcttt gtggactgct tactggaaga tgctcgaaca ccttagacaa ttgggaaacg  28920
aggagactca cgagtcatgg cagagagctg cttgattaat gaactaagac tcccaaaacc  28980
accttccctg tgacagttaa accctgctta tacctttcct cctaataatg ttcatctgtc  29040
acacaaacta aaataaataa aatgggagca ataaataaaa tgggagctca tatatttaca  29100
ccatttacac tgtctattat tcaccatgcc aattattact tcataatttt aaaattatgt  29160
catttttaaa aattgcttaa tgatggaaag gattattata agttaaaagt ataacataga  29220
taaactaacc acaaaacaaa tcaatataaa ctaacttact ctcccatcta atttttattt  29280
aaatttcttt acacttctct tccatttcta tttctacaac attatttaac atttttattg  29340
tatttttctt actttctaac tctattcatt tcaaaaatca atatatgttt atcaccacct  29400
ctctaaaaaa aactttacaa tcattggtcc agaaaagtta aatcacgaga tggtcatttt  29460
agcattaaaa caacgattct tgtatcacta tttttcagca tgtagtccat tctcttcaaa  29520
caaagacagc ggctatataa tcgttgtgtt atattcagtc taaaacaact agctagcctc  29580
agctgacgtt acgtaacgct aggtagcgtc acgtgacgtt agctaacgct aggtagcgtc  29640
agctgagctt acgtaagcgc cacgggcagg acatagggac tactacaagc atagtatgct  29700
tcagacaaag agctaggaaa gaactcttga tggaggttaa gagaaaaaag tgctagaggg  29760
```

```
gcatagtaat caaacttgtc aaaaccgtca tcatgatgag ggatgacata atataaaaag  29820
ttgactaagg tcttggtagt actctttgat tagtattata tattggtgag aacatgagtc  29880
aagaggagac aagaaaccga ggaaccatag tttagcaaca agatggaagt tgcaaagttg  29940
agctagccgc tcgattagtt acatctccta agcagtacta caaggaatgg tctctatact  30000
ttcatgttta gcacatggta gtgcggattg acaagttaga aacagtgctt aggagacaaa  30060
gagtcagtaa aggtattgaa agagtgaagt tgatgctcga caggtcagga gaagtccctc  30120
cgccagatgg tgactaccaa ggggttggta tcagctgaga cccaaataag attcttcggt  30180
tgaaccagtg gttcgaccga gactcttagg gtgggatttc actgtaagat ttgtgcattt  30240
tgttgaatat aaattgacaa tttttttat ttaattatag attatttaga atgaattaca  30300
tatttagttt ctaacaagga tagcaatgga tgggtatggg tacaggttaa acatatctat  30360
tacccaccca tctagtcgtc gggttttaca cgtacccacc cgtttacata aaccagaccg  30420
gaattttaaa ccgtacccgt ccgttagcgg gtttcagatt tacccgttta atcgggtaaa  30480
acctgattac taaatatata tttttattt gataaacaaa acaaaaatgt taatattttc  30540
atattggatg caattttaag aaacacatat tcataaattt ccatatttgt aggaaaataa  30600
aaagaaaaat atattcaaga acacaaattt caccgacatg acttttatta cagagttgga  30660
attagatcta acaattgaaa aattaaaatt aagatagaat atgttgagga acatgacata  30720
gtataatgct gggttacccg tcgggtaggt atcgaggcgg atactactaa atccatccca  30780
ctcgctatcc gataatcact ggtttcgggt atacccattc ccgtcaacag gcctttttaa  30840
ccggataatt tcaacttata gtgaatgaat tttgaataaa tagttagaat accaaaatcc  30900
tggattgcat ttgcaatcaa attttgtgaa ccgttaaatt ttgcatgtac ttgggataga  30960
tataatagaa ccgaattttc attagtttaa tttataactt actttgttca aagaaaaaaa  31020
atatctatcc aatttactta taataaaaaa taatctatcc aagttactta ttataatcaa  31080
cttgtaaaaa ggtaagaata caaatgtggt agcgtacgtg tgattatatg tgacgaaatg  31140
ttatatctaa caaaagtcca aattcccatg gtaaaaaaaa tcaaaatgca tggcaggctg  31200
tttgtaacct tggaataaga tgttggccaa ttctggagcc gccacgtacg caagactcag  31260
ggccacgttc tcttcatgca aggatagtag aacaccactc cacccacctc ctatattaga  31320
cctttgccca accctcccca actttcccat cccatccaca aagaaaccga catttttatc  31380
ataaatcagg gtttcgtttt tgtttcatcg ataaactcaa aggtgatgat tttagggtct  31440
tgtgagtgtg ctttttgtt tgattctact gtagggttta tgttctttag ctcataggtt  31500
ttgtgtattt cttagaaatg tggcttcttt aatctctggg tttgtgactt tttgtgtggt  31560
ttctgtgttt ttcatatcaa aaacctattt tttccgagtt tttttaca aattcttact  31620
ctcaagcttg aatacttcac atgcagtgtt cttttgtaga ttttagagtt aatgtgttaa  31680
aaagtttgga tttttcttgc ttatagagct tcttcacttt gattttgtgg gtttttttgt  31740
tttaaaggtg agatttttga tgaggttttt gcttcaaaga tgtcaccttt ctgggtttgt  31800
cttttgaata aagctatgaa ctgtcacatg gctgacgcaa ttttgttact atgtcatgaa  31860
agctgacgtt tttccgtgtt atacatgttt gcttacactt gcatgcgtca aaaaaattgg  31920
ggctttttag ttttagtcaa agattttact tctcttttgg gatttatgaa ggaaagttgc  31980
aaactttctc aaattttacc atttttgctt tgatgtttgt ttagattgcg acagaacaaa  32040
ctcatatatg ttgaaatttt tgcttggttt tgtataggat tgtgtctttt gcttataaat  32100
```

gttgaaatct gaactttttt tttgtttggt ttctttgagc aggagataag gcgcaccacc 32160
atggcttcta catctgctgc tcaagacgct gctccttacg agttcccttc tctcactgag 32220
atcaagaggg ctcttccttc tgagtgtttc gaggcttctg ttcctctttc tctctactac 32280
accgctagat ctcttgctct tgctggatct ctcgctgttg ctctctctta cgctagagct 32340
ttgcctcttg ttcaggctaa cgctcttctt gatgctactc tctgcactgg atacgttctt 32400
ctccagggaa tcgttttctg ggattcttc accgttggtc acgattgtgg acacggagct 32460
ttctctagat ctcacgtgct caacttctct gttggaaccc tcatgcactc tatcatcctt 32520
acccctttcg agtcttggaa gctctctcac agacaccacc acaagaacac cggaaacatc 32580
gataaggacg agatcttcta ccctcaaaga gaggctgatt ctcaccctgt ttctagacac 32640
cttgtgatgt ctcttggatc tgcttggttc gcttaccttt tcgctggatt ccctcctaga 32700
accatgaacc acttcaaccc ttgggaggct atgtatgtta gaagagtggc tgctgtgatc 32760
atctctctcg gagttctttt cgctttcgct ggactctact cttacctcac cttcgttctt 32820
ggattcacca ctatggctat ctactacttc ggacctctct tcatcttcgc taccatgctt 32880
gttgttacca ctttcctcca ccacaacgat gaggagacac cttggtacgc tgattctgag 32940
tggacttacg tgaagggaaa cctctcttct gtggacagat cttacggtgc tctcatcgac 33000
aaccttagcc acaacatcgg aactcaccag atccaccacc tcttccctat catccctcac 33060
tacaagctca acgatgctac tgctgctttc gctaaggctt tccctgagct tgttaggaaa 33120
aacgctgctc ctatcatccc aactttcttc aggatggctg ctatgtacgc taagtacgga 33180
gttgttgaca ctgatgctaa gaccttcact ctcaaggagg ctaaggctgc tgctaagact 33240
aagtcatctt gatgattaat gaaggccgca gatatcagat ctggtcgacc tagaggatcc 33300
ccggccgcaa agataataac aaaagcctac tatataacgt acatgcaagt attgtatgat 33360
attaatgttt ttacgtacgt gtaaacaaaa ataattacgt ttgtaacgta tggtgatgat 33420
gtggtgcact aggtgtaggc cttgtattaa taaaaagaag tttgttctat atagagtggt 33480
ttagtacgac gatttattta ctagtcggat tggaatagag aaccgaattc ttcaatcctt 33540
gcttttgatc aagaattgaa accgaatcaa atgtaaaagt tgatatattt gaaaaacgta 33600
ttgagcttat gaaaatgcta atactctcat ctgtatggaa aagtgacttt aaaaccgaac 33660
ttaaaagtga caaaagggga atatcgcatc aaaccgaatg aaaccgatct acgtaggctc 33720
agctgagctt acctaaggct acgtaggctc acgtgacgtt acgtaaggct acgtagcgtc 33780
acgtgagctt acctaactct agctagcctc acgtgacctt agctaacact aggtagcgtc 33840
agcttagcag atatttggtg tctaaatgtt tattttgtga tatgttcatg tttgaaatgg 33900
tggtttcgaa accagggaca acgttgggat ctgatagggt gtcaaagagt attatggatt 33960
gggacaattt cggtcatgag ttgcaaattc aagtatatcg ttcgattatg aaaattttcg 34020
aagaatatcc catttgagag agtctttacc tcattaatgt ttttagatta tgaaatttta 34080
tcatagttca tcgtagtctt tttggtgtaa aggctgtaaa aagaaattgt tcacttttgt 34140
tttcgtttat gtgaaggctg taaaagattg taaaagacta ttttggtgtt ttggataaaa 34200
tgatagtttt tatagattct tttgctttta gaagaaatac atttgaaatt ttttccatgt 34260
tgagtataaa ataccgaaat cgattgaaga tcatagaaat attttaactg aaaacaaatt 34320
tataactgat tcaattctct ccatttttat acctatttaa ccgtaatcga ttctaataga 34380
tgatcgattt tttatataat cctaattaac caacggcatg tattggataa ttaaccgatc 34440
aactctcacc cctaatagaa tcagtatttt ccttcgacgt taattgatcc tacactatgt 34500

```
aggtcatatc catcgtttta atttttggcc accattcaat tctgtcttgc ctttagggat  34560
gtgaatatga acggccaagg taagagaata aaaataatcc aaattaaagc aagagaggcc  34620
aagtaagata atccaaatgt acacttgtca ttgccaaaat tagtaaaata ctcggcatat  34680
tgtattccca cacattatta aaataccgta tatgtattgg ctgcatttgc atgaataata  34740
ctacgtgtaa gcccaaaaga acccacgtgt agcccatgca aagttaacac tcacgacccc  34800
attcctcagt ctccactata taaacccacc atccccaatc tcaccaaacc caccacacaa  34860
ctcacaactc actctcacac cttaaagaac caatcaccac caaaaaaagt tctttgcttt  34920
cgaagttgcc gcaacctaaa caggtttttc cttcttcttt cttcttatta actacgacct  34980
tgtcctttgc ctatgtaaaa ttactaggtt ttcatcagtt acactgatta agttcgttat  35040
agtggaagat aaaatgccct caaagcattt tgcaggatat ctttgatttt tcaaagatat  35100
ggaactgtag agtttgatag tgttcttgaa tgtggttgca tgaagttttt ttggtctgca  35160
tgttattttt tcctcgaaat atgttttgag tccaacaagt gattcacttg ggattcagaa  35220
agttgttttc tcaatatgta acagtttttt tctatggaga aaaatcatag ggaccgttgg  35280
ttttggcttc tttaattttg agctcagatt aaacccattt tacccggtgt tcttggcaga  35340
attgaaaaca gtacgtagta ccgcgcctac catgccacct agtgctgcta gtgaaggtgg  35400
tgttgctgaa cttagagctg ctgaagttgc tagctacact agaaaggctg ttgacgaaag  35460
acctgacctc actatagttg gtgacgctgt ttacgacgct aaggctttta gggacgagca  35520
ccctggtggt gctcacttcg ttagcctttt cggaggtagg gacgctactg aggcttttat  35580
ggaatatcac cgtagagctt ggcctaaggc taggatgtct aagttcttcg ttggttcact  35640
tgacgctagc gagaagccta ctcaagctga ttcagcttac cttagacttt gcgctgaggt  35700
taacgctctt ttgcctaagg gtagcggagg attcgctcct cctagctact ggcttaaggc  35760
tgctgctctt gttgttgctg ctgttagtat agagggttat atgctcctta ggggtaagac  35820
ccttttgctt agcgttttcc ttggactcgt gttcgcttgg ataggactta atattcagca  35880
cgacgctaat cacggtgctc ttagtagaca ctcagtgatt aactactgcc tcggttacgc  35940
tcaggattgg ataggtggta atatggtgct ttggcttcaa gagcacgttg tgatgcacca  36000
cctccacact aacgacgttg acgctgatcc tgatcaaaag gctcacggtg ttcttagact  36060
taagcctact gacggttgga tgccttggca cgcacttcaa caactctata tccttcctgg  36120
tgaggctatg tacgctttta agcttctttt cttggacgcc cttgagcttc ttgcttggag  36180
gtgggagggt gagaagatta gccctcttgc tagagctttg ttcgctcctg ctgttgcttg  36240
taagcttgga ttctgggcta gattcgttgc tctccctctc tggcttcaac ctactgttca  36300
cactgctttg tgtatctgtg ctactgtgtg tactggtagc ttctacctcg ccttcttctt  36360
ctttatctct cacaacttcg acggtgttgg tagcgttgga cctaagggat cacttcctag  36420
atcagctact ttcgttcaac gtcaggttga gactagctct aacgttggtg gttactggct  36480
tggagttctt aacggtggac ttaactttca gatagagcac cacttgttcc ctaggcttca  36540
ccactcttac tacgctcaaa tagctcctgt ggttaggact cacatagaga agctcggttt  36600
taagtaccgt cacttcccta ccgttggatc taaccttagc tcaatgcttc agcatatggg  36660
taagatggga actagacctg gtgctgagaa gggtggtaag gctgagtagt gattaatgaa  36720
taattgattg ctgctttaat gagatatgcg agacgcctat gatcgcatga tatttgcttt  36780
caattctgtt gtgcacgttg taaaaaacct gagcatgtgt agctcagatc cttaccgccg  36840
```

```
gtttcggttc attctaatga atatatcacc cgttactatc gtatttttat gaataatatt  36900
ctccgttcaa tttactgatt gtctacgtag cgtcacctga cgttacgtaa ggctacctag  36960
gctcacgtga cgttacgtaa cgctacgtag cgtcaggtga ggttagctaa cgctagctag  37020
cctcacctga cgttaggtaa ggctacgtag cgtcacctga gattagctaa gcctacctag  37080
actcacgtga ccttaggtaa cgctacgtag cgtcaaagct ttacaacgct acacaaaact  37140
tataaccgta atcaccattc attaacttaa ctactatcac atgcattcat gaattgaaac  37200
gagaaggatg taaatagttg ggaagttatc tccacgttga agagatcgtt agcgagagct  37260
gaaagaccga gggaggagac gccgtcaaca cggacagagt cgtcgaccct cacatgaagt  37320
aggaggaatc tccgtgagga gccagagaga cgtctttggt cttcggtttc gatccttgat  37380
ctgacggaga agacgagaga agtgcgactg gactccgtga ggaccaacag agtcgtcctc  37440
ggtttcgatc gtcggtattg gtggagaagg cggaggaatc tccgtgacga gccagagaga  37500
tgtcgtcggt cttcggtttc gatccttgat ctgacggaga agacgagaga agtgcgacga  37560
gactccgtga ggaccaacag agttgtcctc ggtttcgatc gtcggtttcg gcggagaagg  37620
cggaggaatc tccgtgagga gccagagaga cgtcgttggt cttcggtttc gatccttgat  37680
ctgttggaga agacgagaca agtgggacga gactcaacga cggagtcaga gacgtcgtcg  37740
gtcttcggtt tcggccgaga aggcggagtc ggtcttcggt ttcggccgag aaggcggagg  37800
agacgtcttc gatttgggtc tctcctcttg acgaagaaaa caaagaacac gagaaataat  37860
gagaaagaga acaaaagaaa aaaaaataaa aataaaaata aaatttggtc ctcttatgtg  37920
gtgacacgtg gtttgaaacc caccaaataa tcgatcacaa aaaacctaag ttaaggatcg  37980
gtaataacct ttctaattaa ttttgattta tattaaatca ctctttttat ttataaaccc  38040
cactaaatta tgcgatattg attgtctaag tacaaaaatt ctctcgaatt caatacacat  38100
gtttcatata tttagccctg ttcatttaat attactagcg catttttaat ttaaaatttt  38160
gtaaactttt ttggtcaaag aacatttttt taattagaga cagaaatcta gactctttat  38220
ttggaataat agtaataaag atatattagg caatgagttt atgatgttat gtttatatag  38280
tttatttcat tttaaattga aaagcattat ttttatcgaa atgaatctag tatacaatca  38340
atatttatgt tttttcatca gatactttcc tattttttgg cacctttcat cggactactg  38400
atttatttca atgtgtatgc atgcatgagc atgagtatac acatgtcttt taaaatgcat  38460
gtaaagcgta acggaccaca aaagaggatc catacaaata catctcatcg cttcctctac  38520
tattctccga cacacacact gagcatggtg cttaaacact ctggtgagtt ctagtacttc  38580
tgctatgatc gatctcatta ccatttctta aatttctctc cctaaatatt ccgagttctt  38640
gatttttgat aacttcaggt tttctctttt tgataaatct ggtctttcca tttttttttt  38700
tttgtggtta atttagtttc ctatgttctt cgattgtatt atgcatgatc tgtgtttgga  38760
ttctgttaga ttatgtattg gtgaatatgt atgtgttttt gcatgtctgg ttttggtctt  38820
aaaaatgttc aaatctgatg atttgattga agctttttta gtgttggttt gattcttctc  38880
aaaactactg ttaatttact atcatgtttt ccaactttga ttcatgatga cacttttgtt  38940
ctgctttgtt ataaaatttt ggttggtttg attttgtaat tatagtgtaa ttttgttagg  39000
aatgaacatg ttttaatact ctgttttcga tttgtcacac attcgaatta ttaatcgata  39060
atttaactga aaattcatgg ttctagatct tgttgtcatc agattatttg tttcgataat  39120
tcatcaaata tgtagtcctt ttgctgattt gcgactgttt catttttct caaaattgtt  39180
ttttgttaag tttatctaac agttatcgtt gtcaaaagtc tctttcattt tgcaaaatct  39240
```

```
tcttttttt tttgtttgta actttgtttt ttaagctaca catttagtct gtaaaatagc  39300
atcgaggaac agttgtctta gtagacttgc atgttcttgt aacttctatt tgtttcagtt  39360
tgttgatgac tgctttgatt ttgtaggtca aaccgcgcca tgtctgctag cggagctttg  39420
ttgcctgcta tagctttcgc tgcttacgct tacgctacct acgcttatgc tttcgagtgg  39480
agccacgcta acggaatcga taacgtggat gctagagagt ggattggagc tttgtctttg  39540
agactccctg caattgcaac cacaatgtac ctcttgttct gccttgtggg acctagattg  39600
atggctaaga gggaggcttt tgatcctaag ggatttatgc tcgcttacaa cgcttaccaa  39660
accgctttca acgttgtggt gctcggaatg ttcgctagag agatctctgg attgggacaa  39720
cctgtttggg gatctactat gccttggagc gataggaagt ccttcaagat tttgttggga  39780
gtgtggctcc actacaacaa taagtacctc gagttgttgg atactgtgtt catggtggct  39840
aggaaaaaga ccaagcagct ctctttcttg cacgtgtacc accacgcttt gttgatttgg  39900
gcttggtggc ttgtttgtca cctcatggct accaacgatt gcatcgatgc ttatttcgga  39960
gctgcttgca actctttcat ccacatcgtg atgtactcct actacctcat gtctgctttg  40020
ggaattaggt gcccttggaa gagatatatc acccaggctc agatgttgca attcgtgatc  40080
gtgttcgctc acgctgtttt cgtgctcaga caaaagcact gccctgttac tttgccttgg  40140
gcacaaatgt tcgtgatgac aaatatgttg gtgctcttcg gaaacttcta cctcaaggct  40200
tactctaaca agtctagggg agatggagct tcttctgtta agcctgctga gactactaga  40260
gcaccttctg tgagaagaac caggtcaagg aagatcgatt gatagttaat gaactaagtt  40320
tgatgtatct gagtgccaac gtttactttg tctttccttt cttttattgg ttatgattag  40380
atgtttacta tgttctctct ttttcgttat aaataaagaa gttcaattct tctatagttt  40440
caaacgcgat tttaagcgtt tctatttagg tttacatgat ttcttttaca aaatcatctt  40500
taaaatacag tatattttta gttttcataa aatatttaaa gaaatgaaag tttataaaca  40560
ttcactccta ttctctaatt aaggatttgt aaaacaaaaa ttttgtaagc atatcgattt  40620
atgcgttttg tcttaattag ctcactaaat aataaataat agcttatgtt gtgggactgt  40680
ttaattacct aacttagaac taaaatcaac tctttgtgct agctagcctc agctgacgtt  40740
acgtaacgct aggtagcgtc acgtgacgtt agctaacgct aggtagcgtc agctgagctt  40800
acgtaagcgc ttaattaaag tactgatatc ggtaccaaat cgaatccaaa aattacggat  40860
atgaatatag gcatatccgt atccgaatta tccgtttgac agctagcaac gattgtacaa  40920
ttgcttcttt aaaaaaggaa gaaagaaaga aagaaaagaa tcaacatcag cgttaacaaa  40980
cggccccgtt acggcccaaa cggtcatata gagtaacggc gttaagcgtt gaaagactcc  41040
tatcgaaata cgtaaccgca aacgtgtcat agtcagatcc cctcttcctt caccgcctca  41100
aacacaaaaa taatcttcta cagcctatat atacaacccc cccttctatc tctcctttct  41160
cacaattcat catctttctt tctctacccc caattttaag aaatcctctc ttctcctctt  41220
cattttcaag gtaaatctct ctctctctct ctctctctgt tattccttgt tttaattagg  41280
tatgtattat tgctagtttg ttaatctgct tatcttatgt atgccttatg tgaatatctt  41340
tatcttgttc atctcatccg tttagaagct ataaatttgt tgatttgact gtgtatctac  41400
acgtggttat gtttatatct aatcagatat gaatttcttc atattgttgc gtttgtgtgt  41460
accaatccga aatcgttgat ttttttcatt taatcgtgta gctaattgta cgtatacata  41520
tggatctacg tatcaattgt tcatctgttt gtgtttgtat gtatacagat ctgaaaacat  41580
```

```
cacttctctc atctgattgt gttgttacat acatagatat agatctgtta tatcattttt  41640
tttattaatt gtgtatatat atatgtgcat agatctggat tacatgattg tgattattta  41700
catgattttg ttatttacgt atgtatatat gtagatctgg actttttgga gttgttgact  41760
tgattgtatt tgtgtgtgta tatgtgtgtt ctgatcttga tatgttatgt atgtgcagct  41820
gaaccatggc ggcggcaaca acaacaacaa caacatcttc ttcgatctcc ttctccacca  41880
aaccatctcc ttcctcctcc aaatcaccat taccaatctc cagattctcc ctcccattct  41940
ccctaaaccc caacaaatca tcctcctcct cccgccgccg cggtatcaaa tccagctctc  42000
cctcctccat ctccgccgtg ctcaacacaa ccaccaatgt cacaaccact ccctctccaa  42060
ccaaacctac caaacccgaa acattcatct cccgattcgc tccagatcaa ccccgcaaag  42120
gcgctgatat cctcgtcgag gctttagaac gtcaaggcgt agaaaccgta ttcgcttacc  42180
ctggaggtac atcaatggag attcaccaag ccttaacccg ctcttcctca atccgtaacg  42240
tccttcctcg tcacgaacaa ggaggtgtat tcgcagcaga aggatacgct cgatcctcag  42300
gtaaaccagg tatctgtata gccacttcag gtcccggagc tacaaatctc gttagcggat  42360
tagccgatgc gttgttagat agtgttcctc ttgtagcaat cacaggacaa gtccctcgtc  42420
gtatgattgg tacagatgcg tttcaagaga ctccgattgt tgaggtaacg cgttcgatta  42480
cgaagcataa ctatcttgtg atggatgttg aagatatccc aaggattatt gaagaggctt  42540
tctttttagc tacttctggt agacctggac ctgttttggt tgatgttcct aaagatattc  42600
aacaacagct tgcgattcct aattgggaac aggctatgag attacctggt tatatgtcta  42660
ggatgcctaa acctccggaa gattctcatt tggagcagat tgttaggttg atttctgagt  42720
ctaagaagcc tgtgttgtat gttggtggtg gttgtcttaa ttctagcgat gaattgggta  42780
ggtttgttga gcttacgggc atccctgttg cgagtacgtt gatggggctg ggatcttatc  42840
cttgtgatga tgagttgtcg ttacatatgc ttggaatgca tgggactgtg tatgcaaatt  42900
acgctgtgga gcatagtgat ttgttgttgg cgtttggggt aaggtttgat gatcgtgtca  42960
cgggtaaact tgaggctttt gctagtaggg ctaagattgt tcatattgat attgactcgg  43020
ctgagattgg gaagaataag actcctcatg tgtctgtgtg tggtgatgtt aagctggctt  43080
tgcaagggat gaataaggtt cttgagaacc gagcggagga gcttaaactt gattttggag  43140
tttggaggaa tgagttgaac gtacagaaac agaagtttcc gttgagcttt aagacgtttg  43200
gggaagctat tcctccacag tatgcgatta aggtccttga tgagttgact gatggaaaag  43260
ccataataag tactggtgtc gggcaacatc aaatgtgggc ggcgcagttc tacaattaca  43320
agaaaccaag gcagtggcta tcatcaggag gccttggagc tatgggattt ggacttcctg  43380
ctgcgattgg agcgtctgtt gctaaccctg atgcgatagt tgtggatatt gacggagatg  43440
gaagttttat aatgaatgtg caagagctag ccactattcg tgtagagaat cttccagtga  43500
aggtactttt attaaacaac cagcatcttg gcatggttat gcaatgggaa gatcggttct  43560
acaaagctaa ccgagctcac acatttctcg ggacccggc tcaggaggac gagatattcc  43620
cgaacatgtt gctgtttgca gcagcttgcg ggattccagc ggcgagggtg acaaagaaag  43680
cagatctccg agaagctatt cagacaatgc tggatacacc aggaccttac ctgttggatg  43740
tgatttgtcc gcaccaagaa catgtgttgc cgatgatccc gaatggtggc actttcaacg  43800
atgtcataac ggaaggagat ggccggatta aatactgaga gatgaaaccg gtgattatca  43860
gaacctttta tggtctttgt atgcatatgg taaaaaaact tagtttgcaa tttcctgttt  43920
gttttggtaa tttgagtttc ttttagttgt tgatctgcct gctttttggt ttacgtcaga  43980
```

```
ctactactgc tgttgttgtt tggtttcctt tctttcattt tataaataaa taatccggtt  44040
cggtttactc cttgtgactg gctcagtttg gttattgcga aatgcgaatg gtaaattgag  44100
taattgaaat tcgttattag ggttctaagc tgttttaaca gtcactgggt taatatctct  44160
cgaatcttgc atggaaaatg ctcttaccat tggtttttaa ttgaaatgtg ctcatatggg  44220
ccgtggtttc caaattaaat aaaactacga tgtcatcgag aagtaaaatc aactgtgtcc  44280
acattatcag ttttgtgtat acgatgaaat agggtaattc aaaatctagc ttgatatgcc  44340
ttttggttca ttttaacctt ctgtaaacat tttttcagat tttgaacaag taaatccaaa  44400
aaaaaaaaaa aaaatctcaa ctcaacacta aattatttta atgtataaaa gatgcttaaa  44460
acatttggct taaaagaaag aagctaaaaa catagagaac tcttgtaaat tgaagtatga  44520
aaatatactg aattgggtat tatatgaatt tttctgattt aggattcaca tgatccaaaa  44580
aggaaatcca gaagcactaa tcagacattg gaagtaggat taatcagtga tcagtaacta  44640
ttaaattcaa ttaaccgcgg acatctacat ttttgaattg aaaaaaaatt ggtaattact  44700
ctttcttttt ctccatattg accatcatac tcattgtaag acacacagat gaagaagtca  44760
aatagctcga cattcctttg gtctggtcca gtgatgtcga ctcacaaagc gaagattgca  44820
tgaatagact atcatgtgtt tgctatgtat gagtactatg gaatcgaggg atcatttatt  44880
tttcatgtca ttgttcttgg aggttgtgtg gagaggcatc accattaatc ttctgaacat  44940
cagctatact aatcattaat tggaatcagc gactgcaaat tatggcagag gatgttggaa  45000
atagtaccac cacattccta atccactatg ctttccaagc tgcagtaatt tgagttggag  45060
acgggagttt tgctcattta ctcaggctct tggacaaaca aatgtgaaat cgcatatctg  45120
ctcaatccga catactaatc aaaggtcaag aatttttttt agagaagatg aaaaccataa  45180
tgaaagcatc taatgtttat agaaaattac caaaaatacc acatttatga aaaattatca  45240
aaaatacaat attcatagta tcacttttca tatttacaat aaccacgttt gttctcaatt  45300
ttaacgaaga acaaacgaca tttataatcc taagataatt ttttctaatt caaaaataat  45360
tttcgatttt caaaaaaaaa attgaaaaaa aaattgaaaa gaaaaattca aaacaaaatt  45420
atatgaaagt tcaaatttga aaaatgataa ttcaaaaaca taaaaaaata tatttttatt  45480
taaataatta tttattatat atatatagac catggagcaa gggggcgtgg gccccggggc  45540
ccaaactttt tttcccatat ataatgtcaa caaggacccg atttttagaa aaaaaaatag  45600
gtataaagga gtccaaaaaa ttcaaattag ttatatatgt atgtaaaaaa atattaaaat  45660
ttattttgcc caagggccta tagattcatt gggccgaccc tggggttggg gttgtgtgtg  45720
tgtcattcta taattaaccg gcaaaaactc caaaattttt atttaacaaa tgtataa     45777
```

```
<210> SEQ ID NO 21
<211> LENGTH: 43720
<212> TYPE: DNA
<213> ORGANISM: Artificial sequence
<220> FEATURE:
<223> OTHER INFORMATION: T-DNA insertion in LBFDAU Locus 1, including
      left and right border sequences

<400> SEQUENCE: 21
```

```
cagtcagcat catcacacca aaagttaggc ccgaatagtt tgaaattaga aagctcgcaa     60
ttgaggtcta caggccaaat tcgctcttag ccgtacaata ttactcaccg gtgcgatgcc    120
ccccatcgta ggtgaaggtg gaaattaatg gcgcgcctga tcactgatta gtaactatta    180
cgtaagccta cgtagcgtca cgtgacgtta gctaacgcta cgtagcctca gctgacgtta    240
```

```
cgtaagccta cgtagcgtca cgtgagctta gctaacgcta cctaggctca gctgacgtta    300
cgtaacgcta gctagcgtca ctcctgcagc aaatttacac attgccacta aacgtctaaa    360
cccttgtaat ttgtttttgt tttactatgt gtgttatgta tttgatttgc gataaatttt    420
tatatttggt actaaattta taacaccttt tatgctaacg tttgccaaca cttagcaatt    480
tgcaagttga ttaattgatt ctaaattatt tttgtcttct aaatacatat actaatcaac    540
tggaaatgta aatatttgct aatatttcta ctataggaga attaaagtga gtgaatatgg    600
taccacaagg tttggagatt taattgttgc aatgctgcat ggatggcata tacaccaaac    660
attcaataat tcttgaggat aataatggta ccacacaaga tttgaggtgc atgaacgtca    720
cgtggacaaa aggtttagta atttttcaag acaacaatgt taccacacac aagttttgag    780
gtgcatgcat ggatgccctg tggaaagttt aaaaatattt tggaaatgat ttgcatggaa    840
gccatgtgta aaaccatgac atccacttgg aggatgcaat aatgaagaaa actacaaatt    900
tacatgcaac tagttatgca tgtagtctat ataatgagga ttttgcaata ctttcattca    960
tacacactca ctaagtttta cacgattata atttcttcat agccagtact gtttaagctt   1020
cactgtctct gaatcggcaa aggtaaacgt atcaattatt ctacaaaccc ttttattttt   1080
cttttgaatt accgtcttca ttggttatat gataacttga taagtaaagc ttcaataatt   1140
gaatttgatc tgtgtttttt tggccttaat actaaatcct tacataagct ttgttgcttc   1200
tcctcttgtg agttgagtgt taagttgtaa taatggttca ctttcagctt tagaagaaac   1260
catggaagtt gttgagaggt tctacggaga gttggatgga aaggtttccc aaggagtgaa   1320
cgctttgttg ggatctttcg gagttgagtt gactgatacc ccaactacta agggattgcc   1380
actcgttgat tctccaactc caattgtgtt gggagtgtct gtttacttga ccatcgtgat   1440
cggaggattg ctttggatca aggctagaga tctcaagcca agagcttctg agccattctt   1500
gttgcaagct ttggtgttgg tgcacaactt gttctgcttc gctttgtctc tttacatgtg   1560
cgtgggtatc gcttaccaag ctatcacctg gagatattcc ttgtggggaa acgcttataa   1620
cccaaagcac aaggagatgg ctatcctcgt ttacctcttc tacatgtcca agtacgtgga   1680
gttcatggat accgtgatca tgatcctcaa gagatccacc agacagattt ctttcctcca   1740
cgtgtaccac cactcttcta tctcccttat ctggtgggct attgctcacc acgctccagg   1800
aggagaggct tattggagtg ctgctctcaa ctctggagtg cacgtgttga tgtacgctta   1860
ctacttcttg gctgcttgct tgagatcttc cccaaagctc aagaacaagt acctcttctg   1920
gggaagatac ctcacccaat tccagatgtt ccagttcatg ctcaacttgg tgcaagctta   1980
ctacgatatg aaaaccaacg ctccatatcc acaatggctc atcaagatcc tcttctacta   2040
catgatctcc ctcttgttcc tcttcggaaa cttctacgtg caaaagtaca tcaagccatc   2100
cgatggaaag caaaagggag ctaagaccga gtgatcgaca agctcgagtt tctccataat   2160
aatgtgtgag tagttcccag ataagggaat tagggttcct atagggtttc gctcatgtgt   2220
tgagcatata agaaaccctt agtatgtatt tgtatttgta aaatacttct atcaataaaa   2280
tttctaattc ctaaaaccaa aatccagtac taaaatccag atcccccgaa ttaattcggc   2340
gttaattcag ctagctagcc tcagctgacg ttacgtaacg ctaggtagcg tcacgtgacg   2400
ttagctaacg ctaggtagcg tcagctgagc ttacgtaagc gcttagcaga tatttggtgt   2460
ctaaatgttt attttgtgat atgttcatgt ttgaaatggt ggtttcgaaa ccagggacaa   2520
cgttgggatc tgatagggtg tcaaagagta ttatggattg ggacaatttc ggtcatgagt   2580
```

```
tgcaaattca agtatatcgt tcgattatga aaattttcga agaatatccc atttgagaga   2640
gtctttacct cattaatgtt tttagattat gaaattttat catagttcat cgtagtcttt   2700
ttggtgtaaa ggctgtaaaa agaaattgtt cacttttgtt ttcgtttatg tgaaggctgt   2760
aaaagattgt aaaagactat tttggtgttt tggataaaat gatagttttt atagattctt   2820
ttgcttttag aagaaataca tttgaaattt tttccatgtt gagtataaaa taccgaaatc   2880
gattgaagat catagaaata ttttaactga aaacaaattt ataactgatt caattctctc   2940
catttttata cctatttaac cgtaatcgat tctaatagat gatcgatttt ttatataatc   3000
ctaattaacc aacggcatgt attggataat taaccgatca actctcaccc ctaatagaat   3060
cagtattttc cttcgacgtt aattgatcct acactatgta ggtcatatcc atcgttttaa   3120
tttttggcca ccattcaatt ctgtcttgcc tttagggatg tgaatatgaa cggccaaggt   3180
aagagaataa aaataatcca aattaaagca agagaggcca agtaagataa tccaaatgta   3240
cacttgtcat tgccaaaatt agtaaaatac tcggcatatt gtattcccac acattattaa   3300
aataccgtat atgtattggc tgcatttgca tgaataatac tacgtgtaag cccaaaagaa   3360
cccacgtgta gcccatgcaa agttaacact cacgacccca ttcctcagtc tccactatat   3420
aaacccacca tccccaatct caccaaaccc accacacaac tcacaactca ctctcacacc   3480
ttaaagaacc aatcaccacc aaaaaatttc acgatttgga atttgattcc tgcgatcaca   3540
ggtatgacag gttagatttt gttttgtata gttgtataca tacttctttg tgatgttttg   3600
tttacttaat cgaatttttg gagtgtttta aggtctctcg tttagaaatc gtggaaaata   3660
tcactgtgtg tgtgttctta tgattcacag tgtttatggg tttcatgttc tttgttttat   3720
cattgaatgg gaagaaattt cgttgggata caaatttctc atgttcttac tgatcgttat   3780
taggagtttg gggaaaaagg aagagttttt ttggttggtt cgagtgatta tgaggttatt   3840
tctgtatttg atttatgagt taatggtcgt tttaatgttg tagaccatgg gaaaaggatc   3900
tgagggaaga tctgctgcta gagagatgac tgctgaggct aacggagata agagaaagac   3960
catcctcatt gagggagtgt tgtacgatgc taccaacttc aaacacccag gaggttccat   4020
tattaacttc ctcaccgagg gagaagctgg agttgatgct acccaagctt acagagagtt   4080
ccatcagaga tccggaaagg ctgataagta cctcaagtcc ctcccaaagt tggatgcttc   4140
taaggtggag tctaggttct ctgctaagga gcaggctaga agggacgcta tgaccaggga   4200
ttacgctgct ttcagagagg agttggttgc tgagggatac ttcgatccat ctatcccaca   4260
catgatctac agagtggtgg agattgtggc tttgttcgct ttgtctttct ggttgatgtc   4320
taaggcttct ccaacctctt tggttttggg agtggtgatg aacggaatcg ctcaaggaag   4380
atgcggatgg gttatgcacg agatgggaca cggatctttc actggagtta tctggctcga   4440
tgataggatg tgcgagttct tctacggagt tggatgtgga atgtctggac actactggaa   4500
gaaccagcac tctaagcacc acgctgctcc aaacagattg gagcacgatg tggatttgaa   4560
caccttgcca ctcgttgctt tcaacgagag agttgtgagg aaggttaagc caggatcttt   4620
gttggctttg tggctcagag ttcaggctta tttgttcgct ccagtgtctt gcttgttgat   4680
cggattggga tggaccttgt acttgcaccc aagatatatg ctcaggacca agagacacat   4740
ggagtttgtg tggatcttcg ctagatatat cggatggttc tccttgatgg gagctttggg   4800
atattctcct ggaacttctg tgggaatgta cctctgctct ttcggacttg gatgcatcta   4860
catcttcctc caattcgctg tgtctcacac ccacttgcca gttaccaacc cagaggatca   4920
attgcactgg cttgagtacg ctgctgatca caccgtgaac atctctacca agtcttggtt   4980
```

```
ggttacctgg tggatgtcta acctcaactt ccaaatcgag caccacttgt tcccaaccgc   5040

tccacaattc aggttcaagg agatctctcc aagagttgag gctctcttca agagacacaa   5100

cctcccttac tacgatttgc catacacctc tgctgtttct actaccttcg ctaacctcta   5160

ctctgttgga cactctgttg gagctgatac caagaagcag gattgactgc tttaatgaga   5220

tatgcgagac gcctatgatc gcatgatatt tgctttcaat tctgttgtgc acgttgtaaa   5280

aaacctgagc atgtgtagct cagatcctta ccgccggttt cggttcattc taatgaatat   5340

atcacccgtt actatcgtat ttttatgaat aatattctcc gttcaattta ctgattgtct   5400

acgtaggctc agctgagctt acctaaggct acgtaggctc acgtgacgtt acgtaaggct   5460

acgtagcgtc acgtgagctt acctaactct agctagcctc acgtgacctt agctaacact   5520

aggtagcgtc agctcgacgg cccggactgt atccaacttc tgatctttga atctctctgt   5580

tccaacatgt tctgaaggag ttctaagact tttcagaaag cttgtaacat gctttgtaga   5640

ctttctttga attactcttg caaactctga ttgaacctac gtgaaaactg ctccagaagt   5700

tctaaccaaa ttccgtcttg ggaaggccca aaatttattg agtacttcag tttcatggac   5760

gtgtcttcaa agatttataa cttgaaatcc catcattttt aagagaagtt ctgttccgca   5820

atgtcttaga tctcattgaa atctacaact cttgtgtcag aagttcttcc agaatcaact   5880

tgcatcatgg tgaaaatctg gccagaagtt ctgaacttgt catatttctt aacagttaga   5940

aaaatttcta agtgtttaga attttgactt ttccaaagca aacttgactt ttgactttct   6000

taataaaaca aacttcatat tctaacatgt cttgatgaaa tgtgattctt gaaatttgat   6060

gttgatgcaa aagtcaaagt ttgacttttc agtgtgcaat tgaccatttt gctcttgtgc   6120

caattccaaa cctaaattga tgtatcagtg ctgcaaactt gatgtcatgg aagatcttat   6180

gagaaaattc ttgaagactg agaggaaaaa ttttgtagta caacacaaag aatcctgttt   6240

ttcatagtcg gactagacac attaacataa aacaccactt cattcgaaga gtgattgaag   6300

aaggaaatgt gcagttacct ttctgcagtt cataagagca acttacagac acttttacta   6360

aaatactaca aagaggaaga ttttaacaac ttagagaagt aatgggagtt aaagagcaac   6420

acattaaggg ggagtgttaa aattaatgtg ttgtaaccac cactaccttt agtaagtatt   6480

ataagaaaat tgtaatcatc acattataat tattgtcctt atttaaaatt atgataaagt   6540

tgtatcatta agattgagaa aaccaaatag tcctcgtctt gatttttgaa ttattgtttt   6600

ctatgttact tttcttcaag cctatataaa aactttgtaa tgctaaattg tatgctggaa   6660

aaaaatgtgt aatgaattga atagaaatta tggtatttca aagtccaaaa tccatcaata   6720

gaaatttagt acaaaacgta actcaaaaat attctcttat tttaaatttt acaacaatat   6780

aaaaatattc tcttatttta aattttacaa taatataatt tatcacctgt cacctttaga   6840

ataccaccaa caatattaat acttagatat tttattctta ataattttga gatctctcaa   6900

tatatctgat atttatttta tatttgtgtc atattttctt atgttttaga gttaaccctt   6960

atatcttggt caaactagta attcaatata tgagtttgtg aaggacacat tgacatcttg   7020

aaacattggt tttaaccttg ttggaatgtt aaaggtaata aaacattcag aattatgacc   7080

atctattaat atacttcctt tgtcttttaa aaaagtgtgc atgaaaatgc tctatggtaa   7140

gctagagtgt cttgctggcc tgtgtatatc aattccattt ccagatggta gaaactgcca   7200

ctacgaataa ttagtcataa gacacgtatg ttaacacacg tccccttgca tgtttttttgc   7260

catatattcc gtctctttct tttcttcac gtataaaaca atgaactaat taatagagcg   7320
```

```
atcaagctga acagttcttt gctttcgaag ttgccgcaac ctaaacaggt ttttccttct   7380
tctttcttct tattaactac gaccttgtcc tttgcctatg taaaattact aggttttcat   7440
cagttacact gattaagttc gttatagtgg aagataaaat gccctcaaag cattttgcag   7500
gatatctttg atttttcaaa gatatggaac tgtagagttt gatagtgttc ttgaatgtgg   7560
ttgcatgaag ttttttggt ctgcatgtta ttttttcctc gaaatatgtt ttgagtccaa   7620
caagtgattc acttgggatt cagaaagttg ttttctcaat atgtaacagt ttttttctat   7680
ggagaaaaat catagggacc gttggttttg gcttctttaa ttttgagctc agattaaacc   7740
cattttaccc ggtgttcttg gcagaattga aaacagtacg tagtaccgcg cctaccatgt   7800
gtgttgagac cgagaacaac gatggaatcc ctactgtgga gatcgctttc gatggagaga   7860
gagaaagagc tgaggctaac gtgaagttgt ctgctgagaa gatggaacct gctgctttgg   7920
ctaagacctt cgctagaaga tacgtggtta tcgagggagt tgagtacgat gtgaccgatt   7980
tcaaacatcc tggaggaacc gtgattttct acgctctctc taacactgga gctgatgcta   8040
ctgaggcttt caaggagttc caccacagat ctagaaaggc taggaaggct ttggctgctt   8100
tgccttctag acctgctaag accgctaaag tggatgatgc tgagatgctc caggatttcg   8160
ctaagtggag aaaggagttg gagagggacg gattcttcaa gccttctcct gctcatgttg   8220
cttacagatt cgctgagttg gctgctatgt acgctttggg aacctacttg atgtacgcta   8280
gatacgttgt gtcctctgtg ttggtttacg cttgcttctt cggagctaga tgtggatggg   8340
ttcaacacga gggaggacac tcttctttga ccggaaacat ctggtgggat aagagaatcc   8400
aagctttcac tgctggattc ggattggctg gatctggaga tatgtggaac tccatgcaca   8460
acaagcacca cgctactcct caaaaagtga ggcacgatat ggatttggat accactcctg   8520
ctgttgcttt cttcaacacc gctgtggagg ataatagacc taggggattc tctaagtact   8580
ggctcagatt gcaagcttgg accttcattc ctgtgacttc tggattggtg ttgctcttct   8640
ggatgttctt cctccaccct tctaaggctt tgaagggagg aaagtacgag gagcttgtgt   8700
ggatgttggc tgctcacgtg attagaacct ggaccattaa ggctgttact ggattcaccg   8760
ctatgcaatc ctacggactc ttcttggcta cttcttgggt ttccggatgc tacttgttcg   8820
ctcacttctc tacttctcac acccacttgg atgttgttcc tgctgatgag cacttgtctt   8880
gggttaggta cgctgtggat cacaccattg atatcgatcc ttctcaggga tgggttaact   8940
ggttgatggg atacttgaac tgccaagtga ttcaccacct cttccccttct atgcctcaat   9000
tcagacaacc tgaggtgtcc agaagattcg ttgctttcgc taagaagtgg aacctcaact   9060
acaaggtgat gacttatgct ggagcttgga aggctacttt gggaaacctc gataatgtgg   9120
gaaagcacta ctacgtgcac ggacaacact ctggaaagac cgcttgatta atgaaggccg   9180
cctcgaccgt accccctgca gatagactat actatgtttt agcctgcctg ctggctagct   9240
actatgttat gttatgttgt aaaataaaca cctgctaagg tatatctatc tatattttag   9300
catggctttc tcaataaatt gtctttcctt atcgtttact atcttatacc taataatgaa   9360
ataataatat cacatatgag gaacggggca ggtttaggca tatatatacg agtgtagggc   9420
ggagtggggc tacgtagcgt cacgtgacgt tacctaagcc taggtagcct cagctgacgt   9480
tacgtaacgc taggtaggct cagctgacac gggcaggaca tagggactac tacaagcata   9540
gtatgcttca gacaaagagc taggaaagaa ctcttgatgg aggttaagag aaaaaagtgc   9600
tagaggggca tagtaatcaa acttgtcaaa accgtcatca tgatgaggga tgacataata   9660
taaaaagttg actaaggtct tggtagtact ctttgattag tattatatat tggtgagaac   9720
```

```
atgagtcaag aggagacaag aaaccgagga accatagttt agcaacaaga tggaagttgc   9780
aaagttgagc tagccgctcg attagttaca tctcctaagc agtactacaa ggaatggtct   9840
ctatactttc atgtttagca catggtagtg cggattgaca agttagaaac agtgcttagg   9900
agacaaagag tcagtaaagg tattgaaaga gtgaagttga tgctcgacag gtcaggagaa   9960
gtccctccgc cagatggtga ctaccaaggg gttggtatca gctgagaccc aaataagatt  10020
cttcggttga accagtggtt cgaccgagac tcttagggtg ggatttcact gtaagatttg  10080
tgcattttgt tgaatataaa ttgacaattt tttttattta attatagatt atttagaatg  10140
aattacatat ttagtttcta acaaggatag caatggatgg gtatgggtac aggttaaaca  10200
tatctattac ccacccatct agtcgtcggg ttttacacgt acccacccgt ttacataaac  10260
cagaccggaa ttttaaaccg tacccgtccg ttagcgggtt tcagatttac ccgtttaatc  10320
gggtaaaacc tgattactaa atatatattt tttatttgat aaacaaaaca aaaatgttaa  10380
tattttcata ttggatgcaa ttttaagaaa cacatattca taaatttcca tatttgtagg  10440
aaaataaaaa gaaaaatata ttcaagaaca caaatttcac cgacatgact tttattacag  10500
agttggaatt agatctaaca attgaaaaat taaaattaag atagaatatg ttgaggaaca  10560
tgacatagta taatgctggg ttacccgtcg ggtaggtatc gaggcggata ctactaaatc  10620
catcccactc gctatccgat aatcactggt ttcgggtata cccattcccg tcaacaggcc  10680
tttttaaccg gataatttca acttatagtg aatgaatttt gaataaatag ttagaatacc  10740
aaaatcctgg attgcatttg caatcaaatt ttgtgaaccg ttaaattttg catgtacttg  10800
ggatagatat aatagaaccg aattttcatt agtttaattt ataacttact ttgttcaaag  10860
aaaaaaaata tctatccaat ttacttataa taaaaaataa tctatccaag ttacttatta  10920
taatcaactt gtaaaaaggt aagaatacaa atgtggtagc gtacgtgtga ttatatgtga  10980
cgaaatgtta tatctaacaa aagtccaaat tcccatggta aaaaaaatca aaatgcatgg  11040
caggctgttt gtaaccttgg aataagatgt tggccaattc tggagccgcc acgtacgcaa  11100
gactcagggc cacgttctct tcatgcaagg atagtagaac accactccac ccacctccta  11160
tattagacct ttgcccaacc ctccccaact ttcccatccc atccacaaag aaaccgacat  11220
ttttatcata aatctggtgc ttaaacactc tggtgagttc tagtacttct gctatgatcg  11280
atctcattac catttcttaa atttctctcc ctaaatattc cgagttcttg atttttgata  11340
acttcaggtt ttctcttttt gataaatctg gtctttccat tttttttttt tgtggttaat  11400
ttagtttcct atgttcttcg attgtattat gcatgatctg tgtttggatt ctgttagatt  11460
atgtattggt gaatatgtat gtgtttttgc atgtctggtt ttggtcttaa aaatgttcaa  11520
atctgatgat ttgattgaag ctttttttagt gttggtttga ttcttctcaa aactactgtt  11580
aatttactat catgttttcc aactttgatt catgatgaca cttttgttct gctttgttat  11640
aaaattttgg ttggtttgat tttgtaatta tagtgtaatt ttgttaggaa tgaacatgtt  11700
ttaatactct gttttcgatt tgtcacacat tcgaattatt aatcgataat ttaactgaaa  11760
attcatggtt ctagatcttg ttgtcatcag attatttgtt tcgataattc atcaaatatg  11820
tagtcctttt gctgatttgc gactgtttca ttttttctca aaattgtttt ttgttaagtt  11880
tatctaacag ttatcgttgt caaaagtctc tttcattttg caaaatcttc tttttttttt  11940
tgtttgtaac tttgtttttt aagctacaca tttagtctgt aaaatagcat cgaggaacag  12000
ttgtcttagt agacttgcat gttcttgtaa cttctatttg tttcagtttg ttgatgactg  12060
```

```
ctttgatttt gtaggtcaaa ggcgcaccct accatggatg cttataacgc tgctatggat  12120
aagattggag ctgctatcat cgattggagt gatccagatg gaaagttcag agctgatagg  12180
gaggattggt ggttgtgcga tttcagatcc gctatcacca ttgctctcat ctacatcgct  12240
ttcgtgatct tgggatctgc tgtgatgcaa tctctcccag ctatggaccc ataccctatc  12300
aagttcctct acaacgtgtc tcaaatcttc ctctgcgctt acatgactgt tgaggctgga  12360
ttcctcgctt ataggaacgg atacaccgtt atgccatgca accacttcaa cgtgaacgat  12420
ccaccagttg ctaacttgct ctggctcttc tacatctcca aagtgtggga tttctgggat  12480
accatcttca ttgtgctcgg aaagaagtgg agacaactct ctttcttgca cgtgtaccac  12540
cacaccacca tcttcctctt ctactggttg aacgctaacg tgctctacga tggagatatc  12600
ttcttgacca tcctcctcaa cggattcatt cacaccgtga tgtacaccta ctacttcatc  12660
tgcatgcaca ccaaggattc taagaccgga aagtctttgc caatctggtg gaagtcatct  12720
ttgaccgctt tccaactctt gcaattcacc atcatgatgt cccaagctac ctacttggtt  12780
ttccacggat gcgataaggt ttccctcaga atcaccatcg tgtacttcgt gtacattctc  12840
tccctttttct tcctcttcgc tcagttcttc gtgcaatcct acatggctcc aaagaagaag  12900
aagtccgctt gatgttaatg aaggccgcag atatcagatc tggtcgacct agaggatccc  12960
cggccgcaaa gataataaca aaagcctact atataacgta catgcaagta ttgtatgata  13020
ttaatgtttt tacgtacgtg taaacaaaaa taattacgtt tgtaacgtat ggtgatgatg  13080
tggtgcacta ggtgtaggcc ttgtattaat aaaaagaagt ttgttctata tagagtggtt  13140
tagtacgacg atttatttac tagtcggatt ggaatagaga accgaattct tcaatccttg  13200
cttttgatca agaattgaaa ccgaatcaaa tgtaaaagtt gatatatttg aaaaacgtat  13260
tgagcttatg aaaatgctaa tactctcatc tgtatggaaa agtgacttta aaaccgaact  13320
taaaagtgac aaaaggggaa tatcgcatca aaccgaatga aaccgatcta cgtaggctca  13380
gctgagctta gctaagccta cctagcctca cgtgagatta tgtaaggcta ggtagcgtca  13440
cgtgacgtta cctaacacta gctagcgtca gctgagctta gctaacccta cgtagcctca  13500
cgtgagctta cctaacgcta cgtagcctca cgtgactaag gatgacctac ccattcttga  13560
gacaaatgtt acattttagt atcagagtaa aatgtgtacc tataactcaa attcgattga  13620
catgtatcca ttcaacataa aattaaacca gcctgcacct gcatccacat ttcaagtatt  13680
ttcaaaccgt tcggctccta tccaccgggt gtaacaagac ggattccgaa tttggaagat  13740
tttgactcaa attcccaatt tatattgacc gtgactaaat caactttaac ttctataatt  13800
ctgattaagc tcccaattta tattcccaac ggcactacct ccaaaattta tagactctca  13860
tcccctttta aaccaactta gtaaacgttt ttttttaat tttatgaagt taagttttta  13920
ccttgttttt aaaaagaatc gttcataaga tgccatgcca gaacattagc tacacgttac  13980
acatagcatg cagccgcgga gaattgtttt tcttcgccac ttgtcactcc cttcaaacac  14040
ctaagagctt ctctctcaca gcacacacat acaatcacat gcgtgcatgc attattacac  14100
gtgatcgcca tgcaaatctc ctttatagcc tataaattaa ctcatcggct tcactcttta  14160
ctcaaaccaa aactcatcaa tacaaacaag attaaaaaca tttcacgatt tggaatttga  14220
ttcctgcgat cacaggtatg acaggttaga ttttgttttg tatagttgta tacatacttc  14280
tttgtgatgt tttgtttact taatcgaatt tttggagtgt tttaaggtct ctcgtttaga  14340
aatcgtggaa aatatcactg tgtgtgtgtt cttatgattc acagtgttta tgggtttcat  14400
gttctttgtt ttatcattga atgggaagaa atttcgttgg gatacaaatt tctcatgttc  14460
```

```
ttactgatcg ttattaggag tttggggaaa aaggaagagt ttttttggtt ggttcgagtg  14520
attatgaggt tatttctgta tttgatttat gagttaatgg tcgttttaat gttgtagacc  14580
gccatggcta ttttgaaccc tgaggctgat tctgctgcta acctcgctac tgattctgag  14640
gctaagcaaa gacaattggc tgaggctgga tacactcacg ttgagggtgc tcctgctcct  14700
ttgcctttgg agttgcctca cttctctctc agagatctca gagctgctat tcctaagcac  14760
tgcttcgaga gatctttcgt gacctccacc tactacatga tcaagaacgt gttgacttgc  14820
gctgctttgt tctacgctgc taccttcatt gatagagctg gagctgctgc ttatgttttg  14880
tggcctgtgt actggttctt ccagggatct tacttgactg gagtgtgggt tatcgctcac  14940
gagtgtggac accaggctta ttgctcttct gaggtggtga acaacttgat tggactcgtg  15000
ttgcactctg ctttgttggt gccttaccac tcttggagaa tctctcacag aaagcaccac  15060
tccaacactg gatcttgcga gaacgatgag gttttcgttc ctgtgaccag atctgtgttg  15120
gcttcttctt ggaacgagac cttggaggat tctcctctct accaactcta ccgtatcgtg  15180
tacatgttgg ttgttggatg gatgcctgga tacctcttct tcaacgctac tggacctact  15240
aagtactggg gaaagtctag gtctcacttc aacccttact ccgctatcta tgctgatagg  15300
gagaggtgga tgatcgtgct ctccgatatt ttcttggtgg ctatgttggc tgttttggct  15360
gctttggtgc acactttctc cttcaacacg atggtgaagt tctacgtggt gccttacttc  15420
attgtgaacg cttacttggt gttgattacc tacctccaac acaccgatac ctacatccct  15480
cacttcagag agggagagtg gaattggttg agaggagctt tgtgcactgt ggatagatca  15540
tttggtccat tcctcgattc tgtggtgcat agaatcgtgg atacccacgt ttgccaccat  15600
atcttctcca agatgccttt ctatcactgc gaggaggcta ccaacgctat taagcctctc  15660
ctcggaaagt tctacttgaa ggatactact cctgttcctg ttgctctctg gagatcttac  15720
acccactgca agttcgttga ggatgatgga aaggtggtgt tctacaagaa caagttatag  15780
ttaatgaata attgattggt tcgagtatta tggcattggg aaaactgttt ttcttgtacc  15840
atttgttgtg cttgtaattt actgtgtttt ttattcggtt ttcgctatcg aactgtgaaa  15900
tggaaatgga tggagaagag ttaatgaatg atatggtcct tttgttcatt ctcaaattaa  15960
tattatttgt tttttctctt atttgttgtg tgttgaattt gaaattataa gagatatgca  16020
aacattttgt tttgagtaaa aatgtgtcaa atcgtggcct ctaatgaccg aagttaatat  16080
gaggagtaaa acacttgtag ttgtaccatt atgcttattc actaggcaac aaatatattt  16140
tcagacctag aaaagctgca aatgttactg aatacaagta tgtcctcttg tgttttagac  16200
atttatgaac tttcctttat gtaattttcc agaatccttg tcagattcta atcattgctt  16260
tataattata gttatactca tggatttgta gttgagtatg aaaatatttt ttaatgcatt  16320
ttatgacttg ccaattgatt gacaacatgc atcaatctag ctagcctcag ctgacgttac  16380
gtaacgctag gtagcgtcac gtgacgttag ctaacgctag gtagcgtcag ctgagcttac  16440
gtaagcgcac agatgaatac tagctgttgt tcacagttct agtgtctcct cattacgtga  16500
attcaagcta cgatcactat ctcaactcct acataaacat cagaatgcta caaaactatg  16560
cacaaaaaca aaagctacat ctaatacgtg aatcaattac tctcatcaca agaaagaaga  16620
tttcaatcac cgtcgagaag gaggattcag ttaattgaat caaagttccg atcaaactcg  16680
aagactggtg agcacgagga cgacgaagaa gagtgtctcg aagatacaac aagcaagaaa  16740
tctactgagt gacctcctga agttattggc gcgattgaga gaatcaatcc gaattaattt  16800
```

```
cggggaaaaa gataaattag atactaagcg atgggcttgg gctgggctaa gaaacaggtg  16860
gcaattgggc tggaggaccc cgcgattcat agcttccgat agcccaaaaa aaaacggata  16920
acatatttat cgggtatttg aatttcagtg aaataagata ttttcttttt gttaggaaaa  16980
ttttagaaaa taatggaaat taaatagcga ttatgttaca agatacgatc agcatcgggc  17040
agtgcaaaat gctatagctt cccaagattt gatccttttg ggttatctcc taatgacaat  17100
tagtttagga ttttgaaact tatattaata ctattatccg acaacacttg tttcagcttc  17160
ttattttaac attttttgtt tttttctatt cttcttccca tcagcatttt ctttttaaaa  17220
aattgaatac tttaactttt taaaaatttc acaatgatca gatgatatta tggaagatct  17280
caagagttaa atgtatccat cttggggcat taaaaccggt gtacgggatg ataaatacag  17340
actttatatc atatgatagc tcagtaattc atatttatca cgttgctaaa aaaattataa  17400
ggtactagta gtcaacaaaa tcaattaaag agaaagaaag aaacgcatgt gaagagagtt  17460
tacaactgga aaagtaaaat aaaaattaac gcatgttgaa tgctgacatg tcagtatgtc  17520
catgaatcca cgtatcaagc gccattcatc gatcgtcttc ctctttctaa atgaaaacaa  17580
cttcacacat cacaacaaac aatacacaca agaccccctc tctctcgttg tctctctgcc  17640
agcgaccaaa tcgaagcttg agaagaacaa gaaggggtca aaccatggct tctacatctg  17700
ctgctcaaga cgctgctcct tacgagttcc cttctctcac tgagatcaag agggctcttc  17760
cttctgagtg tttcgaggct tctgttcctc tttctctcta ctacaccgct agatctcttg  17820
ctcttgctgg atctctcgct gttgctctct cttacgctag agctttgcct cttgttcagg  17880
ctaacgctct tcttgatgct actctctgca ctggatacgt tcttctccag ggaatcgttt  17940
tctggggatt cttcaccgtt ggtcacgatt gtggacacgg agctttctct agatctcacg  18000
tgctcaactt ctctgttgga accctcatgc actctatcat ccttacccct ttcgagtctt  18060
ggaagctctc tcacagacac caccacaaga acaccggaaa catcgataag gacgagatct  18120
tctaccctca aagagaggct gattctcacc ctgtttctag acaccttgtg atgtctcttg  18180
gatctgcttg gttcgcttac cttttcgctg gattccctcc tagaaccatg aaccacttca  18240
acccttggga ggctatgtat gttagaagag tggctgctgt gatcatctct ctcggagttc  18300
ttttcgcttt cgctggactc tactcttacc tcaccttcgt tcttggattc accactatgg  18360
ctatctacta cttcggacct ctcttcatct tcgctaccat gcttgttgtt accactttcc  18420
tccaccacaa cgatgaggag acaccttggt acgctgattc tgagtggact tacgtgaagg  18480
gaaacctctc ttctgtggac agatcttacg gtgctctcat cgacaacctt agccacaaca  18540
tcggaactca ccagatccac cacctcttcc ctatcatccc tcactacaag ctcaacgatg  18600
ctactgctgc tttcgctaag gctttccctg agcttgttag gaaaaacgct gctcctatca  18660
tcccaacttt cttcaggatg gctgctatgt acgctaagta cggagttgtt gacactgatg  18720
ctaagacctt cactctcaag gaggctaagg ctgctgctaa gactaagtca tcttgatgat  18780
taatgaataa ttgattgtac atactatatt ttttgtttac cttgtgttag tttaatgttc  18840
agtgtcctct ctttattgtg gcacgtctct ttgttgtatg ttgtgtctat acaaagttga  18900
aataatggaa agaaaaggaa gagtgtaatt tgttttgttt taagtgttta taaatatata  18960
tatataggtc atttagatag ttctaggttt ctataaaact ctctctctgg aagtagaatc  19020
tgtttttgag aggatccagt tgcctactaa tctcccccaa aacccttcaa gcttaacctt  19080
cctcttcaca acaacagagg aaacacatct cttgagctct gagttctctt ctttgagcat  19140
gtctatcgct aaactcatct gccttatagc ttccctcttc tcttcatctc tctctctcac  19200
```

```
catttcgctg taaaacttat tctcctccct cagcctctct atctcttcct tcagcatctc  19260
acaattccca ccataatcga ctgaggatga ttcaccgtca tcaacttcag actcagcgtt  19320
gtagtcgtca tgagtctcac aagccttgga ccaagaagac tcatcatcgc aagttgatga  19380
tttatcatga tgcttctctg agccgtgttt gctacgtagc gtcacgtgac gttacctaag  19440
cctaggtagc ctcagctgac gttacgtaac gctaggtagg ctcagctgac tgcagcaaat  19500
ttacacattg ccactaaacg tctaaaccct tgtaatttgt ttttgtttta ctatgtgtgt  19560
tatgtatttg atttgcgata aatttttata tttggtacta aatttataac accttttatg  19620
ctaacgtttg ccaacactta gcaatttgca agttgattaa ttgattctaa attatttttg  19680
tcttctaaat acatatacta atcaactgga aatgtaaata tttgctaata tttctactat  19740
aggagaatta aagtgagtga atatggtacc acaaggtttg gagatttaat tgttgcaatg  19800
ctgcatggat ggcatataca ccaaacattc aataattctt gaggataata atggtaccac  19860
acaagatttg aggtgcatga acgtcacgtg gacaaaaggt ttagtaattt ttcaagacaa  19920
caatgttacc acacacaagt tttgaggtgc atgcatggat gccctgtgga aagtttaaaa  19980
atattttgga aatgatttgc atggaagcca tgtgtaaaac catgacatcc acttggagga  20040
tgcaataatg aagaaaacta caaatttaca tgcaactagt tatgcatgta gtctatataa  20100
tgaggatttt gcaatacttt cattcataca cactcactaa gttttacacg attataattt  20160
cttcatagcc agtactgttt aagcttcact gtctctgaat cggcaaaggt aaacgtatca  20220
attattctac aaaccctttt atttttcttt tgaattaccg tcttcattgg ttatatgata  20280
acttgataag taaagcttca ataattgaat ttgatctgtg tttttttggc cttaatacta  20340
aatccttaca taagctttgt tgcttctcct cttgtgagtt gagtgttaag ttgtaataat  20400
ggttcacttt cagctttaga agaaacgcgc cttccatggc tacaaaggag gcttacgttt  20460
tcccaactct caccgagatc aagagatctc tcccaaagga ttgcttcgag gcttctgtgc  20520
ctttgtctct ctactacact gtgagatgct tggttattgc tgtggctttg accttcggat  20580
tgaactacgc tagagctttg ccagaggttg agtctttctg ggctttggat gctgctttgt  20640
gcactggata tatcctcctc cagggaattg tgttctgggg attcttcact gttggacacg  20700
atgctggaca cggagctttc tctagatacc acctcttgaa cttcgttgtg ggaaccttca  20760
tgcactctct catcttgacc ccattcgagt cttggaagtt gacccacaga caccaccaca  20820
agaacaccgg aaacatcgat agagatgagg tgttctaccc acagagaaag gctgatgatc  20880
acccattgtc caggaacttg atcttggctt tgggagctgc ttggcttgct tatttggtgg  20940
agggattccc accaagaaag gtgaaccact tcaacccatt cgagccactt tttgtgagac  21000
aagtgtccgc tgtggttatc tctttgctcg ctcacttctt cgttgctgga ctctctatct  21060
acttgtctct ccagttggga cttaagacca tggctatcta ctactacgga ccagttttcg  21120
tgttcggatc tatgttggtg attaccacct tcttgcacca caacgatgag gagactccat  21180
ggtatgctga ttctgagtgg acttacgtga agggaaactt gtcctctgtg gatagatctt  21240
acggtgctct catcgataac ctctcccaca acatcggaac tcaccagatc caccacctct  21300
tcccaattat cccacactac aagctcaaga aggctactgc tgctttccac caagctttcc  21360
cagagcttgt gagaaagtcc gatgagccaa tcatcaaggc tttcttcaga gtgggaaggt  21420
tgtatgctaa ctacggagtg gttgatcaag aggctaagct cttcactttg aaggaggcta  21480
aggctgctac tgaagctgct gctaagacca agtctacctg attaatgaat cgacaagctc  21540
```

```
gagtttctcc ataataatgt gtgagtagtt cccagataag ggaattaggg ttcctatagg  21600
gtttcgctca tgtgttgagc atataagaaa cccttagtat gtatttgtat ttgtaaaata  21660
cttctatcaa taaaatttct aattcctaaa accaaaatcc agtactaaaa tccagatccc  21720
ccgaattaat tcggcgttaa ttcagctacg taggctcagc tgagcttacc taaggctacg  21780
taggctcacg tgacgttacg taaggctacg tagcgtcacg tgagcttacc taactctagc  21840
tagcctcacg tgaccttagc taacactagg tagcgtcagc acagatgaat actagctgtt  21900
gttcacagtt ctagtgtctc ctcattacgt gaattcaagc tacgatcact atctcaactc  21960
ctacataaac atcagaatgc tacaaaacta tgcacaaaaa caaaagctac atctaatacg  22020
tgaatcaatt actctcatca caagaaagaa gatttcaatc accgtcgaga aggaggattc  22080
agttaattga atcaaagttc cgatcaaact cgaagactgg tgagcacgag gacgacgaag  22140
aagagtgtct cgaagataca acaagcaaga aatctactga gtgacctcct gaagttattg  22200
gcgcgattga gagaatcaat ccgaattaat ttcggggaaa aagataaatt agatactaag  22260
cgatgggctt gggctgggct aagaaacagg tggcaattgg gctggaggac cccgcgattc  22320
atagcttccg atagcccaaa aaaaaacgga taacatattt atcgggtatt tgaatttcag  22380
tgaaataaga tattttcttt ttgttaggaa aattttagaa aataatggaa attaaatagc  22440
gattatgtta caagatacga tcagcatcgg gcagtgcaaa atgctatagc ttcccaagat  22500
ttgatccttt tgggttatct cctaatgaca attagtttag gattttgaaa cttatattaa  22560
tactattatc cgacaacact tgtttcagct tcttatttta acattttttg ttttttttcta  22620
ttcttcttcc catcagcatt ttctttttaa aaaattgaat actttaactt tttaaaaatt  22680
tcacaatgat cagatgatat tatggaagat ctcaagagtt aaatgtatcc atcttggggc  22740
attaaaaccg gtgtacggga tgataaatac agactttata tcatatgata gctcagtaat  22800
tcatatttat cacgttgcta aaaaaattat aaggtactag tagtcaacaa aatcaattaa  22860
agagaaagaa agaaacgcat gtgaagagag tttacaactg gaaaagtaaa ataaaaatta  22920
acgcatgttg aatgctgaca tgtcagtatg tccatgaatc cacgtatcaa gcgccattca  22980
tcgatcgtct tcctctttct aaatgaaaac aacttcacac atcacaacaa acaatacaca  23040
caagaccccc tctctctcgt tgtctctctg ccagcgacca aatcgaagct tgagaagaac  23100
aagaaggggt caaaccatgg gaaaaggatc tgagggaaga tctgctgcta gagagatgac  23160
tgctgaggct aacggagata agagaaagac catcctcatt gagggagtgt tgtacgatgc  23220
taccaacttc aaacacccag gaggttccat tattaacttc ctcaccgagg gagaagctgg  23280
agttgatgct acccaagctt acagagagtt ccatcagaga tccggaaagg ctgataagta  23340
cctcaagtcc ctcccaaagt tggatgcttc taaggtggag tctaggttct ctgctaagga  23400
gcaggctaga agggacgcta tgaccaggga ttacgctgct ttcagagagg agttggttgc  23460
tgagggatac ttcgatccat ctatcccaca catgatctac agagtggtgg agattgtggc  23520
tttgttcgct ttgtctttct ggttgatgtc taaggcttct ccaacctctt tggttttggg  23580
agtggtgatg aacggaatcg ctcaaggaag atgcggatgg gttatgcacg agatgggaca  23640
cggatctttc actggagtta tctggctcga tgataggatg tgcgagttct tctacggagt  23700
tggatgtgga atgtctggac actactggaa gaaccagcac tctaagcacc acgctgctcc  23760
aaacagattg gagcacgatg tggatttgaa caccttgcca ctcgttgctt tcaacgagag  23820
agttgtgagg aaggttaagc caggatcttt gttggctttg tggctcagag ttcaggctta  23880
tttgttcgct ccagtgtctt gcttgttgat cggattggga tggaccttgt acttgcaccc  23940
```

aagatatatg ctcaggacca agagacacat ggagtttgtg tggatcttcg ctagatatat 24000
cggatggttc tccttgatgg gagctttggg atattctcct ggaacttctg tgggaatgta 24060
cctctgctct ttcggacttg gatgcatcta catcttcctc caattcgctg tgtctcacac 24120
ccacttgcca gttaccaacc cagaggatca attgcactgg cttgagtacg ctgctgatca 24180
caccgtgaac atctctacca agtcttggtt ggttacctgg tggatgtcta acctcaactt 24240
ccaaatcgag caccacttgt tcccaaccgc tccacaattc aggttcaagg agatctctcc 24300
aagagttgag gctctcttca agagacacaa cctcccttac tacgatttgc catacacctc 24360
tgctgtttct actaccttcg ctaacctcta ctctgttgga cactctgttg gagctgatac 24420
caagaagcag gattgatgat taatgaataa ttgattgtac atactatatt ttttgtttac 24480
cttgtgttag tttaatgttc agtgtcctct ctttattgtg gcacgtctct ttgttgtatg 24540
ttgtgtctat acaaagttga aataatggaa agaaaaggaa gagtgtaatt tgttttgttt 24600
taagtgttta taaatatata tatataggtc atttagatag ttctaggttt ctataaaact 24660
ctctctctgg aagtagaatc tgtttttgag aggatccagt tgcctactaa tctcccccaa 24720
aacccttcaa gcttaacctt cctcttcaca acaacagagg aaacacatct cttgagctct 24780
gagttctctt ctttgagcat gtctatcgct aaactcatct gccttatagc ttccctcttc 24840
tcttcatctc tctctctcac catttcgctg taaaacttat tctcctccct cagcctctct 24900
atctcttcct tcagcatctc acaattccca ccataatcga ctgaggatga ttcaccgtca 24960
tcaacttcag actcagcgtt gtagtcgtca tgagtctcac aagccttgga ccaagaagac 25020
tcatcatcgc aagttgatga tttatcatga tgcttctctg agccgtgttt gctacctaga 25080
gtcagctgag cttagctaac gctagctagt gtcagctgac gttacgtaag gctaactagc 25140
gtcacgtgac cttacgtaac gctacgtagg ctcagctgag cttagctaac cctagctagt 25200
gtcacgtgag cttacgctac tatagaaaat gtgttatatc gacatgacca gacaaagggg 25260
caacagttaa caaaacaatt aattctttca tttgagatta aggaaggtaa ggtactaaaa 25320
agattaaaaa aaatgagctt atctctttgt ttctgtaata ataatataag tgtgataaac 25380
ttttaatata ataattgtaa ttaggttttc tacagatgag caccactcag agacaagata 25440
agaagaaaac aattttgtta aacatgatta tagaaacttt tagttaagtc ttgaagtatc 25500
aatataacaa aaaaaagtac acacgactat gacaataaac ccactaccgt caggttatca 25560
tttcgatgaa atgttttgat atcattaaat ataacagtca caaaaaatca tctaattata 25620
acaatataac ttatacatat atttaactaa aaacttagag tttttgtaat gattctaatt 25680
gatgattaga gtttatagaa atacaattaa ataaaaaata taattttaaa aaaacatagt 25740
aaagtcaatg agatcctctc tgacctcagt gatcatttag tcatgtatgt acaacaatca 25800
ttgttcatca catgactgta aaataaataa ggataaactt gggaatatat ataatatatt 25860
gtattaaata aaaaagggaa atacaaatat caattttaga ttcccgagtt gacacaactc 25920
accatgcacg ctgccacctc agctcccagc tctcgtcaca tgtctcatgt cagttaggtc 25980
tttggttttt agtctttgac acaactcgcc atgcatgttg ccacgtgagc tcgttcctct 26040
tcccatgatc tcaccactgg gcatgcatgc tgccacctca gctggcacct cttctctata 26100
tgtccctaga ggccatgcac agtgccacct cagcactcct ctcagaaccc atacgtacct 26160
gccaatcggc ttctctccat aaatatctat ttaaattata actaattatt tcatatactt 26220
aattgatgac gtggatgcat tgccatcgtt gtttaataat tgttaattac gacatgataa 26280

```
ataaaatgaa agtaaaaagt acgaaagatt ttccatttgt tgttgtataa atagagaagt  26340
gagtgatgca taatgcatga atgcatgacc gcgccaccat gactgttgga tacgacgagg  26400
agatcccatt cgagcaagtt agggctcata acaagccaga cgacgcttgg tgtgctattc  26460
acggacacgt gtacgacgtt accaagttcg cttcagttca cccaggagga gatattatct  26520
tgctcgctgc tggaaaggaa gctactgtcc tctacgagac ctaccatgtt agaggagtgt  26580
ctgacgctgt gctcagaaag tacagaatag gaaagttgcc agacggacaa ggaggagcta  26640
acgagaagga gaagagaacc ttgtctggat tgtcctctgc ttcttactac acctggaact  26700
ccgatttcta cagagtgatg agggagagag ttgtggctag attgaaggag agaggaaagg  26760
ctagaagagg aggatacgaa ctctggatca aggctttctt gctccttgtt ggattctggt  26820
cctctcttta ctggatgtgc accctcgatc catctttcgg agctatcttg gctgctatgt  26880
ctttgggagt gttcgctgct tttgttggaa cctgcatcca acacgatgga aaccacggag  26940
ctttcgctca atctagatgg gttaacaagg tggcaggatg gactttggat atgatcggag  27000
cttctggaat gacttgggag ttccaacacg tgttgggaca ccacccatac actaacttga  27060
tcgaggagga gaacggattg caaaaggtgt ccggaaagaa gatggatacc aagttggctg  27120
atcaagagtc tgatccagat gtgttctcca cctacccaat gatgagattg caccccttggc  27180
accagaagag gtggtatcac aggttccagc acatctacgg acctttcatc ttcggattca  27240
tgaccatcaa caaggtggtg actcaagatg ttggagtggt gttgagaaag agactcttcc  27300
aaatcgatgc tgagtgcaga tatgcttccc caatgtacgt tgctaggttc tggattatga  27360
aggctttgac cgtgttgtat atggttgctt tgccttgtta tatgcaagga ccttggcacg  27420
gattgaaact cttcgctatc gctcacttca cttgcggaga ggttttggct accatgttca  27480
tcgtgaacca cattatcgag ggagtgtctt acgcttctaa ggatgctgtt aagggaacta  27540
tggctccacc aaagactatg cacggagtga ccccaatgaa caacactaga aaggaggttg  27600
aggctgaggc ttctaagtct ggagctgtgg ttaagtctgt gccattggat gattgggctg  27660
ctgttcagtg ccaaacctct gtgaactggt ctgttggatc ttggttttgg aaccacttct  27720
ctggaggact caaccaccaa atcgagcacc acctcttccc aggattgtct cacgagacct  27780
actaccacat ccaagacgtg gttcaatcta cctgtgctga gtacggagtt ccataccaac  27840
acgagccatc tttgtggact gcttactgga agatgctcga acaccttaga caattgggaa  27900
acgaggagac tcacgagtca tggcagagag ctgcttgatt aatgaactaa gactcccaaa  27960
accaccttcc ctgtgacagt taaaccctgc ttatacctt cctcctaata atgttcatct  28020
gtcacacaaa ctaaaataaa taaaatggga gcaataaata aaatgggagc tcatatattt  28080
acaccattta cactgtctat tattcaccat gccaattatt acttcataat tttaaaatta  28140
tgtcattttt aaaaattgct taatgatgga aaggattatt ataagttaaa agtataacat  28200
agataaacta accacaaaac aaatcaatat aaactaactt actctcccat ctaattttta  28260
tttaaatttc tttacacttc tcttccattt ctatttctac aacattattt aacattttta  28320
ttgtattttt cttactttct aactctattc atttcaaaaa tcaatatatg tttatcacca  28380
cctctctaaa aaaaacttta caatcattgg tccagaaaag ttaaatcacg agatggtcat  28440
tttagcatta aaacaacgat tcttgtatca ctatttttca gcatgtagtc cattctcttc  28500
aaacaaagac agcggctata taatcgttgt gttatattca gtctaaaaca actagctagc  28560
ctcagctgac gttacgtaac gctaggtagc gtcacgtgac gttagctaac gctaggtagc  28620
gtcagctgag cttacgtaag cgccacgggc aggacatagg gactactaca agcatagtat  28680
```

```
gcttcagaca aagagctagg aaagaactct tgatggaggt taagagaaaa aagtgctaga  28740
ggggcatagt aatcaaactt gtcaaaaccg tcatcatgat gagggatgac ataatataaa  28800
aagttgacta aggtcttggt agtactcttt gattagtatt atatattggt gagaacatga  28860
gtcaagagga gacaagaaac cgaggaacca tagtttagca acaagatgga agttgcaaag  28920
ttgagctagc cgctcgatta gttacatctc ctaagcagta ctacaaggaa tggtctctat  28980
actttcatgt ttagcacatg gtagtgcgga ttgacaagtt agaaacagtg cttaggagac  29040
aaagagtcag taaaggtatt gaaagagtga agttgatgct cgacaggtca ggagaagtcc  29100
ctccgccaga tggtgactac caaggggttg gtatcagctg agacccaaat aagattcttc  29160
ggttgaacca gtggttcgac cgagactctt agggtgggat ttcactgtaa gatttgtgca  29220
ttttgttgaa tataaattga caattttttt tatttaatta tagattattt agaatgaatt  29280
acatatttag tttctaacaa ggatagcaat ggatgggtat gggtacaggt taaacatatc  29340
tattacccac ccatctagtc gtcgggtttt acacgtaccc acccgtttac ataaaccaga  29400
ccggaatttt aaaccgtacc cgtccgttag cgggtttcag atttacccgt ttaatcgggt  29460
aaaacctgat tactaaatat atattttta tttgataaac aaaacaaaaa tgttaatatt  29520
ttcatattgg atgcaatttt aagaaacaca tattcataaa tttccatatt tgtaggaaaa  29580
taaaaagaaa aatatattca agaacacaaa tttcaccgac atgactttta ttacagagtt  29640
ggaattagat ctaacaattg aaaaattaaa attaagatag aatatgttga ggaacatgac  29700
atagtataat gctgggttac ccgtcgggta ggtatcgagg cggatactac taaatccatc  29760
ccactcgcta tccgataatc actggtttcg ggtataccca ttcccgtcaa caggcctttt  29820
taaccggata atttcaactt atagtgaatg aattttgaat aaatagttag aataccaaaa  29880
tcctggattg catttgcaat caaattttgt gaaccgttaa attttgcatg tacttgggat  29940
agatataata gaaccgaatt ttcattagtt taatttataa cttactttgt tcaaagaaaa  30000
aaaatatcta tccaatttac ttataataaa aaataatcta tccaagttac ttattataat  30060
caacttgtaa aaaggtaaga atacaaatgt ggtagcgtac gtgtgattat atgtgacgaa  30120
atgttatatc taacaaaagt ccaaattccc atggtaaaaa aaatcaaaat gcatggcagg  30180
ctgtttgtaa ccttggaata agatgttggc caattctgga gccgccacgt acgcaagact  30240
cagggccacg ttctcttcat gcaaggatag tagaacacca ctccacccac ctcctatatt  30300
agacctttgc ccaaccctcc ccaactttcc catcccatcc acaaagaaac cgacattttt  30360
atcataaatc agggtttcgt ttttgtttca tcgataaact caaaggtgat gattttaggg  30420
tcttgtgagt gtgctttttt gtttgattct actgtagggt ttatgttctt tagctcatag  30480
gttttgtgta tttcttagaa atgtggcttc tttaatctct gggtttgtga ctttttgtgt  30540
ggtttctgtg tttttcatat caaaaaccta ttttttccga gttttttttt acaaattctt  30600
actctcaagc ttgaatactt cacatgcagt gttcttttgt agattttaga gttaatgtgt  30660
taaaaagttt ggatttttct tgcttataga gcttcttcac tttgattttg tgggtttttt  30720
tgttttaaag gtgagatttt tgatgaggtt tttgcttcaa agatgtcacc tttctgggtt  30780
tgtcttttga ataaagctat gaactgtcac atggctgacg caattttgtt actatgtcat  30840
gaaagctgac gtttttccgt gttatacatg tttgcttaca cttgcatgcg tcaaaaaaat  30900
tggggctttt tagttttagt caaagatttt acttctcttt tgggatttat gaaggaaagt  30960
tgcaaacttt ctcaaatttt accattttg ctttgatgtt tgtttagatt gcgacagaac  31020
```

```
aaactcatat atgttgaaat ttttgcttgg ttttgtatag gattgtgtct tttgcttata  31080
aatgttgaaa tctgaacttt ttttttgttt ggtttctttg agcaggagat aaggcgcacc  31140
accatggctt ctacatctgc tgctcaagac gctgctcctt acgagttccc ttctctcact  31200
gagatcaaga gggctcttcc ttctgagtgt ttcgaggctt ctgttcctct ttctctctac  31260
tacaccgcta gatctcttgc tcttgctgga tctctcgctg ttgctctctc ttacgctaga  31320
gctttgcctc ttgttcaggc taacgctctt cttgatgcta ctctctgcac tggatacgtt  31380
cttctccagg gaatcgtttt ctggggattc ttcaccgttg gtcacgattg tggacacgga  31440
gctttctcta gatctcacgt gctcaacttc tctgttggaa ccctcatgca ctctatcatc  31500
cttacccctt tcgagtcttg gaagctctct cacagacacc accacaagaa caccggaaac  31560
atcgataagg acgagatctt ctaccctcaa agagaggctg attctcaccc tgtttctaga  31620
caccttgtga tgtctcttgg atctgcttgg ttcgcttacc ttttcgctgg attccctcct  31680
agaaccatga accacttcaa cccttgggag gctatgtatg ttagaagagt ggctgctgtg  31740
atcatctctc tcggagttct tttcgctttc gctggactct actcttacct caccttcgtt  31800
cttggattca ccactatggc tatctactac ttcggacctc tcttcatctt cgctaccatg  31860
cttgttgtta ccactttcct ccaccacaac gatgaggaga caccttggta cgctgattct  31920
gagtggactt acgtgaaggg aaacctctct tctgtggaca gatcttacgg tgctctcatc  31980
gacaacctta gccacaacat cggaactcac cagatccacc acctcttccc tatcatccct  32040
cactacaagc tcaacgatgc tactgctgct ttcgctaagg ctttccctga gcttgttagg  32100
aaaaacgctg ctcctatcat cccaactttc ttcaggatgg ctgctatgta cgctaagtac  32160
ggagttgttg acactgatgc taagaccttc actctcaagg aggctaaggc tgctgctaag  32220
actaagtcat cttgatgatt aatgaaggcc gcagatatca gatctggtcg acctagagga  32280
tccccggccg caaagataat aacaaaagcc tactatataa cgtacatgca agtattgtat  32340
gatattaatg tttttacgta cgtgtaaaca aaaataatta cgtttgtaac gtatggtgat  32400
gatgtggtgc actaggtgta ggccttgtat taataaaaag aagtttgttc tatatagagt  32460
ggtttagtac gacgatttat ttactagtcg gattggaata gagaaccgaa ttcttcaatc  32520
cttgcttttg atcaagaatt gaaaccgaat caaatgtaaa agttgatata tttgaaaaac  32580
gtattgagct tatgaaaatg ctaatactct catctgtatg gaaaagtgac tttaaaaccg  32640
aacttaaaag tgacaaaagg ggaatatcgc atcaaaccga atgaaaccga tctacgtagg  32700
ctcagctgag cttacctaag gctacgtagg ctcacgtgac gttacgtaag gctacgtagc  32760
gtcacgtgag cttacctaac tctagctagc ctcacgtgac cttagctaac actaggtagc  32820
gtcagcttag cagatatttg gtgtctaaat gtttattttg tgatatgttc atgtttgaaa  32880
tggtggtttc gaaaccaggg acaacgttgg gatctgatag ggtgtcaaag agtattatgg  32940
attgggacaa tttcggtcat gagttgcaaa ttcaagtata tcgttcgatt atgaaaattt  33000
tcgaagaata tcccatttga gagagtcttt acctcattaa tgtttttaga ttatgaaatt  33060
ttatcatagt tcatcgtagt ctttttggtg taaaggctgt aaaaagaaat tgttcacttt  33120
tgttttcgtt tatgtgaagg ctgtaaaaga ttgtaaaaga ctattttggt gttttggata  33180
aaatgatagt ttttatagat tcttttgctt ttagaagaaa tacatttgaa atttttttcca  33240
tgttgagtat aaaataccga aatcgattga agatcataga aatattttaa ctgaaaacaa  33300
atttataact gattcaattc tctccatttt tatacctatt taaccgtaat cgattctaat  33360
agatgatcga ttttttatat aatcctaatt aaccaacggc atgtattgga taattaaccg  33420
```

```
atcaactctc accoctaata gaatcagtat tttccttcga cgttaattga tcctacacta  33480
tgtaggtcat atccatcgtt ttaatttttg gccaccattc aattctgtct tgcctttagg  33540
gatgtgaata tgaacggcca aggtaagaga ataaaaataa tccaaattaa agcaagagag  33600
gccaagtaag ataatccaaa tgtacacttg tcattgccaa aattagtaaa atactcggca  33660
tattgtattc ccacacatta ttaaaatacc gtatatgtat tggctgcatt tgcatgaata  33720
atactacgtg taagcccaaa agaacccacg tgtagcccat gcaaagttaa cactcacgac  33780
cccattcctc agtctccact atataaaccc accatcccca atctcaccaa acccaccaca  33840
caactcacaa ctcactctca caccttaaag aaccaatcac caccaaaaaa agttctttgc  33900
tttcgaagtt gccgcaacct aaacaggttt ttccttcttc tttcttctta ttaactacga  33960
ccttgtcctt tgcctatgta aaattactag gttttcatca gttacactga ttaagttcgt  34020
tatagtggaa gataaaatgc cctcaaagca ttttgcagga tatctttgat ttttcaaaga  34080
tatggaactg tagagtttga tagtgttctt gaatgtggtt gcatgaagtt tttttggtct  34140
gcatgttatt ttttcctcga aatatgtttt gagtccaaca agtgattcac ttgggattca  34200
gaaagttgtt ttctcaatat gtaacagttt ttttctatgg agaaaaatca tagggaccgt  34260
tggttttggc ttctttaatt ttgagctcag attaaaccca ttttacccgg tgttcttggc  34320
agaattgaaa acagtacgta gtaccgcgcc taccatgcca cctagtgctg ctagtgaagg  34380
tggtgttgct gaacttagag ctgctgaagt tgctagctac actagaaagg ctgttgacga  34440
aagacctgac ctcactatag ttggtgacgc tgtttacgac gctaaggctt ttagggacga  34500
gcaccctggt ggtgctcact tcgttagcct tttcggaggt agggacgcta ctgaggcttt  34560
tatggaatat caccgtagag cttggcctaa ggctaggatg tctaagttct tcgttggttc  34620
acttgacgct agcgagaagc ctactcaagc tgattcagct taccttagac tttgcgctga  34680
ggttaacgct cttttgccta agggtagcgg aggattcgct cctcctagct actggcttaa  34740
ggctgctgct cttgttgttg ctgctgttag tatagagggt tatatgctcc ttaggggtaa  34800
gaccctttttg cttagcgttt tccttggact cgtgttcgct tggataggac ttaatattca  34860
gcacgacgct aatcacggtg ctcttagtag acactcagtg attaactact gcctcggtta  34920
cgctcaggat tggataggtg gtaatatggt gctttggctt caagagcacg ttgtgatgca  34980
ccacctccac actaacgacg ttgacgctga tcctgatcaa aaggctcacg gtgttcttag  35040
acttaagcct actgacggtt ggatgccttg gcacgcactt caacaactct atatccttcc  35100
tggtgaggct atgtacgctt ttaagcttct tttcttggac gcccttgagc ttcttgcttg  35160
gaggtgggag ggtgagaaga ttagccctct tgctagagct ttgttcgctc ctgctgttgc  35220
ttgtaagctt ggattctggg ctagattcgt tgctctccct ctctggcttc aacctactgt  35280
tcacactgct ttgtgtatct gtgctactgt gtgtactggt agcttctacc tcgccttctt  35340
cttctttatc tctcacaact tcgacggtgt tggtagcgtt ggacctaagg gatcacttcc  35400
tagatcagct actttcgttc aacgtcaggt tgagactagc tctaacgttg gtggttactg  35460
gcttggagtt cttaacggtg gacttaactt tcagatagag caccacttgt tccctaggct  35520
tcaccactct tactacgctc aaatagctcc tgtggttagg actcacatag agaagctcgg  35580
ttttaagtac cgtcacttcc ctaccgttgg atctaacctt agctcaatgc ttcagcatat  35640
gggtaagatg ggaactagac ctggtgctga gaagggtggt aaggctgagt agtgattaat  35700
gaataattga ttgctgcttt aatgagatat gcgagacgcc tatgatcgca tgatatttgc  35760
```

```
tttcaattct gttgtgcacg ttgtaaaaaa cctgagcatg tgtagctcag atccttaccg  35820
ccggtttcgg ttcattctaa tgaatatatc acccgttact atcgtatttt tatgaataat  35880
attctccgtt caatttactg attgtctacg tagcgtcacc tgacgttacg taaggctacc  35940
taggctcacg tgacgttacg taacgctacg tagcgtcagg tgaggttagc taacgctagc  36000
tagcctcacc tgacgttagg taaggctacg tagcgtcacc tgagattagc taagcctacc  36060
tagactcacg tgaccttagg taacgctacg tagcgtcaaa gctttacaac gctacacaaa  36120
acttataacc gtaatcacca ttcattaact taactactat cacatgcatt catgaattga  36180
aacgagaagg atgtaaatag ttgggaagtt atctccacgt tgaagagatc gttagcgaga  36240
gctgaaagac cgagggagga gacgccgtca acacggacag agtcgtcgac cctcacatga  36300
agtaggagga atctccgtga ggagccagag agacgtcttt ggtcttcggt ttcgatcctt  36360
gatctgacgg agaagacgag agaagtgcga ctggactccg tgaggaccaa cagagtcgtc  36420
ctcggtttcg atcgtcggta ttggtggaga aggcggagga atctccgtga cgagccagag  36480
agatgtcgtc ggtcttcggt ttcgatcctt gatctgacgg agaagacgag agaagtgcga  36540
cgagactccg tgaggaccaa cagagttgtc ctcggtttcg atcgtcggtt tcggcggaga  36600
aggcggagga atctccgtga ggagccagag agacgtcgtt ggtcttcggt ttcgatcctt  36660
gatctgttgg agaagacgag acaagtggga cgagactcaa cgacggagtc agagacgtcg  36720
tcggtcttcg gtttcggccg agaaggcgga gtcggtcttc ggtttcggcc gagaaggcgg  36780
aggagacgtc ttcgatttgg gtctctcctc ttgacgaaga aaacaaagaa cacgagaaat  36840
aatgagaaag agaacaaaag aaaaaaaaat aaaaataaaa ataaaatttg gtcctcttat  36900
gtggtgacac gtggtttgaa acccaccaaa taatcgatca caaaaaacct aagttaagga  36960
tcggtaataa cctttctaat taattttgat ttatattaaa tcactctttt tatttataaa  37020
ccccactaaa ttatgcgata ttgattgtct aagtacaaaa attctctcga attcaataca  37080
catgtttcat atatttagcc ctgttcattt aatattacta gcgcattttt aatttaaaat  37140
tttgtaaact tttttggtca aagaacattt ttttaattag agacagaaat ctagactctt  37200
tatttggaat aatagtaata aagatatatt aggcaatgag tttatgatgt tatgtttata  37260
tagtttattt cattttaaat tgaaaagcat tatttttatc gaaatgaatc tagtatacaa  37320
tcaatattta tgttttttca tcagatactt tcctattttt tggcaccttt catcggacta  37380
ctgatttatt tcaatgtgta tgcatgcatg agcatgagta tacacatgtc ttttaaaatg  37440
catgtaaagc gtaacggacc acaaaagagg atccatacaa atacatctca tcgcttcctc  37500
tactattctc cgacacacac actgagcatg gtgcttaaac actctggtga gttctagtac  37560
ttctgctatg atcgatctca ttaccatttc ttaaatttct ctccctaaat attccgagtt  37620
cttgattttt gataacttca ggttttctct ttttgataaa tctggtcttt ccattttttt  37680
ttttttgtgg ttaatttagt ttcctatgtt cttcgattgt attatgcatg atctgtgttt  37740
ggattctgtt agattatgta ttggtgaata tgtatgtgtt tttgcatgtc tggttttggt  37800
cttaaaaatg ttcaaatctg atgatttgat tgaagctttt ttagtgttgg tttgattctt  37860
ctcaaaacta ctgttaattt actatcatgt tttccaactt tgattcatga tgacactttt  37920
gttctgcttt gttataaaat tttggttggt ttgattttgt aattatagtg taattttgtt  37980
aggaatgaac atgttttaat actctgtttt cgatttgtca cacattcgaa ttattaatcg  38040
ataatttaac tgaaaattca tggttctaga tcttgttgtc atcagattat ttgtttcgat  38100
aattcatcaa atatgtagtc cttttgctga tttgcgactg tttcattttt tctcaaaatt  38160
```

```
gttttttgtt aagtttatct aacagttatc gttgtcaaaa gtctctttca ttttgcaaaa  38220
tcttcttttt ttttttgttt gtaactttgt tttttaagct acacatttag tctgtaaaat  38280
agcatcgagg aacagttgtc ttagtagact tgcatgttct tgtaacttct atttgtttca  38340
gtttgttgat gactgctttg attttgtagg tcaaaccgcg ccatgtctgc tagcggagct  38400
ttgttgcctg ctatagcttt cgctgcttac gcttacgcta cctacgctta tgctttcgag  38460
tggagccacg ctaacggaat cgataacgtg gatgctagag agtggattgg agctttgtct  38520
ttgagactcc ctgcaattgc aaccacaatg tacctcttgt tctgccttgt gggacctaga  38580
ttgatggcta agagggaggc ttttgatcct aagggattta tgctcgctta caacgcttac  38640
caaaccgctt tcaacgttgt ggtgctcgga atgttcgcta gagagatctc tggattggga  38700
caacctgttt ggggatctac tatgccttgg agcgatagga agtccttcaa gattttgttg  38760
ggagtgtggc tccactacaa caataagtac ctcgagttgt tggatactgt gttcatggtg  38820
gctaggaaaa agaccaagca gctctctttc ttgcacgtgt accaccacgc tttgttgatt  38880
tgggcttggt ggcttgtttg tcacctcatg gctaccaacg attgcatcga tgcttatttc  38940
ggagctgctt gcaactcttt catccacatc gtgatgtact cctactacct catgtctgct  39000
ttgggaatta ggtgcccttg gaagagatat atcacccagg ctcagatgtt gcaattcgtg  39060
atcgtgttcg ctcacgctgt tttcgtgctc agacaaaagc actgccctgt tactttgcct  39120
tgggcacaaa tgttcgtgat gacaaatatg ttggtgctct tcggaaactt ctacctcaag  39180
gcttactcta acaagtctag gggagatgga gcttcttctg ttaagcctgc tgagactact  39240
agagcacctt ctgtgagaag aaccaggtca aggaagatcg attgatagtt aatgaactaa  39300
gtttgatgta tctgagtgcc aacgtttact ttgtctttcc tttcttttat tggttatgat  39360
tagatgttta ctatgttctc tctttttcgt tataaataaa gaagttcaat tcttctatag  39420
tttcaaacgc gattttaagc gtttctattt aggtttacat gatttctttt acaaaatcat  39480
ctttaaaata cagtatattt ttagttttca taaaatattt aaagaaatga aagtttataa  39540
acattcactc ctattctcta attaaggatt tgtaaaacaa aaattttgta agcatatcga  39600
tttatgcgtt ttgtcttaat tagctcacta aataataaat aatagcttat gttgtgggac  39660
tgtttaatta cctaacttag aactaaaatc aactctttgt gctagctagc ctcagctgac  39720
gttacgtaac gctaggtagc gtcacgtgac gttagctaac gctaggtagc gtcagctgag  39780
cttacgtaag cgcttaatta aagtactgat atcggtacca aatcgaatcc aaaaattacg  39840
gatatgaata taggcatatc cgtatccgaa ttatccgttt gacagctagc aacgattgta  39900
caattgcttc tttaaaaaag gaagaaagaa agaaagaaaa gaatcaacat cagcgttaac  39960
aaacggcccc gttacggccc aaacggtcat atagagtaac ggcgttaagc gttgaaagac  40020
tcctatcgaa atacgtaacc gcaaacgtgt catagtcaga tcccctcttc cttcaccgcc  40080
tcaaacacaa aaataatctt ctacagccta tatatacaac ccccccttct atctctcctt  40140
tctcacaatt catcatcttt ctttctctac ccccaatttt aagaaatcct ctcttctcct  40200
cttcattttc aaggtaaatc tctctctctc tctctctctc tgttattcct tgttttaatt  40260
aggtatgtat tattgctagt ttgttaatct gcttatctta tgtatgcctt atgtgaatat  40320
ctttatcttg ttcatctcat ccgtttagaa gctataaatt tgttgatttg actgtgtatc  40380
tacacgtggt tatgtttata tctaatcaga tatgaatttc ttcatattgt tgcgtttgtg  40440
tgtaccaatc cgaaatcgtt gatttttttc atttaatcgt gtagctaatt gtacgtatac  40500
```

```
atatggatct acgtatcaat tgttcatctg tttgtgtttg tatgtataca gatctgaaaa  40560
catcacttct ctcatctgat tgtgttgtta catacataga tatagatctg ttatatcatt  40620
tttttatta attgtgtata tatatatgtg catagatctg gattacatga ttgtgattat  40680
ttacatgatt ttgttattta cgtatgtata tatgtagatc tggacttttt ggagttgttg  40740
acttgattgt atttgtgtgt gtatatgtgt gttctgatct tgatatgtta tgtatgtgca  40800
gctgaaccat ggcggcggca acaacaacaa caacaacatc ttcttcgatc tccttctcca  40860
ccaaaccatc tccttcctcc tccaaatcac cattaccaat ctccagattc tccctcccat  40920
tctccctaaa ccccaacaaa tcatcctcct cctcccgccg ccgcggtatc aaatccagct  40980
ctccctcctc catctccgcc gtgctcaaca caaccaccaa tgtcacaacc actccctctc  41040
caaccaaacc taccaaaccc gaaacattca tctcccgatt cgctccagat caaccccgca  41100
aaggcgctga tatcctcgtc gaggctttag aacgtcaagg cgtagaaacc gtattcgctt  41160
accctggagg tacatcaatg gagattcacc aagccttaac ccgctcttcc tcaatccgta  41220
acgtccttcc tcgtcacgaa caaggaggtg tattcgcagc agaaggatac gctcgatcct  41280
caggtaaacc aggtatctgt atagccactt caggtcccgg agctacaaat ctcgttagcg  41340
gattagccga tgcgttgtta gatagtgttc ctcttgtagc aatcacagga caagtccctc  41400
gtcgtatgat tggtacagat gcgtttcaag agactccgat tgttgaggta acgcgttcga  41460
ttacgaagca taactatctt gtgatggatg ttgaagatat cccaaggatt attgaagagg  41520
ctttcttttt agctacttct ggtagacctg gacctgtttt ggttgatgtt cctaaagata  41580
ttcaacaaca gcttgcgatt cctaattggg aacaggctat gagattacct ggttatatgt  41640
ctaggatgcc taaacctccg gaagattctc atttggagca gattgttagg ttgatttctg  41700
agtctaagaa gcctgtgttg tatgttggtg gtggttgtct taattctagc gatgaattgg  41760
gtaggtttgt tgagcttacg ggcatccctg ttgcgagtac gttgatgggg ctgggatctt  41820
atccttgtga tgatgagttg tcgttacata tgcttggaat gcatgggact gtgtatgcaa  41880
attacgctgt ggagcatagt gatttgttgt tggcgtttgg ggtaaggttt gatgatcgtg  41940
tcacgggtaa acttgaggct tttgctagta gggctaagat tgttcatatt gatattgact  42000
cggctgagat tgggaagaat aagactcctc atgtgtctgt gtgtggtgat gttaagctgg  42060
ctttgcaagg gatgaataag gttcttgaga accgagcgga ggagcttaaa cttgattttg  42120
gagtttggag gaatgagttg aacgtacaga aacagaagtt tccgttgagc tttaagacgt  42180
ttggggaagc tattcctcca cagtatgcga ttaaggtcct tgatgagttg actgatggaa  42240
aagccataat aagtactggt gtcgggcaac atcaaatgtg ggcggcgcag ttctacaatt  42300
acaagaaacc aaggcagtgg ctatcatcag gaggccttgg agctatggga tttggacttc  42360
ctgctgcgat tggagcgtct gttgctaacc ctgatgcgat agttgtggat attgacggag  42420
atggaagttt tataatgaat gtgcaagagc tagccactat tcgtgtagag aatcttccag  42480
tgaaggtact tttattaaac aaccagcatc ttggcatggt tatgcaatgg gaagatcggt  42540
tctacaaagc taaccgagct cacacatttc tcggggaccc ggctcaggag gacgagatat  42600
tcccgaacat gttgctgttt gcagcagctt gcgggattcc agcggcgagg gtgacaaaga  42660
aagcagatct ccgagaagct attcagacaa tgctggatac accaggacct tacctgttgg  42720
atgtgatttg tccgcaccaa gaacatgtgt tgccgatgat cccgaatggt ggcactttca  42780
acgatgtcat aacggaagga gatggccgga ttaaatactg agagatgaaa ccggtgatta  42840
tcagaacctt ttatggtctt tgtatgcata tggtaaaaaa acttagtttg caatttcctg  42900
```

```
tttgttttgg taatttgagt ttcttttagt tgttgatctg cctgcttttt ggtttacgtc  42960

agactactac tgctgttgtt gtttggtttc ctttctttca ttttataaat aaataatccg  43020

gttcggttta ctccttgtga ctggctcagt ttggttattg cgaaatgcga atggtaaatt  43080

gagtaattga aattcgttat tagggttcta agctgtttta acagtcactg ggttaatatc  43140

tctcgaatct tgcatggaaa atgctcttac cattggtttt taattgaaat gtgctcatat  43200

gggccgtggt ttccaaatta aataaaacta cgatgtcatc gagaagtaaa atcaactgtg  43260

tccacattat cagttttgtg tatacgatga aatagggtaa ttcaaaatct agcttgatat  43320

gccttttggt tcattttaac cttctgtaaa catttttca gattttgaac aagtaaatcc  43380

aaaaaaaaaa aaaaaaatct caactcaaca ctaaattatt ttaatgtata aaagatgctt  43440

aaaacatttg gcttaaaaga aagaagctaa aaacatagag aactcttgta aattgaagta  43500

tgaaaatata ctgaattggg tattatatga atttttctga tttaggattc acatgatcca  43560

aaaaggaaat ccagaagcac taatcagaca ttggaagtag gattaatcag tgatcagtaa  43620

ctattaaatt caattaaccg cggacatcta catttttgaa ttgaaaaaaa attggtaatt  43680

actctttctt tttctccata ttgaccatca tactcattgt                        43720
```

<210> SEQ ID NO 22
<211> LENGTH: 20
<212> TYPE: DNA
<213> ORGANISM: Artificial sequence
<220> FEATURE:
<223> OTHER INFORMATION: LBFDAU Locus 1 RB junction region

<400> SEQUENCE: 22

```
tataaataag cagtcagcat                                                 20
```

<210> SEQ ID NO 23
<211> LENGTH: 20
<212> TYPE: DNA
<213> ORGANISM: Artificial sequence
<220> FEATURE:
<223> OTHER INFORMATION: LBFDAU Locus 1 LB junction region

<400> SEQUENCE: 23

```
tactcattgt aagacacaca                                                 20
```

<210> SEQ ID NO 24
<211> LENGTH: 1600
<212> TYPE: DNA
<213> ORGANISM: Artificial sequence
<220> FEATURE:
<223> OTHER INFORMATION: LBFDAU Locus 1 flanking sequence up to and including the right border of the T-DNA

<400> SEQUENCE: 24

```
aaaagaaata taaaagaata tgaccaaaaa agtaaacgtg agtgagagaa taagaaaatg     60

actacaaaat ataatagcct caattatctt caaaactaag ttgacattta attatgcttt    120

tgcaagatat ttacttttgt tgttcgatca tatttaatga ttattttggt tttgaaacaa    180

atattaacat tatatatatt gtgtctatat tgaactgttg taaattataa acatcaaaat    240

tttaatgtta tcttaattat aatttctaat actagtatat tcaaaaatca aaataaacat    300

attttataaa atagtgccag tacgtagtat gggagataat actagtggct ttataaaggg    360

aaacattgtc tctaaaatct cagataaaat gttaaaacac acttattcac aattatgaag    420

atttgaaata tctgaaattt caaattgatg cacttggtag aaagcaaagg ttcaacgcta    480
```

```
agtctacaag gtgtaataat gaagtgaaaa tgctagttta gattaccctt gatatgtgac    540
tgaacatagg gtggagcgtc agtgagtcca tggagtacag aagctaaaca agagacatgg    600
ttaagcacca gaatcaactc gttctccata gagtccagct tttgagatat atgtgaatag    660
ccttgttgca atatacttgt gagtggcagg cgtgatctta ttaacgaaag tccaaattct    720
gaacaaagtt tatatcaagc tacgatggaa atatggaatc cgtatcaaaa tcaactgtac    780
tgtatcatac ggtgcagatt tttagctcga ctctaccacc ttgcgtttac ttttgtgatg    840
aacattgcga ttatatatga ggacctaaat agagggaaaa tgtatgaaga caggatccta    900
agaatgaaaa accagcatcc ccaagatgtg gcaccaagtg ctatcgacca caaactacgc    960
tggacatact ctgatatagt tcgttaagaa atcaaaatgt caacacatat aaataagcag   1020
tcagcatcat cacaccaaaa gttaggcccg aatagtttga aattagaaag ctcgcaattg   1080
aggtctacag gccaaattcg ctcttagccg tacaatatta ctcaccggtg cgatgccccc   1140
catcgtaggt gaaggtggaa attaatggcg cgcctgatca ctgattagta actattacgt   1200
aagcctacgt agcgtcacgt gacgttagct aacgctacgt agcctcagct gacgttacgt   1260
aagcctacgt agcgtcacgt gagcttagct aacgctacct aggctcagct gacgttacgt   1320
aacgctagct agcgtcactc ctgcagcaaa tttacacatt gccactaaac gtctaaaccc   1380
ttgtaatttg tttttgtttt actatgtgtg ttatgtattt gatttgcgat aaatttttat   1440
atttggtact aaatttataa caccttttat gctaacgttt gccaacactt agcaatttgc   1500
aagttgatta attgattcta aattattttt gtcttctaaa tacatatact aatcaactgg   1560
aaatgtaaat atttgctaat atttctacta taggagaatt                          1600
```

```
<210> SEQ ID NO 25
<211> LENGTH: 1677
<212> TYPE: DNA
<213> ORGANISM: Artificial sequence
<220> FEATURE:
<223> OTHER INFORMATION: LBFDAU  Locus 1 flanking sequence up to and
      including the left border of the T-DNA

<400> SEQUENCE: 25
```

```
taattgaaat tcgttattag ggttctaagc tgttttaaca gtcactgggt taatatctct     60
cgaatcttgc atggaaaatg ctcttaccat tggtttttaa ttgaaatgtg ctcatatggg    120
ccgtggtttc caaattaaat aaaactacga tgtcatcgag aagtaaaatc aactgtgtcc    180
acattatcag ttttgtgtat acgatgaaat agggtaattc aaaatctagc ttgatatgcc    240
ttttggttca ttttaacctt ctgtaaacat tttttcagat tttgaacaag taaatccaaa    300
aaaaaaaaaa aaaatctcaa ctcaacacta aattatttta atgtataaaa gatgcttaaa    360
acatttggct taaaagaaag aagctaaaaa catagagaac tcttgtaaat tgaagtatga    420
aaatatactg aattgggtat tatatgaatt tttctgattt aggattcaca tgatccaaaa    480
aggaaatcca gaagcactaa tcagacattg gaagtaggat taatcagtga tcagtaacta    540
ttaaattcaa ttaaccgcgg acatctacat ttttgaattg aaaaaaaatt ggtaattact    600
ctttcttttt ctccatattg accatcatac tcattgtaag acacacagat gaagaagtca    660
aatagctcga cattcctttg gtctggtcca gtgatgtcga ctcacaaagc gaagattgca    720
tgaatagact atcatgtgtt tgctatgtat gagtactatg gaatcgaggg atcatttatt    780
tttcatgtca ttgttcttgg aggttgtgtg gagaggcatc accattaatc ttctgaacat    840
cagctatact aatcattaat tggaatcagc gactgcaaat tatggcagag gatgttggaa    900
```

atagtaccac cacattccta atccactatg ctttccaagc tgcagtaatt tgagttggag 960
acgggagttt tgctcattta ctcaggctct tggacaaaca aatgtgaaat cgcatatctg 1020
ctcaatccga catactaatc aaaggtcaag aatttttttt agagaagatg aaaaccataa 1080
tgaaagcatc taatgtttat agaaaattac caaaaatacc acatttatga aaaattatca 1140
aaaatacaat attcatagta tcacttttca tatttacaat aaccacgttt gttctcaatt 1200
ttaacgaaga acaaacgaca tttataatcc taagataatt ttttctaatt caaaaataat 1260
tttcgatttt caaaaaaaaa attgaaaaaa aaattgaaaa gaaaaattca aaacaaaatt 1320
atatgaaagt tcaaatttga aaaatgataa ttcaaaaaca taaaaaaata tatttttatt 1380
taaataatta tttattatat atatatagac catggagcaa gggggcgtgg gccccggggc 1440
ccaaactttt tttcccatat ataatgtcaa caaggacccg atttttagaa aaaaaaatag 1500
gtataaagga gtccaaaaaa ttcaaattag ttatatatgt atgtaaaaaa atattaaaat 1560
ttattttgcc caagggccta tagattcatt gggccgaccc tggggttggg gttgtgtgtg 1620
tgtcattcta taattaaccg gcaaaaactc caaaattttt atttaacaaa tgtataa 1677

<210> SEQ ID NO 26
<211> LENGTH: 24
<212> TYPE: DNA
<213> ORGANISM: Artificial sequence
<220> FEATURE:
<223> OTHER INFORMATION: LBFDAU Locus 1_Forward primer

<400> SEQUENCE: 26
gcggacatct acatttttga attg 24

<210> SEQ ID NO 27
<211> LENGTH: 28
<212> TYPE: DNA
<213> ORGANISM: Artificial sequence
<220> FEATURE:
<223> OTHER INFORMATION: LBFDAU Locus 1_Reverse primer

<400> SEQUENCE: 27
gctatttgac ttcttcatct gtgtgtct 28

<210> SEQ ID NO 28
<211> LENGTH: 22
<212> TYPE: DNA
<213> ORGANISM: Artificial sequence
<220> FEATURE:
<223> OTHER INFORMATION: LBFDAU locus 1_Probe

<400> SEQUENCE: 28
tttctccata ttgaccatca ta 22

<210> SEQ ID NO 29
<211> LENGTH: 39620
<212> TYPE: DNA
<213> ORGANISM: Artificial sequence
<220> FEATURE:
<223> OTHER INFORMATION: contig of insert and flanking sequences of LBFDAU T-DNA Locus 2

<400> SEQUENCE: 29
attttagatt tagtcatatt tttaacttaa ttattaatta taataaatat ttttagtgat 60
ttagatgata aattttcatt gtcttgagaa taataaaaaa aaaatctaag gataatatca 120
tagttaaatt tatatgatat ttacttcagt aatattaaaa tattatatac atttttatta 180

```
tatttggttt agtaatatta aatggattct attttaaatt tcttatgaca atcaaaacca    240
cttagtgtga taatttctga aaaaaattgg caaaaaaatc aaaaatactt atcttattat    300
ttgtagtgat ttttctctct ctcatgttaa aattttgaat gtttaaagtc tttattatct    360
ttaataaata attagattaa atttttaata tataattacc cataatttaa aacaaatttc    420
attaatttta aaatcatcat tatctaaaaa gattatatat tatgttatcc aaaaatattt    480
tacatcataa tattttaaaa taaatataaa tttatgtata ttgttttatg tatatatgaa    540
tgtttttaag tttattttac ataatcaaat atattttaca aaaataattt ttatcatata    600
taaaatttaa catttaatta attattaaat atttcaaaag tatgaatata acttattctc    660
atggttttta attgataata tatctattta caatttttttg taaaattatt aaacccgcaa    720
gtatggacaa aacacctagt atatatattt ggaacaaaga atacagacaa aacacctagt    780
atatatattt ggaacaaaaa atatacgtac atattttata tacatgaata acttatatat    840
cacttagaaa taggataatc aattgacatt aaactctctt aaattatata ttgtatagaa    900
gaactataga tatacgtata aaatatttat aaaagataac tacactatat atagaaacag    960
ataacgatac atccacgaaa attcttctgg aaaagaaaca gagtggtttc gcgtcagcac   1020
acctacgttg atcattggaa attggaatat tgaaacacgc ttcaaatcaa cgactattaa   1080
ttaccaatac accctggctt tggggtgaga gttgatcggt taattatcca atacatgccg   1140
ttggttaatt aggattatat aaaaaatcga tcatctatta gaatcgatta cggttaaata   1200
ggtataaaaa tggagagaat tgaatcagtt ataaatttgt tttcagttaa aatatttcta   1260
tgatcttcaa tcgatttcgg tattttatac tcaacatgga aaaaatttca aatgtatttc   1320
ttctaaaagc aaaagaatct ataaaaacta tcattttatc caaaacacca aaatagtctt   1380
ttacaatctt ttacagcctt cacataaacg aaaacaaaag tgaacaattt ctttttacag   1440
cctttacacc aaaaagacta cgatgaacta tgataaaatt tcataatcta aaaacattaa   1500
tgaggtaaag actctctcaa atgggatatt cttcgaaaat tttcataatc gaacgatata   1560
cttgaatttg caactcatga ccgaaattgt cccaatccat aatactcttt gacaccctat   1620
cagatcccaa cgttgtccct ggtttcgaaa ccaccatttc aaacatgaac atatcacaaa   1680
ataaacattt agacaccaaa tatctgctaa gcgcttacgt aagctcagct gacgctacct   1740
agcgttagct aacgtcacgt gacgctacct agcgttacgt aacgtcagct gaggctagct   1800
agctgaatta acgccgaatt aattcggggg atctggattt tagtactgga ttttggtttt   1860
aggaattaga aattttattg atagaagtat tttacaaata caaatacata ctaagggttt   1920
cttatatgct caacacatga gcgaaaccct ataggaaccc taattccctt atctgggaac   1980
tactcacaca ttattatgga gaaactcgag cttgtcgatc actcggtctt agctcccttt   2040
tgctttccat cggatggctt gatgtacttt tgcacgtaga agtttccgaa gaggaacaag   2100
agggagatca tgtagtagaa gaggatcttg atgagccatt gtggatatgg agcgttggtt   2160
ttcatatcgt agtaagcttg caccaagttg agcatgaact ggaacatctg gaattgggtg   2220
aggtatcttc cccagaagag gtacttgttc ttgagctttg gggaagatct caagcaagca   2280
gccaagaagt agtaagcgta catcaacacg tgcactccag agttgagagc agcactccaa   2340
taagcctctc ctcctggagc gtggtgagca atagcccacc agataaggga gatagaagag   2400
tggtggtaca cgtggaggaa agaaatctgt ctggtggatc tcttgaggat catgatcacg   2460
gtatccatga actccacgta cttggacatg tagaagaggt aaacgaggat agccatctcc   2520
```

```
ttgtgctttg ggttataagc gtttccccac aaggaatatc tccaggtgat agcttggtaa   2580
gcgataccca cgcacatgta aagagacaaa gcgaagcaga acaagttgtg caccaacacc   2640
aaagcttgca acaagaatgg ctcagaagct cttggcttga gatctctagc cttgatccaa   2700
agcaatcctc cgatcacgat ggtcaagtaa acagacactc ccaacacaat tggagttgga   2760
gaatcaacga gtggcaatcc cttagtagtt ggggtatcag tcaactcaac tccgaaagat   2820
cccaacaaag cgttcactcc ttgggaaacc tttccatcca actctccgta gaacctctca   2880
acaacttcca tggtttcttc taaagctgaa agtgaaccat tattacaact taacactcaa   2940
ctcacaagag gagaagcaac aaagcttatg taaggattta gtattaaggc caaaaaaaca   3000
cagatcaaat tcaattattg aagctttact tatcaagtta tcatataacc aatgaagacg   3060
gtaattcaaa agaaaaataa aagggtttgt agaataattg atacgtttac ctttgccgat   3120
tcagagacag tgaagcttaa acagtactgg ctatgaagaa attataatcg tgtaaaactt   3180
agtgagtgtg tatgaatgaa agtattgcaa aatcctcatt atatagacta catgcataac   3240
tagttgcatg taaatttgta gtttcttcca ttattgcatc ctccaagtgg atgtcatggt   3300
tttacacatg gcttccatgc aaatcatttc caaaatattt ttaaactttc cacagggcat   3360
ccatgcatgc acctcaaaac ttgtgtgtgg taacattgtt gtcttgaaaa attactaaac   3420
cttttgtcca cgtgacgttc atgcacctca aatcttgtgt ggtaccatta ttatcctcaa   3480
gaattattga atgtttggtg tatatgccat ccatgcagca ttgcaacaat taaatctcca   3540
aaccttgtgg taccatattc actcacttta attctcctat agtagaaata ttagcaaata   3600
tttacatttc cagttgatta gtatatgtat ttagaagaca aaaataattt agaatcaatt   3660
aatcaacttg caaattgcta agtgttggca aacgttagca taaaaggtgt tataaattta   3720
gtaccaaata taaaaattta tcgcaaatca aatacataac acacatagta aaacaaaaac   3780
aaattacaag ggtttagacg tttagtggca atgtgtaaat ttgctgcagg agtgacgcta   3840
gctagcgtta cgtaacgtca gctgagccta ggtagcgtta gctaagctca cgtgacgcta   3900
cgtaggctta cgtaacgtca gctgaggcta cgtagcgtta gctaacgtca cgtgacgcta   3960
cgtaggctta cgtaatagtt actaatcagt gatcaggcgc gccattaatt tccaccttca   4020
cctacgatgg ggggcatcgc accggtgagt aatattgtac ggctaagagc gaatttggcc   4080
tgtagacctc aattgcgagc tttctaattt caaactattc gggcctaact tttggtgtga   4140
tgatgctgac tgtttcgacg ttaattgatc ctacactatg taggtcatat ccatcgtttt   4200
aatttttggc caccattcaa ttctgtcttg cctttaggga tgtgaatatg aacggccaag   4260
gtaagagaat aaaaataatc caaattaaag caagagaggc caagtaagat aatccaaatg   4320
tacacttgtc attgccaaaa ttagtaaaat actcggcata ttgtattccc acacattatt   4380
aaaataccgt atatgtattg gctgcatttg catgaataat actacgtgta agcccaaaag   4440
aacccacgtg tagcccatgc aaagttaaca ctcacgaccc cattcctcag tctccactat   4500
ataaacccac catccccaat ctcaccaaac ccaccacaca actcacaact cactctcaca   4560
ccttaaagaa ccaatcacca ccaaaaaatt tcacgatttg gaatttgatt cctgcgatca   4620
caggtatgac aggttagatt ttgttttgta tagttgtata catacttctt tgtgatgttt   4680
tgtttactta atcgaatttt tggagtgttt taaggtctct cgtttagaaa tcgtggaaaa   4740
tatcactgtg tgtgtgttct tatgattcac agtgtttatg ggtttcatgt tctttgtttt   4800
atcattgaat gggaagaaat ttcgttggga tacaaatttc tcatgttctt actgatcgtt   4860
attaggagtt tggggaaaaa ggaagagttt ttttggttgg ttcgagtgat tatgaggtta   4920
```

```
tttctgtatt tgatttatga gttaatggtc gttttaatgt tgtagacatg ggaaaaggat   4980
ctgagggaag atctgctgct agagagatga ctgctgaggc taacggagat aagagaaaga   5040
ccatcctcat tgagggagtg ttgtacgatg ctaccaactt caaacaccca ggaggttcca   5100
ttattaactt cctcaccgag ggagaagctg gagttgatgc tacccaagct tacagagagt   5160
tccatcagag atccggaaag gctgataagt acctcaagtc cctcccaaag ttggatgctt   5220
ctaaggtgga gtctaggttc tctgctaagg agcaggctag aagggacgct atgaccaggg   5280
attacgctgc tttcagagag gagttggttg ctgagggata cttcgatcca tctatcccac   5340
acatgatcta cagagtggtg gagattgtgg ctttgttcgc tttgtctttc tggttgatgt   5400
ctaaggcttc tccaacctct ttggttttgg gagtggtgat gaacggaatc gctcaaggaa   5460
gatgcggatg ggttatgcac gagatgggac acggatcttt cactggagtt atctggctcg   5520
atgataggat gtgcgagttc ttctacggag ttggatgtgg aatgtctgga cactactgga   5580
agaaccagca ctctaagcac cacgctgctc caaacagatt ggagcacgat gtggatttga   5640
acaccttgcc actcgttgct ttcaacgaga gagttgtgag gaaggttaag ccaggatctt   5700
tgttggcttt gtggctcaga gttcaggctt atttgttcgc tccagtgtct tgcttgttga   5760
tcggattggg atggaccttg tacttgcacc caagatatat gctcaggacc aagagacaca   5820
tggagtttgt gtggatcttc gctagatata tcggatggtt ctccttgatg ggagctttgg   5880
gatattctcc tggaacttct gtgggaatgt acctctgctc tttcggactt ggatgcatct   5940
acatcttcct ccaattcgct gtgtctcaca cccacttgcc agttaccaac ccagaggatc   6000
aattgcactg gcttgagtac gctgctgatc acaccgtgaa catctctacc aagtcttggt   6060
tggttacctg gtggatgtct aacctcaact tccaaatcga gcaccacttg ttcccaaccg   6120
ctccacaatt caggttcaag gagatctctc caagagttga ggctctcttc aagagacaca   6180
acctccctta ctacgatttg ccatacacct ctgctgtttc tactaccttc gctaacctct   6240
actctgttgg acactctgtt ggagctgata ccaagaagca ggattgactg ctttaatgag   6300
atatgcgaga cgcctatgat cgcatgatat ttgctttcaa ttctgttgtg cacgttgtaa   6360
aaaacctgag catgtgtagc tcagatcctt accgccggtt tcggttcatt ctaatgaata   6420
tatcacccgt tactatcgta tttttatgaa taatattctc cgttcaattt actgattgtc   6480
tacgtaggct cagctgagct tacctaaggc tacgtaggct cacgtgacgt tacgtaaggc   6540
tacgtagcgt cacgtgagct tacctaactc tagctagcct cacgtgacct tagctaacac   6600
taggtagcgt cagctcgacg gcccggactg tatccaactt ctgatctttg aatctctctg   6660
ttccaacatg ttctgaagga gttctaagac ttttcagaaa gcttgtaaca tgctttgtag   6720
actttctttg aattactctt gcaaactctg attgaaccta cgtgaaaact gctccagaag   6780
ttctaaccaa attccgtctt gggaaggccc aaaatttatt gagtacttca gtttcatgga   6840
cgtgtcttca aagatttata acttgaaatc ccatcatttt taagagaagt tctgttccgc   6900
aatgtcttag atctcattga aatctacaac tcttgtgtca gaagttcttc cagaatcaac   6960
ttgcatcatg gtgaaaatct ggccagaagt tctgaacttg tcatatttct taacagttag   7020
aaaaatttct aagtgtttag aattttgact tttccaaagc aaacttgact tttgactttc   7080
ttaataaaac aaacttcata ttctaacatg tcttgatgaa atgtgattct tgaaatttga   7140
tgttgatgca aaagtcaaag tttgactttt cagtgtgcaa ttgaccattt tgctcttgtg   7200
ccaattccaa acctaaattg atgtatcagt gctgcaaact tgatgtcatg gaagatctta   7260
```

```
tgagaaaatt cttgaagact gagaggaaaa attttgtagt acaacacaaa gaatcctgtt   7320
tttcatagtc ggactagaca cattaacata aaacaccact tcattcgaag agtgattgaa   7380
gaaggaaatg tgcagttacc tttctgcagt tcataagagc aacttacaga cacttttact   7440
aaaatactac aaagaggaag attttaacaa cttagagaag taatgggagt taaagagcaa   7500
cacattaagg gggagtgtta aaattaatgt gttgtaacca ccactacctt tagtaagtat   7560
tataagaaaa ttgtaatcat cacattataa ttattgtcct tatttaaaat tatgataaag   7620
ttgtatcatt aagattgaga aaaccaaata gtcctcgtct tgatttttga attattgttt   7680
tctatgttac ttttcttcaa gcctatataa aaactttgta atgctaaatt gtatgctgga   7740
aaaaaatgtg taatgaattg aatagaaatt atggtatttc aaagtccaaa atccatcaat   7800
agaaatttag tacaaaacgt aactcaaaaa tattctctta ttttaaattt tacaacaata   7860
taaaaatatt ctcttatttt aaattttaca ataatataat ttatcacctg tcacctttag   7920
aataccacca acaatattaa tacttagata ttttattctt aataattttg agatctctca   7980
atatatctga tatttatttt atatttgtgt catattttct tatgttttag agttaaccct   8040
tatatcttgg tcaaactagt aattcaatat atgagtttgt gaaggacaca ttgacatctt   8100
gaaacattgg ttttaacctt gttggaatgt taaaggtaat aaaacattca gaattatgac   8160
catctattaa tatacttcct ttgtctttta aaaaagtgtg catgaaaatg ctctatggta   8220
agctagagtg tcttgctggc ctgtgtatat caattccatt tccagatggt agaaactgcc   8280
actacgaata attagtcata agacacgtat gttaacacac gtccccttgc atgtttttttg   8340
ccatatattc cgtctctttc tttttcttca cgtataaaac aatgaactaa ttaatagagc   8400
gatcaagctg aacagttctt tgctttcgaa gttgccgcaa cctaaacagg tttttccttc   8460
ttctttcttc ttattaacta cgaccttgtc ctttgcctat gtaaaattac taggttttca   8520
tcagttacac tgattaagtt cgttatagtg gaagataaaa tgccctcaaa gcattttgca   8580
ggatatcttt gatttttcaa agatatggaa ctgtagagtt tgatagtgtt cttgaatgtg   8640
gttgcatgaa gtttttttgg tctgcatgtt attttttcct cgaaatatgt tttgagtcca   8700
acaagtgatt cacttgggat tcagaaagtt gttttctcaa tatgtaacag ttttttttcta   8760
tggagaaaaa tcatagggac cgttggtttt ggcttcttta attttgagct cagattaaac   8820
ccattttacc cggtgttctt ggcagaattg aaaacagtac gtagtaccgc gcctaccatg   8880
tgtgttgaga ccgagaacaa cgatggaatc cctactgtgg agatcgcttt cgatggagag   8940
agagaaagag ctgaggctaa cgtgaagttg tctgctgaga agatggaacc tgctgctttg   9000
gctaagacct tcgctagaag atacgtggtt atcgagggag ttgagtacga tgtgaccgat   9060
ttcaaacatc ctggaggaac cgtgattttc tacgctctct ctaacactgg agctgatgct   9120
actgaggctt tcaaggagtt ccaccacaga tctagaaagg ctaggaaggc tttggctgct   9180
ttgccttcta gacctgctaa gaccgctaaa gtggatgatg ctgagatgct ccaggatttc   9240
gctaagtgga gaaaggagtt ggagagggac ggattcttca agccttctcc tgctcatgtt   9300
gcttacagat tcgctgagtt ggctgctatg tacgctttgg gaacctactt gatgtacgct   9360
agatacgttg tgtcctctgt gttggtttac gcttgcttct tcggagctag atgtggatgg   9420
gttcaacacg agggaggaca ctcttctttg accggaaaca tctggtggga taagagaatc   9480
caagctttca ctgctggatt cggattggct ggatctggag atatgtggaa ctccatgcac   9540
aacaagcacc acgctactcc tcaaaaagtg aggcacgata tggatttgga taccactcct   9600
gctgttgctt tcttcaacac cgctgtggag gataatagac ctaggggatt ctctaagtac   9660
```

```
tggctcagat tgcaagcttg gaccttcatt cctgtgactt ctggattggt gttgctcttc   9720
tggatgttct tcctccaccc ttctaaggct ttgaagggag gaaagtacga ggagcttgtg   9780
tggatgttgg ctgctcacgt gattagaacc tggaccatta aggctgttac tggattcacc   9840
gctatgcaat cctacggact cttcttggct acttcttggg tttccggatg ctacttgttc   9900
gctcacttct ctacttctca cacccacttg gatgttgttc ctgctgatga gcacttgtct   9960
tgggttaggt acgctgtgga tcacaccatt gatatcgatc cttctcaggg atgggttaac  10020
tggttgatgg gatacttgaa ctgccaagtg attcaccacc tcttcccttc tatgcctcaa  10080
ttcagacaac ctgaggtgtc cagaagattc gttgctttcg ctaagaagtg gaacctcaac  10140
tacaaggtga tgacttatgc tggagcttgg aaggctactt tgggaaacct cgataatgtg  10200
ggaaagcact actacgtgca cggacaacac tctggaaaga ccgcttgatt aatgaaggcc  10260
gcctcgaccg taccccctgc agatagacta tactatgttt tagcctgcct gctggctagc  10320
tactatgtta tgttatgttg taaaataaac acctgctaag gtatatctat ctatatttta  10380
gcatggcttt ctcaataaat tgtctttcct tatcgtttac tatcttatac ctaataatga  10440
aataataata tcacatatga ggaacggggc aggtttaggc atatatatac gagtgtaggg  10500
cggagtgggg ctacgtagcg tcacgtgacg ttacctaagc ctaggtagcc tcagctgacg  10560
ttacgtaacg ctaggtaggc tcagctgaca cgggcaggac atagggacta ctacaagcat  10620
agtatgcttc agacaaagag ctaggaaaga actcttgatg gaggttaaga gaaaaaagtg  10680
ctagaggggc atagtaatca aacttgtcaa aaccgtcatc atgatgaggg atgacataat  10740
ataaaaagtt gactaaggtc ttggtagtac tctttgatta gtattatata ttggtgagaa  10800
catgagtcaa gaggagacaa gaaaccgagg aaccatagtt tagcaacaag atggaagttg  10860
caaagttgag ctagccgctc gattagttac atctcctaag cagtactaca aggaatggtc  10920
tctatacttt catgtttagc acatggtagt gcggattgac aagttagaaa cagtgcttag  10980
gagacaaaga gtcagtaaag gtattgaaag agtgaagttg atgctcgaca ggtcaggaga  11040
agtccctccg ccagatggtg actaccaagg ggttggtatc agctgagacc caaataagat  11100
tcttcggttg aaccagtggt tcgaccgaga ctcttagggt gggatttcac tgtaagattt  11160
gtgcattttg ttgaatataa attgacaatt ttttttattt aattatagat tatttagaat  11220
gaattacata tttagtttct aacaaggata gcaatggatg ggtatgggta caggttaaac  11280
atatctatta cccacccatc tagtcgtcgg gttttacacg tacccacccg tttacataaa  11340
ccagaccgga attttaaacc gtacccgtcc gttagcgggt ttcagattta cccgtttaat  11400
cgggtaaaac ctgattacta aatatatatt ttttatttga taaacaaaac aaaaatgtta  11460
atattttcat attggatgca attttaagaa acacatattc ataaatttcc atatttgtag  11520
gaaaataaaa agaaaaatat attcaagaac acaaatttca ccgacatgac ttttattaca  11580
gagttggaat tagatctaac aattgaaaaa ttaaaattaa gatagaatat gttgaggaac  11640
atgacatagt ataatgctgg gttacccgtc gggtaggtat cgaggcggat actactaaat  11700
ccatcccact cgctatccga taatcactgg tttcgggtat acccattccc gtcaacaggc  11760
ctttttaacc ggataatttc aacttatagt gaatgaattt tgaataaata gttagaatac  11820
caaaatcctg gattgcattt gcaatcaaat tttgtgaacc gttaaatttt gcatgtactt  11880
gggatagata taatagaacc gaattttcat tagtttaatt tataacttac tttgttcaaa  11940
gaaaaaaaat atctatccaa tttacttata ataaaaaata atctatccaa gttacttatt  12000
```

```
ataatcaact tgtaaaaagg taagaataca aatgtggtag cgtacgtgtg attatatgtg  12060
acgaaatgtt atatctaaca aaagtccaaa ttcccatggt aaaaaaaatc aaaatgcatg  12120
gcaggctgtt tgtaaccttg gaataagatg ttggccaatt ctggagccgc cacgtacgca  12180
agactcaggg ccacgttctc ttcatgcaag gatagtagaa caccactcca cccacctcct  12240
atattagacc tttgcccaac cctccccaac tttcccatcc catccacaaa gaaaccgaca  12300
tttttatcat aaatctggtg cttaaacact ctggtgagtt ctagtacttc tgctatgatc  12360
gatctcatta ccatttctta aatttctctc cctaaatatt ccgagttctt gatttttgat  12420
aacttcaggt tttctctttt tgataaatct ggtctttcca tttttttttt ttgtggttaa  12480
tttagtttcc tatgttcttc gattgtatta tgcatgatct gtgtttggat tctgttagat  12540
tatgtattgg tgaatatgta tgtgtttttg catgtctggt tttggtctta aaaatgttca  12600
aatctgatga tttgattgaa gctttttag tgttggtttg attcttctca aaactactgt  12660
taatttacta tcatgttttc caactttgat tcatgatgac acttttgttc tgctttgtta  12720
taaaattttg gttggtttga ttttgtaatt atagtgtaat tttgttagga atgaacatgt  12780
tttaatactc tgttttcgat ttgtcacaca ttcgaattat taatcgataa tttaactgaa  12840
aattcatggt tctagatctt gttgtcatca gattatttgt ttcgataatt catcaaatat  12900
gtagtccttt tgctgatttg cgactgtttc attttttctc aaaattgttt tttgttaagt  12960
ttatctaaca gttatcgttg tcaaaagtct ctttcatttt gcaaaatctt cttttttttt  13020
ttgtttgtaa ctttgttttt taagctacac atttagtctg taaaatagca tcgaggaaca  13080
gttgtcttag tagacttgca tgttcttgta acttctattt gtttcagttt gttgatgact  13140
gctttgattt tgtaggtcaa aggcgcaccc taccatggat gcttataacg ctgctatgga  13200
taagattgga gctgctatca tcgattggag tgatccagat ggaaagttca gagctgatag  13260
ggaggattgg tggttgtgcg atttcagatc cgctatcacc attgctctca tctacatcgc  13320
tttcgtgatc ttgggatctg ctgtgatgca atctctccca gctatggacc catacccctat  13380
caagttcctc tacaacgtgt ctcaaatctt cctctgcgct tacatgactg ttgaggctgg  13440
attcctcgct tataggaacg gatacaccgt tatgccatgc aaccacttca acgtgaacga  13500
tccaccagtt gctaacttgc tctggctctt ctacatctcc aaagtgtggg atttctggga  13560
taccatcttc attgtgctcg gaaagaagtg gagacaactc tctttcttgc acgtgtacca  13620
ccacaccacc atcttcctct tctactggtt gaacgctaac gtgctctacg atggagatat  13680
cttcttgacc atcctcctca acggattcat tcacaccgtg atgtacacct actacttcat  13740
ctgcatgcac accaaggatt ctaagaccgg aaagtctttg ccaatctggt ggaagtcatc  13800
tttgaccgct ttccaactct tgcaattcac catcatgatg tcccaagcta cctacttggt  13860
tttccacgga tgcgataagg tttccctcag aatcaccatc gtgtacttcg tgtacattct  13920
ctccctttttc ttcctcttcg ctcagttctt cgtgcaatcc tacatggctc caaagaagaa  13980
gaagtccgct tgatgttaat gaaggccgca gatatcagat ctggtcgacc tagaggatcc  14040
ccggccgcaa agataataac aaaagcctac tatataacgt acatgcaagt attgtatgat  14100
attaatgttt ttacgtacgt gtaaacaaaa ataattacgt ttgtaacgta tggtgatgat  14160
gtggtgcact aggtgtaggc cttgtattaa taaaaagaag tttgttctat atagagtggt  14220
ttagtacgac gatttattta ctagtcggat tggaatagag aaccgaattc ttcaatcctt  14280
gcttttgatc aagaattgaa accgaatcaa atgtaaaagt tgatatattt gaaaaacgta  14340
ttgagcttat gaaaatgcta atactctcat ctgtatggaa aagtgacttt aaaaccgaac  14400
```

```
ttaaaagtga caaaagggga atatcgcatc aaaccgaatg aaaccgatct acgtaggctc  14460
agctgagctt agctaagcct acctagcctc acgtgagatt atgtaaggct aggtagcgtc  14520
acgtgacgtt acctaacact agctagcgtc agctgagctt agctaaccct acgtagcctc  14580
acgtgagctt acctaacgct acgtagcctc acgtgactaa ggatgaccta cccattcttg  14640
agacaaatgt tacattttag tatcagagta aaatgtgtac ctataactca aattcgattg  14700
acatgtatcc attcaacata aaattaaacc agcctgcacc tgcatccaca tttcaagtat  14760
tttcaaaccg ttcggctcct atccaccggg tgtaacaaga cggattccga atttggaaga  14820
ttttgactca aattcccaat ttatattgac cgtgactaaa tcaactttaa cttctataat  14880
tctgattaag ctcccaattt atattcccaa cggcactacc tccaaaattt atagactctc  14940
atccccttt aaaccaactt agtaaacgtt tttttttaa ttttatgaag ttaagttttt  15000
accttgtttt taaaaagaat cgttcataag atgccatgcc agaacattag ctacacgtta  15060
cacatagcat gcagccgcgg agaattgttt ttcttcgcca cttgtcactc ccttcaaaca  15120
cctaagagct tctctctcac agcacacaca tacaatcaca tgcgtgcatg cattattaca  15180
cgtgatcgcc atgcaaatct cctttatagc ctataaatta actcatcggc ttcactcttt  15240
actcaaacca aaactcatca atacaaacaa gattaaaaac atttcacgat ttggaatttg  15300
attcctgcga tcacaggtat gacaggttag attttgtttt gtatagttgt atacatactt  15360
ctttgtgatg ttttgtttac ttaatcgaat ttttggagtg ttttaaggtc tctcgtttag  15420
aaatcgtgga aaatatcact gtgtgtgtgt tcttatgatt cacagtgttt atgggtttca  15480
tgttctttgt tttatcattg aatgggaaga aatttcgttg ggatacaaat ttctcatgtt  15540
cttactgatc gttattagga gtttggggaa aaaggaagag ttttttggt tggttcgagt  15600
gattatgagg ttatttctgt atttgattta tgagttaatg gtcgttttaa tgttgtagac  15660
cgccatggct attttgaacc ctgaggctga ttctgctgct aacctcgcta ctgattctga  15720
ggctaagcaa agacaattgg ctgaggctgg atacactcac gttgagggtg ctcctgctcc  15780
tttgcctttg gagttgcctc acttctctct cagagatctc agagctgcta ttcctaagca  15840
ctgcttcgag agatctttcg tgacctccac ctactacatg atcaagaacg tgttgacttg  15900
cgctgctttg ttctacgctg ctaccttcat tgatagagct ggagctgctg cttatgtttt  15960
gtggcctgtg tactggttct tccagggatc ttacttgact ggagtgtggg ttatcgctca  16020
cgagtgtgga caccaggctt attgctcttc tgaggtggtg aacaacttga ttggactcgt  16080
gttgcactct gctttgttgg tgccttacca ctcttggaga atctctcaca gaaagcacca  16140
ctccaacact ggatcttgcg agaacgatga ggttttcgtt cctgtgacca gatctgtgtt  16200
ggcttcttct tggaacgaga ccttggagga ttctcctctc taccaactct accgtatcgt  16260
gtacatgttg gttgttggat ggatgcctgg atacctcttc ttcaacgcta ctggacctac  16320
taagtactgg ggaaagtcta ggtctcactt caaccccttac tccgctatct atgctgatag  16380
ggagaggtgg atgatcgtgc tctccgatat tttcttggtg gctatgttgg ctgttttggc  16440
tgctttggtg cacactttct ccttcaacac gatggtgaag ttctacgtgg tgccttactt  16500
cattgtgaac gcttacttgg tgttgattac ctacctccaa cacaccgata cctacatccc  16560
tcacttcaga gagggagagt ggaattggtt gagaggagct ttgtgcactg tggatagatc  16620
atttggtcca ttcctcgatt ctgtggtgca tagaatcgtg gatacccacg tttgccacca  16680
tatcttctcc aagatgcctt tctatcactg cgaggaggct accaacgcta ttaagcctct  16740
```

```
cctcggaaag ttctacttga aggatactac tcctgttcct gttgctctct ggagatctta  16800
cacccactgc aagttcgttg aggatgatgg aaaggtggtg ttctacaaga acaagttata  16860
gttaatgaat aattgattgg ttcgagtatt atggcattgg gaaaactgtt tttcttgtac  16920
catttgttgt gcttgtaatt tactgtgttt tttattcggt tttcgctatc gaactgtgaa  16980
atggaaatgg atggagaaga gttaatgaat gatatggtcc ttttgttcat tctcaaatta  17040
atattatttg ttttttctct tatttgttgt gtgttgaatt tgaaattata agagatatgc  17100
aaacattttg ttttgagtaa aaatgtgtca aatcgtggcc tctaatgacc gaagttaata  17160
tgaggagtaa aacacttgta gttgtaccat tatgcttatt cactaggcaa caaatatatt  17220
ttcagaccta gaaaagctgc aaatgttact gaatacaagt atgtcctctt gtgttttaga  17280
catttatgaa ctttccttta tgtaattttc cagaatcctt gtcagattct aatcattgct  17340
ttataattat agttatactc atggatttgt agttgagtat gaaaatattt tttaatgcat  17400
tttatgactt gccaattgat tgacaacatg catcaatcta gctagcctca gctgacgtta  17460
cgtaacgcta ggtagcgtca cgtgacgtta gctaacgcta ggtagcgtca gctgagctta  17520
cgtaagcgca cagatgaata ctagctgttg ttcacagttc tagtgtctcc tcattacgtg  17580
aattcaagct acgatcacta tctcaactcc tacataaaca tcagaatgct acaaaactat  17640
gcacaaaaac aaaagctaca tctaatacgt gaatcaatta ctctcatcac aagaaagaag  17700
atttcaatca ccgtcgagaa ggaggattca gttaattgaa tcaaagttcc gatcaaactc  17760
gaagactggt gagcacgagg acgacgaaga agagtgtctc gaagatacaa caagcaagaa  17820
atctactgag tgacctcctg aagttattgg cgcgattgag agaatcaatc cgaattaatt  17880
tcggggaaaa agataaatta gatactaagc gatgggcttg ggctgggcta agaaacaggt  17940
ggcaattggg ctggaggacc ccgcgattca tagcttccga tagcccaaaa aaaaacggat  18000
aacatattta tcgggtattt gaatttcagt gaaataagat attttctttt tgttaggaaa  18060
attttagaaa ataatggaaa ttaaatagcg attatgttac aagatacgat cagcatcggg  18120
cagtgcaaaa tgctatagct tcccaagatt tgatcctttt gggttatctc ctaatgacaa  18180
ttagtttagg attttgaaac ttatattaat actattatcc gacaacactt gtttcagctt  18240
cttattttaa catttttttgt tttttctat tcttcttccc atcagcattt tctttttaaa  18300
aaattgaata ctttaacttt ttaaaaattt cacaatgatc agatgatatt atggaagatc  18360
tcaagagtta aatgtatcca tcttggggca ttaaaaccgg tgtacgggat gataaataca  18420
gactttatat catatgatag ctcagtaatt catatttatc acgttgctaa aaaaattata  18480
aggtactagt agtcaacaaa atcaattaaa gagaaagaaa gaaacgcatg tgaagagagt  18540
ttacaactgg aaaagtaaaa taaaaattaa cgcatgttga atgctgacat gtcagtatgt  18600
ccatgaatcc acgtatcaag cgccattcat cgatcgtctt cctctttcta aatgaaaaca  18660
acttcacaca tcacaacaaa caatacacac aagacccccct ctctctcgtt gtctctctgc  18720
cagcgaccaa atcgaagctt gagaagaaca agaaggggtc aaaccatggc ttctacatct  18780
gctgctcaag acgctgctcc ttacgagttc ccttctctca ctgagatcaa gagggctctt  18840
ccttctgagt gtttcgaggc ttctgttcct ctttctctct actacaccgc tagatctctt  18900
gctcttgctg gatctctcgc tgttgctctc tcttacgcta gagctttgcc tcttgttcag  18960
gctaacgctc ttcttgatgc tactctctgc actggatacg ttcttctcca gggaatcgtt  19020
ttctggggat tcttcaccgt tggtcacgat tgtggacacg gagctttctc tagatctcac  19080
gtgctcaact tctctgttgg aaccctcatg cactctatca tccttacccc tttcgagtct  19140
```

```
tggaagctct ctcacagaca ccaccacaag aacaccggaa acatcgataa ggacgagatc  19200
ttctaccctc aaagagaggc tgattctcac cctgtttcta gacaccttgt gatgtctctt  19260
ggatctgctt ggttcgctta ccttttcgct ggattccctc ctagaaccat gaaccacttc  19320
aacccttggg aggctatgta tgttagaaga gtggctgctg tgatcatctc tctcggagtt  19380
cttttcgctt tcgctggact ctactcttac ctcaccttcg ttcttggatt caccactatg  19440
gctatctact acttcggacc tctcttcatc ttcgctacca tgcttgttgt taccactttc  19500
ctccaccaca acgatgagga gacaccttgg tacgctgatt ctgagtggac ttacgtgaag  19560
ggaaacctct cttctgtgga cagatcttac ggtgctctca tcgacaacct tagccacaac  19620
atcggaactc accagatcca ccacctcttc cctatcatcc ctcactacaa gctcaacgat  19680
gctactgctg ctttcgctaa ggctttccct gagcttgtta ggaaaaacgc tgctcctatc  19740
atcccaactt tcttcaggat ggctgctatg tacgctaagt acggagttgt tgacactgat  19800
gctaagacct tcactctcaa ggaggctaag gctgctgcta agactaagtc atcttgatga  19860
ttaatgaata attgattgta catactatat tttttgttta ccttgtgtta gtttaatgtt  19920
cagtgtcctc tctttattgt ggcacgtctc tttgttgtat gttgtgtcta tacaaagttg  19980
aaataatgga aagaaaagga agagtgtaat ttgttttgtt ttaagtgttt ataaatatat  20040
atatataggt catttagata gttctaggtt tctataaaac tctctctctg gaagtagaat  20100
ctgtttttga gaggatccag ttgcctacta atctccccca aaacccttca agcttaacct  20160
tcctcttcac aacaacagag gaaacacatc tcttgagctc tgagttctct tctttgagca  20220
tgtctatcgc taaactcatc tgccttatag cttccctctt ctcttcatct ctctctctca  20280
ccatttcgct gtaaaactta ttctcctccc tcagcctctc tatctcttcc ttcagcatct  20340
cacaattccc accataatcg actgaggatg attcaccgtc atcaacttca gactcagcgt  20400
tgtagtcgtc atgagtctca caagccttgg accaagaaga ctcatcatcg caagttgatg  20460
atttatcatg atgcttctct gagccgtgtt tgctacgtag cgtcacgtga cgttacctaa  20520
gcctaggtag cctcagctga cgttacgtaa cgctaggtag gctcagctga ctgcagcaaa  20580
tttacacatt gccactaaac gtctaaaccc ttgtaatttg tttttgtttt actatgtgtg  20640
ttatgtattt gatttgcgat aaatttttat atttggtact aaatttataa caccttttat  20700
gctaacgttt gccaacactt agcaatttgc aagttgatta attgattcta aattattttt  20760
gtcttctaaa tacatatact aatcaactgg aaatgtaaat atttgctaat atttctacta  20820
taggagaatt aaagtgagtg aatatggtac cacaaggttt ggagatttaa ttgttgcaat  20880
gctgcatgga tggcatatac accaaacatt caataattct tgaggataat aatggtacca  20940
cacaagattt gaggtgcatg aacgtcacgt ggacaaaagg tttagtaatt tttcaagaca  21000
acaatgttac cacacacaag ttttgaggtg catgcatgga tgccctgtgg aaagtttaaa  21060
aatattttgg aaatgatttg catggaagcc atgtgtaaaa ccatgacatc cacttggagg  21120
atgcaataat gaagaaaact acaaatttac atgcaactag ttatgcatgt agtctatata  21180
atgaggattt tgcaatactt tcattcatac acactcacta agttttacac gattataatt  21240
tcttcatagc cagtactgtt taagcttcac tgtctctgaa tcggcaaagg taaacgtatc  21300
aattattcta caaacccttt tatttttctt ttgaattacc gtcttcattg gttatatgat  21360
aacttgataa gtaaagcttc aataattgaa tttgatctgt gtttttttgg ccttaatact  21420
aaatccttac ataagctttg ttgcttctcc tcttgtgagt tgagtgttaa gttgtaataa  21480
```

```
tggttcactt tcagctttag aagaaacgcg ccttccatgg ctacaaagga ggcttacgtt  21540
ttcccaactc tcaccgagat caagagatct ctcccaaagg attgcttcga ggcttctgtg  21600
cctttgtctc tctactacac tgtgagatgc ttggttattg ctgtggcttt gaccttcgga  21660
ttgaactacg ctagagcttt gccagaggtt gagtctttct gggctttgga tgctgctttg  21720
tgcactggat atatcctcct ccagggaatt gtgttctggg gattcttcac tgttggacac  21780
gatgctggac acggagcttt ctctagatac cacctcttga acttcgttgt gggaaccttc  21840
atgcactctc tcatcttgac cccattcgag tcttggaagt tgacccacag acaccaccac  21900
aagaacaccg gaaacatcga tagagatgag gtgttctacc cacagagaaa ggctgatgat  21960
cacccattgt ccaggaactt gatcttggct ttgggagctg cttggcttgc ttatttggtg  22020
gagggattcc caccaagaaa ggtgaaccac ttcaacccat tcgagccact tttgtgaga  22080
caagtgtccg ctgtggttat ctctttgctc gctcacttct tcgttgctgg actctctatc  22140
tacttgtctc tccagttggg acttaagacc atggctatct actactacgg accagttttc  22200
gtgttcggat ctatgttggt gattaccacc ttcttgcacc acaacgatga ggagactcca  22260
tggtatgctg attctgagtg gacttacgtg aagggaaact tgtcctctgt ggatagatct  22320
tacggtgctc tcatcgataa cctctcccac aacatcggaa ctcaccagat ccaccacctc  22380
ttcccaatta tcccacacta caagctcaag aaggctactg ctgctttcca ccaagctttc  22440
ccagagcttg tgagaaagtc cgatgagcca atcatcaagg ctttcttcag agtgggaagg  22500
ttgtatgcta actacggagt ggttgatcaa gaggctaagc tcttcacttt gaaggaggct  22560
aaggctgcta ctgaagctgc tgctaagacc aagtctacct gattaatgaa tcgacaagct  22620
cgagtttctc cataataatg tgtgagtagt tcccagataa gggaattagg gttcctatag  22680
ggtttcgctc atgtgttgag catataagaa acccttagta tgtatttgta tttgtaaaat  22740
acttctatca ataaaatttc taattcctaa aaccaaaatc cagtactaaa atccagatcc  22800
cccgaattaa ttcggcgtta attcagctac gtaggctcag ctgagcttac ctaaggctac  22860
gtaggctcac gtgacgttac gtaaggctac gtagcgtcac gtgagcttac ctaactctag  22920
ctagcctcac gtgaccttag ctaacactag gtagcgtcag cacagatgaa tactagctgt  22980
tgttcacagt tctagtgtct cctcattacg tgaattcaag ctacgatcac tatctcaact  23040
cctacataaa catcagaatg ctacaaaact atgcacaaaa acaaaagcta catctaatac  23100
gtgaatcaat tactctcatc acaagaaaga agatttcaat caccgtcgag aaggaggatt  23160
cagttaattg aatcaaagtt ccgatcaaac tcgaagactg gtgagcacga ggacgacgaa  23220
gaagagtgtc tcgaagatac aacaagcaag aaatctactg agtgacctcc tgaagttatt  23280
ggcgcgattg agagaatcaa tccgaattaa tttcggggaa aaagataaat tagatactaa  23340
gcgatgggct tgggctgggc taagaaacag gtggcaattg ggctggagga ccccgcgatt  23400
catagcttcc gatagcccaa aaaaaaacgg ataacatatt tatcgggtat ttgaatttca  23460
gtgaaataag atattttctt tttgttagga aaattttaga aaataatgga aattaaatag  23520
cgattatgtt acaagatacg atcagcatcg ggcagtgcaa aatgctatag cttcccaaga  23580
tttgatcctt ttgggttatc tcctaatgac aattagttta ggattttgaa acttatatta  23640
atactattat ccgacaacac ttgtttcagc ttcttatttt aacatttttt gtttttttct  23700
attcttcttc ccatcagcat tttctttttta aaaaattgaa tactttaact ttttaaaaat  23760
ttcacaatga tcagatgata ttatggaaga tctcaagagt taaatgtatc catcttgggg  23820
cattaaaacc ggtgtacggg atgataaata cagactttat atcatatgat agctcagtaa  23880
```

```
ttcatattta tcacgttgct aaaaaaatta taaggtacta gtagtcaaca aaatcaatta  23940
aagagaaaga aagaaacgca tgtgaagaga gtttacaact ggaaaagtaa aataaaaatt  24000
aacgcatgtt gaatgctgac atgtcagtat gtccatgaat ccacgtatca agcgccattc  24060
atcgatcgtc ttcctctttc taaatgaaaa caacttcaca catcacaaca aacaatacac  24120
acaagacccc ctctctctcg ttgtctctct gccagcgacc aaatcgaagc ttgagaagaa  24180
caagaagggg tcaaaccatg ggaaaaggat ctgagggaag atctgctgct agagagatga  24240
ctgctgaggc taacggagat aagagaaaga ccatcctcat tgagggagtg ttgtacgatg  24300
ctaccaactt caaacaccca ggaggttcca ttattaactt cctcaccgag ggagaagctg  24360
gagttgatgc tacccaagct tacagagagt tccatcagag atccggaaag gctgataagt  24420
acctcaagtc cctcccaaag ttggatgctt ctaaggtgga gtctaggttc tctgctaagg  24480
agcaggctag aagggacgct atgaccaggg attacgctgc tttcagagag gagttggttg  24540
ctgagggata cttcgatcca tctatcccac acatgatcta cagagtggtg gagattgtgg  24600
ctttgttcgc tttgtctttc tggttgatgt ctaaggcttc tccaacctct ttggttttgg  24660
gagtggtgat gaacggaatc gctcaaggaa gatgcggatg ggttatgcac gagatgggac  24720
acggatcttt cactggagtt atctggctcg atgataggat gtgcgagttc ttctacggag  24780
ttggatgtgg aatgtctgga cactactgga agaaccagca ctctaagcac cacgctgctc  24840
caaacagatt ggagcacgat gtggatttga acaccttgcc actcgttgct ttcaacgaga  24900
gagttgtgag gaaggttaag ccaggatctt tgttggcttt gtggctcaga gttcaggctt  24960
atttgttcgc tccagtgtct tgcttgttga tcggattggg atggaccttg tacttgcacc  25020
caagatatat gctcaggacc aagagacaca tggagtttgt gtggatcttc gctagatata  25080
tcggatggtt ctccttgatg ggagctttgg gatattctcc tggaacttct gtgggaatgt  25140
acctctgctc tttcggactt ggatgcatct acatcttcct ccaattcgct gtgtctcaca  25200
cccacttgcc agttaccaac ccagaggatc aattgcactg gcttgagtac gctgctgatc  25260
acaccgtgaa catctctacc aagtcttggt tggttacctg gtggatgtct aacctcaact  25320
tccaaatcga gcaccacttg ttcccaaccg ctccacaatt caggttcaag gagatctctc  25380
caagagttga ggctctcttc aagagacaca acctccctta ctacgatttg ccatacacct  25440
ctgctgtttc tactaccttc gctaacctct actctgttgg acactctgtt ggagctgata  25500
ccaagaagca ggattgatga ttaatgaata attgattgta catactatat tttttgttta  25560
ccttgtgtta gtttaatgtt cagtgtcctc tctttattgt ggcacgtctc tttgttgtat  25620
gttgtgtcta tacaaagttg aaataatgga aagaaaagga agagtgtaat ttgttttgtt  25680
ttaagtgttt ataaatatat atatataggt catttagata gttctaggtt tctataaaac  25740
tctctctctg gaagtagaat ctgtttttga gaggatccag ttgcctacta atctccccca  25800
aaacccttca agcttaacct tcctcttcac aacaacagag gaaacacatc tcttgagctc  25860
tgagttctct tctttgagca tgtctatcgc taaactcatc tgccttatag cttccctctt  25920
ctcttcatct ctctctctca ccatttcgct gtaaaactta ttctcctccc tcagcctctc  25980
tatctcttcc ttcagcatct cacaattccc accataatcg actgaggatg attcaccgtc  26040
atcaacttca gactcagcgt tgtagtcgtc atgagtctca caagccttgg accaagaaga  26100
ctcatcatcg caagttgatg atttatcatg atgcttctct gagccgtgtt tgctacctag  26160
agtcagctga gcttagctaa cgctagctag tgtcagctga cgttacgtaa ggctaactag  26220
```

```
cgtcacgtga ccttacgtaa cgctacgtag gctcagctga gcttagctaa ccctagctag  26280
tgtcacgtga gcttacgcta ctatagaaaa tgtgttatat cgacatgacc agacaaaggg  26340
gcaacagtta acaaaacaat taattctttc atttgagatt aaggaaggta aggtactaaa  26400
aagattaaaa aaaatgagct tatctctttg tttctgtaat aataatataa gtgtgataaa  26460
cttttaatat aataattgta attaggtttt ctacagatga gcaccactca gagacaagat  26520
aagaagaaaa caattttgtt aaacatgatt atagaaactt ttagttaagt cttgaagtat  26580
caatataaca aaaaaaagta cacacgacta tgacaataaa cccactaccg tcaggttatc  26640
atttcgatga aatgttttga tatcattaaa tataacagtc acaaaaaatc atctaattat  26700
aacaatataa cttatacata tatttaacta aaaacttaga gtttttgtaa tgattctaat  26760
tgatgattag agtttataga aatacaatta aataaaaaat ataattttaa aaaaacatag  26820
taaagtcaat gagatcctct ctgacctcag tgatcattta gtcatgtatg tacaacaatc  26880
attgttcatc acatgactgt aaaataaata aggataaact tgggaatata tataatatat  26940
tgtattaaat aaaaaaggga aatacaaata tcaattttag attcccgagt tgacacaact  27000
caccatgcac gctgccacct cagctcccag ctctcgtcac atgtctcatg tcagttaggt  27060
ctttggtttt tagtctttga cacaactcgc catgcatgtt gccacgtgag ctcgttcctc  27120
ttcccatgat ctcaccactg ggcatgcatg ctgccacctc agctggcacc tcttctctat  27180
atgtccctag aggccatgca cagtgccacc tcagcactcc tctcagaacc catacgtacc  27240
tgccaatcgg cttctctcca taaatatcta tttaaattat aactaattat ttcatatact  27300
taattgatga cgtggatgca ttgccatcgt tgtttaataa ttgttaatta cgacatgata  27360
aataaaatga aagtaaaaag tacgaaagat tttccatttg ttgttgtata aatagagaag  27420
tgagtgatgc ataatgcatg aatgcatgac cgcgccacca tgactgttgg atacgacgag  27480
gagatcccat tcgagcaagt tagggctcat aacaagccag acgacgcttg gtgtgctatt  27540
cacggacacg tgtacgacgt taccaagttc gcttcagttc acccaggagg agatattatc  27600
ttgctcgctg ctggaaagga agctactgtc ctctacgaga cctaccatgt tagaggagtg  27660
tctgacgctg tgctcagaaa gtacagaata ggaaagttgc cagacggaca aggaggagct  27720
aacgagaagg agaagagaac cttgtctgga ttgtcctctg cttcttacta cacctggaac  27780
tccgatttct acagagtgat gagggagaga gttgtggcta gattgaagga gagaggaaag  27840
gctagaagag gaggatacga actctggatc aaggctttct tgctccttgt tggattctgg  27900
tcctctcttt actggatgtg caccctcgat ccatctttcg gagctatctt ggctgctatg  27960
tctttgggag tgttcgctgc ttttgttgga acctgcatcc aacacgatgg aaaccacgga  28020
gctttcgctc aatctagatg ggttaacaag gtggcaggat ggactttgga tatgatcgga  28080
gcttctggaa tgacttggga gttccaacac gtgttgggac accacccata cactaacttg  28140
atcgaggagg agaacggatt gcaaaaggtg tccggaaaga agatggatac caagttggct  28200
gatcaagagt ctgatccaga tgtgttctcc acctacccaa tgatgagatt gcacccttgg  28260
caccagaaga ggtggtatca caggttccag cacatctacg gacctttcat cttcggattc  28320
atgaccatca acaaggtggt gactcaagat gttggagtgg tgttgagaaa gagactcttc  28380
caaatcgatg ctgagtgcag atatgcttcc ccaatgtacg ttgctaggtt ctggattatg  28440
aaggctttga ccgtgttgta tatggttgct ttgccttgtt atatgcaagg accttggcac  28500
ggattgaaac tcttcgctat cgctcacttc acttgcggag aggttttggc taccatgttc  28560
atcgtgaacc acattatcga gggagtgtct tacgcttcta aggatgctgt taagggaact  28620
```

```
atggctccac caaagactat gcacggagtg accccaatga acaacactag aaaggaggtt  28680
gaggctgagg cttctaagtc tggagctgtg gttaagtctg tgccattgga tgattgggct  28740
gctgttcagt gccaaacctc tgtgaactgg tctgttggat cttggttttg gaaccacttc  28800
tctggaggac tcaaccacca aatcgagcac cacctcttcc caggattgtc tcacgagacc  28860
tactaccaca tccaagacgt ggttcaatct acctgtgctg agtacggagt tccataccaa  28920
cacgagccat ctttgtggac tgcttactgg aagatgctcg aacaccttag acaattggga  28980
aacgaggaga ctcacgagtc atggcagaga gctgcttgat taatgaacta agactcccaa  29040
aaccaccttc cctgtgacag ttaaaccctg cttatacctt tcctcctaat aatgttcatc  29100
tgtcacacaa actaaaataa ataaaatggg agcaataaat aaaatgggag ctcatatatt  29160
tacaccattt acactgtcta ttattcacca tgccaattat tacttcataa ttttaaaatt  29220
atgtcatttt taaaaattgc ttaatgatgg aaaggattat tataagttaa aagtataaca  29280
tagataaact aaccacaaaa caaatcaata taaactaact tactctccca tctaattttt  29340
atttaaattt ctttacactt ctcttccatt tctatttcta caacattatt taacattttt  29400
attgtatttt tcttactttc taactctatt catttcaaaa atcaatatat gtttatcacc  29460
acctctctaa aaaaaacttt acaatcattg gtccagaaaa gttaaatcac gagatggtca  29520
ttttagcatt aaaacaacga ttcttgtatc actatttttc agcatgtagt ccattctctt  29580
caaacaaaga cagcggctat ataatcgttg tgttatattc agtctaaaac aactagctag  29640
cctcagctga cgttacgtaa cgctaggtag cgtcacgtga cgttagctaa cgctaggtag  29700
cgtcagctga gcttacgtaa gcgccacggg caggacatag ggactactac aagcatagta  29760
tgcttcagac aaagagctag gaaagaactc ttgatggagg ttaagagaaa aaagtgctag  29820
aggggcatag taatcaaact tgtcaaaacc gtcatcatga tgagggatga cataatataa  29880
aaagttgact aaggtcttgg tagtactctt tgattagtat tatatattgg tgagaacatg  29940
agtcaagagg agacaagaaa ccgaggaacc atagtttagc aacaagatgg aagttgcaaa  30000
gttgagctag ccgctcgatt agttacatct cctaagcagt actacaagga atggtctcta  30060
tactttcatg tttagcacat ggtagtgcgg attgacaagt tagaaacagt gcttaggaga  30120
caaagagtca gtaaaggtat tgaaagagtg aagttgatgc tcgacaggtc aggagaagtc  30180
cctccgccag atggtgacta ccaaggggtt ggtatcagct gagacccaaa taagattctt  30240
cggttgaacc agtggttcga ccgagactct tagggtggga tttcactgta agatttgtgc  30300
attttgttga atataaattg acaatttttt ttatttaatt atagattatt tagaatgaat  30360
tacatattta gtttctaaca aggatagcaa tggatgggta tgggtacagg ttaaacatat  30420
ctattaccca cccatctagt cgtcgggttt tacacgtacc cacccgttta cataaaccag  30480
accggaattt taaaccgtac ccgtccgtta gcgggtttca gatttacccg tttaatcggg  30540
taaaacctga ttactaaata tatatttttt atttgataaa caaaacaaaa atgttaatat  30600
tttcatattg gatgcaattt taagaaacac atattcataa atttccatat ttgtaggaaa  30660
ataaaaagaa aaatatattc aagaacacaa atttcaccga catgactttt attacagagt  30720
tggaattaga tctaacaatt gaaaaattaa aattaagata gaatatgttg aggaacatga  30780
catagtataa tgctgggtta cccgtcgggt aggtatcgag gcggatacta ctaaatccat  30840
cccactcgct atccgataat cactggtttc gggtataccc attcccgtca acaggccttt  30900
ttaaccggat aatttcaact tatagtgaat gaattttgaa taaatagtta gaataccaaa  30960
```

```
atcctggatt gcatttgcaa tcaaattttg tgaaccgtta aattttgcat gtacttggga  31020
tagatataat agaaccgaat tttcattagt ttaatttata acttactttg ttcaaagaaa  31080
aaaaatatct atccaattta cttataataa aaaataatct atccaagtta cttattataa  31140
tcaacttgta aaaaggtaag aatacaaatg tggtagcgta cgtgtgatta tatgtgacga  31200
aatgttatat ctaacaaaag tccaaattcc catggtaaaa aaaatcaaaa tgcatggcag  31260
gctgtttgta accttggaat aagatgttgg ccaattctgg agccgccacg tacgcaagac  31320
tcagggccac gttctcttca tgcaaggata gtagaacacc actccaccca cctcctatat  31380
tagacctttg cccaaccctc cccaactttc ccatcccatc cacaaagaaa ccgacatttt  31440
tatcataaat cagggtttcg tttttgtttc atcgataaac tcaaaggtga tgattttagg  31500
gtcttgtgag tgtgcttttt tgtttgattc tactgtaggg tttatgttct ttagctcata  31560
ggttttgtgt atttcttaga aatgtggctt ctttaatctc tgggtttgtg actttttgtg  31620
tggtttctgt gtttttcata tcaaaaacct attttttccg agtttttttt tacaaattct  31680
tactctcaag cttgaatact tcacatgcag tgttcttttg tagattttag agttaatgtg  31740
ttaaaaagtt tggattttc ttgcttatag agcttcttca ctttgatttt gtgggttttt  31800
ttgttttaaa ggtgagattt ttgatgaggt ttttgcttca aagatgtcac ctttctgggt  31860
ttgtcttttg aataaagcta tgaactgtca catggctgac gcaattttgt tactatgtca  31920
tgaaagctga cgtttttccg tgttatacat gtttgcttac acttgcatgc gtcaaaaaaa  31980
ttggggcttt ttagttttag tcaaagattt tacttctctt ttgggattta tgaaggaaag  32040
ttgcaaactt tctcaaattt taccattttt gctttgatgt ttgtttagat tgcgacagaa  32100
caaactcata tatgttgaaa tttttgcttg gttttgtata ggattgtgtc ttttgcttat  32160
aaatgttgaa atctgaactt ttttttgtt tggtttcttt gagcaggaga taaggcgcac  32220
caccatggct tctacatctg ctgctcaaga cgctgctcct tacgagttcc cttctctcac  32280
tgagatcaag agggctcttc cttctgagtg tttcgaggct tctgttcctc tttctctcta  32340
ctacaccgct agatctcttg ctcttgctgg atctctcgct gttgctctct cttacgctag  32400
agctttgcct cttgttcagg ctaacgctct tcttgatgct actctctgca ctggatacgt  32460
tcttctccag ggaatcgttt tctggggatt cttcaccgtt ggtcacgatt gtggacacgg  32520
agctttctct agatctcacg tgctcaactt ctctgttgga accctcatgc actctatcat  32580
ccttacccct ttcgagtctt ggaagctctc tcacagacac caccacaaga acaccggaaa  32640
catcgataag gacgagatct tctaccctca aagagaggct gattctcacc ctgtttctag  32700
acaccttgtg atgtctcttg gatctgcttg gttcgcttac cttttcgctg gattccctcc  32760
tagaaccatg aaccacttca acccttggga ggctatgtat gttagaagag tggctgctgt  32820
gatcatctct ctcggagttc ttttcgcttt cgctggactc tactcttacc tcaccttcgt  32880
tcttggattc accactatgg ctatctacta cttcggacct ctcttcatct tcgctaccat  32940
gcttgttgtt accactttcc tccaccacaa cgatgaggag acaccttggt acgctgattc  33000
tgagtggact tacgtgaagg gaaacctctc ttctgtggac agatcttacg gtgctctcat  33060
cgacaacctt agccacaaca tcggaactca ccagatccac cacctcttcc ctatcatccc  33120
tcactacaag ctcaacgatg ctactgctgc tttcgctaag gctttccctg agcttgttag  33180
gaaaaacgct gctcctatca tcccaacttt cttcaggatg gctgctatgt acgctaagta  33240
cggagttgtt gacactgatg ctaagacctt cactctcaag gaggctaagg ctgctgctaa  33300
gactaagtca tcttgatgat taatgaaggc cgcagatatc agatctggtc gacctagagg  33360
```

```
atccccggcc gcaaagataa taacaaaagc ctactatata acgtacatgc aagtattgta  33420
tgatattaat gtttttacgt acgtgtaaac aaaaataatt acgtttgtaa cgtatggtga  33480
tgatgtggtg cactaggtgt aggccttgta ttaataaaaa gaagtttgtt ctatatagag  33540
tggtttagta cgacgattta tttactagtc ggattggaat agagaaccga attcttcaat  33600
ccttgctttt gatcaagaat tgaaaccgaa tcaaatgtaa aagttgatat atttgaaaaa  33660
cgtattgagc ttatgaaaat gctaatactc tcatctgtat ggaaaagtga ctttaaaacc  33720
gaacttaaaa gtgacaaaag gggaatatcg catcaaaccg aatgaaaccg atctacgtag  33780
gctcagctga gcttacctaa ggctacgtag gctcacgtga cgttacgtaa ggctacgtag  33840
cgtcacgtga gcttacctaa ctctagctag cctcacgtga ccttagctaa cactaggtag  33900
cgtcagctta gcagatattt ggtgtctaaa tgtttatttt gtgatatgtt catgtttgaa  33960
atggtggttt cgaaaccagg gacaacgttg ggatctgata gggtgtcaaa gagtattatg  34020
gattgggaca atttcggtca tgagttgcaa attcaagtat atcgttcgat tatgaaaatt  34080
ttcgaagaat atcccatttg agagagtctt tacctcatta atgtttttag attatgaaat  34140
tttatcatag ttcatcgtag tctttttggt gtaaaggctg taaaaagaaa ttgttcactt  34200
ttgttttcgt ttatgtgaag gctgtaaaag attgtaaaag actattttgg tgttttggat  34260
aaaatgatag tttttataga ttcttttgct tttagaagaa atacatttga aatttttttcc  34320
atgttgagta taaaataccg aaatcgattg aagatcatag aaatatttta actgaaaaca  34380
aatttataac tgattcaatt ctctccattt ttatacctat ttaaccgtaa tcgattctaa  34440
tagatgatcg atttttttata taatcctaat taaccaacgg catgtattgg ataattaacc  34500
gatcaactct caccccctaat agaatcagta ttttccttcg acgttaattg atcctacact  34560
atgtaggtca tatccatcgt tttaattttt ggccaccatt caattctgtc ttgcctttag  34620
ggatgtgaat atgaacggcc aaggtaagag aataaaaata atccaaatta aagcaagaga  34680
ggccaagtaa gataatccaa atgtacactt gtcattgcca aaattagtaa aatactcggc  34740
atattgtatt cccacacatt attaaaatac cgtatatgta ttggctgcat ttgcatgaat  34800
aatactacgt gtaagcccaa aagaacccac gtgtagccca tgcaaagtta acactcacga  34860
ccccattcct cagtctccac tatataaacc caccatcccc aatctcacca aacccaccac  34920
acaactcaca actcactctc acaccttaaa gaaccaatca ccaccaaaaa aagttctttg  34980
ctttcgaagt tgccgcaacc taaacaggtt tttccttctt ctttcttctt attaactacg  35040
accttgtcct ttgcctatgt aaaattacta ggttttcatc agttacactg attaagttcg  35100
ttatagtgga agataaaatg ccctcaaagc attttgcagg atatctttga tttttcaaag  35160
atatggaact gtagagtttg atagtgttct tgaatgtggt tgcatgaagt ttttttggtc  35220
tgcatgttat tttttcctcg aaatatgttt tgagtccaac aagtgattca cttgggattc  35280
agaaagttgt tttctcaata tgtaacagtt tttttctatg gagaaaaatc atagggaccg  35340
ttggttttgg cttctttaat tttgagctca gattaaaccc attttacccg gtgttcttgg  35400
cagaattgaa aacagtacgt agtaccgcgc ctaccatgcc acctagtgct gctagtgaag  35460
gtggtgttgc tgaacttaga gctgctgaag ttgctagcta cactagaaag gctgttgacg  35520
aaagacctga cctcactata gttggtgacg ctgtttacga cgctaaggct tttagggacg  35580
agcaccctgg tggtgctcac ttcgttagcc ttttcggagg tagggacgct actgaggctt  35640
ttatggaata tcaccgtaga gcttggccta aggctaggat gtctaagttc ttcgttggtt  35700
```

```
cacttgacgc tagcgagaag cctactcaag ctgattcagc ttaccttaga ctttgcgctg  35760
aggttaacgc tcttttgcct aagggtagcg gaggattcgc tcctcctagc tactggctta  35820
aggctgctgc tcttgttgtt gctgctgtta gtatagaggg ttatatgctc cttaggggta  35880
agaccctttt gcttagcgtt ttccttggac tcgtgttcgc ttggatagga cttaatattc  35940
agcacgacgc taatcacggt gctcttagta gacactcagt gattaactac tgcctcggtt  36000
acgctcagga ttggataggt ggtaatatgg tgctttggct tcaagagcac gttgtgatgc  36060
accacctcca cactaacgac gttgacgctg atcctgatca aaaggctcac ggtgttctta  36120
gacttaagcc tactgacggt tggatgcctt ggcacgcact tcaacaactc tatatccttc  36180
ctggtgaggc tatgtacgct tttaagcttc ttttcttgga cgcccttgag cttcttgctt  36240
ggaggtggga gggtgagaag attagccctc ttgctagagc tttgttcgct cctgctgttg  36300
cttgtaagct tggattctgg gctagattcg ttgctctccc tctctggctt caacctactg  36360
ttcacactgc tttgtgtatc tgtgctactg tgtgtactgg tagcttctac ctcgccttct  36420
tcttctttat ctctcacaac ttcgacggtg ttggtagcgt tggacctaag ggatcacttc  36480
ctagatcagc tactttcgtt caacgtcagg ttgagactag ctctaacgtt ggtggttact  36540
ggcttggagt tcttaacggt ggacttaact ttcagataga gcaccacttg ttccctaggc  36600
ttcaccactc ttactacgct caaatagctc ctgtggttag gactcacata gagaagctcg  36660
gttttaagta ccgtcacttc cctaccgttg gatctaacct tagctcaatg cttcagcata  36720
tgggtaagat gggaactaga cctggtgctg agaagggtgg taaggctgag tagtgattaa  36780
tgaataattg attgctgctt taatgagata tgcgagacgc ctatgatcgc atgatatttg  36840
ctttcaattc tgttgtgcac gttgtaaaaa acctgagcat gtgtagctca gatccttacc  36900
gccggtttcg gttcattcta atgaatatat cacccgttac tatcgtattt ttatgaataa  36960
tattctccgt tcaatttact gattgtctac gtagcgtcac ctgacgttac gtaaggctac  37020
ctaggctcac gtgacgttac gtaacgctac gtagcgtcag gtgaggttag ctaacgctag  37080
ctagcctcac ctgacgttag gtaaggctac gtagcgtcac ctgagattag ctaagcctac  37140
ctagactcac gtgaccttag gtaacgctac gtagcgtcaa agctttacaa cgctacacaa  37200
aacttataac cgtaatcacc attcattaac ttaactacta tcacatgcat tcatgaattg  37260
aaacgagaag gatgtaaata gttgggaagt tatctccacg ttgaagagat cgttagcgag  37320
agctgaaaga ccgagggagg agacgccgtc aacacggaca gagtcgtcga ccctcacatg  37380
aagtaggagg aatctccgtg aggagccaga gagacgtctt tggtcttcgg tttcgatcct  37440
tgatctgacg gagaagacga gagaagtgcg actggactcc gtgaggacca acagagtcgt  37500
cctcggtttc gatcgtcggt attggtggag aaggcggagg aatctccgtg acgagccaga  37560
gagatgtcgt cggtcttcgg tttcgatcct tgatctgacg gagaagacga gagaagtgcg  37620
acgagactcc gtgaggacca acagagttgt cctcggtttc gatcgtcggt ttcggcggag  37680
aaggcggagg aatctccgtg aggagccaga gagacgtcgt tggtcttcgg tttcgatcct  37740
tgatctgttg gagaagacga gacaagtggg acgagactca acgacggagt cagagacgtc  37800
gtcggtcttc ggtttcggcc gagaaggcgg agtcggtctt cggtttcggc cgagaaggcg  37860
gaggagacgt cttcgatttg ggtctctcct cttgacgaag aaaacaaaga acacgagaaa  37920
taatgagaaa gagaacaaaa gaaaaaaaaa taaaaataaa aataaaattt ggtcctctta  37980
tgtggtgaca cgtggtttga aacccaccaa ataatcgatc acaaaaaacc taagttaagg  38040
atcggtaata acctttctaa ttaattttga tttatattaa atcactcttt ttatttataa  38100
```

```
accccactaa attatgcgat attgattgtc taagtacaaa aattctctcg aattcaatac  38160
acatgtttca tatatttagc cctgttcatt taatattact agcgcatttt taatttaaaa  38220
ttttgtaaac ttttttggtc aaagaacatt tttttaatta gagacagaaa tctagactct  38280
ttatttggaa taatagtaat aaagatatat taggcaatga gtttatgatg ttatgtttat  38340
atagtttatt tcattttaaa ttgaaaagca ttatttttat cgaaatgaat ctagtataca  38400
atcaatattt atgtttttc atcagatact ttcctatttt ttggcacctt tcatcggact  38460
actgatttat ttcaatgtgt atgcatgcat gagcatgagt atacacatgt cttttaaaat  38520
gcatgtaaag cgtaacggac cacaaaagag gatccataca aatacatctc atcgcttcct  38580
ctactattct ccgacacaca cactgagcat ggtgcttaaa cactctggtg agttctagta  38640
cttctgctat gatgttaaat tttatattat atacctactt cctctctctc gctctgttat  38700
gttcgatttc gaaaggattt caagatcaaa gatgatgaga aaaggtacct tttcgatatt  38760
taagacaagg aaagaaagga cgaggttgaa attttcggga cttggagggc taaagtggaa  38820
gagactgaat ctgaagatgt cgtttctcga aactttgaga tacagaatca tgtctatcat  38880
tgaaggaatg gttttggttt ctaagcttgc tttcttcttt ctctgttgcg gttgcagatt  38940
ttaacacgtt agttttttt ttttcgtttt tttgaacgtc aacaatgtct tttttgtact  39000
ctttagctca tgtgtaaaat tctaaattct tccaataaca tacccaacaa attattcgta  39060
tctgattttt atagttttta acctgttaat gtaattaatc taagtgtaat ttttaggcta  39120
aatgttaaat tttatattaa agttttgtaa cttgaaatta cattcttctt atagcggata  39180
aacagaaaat gctcttaaac aaatcctgaa acaagtaaaa aatacaacag aaaaatctaa  39240
cgtttaattc ttaaaacctc aaaatcctta tttttacagc tttcaaagtt taacagctgg  39300
aaacctgtag aaaatcagac acagcctctc aagttttctg gacaataaat actggtaacg  39360
taagaaaacc aattaatgat accgtcgttc agtagataga actgacgatg tgaagattaa  39420
ttgtttctgt aatatactga atttgaaaat ttatcatcat catgttaacg gaagttgtct  39480
gtaaaagtag ttgattacct gttatcgtgt aaagtagtta gtaatttctt gcttatttga  39540
aaaatagaga acatttaaca tgtattttta aataggcacg accatgctac tgaactttat  39600
gaaatgcttt ggaatcttat                                             39620
```

<210> SEQ ID NO 30
<211> LENGTH: 37487
<212> TYPE: DNA
<213> ORGANISM: Artificial Sequence
<220> FEATURE:
<223> OTHER INFORMATION: T-DNA insertion in LBFDAU Locus 2, including left and right border sequences

<400> SEQUENCE: 30

```
ttggggtgag agttgatcgg ttaattatcc aatacatgcc gttggttaat taggattata     60
taaaaaatcg atcatctatt agaatcgatt acggttaaat aggtataaaa atggagagaa    120
ttgaatcagt tataaatttg ttttcagtta aaatatttct atgatcttca atcgatttcg    180
gtattttata ctcaacatgg aaaaaatttc aaatgtattt cttctaaaag caaaagaatc    240
tataaaaact atcattttat ccaaaacacc aaaatagtct tttacaatct tttacagcct    300
tcacataaac gaaaacaaaa gtgaacaatt tctttttaca gcctttacac caaaaagact    360
acgatgaact atgataaaat ttcataatct aaaaacatta atgaggtaaa gactctctca    420
aatgggatat tcttcgaaaa ttttcataat cgaacgatat acttgaattt gcaactcatg    480
```

```
accgaaattg tcccaatcca taatactctt tgacacccta tcagatccca acgttgtccc    540
tggtttcgaa accaccattt caaacatgaa catatcacaa aataaacatt tagacaccaa    600
atatctgcta agcgcttacg taagctcagc tgacgctacc tagcgttagc taacgtcacg    660
tgacgctacc tagcgttacg taacgtcagc tgaggctagc tagctgaatt aacgccgaat    720
taattcgggg gatctggatt ttagtactgg attttggttt taggaattag aaattttatt    780
gatagaagta ttttacaaat acaaatacat actaagggtt tcttatatgc tcaacacatg    840
agcgaaaccc tataggaacc ctaattccct tatctgggaa ctactcacac attattatgg    900
agaaactcga gcttgtcgat cactcggtct tagctccctt ttgctttcca tcggatggct    960
tgatgtactt ttgcacgtag aagtttccga agaggaacaa gagggagatc atgtagtaga   1020
agaggatctt gatgagccat tgtggatatg gagcgttggt tttcatatcg tagtaagctt   1080
gcaccaagtt gagcatgaac tggaacatct ggaattgggt gaggtatctt ccccagaaga   1140
ggtacttgtt cttgagcttt ggggaagatc tcaagcaagc agccaagaag tagtaagcgt   1200
acatcaacac gtgcactcca gagttgagag cagcactcca ataagcctct cctcctggag   1260
cgtggtgagc aatagcccac cagataaggg agatagaaga gtggtggtac acgtggagga   1320
aagaaatctg tctggtggat ctcttgagga tcatgatcac ggtatccatg aactccacgt   1380
acttggacat gtagaagagg taaacgagga tagccatctc cttgtgcttt gggttataag   1440
cgtttcccca caaggaatat ctccaggtga tagcttggta agcgataccc acgcacatgt   1500
aaagagacaa agcgaagcag aacaagttgt gcaccaacac caaagcttgc aacaagaatg   1560
gctcagaagc tcttggcttg agatctctag ccttgatcca aagcaatcct ccgatcacga   1620
tggtcaagta aacagacact cccaacacaa ttggagttgg agaatcaacg agtggcaatc   1680
ccttagtagt tggggtatca gtcaactcaa ctccgaaaga tcccaacaaa gcgttcactc   1740
cttgggaaac ctttccatcc aactctccgt agaacctctc aacaacttcc atggtttctt   1800
ctaaagctga aagtgaacca ttattacaac ttaacactca actcacaaga ggagaagcaa   1860
caaagcttat gtaaggattt agtattaagg ccaaaaaaac acagatcaaa ttcaattatt   1920
gaagctttac ttatcaagtt atcatataac caatgaagac ggtaattcaa aagaaaaata   1980
aaagggtttg tagaataatt gatacgttta cctttgccga ttcagagaca gtgaagctta   2040
aacagtactg gctatgaaga aattataatc gtgtaaaact tagtgagtgt gtatgaatga   2100
aagtattgca aaatcctcat tatatagact acatgcataa ctagttgcat gtaaatttgt   2160
agttttcttc attattgcat cctccaagtg gatgtcatgg ttttacacat ggcttccatg   2220
caaatcattt ccaaaatatt tttaaacttt ccacagggca tccatgcatg cacctcaaaa   2280
cttgtgtgtg gtaacattgt tgtcttgaaa aattactaaa ccttttgtcc acgtgacgtt   2340
catgcacctc aaatcttgtg tggtaccatt attatcctca agaattattg aatgtttggt   2400
gtatatgcca tccatgcagc attgcaacaa ttaaatctcc aaaccttgtg gtaccatatt   2460
cactcacttt aattctccta tagtagaaat attagcaaat atttacattt ccagttgatt   2520
agtatatgta tttagaagac aaaaataatt tagaatcaat taatcaactt gcaaattgct   2580
aagtgttggc aaacgttagc ataaaaggtg ttataaattt agtaccaaat ataaaaattt   2640
atcgcaaatc aaatacataa cacacatagt aaaacaaaaa caaattacaa gggtttagac   2700
gtttagtggc aatgtgtaaa tttgctgcag gagtgacgct agctagcgtt acgtaacgtc   2760
agctgagcct aggtagcgtt agctaagctc acgtgacgct acgtaggctt acgtaacgtc   2820
```

-continued

```
agctgaggct acgtagcgtt agctaacgtc acgtgacgct acgtaggctt acgtaatagt   2880
tactaatcag tgatcaggcg cgccattaat ttccaccttc acctacgatg gggggcatcg   2940
caccggtgag taatattgta cggctaagag cgaatttggc ctgtagacct caattgcgag   3000
ctttctaatt tcaaactatt cgggcctaac ttttggtgtg atgatgctga ctgtttcgac   3060
gttaattgat cctacactat gtaggtcata tccatcgttt taatttttgg ccaccattca   3120
attctgtctt gcctttaggg atgtgaatat gaacggccaa ggtaagagaa taaaaataat   3180
ccaaattaaa gcaagagagg ccaagtaaga taatccaaat gtacacttgt cattgccaaa   3240
attagtaaaa tactcggcat attgtattcc cacacattat taaaataccg tatatgtatt   3300
ggctgcattt gcatgaataa tactacgtgt aagcccaaaa gaacccacgt gtagcccatg   3360
caaagttaac actcacgacc ccattcctca gtctccacta tataaaccca ccatccccaa   3420
tctcaccaaa cccaccacac aactcacaac tcactctcac accttaaaga accaatcacc   3480
accaaaaaat ttcacgattt ggaatttgat tcctgcgatc acaggtatga caggttagat   3540
tttgttttgt atagttgtat acatacttct ttgtgatgtt ttgtttactt aatcgaattt   3600
ttggagtgtt ttaaggtctc tcgtttagaa atcgtggaaa atatcactgt gtgtgtgttc   3660
ttatgattca cagtgtttat gggtttcatg ttctttgttt tatcattgaa tgggaagaaa   3720
tttcgttggg atacaaattt ctcatgttct tactgatcgt tattaggagt ttggggaaaa   3780
aggaagagtt tttttggttg gttcgagtga ttatgaggtt atttctgtat ttgatttatg   3840
agttaatggt cgttttaatg ttgtagacat gggaaaagga tctgagggaa gatctgctgc   3900
tagagagatg actgctgagg ctaacggaga taagagaaag accatcctca ttgagggagt   3960
gttgtacgat gctaccaact tcaaacaccc aggaggttcc attattaact tcctcaccga   4020
gggagaagct ggagttgatg ctacccaagc ttacagagag ttccatcaga gatccggaaa   4080
ggctgataag tacctcaagt ccctcccaaa gttggatgct tctaaggtgg agtctaggtt   4140
ctctgctaag gagcaggcta gaagggacgc tatgaccagg gattacgctg ctttcagaga   4200
ggagttggtt gctgagggat acttcgatcc atctatccca cacatgatct acagagtggt   4260
ggagattgtg gctttgttcg ctttgtcttt ctggttgatg tctaaggctt ctccaacctc   4320
tttggttttg ggagtggtga tgaacggaat cgctcaagga agatgcggat gggttatgca   4380
cgagatggga cacggatctt tcactggagt tatctggctc gatgatagga tgtgcgagtt   4440
cttctacgga gttggatgtg gaatgtctgg acactactgg aagaaccagc actctaagca   4500
ccacgctgct ccaaacagat tggagcacga tgtggatttg aacaccttgc cactcgttgc   4560
tttcaacgag agagttgtga ggaaggttaa gccaggatct ttgttggctt tgtggctcag   4620
agttcaggct tatttgttcg ctccagtgtc ttgcttgttg atcggattgg gatggacctt   4680
gtacttgcac ccaagatata tgctcaggac caagagacac atggagtttg tgtggatctt   4740
cgctagatat atcggatggt tctccttgat gggagctttg ggatattctc ctggaacttc   4800
tgtgggaatg tacctctgct ctttcggact tggatgcatc tacatcttcc tccaattcgc   4860
tgtgtctcac acccacttgc cagttaccaa cccagaggat caattgcact ggcttgagta   4920
cgctgctgat cacaccgtga acatctctac caagtcttgg ttggttacct ggtggatgtc   4980
taacctcaac ttccaaatcg agcaccactt gttcccaacc gctccacaat tcaggttcaa   5040
ggagatctct ccaagagttg aggctctctt caagagacac aacctccctt actacgattt   5100
gccatacacc tctgctgttt ctactacctt cgctaacctc tactctgttg gacactctgt   5160
tggagctgat accaagaagc aggattgact gctttaatga gatatgcgag acgcctatga   5220
```

```
tcgcatgata tttgctttca attctgttgt gcacgttgta aaaaacctga gcatgtgtag   5280
ctcagatcct taccgccggt ttcggttcat tctaatgaat atatcacccg ttactatcgt   5340
atttttatga ataatattct ccgttcaatt tactgattgt ctacgtaggc tcagctgagc   5400
ttacctaagg ctacgtaggc tcacgtgacg ttacgtaagg ctacgtagcg tcacgtgagc   5460
ttacctaact ctagctagcc tcacgtgacc ttagctaaca ctaggtagcg tcagctcgac   5520
ggcccggact gtatccaact tctgatcttt gaatctctct gttccaacat gttctgaagg   5580
agttctaaga cttttcagaa agcttgtaac atgctttgta gactttcttt gaattactct   5640
tgcaaactct gattgaacct acgtgaaaac tgctccagaa gttctaacca aattccgtct   5700
tgggaaggcc caaaatttat tgagtacttc agtttcatgg acgtgtcttc aaagatttat   5760
aacttgaaat cccatcattt ttaagagaag ttctgttccg caatgtctta gatctcattg   5820
aaatctacaa ctcttgtgtc agaagttctt ccagaatcaa cttgcatcat ggtgaaaatc   5880
tggccagaag ttctgaactt gtcatatttc ttaacagtta gaaaaatttc taagtgttta   5940
gaattttgac ttttccaaag caaacttgac ttttgacttt cttaataaaa caaacttcat   6000
attctaacat gtcttgatga aatgtgattc ttgaaatttg atgttgatgc aaaagtcaaa   6060
gtttgacttt tcagtgtgca attgaccatt ttgctcttgt gccaattcca aacctaaatt   6120
gatgtatcag tgctgcaaac ttgatgtcat ggaagatctt atgagaaaat tcttgaagac   6180
tgagaggaaa aattttgtag tacaacacaa agaatcctgt ttttcatagt cggactagac   6240
acattaacat aaaacaccac ttcattcgaa gagtgattga agaaggaaat gtgcagttac   6300
ctttctgcag ttcataagag caacttacag acacttttac taaaatacta caaagaggaa   6360
gattttaaca acttagagaa gtaatgggag ttaaagagca acacattaag gggagtgtt    6420
aaaattaatg tgttgtaacc accactacct ttagtaagta ttataagaaa attgtaatca   6480
tcacattata attattgtcc ttatttaaaa ttatgataaa gttgtatcat taagattgag   6540
aaaaccaaat agtcctcgtc ttgatttttg aattattgtt ttctatgtta cttttcttca   6600
agcctatata aaaactttgt aatgctaaat tgtatgctgg aaaaaaatgt gtaatgaatt   6660
gaatagaaat tatggtattt caaagtccaa aatccatcaa tagaaattta gtacaaaacg   6720
taactcaaaa atattctctt attttaaatt ttacaacaat ataaaaatat tctcttattt   6780
taaattttac aataatataa tttatcacct gtcaccttta gaataccacc aacaatatta   6840
atacttagat attttattct taataatttt gagatctctc aatatatctg atatttattt   6900
tatatttgtg tcatatttc ttatgtttta gagttaaccc ttatatcttg gtcaaactag    6960
taattcaata tatgagtttg tgaaggacac attgacatct tgaaacattg gttttaacct   7020
tgttggaatg ttaaaggtaa taaaacattc agaattatga ccatctatta atatacttcc   7080
tttgtctttt aaaaaagtgt gcatgaaaat gctctatggt aagctagagt gtcttgctgg   7140
cctgtgtata tcaattccat ttccagatgg tagaaactgc cactacgaat aattagtcat   7200
aagacacgta tgttaacaca cgtcccttg catgtttttt gccatatatt ccgtctcttt    7260
ctttttcttc acgtataaaa caatgaacta attaatagag cgatcaagct gaacagttct   7320
ttgctttcga agttgccgca acctaaacag gtttttcctt cttctttctt cttattaact   7380
acgaccttgt cctttgccta tgtaaaatta ctaggttttc atcagttaca ctgattaagt   7440
tcgttatagt ggaagataaa atgccctcaa agcattttgc aggatatctt tgatttttca   7500
aagatatgga actgtagagt ttgatagtgt tcttgaatgt ggttgcatga agttttttg    7560
```

```
gtctgcatgt tattttttcc tcgaaatatg ttttgagtcc aacaagtgat tcacttggga   7620
ttcagaaagt tgttttctca atatgtaaca gttttttttct atggagaaaa atcataggga   7680
ccgttggttt tggcttcttt aattttgagc tcagattaaa cccattttac ccggtgttct   7740
tggcagaatt gaaaacagta cgtagtaccg cgcctaccat gtgtgttgag accgagaaca   7800
acgatggaat ccctactgtg gagatcgctt tcgatggaga gagagaaaga gctgaggcta   7860
acgtgaagtt gtctgctgag aagatggaac ctgctgcttt ggctaagacc ttcgctagaa   7920
gatacgtggt tatcgaggga gttgagtacg atgtgaccga tttcaaacat cctggaggaa   7980
ccgtgatttt ctacgctctc tctaacactg gagctgatgc tactgaggct ttcaaggagt   8040
tccaccacag atctagaaag gctaggaagg ctttggctgc tttgccttct agacctgcta   8100
agaccgctaa agtggatgat gctgagatgc tccaggattt cgctaagtgg agaaaggagt   8160
tggagaggga cggattcttc aagccttctc ctgctcatgt tgcttacaga ttcgctgagt   8220
tggctgctat gtacgctttg ggaacctact tgatgtacgc tagatacgtt gtgtcctctg   8280
tgttggttta cgcttgcttc ttcggagcta gatgtggatg ggttcaacac gagggaggac   8340
actcttcttt gaccggaaac atctggtggg ataagagaat ccaagctttc actgctggat   8400
tcggattggc tggatctgga gatatgtgga actccatgca caacaagcac cacgctactc   8460
ctcaaaaagt gaggcacgat atggatttgg ataccactcc tgctgttgct ttcttcaaca   8520
ccgctgtgga ggataataga cctaggggat tctctaagta ctggctcaga ttgcaagctt   8580
ggaccttcat tcctgtgact tctggattgg tgttgctctt ctggatgttc ttcctccacc   8640
cttctaaggc tttgaaggga ggaaagtacg aggagcttgt gtggatgttg gctgctcacg   8700
tgattagaac ctggaccatt aaggctgtta ctggattcac cgctatgcaa tcctacggac   8760
tcttcttggc tacttcttgg gtttccggat gctacttgtt cgctcacttc tctacttctc   8820
acacccactt ggatgttgtt cctgctgatg agcacttgtc ttgggttagg tacgctgtgg   8880
atcacaccat tgatatcgat ccttctcagg gatgggttaa ctggttgatg ggatacttga   8940
actgccaagt gattcaccac ctcttccctt ctatgcctca attcagacaa cctgaggtgt   9000
ccagaagatt cgttgctttc gctaagaagt ggaacctcaa ctacaaggtg atgacttatg   9060
ctggagcttg gaaggctact ttgggaaacc tcgataatgt gggaaagcac tactacgtgc   9120
acggacaaca ctctggaaag accgcttgat taatgaaggc cgcctcgacc gtacccccctg   9180
cagatagact atactatgtt ttagcctgcc tgctggctag ctactatgtt atgttatgtt   9240
gtaaaataaa cacctgctaa ggtatatcta tctatatttt agcatggctt tctcaataaa   9300
ttgtctttcc ttatcgttta ctatcttata cctaataatg aaataataat atcacatatg   9360
aggaacgggg caggtttagg catatatata cgagtgtagg gcggagtggg gctacgtagc   9420
gtcacgtgac gttacctaag cctaggtagc ctcagctgac gttacgtaac gctaggtagg   9480
ctcagctgac acgggcagga catagggact actacaagca tagtatgctt cagacaaaga   9540
gctaggaaag aactcttgat ggaggttaag agaaaaaagt gctagagggg catagtaatc   9600
aaacttgtca aaaccgtcat catgatgagg gatgacataa tataaaaagt tgactaaggt   9660
cttggtagta ctctttgatt agtattatat attggtgaga acatgagtca agaggagaca   9720
agaaaccgag gaaccatagt ttagcaacaa gatggaagtt gcaaagttga gctagccgct   9780
cgattagtta catctcctaa gcagtactac aaggaatggt ctctatactt tcatgtttag   9840
cacatggtag tgcggattga caagttagaa acagtgctta ggagacaaag agtcagtaaa   9900
ggtattgaaa gagtgaagtt gatgctcgac aggtcaggag aagtccctcc gccagatggt   9960
```

gactaccaag gggttggtat cagctgagac ccaaataaga ttcttcggtt gaaccagtgg 10020
ttcgaccgag actcttaggg tgggatttca ctgtaagatt tgtgcatttt gttgaatata 10080
aattgacaat tttttttatt taattataga ttatttagaa tgaattacat atttagtttc 10140
taacaaggat agcaatggat gggtatgggt acaggttaaa catatctatt acccacccat 10200
ctagtcgtcg ggttttacac gtacccaccc gtttacataa accagaccgg aattttaaac 10260
cgtacccgtc cgttagcggg tttcagattt acccgtttaa tcgggtaaaa cctgattact 10320
aaatatatat tttttatttg ataaacaaaa caaaaatgtt aatattttca tattggatgc 10380
aattttaaga aacacatatt cataaatttc catatttgta ggaaaataaa aagaaaaata 10440
tattcaagaa cacaaatttc accgacatga cttttattac agagttggaa ttagatctaa 10500
caattgaaaa attaaaatta agatagaata tgttgaggaa catgacatag tataatgctg 10560
ggttacccgt cgggtaggta tcgaggcgga tactactaaa tccatcccac tcgctatccg 10620
ataatcactg gtttcgggta tacccattcc cgtcaacagg ccttttttaac cggataattt 10680 caacttatag tgaatgaatt ttgaataaat agttagaata ccaaaatcct ggattgcatt 10740
tgcaatcaaa ttttgtgaac cgttaaattt tgcatgtact tgggatagat ataatagaac 10800
cgaattttca ttagtttaat ttataactta ctttgttcaa agaaaaaaaa tatctatcca 10860
atttacttat aataaaaaat aatctatcca agttacttat tataatcaac ttgtaaaaag 10920
gtaagaatac aaatgtggta gcgtacgtgt gattatatgt gacgaaatgt tatatctaac 10980
aaaagtccaa attcccatgg taaaaaaaat caaaatgcat ggcaggctgt ttgtaacctt 11040
ggaataagat gttggccaat tctggagccg ccacgtacgc aagactcagg gccacgttct 11100
cttcatgcaa ggatagtaga acaccactcc acccacctcc tatattagac ctttgcccaa 11160
ccctccccaa ctttcccatc ccatccacaa agaaaccgac atttttatca taaatctggt 11220
gcttaaacac tctggtgagt tctagtactt ctgctatgat cgatctcatt accatttctt 11280
aaatttctct ccctaaatat tccgagttct tgatttttga taacttcagg ttttctcttt 11340
ttgataaatc tggtctttcc attttttttt tttgtggtta atttagtttc ctatgttctt 11400
cgattgtatt atgcatgatc tgtgtttgga ttctgttaga ttatgtattg gtgaatatgt 11460
atgtgttttt gcatgtctgg ttttggtctt aaaaatgttc aaatctgatg atttgattga 11520 agcttttttta gtgttggttt gattcttctc aaaactactg ttaatttact atcatgtttt 11580
ccaactttga ttcatgatga cacttttgtt ctgctttgtt ataaaatttt ggttggtttg 11640
attttgtaat tatagtgtaa ttttgttagg aatgaacatg ttttaatact ctgttttcga 11700
tttgtcacac attcgaatta ttaatcgata atttaactga aaattcatgg ttctagatct 11760
tgttgtcatc agattatttg tttcgataat tcatcaaata tgtagtcctt ttgctgattt 11820
gcgactgttt cattttttct caaaattgtt ttttgttaag tttatctaac agttatcgtt 11880
gtcaaaagtc tctttcattt tgcaaaatct tcttttttttt tttgtttgta actttgtttt 11940
ttaagctaca catttagtct gtaaaatagc atcgaggaac agttgtctta gtagacttgc 12000
atgttcttgt aacttctatt tgtttcagtt tgttgatgac tgctttgatt ttgtaggtca 12060
aaggcgcacc ctaccatgga tgcttataac gctgctatgg ataagattgg agctgctatc 12120
atcgattgga gtgatccaga tggaaagttc agagctgata gggaggattg gtggttgtgc 12180
gatttcagat ccgctatcac cattgctctc atctacatcg ctttcgtgat cttgggatct 12240
gctgtgatgc aatctctccc agctatggac ccatacccta tcaagttcct ctacaacgtg 12300

```
tctcaaatct tcctctgcgc ttacatgact gttgaggctg gattcctcgc ttataggaac  12360
ggatacaccg ttatgccatg caaccacttc aacgtgaacg atccaccagt tgctaacttg  12420
ctctggctct tctacatctc caaagtgtgg gatttctggg ataccatctt cattgtgctc  12480
ggaaagaagt ggagacaact ctctttcttg cacgtgtacc accacaccac catcttcctc  12540
ttctactggt tgaacgctaa cgtgctctac gatggagata tcttcttgac catcctcctc  12600
aacggattca ttcacaccgt gatgtacacc tactacttca tctgcatgca caccaaggat  12660
tctaagaccg gaaagtcttt gccaatctgg tggaagtcat ctttgaccgc tttccaactc  12720
ttgcaattca ccatcatgat gtcccaagct acctacttgg ttttccacgg atgcgataag  12780
gtttccctca gaatcaccat cgtgtacttc gtgtacattc tctccctttt cttcctcttc  12840
gctcagttct tcgtgcaatc ctacatggct ccaaagaaga agaagtccgc ttgatgttaa  12900
tgaaggccgc agatatcaga tctggtcgac ctagaggatc cccggccgca aagataataa  12960
caaaagccta ctatataacg tacatgcaag tattgtatga tattaatgtt tttacgtacg  13020
tgtaaacaaa aataattacg tttgtaacgt atggtgatga tgtggtgcac taggtgtagg  13080
ccttgtatta ataaaaagaa gtttgttcta tatagagtgg tttagtacga cgatttattt  13140
actagtcgga ttggaataga gaaccgaatt cttcaatcct tgcttttgat caagaattga  13200
aaccgaatca aatgtaaaag ttgatatatt tgaaaaacgt attgagctta tgaaaatgct  13260
aatactctca tctgtatgga aaagtgactt taaaaccgaa cttaaaagtg acaaaagggg  13320
aatatcgcat caaaccgaat gaaaccgatc tacgtaggct cagctgagct tagctaagcc  13380
tacctagcct cacgtgagat tatgtaaggc taggtagcgt cacgtgacgt tacctaacac  13440
tagctagcgt cagctgagct tagctaaccc tacgtagcct cacgtgagct tacctaacgc  13500
tacgtagcct cacgtgacta aggatgacct acccattctt gagacaaatg ttacatttta  13560
gtatcagagt aaaatgtgta cctataactc aaattcgatt gacatgtatc cattcaacat  13620
aaaattaaac cagcctgcac ctgcatccac atttcaagta ttttcaaacc gttcggctcc  13680
tatccaccgg gtgtaacaag acggattccg aatttggaag attttgactc aaattcccaa  13740
tttatattga ccgtgactaa atcaacttta acttctataa ttctgattaa gctcccaatt  13800
tatattccca acggcactac ctccaaaatt tatagactct catccccttt taaaccaact  13860
tagtaaacgt tttttttta attttatgaa gttaagtttt taccttgttt ttaaaaagaa  13920
tcgttcataa gatgccatgc cagaacatta gctacacgtt acacatagca tgcagccgcg  13980
gagaattgtt tttcttcgcc acttgtcact cccttcaaac acctaagagc ttctctctca  14040
cagcacacac atacaatcac atgcgtgcat gcattattac acgtgatcgc catgcaaatc  14100
tcctttatag cctataaatt aactcatcgg cttcactctt tactcaaacc aaaactcatc  14160
aatacaaaca agattaaaaa catttcacga tttggaattt gattcctgcg atcacaggta  14220
tgacaggtta gattttgttt tgtatagttg tatacatact tctttgtgat gttttgttta  14280
cttaatcgaa tttttggagt gttttaaggt ctctcgttta gaaatcgtgg aaaatatcac  14340
tgtgtgtgtg ttcttatgat tcacagtgtt tatgggtttc atgttctttg ttttatcatt  14400
gaatgggaag aaatttcgtt gggatacaaa tttctcatgt tcttactgat cgttattagg  14460
agtttgggga aaaaggaaga gttttttgg ttggttcgag tgattatgag gttatttctg  14520
tatttgattt atgagttaat ggtcgtttta atgttgtaga ccgccatggc tattttgaac  14580
cctgaggctg attctgctgc taacctcgct actgattctg aggctaagca aagacaattg  14640
gctgaggctg gatacactca cgttgagggt gctcctgctc ctttgccttt ggagttgcct  14700
```

```
cacttctctc tcagagatct cagagctgct attcctaagc actgcttcga gagatctttc  14760
gtgacctcca cctactacat gatcaagaac gtgttgactt gcgctgcttt gttctacgct  14820
gctaccttca ttgatagagc tggagctgct gcttatgttt tgtggcctgt gtactggttc  14880
ttccagggat cttacttgac tggagtgtgg gttatcgctc acgagtgtgg acaccaggct  14940
tattgctctt ctgaggtggt gaacaacttg attggactcg tgttgcactc tgctttgttg  15000
gtgccttacc actcttggag aatctctcac agaaagcacc actccaacac tggatcttgc  15060
gagaacgatg aggttttcgt tcctgtgacc agatctgtgt tggcttcttc ttggaacgag  15120
accttggagg attctcctct ctaccaactc taccgtatcg tgtacatgtt ggttgttgga  15180
tggatgcctg gatacctctt cttcaacgct actggaccta ctaagtactg ggggaaagtct  15240
aggtctcact tcaaccctta ctccgctatc tatgctgata gggagaggtg gatgatcgtg  15300
ctctccgata ttttcttggt ggctatgttg gctgttttgg ctgctttggt gcacactttc  15360
tccttcaaca cgatggtgaa gttctacgtg gtgccttact tcattgtgaa cgcttacttg  15420
gtgttgatta cctacctcca acacaccgat acctacatcc ctcacttcag agagggagag  15480
tggaattggt tgagaggagc tttgtgcact gtggatagat catttggtcc attcctcgat  15540
tctgtggtgc atagaatcgt ggatacccac gtttgccacc atatcttctc caagatgcct  15600
ttctatcact gcgaggaggc taccaacgct attaagcctc tcctcggaaa gttctacttg  15660
aaggatacta ctcctgttcc tgttgctctc tggagatctt acacccactg caagttcgtt  15720
gaggatgatg gaaaggtggt gttctacaag aacaagttat agttaatgaa taattgattg  15780
gttcgagtat tatggcattg ggaaaactgt ttttcttgta ccatttgttg tgcttgtaat  15840
ttactgtgtt ttttattcgg ttttcgctat cgaactgtga aatggaaatg gatggagaag  15900
agttaatgaa tgatatggtc cttttgttca ttctcaaatt aatattattt gtttttttctc  15960
ttatttgttg tgtgttgaat ttgaaattat aagagatatg caaacatttt gttttgagta  16020
aaaatgtgtc aaatcgtggc ctctaatgac cgaagttaat atgaggagta aaacacttgt  16080
agttgtacca ttatgcttat tcactaggca acaaatatat tttcagacct agaaaagctg  16140
caaatgttac tgaatacaag tatgtcctct tgtgttttag acatttatga actttccttt  16200
atgtaatttt ccagaatcct tgtcagattc taatcattgc tttataatta tagttatact  16260
catggatttg tagttgagta tgaaaatatt ttttaatgca ttttatgact tgccaattga  16320
ttgacaacat gcatcaatct agctagcctc agctgacgtt acgtaacgct aggtagcgtc  16380
acgtgacgtt agctaacgct aggtagcgtc agctgagctt acgtaagcgc acagatgaat  16440
actagctgtt gttcacagtt ctagtgtctc ctcattacgt gaattcaagc tacgatcact  16500
atctcaactc ctacataaac atcagaatgc tacaaaacta tgcacaaaaa caaaagctac  16560
atctaatacg tgaatcaatt actctcatca caagaaagaa gatttcaatc accgtcgaga  16620
aggaggattc agttaattga atcaaagttc cgatcaaact cgaagactgg tgagcacgag  16680
gacgacgaag aagagtgtct cgaagataca acaagcaaga aatctactga gtgacctcct  16740
gaagttattg gcgcgattga gagaatcaat ccgaattaat ttcggggaaa aagataaatt  16800
agatactaag cgatgggctt gggctgggct aagaaacagg tggcaattgg gctggaggac  16860
cccgcgattc atagcttccg atagcccaaa aaaaaacgga taacatattt atcgggtatt  16920
tgaatttcag tgaaataaga tattttcttt ttgttaggaa aattttagaa aataatggaa  16980
attaaatagc gattatgtta caagatacga tcagcatcgg gcagtgcaaa atgctatagc  17040
```

```
ttcccaagat ttgatccttt tgggttatct cctaatgaca attagtttag gattttgaaa  17100
cttatattaa tactattatc cgacaacact tgtttcagct tcttatttta acatttttttg  17160
tttttttcta ttcttcttcc catcagcatt ttctttttaa aaaattgaat actttaactt  17220
tttaaaaatt tcacaatgat cagatgatat tatggaagat ctcaagagtt aaatgtatcc  17280
atcttggggc attaaaaccg gtgtacggga tgataaatac agactttata tcatatgata  17340
gctcagtaat tcatatttat cacgttgcta aaaaaattat aaggtactag tagtcaacaa  17400
aatcaattaa agagaaagaa agaaacgcat gtgaagagag tttacaactg gaaaagtaaa  17460
ataaaaatta acgcatgttg aatgctgaca tgtcagtatg tccatgaatc cacgtatcaa  17520
gcgccattca tcgatcgtct tcctctttct aaatgaaaac aacttcacac atcacaacaa  17580
acaatacaca caagacccc tctctctcgt tgtctctctg ccagcgacca aatcgaagct  17640
tgagaagaac aagaaggggt caaaccatgg cttctacatc tgctgctcaa gacgctgctc  17700
cttacgagtt cccttctctc actgagatca agagggctct tccttctgag tgtttcgagg  17760
cttctgttcc tctttctctc tactacaccg ctagatctct tgctcttgct ggatctctcg  17820
ctgttgctct ctcttacgct agagctttgc ctcttgttca ggctaacgct cttcttgatg  17880
ctactctctg cactggatac gttcttctcc agggaatcgt tttctgggga ttcttcaccg  17940
ttggtcacga ttgtggacac ggagctttct ctagatctca cgtgctcaac ttctctgttg  18000
gaaccctcat gcactctatc atccttaccc ctttcgagtc ttggaagctc tctcacagac  18060
accaccacaa gaacaccgga aacatcgata aggacgagat cttctaccct caaagagagg  18120
ctgattctca ccctgtttct agacaccttg tgatgtctct tggatctgct tggttcgctt  18180
accttttcgc tggattccct cctagaacca tgaaccactt caacccttgg gaggctatgt  18240
atgttagaag agtggctgct gtgatcatct ctctcggagt tcttttcgct ttcgctggac  18300
tctactctta cctcaccttc gttcttggat tcaccactat ggctatctac tacttcggac  18360
ctctcttcat cttcgctacc atgcttgttg ttaccacttt cctccaccac aacgatgagg  18420
agacaccttg gtacgctgat tctgagtgga cttacgtgaa gggaaacctc tcttctgtgg  18480
acagatctta cggtgctctc atcgacaacc ttagccacaa catcggaact caccagatcc  18540
accacctctt ccctatcatc cctcactaca agctcaacga tgctactgct gctttcgcta  18600
aggctttccc tgagcttgtt aggaaaaacg ctgctcctat catcccaact ttcttcagga  18660
tggctgctat gtacgctaag tacggagttg ttgacactga tgctaagacc ttcactctca  18720
aggaggctaa ggctgctgct aagactaagt catcttgatg attaatgaat aattgattgt  18780
acatactata ttttttgttt accttgtgtt agtttaatgt tcagtgtcct ctctttattg  18840
tggcacgtct ctttgttgta tgttgtgtct atacaaagtt gaaataatgg aaagaaaagg  18900
aagagtgtaa tttgttttgt tttaagtgtt tataaatata tatatatagg tcatttagat  18960
agttctaggt ttctataaaa ctctctctct ggaagtagaa tctgtttttg agaggatcca  19020
gttgcctact aatctccccc aaaacccttc aagcttaacc ttcctcttca caacaacaga  19080
ggaaacacat ctcttgagct ctgagttctc ttctttgagc atgtctatcg ctaaactcat  19140
ctgccttata gcttccctct tctcttcatc tctctctctc accatttcgc tgtaaaactt  19200
attctcctcc ctcagcctct ctatctcttc cttcagcatc tcacaattcc caccataatc  19260
gactgaggat gattcaccgt catcaacttc agactcagcg ttgtagtcgt catgagtctc  19320
acaagccttg gaccaagaag actcatcatc gcaagttgat gatttatcat gatgcttctc  19380
tgagccgtgt ttgctacgta gcgtcacgtg acgttaccta agcctaggta gcctcagctg  19440
```

```
acgttacgta acgctaggta ggctcagctg actgcagcaa atttacacat tgccactaaa  19500
cgtctaaacc cttgtaattt gtttttgttt tactatgtgt gttatgtatt tgatttgcga  19560
taaattttta tatttggtac taaatttata acacctttta tgctaacgtt tgccaacact  19620
tagcaatttg caagttgatt aattgattct aaattatttt tgtcttctaa atacatatac  19680
taatcaactg gaaatgtaaa tatttgctaa tatttctact ataggagaat taaagtgagt  19740
gaatatggta ccacaaggtt tggagattta attgttgcaa tgctgcatgg atggcatata  19800
caccaaacat tcaataattc ttgaggataa taatggtacc acacaagatt tgaggtgcat  19860
gaacgtcacg tggacaaaag gtttagtaat ttttcaagac aacaatgtta ccacacacaa  19920
gttttgaggt gcatgcatgg atgccctgtg gaaagtttaa aaatattttg gaaatgattt  19980
gcatggaagc catgtgtaaa accatgacat ccacttggag gatgcaataa tgaagaaaac  20040
tacaaattta catgcaacta gttatgcatg tagtctatat aatgaggatt ttgcaatact  20100
ttcattcata cacactcact aagttttaca cgattataat ttcttcatag ccagtactgt  20160
ttaagcttca ctgtctctga atcggcaaag gtaaacgtat caattattct acaaaccctt  20220
ttatttttct tttgaattac cgtcttcatt ggttatatga taacttgata agtaaagctt  20280
caataattga atttgatctg tgttttttttg gccttaatac taaatcctta cataagcttt  20340
gttgcttctc ctcttgtgag ttgagtgtta agttgtaata atggttcact ttcagcttta  20400
gaagaaacgc gccttccatg gctacaaagg aggcttacgt tttcccaact ctcaccgaga  20460
tcaagagatc tctcccaaag gattgcttcg aggcttctgt gcctttgtct ctctactaca  20520
ctgtgagatg cttggttatt gctgtggctt tgaccttcgg attgaactac gctagagctt  20580
tgccagaggt tgagtctttc tgggctttgg atgctgcttt gtgcactgga tatatcctcc  20640
tccagggaat tgtgttctgg ggattcttca ctgttggaca cgatgctgga cacggagctt  20700
tctctagata ccacctcttg aacttcgttg tgggaacctt catgcactct ctcatcttga  20760
ccccattcga gtcttggaag ttgacccaca gacaccacca caagaacacc ggaaacatcg  20820
atagagatga ggtgttctac ccacagagaa aggctgatga tcacccattg tccaggaact  20880
tgatcttggc tttgggagct gcttggcttg cttatttggt ggagggattc ccaccaagaa  20940
aggtgaacca cttcaaccca ttcgagccac tttttgtgag acaagtgtcc gctgtggtta  21000
tctctttgct cgctcacttc ttcgttgctg gactctctat ctacttgtct ctccagttgg  21060
gacttaagac catggctatc tactactacg gaccagtttt cgtgttcgga tctatgttgg  21120
tgattaccac cttcttgcac cacaacgatg aggagactcc atggtatgct gattctgagt  21180
ggacttacgt gaagggaaac ttgtcctctg tggatagatc ttacggtgct ctcatcgata  21240
acctctccca caacatcgga actcaccaga tccaccacct cttcccaatt atcccacact  21300
acaagctcaa gaaggctact gctgctttcc accaagcttt cccagagctt gtgagaaagt  21360
ccgatgagcc aatcatcaag gctttcttca gagtgggaag gttgtatgct aactacggag  21420
tggttgatca agaggctaag ctcttcactt tgaaggaggc taaggctgct actgaagctg  21480
ctgctaagac caagtctacc tgattaatga atcgacaagc tcgagtttct ccataataat  21540
gtgtgagtag ttcccagata agggaattag ggttcctata gggtttcgct catgtgttga  21600
gcatataaga aacccttagt atgtatttgt atttgtaaaa tacttctatc aataaaattt  21660
ctaattccta aaaccaaaat ccagtactaa aatccagatc ccccgaatta attcggcgtt  21720
aattcagcta cgtaggctca gctgagctta cctaaggcta cgtaggctca cgtgacgtta  21780
```

```
cgtaaggcta cgtagcgtca cgtgagctta cctaactcta gctagcctca cgtgacctta  21840

gctaacacta ggtagcgtca gcacagatga atactagctg ttgttcacag ttctagtgtc  21900

tcctcattac gtgaattcaa gctacgatca ctatctcaac tcctacataa acatcagaat  21960

gctacaaaac tatgcacaaa aacaaaagct acatctaata cgtgaatcaa ttactctcat  22020

cacaagaaag aagatttcaa tcaccgtcga gaaggaggat tcagttaatt gaatcaaagt  22080

tccgatcaaa ctcgaagact ggtgagcacg aggacgacga agaagagtgt ctcgaagata  22140

caacaagcaa gaaatctact gagtgacctc ctgaagttat tggcgcgatt gagagaatca  22200

atccgaatta atttcgggga aaaagataaa ttagatacta agcgatgggc ttgggctggg  22260

ctaagaaaca ggtggcaatt gggctggagg accccgcgat tcatagcttc cgatagccca  22320

aaaaaaaacg gataacatat ttatcgggta tttgaatttc agtgaaataa gatattttct  22380

ttttgttagg aaaattttag aaaataatgg aaattaaata gcgattatgt tacaagatac  22440

gatcagcatc gggcagtgca aaatgctata gcttcccaag atttgatcct tttgggttat  22500

ctcctaatga caattagttt aggattttga aacttatatt aatactatta tccgacaaca  22560

cttgtttcag cttcttattt taacattttt tgtttttttc tattcttctt cccatcagca  22620

ttttcttttt aaaaaattga atactttaac tttttaaaaa tttcacaatg atcagatgat  22680

attatggaag atctcaagag ttaaatgtat ccatcttggg gcattaaaac cggtgtacgg  22740

gatgataaat acagacttta tatcatatga tagctcagta attcatattt atcacgttgc  22800

taaaaaaatt ataaggtact agtagtcaac aaaatcaatt aaagagaaag aaagaaacgc  22860

atgtgaagag agtttacaac tggaaaagta aaataaaaat taacgcatgt tgaatgctga  22920

catgtcagta tgtccatgaa tccacgtatc aagcgccatt catcgatcgt cttcctcttt  22980

ctaaatgaaa acaacttcac acatcacaac aaacaataca cacaagaccc cctctctctc  23040

gttgtctctc tgccagcgac caaatcgaag cttgagaaga acaagaaggg gtcaaaccat  23100

gggaaaagga tctgagggaa gatctgctgc tagagagatg actgctgagg ctaacggaga  23160

taagagaaag accatcctca ttgagggagt gttgtacgat gctaccaact tcaaacaccc  23220

aggaggttcc attattaact tcctcaccga gggagaagct ggagttgatg ctacccaagc  23280

ttacagagag ttccatcaga gatccggaaa ggctgataag tacctcaagt ccctcccaaa  23340

gttggatgct tctaaggtgg agtctaggtt ctctgctaag gagcaggcta gaagggacgc  23400

tatgaccagg gattacgctg ctttcagaga ggagttggtt gctgagggat acttcgatcc  23460

atctatccca cacatgatct acagagtggt ggagattgtg gctttgttcg ctttgtcttt  23520

ctggttgatg tctaaggctt ctccaacctc tttggttttg ggagtggtga tgaacggaat  23580

cgctcaagga agatgcggat gggttatgca cgagatggga cacggatctt tcactggagt  23640

tatctggctc gatgatagga tgtgcgagtt cttctacgga gttggatgtg gaatgtctgg  23700

acactactgg aagaaccagc actctaagca ccacgctgct ccaaacagat tggagcacga  23760

tgtggatttg aacaccttgc cactcgttgc tttcaacgag agagttgtga ggaaggttaa  23820

gccaggatct ttgttggctt tgtggctcag agttcaggct tatttgttcg ctccagtgtc  23880

ttgcttgttg atcggattgg gatggacctt gtacttgcac ccaagatata tgctcaggac  23940

caagagacac atggagtttg tgtggatctt cgctagatat atcggatggt tctccttgat  24000

gggagctttg ggatattctc ctggaacttc tgtgggaatg tacctctgct ctttcggact  24060

tggatgcatc tacatcttcc tccaattcgc tgtgtctcac acccacttgc cagttaccaa  24120

cccagaggat caattgcact ggcttgagta cgctgctgat cacaccgtga acatctctac  24180
```

```
caagtcttgg ttggttacct ggtggatgtc taacctcaac ttccaaatcg agcaccactt  24240
gttcccaacc gctccacaat tcaggttcaa ggagatctct ccaagagttg aggctctctt  24300
caagagacac aacctccctt actacgattt gccatacacc tctgctgttt ctactacctt  24360
cgctaacctc tactctgttg gacactctgt tggagctgat accaagaagc aggattgatg  24420
attaatgaat aattgattgt acatactata ttttttgttt accttgtgtt agtttaatgt  24480
tcagtgtcct ctctttattg tggcacgtct ctttgttgta tgttgtgtct atacaaagtt  24540
gaaataatgg aaagaaaagg aagagtgtaa tttgttttgt tttaagtgtt tataaatata  24600
tatatatagg tcatttagat agttctaggt ttctataaaa ctctctctct ggaagtagaa  24660
tctgtttttg agaggatcca gttgcctact aatctccccc aaaacccttc aagcttaacc  24720
ttcctcttca caacaacaga ggaaacacat ctcttgagct ctgagttctc ttctttgagc  24780
atgtctatcg ctaaactcat ctgccttata gcttccctct tctcttcatc tctctctctc  24840
accatttcgc tgtaaaactt attctcctcc ctcagcctct ctatctcttc cttcagcatc  24900
tcacaattcc caccataatc gactgaggat gattcaccgt catcaacttc agactcagcg  24960
ttgtagtcgt catgagtctc acaagccttg gaccaagaag actcatcatc gcaagttgat  25020
gatttatcat gatgcttctc tgagccgtgt ttgctaccta gagtcagctg agcttagcta  25080
acgctagcta gtgtcagctg acgttacgta aggctaacta gcgtcacgtg accttacgta  25140
acgctacgta ggctcagctg agcttagcta accctagcta gtgtcacgtg agcttacgct  25200
actatagaaa atgtgttata tcgacatgac cagacaaagg ggcaacagtt aacaaaacaa  25260
ttaattcttt catttgagat taaggaaggt aaggtactaa aaagattaaa aaaaatgagc  25320
ttatctcttt gtttctgtaa taataatata agtgtgataa acttttaata taataattgt  25380
aattaggttt tctacagatg agcaccactc agagacaaga taagaagaaa acaattttgt  25440
taaacatgat tatagaaact tttagttaag tcttgaagta tcaatataac aaaaaaaagt  25500
acacacgact atgacaataa acccactacc gtcaggttat catttcgatg aaatgttttg  25560
atatcattaa atataacagt cacaaaaaat catctaatta taacaatata acttatacat  25620
atatttaact aaaaacttag agtttttgta atgattctaa ttgatgatta gagtttatag  25680
aaatacaatt aaataaaaaa tataatttta aaaaaacata gtaaagtcaa tgagatcctc  25740
tctgacctca gtgatcattt agtcatgtat gtacaacaat cattgttcat cacatgactg  25800
taaaataaat aaggataaac ttgggaatat atataatata ttgtattaaa taaaaaaggg  25860
aaatacaaat atcaatttta gattcccgag ttgacacaac tcaccatgca cgctgccacc  25920
tcagctccca gctctcgtca catgtctcat gtcagttagg tctttggttt ttagtctttg  25980
acacaactcg ccatgcatgt tgccacgtga gctcgttcct cttcccatga tctcaccact  26040
gggcatgcat gctgccacct cagctggcac ctcttctcta tatgtcccta gaggccatgc  26100
acagtgccac ctcagcactc ctctcagaac ccatacgtac ctgccaatcg gcttctctcc  26160
ataaatatct atttaaatta taactaatta tttcatatac ttaattgatg acgtggatgc  26220
attgccatcg ttgtttaata attgttaatt acgacatgat aaataaaatg aaagtaaaaa  26280
gtacgaaaga ttttccattt gttgttgtat aaatagagaa gtgagtgatg cataatgcat  26340
gaatgcatga ccgcgccacc atgactgttg gatacgacga ggagatccca ttcgagcaag  26400
ttagggctca taacaagcca gacgacgctt ggtgtgctat tcacggacac gtgtacgacg  26460
ttaccaagtt cgcttcagtt cacccaggag gagatattat cttgctcgct gctggaaagg  26520
```

```
aagctactgt cctctacgag acctaccatg ttagaggagt gtctgacgct gtgctcagaa  26580
agtacagaat aggaaagttg ccagacggac aaggaggagc taacgagaag gagaagagaa  26640
ccttgtctgg attgtcctct gcttcttact acacctggaa ctccgatttc tacagagtga  26700
tgagggagag agttgtggct agattgaagg agagaggaaa ggctagaaga ggaggatacg  26760
aactctggat caaggctttc ttgctccttg ttggattctg gtcctctctt tactggatgt  26820
gcaccctcga tccatctttc ggagctatct tggctgctat gtctttggga gtgttcgctg  26880
cttttgttgg aacctgcatc caacacgatg gaaaccacgg agctttcgct caatctagat  26940
gggttaacaa ggtggcagga tggactttgg atatgatcgg agcttctgga atgacttggg  27000
agttccaaca cgtgttggga caccacccat acactaactt gatcgaggag gagaacggat  27060
tgcaaaaggt gtccggaaag aagatggata ccaagttggc tgatcaagag tctgatccag  27120
atgtgttctc cacctaccca atgatgagat tgcacccttg gcaccagaag aggtggtatc  27180
acaggttcca gcacatctac ggacctttca tcttcggatt catgaccatc aacaaggtgg  27240
tgactcaaga tgttggagtg gtgttgagaa agagactctt ccaaatcgat gctgagtgca  27300
gatatgcttc cccaatgtac gttgctaggt tctggattat gaaggctttg accgtgttgt  27360
atatggttgc tttgccttgt tatatgcaag gaccttggca cggattgaaa ctcttcgcta  27420
tcgctcactt cacttgcgga gaggttttgg ctaccatgtt catcgtgaac cacattatcg  27480
agggagtgtc ttacgcttct aaggatgctg ttaagggaac tatggctcca ccaaagacta  27540
tgcacggagt gaccccaatg aacaacacta gaaaggaggt tgaggctgag gcttctaagt  27600
ctggagctgt ggttaagtct gtgccattgg atgattgggc tgctgttcag tgccaaacct  27660
ctgtgaactg gtctgttgga tcttggtttt ggaaccactt ctctggagga ctcaaccacc  27720
aaatcgagca ccacctcttc ccaggattgt ctcacgagac ctactaccac atccaagacg  27780
tggttcaatc tacctgtgct gagtacggag ttccatacca acacgagcca tctttgtgga  27840
ctgcttactg gaagatgctc gaacacctta gacaattggg aaacgaggag actcacgagt  27900
catggcagag agctgcttga ttaatgaact aagactccca aaaccacctt ccctgtgaca  27960
gttaaaccct gcttatacct ttcctcctaa taatgttcat ctgtcacaca aactaaaata  28020
aataaaatgg gagcaataaa taaaatggga gctcatatat ttacaccatt tacactgtct  28080
attattcacc atgccaatta ttacttcata attttaaaat tatgtcattt ttaaaaattg  28140
cttaatgatg gaaaggatta ttataagtta aaagtataac atagataaac taaccacaaa  28200
acaaatcaat ataaactaac ttactctccc atctaatttt tatttaaatt tctttacact  28260
tctcttccat ttctatttct acaacattat ttaacatttt tattgtattt ttcttacttt  28320
ctaactctat tcatttcaaa aatcaatata tgtttatcac cacctctcta aaaaaaactt  28380
tacaatcatt ggtccagaaa agttaaatca cgagatggtc attttagcat taaaacaacg  28440
attcttgtat cactattttt cagcatgtag tccattctct tcaaacaaag acagcggcta  28500
tataatcgtt gtgttatatt cagtctaaaa caactagcta gcctcagctg acgttacgta  28560
acgctaggta gcgtcacgtg acgttagcta acgctaggta gcgtcagctg agcttacgta  28620
agcgccacgg gcaggacata gggactacta caagcatagt atgcttcaga caaagagcta  28680
ggaaagaact cttgatggag gttaagagaa aaaagtgcta gaggggcata gtaatcaaac  28740
ttgtcaaaac cgtcatcatg atgagggatg acataatata aaaagttgac taaggtcttg  28800
gtagtactct ttgattagta ttatatattg gtgagaacat gagtcaagag gagacaagaa  28860
accgaggaac catagtttag caacaagatg gaagttgcaa agttgagcta gccgctcgat  28920
```

```
tagttacatc tcctaagcag tactacaagg aatggtctct atactttcat gtttagcaca  28980
tggtagtgcg gattgacaag ttagaaacag tgcttaggag acaaagagtc agtaaaggta  29040
ttgaaagagt gaagttgatg ctcgacaggt caggagaagt ccctccgcca gatggtgact  29100
accaaggggt tggtatcagc tgagacccaa ataagattct tcggttgaac cagtggttcg  29160
accgagactc ttagggtggg atttcactgt aagatttgtg cattttgttg aatataaatt  29220
gacaattttt tttatttaat tatagattat ttagaatgaa ttacatattt agtttctaac  29280
aaggatagca atggatgggt atgggtacag gttaaacata tctattaccc acccatctag  29340
tcgtcgggtt ttacacgtac ccacccgttt acataaacca gaccggaatt ttaaaccgta  29400
cccgtccgtt agcgggtttc agatttaccc gtttaatcgg gtaaaacctg attactaaat  29460
atatattttt tatttgataa acaaaacaaa aatgttaata ttttcatatt ggatgcaatt  29520
ttaagaaaca catattcata aatttccata tttgtaggaa aataaaaaga aaaatatatt  29580
caagaacaca aatttcaccg acatgacttt tattacagag ttggaattag atctaacaat  29640
tgaaaaatta aaattaagat agaatatgtt gaggaacatg acatagtata atgctgggtt  29700
acccgtcggg taggtatcga ggcggatact actaaatcca tcccactcgc tatccgataa  29760
tcactggttt cgggtatacc cattcccgtc aacaggcctt tttaaccgga taatttcaac  29820
ttatagtgaa tgaattttga ataaatagtt agaataccaa aatcctggat tgcatttgca  29880
atcaaatttt gtgaaccgtt aaattttgca tgtacttggg atagatataa tagaaccgaa  29940
ttttcattag tttaatttat aacttacttt gttcaaagaa aaaaaatatc tatccaattt  30000
acttataata aaaaataatc tatccaagtt acttattata atcaacttgt aaaaaggtaa  30060
gaatacaaat gtggtagcgt acgtgtgatt atatgtgacg aaatgttata tctaacaaaa  30120
gtccaaattc ccatggtaaa aaaaatcaaa atgcatggca ggctgtttgt aaccttggaa  30180
taagatgttg gccaattctg gagccgccac gtacgcaaga ctcagggcca cgttctcttc  30240
atgcaaggat agtagaacac cactccaccc acctcctata ttagaccttt gcccaaccct  30300
ccccaacttt cccatcccat ccacaaagaa accgacattt ttatcataaa tcagggtttc  30360
gtttttgttt catcgataaa ctcaaaggtg atgattttag ggtcttgtga gtgtgctttt  30420
ttgtttgatt ctactgtagg gtttatgttc tttagctcat aggttttgtg tatttcttag  30480
aaatgtggct tctttaatct ctgggtttgt gactttttgt gtggtttctg tgtttttcat  30540
atcaaaaacc tattttttcc gagttttttt ttacaaattc ttactctcaa gcttgaatac  30600
ttcacatgca gtgttctttt gtagatttta gagttaatgt gttaaaaagt ttggattttt  30660
cttgcttata gagcttcttc actttgattt tgtgggtttt tttgttttaa aggtgagatt  30720
tttgatgagg tttttgcttc aaagatgtca cctttctggg tttgtctttt gaataaagct  30780
atgaactgtc acatggctga cgcaattttg ttactatgtc atgaaagctg acgtttttcc  30840
gtgttataca tgtttgctta cacttgcatg cgtcaaaaaa attggggctt tttagtttta  30900
gtcaaagatt ttacttctct tttgggattt atgaaggaaa gttgcaaact ttctcaaatt  30960
ttaccatttt tgctttgatg tttgtttaga ttgcgacaga acaaactcat atatgttgaa  31020
atttttgctt ggttttgtat aggattgtgt cttttgctta taaatgttga aatctgaact  31080
tttttttgt ttggtttctt tgagcaggag ataaggcgca ccaccatggc ttctacatct  31140
gctgctcaag acgctgctcc ttacgagttc ccttctctca ctgagatcaa gagggctctt  31200
ccttctgagt gtttcgaggc ttctgttcct ctttctctct actacaccgc tagatctctt  31260
```

```
gctcttgctg gatctctcgc tgttgctctc tcttacgcta gagctttgcc tcttgttcag  31320
gctaacgctc ttcttgatgc tactctctgc actggatacg ttcttctcca gggaatcgtt  31380
ttctggggat tcttcaccgt tggtcacgat tgtggacacg gagctttctc tagatctcac  31440
gtgctcaact tctctgttgg aaccctcatg cactctatca tccttacccc tttcgagtct  31500
tggaagctct ctcacagaca ccaccacaag aacaccggaa acatcgataa ggacgagatc  31560
ttctaccctc aaagagaggc tgattctcac cctgtttcta gacaccttgt gatgtctctt  31620
ggatctgctt ggttcgctta ccttttcgct ggattccctc ctagaaccat gaaccacttc  31680
aacccttggg aggctatgta tgttagaaga gtggctgctg tgatcatctc tctcggagtt  31740
cttttcgctt tcgctggact ctactcttac ctcaccttcg ttcttggatt caccactatg  31800
gctatctact acttcggacc tctcttcatc ttcgctacca tgcttgttgt taccactttc  31860
ctccaccaca acgatgagga gacaccttgg tacgctgatt ctgagtggac ttacgtgaag  31920
ggaaacctct cttctgtgga cagatcttac ggtgctctca tcgacaacct tagccacaac  31980
atcggaactc accagatcca ccacctcttc cctatcatcc ctcactacaa gctcaacgat  32040
gctactgctg ctttcgctaa ggctttccct gagcttgtta ggaaaaacgc tgctcctatc  32100
atcccaactt tcttcaggat ggctgctatg tacgctaagt acggagttgt tgacactgat  32160
gctaagacct tcactctcaa ggaggctaag gctgctgcta agactaagtc atcttgatga  32220
ttaatgaagg ccgcagatat cagatctggt cgacctagag gatccccggc cgcaaagata  32280
ataacaaaag cctactatat aacgtacatg caagtattgt atgatattaa tgtttttacg  32340
tacgtgtaaa caaaaataat tacgtttgta acgtatggtg atgatgtggt gcactaggtg  32400
taggccttgt attaataaaa agaagtttgt tctatataga gtggtttagt acgacgattt  32460
atttactagt cggattggaa tagagaaccg aattcttcaa tccttgcttt tgatcaagaa  32520
ttgaaaccga atcaaatgta aaagttgata tatttgaaaa acgtattgag cttatgaaaa  32580
tgctaatact ctcatctgta tggaaaagtg actttaaaac cgaacttaaa agtgacaaaa  32640
ggggaatatc gcatcaaacc gaatgaaacc gatctacgta ggctcagctg agcttaccta  32700
aggctacgta ggctcacgtg acgttacgta aggctacgta gcgtcacgtg agcttaccta  32760
actctagcta gcctcacgtg accttagcta acactaggta gcgtcagctt agcagatatt  32820
tggtgtctaa atgtttattt tgtgatatgt tcatgtttga aatggtggtt tcgaaaccag  32880
ggacaacgtt gggatctgat agggtgtcaa agagtattat ggattgggac aatttcggtc  32940
atgagttgca aattcaagta tatcgttcga ttatgaaaat tttcgaagaa tatcccattt  33000
gagagagtct ttacctcatt aatgttttta gattatgaaa ttttatcata gttcatcgta  33060
gtctttttgg tgtaaaggct gtaaaaagaa attgttcact tttgttttcg tttatgtgaa  33120
ggctgtaaaa gattgtaaaa gactattttg gtgttttgga taaaatgata gtttttatag  33180
attcttttgc ttttagaaga aatacatttg aaattttttc catgttgagt ataaaatacc  33240
gaaatcgatt gaagatcata gaaatatttt aactgaaaac aaatttataa ctgattcaat  33300
tctctccatt tttataccta tttaaccgta atcgattcta atagatgatc gatttttat   33360
ataatcctaa ttaaccaacg gcatgtattg gataattaac cgatcaactc tcacccctaa  33420
tagaatcagt attttccttc gacgttaatt gatcctacac tatgtaggtc atatccatcg  33480
ttttaatttt tggccaccat tcaattctgt cttgccttta gggatgtgaa tatgaacggc  33540
caaggtaaga gaataaaaat aatccaaatt aaagcaagag aggccaagta agataatcca  33600
aatgtacact tgtcattgcc aaaattagta aaatactcgg catattgtat tcccacacat  33660
```

```
tattaaaata ccgtatatgt attggctgca tttgcatgaa taatactacg tgtaagccca  33720
aaagaaccca cgtgtagccc atgcaaagtt aacactcacg accccattcc tcagtctcca  33780
ctatataaac ccaccatccc caatctcacc aaacccacca cacaactcac aactcactct  33840
cacaccttaa agaaccaatc accaccaaaa aaagttcttt gctttcgaag ttgccgcaac  33900
ctaaacaggt tttccttct tctttcttct tattaactac gaccttgtcc tttgcctatg  33960
taaaattact aggttttcat cagttacact gattaagttc gttatagtgg aagataaaat  34020
gccctcaaag cattttgcag gatatctttg atttttcaaa gatatggaac tgtagagttt  34080
gatagtgttc ttgaatgtgg ttgcatgaag ttttttggt ctgcatgtta tttttcctc  34140
gaaatatgtt ttgagtccaa caagtgattc acttgggatt cagaaagttg ttttctcaat  34200
atgtaacagt ttttttctat ggagaaaaat catagggacc gttggttttg gcttctttaa  34260
ttttgagctc agattaaacc cattttaccc ggtgttcttg gcagaattga aaacagtacg  34320
tagtaccgcg cctaccatgc cacctagtgc tgctagtgaa ggtggtgttg ctgaacttag  34380
agctgctgaa gttgctagct acactagaaa ggctgttgac gaaagacctg acctcactat  34440
agttggtgac gctgtttacg acgctaaggc ttttagggac gagcaccctg gtggtgctca  34500
cttcgttagc cttttcggag gtagggacgc tactgaggct tttatggaat atcaccgtag  34560
agcttggcct aaggctagga tgtctaagtt cttcgttggt tcacttgacg ctagcgagaa  34620
gcctactcaa gctgattcag cttaccttag actttgcgct gaggttaacg ctcttttgcc  34680
taagggtagc ggaggattcg ctcctcctag ctactggctt aaggctgctg ctcttgttgt  34740
tgctgctgtt agtatagagg gttatatgct ccttaggggt aagaccccttt tgcttagcgt  34800
tttccttgga ctcgtgttcg cttggatagg acttaatatt cagcacgacg ctaatcacgg  34860
tgctcttagt agacactcag tgattaacta ctgcctcggt tacgctcagg attggatagg  34920
tggtaatatg gtgctttggc ttcaagagca cgttgtgatg caccacctcc acactaacga  34980
cgttgacgct gatcctgatc aaaaggctca cggtgttctt agacttaagc ctactgacgg  35040
ttggatgcct tggcacgcac ttcaacaact ctatatcctt cctggtgagg ctatgtacgc  35100
ttttaagctt cttttcttgg acgcccttga gcttcttgct tggaggtggg agggtgagaa  35160
gattagccct cttgctagag ctttgttcgc tcctgctgtt gcttgtaagc ttggattctg  35220
ggctagattc gttgctctcc ctctctggct tcaacctact gttcacactg ctttgtgtat  35280
ctgtgctact gtgtgtactg gtagcttcta cctcgccttc ttcttcttta tctctcacaa  35340
cttcgacggt gttggtagcg ttggacctaa gggatcactt cctagatcag ctactttcgt  35400
tcaacgtcag gttgagacta gctctaacgt tggtggttac tggcttggag ttcttaacgg  35460
tggacttaac tttcagatag agcaccactt gttccctagg cttcaccact cttactacgc  35520
tcaaatagct cctgtggtta ggactcacat agagaagctc ggttttaagt accgtcactt  35580
ccctaccgtt ggatctaacc ttagctcaat gcttcagcat atgggtaaga tgggaactag  35640
acctggtgct gagaagggtg gtaaggctga gtagtgatta atgaataatt gattgctgct  35700
ttaatgagat atgcgagacg cctatgatcg catgatattt gctttcaatt ctgttgtgca  35760
cgttgtaaaa aacctgagca tgtgtagctc agatccttac cgccggtttc ggttcattct  35820
aatgaatata tcacccgtta ctatcgtatt tttatgaata atattctccg ttcaatttac  35880
tgattgtcta cgtagcgtca cctgacgtta cgtaaggcta cctaggctca cgtgacgtta  35940
cgtaacgcta cgtagcgtca ggtgaggtta gctaacgcta gctagcctca cctgacgtta  36000
```

ggtaaggcta cgtagcgtca cctgagatta gctaagccta cctagactca cgtgacctta 36060
ggtaacgcta cgtagcgtca aagctttaca acgctacaca aaacttataa ccgtaatcac 36120
cattcattaa cttaactact atcacatgca ttcatgaatt gaaacgagaa ggatgtaaat 36180
agttgggaag ttatctccac gttgaagaga tcgttagcga gagctgaaag accgagggag 36240
gagacgccgt caacacggac agagtcgtcg accctcacat gaagtaggag gaatctccgt 36300
gaggagccag agagacgtct ttggtcttcg gtttcgatcc ttgatctgac ggagaagacg 36360
agagaagtgc gactggactc cgtgaggacc aacagagtcg tcctcggttt cgatcgtcgg 36420
tattggtgga gaaggcggag gaatctccgt gacgagccag agagatgtcg tcggtcttcg 36480
gtttcgatcc ttgatctgac ggagaagacg agagaagtgc gacgagactc cgtgaggacc 36540
aacagagttg tcctcggttt cgatcgtcgg tttcggcgga gaaggcggag gaatctccgt 36600
gaggagccag agagacgtcg ttggtcttcg gtttcgatcc ttgatctgtt ggagaagacg 36660
agacaagtgg gacgagactc aacgacggag tcagagacgt cgtcggtctt cggtttcggc 36720
cgagaaggcg gagtcggtct tcggtttcgg ccgagaaggc ggaggagacg tcttcgattt 36780
gggtctctcc tcttgacgaa gaaaacaaag aacacgagaa ataatgagaa agagaacaaa 36840
agaaaaaaaa ataaaaataa aaataaaatt tggtcctctt atgtggtgac acgtggtttg 36900
aaacccacca aataatcgat cacaaaaaac ctaagttaag gatcggtaat aacctttcta 36960
attaattttg atttatatta aatcactctt tttatttata aaccccacta aattatgcga 37020
tattgattgt ctaagtacaa aaattctctc gaattcaata cacatgtttc atatatttag 37080
ccctgttcat ttaatattac tagcgcattt ttaatttaaa attttgtaaa ctttttttggt 37140 caaagaacat ttttttaatt agagacagaa atctagactc tttatttgga ataatagtaa 37200
taaagatata ttaggcaatg agtttatgat gttatgttta tatagtttat ttcattttaa 37260
attgaaaagc attattttta tcgaaatgaa tctagtatac aatcaatatt tatgtttttt 37320
catcagatac tttcctattt tttggcacct ttcatcggac tactgattta tttcaatgtg 37380
tatgcatgca tgagcatgag tatacacatg tcttttaaaa tgcatgtaaa gcgtaacgga 37440
ccacaaaaga ggatccatac aaatacatct catcgcttcc tctacta 37487

<210> SEQ ID NO 31
<211> LENGTH: 20
<212> TYPE: DNA
<213> ORGANISM: Artificial sequence
<220> FEATURE:
<223> OTHER INFORMATION: LBFDAU Locus 2 RB junction region

<400> SEQUENCE: 31
caccctggct ttggggtgag 20

<210> SEQ ID NO 32
<211> LENGTH: 20
<212> TYPE: DNA
<213> ORGANISM: Artificial sequence
<220> FEATURE:
<223> OTHER INFORMATION: LBFDAU Locus 2 LB junction region

<400> SEQUENCE: 32
tcctctacta ttctccgaca 20

<210> SEQ ID NO 33
<211> LENGTH: 5600
<212> TYPE: DNA
<213> ORGANISM: Artificial sequence
<220> FEATURE:
<223> OTHER INFORMATION: LBFDAU Locus 2 flanking sequence up to and including the right border of the T-DNA

<400> SEQUENCE: 33

```
attttagatt tagtcatatt tttaacttaa ttattaatta taataaatat ttttagtgat     60
ttagatgata aattttcatt gtcttgagaa taataaaaaa aaaatctaag gataatatca    120
tagttaaatt tatatgatat ttacttcagt aatattaaaa tattatatac atttttatta    180
tatttggttt agtaatatta aatggattct attttaaatt tcttatgaca atcaaaacca    240
cttagtgtga taatttctga aaaaaattgg caaaaaaatc aaaaatactt atcttattat    300
ttgtagtgat ttttctctct ctcatgttaa aattttgaat gtttaaagtc tttattatct    360
ttaataaata attagattaa atttttaata tataattacc cataatttaa aacaaatttc    420
attaatttta aaatcatcat tatctaaaaa gattatatat tatgttatcc aaaaatattt    480
tacatcataa tattttaaaa taaatataaa tttatgtata ttgttttatg tatatatgaa    540
tgtttttaag tttattttac ataatcaaat atattttaca aaaataattt ttatcatata    600
taaaatttaa catttaatta attattaaat atttcaaaag tatgaatata acttattctc    660
atggttttta attgataata tatctattta caatttttg taaaattatt aaacccgcaa     720
gtatggacaa aacacctagt atatatattt ggaacaaaga atacagacaa aacacctagt    780
atatatattt ggaacaaaaa atatacgtac atattttata tacatgaata acttatatat    840
cacttagaaa taggataatc aattgacatt aaactctctt aaattatata ttgtatagaa    900
ctatagatat acgtataaaa tatttataaa agataactac actatatata gaaacagata    960
atgatacatc cacgaaaatt cttctggaaa agaaacagag tggtttcgcg tcagcacacc   1020
tacgttgatc attggaaatt ggaatattga aacacgcttc aaatcaacga ctattaatta   1080
ccaatacacc ctggctttgg ggtgagagtt gatcggttaa ttatccaata catgccgttg   1140
gttaattagg attatataaa aaatcgatca tctattagaa tcgattacgg ttaaataggt   1200
ataaaaatgg agagaattga atcagttata aatttgtttt cagttaaaat atttctatga   1260
tcttcaatcg atttcggtat tttatactca acatggaaaa aatttcaaat gtatttcttc   1320
taaaagcaaa agaatctata aaaactatca ttttatccaa aacaccaaaa tagtctttta   1380
caatctttta cagccttcac ataaacgaaa acaaaagtga acaatttctt tttacagcct   1440
ttacaccaaa aagactacga tgaactatga taaaatttca taatctaaaa acattaatga   1500
ggtaaagact ctctcaaatg ggatattctt cgaaaatttt cataatcgaa cgatatactt   1560
gaatttgcaa ctcatgaccg aaattgtccc aatccataat actctttgac accctatcag   1620
atcccaacgt tgtccctggt ttcgaaacca ccatttcaaa catgaacata tcacaaaata   1680
aacatttaga caccaaatat ctgctaagcg cttacgtaag ctcagctgac gctacctagc   1740
gttagctaac gtcacgtgac gctacctagc gttacgtaac gtcagctgag gctagctagc   1800
tgaattaacg ccgaattaat tcgggggatc tggattttag tactggattt tggttttagg   1860
aattagaaat tttattgata gaagtatttt acaaatacaa atacatacta agggtttctt   1920
atatgctcaa cacatgagcg aaaccctata ggaaccctaa ttcccttatc tgggaactac   1980
tcacacatta ttatggagaa actcgagctt gtcgatcact cggtcttagc tccctttttgc  2040
tttccatcgg atggcttgat gtacttttgc acgtagaagt ttccgaagag gaacaagagg   2100
gagatcatgt agtagaagag gatcttgatg agccattgtg gatatggagc gttggttttc   2160
atatcgtagt aagcttgcac caagttgagc atgaactgga acatctggaa ttgggtgagg   2220
```

```
tatcttcccc agaagaggta cttgttcttg agctttgggg aagatctcaa gcaagcagcc   2280
aagaagtagt aagcgtacat caacacgtgc actccagagt tgagagcagc actccaataa   2340
gcctctcctc ctggagcgtg gtgagcaata gcccaccaga taagggagat agaagagtgg   2400
tggtacacgt ggaggaaaga aatctgtctg gtggatctct tgaggatcat gatcacggta   2460
tccatgaact ccacgtactt ggacatgtag aagaggtaaa cgaggatagc catctccttg   2520
tgctttgggt tataagcgtt tccccacaag gaatatctcc aggtgatagc ttggtaagcg   2580
atacccacgc acatgtaaag agacaaagcg aagcagaaca agttgtgcac caacaccaaa   2640
gcttgcaaca agaatggctc agaagctctt ggcttgagat ctctagcctt gatccaaagc   2700
aatcctccga tcacgatggt caagtaaaca gacactccca acacaattgg agttggagaa   2760
tcaacgagtg gcaatccctt agtagttggg gtatcagtca actcaactcc gaaagatccc   2820
aacaaagcgt tcactccttg ggaaaccttt ccatccaact ctccgtagaa cctctcaaca   2880
acttccatgg tttcttctaa agctgaaagt gaaccattat tacaacttaa cactcaactc   2940
acaagaggag aagcaacaaa gcttatgtaa ggatttagta ttaaggccaa aaaaacacag   3000
atcaaattca attattgaag ctttacttat caagttatca tataaccaat gaagacggta   3060
attcaaaaga aaaataaaag ggtttgtaga ataattgata cgtttacctt tgccgattca   3120
gagacagtga agcttaaaca gtactggcta tgaagaaatt ataatcgtgt aaaacttagt   3180
gagtgtgtat gaatgaaagt attgcaaaat cctcattata tagactacat gcataactag   3240
ttgcatgtaa atttgtagtt ttcttcatta ttgcatcctc caagtggatg tcatggtttt   3300
acacatggct tccatgcaaa tcatttccaa aatattttta aactttccac agggcatcca   3360
tgcatgcacc tcaaaacttg tgtgtggtaa cattgttgtc ttgaaaaatt actaaacctt   3420
ttgtccacgt gacgttcatg cacctcaaat cttgtgtggt accattatta tcctcaagaa   3480
ttattgaatg tttggtgtat atgccatcca tgcagcattg caacaattaa atctccaaac   3540
cttgtggtac catattcact cactttaatt ctcctatagt agaaatatta gcaaatattt   3600
acatttccag ttgattagta tatgtattta gaagacaaaa ataatttaga atcaattaat   3660
caacttgcaa attgctaagt gttggcaaac gttagcataa aaggtgttat aaatttagta   3720
ccaaatataa aaatttatcg caaatcaaat acataacaca catagtaaaa caaaaacaaa   3780
ttacaagggt ttagacgttt agtggcaatg tgtaaatttg ctgcaggagt gacgctagct   3840
agcgttacgt aacgtcagct gagcctaggt agcgttagct aagctcacgt gacgctacgt   3900
aggcttacgt aacgtcagct gaggctacgt agcgttagct aacgtcacgt gacgctacgt   3960
aggcttacgt aatagttact aatcagtgat caggcgcgcc attaatttcc accttcacct   4020
acgatggggg gcatcgcacc ggtgagtaat attgtacggc taagagcgaa tttggcctgt   4080
agacctcaat tgcgagcttt ctaatttcaa actattcggg cctaactttt ggtgtgatga   4140
tgctgactgt ttcgacgtta attgatccta cactatgtag gtcatatcca tcgttttaat   4200
ttttggccac cattcaattc tgtcttgcct ttagggatgt gaatatgaac ggccaaggta   4260
agagaataaa aataatccaa attaaagcaa gagaggccaa gtaagataat ccaaatgtac   4320
acttgtcatt gccaaaatta gtaaaatact cggcatattg tattcccaca cattattaaa   4380
ataccgtata tgtattggct gcatttgcat gaataatact acgtgtaagc ccaaaagaac   4440
ccacgtgtag cccatgcaaa gttaacactc acgaccccat tcctcagtct ccactatata   4500
aacccaccat ccccaatctc accaaaccca ccacacaact cacaactcac tctcacacct   4560
```

```
taaagaacca atcaccacca aaaaatttca cgatttggaa tttgattcct gcgatcacag   4620

gtatgacagg ttagattttg ttttgtatag ttgtatacat acttctttgt gatgttttgt   4680

ttacttaatc gaatttttgg agtgttttaa ggtctctcgt ttagaaatcg tggaaaatat   4740

cactgtgtgt gtgttcttat gattcacagt gtttatgggt ttcatgttct ttgttttatc   4800

attgaatggg aagaaatttc gttgggatac aaatttctca tgttcttact gatcgttatt   4860

aggagtttgg ggaaaaagga agagtttttt tggttggttc gagtgattat gaggttattt   4920

ctgtatttga tttatgagtt aatggtcgtt ttaatgttgt agacatggga aaaggatctg   4980

agggaagatc tgctgctaga gagatgactg ctgaggctaa cggagataag agaaagacca   5040

tcctcattga gggagtgttg tacgatgcta ccaacttcaa acacccagga ggttccatta   5100

ttaacttcct caccgaggga gaagctggag ttgatgctac ccaagcttac agagagttcc   5160

atcagagatc cggaaaggct gataagtacc tcaagtccct cccaaagttg gatgcttcta   5220

aggtggagtc taggttctct gctaaggagc aggctagaag ggacgctatg accagggatt   5280

acgctgcttt cagagaggag ttggttgctg agggatactt cgatccatct atcccacaca   5340

tgatctacag agtggtggag attgtggctt tgttcgcttt gtctttctgg ttgatgtcta   5400

aggcttctcc aacctctttg gttttgggag tggtgatgaa cggaatcgct caaggaagat   5460

gcggatgggt tatgcacgag atgggacacg gatctttcac tggagttatc tggctcgatg   5520

ataggatgtg cgagttcttc tacggagttg gatgtggaat gtctggacac tactggaaga   5580

accagcactc taagcaccac                                               5600
```

<210> SEQ ID NO 34
<211> LENGTH: 1321
<212> TYPE: DNA
<213> ORGANISM: Artificial sequence
<220> FEATURE:
<223> OTHER INFORMATION: LBFDAU Locus 2 flanking sequence up to and including the left border of the T-DNA

<400> SEQUENCE: 34

```
taaagatata ttaggcaatg agtttatgat gttatgttta tatagtttat ttcattttaa     60

attgaaaagc attattttta tcgaaatgaa tctagtatac aatcaatatt tatgtttttt    120

catcagatac tttcctattt tttggcacct ttcatcggac tactgattta tttcaatgtg    180

tatgcatgca tgagcatgag tatacacatg tcttttaaaa tgcatgtaaa gcgtaacgga    240

ccacaaaaga ggatccatac aaatacatct catcgcttcc tctactattc tccgacacac    300

acactgagca tggtgcttaa acactctggt gagttctagt acttctgcta taatgttaaa    360

ttttatatta tatacctact tcctctctct cgctctgtta tgttcgattt cgaaaggatt    420

tcaagatcaa agatgatgag aaaaggtacc ttttcgatat ttaagacaag gaaagaaagg    480

acgaggttga aattttcggg acttggaggg ctaaagtgga agagactgaa tctgaagatg    540

tcgtttctcg aaactttgag atacagaatc atgtctatca ttgaaggaat ggttttggtt    600

tctaagcttg ctttcttctt tctctgttgc ggttgcagat tttaacacgt tagttttttt    660

tttttcgttt ttttgaacgt caacaatgtc ttttttgtac tctttagctc atgtgtaaaa    720

ttctaaattc ttccaataac atacccaaca aattattcgt atctgatttt tatagttttt    780

aacctgttaa tgtaattaat ctaagtgtaa tttttaggct aaatgttaaa ttttatatta    840

aagttttgta acttgaaatt acattcttct tatagcggat aaacagaaaa tgctcttaaa    900

caaatcctga aacaagtaaa aaatacaaca gaaaaatcta acgtttaatt cttaaaacct    960
```

```
caaaatcctt atttttacag ctttcaaagt ttaacagctg gaaacctgta gaaaatcaga   1020

cacagcctct caagttttct ggacaataaa tactggtaac gtaagaaaac caattaatga   1080

taccgtcgtt cagtagatag aactgacgat gtgaagatta attgtttctg taatatactg   1140

aatttgaaaa tttatcatca tcatgttaac ggaagttgtc tgtaaaagta gttgattacc   1200

tgttatcgtg taaagtagtt agtaatttct tgcttatttg aaaaatagag aacatttaac   1260

atgtattttt aaataggcac gaccatgcta ctgaacttta tgaaatgctt tggaatctta   1320

t                                                                   1321


<210> SEQ ID NO 35
<211> LENGTH: 23
<212> TYPE: DNA
<213> ORGANISM: Artificial sequence
<220> FEATURE:
<223> OTHER INFORMATION: LBFDAU Locus 2_Forward primer

<400> SEQUENCE: 35

cactgagcat ggtgcttaaa cac                                             23


<210> SEQ ID NO 36
<211> LENGTH: 29
<212> TYPE: DNA
<213> ORGANISM: Artificial sequence
<220> FEATURE:
<223> OTHER INFORMATION: LBFDAU Locus 2_Reverse primer

<400> SEQUENCE: 36

agagcgagag agaggaagta ggtatataa                                       29


<210> SEQ ID NO 37
<211> LENGTH: 19
<212> TYPE: DNA
<213> ORGANISM: Artificial sequence
<220> FEATURE:
<223> OTHER INFORMATION: LBFDAU locus 2_Probe

<400> SEQUENCE: 37

ctggtgagtt ctagtactt                                                  19


<210> SEQ ID NO 38
<211> LENGTH: 19
<212> TYPE: DNA
<213> ORGANISM: Artificial sequence
<220> FEATURE:
<223> OTHER INFORMATION: Primer for determining zygosity of LBFLFK Locus
      1

<400> SEQUENCE: 38

agaagtgtac gcgacgaga                                                  19


<210> SEQ ID NO 39
<211> LENGTH: 21
<212> TYPE: DNA
<213> ORGANISM: Artificial sequence
<220> FEATURE:
<223> OTHER INFORMATION: Primer for determining zygosity of LBFLFK Locus
      1

<400> SEQUENCE: 39

tcaggagcga gaatgcgaaa g                                               21


<210> SEQ ID NO 40
<211> LENGTH: 21
```

```
<212> TYPE: DNA
<213> ORGANISM: Artificial sequence
<220> FEATURE:
<223> OTHER INFORMATION: Primer for determining zygosity of LBFLFK Locus
      2

<400> SEQUENCE: 40

acccatacat acgcataagt g                                                21


<210> SEQ ID NO 41
<211> LENGTH: 19
<212> TYPE: DNA
<213> ORGANISM: Artificial sequence
<220> FEATURE:
<223> OTHER INFORMATION: Primer for determining zygosity of LBFLFK Locus
      2

<400> SEQUENCE: 41

aatatatggg ctacattga                                                   19


<210> SEQ ID NO 42
<211> LENGTH: 18
<212> TYPE: DNA
<213> ORGANISM: Artificial sequence
<220> FEATURE:
<223> OTHER INFORMATION: Primer for determining zygosity of LBFDAU Locus
      1

<400> SEQUENCE: 42

ggcaggcgtg atcttatt                                                    18


<210> SEQ ID NO 43
<211> LENGTH: 21
<212> TYPE: DNA
<213> ORGANISM: Artificial sequence
<220> FEATURE:
<223> OTHER INFORMATION: Primer for determining zygosity of LBFDAU Locus
      1

<400> SEQUENCE: 43

cataatttgc agtcgctgat t                                                21


<210> SEQ ID NO 44
<211> LENGTH: 21
<212> TYPE: DNA
<213> ORGANISM: Artificial sequence
<220> FEATURE:
<223> OTHER INFORMATION: Primer for determining zygosity of LBFDAU Locus
      2

<400> SEQUENCE: 44

agataacgat acatccacga a                                                21


<210> SEQ ID NO 45
<211> LENGTH: 21
<212> TYPE: DNA
<213> ORGANISM: Artificial sequence
<220> FEATURE:
<223> OTHER INFORMATION: Primer for determining zygosity of LBFDAU Locus
      2

<400> SEQUENCE: 45

cgaacataac agagcgagag a                                                21
```

UNITED STATES PATENT AND TRADEMARK OFFICE
CERTIFICATE OF CORRECTION

| | | |
|---|---|---|
| PATENT NO. | : 11,033,593 B2 | |
| APPLICATION NO. | : 15/526443 | |
| DATED | : June 15, 2021 | |
| INVENTOR(S) | : Toralf Senger et al. | |

It is certified that error appears in the above-identified patent and that said Letters Patent is hereby corrected as shown below:

In the Claims

At Column 412, Line 48 (Claim 12, last line), "SEQ ID NO: 13." should be -- SEQ ID NO: 12. --

Signed and Sealed this
Twentieth Day of June, 2023

Katherine Kelly Vidal
*Director of the United States Patent and Trademark Office*